United States Patent
Yeung et al.

(10) Patent No.: US 10,144,706 B2
(45) Date of Patent: Dec. 4, 2018

(54) COMPOUNDS USEFUL AS IMMUNOMODULATORS

(71) Applicant: BRISTOL-MYERS SQUIBB COMPANY, Princeton, NJ (US)

(72) Inventors: Kap-Sun Yeung, Madison, CT (US); Katharine A. Grant-Young, Madison, CT (US); Juliang Zhu, North Haven, CT (US); Mark G. Saulnier, Higganum, CT (US); David B. Frennesson, Naugatuck, CT (US); David R. Langley, Meriden, CT (US); Piyasena Hewawasam, Middletown, CT (US); Tao Wang, Farmington, CT (US); Zhongxing Zhang, Madison, CT (US); Zhaoxing Meng, Middletown, CT (US); Li-Qiang Sun, Glastonbury, CT (US); Eric Mull, Guilford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/689,115

(22) Filed: Aug. 29, 2017

(65) Prior Publication Data
US 2018/0057455 A1 Mar. 1, 2018

Related U.S. Application Data

(60) Provisional application No. 62/382,480, filed on Sep. 1, 2016.

(51) Int. Cl.
*C07D 207/12* (2006.01)
*C07D 217/18* (2006.01)
(Continued)

(52) U.S. Cl.
CPC .......... *C07D 207/12* (2013.01); *C07C 217/18* (2013.01); *C07C 217/28* (2013.01); *C07C 217/58* (2013.01); *C07C 229/14* (2013.01); *C07C 235/08* (2013.01); *C07C 237/04* (2013.01); *C07C 237/06* (2013.01); *C07C 255/24* (2013.01); *C07C 255/25* (2013.01); *C07D 205/04* (2013.01); *C07D 207/14* (2013.01); *C07D 207/16* (2013.01); *C07D 211/22* (2013.01); *C07D 211/46* (2013.01); *C07D 211/58* (2013.01); *C07D 211/60* (2013.01); *C07D 211/66* (2013.01); *C07D 211/90* (2013.01); *C07D 213/38* (2013.01); *C07D 213/42* (2013.01); *C07D 213/55* (2013.01); *C07D 213/73* (2013.01); *C07D 213/79* (2013.01); *C07D 213/85* (2013.01); *C07D 231/12* (2013.01); *C07D 239/26* (2013.01); *C07D 277/28* (2013.01); *C07D 295/088* (2013.01); *C07D 401/04* (2013.01); *C07D 401/12* (2013.01); *C07D 401/14* (2013.01); *C07D 403/12* (2013.01); *C07D 405/06* (2013.01); *C07D 405/12* (2013.01);
(Continued)

(58) Field of Classification Search
CPC ... C07C 217/18; C07C 217/28; C07C 217/58; C07C 229/14; C07C 237/04; C07C 237/06; C07C 255/24; C07C 255/25; C07C 2601/02; C07C 2601/04; C07C 2601/08; C07D 205/04; C07D 207/12; C07D 207/14; C07D 207/16; C07D 211/22; C07D 211/46; C07D 211/58; C07D 211/60; C07D 211/66; C07D 211/90; C07D 213/38; C07D 213/42; C07D 213/55; C07D 213/73; C07D 213/79; C07D 213/85; C07D 231/12; C07D 239/26; C07D 277/28; C07D 295/088; C07D 401/04; C07D 401/12; C07D 401/14; C07D 403/12; C07D 405/06; C07D 405/12; C07D 405/14; C07D 413/14; C07D 417/12
See application file for complete search history.

(56) References Cited

U.S. PATENT DOCUMENTS

| 4,564,479 A | 1/1986 | Spencer |
| 5,977,117 A | 11/1999 | Chan et al. |

(Continued)

FOREIGN PATENT DOCUMENTS

| DE | 2736889 | 2/1978 |
| EP | 2216330 A1 | 8/2010 |

(Continued)

OTHER PUBLICATIONS

Jaquinod, et al., Biphenyl-strapped Diphenylporphyrins: Synthesis and Spectroscopic Characterization of a Series of Porphyrins with Ether-linked straps. Preliminary CO binding properties of their Iron(II) derivatives, Inorg. Chem., 37, 1142-1149, table II (1998). (Year: 1998).*

(Continued)

*Primary Examiner* — Erich A Leeser
(74) *Attorney, Agent, or Firm* — Pamela A. Mingo

(57) ABSTRACT

The present disclosure generally relates to compounds useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

8 Claims, No Drawings

Specification includes a Sequence Listing.

(51) Int. Cl.

| | |
|---|---|
| *C07D 237/06* | (2006.01) |
| *C07D 205/04* | (2006.01) |
| *C07D 207/14* | (2006.01) |
| *C07D 207/16* | (2006.01) |
| *C07D 211/22* | (2006.01) |
| *C07D 211/66* | (2006.01) |
| *C07D 211/90* | (2006.01) |
| *C07D 213/38* | (2006.01) |
| *C07D 213/73* | (2006.01) |
| *C07D 213/79* | (2006.01) |
| *C07D 213/85* | (2006.01) |
| *C07D 231/12* | (2006.01) |
| *C07D 239/26* | (2006.01) |
| *C07D 277/28* | (2006.01) |
| *C07D 295/088* | (2006.01) |
| *C07D 401/12* | (2006.01) |
| *C07D 401/14* | (2006.01) |
| *C07D 403/12* | (2006.01) |
| *C07D 405/12* | (2006.01) |
| *C07D 405/14* | (2006.01) |
| *C07D 413/14* | (2006.01) |
| *C07D 401/04* | (2006.01) |
| *C07D 405/06* | (2006.01) |
| *C07D 417/12* | (2006.01) |
| *C07D 211/46* | (2006.01) |
| *C07D 211/58* | (2006.01) |
| *C07D 211/60* | (2006.01) |
| *C07D 213/42* | (2006.01) |
| *C07D 213/55* | (2006.01) |
| *C07C 237/04* | (2006.01) |
| *C07C 235/08* | (2006.01) |
| *C07C 229/14* | (2006.01) |
| *C07C 217/58* | (2006.01) |
| *C07C 217/28* | (2006.01) |
| *C07C 217/18* | (2006.01) |
| *C07C 237/06* | (2006.01) |
| *C07C 255/24* | (2006.01) |
| *C07C 255/25* | (2006.01) |

(52) U.S. Cl.
CPC ......... *C07D 405/14* (2013.01); *C07D 413/14* (2013.01); *C07D 417/12* (2013.01); *C07C 2601/02* (2017.05); *C07C 2601/04* (2017.05); *C07C 2601/08* (2017.05)

(56) References Cited

U.S. PATENT DOCUMENTS

| | | | |
|---|---|---|---|
| 7,968,552 | B2 | 6/2011 | Negoro et al. |
| 9,850,225 | B2 | 12/2017 | Chupak et al. |
| 9,872,852 | B2 | 1/2018 | Chupak et al. |

FOREIGN PATENT DOCUMENTS

| | | |
|---|---|---|
| EP | 2390304 B1 | 11/2011 |
| JP | 2005-179281 A | 7/2005 |
| WO | WO 97/25321 A2 | 7/1997 |
| WO | WO 2004/007439 A1 | 1/2004 |
| WO | WO 2004/080377 A2 | 9/2004 |
| WO | WO 2005/080367 A1 | 9/2005 |
| WO | WO 2007/017687 A2 | 2/2007 |
| WO | WO 2008/130514 A1 | 10/2008 |
| WO | WO 2017/066227 A1 | 4/2017 |
| WO | WO 2018/009505 A1 | 1/2018 |

OTHER PUBLICATIONS

Guzik, K. et al., "Small-Molecule Inhibitors of the Programmed Cell Death-1/Programmed Death-Ligand 1 (PD-1/PD-1) Interaction via Transiently Induced Protein States and Dimerization of PD-L1," Journal of Medicinal Chemistry, 60, pp. 5857-5867 (2017).

Liu, Kefang, et al., "Structural basis of anti-PD-L1 monoclonal antibody avelumab for tumor therapy," Cell Research, 27, pp. 151-153 (2017).

Ohaegbulam, K.C., et al., "Human cancer immunotherapy with antibodies to the PD-1 and PD-L1 pathway," Trends in Molecular Medicine, vol. 21, No. 1, pp. 24-33 (Jan. 2015).

Zak, K.M., et al., "Structural basis for small molecule targeting of the programmed death ligand 1 (PD-L1)," Oncotarget, vol. 7, No. 21, pp. 30323-30335 (2016).

Chen, Li, et al., "Toward Supramolecular Ion Channels Formed by Oligonucleotide Analogs: Hydrophobic Guanine Dimers," Tetrahedron Letters, vol. 39, pp. 3627-3630 (1998).

Teranishi, Katsunori, "Regioselective $2^A$, $2^D$-Disulfonyl Capping of Beta-cyclodetrin for Practical Bifunctionalization on the Secondary Hydroxyl Face," Tetrahedron Letters, vol. 42, pp. 5477-5480 (2001).

Gao, B., et al., "A High-Yield Synthesis of [m]Biphenyl-Extended Pillar[n]arenes for an Efficient Selective Inclusion of Toluene and m-Xyene in the Solid State," Chem. Commun., vol. 52, pp. 5804-5807 (2016).

Windisch, B., et al., "Macrocyclic Hydrocarbons with Rigid and Flexible Building Blocks," J. Prakt. Chem., vol. 342, No. 7, 642-653 (2000).

* cited by examiner

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270
```

```
Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
                340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
        370                 375                 380

<210> SEQ ID NO 2
<211> LENGTH: 238
<212> TYPE: PRT
<213> ORGANISM: Homo sapiens

<400> SEQUENCE: 2

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
                20                  25                  30

Leu Ala Ala Leu Ile Val Tyr Trp Glu Met Glu Asp Lys Asn Ile Ile
            35                  40                  45

Gln Phe Val His Gly Glu Glu Asp Leu Lys Val Gln His Ser Ser Tyr
        50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu Pro Leu Ala His Pro Pro Asn Glu Arg Thr Gly Ser
    210                 215                 220

Ser Glu Thr Val Arg Phe Gln Gly His His His His His
225                 230                 235
```

COMPOUNDS USEFUL AS IMMUNOMODULATORS

CROSS-REFERENCE TO RELATED APPLICATIONS

This application claims the benefit of U.S. provisional patent application Ser. No. 62/382,480, filed on Sep. 1, 2016, hereby incorporated by reference in its entirety.

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., Nat. Imm. 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir Me, Butte M J, Freeman G J, et al. PD-1 and its ligands in tolerance and immunity. *Annu. Rev. Immunol.* 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al, *Immunity;* 27:111-122 (2007)). The interaction of PD-L1/CD80 on expressing immune cells has been shown to be an inhibitory one. Blockade of this interaction has been shown to abrogate this inhibitory interaction (Paterson A M, et al., *J Immunol.*, 187:1097-1105 (2011); Yang J, et al. *J Immunol.* August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., *New Engl J Med* 2012). Preclinical animal models of tumors have shown that blockade of the PD-1/PD-L1 pathway by monoclonal antibodies can enhance the immune response and result in the immune response to a number of histologically distinct tumors (Dong H, Chen L. B7-H1 pathway and its role in the Evasion of tumor immunity. *J Mol Med.* 2003; 81(5):281-287; Dong H, Strome S E, Salamoa D R, et al. Tumor-associated B7-H1 promotes T-cell apoptosis: a potential mechanism of immune evasion. *Nat Med.* 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. Restoring function in exhausted CD8 T cells during chronic viral infection. *Nature.* 2006; 439 (7077):682-687). Humanized mice infected with HIV-1 show enhanced protection against viremia and reduced viral depletion of CD4+ T cells (Palmer et al., *J. Immunol* 2013). Blockade of PD-1/PD-L1 through monoclonal antibodies to PD-L1 can restore in vitro antigen-specific functionality to T cells from HIV patients (Day, *Nature* 2006; Petrovas, *J. Exp. Med.* 2006; Trautman, *Nature Med.* 2006; D'Souza, *J. Immunol.* 2007; Zhang, *Blood* 2007; Kaufmann, *Nature Imm.* 2007; Kasu, *J. Immunol.* 2010; Porichis, Blood 2011), HCV patients [Golden-Mason, J. Virol. 2007; Jeung, J. Leuk. Biol. 2007; Urbani, *J. Hepatol.* 2008; Nakamoto, PLoS Path. 2009; Nakamoto, Gastroenterology 2008] or HBV patients (Boni, *J. Virol.* 2007; Fisicaro, Gastro. 2010; Fisicaro et al., *Gastroenterology,* 2012; Boni et al., *Gastro.,* 2012; Penna et al., *J Hep,* 2012; Raziorrough, Hepatology 2009; Liang, World J *Gastro.* 2010; Zhang, *Gastro.* 2008).

Blockade of the PD-L1/CD80 interaction has also been shown to stimulate immunity (Yang J., et al., *J Immunol.* August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., *Nat Rev Immunol* (2013)). These include increased levels of PD-1 and PD-L1 and T ceoll apoptosis (Guignant, et al, *Crit. Care* (2011)). Antibodies directed to PD-L1 can reduce the level of Immune cell apoptosis (Zhang et al, *Crit. Care* (2011)). Furthermore, mice lacking PD-1 expression are more resistant to septic shock symptoms than wildtype mice (Yang J., et al. *J Immunol.* August 1; 187(3):1113-9 (2011)). Studies have revealed that blockade of the interactions of PD-L1 using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., "Enhancing therapeutic vaccination by blocking PD-1-mediated inhibitory signals during chronic infection," *The Journal of Experimental Medicine,* vol. 205, no. 3, pp. 543-555, 2008; A. C. Finnefrock, A. Tang, F. Li et al., "PD-1 blockade in rhesus macaques: impact on chronic infection and prophylactic vaccination," *The Journal of Immunology,* vol. 182, no. 2, pp. 980-987, 2009; M.-Y. Song, S.-H. Park, H. J. Nam, D.-H. Choi, and Y.-C. Sung, "Enhancement of vaccine-induced primary and memory CD8+t-cell responses by soluble PD-1," The *Journal of Immunotherapy,* vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection. Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

The present disclosure also provides pharmaceutical compositions comprising a compound of formula (I) and/or a pharmaceutically acceptable salt thereof; and a pharmaceutically acceptable carrier.

The present disclosure also provides a method of treating a disease or disorder associated with the activity of PD-L1 including its interaction with other proteins such as PD-1 and B7-1(CD80), the method comprising administering to a patient in need thereof a compound of formula (I) and/or a pharmaceutically acceptable salt thereof. The present disclosure also provides processes and intermediates for making the compounds of formula (I) and/or salts thereof.

The present disclosure also provides a compound of formula (I) and/or a pharmaceutically acceptable salt thereof, for use in therapy.

The present disclosure also provides the use of the compounds of formula (I) and/or pharmaceutically acceptable salts thereof, for the manufacture of a medicament for the treatment or prophylaxis of PD-L1 related conditions, such as cancer and infectious diseases.

The compounds of formula (I) and compositions comprising the compounds of formula (I) may be used in treating, preventing, or curing various infectious diseases and cancer. Pharmaceutical compositions comprising these compounds are useful in treating, preventing, or slowing the progression of diseases or disorders in a variety of therapeutic areas, such as cancer and infectious diseases.

These and other features of the disclosure will be set forth in expanded form as the disclosure continues.

In a first aspect the present disclosure provides a compound of formula (I)

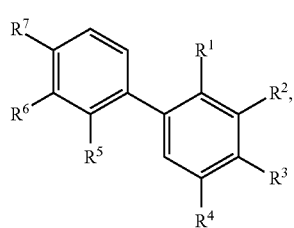

(I)

or a pharmaceutically acceptable salt thereof, wherein:

$R^1$ and $R^5$ are independently selected from hydrogen, —$CH_3$, cyano, halo, halomethyl, dihalomethyl, and trihalomethyl;

$R^2$ and $R^3$ are independently selected from hydrogen, —$O(CH_2)_m$Ph, —$(CH_2)_m$OPh, —$O(CH_2)_n NR^a R^b$, —$(CH_2)_m$ Ph, -(alkenylene)Ph, —$S(O)_2NH(CH_2)_n NR^a R^b$, —$S(O)_2NH(CH_2)_n CO_2H$, —$O(CH_2)$piperidinyl, —$O(CH_2)_m$ pyridinyl, —$(CH_2)_m NH(CH_2)_n NR^a R^b$, —$NH(CH_2)_n NR^a R^b$, —$C(O)NH(CH_2)_n NR^a R^b$, —$NHC(O)(CH_2)_n NR^a R^b$, —$NHC(O)NH(CH_2)_n NR^a R^b$, and —$NHC(O)NH(CH_2)_n CO_2H$; wherein each piperidinyl group is optionally substituted with a $C_1$-$C_3$alkyl group; and wherein the pyridinyl group is optionally substituted with a cyano group; and wherein each Ph group is optionally substituted with one, two, or three groups independently selected from $C_1$-$C_3$alkoxy, $C_1$-$C_3$alkyl, $C_1$-$C_3$alkylcarbonyl, amino, carboxy, cyano, ($C_3$-$C_6$cycloalkyl)alkoxy, halo, hydroxy, hydroxymethyl, —CHO, —$C(O)NR^a R^b$, —$(CH_2)_m NR^a R^b$, —$OCH_2$phenyl wherein the phenyl is optionally substituted with one or two halo groups, and —$OCH_2$pyridinyl optionally substituted with a cyano group, aminocarbonyl group, or a pyrazole ring; or $R^2$ and $R^3$, together with the atoms to which they are attached, form a 1,4-dioxane ring optionally substituted with —$O(CH_2)_n NR^a R^b$;

$R^4$ is selected from hydrogen; —$O(CH_2)_m$Ph, —$(CH_2)_m$OPh, —$O(CH_2)_n NR^a R^b$, —$(CH_2)_m$Ph, -(alkenylene)Ph, —$S(O)_2NH(CH_2)_n NR^a R^b$, —$S(O)_2NH(CH_2)_n CO_2H$, —$O(CH_2)$piperidinyl, —$O(CH_2)_m$pyridinyl, —$NH(CH_2)_n NR^a R^b$, —$C(O)NH(CH_2)_n NR^a R^b$, $NHC(O)(CH_2)_n NR^a R^b$, —$NHC(O)NH(CH_2)_n NR^a R^b$, and —$NHC(O)NH(CH_2)_n CO_2H$; wherein each piperidinyl group is optionally substituted with a $C_1$-$C_3$alkyl group; and wherein the pyridinyl group is optionally substituted with a cyano group; and wherein each Ph group is optionally substituted with one, two, or three groups independently selected from $C_1$-$C_3$alkoxy, $C_1$-$C_3$alkyl, $C_1$-$C_3$alkylcarbonyl, amino, carboxy, cyano, ($C_3$-$C_6$cycloalkyl)alkoxy, halo, hydroxy, hydroxymethyl, —$C(O)NR^a R^b$, —$(CH_2)_m NR^a R^b$, —$OCH_2$phenyl wherein the phenyl is optionally substituted with one or two halo groups, and —$OCH_2$pyridinyl optionally substituted with a cyano group, aminocarbonyl group, or a pyrazole ring;

$R^6$ and $R^7$ are independently selected from hydrogen, —$O(CH_2)_m$Ph, —$(CH_2)_m$OPh, —$O(CH_2)_n NR^a R^b$, —$(CH_2)_m$ Ph, -(alkenylene)Ph, —$S(O)_2NH(CH_2)_n NR^a R^b$, $S(O)_2NH(CH_2)_n CO_2H$, —$O(CH_2)$piperidinyl, —$O(CH_2)_m$pyridinyl, —$(CH_2)_m NH(CH_2)_n NR^a R^b$, —$NH(CH_2)_n NR^a R^b$, —$C(O)NH(CH_2)_n NR^a R^b$, $NHC(O)(CH_2)_n NR^a R^b$, —$NHC(O)NH(CH_2)_n NR^a R^b$, and —$NHC(O)NH(CH_2)_n CO_2H$; wherein the piperidinyl group is optionally substituted with a $C_1$-$C_3$alkyl group; and wherein the pyridinyl group is optionally substituted with a cyano group; and wherein each Ph group is optionally substituted with one, two, or three groups independently selected from $C_1$-$C_3$alkoxy, $C_1$-$C_3$alkyl, $C_1$-$C_3$alkylcarbonyl, amino, carboxy, cyano, ($C_3$-$C_6$cycloalkyl)alkoxy, halo, hydroxy, hydroxymethyl, —$C(O)NR^a R^b$, —$(CH_2)_m NR^a R^b$, —$OCH_2$phenyl wherein the phenyl is optionally substituted with one or two halo groups; and —$OCH_2$pyridinyl optionally substituted with a cyano group, aminocarbonyl group, or a pyrazole ring; or $R^6$ and $R^7$, together with the atoms to which they are attached, form a 1,4-dioxane ring optionally substituted with —$O(CH_2)_n NR^a R^b$;

provided that at least two of $R^2$, $R^3$, $R^4$, $R^6$, and $R^7$ are other than hydrogen; and provided that when $R^2$ is —$(CH_2)_m$OPh, —$(CH_2)_m$Ph, or -(alkenylene)Ph then $R^6$ is selected from —$(CH_2)_m$OPh, —$(CH_2)_m$Ph, and -(alkenylene)Ph;

m is 1, 2, or 3;

n is 2, 3, 4, 5;

$R^a$ and $R^b$ are independently selected from hydrogen, $C_1$-$C_3$alkyl, $C_1$-$C_3$alkylsulfonyl$C_1$-$C_3$alkyl, aminocarbonyl$C_1$-$C_6$alkyl, carboxy$C_2$-$C_6$alkenyl, carboxy$C_1$-$C_6$alkyl, (carboxy$C_1$-$C_3$alkyl)carbonyl, cyano$C_1$-$C_3$alkyl, ($C_3$-$C_6$cycloalkyl)$C_1$-$C_3$alkyl, $C_3$-$C_6$cycloalkyl, halo$C_1$-$C_3$alkyl, hydroxy$C_1$-$C_6$alkyl, (hydroxy$C_1$-$C_6$alkyl)carbonyl, imidazolyl$C_1$-$C_3$alkyl, morpholinyl$C_1$-$C_3$alkyl, oxeranyl, phenyl, phenyl$C_1$-$C_3$alkyl, piperidinyl, piperidinyl$C_1$-$C_3$alkyl, pyridinyl$C_1$-$C_3$alkyl, pyrimidinyl$C_1$-$C_3$alkyl, pyrazolyl$C_1$-$C_3$alkyl, tetrahydrofuryl$C_1$-$C_3$alkyl, thiazolyl, thiazolyl$C_1$-$C_3$alkyl, ($NR^c R^d$)$C_1$-$C_3$alkyl,

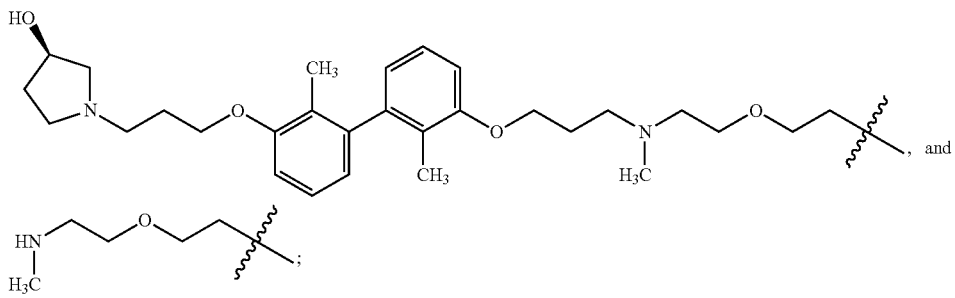

, and

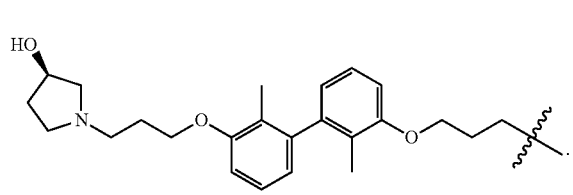 [SMILES: *CCCOc1cccc(-c2cccc(OCCCN3CC[C@@H](O)C3)c2C)c1C]

;

wherein the alkyl part of the carboxyC$_1$-C$_3$alkyl is further optionally substituted with one or two groups selected from C$_1$-C$_3$alkoxy, C$_1$-C$_3$alkylsulfanyl, cyano, hydroxy, indolyl, phenylC$_1$-C$_3$alkoxy, phenyl optionally substituted with one halo, and pyridinyl; and wherein the alkyl part of the (C$_3$-C$_6$cycloalkyl)C$_1$-C$_3$alkyl, the haloC$_1$-C$_3$alkyl, the imidazolylC$_1$-C$_3$alkyl, and the phenylC$_1$-C$_3$alkyl is optionally substituted with a aminocarbonyl or carboxy group;

wherein the alkyl part of, the is optionally substituted with an aminocarbonyl group;

wherein the C$_3$-C$_6$cycloalkyl and the cycloalkyl part of the (C$_3$-C$_6$cycloalkyl)C$_1$-C$_3$alkyl is optionally substituted with one, two, or three groups independently selected from hydroxy and hydroxyC$_1$-C$_3$alkyl; and wherein the alkyl part of the hydroxyC$_1$-C$_6$alkyl is further optionally substituted with one group selected from C$_1$-C$_3$alkoxy, C$_1$-C$_6$alkoxycarbonyl, C$_3$-C$_6$cycloalkyl, phenylC$_1$-C$_3$alkoxycarbonyl, tetrahydrofuryl, imidazolyl optionally substituted with one or two groups independently selected from C$_1$-C$_3$alkyl and halo, pyridinyl, phenyl optionally substituted with two halo groups, and thiazolyl; and wherein the imidazolyl part of the imidazolylC$_1$-C$_3$alkyl, the piperidinyl, the piperidinyl part of the piperidinylC$_1$-C$_3$alkyl, the pyrazolyl part of the pyrazolylC$_1$-C$_3$alkyl, and the pyridinyl part of the pyridinylC$_1$-C$_3$alkyl are optionally substituted with one, two, or three groups independently selected from C$_1$-C$_3$alkyl, cyano, halo, and hydroxyC$_1$-C$_3$alkyl; and wherein the phenyl and the phenyl part of the phenylC$_1$-C$_3$alkyl is optionally substituted with one or two groups independently selected from C$_1$-C$_3$alkoxy, amino and halo; or R$^a$ and R$^b$, together with the nitrogen atom to which they are attached, form a four-, five-, or six-membered ring optionally containing one additional heteroatom selected from nitrogen, oxygen, and sulfur; wherein the ring is optionally fused to a phenyl group to form a bicyclic structure and wherein the ring and bicyclic structure are optionally substituted with one or two groups selected from C$_1$-C$_3$alkoxy, C$_1$-C$_3$alkoxycarbonyl, C$_1$-C$_3$alkyl, C$_1$-C$_3$alkylcarbonyl, aminocarbonyl, carboxy, carboxyC$_1$-C$_3$alkyl, halo, hydroxy, hydroxyC$_1$-C$_3$alkyl, —NR$^c$R$^d$, (NR$^c$R$^d$)carbonyl, (NR$^c$R$^d$)carbonylC$_1$-C$_3$alkyl, oxo, pyridinyl, and phenyl optionally substituted with a halo or methoxy group; and R$^c$ and R$^d$ are independently selected from hydrogen, C$_1$-C$_3$alkyl, C$_1$-C$_3$alkylcarbonyl; and In a first embodiment of the first aspect the present disclosure provides a compound of formula (I), or a pharmaceutically acceptable salt thereof, wherein R$^4$ is hydrogen. In a second embodiment, the present disclosure provides a compound of formula (I) wherein R$^4$ is hydrogen and wherein R$^1$ and R$^5$ are independently selected from hydrogen, —CH$_3$ and halo.

In a third embodiment of the first aspect the present disclosure provides a compound of formula (I), or a pharmaceutically acceptable salt thereof, wherein:

R$^4$ is hydrogen;

R$^1$ and R$^5$ are independently selected from hydrogen, —CH$_3$ and halo, one of R$^2$ and R$^3$ is hydrogen and the other is selected from —(CH$_2$)$_m$OPh, —O(CH$_2$)$_m$Ph, —O(CH$_2$)$_n$NR$^a$R$^b$, —S(O)$_2$NH(CH$_2$)$_n$NR$^a$R$^b$, —S(O)$_2$NH(CH$_2$)$_n$CO$_2$H, —O(CH$_2$)$_m$pyridinyl, —(CH$_2$)$_m$NH(CH$_2$)$_n$NR$^a$R$^b$, —C(O)NH(CH$_2$)$_n$NR$^a$R$^b$, —NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H; wherein each piperidinyl group is optionally substituted with a C$_1$-C$_3$alkyl group; and wherein the pyridinyl group is optionally substituted with a cyano group; and wherein each Ph group is optionally substituted with one, two, or three groups independently selected from C$_1$-C$_3$alkoxy, C$_1$-C$_3$alkyl, C$_1$-C$_3$alkylcarbonyl, amino, carboxy, (C$_3$-C$_6$cycloalkyl)alkoxy, cyano, halo, hydroxy, hydroxymethyl, —CHO, —C(O)NR$^a$R$^b$, —(CH$_2$)$_m$NR$^a$R$^b$; —OCH$_2$phenyl wherein the phenyl is optionally substituted with one or two halo groups, and —OCH$_2$pyridinyl optionally substituted with a cyano group, aminocarbonyl group, or a pyrazole ring; and one of R$^6$ and R$^7$ is hydrogen and the other is selected from —(CH$_2$)$_m$OPh, —O(CH$_2$)$_m$Ph, —O(CH$_2$)$_n$NR$^a$R$^b$, —S(O)$_2$NH(CH$_2$)$_n$NR$^a$R$^b$, —S(O)$_2$NH(CH$_2$)$_n$CO$_2$H, —O(CH$_2$)$_m$pyridinyl, —(CH$_2$)$_m$NH(CH$_2$)$_n$NR$^a$R$^b$, —C(O)NH(CH$_2$)$_n$NR$^a$R$^b$, —NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H; wherein the pyridinyl group is optionally substituted with a cyano group; and wherein each Ph group is optionally substituted with one, two, or three groups independently selected from C$_1$-C$_3$alkoxy, C$_1$-C$_3$alkyl, C$_1$-C$_3$alkylcarbonyl, amino, carboxy, cyano, (C$_3$-C$_6$cycloalkyl)alkoxy, halo, hydroxy, hydroxymethyl, —C(O)NR$^a$R$^b$, —(CH$_2$)$_m$NR$^a$R$^b$; —OCH$_2$phenyl wherein the phenyl is optionally substituted with one or two halo groups; and —OCH$_2$pyridinyl optionally substituted with a cyano group, aminocarbonyl group, or a pyrazole ring.

In a fourth embodiment of the first aspect the present disclosure provides a compound of formula (I), or a pharmaceutically acceptable salt thereof, wherein:

$R^4$ is hydrogen;

$R^1$ and $R^5$ are independently selected from hydrogen, —CH$_3$ and halo, one of $R^2$ and $R^3$ is hydrogen and the other is selected from —(CH$_2$)$_m$OPh and —O(CH$_2$)$_n$NR$^a$R$^b$; wherein the Ph group is optionally substituted with one, two, or three groups independently selected from C$_1$-C$_3$alkoxy, C$_1$-C$_3$alkyl, C$_1$-C$_3$alkylcarbonyl, amino, carboxy, (C$_3$-C$_6$cycloalkyl) alkoxy, cyano, halo, hydroxy, hydroxymethyl, —CHO, —C(O)NR$^a$R$^b$, —(CH$_2$)$_m$NR$^a$R$^b$; —OCH$_2$phenyl wherein the phenyl is optionally substituted with one or two halo groups, and —OCH$_2$pyridinyl optionally substituted with a cyano group, aminocarbonyl group, or a pyrazole ring; and one of $R^6$ and $R^7$ is hydrogen and the other is selected from —(CH$_2$)$_m$OPh and —O(CH$_2$)$_n$NR$^a$R$^b$; wherein the Ph group is optionally substituted with one, two, or three groups independently selected from C$_1$-C$_3$alkoxy, C$_1$-C$_3$alkyl, C$_1$-C$_3$alkylcarbonyl, amino, carboxy, (C$_3$-C$_6$cycloalkyl) alkoxy, cyano, halo, hydroxy, hydroxymethyl, —CHO, —C(O)NR$^a$R$^b$, —(CH$_2$)$_m$NR$^a$R$^b$, —OCH$_2$phenyl wherein the phenyl is optionally substituted with one or two halo groups, and —OCH$_2$pyridinyl optionally substituted with a cyano group, aminocarbonyl group, or a pyrazole ring.

In another aspect the present disclosure provides a compound of formula (I)

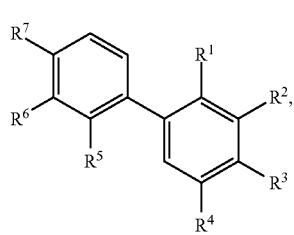

(I)

or a pharmaceutically acceptable salt thereof, wherein:

$R^1$ and $R^5$ are independently selected from hydrogen, —CH$_3$, cyano, halo, halomethyl, dihalomethyl, and trihalomethyl;

$R^2$ and $R^3$ are independently selected from hydrogen, —O(CH$_2$)$_m$Ph, —(CH$_2$)$_m$OPh, —O(CH$_2$)$_n$NR$^a$R$^b$, —(CH$_2$)$_m$ Ph, -(alkenylene)Ph, —S(O)$_2$NH(CH$_2$)$_n$NR$^a$R$^b$, —S(O)$_2$NH(CH$_2$)$_n$CO$_2$H, —O(CH$_2$)piperidinyl, —O(CH$_2$)$_m$ pyridinyl, —NH(CH$_2$)$_n$NR$^a$R$^b$, C(O)NH(CH$_2$)$_n$NR$^a$R$^b$, —NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H; wherein each piperidinyl group is optionally substituted with a C$_1$-C$_3$alkyl group; and wherein the pyridinyl group is optionally substituted with a cyano group; and wherein each Ph group is optionally substituted with one, two, or three groups independently selected from C$_1$-C$_3$alkoxy, cyano, halo, hydroxymethyl, —(CH$_2$)$_n$NR$^a$R$^b$, and —OCH$_2$pyridinyl optionally substituted with a cyano group; or $R^2$ and $R^3$, together with the atoms to which they are attached, form a 1,4-dioxane ring optionally substituted with —O(CH$_2$)$_n$NR$^a$R$^b$;

$R^4$ is selected from hydrogen, —O(CH$_2$)$_m$Ph, —(CH$_2$)$_m$OPh, —O(CH$_2$)$_n$NR$^a$R$^b$, —(CH$_2$)$_m$Ph, -(alkenylene)Ph, —S(O)$_2$NH(CH$_2$)$_n$NR$^a$R$^b$, —S(O)$_2$NH(CH$_2$)$_n$CO$_2$H, —O(CH$_2$)piperidinyl, —O(CH$_2$)$_m$pyridinyl, —NH(CH$_2$)$_n$NR$^a$R$^b$, —C(O)NH(CH$_2$)$_n$NR$^a$R$^b$, NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H, wherein each piperidinyl group is optionally substituted with a C$_1$-C$_3$alkyl group; and wherein the pyridinyl group is optionally substituted with a cyano group; and wherein each Ph group is optionally substituted with one, two, or three groups independently selected from C$_1$-C$_3$alkoxy, cyano, halo, hydroxymethyl, —(CH$_2$)$_n$NR$^a$R$^b$, and —OCH$_2$pyridinyl optionally substituted with a cyano group;

$R^6$ and $R^7$ are independently selected from hydrogen, —O(CH$_2$)$_m$Ph, —(CH$_2$)$_m$OPh, —O(CH$_2$)$_n$NR$^a$R$^b$, —(CH$_2$)$_m$ Ph, -(alkenylene)Ph, —S(O)$_2$NH(CH$_2$)$_n$NR$^a$R$^b$, S(O)$_2$NH(CH$_2$)$_n$CO$_2$H, —O(CH$_2$)piperidinyl, —O(CH$_2$)$_m$pyridinyl, —NH(CH$_2$)$_n$NR$^a$R$^b$, C(O)NH(CH$_2$)$_n$NR$^a$R$^b$, NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H; wherein the piperidinyl group is optionally substituted with a C$_1$-C$_3$alkyl group; and wherein the pyridinyl group is optionally substituted with a cyano group; and wherein each Ph group is optionally substituted with one, two, or three groups independently selected from C$_1$-C$_3$alkoxy, cyano, halo, hydroxymethyl, —(CH$_2$)$_n$NR$^a$R$^b$; and —OCH$_2$pyridinyl optionally substituted with a cyano group; or $R^6$ and $R^7$, together with the atoms to which they are attached, form a 1,4-dioxane ring optionally substituted with —O(CH$_2$)NR$^a$R$^b$;

provided that at least two of $R^2$, $R^3$, $R^4$, $R^6$, and $R^7$ are other than hydrogen; and provided that when $R^2$ is —(CH$_2$)$_m$OPh, —(CH$_2$)$_m$Ph, or -(alkenylene)Ph then $R^6$ is selected from —(CH$_2$)$_m$OPh, —(CH$_2$)$_m$Ph, and -(alkenylene)Ph;

m is 1, 2, or 3;

n is 2, 3, 4, 5;

$R^a$ and $R^b$ are independently selected from hydrogen, C$_1$-C$_3$alkyl, C$_1$-C$_3$alkylsulfonylC$_1$-C$_3$alkyl, aminocarbonylC$_1$-C$_3$alkyl, C$_3$-C$_6$cycloalkyl, carboxyC$_1$-C$_3$alkyl, cyanoC$_1$-C$_3$alkyl, hydroxyC$_1$-C$_6$alkyl, imidazolylC$_1$-C$_3$alkyl, morpholinylC$_1$-C$_3$alkyl, phenylC$_1$-C$_3$alkyl, piperidinyl, piperidinylC$_1$-C$_3$alkyl, pyridinylC$_1$-C$_3$alkyl, pyrazolylC$_1$-C$_3$alkyl, (NR$^c$R$^d$)C$_1$-C$_3$alkyl,

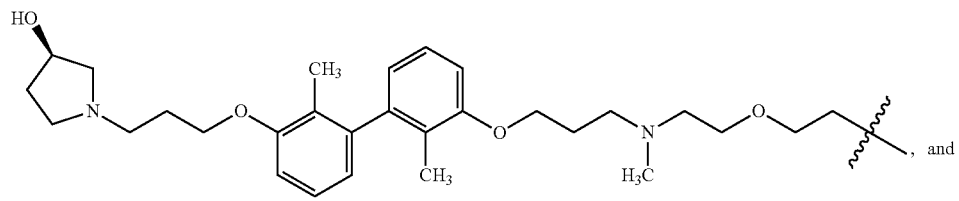

, and

-continued

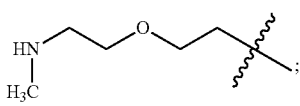

wherein the alkyl part of the carboxyC$_1$-C$_3$alkyl is further optionally substituted with one group selected from hydroxy and pyridinyl; and wherein the C$_3$-C$_6$cycloalkyl is optionally substituted with one, two, or three groups independently selected from hydroxy and hydroxyC$_1$-C$_3$alkyl; and wherein the alkyl part of the hydroxyC$_1$-C$_6$alkyl is further optionally substituted with one group selected from C$_1$-C$_3$alkoxy, imidazolyl optionally substituted with one or two groups independently selected from C$_1$-C$_3$alkyl and halo, pyridinyl, and phenyl optionally substituted with two halo; and wherein the imidazolyl part of the imidazolylC1-C3alkyl, the piperidinyl, the piperidinyl part of the piperidinylC$_1$-C$_3$alkyl, the pyrazolyl part of the pyrazolylC$_1$-C$_3$alkyl, and the pyridinyl part of the pyridinylC$_1$-C$_3$alkyl are optionally substituted with one, two, or three groups independently selected from C$_1$-C$_3$alkyl, cyano, halo, and hydroxyC$_1$-C$_3$alkyl; and wherein the phenyl part of the phenylC$_1$-C$_3$alkyl is optionally substituted with one or two groups independently selected from amino and halo; or R$^a$ and R$^b$, together with the nitrogen atom to which they are attached, form a four-, five-, or six-membered ring optionally containing one additional heteroatom selected from nitrogen, oxygen, and sulfur; wherein the ring is optionally fused to a phenyl group to form a bicyclic structure and wherein the ring and bicyclic structure are optionally substituted with one or two groups selected from C$_1$-C$_3$alkoxy, C$_1$-C$_3$alkyl, C$_1$-C$_3$alkylcarbonyl, aminocarbonyl, carboxy, carboxyC$_1$-C$_3$alkyl, hydroxy, hydroxyC$_1$-C$_3$alkyl, —NR$^c$R$^d$, (NR$^c$R$^d$)carbonyl, (NR$^c$R$^d$)carbonylC$_1$-C$_3$alkyl, oxo, pyridinyl, and phenyl optionally substituted with methoxy; and R$^c$ and R$^d$ are independently selected from hydrogen, C$_1$-C$_3$alkyl, C$_1$-C$_3$alkylcarbonyl; and

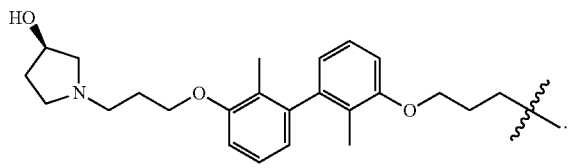 [SMILES: *CCCOc1cccc(-c2cccc(OCCCN3CC[C@@H](O)C3)c2C)c1C]

In a second aspect the present disclosure provides a pharmaceutical composition comprising a compound of formula (I), or a pharmaceutically acceptable salt thereof, and a pharmaceutically acceptable carrier.

In a third aspect the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the third aspect the method further comprises administering an additional agent prior to, after, or simultaneously with the compound of formula (I), or the pharmaceutically acceptable salt thereof. In a second embodiment of the third aspect the additional agent is an antimicrobial agent, an antiviral agent, an agent that modifies gene expression, a cytotoxic agent, and/or an immune response modifier.

In a fourth aspect the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment of the fourth aspect the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In a fifth aspect the present disclosure provides a method of treating an infectious disease in a subject in need thereof, the method comprising administering to the subject a therapeutically effective amount of a compound of formula (I), or a pharmaceutically acceptable salt thereof. In a first embodiment of the fifth aspect the infectious disease is caused by a virus. In a second embodiment of the fifth aspect the virus is selected from HIV, Hepatitis A, Hepatitis B, Hepatitis C, Hepatitis D, herpes viruses, papillomaviruses and influenza.

In a sixth aspect the present disclosure provides a method of treating septic shock in a subject in need thereof, the method comprising administering to the subject a therapeutically effective amount of a compound of formula (I), or a pharmaceutically acceptable salt thereof.

In a seventh aspect the present disclosure provides a method blocking the interaction of PD-L1 with PD-1 and/or CD80 in a subject, said method comprising administering to the subject a therapeutically effective amount of a compound of formula (I), or a pharmaceutically acceptable salt thereof.

The features and advantages of the disclosure may be more readily understood by those of ordinary skill in the art upon reading the following detailed description. It is to be appreciated that certain features of the disclosure that are, for clarity reasons, described above and below in the context of separate embodiments, may also be combined to form a single embodiment. Conversely, various features of the disclosure that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

The term "$C_2$-$C_6$alkenyl," as used herein, refers to a group derived from a straight or branched hydrocarbon containing from two to six carbon atoms and at least one double bond.

The term "alkenylene," as used herein, refers to a divalent hydrocarbon containing from two to six carbon atoms and at least one double bond.

The term "$C_1$-$C_3$alkoxy," as used herein, refers to a $C_1$-$C_3$alkyl group attached to the parent molecular moiety through an oxygen atom.

The term "$C_1$-$C_6$alkoxy," as used herein, refers to a $C_1$-$C_6$alkyl group attached to the parent molecular moiety through an oxygen atom.

The term "$C_1$-$C_6$alkoxycarbonyl," as used herein, refers to a $C_1$-$C_6$alkoxy group attached to the parent molecular moiety through a carbonyl group.

The term "$C_1$-$C_3$alkyl," as used herein, refers to a group derived from a straight or branched chain saturated hydrocarbon containing from one to three carbon atoms.

The term "$C_1$-$C_6$alkyl," as used herein, refers to a group derived from a straight or branched chain saturated hydrocarbon containing from one to six carbon atoms.

The term "$C_1$-$C_3$alkylcarbonyl," as used herein, refers to a $C_1$-$C_3$alkyl group attached to the parent molecular moiety through a carbonyl group.

The term "$C_1$-$C_3$alkylsulfanyl," as used herein, refers to a $C_1$-$C_3$alkyl group attached to the parent molecular moiety through a sulfanyl group.

The term "$C_1$-$C_3$alkylsulfonyl," as used herein, refers to a $C_1$-$C_3$alkyl group attached to the parent molecular moiety through a sulfonyl group.

The term "$C_1$-$C_3$alkylsulfonyl$C_1$-$C_3$alkyl," as used herein, refers to a $C_1$-$C_3$alkylsulfonyl group attached to the parent molecular moiety through a $C_1$-$C_3$alkyl group.

The term "amino," as used herein, refers to —$NH_2$.

The term "aminocarbonyl," as used herein, refers to an amino group attached to the parent molecular moiety through a carbonyl group.

The term "aminocarbonyl($C_1$-$C_3$alkyl)," as used herein, refers to an aminocarbonyl group attached to the parent molecular moiety through a $C_1$-$C_3$alkyl group.

The term "carbonyl," as used herein, refers to —C(O)—.

The term "carboxy," as used herein, refers to —$CO_2H$.

The term "carboxy$C_2$-$C_6$alkenyl," as used herein, refers to a carboxy group attached to the parent molecular moiety through a $C_2$-$C_6$alkenyl group.

The term "carboxy$C_1$-$C_3$alkyl," as used herein, refers to a carboxy group attached to the parent molecular moiety through a $C_1$-$C_3$alkyl group.

The term "(carboxy$C_1$-$C_3$alkyl)carbonyl," as used herein, refers to a carboxy$C_1$-$C_3$alkyl group attached to the parent molecular moiety through a carbonyl group.

The term "cyano," as used herein, refers to —CN.

The term "cyano$C_1$-$C_3$alkyl," as used herein, refers to a cyano group attached to the parent molecular moiety through a $C_1$-$C_3$alkyl group.

The term "$C_3$-$C_6$cycloalkyl," as used herein, refers to a saturated monocyclic or bicyclic hydrocarbon ring system having three to six carbon atoms and zero heteroatoms. Representative examples of cycloalkyl groups include, but are not limited to, cyclopropyl, cyclobutyl, and cyclopentyl.

The term "($C_3$-$C_6$cycloalkyl)alkoxy," as used herein, refers to a $C_3$-$C_6$cycloalkyl group attached to the parent molecular group through a $C_1$-$C_3$alkoxy group.

The term "($C_3$-$C_6$cycloalkyl)$C_1$-$C_3$alkyl," as used herein, refers to a $C_3$-$C_6$cycloalkyl group attached to the parent molecular group through a $C_1$-$C_3$alkyl group.

The terms "halo" and "halogen," as used herein, refer to F, Cl, Br, or I.

The term "halo$C_1$-$C_3$alkyl," as used herein, refers to a $C_1$-$C_3$alkyl group substituted with at least one halo group.

The term "hydroxy," as used herein, refers to —OH.

The term "hydroxy$C_1$-$C_3$alkyl," as used herein, refers to a $C_1$-$C_3$alkyl group substituted with one or two hydroxy groups.

The term "hydroxy$C_1$-$C_6$alkyl," as used herein, refers to a hydroxy group attached to the parent molecular moiety through a $C_1$-$C_6$alkyl group.

The term "(hydroxy$C_1$-$C_6$alkyl)carbonyl," as used herein, refers to a hydroxy$C_1$-$C_6$alkyl group attached to the parent molecular moiety through a carbonyl group.

The term "imidazolyl$C_1$-$C_3$alkyl," as used herein, refers to an imidazolyl group attached to the parent molecular moiety through a $C_1$-$C_3$alkyl group.

The term "morpholinyl$C_1$-$C_3$alkyl," as used herein, refers to a morpholinyl group attached to the parent molecular moiety through a $C_1$-$C_3$alkyl group.

The term "(NR$^c$R$^d$)$C_1$-$C_3$alkyl," as used herein, refers to an —NR$^c$R$^d$ group attached to the parent molecular moiety through a $C_1$-$C_3$alkyl group.

The term "(NR$^c$R$^d$)carbonyl," as used herein, refers to an —NR$^c$R$^d$ group attached to the parent molecular moiety through a carbonyl group.

The term "(NR$^c$R$^d$)carbonyl$C_1$-$C_3$alkyl," as used herein, refers to an (NR$^c$R$^d$)carbonyl group attached to the parent molecular moiety through a $C_1$-$C_3$alkyl group.

The term "oxo," as used herein, refers to =O.

The term "phenyl$C_1$-$C_3$alkoxy," as used herein, refers to a phenyl group attached to the parent molecular moiety through a $C_1$-$C_3$alkoxy group.

The term "phenyl$C_1$-$C_3$alkoxycarbonyl," as used herein, refers to a phenyl$C_1$-$C_3$alkoxy group attached to the parent molecular moiety through a carbonyl group.

The term "phenyl$C_1$-$C_3$alkyl," as used herein, refers to a phenyl group attached to the parent molecular moiety through a $C_1$-$C_3$alkyl group.

The term "piperidinyl$C_1$-$C_3$alkyl," as used herein, refers to a piperidinyl group attached to the parent molecular moiety through a $C_1$-$C_3$alkyl group.

The term "pyrazolyl$C_1$-$C_3$alkyl," as used herein, refers to a pyrazolyl ring attached to the parent molecular moiety through a $C_1$-$C_3$alkyl group.

The term "pyridinyl$C_1$-$C_3$alkyl," as used herein, refers to a pyridinyl ring attached to the parent molecular moiety through a $C_1$-$C_3$alkyl group.

The term "pyrimidinyl$C_1$-$C_3$alkyl," as used herein, refers to a pyrimidinyl ring attached to the parent molecular moiety through a $C_1$-$C_3$alkyl group.

The term "sulfonyl," as used herein, refers to —$SO_2$—.

The term "tetrahydrofurylC$_1$-C$_3$alkyl," as used herein, refers to a tetrahydrofuryl ring attached to the parent molecular moiety through a C$_1$-C$_3$alkyl group.

The term "thiazolylC$_1$-C$_3$alkyl," as used herein, refers to a thiazolyl ring attached to the parent molecular moiety through a C$_1$-C$_3$alkyl group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as HIV or Hepatitis B, Hepatitis C, and Hepatitis D.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrastemally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) Int. Immunol. 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) Nature 393: 474-478) and can be used in conjunction with PD-L1 blockade (Ito, N. et al. (2000) Immunobiology 201 (5) 527-40). Activating compounds to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), Influenza, Herpes, Giardia, Malaria, *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7, HHV-8, HSV-2, CMV, and Epstein Barr virus), adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *chlamydia*, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the disclosure include Candida (albicans, krusei, glabrata, tropicalis, etc.), Cryptococcus neoformans, Aspergillus (fumigatus, niger, etc.), Genus Mucorales (mucor, absidia, rhizophus), Sporothrix schenkii, Blastomyces dermatitidis, Paracoccidioides brasiliensis, Coccidioides immitis and Histoplasma capsulatum.

Some examples of pathogenic parasites causing infections treatable by methods of the disclosure include Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi, and Nippostrongylus brasiliensis.

In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123), vaccines, or agents that modify gene expression.

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) Proc. Natl. Acad. Sci. U.S.A. 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) J. Immunother Emphasis Tumor Immunol 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

The compounds described herein can also be used in the treatment of severe sepsis, or septic shock.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

In one embodiment, the compounds of formula (I) inhibit the PD-1/PD-L1 interaction with $IC_{50}$ values of 20 μM or less, for example, from 0.006 to 20 μM, as measured by the PD-1/PD-L1 Homogenous Time-Resolved Fluorescence (HTRF) binding assay. Preferably, the compounds of formula (I) inhibit the PD-1/PD-L1 interaction with $IC_{50}$ values from 0.006 to 100 nM.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

As used in the present specification, the following terms have the meanings indicated: DCM for dichloromethane; DMF for N,N-dimethylformamide; THF for tetrahydrofuran; EtOAc for ethyl acetate; n-BuLi for n-butyllithium; O$^i$Pr for isopropyloxy; h or hr or hrs for hours; min or mins for minutes; sec for seconds; TFA for trifluoroacetic acid; MeOH for methanol; ACN or MeCN for acetonitrile; sat. or satd. for saturated; RT or rt for room temperature or retention time (context will dictate); R$_t$ for retention time; evap'd for evaporated; DIAD for diisorpropyl azodicarboxylate; DMSO for dimethylsulfoxide; NMP for N-methylpyrrolidinone; HATU for (1-[bis(dimethylamino)methylene]-1H-1,2,3-triazolo[4,5-b]pyridinium 3-oxidhexafluorophosphate); dppf for 1,1'-bis(diphenylphosphino)ferrocene; OAc for acetate; RBF for round-bottomed flask; DIEA or iPr$_2$NEt for diisopropylethylamine; EDC for 1-ethyl-3-(3-dimethylaminopropyl)carbodiimide; DCE for 1,2-dichloroethane; NCS for N-chlorosuccinimide; Et$_3$N for triethylamine; EtOH for ethanol; HCTU for (1-[Bis(dimethylamino)methylene]-1H-1,2,3-triazolo[4,5-b]pyridinium 3-oxidhexafluorophosphate); and HOBt for hydroxybenzotriazole.

Examples 1001 to 1004 were prepared as described below:

LC-MS conditions P-1: Column: Phenomenex LUNA C18, 30×2, 3 u; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0% B, 0-100% B over 2 minutes, then a 1.0-minute hold at 100% B; Flow rate: 1 mL/min; Detection: UV at 254 nm.

Preparation of 2-chloro-3,3'-bis(3-chloropropoxy)-2'-methyl-1,1'-biphenyl

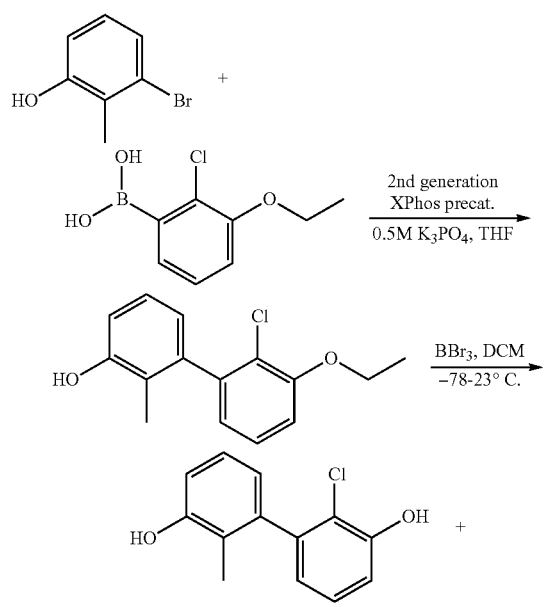

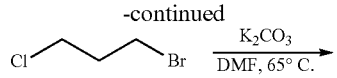

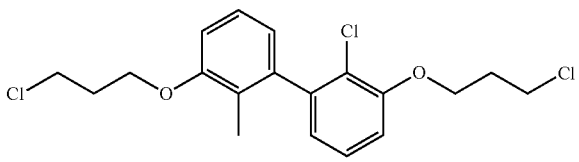

A mixture of 3-bromo-2-methylphenol (0.374 g, 2.000 mmol) and 2-chloro-3-ethoxyphenylboronic acid (0.401 g, 2 mmol) in THF (10 mL) and 0.5 M aq. potassium phosphate, tribasic (12.00 mL, 6.00 mmol) was stirred under nitrogen sparging for 10 min and then added 2nd gen. XPhos precatalyst (0.047 g, 0.060 mmol) and sparging was continued for another 5 min. The reaction mixture was stirred at rt under nitrogen for 16 h and diluted with EtOAc, washed with water, brine, dried (Na$_2$SO$_4$), concentrated and purified by silica gel FCC (flash column chromatography) (0-20% EtOAc-hexanes) to yield 2'-chloro-3'-ethoxy-2-methyl-[1,1'-biphenyl]-3-ol (~0.5 g, 95% yield) as a white solid. LC-MS (method P-1): R$_t$ (Retention time)=1.748 min, m/z 261.1 (M−H)$^-$; $^1$H NMR (400 MHz, CHLOROFORM-d) δ 7.28-7.23 (m, 1H), 7.14 (t, J=7.8 Hz, 1H), 6.96 (dd, J=8.3, 1.3 Hz, 1H), 6.88-6.83 (m, 2H), 6.80-6.75 (m, 1H), 4.81 (s, 1H), 4.20-4.14 (m, 2H), 2.03 (s, 3H), 1.53 (t, J=7.0 Hz, 3H).

To a cold (−78° C.) stirred solution of 2'-chloro-3'-ethoxy-2-methyl-[1,1'-biphenyl]-3-ol (0.5 g) in DCM (12 mL) was added a solution of boron tribromide (4.40 mL, 4.40 mmol) in DCM under nitrogen. The mixture was allowed to warm to rt and stirred for 2-3 h and then quenched with ice and neutralized with satd. NaHCO$_3$. The organic layer was separated and washed with water, brine, dried (MgSO$_4$) and concentrated to afford 2-chloro-2'-methyl-[1,1'-biphenyl]-3,3'-diol (0.41 g, 1.747 mmol, 87% yield) as a tan solid. LC-MS (method P-1): R$_t$=1.407 min, m/z 233.1 (M−H)$^-$; $^1$H NMR (400 MHz, CHLOROFORM-d) δ 7.24 (t, J=7.8 Hz, 1H), 7.15 (t, J=7.8 Hz, 1H), 7.07 (dd, J=8.2, 1.6 Hz, 1H), 6.86 (d, J=7.8 Hz, 1H), 6.83 (dd, J=7.7, 1.6 Hz, 1H), 6.80-6.77 (m, 1H), 5.71 (s, 1H), 4.79 (s, 1H), 2.03 (s, 3H).

Neat potassium carbonate (0.353 g, 2.56 mmol) was added to a stirred solution of 2-chloro-2'-methyl-[1,1'-biphenyl]-3,3'-diol (0.25 g, 1.065 mmol) and 1-bromo-3-chloropropane (0.419 mL, 4.26 mmol) in DMF (4 mL), and the mixture heated at 65° C. overnight. The reaction mixture was cooled to rt and diluted with ether and water. The organic phase was separated and washed with water, brine, dried (Na$_2$SO$_4$), concentrated and purified by silica gel chromatography (0-10% EtOAc/hexane) to yield 2-chloro-3,3'-bis(3-chloropropoxy)-2'-methyl-1,1'-biphenyl (0.351 g, 0.905 mmol, 85% yield, contains ~10% mono-bromopropoxy and bis-bromopropoxy isomers) as a clear viscous oil which was used in subsequent steps as a mixture without further purification.

Preparation of 3,5'-bis(3-chloropropoxy)-2,2'-dimethyl-1,1'-biphenyl and 3-chloropropoxy-5'-bromopropoxy-2,2'-dimethyl-1,1'-biphenyl

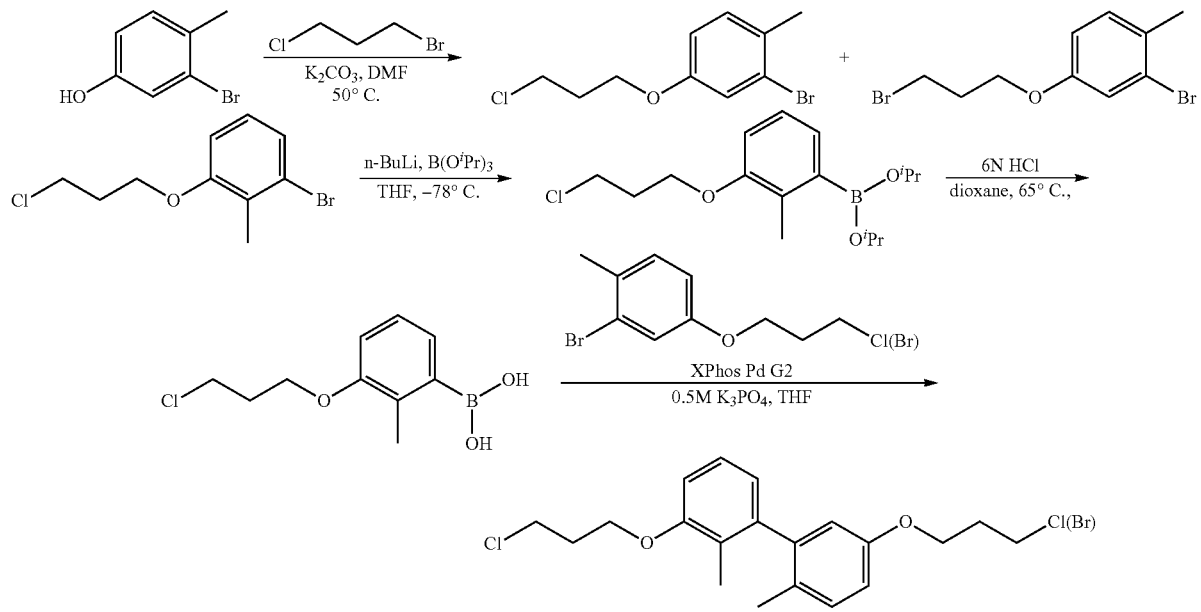

Neat potassium carbonate (0.829 g, 6.00 mmol) was added to a stirred solution of 3-bromo-4-methylphenol (0.935 g, 5 mmol) and 1-bromo-3-chloropropane (0.590 mL, 6.00 mmol) in DMF (10 mL), and the mixture heated at 50° C. overnight. The reaction mixture was cooled to rt and diluted with ether and added water. The organic phase was washed with water, brine, dried (Na$_2$SO$_4$) and concentrated. The residue was purified by silica gel chromatography (0-10% EtOAc/hexane) to yield a mixture of 2-bromo-4-(3-chloropropoxy)-1-methylbenzene and 2-bromo-4-(3-bromopropoxy)-1-methylbenzene in ~7:3 ratio as a clear viscous oil (~1.3 g). $^1$H NMR (500 MHz, CHLOROFORM-d) δ 7.16-7.12 (m, 2H), 6.79 (dd, J=8.4, 2.6 Hz, 1H), 4.10 (t, J=5.7 Hz, 2H), 3.75 (t, J=6.3 Hz, 2H), 2.35 (s, 3H), 2.28-2.18 (m, 2H).

n-Butyllithium (0.442 mL, 1.106 mmol) in hexanes was added to a cold (−78° C.) stirred solution of 1-bromo-3-(3-chloropropoxy)-2-methylbenzene (0.265 g, 1.005 mmol) in THF (3 mL) and the mixture was stirred at −78° C. for 15 min. A solution of triisopropyl borate (0.277 mL, 1.207 mmol) in THF (1 mL) was then added, and the mixture was stirred at −78° C. for 2 h and then allowed to warm to 0° C. The reaction mixture was evaporated to dryness under reduced pressure to afford crude isopropyl (3-(3-chloropropoxy)-2-methylphenyl)boronate (0.23 g) which was dissolved in dioxane (5 ml) and added 6N HCl (5 mL), and the mixture was heated at 65° C. for 1 h. The reaction mixture was evaporated to dryness and azeotroped with toluene to afford crude (3-(3-chloropropoxy)-2-methylphenyl)boronic acid (0.195 g, 0.853 mmol, 85% yield) as a light brown semi-solid which was used in the next step without further purification.

A mixture of (3-(3-chloropropoxy)-2-methylphenyl)boronic acid (0.195 g, 0.853 mmol) and 2-bromo-4-(3-chloropropoxy)-1-methylbenzene/2-bromo-4-(3-bromopropoxy)-1-methylbenzene (0.225 g) in THF (6 mL)/dioxane (2 mL) and 0.5 M aq potassium phosphate, tribasic (5.12 mL, 2.56 mmol) was stirred under N$_2$ sparging for 15 min. 2nd gen. XPhos precatalyst (0.020 g, 0.026 mmol) was then added to the mixture, and sparging was continued for another 10 min. The reaction mixture was stirred at rt under N$_2$ for 16 h, and diluted with EtOAc, washed with water, brine, dried (Na$_2$SO$_4$) and concentrated. The crude isolate was purified by silica gel chromatography (10-30% EtOAc-hex) to yield a mixture of 3,5'-bis(3-chloropropoxy)-2,2'-dimethyl-1,1'-biphenyl and 3-chloropropoxy-5'-bromopropoxy-2,2'-dimethyl-1,1'-biphenyl (0.276 g) which was used in the next step as a mixture. $^1$H NMR (400 MHz, CHLOROFORM-d) δ 7.20 (d, J=7.5 Hz, 1H), 7.16 (d, J=2.8 Hz, 1H), 7.14-7.12 (m, 1H), 6.88 (d, J=7.8 Hz, 1H), 6.82 (dd, J=11.2, 2.6 Hz, 1H), 6.70 (d, J=2.8 Hz, 1H), 4.15-4.06 (m, 4H), 3.82-3.73 (m, 4H), 2.35 (s, 3H), 2.34-2.27 (m, 2H), 2.27-2.23 (m, 2H), 2.01 (s, 3H).

The following preparative HPLC method was used for the purification of Examples 1001 to 1004:

Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 5-40% B over 20 minutes, then a 5-minute hold at 100% B; Flow: 20 mL/min. Fractions containing the desired product were combined and dried via centrifugal evaporation.

The following two analytical LC-MS conditions were used to determine the final purity:

LC-MS conditions-1: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

LC-MS conditions-2: Column: Waters Acquity UPLC BEH C18, 2.1×50 mm, 1.7-μm particles; Mobile Phase A: 5:95 acetonitrile:water with 0.1% trifluoroacetic acid;

Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 1001: 2,2'-(((((2-chloro-2'-methyl-[1,1'-biphenyl]-3,3'-diyl)bis(oxy))bis(propane-3,1-diyl))bis(3-hydroxypyrrolidine-1,3-diyl))diacetic acid (MgSO$_4$) and concentrated to afford diethyl 2,2'-(1,1'-(((2-chloro-2'-methyl-[1,1'-biphenyl]-3,3'-diyl)bis(oxy))bis(propane-3,1-diyl))bis(3-hydroxypyrrolidine-3,1-diyl))diacetate (55 mg) as a clear oil which was saponified (LiOH.H$_2$O, THF-MeOH—H$_2$O) and purified by prep. HPLC to afford 2,2'-(((((2-chloro-2'-methyl-[1,1'-biphenyl]-3,3'-diyl)bis(oxy))bis(propane-3,1-diyl))bis(3-hydroxypyrrolidine-1,3-

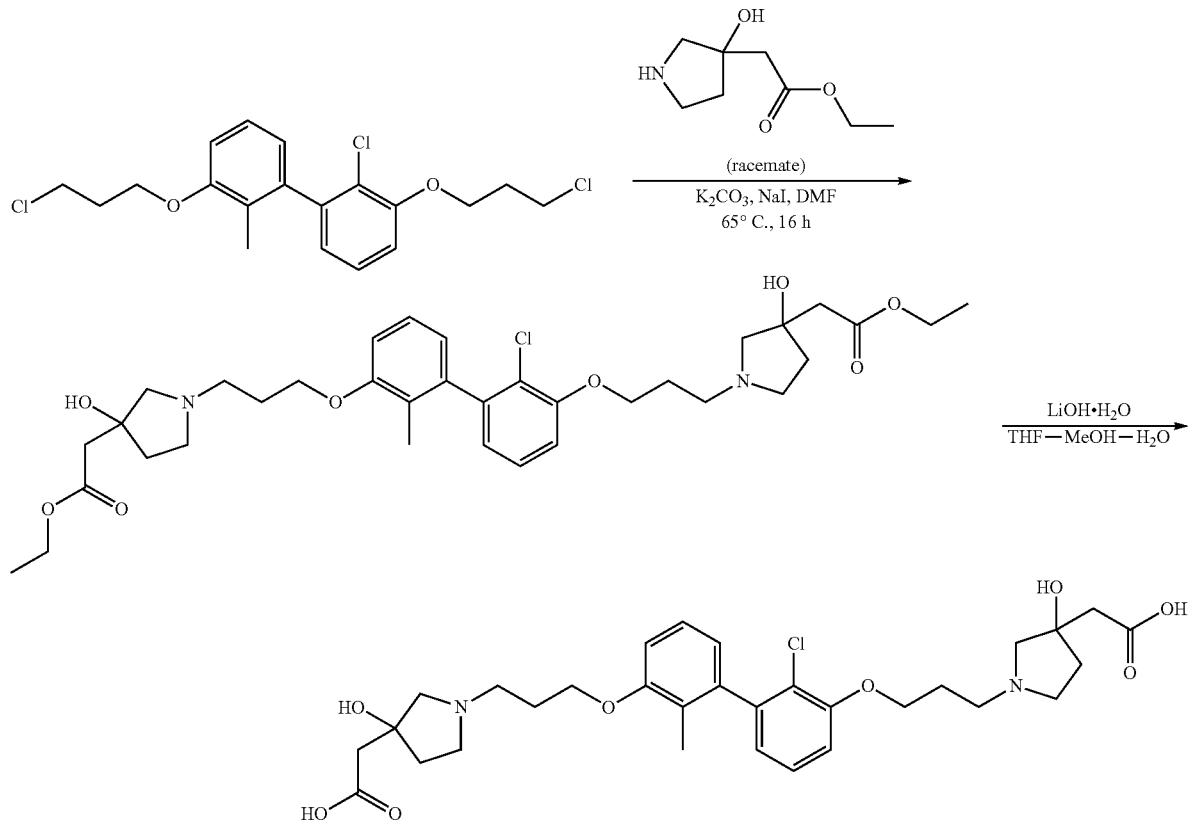

Example 1001

A stirred mixture of 2-chloro-3,3'-bis(3-chloropropoxy)-2'-methyl-1,1'-biphenyl (27.6 mg, 0.071 mmol), ethyl 2-(3-hydroxypyrrolidin-3-yl)acetate, TFA (45 mg, 0.157 mmol), potassium carbonate (49.2 mg, 0.356 mmol) and sodium iodide (10.67 mg, 0.071 mmol) in DMF (2 mL) was heated at 65° C. overnight. The reaction mixture was cooled and diluted with EtOAc, washed with water, brine, dried diyl))diacetic acid. LC-MS (conditions-1): R$_t$=1.455 min, m/z 605.1 [M+H]$^+$ Example 1002: 1,1'-(((2-chloro-2'-methyl-[1,1'-biphenyl]-3,3'-diyl)bis(oxy))bis(propane-3,1-diyl))bis(4-hydroxypiperidine-4-carboxylic acid)

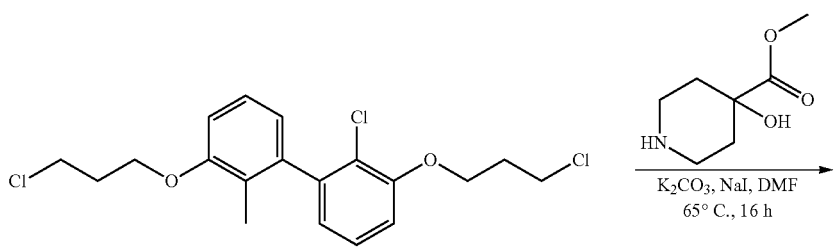

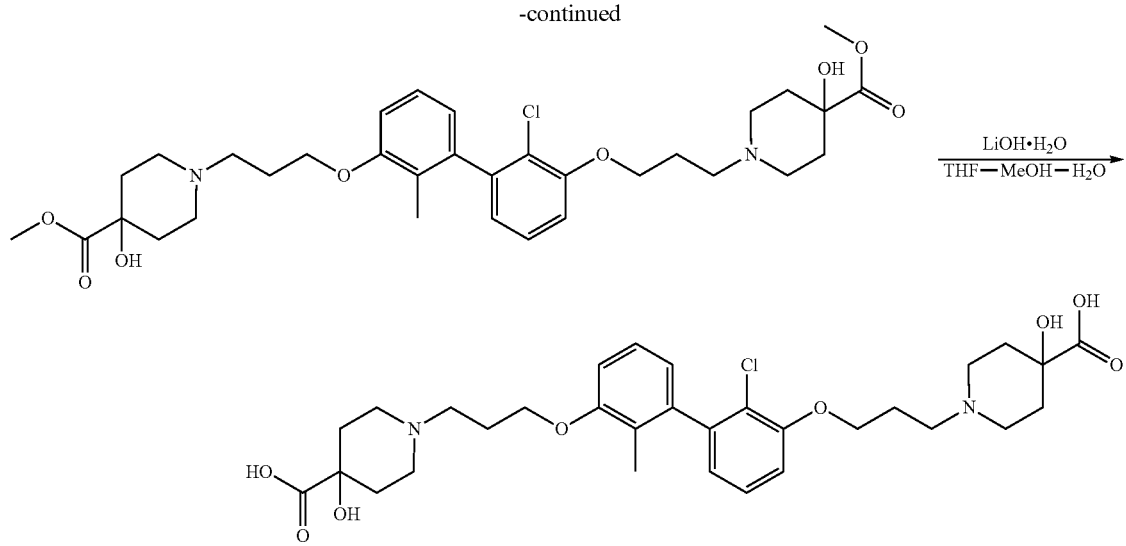

Example 1002

A stirred mixture of 2-chloro-3,3'-bis(3-chloropropoxy)-2'-methyl-1,1'-biphenyl (39.6 mg, 0.102 mmol), methyl 4-hydroxypiperidine-4-carboxylate (35.8 mg, 0.225 mmol), potassium carbonate (70.6 mg, 0.511 mmol) and sodium iodide (15.31 mg, 0.102 mmol) in DMF (2 mL) was heated at 65° C. overnight. The reaction mixture was cooled and diluted with EtOAc, washed with water, brine, dried (MgSO$_4$), concentrated to afford dimethyl 1,1'-(((2-chloro-2'-methyl-[1,1'-biphenyl]-3,3'-diyl)bis(oxy))bis(propane-3,1-diyl))bis(4-hydroxypiperidine-4-carboxylate) (~59 mg) as a clear oil which was saponified (LiOH.H$_2$O, THF-MeOH—H$_2$O) and purified by prep. HPLC to afford 1,1'-(((2-chloro-2'-methyl-[1,1'-biphenyl]-3,3'-diyl)bis(oxy))bis(propane-3,1-diyl))bis(4-hydroxypiperidine-4-carboxylic acid). LC-MS (conditions-1): R$_t$=1.059 min, m/z 605.10 [M+H]$^+$ Example 1003: (2S,2'S,4R,4'R)-1,1'-(((2-chloro-2'-methyl-[1,1'-biphenyl]-3,3'-diyl)bis(oxy))bis(propane-3,1-diyl))bis(4-hydroxypyrrolidine-2-carboxylic acid)

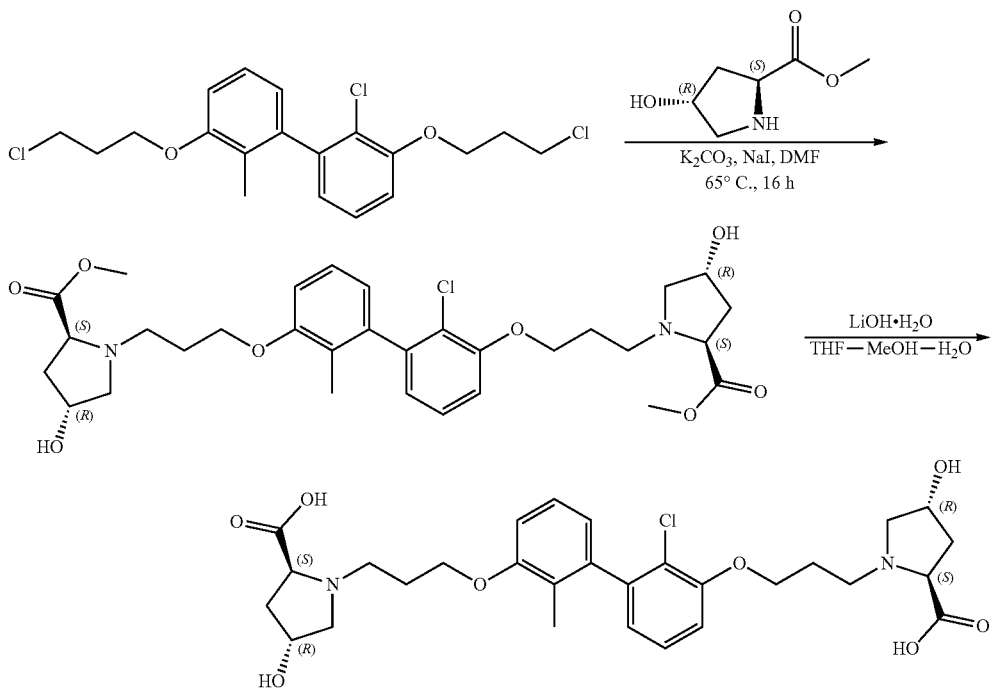

Example 1003

A stirred mixture of 2-chloro-3,3'-bis(3-chloropropoxy)-2'-methyl-1,1'-biphenyl (36.6 mg, 0.094 mmol), (2S,4R)-methyl 4-hydroxypyrrolidine-2-carboxylate, HCl (44.6 mg, 0.245 mmol), potassium carbonate (65.2 mg, 0.472 mmol) and sodium iodide (14.15 mg, 0.094 mmol) in DMF (1 mL) was heated at 65° C. overnight. The reaction mixture was cooled and diluted with EtOAc, washed with water, brine, dried (MgSO$_4$) and concentrated to afford (2S,2'S,4R,4'R)-dimethyl 1,1'-(((2-chloro-2'-methyl-[1,1'-biphenyl]-3,3'-diyl)bis(oxy))bis(propane-3,1-diyl))bis(4-hydroxypyrrolidine-2-carboxylate) (53 mg) as a clear oil which was saponified (LiOH.H$_2$O, THF-MeOH—H$_2$O) and purified by prep. HPLC to afford (2S,2'S,4R,4'R)-1,1'-(((2-chloro-2'-methyl-[1,1'-biphenyl]-3,3'-diyl)bis(oxy))bis(propane-3,1-diyl))bis(4-hydroxypyrrolidine-2-carboxylic acid). LC-MS (conditions-1): R$_t$=1.008 min, m/z 577.1 [M+H]$^+$ Example 1004: (3R,3'R)-1,1'-(((2,6'-dimethyl-[1,1'-biphenyl]-3,3'-diyl)bis(oxy))bis(propane-3,1-diyl))bis(pyrrolidin-3-ol)

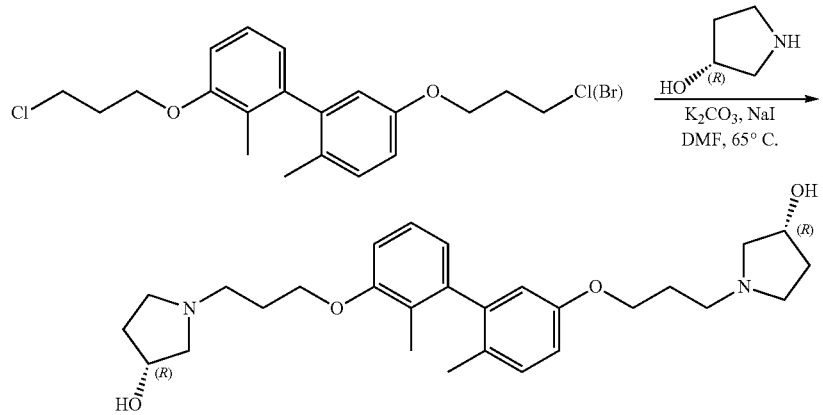

Example 1004

A stirred mixture of 3,5'-bis(3-chloropropoxy)-2,2'-dimethyl-1,1'-biphenyl/3-chloropropoxy-5'-bromopropoxy-2,2'-dimethyl-1,1'-biphenyl (0.050 g, 0.136 mmol, based on Cl isomer), (R)-pyrrolidin-3-ol, HCl (0.050 g, 0.408 mmol), potassium carbonate (0.113 g, 0.817 mmol) and sodium iodide (0.041 g, 0.272 mmol) in DMF (2 mL) was heated at 75° C. for 16 h. The reaction mixture was cooled, diluted with EtOAc, washed with water, brine, dried (MgSO$_4$), concentrated and purified by prep. HPLC to afford (3R,3'R)-1,1'-(((2,6'-dimethyl-[1,1'-biphenyl]-3,3'-diyl)bis(oxy))bis(propane-3,1-diyl))bis(pyrrolidin-3-ol). LC-MS (conditions-1): R$_t$=1.201 min, m/z 469.2 [M+H]$^+$ Examples 2001 to 2131 were prepared as described below, and the HPLC LC/MS conditions employed for these examples were listed below:

LC/MS Condition A:
Column=Waters Aquity UPLC BEH C18, 2.1×50 mm, 1.7 μm
Start % B=2; Final % B=98
Gradient time=1.5 min; Stop time=2 or 2.5 min
Flow Rate=0.8 mL/min; Wavelength=220 nm or 254 nm
Solvent A=100% water/0.05% TFA
Solvent B=100% ACN/0.05% TFA
Oven temp.=40° C.

LC/MS Condition B:
Column=Phenomenex-Luna C18, 2.0×50 mm, 3 μm
Start % B=0; Final % B=100
Gradient time=4 min; Stop time=5 or 6 min
Flow Rate=0.8 mL/min; Wavelength=220 nm or 254 nm
Solvent A=5% ACN/95% water/10 mM NH$_4$OAc
Solvent B=95% ACN/5% water/10 mM NH$_4$OAc
Oven temp.=40° C.

LC/MS Condition C:
Column=Phenomenex-Luna C18, 2.0×50 mm, 3 μm
Start % B=0; Final % B=100
Gradient time=4 min; Stop time=5 or 6 min
Flow Rate=0.8 mL/min; Wavelength=220 nm or 254 nm
Solvent A=10% MeOH/90% H2O/0.1% TFA
Solvent B=90% MeOH/10% H$_2$O/0.1% TFA
Oven temp.=40° C.

LC/MS Condition D:
Column=Waters Aquity UPLC BEH C18, 2.1×50 mm, 1.7 μm
Start % B=2; Final % B=98
Gradient time=1.5 min; Stop time=1.6 min
Flow Rate=0.8 mL/min; Wavelength=220 nm or 254 nm
Solvent A=100% water/0.05% TFA
Solvent B=100% ACN/0.05% TFA
Oven temp.=50° C.

LC/MS Condition E:
Column=Waters Acquity UPLC BEH C18, 2.1×50 mm, 1.7-μm
Start % B=0; Final % B=100
Gradient time=3 min; Stop time=3.75 min
Flow rate=1.0 mL/min: Wavelength=220 nm
Solvent A=5% ACN/95% water/10 mM NH$_4$OAc
Solvent B=95% ACN/5% water/10 mM NH$_4$OAc
Oven temp.=50° C.

LC/MS Condition F:
Column=Waters Acquity UPLC BEH C18, 2.1×50 mm, 1.7-μm
Start % B=0; Final % B=100
Gradient time=3 min; Stop time=3.75 min
Flow rate=1.0 mL/min: Wavelength=220 nm
Solvent A=5% ACN/95% water/0.1% TFA
Solvent B=95% ACN/5% water/0.1% TFA
Oven temp.=50° C.

Intermediate:
1-bromo-3-(3-bromopropoxy)-2-methylbenzene

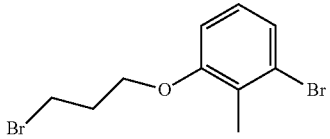

A magnetically stirred solution of 1,3-dibromopropane (61 g, 302 mmol) and 3-bromo-2-methylphenol (5.00 g, 26.7 mmol) in acetone (200 mL) is treated with potassium carbonate (9.8 g, 70.9 mmol). The mixture was stirred at rt for seven days. The solids were filtered and washed with acetone (800 mL), and the filtrate evap'd (evaporated) in vacuo and then on high vacuum to remove excess 1,3-dibromopropane. The crude liquid was applied to the head of a 330 g Teledyne Isco Silica Flash Column (some hexanes, very little DCM mixed with mostly hexanes used to apply) and purified on Biotage using a gradient from 100% hexanes to 100% $CH_2Cl_2$ over 10 col vols (column volumes). The fractions containing the product were evaporated in vacuo then dried on high vacuum to give 13.35 g (92%) of the pure title compound as a colorless liquid. $^1$H NMR (400 MHz, CHLOROFORM-d) δ 7.18 (dd, J=8.0, 0.8 Hz, 1H), 7.02 (t, J=8.2 Hz, 1H), 6.81 (d, J=8.3 Hz, 1H), 4.11 (t, J=5.8 Hz, 2H), 3.64 (t, J=6.4 Hz, 2H), 2.36 (t, J=5.9 Hz, 2H), 2.33 (s, 3H).

Intermediate: 2-(3-(3-bromopropoxy)-2-methylphenyl)-4,4,5,5-tetramethyl-1,3,2-dioxaborolane

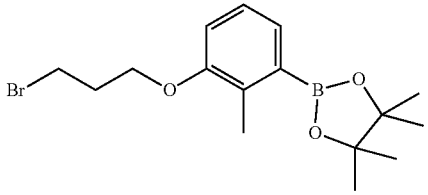 [SMILES: Cc1c(OCCCBr)cccc1B1OC(C)(C)C(C)(C)O1]

An oven dried 150 mL pressure bottle is charged with 1-bromo-3-(3-bromopropoxy)-2-methylbenzene (5.3 g, 17.21 mmol) (5.30 g, 17.2 mmol), 4,4,4',4',5,5,5',5'-octamethyl-2,2'-bi(1,3,2-dioxaborolane) (7.3 g, 28.7 mmol), and potassium acetate (5.3 g, 54.0 mmol). After adding dioxane (100 mL), argon was bubbled into the mixture for 10 min, and [1,1'-bis(diphenylphosphino)ferrocene]dichloropalladium(II) (825 mg, 1.128 mmol) then added to the mixture. The reaction is sealed and heated in a 80° C. oil bath for 21 h. The reaction was treated with water (300 mL) and EtOAc (250 L), and filtered through diatomaceous earth (Celite®) to remove some dark solids. The pad was washed with ethyl acetate (300 mL). The layers were partitioned. The organic layer was washed with brine, dried over sodium sulfate, filtered and evaporated to a dark oily solid. The crude product dissolved in $CH_2Cl_2$/hexane was applied to the head of a 330 g Teledyne Isco Silica Flash Column and purified on Biotage using a gradient from 100% hexanes to 100% $CH_2Cl_2$ over 11 col vols. The fractions containing the product were evaporated in vacuo and dried on high vacuum to give 4.36 g (71%) of the pure title compound as a white solid. $^1$H NMR (500 MHz, CHLOROFORM-d) δ 7.38 (d, J=7.3 Hz, 1H), 7.16 (t, J=7.8 Hz, 1H), 6.94 (d, J=8.1 Hz, 1H), 4.11 (t, J=5.7 Hz, 2H), 3.66 (t, J=6.5 Hz, 2H), 2.44 (s, 3H), 2.36 (quin, J=6.1 Hz, 2H), 1.37 (s, 12H).

Intermediate: (R)-1-(3-(3-bromo-2-methylphenoxy)propyl)pyrrolidin-3-ol

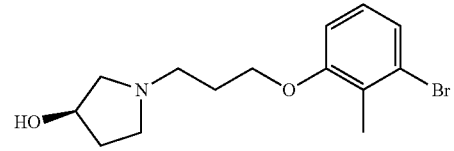 [SMILES: Cc1c(Br)cccc1OCCCN1CC[C@@H](O)C1]

A magnetically stirred solution of 1-bromo-3-(3-bromopropoxy)-2-methylbenzene (3.00 g, 9.74 mmol) and (R)-pyrrolidin-3-ol, HCl (2.41 g, 19.50 mmol) in MeOH (40 mL) under $N_2$ in a 150 mL pressure bottle was treated with Hunig's base (6 ml, 34.4 mmol), sealed, and placed in a 70° C. oil bath overnight. The solvent was evaporated and the residue was partitioned with EtOAc (250 mL) and sat. aq NaHCO$_3$ (200 mL). The layers was separated, the organic layer washed with water (75 mL) and brine (50 mL). This first extract was dried over $Na_2SO_4$, filtered and evapd to give 2.81 g of the title compound. The non-brine aqueous layers were combined and again extracted with fresh EtOAc (250 mL). This was washed with 50 mL water, 50 mL brine, dried over $Na_2SO_4$ and evapd separately to give 180 mg of the pure title compound. $^1$H NMR (500 MHz, CHLOROFORM-d) δ 7.20-7.14 (m, 1H), 7.01 (t, J=8.2 Hz, 1H), 6.79 (d, J=8.2 Hz, 1H), 4.38 (ddt, J=7.2, 4.9, 2.3 Hz, 1H), 4.04 (t, J=6.3 Hz, 2H), 2.96 (td, J=8.6, 5.2 Hz, 1H), 2.76 (d, J=10.1 Hz, 1H), 2.69 (t, J=7.4 Hz, 2H), 2.58 (dd, J=10.1, 5.2 Hz, 1H), 2.40-2.34 (m, 1H), 2.22 (dddd, J=13.8, 8.7, 7.1, 5.2 Hz, 1H), 2.10-1.99 (m, 2H), 1.87-1.73 (m, 1H). LC/MS Condition B: ret time (retention time) 2.53 min; m/e=314 (M+H)$^+$.

Intermediate: (R)-1-(3-((3'-(3-bromopropoxy)-2,2'-dimethyl-[1,1'-biphenyl]-3-yl)oxy)propyl)pyrrolidin-3-ol

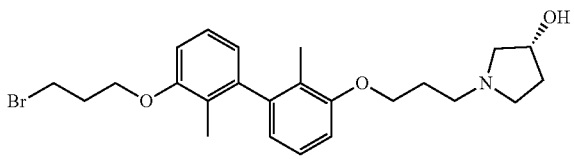 [SMILES: Cc1c(OCCCBr)cccc1-c1cccc(OCCCN2CC[C@@H](O)C2)c1C]

To a solution of 2-(3-(3-bromopropoxy)-2-methylphenyl)-4,4,5,5-tetramethyl-1,3,2-dioxaborolane (1.82 g, 5.13 mmol) and (R)-1-(3-(3-bromo-2-methylphenoxy)propyl)pyrrolidin-3-ol (1.74 g, 5.54 mmol) in THF (110 mL) was added aqueous potassium phosphate tribasic 0.5M (25.4 mL, 12.70 mmol) (degassed with $N_2$ for 1 h before use) and then flushed with argon and added 2nd Generation XPhos Precatalyst (200 mg, 0.254 mmol). The resulting mixture was flushed with argon for a few min, sealed, and stirred at rt overnight. The mixture was partioned with $CH_2Cl_2$ (350 mL) and water (200 mL). The organic layer was washed with brine (100 mL), dried with Na$_2$SO$_4$, filtered, and evap'd in vacuo, and then dried 5 min on high vacuum to a weight of ~3.3 g and immediately froze at −20° C. LCMS showed about 60-70% product. The product was dissolved in a total of 90 mL MeOH in a 100 mL round bottomed flask and used 1 mL for most of the reactions indicated below: LC/MS Condition A: ret time 1.32 min; m/e=462 (M+H)$^+$.

Intermediate: 3,3'-bis(3-bromopropoxy)-2,2'-dimethyl-1,1'-biphenyl

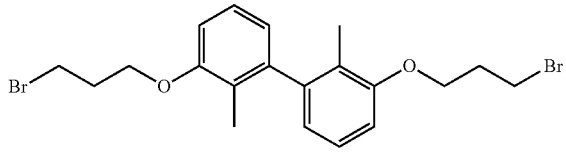 [SMILES: Cc1c(OCCCBr)cccc1-c1cccc(OCCCBr)c1C]

To a solution of 2-(3-(3-bromopropoxy)-2-methylphenyl)-4,4,5,5-tetramethyl-1,3,2-dioxaborolane (600 mg, 1.690 mmol) and 1-bromo-3-(3-bromopropoxy)-2-methylbenzene (521 mg, 1.692 mmol) in anhydrous THF (40 mL) was added potassium phosphate tribasic 0.5 M (8.5 mL, 4.25 mmol). The reaction mixture was flushed well with argon, treated with 2$^{nd}$ generation xphos precatalyst (66 mg, 0.084 mmol). The mixture was flushed with argon again, securely capped and stirred at room temperature for 8 h. The reaction was diluted with dichloromethane (300 mL) and water (150 mL). The organic layer was washed with brine (1×100 mL), dried over Na$_2$SO$_4$, filtered and evaporated to dryness to give 600 mg (78%) of the crude title compound that was used without further purification.

LC/MS condition B: ret time=4.45 min; m/e=457 (M+H)$^+$

Intermediate: (2,2'-dimethyl-[1,1'-biphenyl]-3,3'-diyl)dimethanol

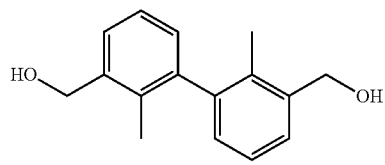 [SMILES: Cc1c(CO)cccc1-c1cccc(CO)c1C]

To a solution of (2-methyl-3-(4,4,5,5-tetramethyl-1,3,2-dioxaborolan-2-yl)phenyl)methanol (5.0 g, 20.15 mmol) and (3-bromo-2-methylphenyl)methanol (4.05 g, 20.15 mmol) in THF (350 mL) was added potassium phosphate tribasic 0.5 M (100 mL, 50.0 mmol). The reaction mixture was flushed well with argon, treated with 2$^{nd}$ generation xphos precatalyst (420 mg, 0.534 mmol). The mixture was flushed with argon again and stirred at rt overnight. The mixture was diluted with dichloromethane (600 mL) and water (75 mL), and the organic layer was drained off. The water layer was extracted with dichloromethane (2×150 mL). The organic layers were combined, dried over Na$_2$SO$_4$/MgSO$_4$, filtered and evaporated to dryness. The crude residue was dissolved in dichloromethane (35 mL) and the white precipitate was collected by filtration to give 3.58 g (73%) of the pure title compound as a white solid.

$^1$H NMR (500 MHz, DMSO-d$_6$) δ 7.39 (d, J=7.2 Hz, 2H), 7.22 (t, J=7.6 Hz, 2H), 6.97-6.92 (m, 2H), 5.11 (t, J=5.4 Hz, 2H), 4.55 (d, J=5.3 Hz, 4H), 1.90 (s, 6H).

Intermediate: 4,4'-(((2,2'-dimethyl-[1,1'-biphenyl]-3,3'-diyl)bis(methylene))bis(oxy))bis(5-chloro-2-hydroxybenzaldehyde)

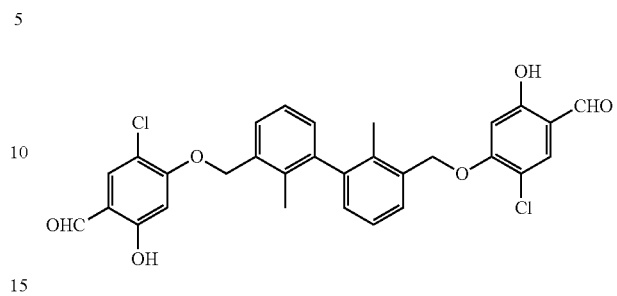

To a magnetically stirred ice cold mixture of (2,2'-dimethyl-[1,1'-biphenyl]-3,3'-diyl)dimethanol (2.1 g, 8.67 mmol), 5-chloro-2,4-dihydroxybenzaldehyde (3.1 g, 17.96 mmol), and triphenylphosphine (5.0 g, 19.06 mmol) in THF (150 mL) under continuos argon flush is slowly added over 35 min DIAD (3.6 mL, 18.52 mmol). After the addition was complete, the cooling bath is removed and the reaction flask was securely capped and the mixture allowed to stir overnight at room temperature. The solvent was removed in vacuo, and the residue suspended in dichloromethane (30 mL) and evaporated to dryness. Ice cold THF (25 mL) was added to the residue which was then placed in a −20° C. freezer for 15 min, and during which time much solid precipitated out. The solid was collected by filtration to give 3.46 g (72%) of the pure title compound as a white solid. $^1$H NMR (500 MHz, DMSO-d$_6$) δ 10.04 (s, 2H), 7.72 (s, 2H), 7.53 (d, J=8.7 Hz, 2H), 7.33 (t, J=7.6 Hz, 2H), 7.17-7.11 (m, 2H), 6.88 (s, 2H), 5.34 (s, 4H), 2.02 (s, 6H).

Intermediate: 5,5'-((((((2,2'-dimethyl-[1,1'-biphenyl]-3,3'-diyl)bis(methylene))bis(oxy))bis(4-chloro-6-formyl-3,1-phenylene))bis(oxy))bis(methylene))dinicotinonitrile

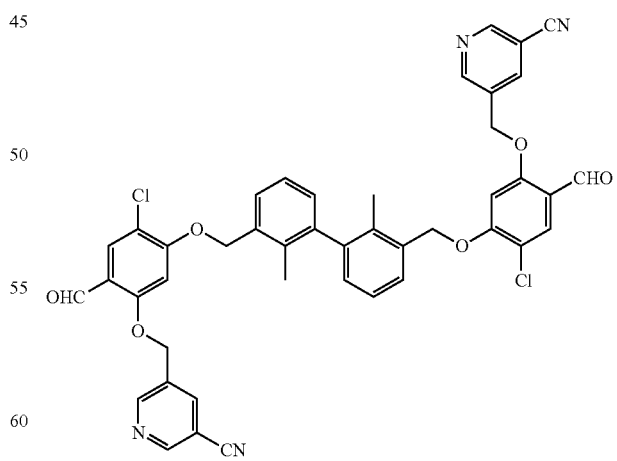

To a rapidly stirred solution of 4,4'-(((2,2'-dimethyl-[1,1'-biphenyl]-3,3'-diyl)bis(methylene))bis(oxy))bis(5-chloro-2-hydroxybenzaldehyde) (1.25 g, 2.267 mmol), and 5-(chloromethyl)nicotinonitrile (0.866 g, 5.68 mmol) in anhydrous DMF (8 mL) was added cesium carbonate (1.87 g, 5.74 mmol), and sodium iodide (77 mg, 0.514 mmol). The reaction mixture was flushed well with argon, securely capped, and placed in a 75° C. oil bath with good magnetic stirring for 2 h 45 min. The reaction mixture was poured into ice water and the resulting yellow precipitate was collected by filtration to give 1.47 g (83%) of the pure title compound as a yellow solid. $^1$H NMR (500 MHz, DMSO-$d_6$) δ 10.24 (s, 2H), 9.05-9.03 (m, 4H), 8.56 (t, J=2.0 Hz, 2H), 7.74 (s, 2H), 7.56 (d, J=7.0 Hz, 2H), 7.34 (t, J=7.6 Hz, 2H), 7.30 (s, 2H), 7.17 (d, J=6.9 Hz, 2H), 5.50 (s, 4H), 5.48-5.42 (m, 4H), 2.05 (s, 6H).

Silica Flash Column and purified on Biotage using a gradient from 100% dichloromethane to 15% ethyl acetate/dichloromethane over 12 column volumes. The fractions containing the product were evaporated in vacuo and then dried on high vacuum to give 187.6 mg (71%) of the pure title compound as a white solid. $^1$H NMR (500 MHz, CHLOROFORM-d) δ 10.29 (s, 2H), 7.90 (s, 2H), 7.53 (d, J=6.9 Hz, 2H), 7.33 (t, J=7.6 Hz, 2H), 7.20 (dd, J=7.6, 1.1 Hz, 2H), 6.63 (s, 2H), 5.29 (s, 4H), 3.96 (s, 6H), 2.10 (s, 6H).

Example 2001: (R)-1-(4-(3-((3'-(3-(3-hydroxypyrrolidin-1-yl)propoxy)-2,2'-dimethyl-[1,1'-biphenyl]-3-yl)oxy)propyl)piperazin-1-yl)ethan-1-one

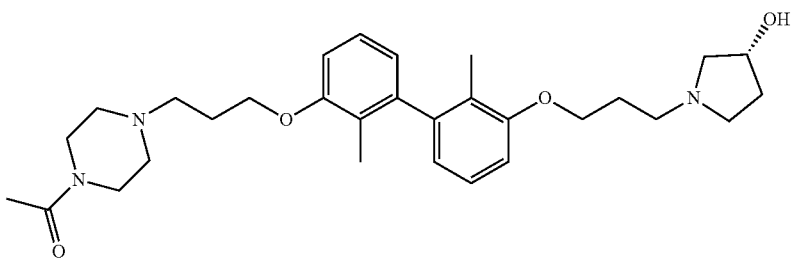

Intermediate: 4,4'-(((2,2'-dimethyl-[1,1'-biphenyl]-3,3'-diyl)bis(methylene))bis(oxy))bis(5-chloro-2-methoxybenzaldehyde)

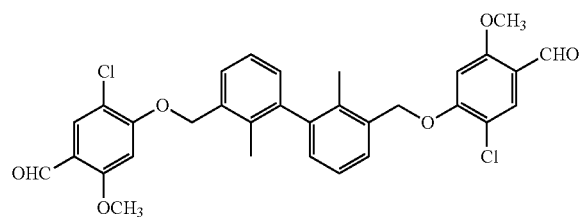 [SMILES: COc1cc(OCc2cccc(-c3cccc(COc4cc(OC)c(C=O)cc4Cl)c3C)c2C)c(Cl)cc1C=O]

To a rapidly stirred solution of 4,4'-(((2,2'-dimethyl-[1,1'-biphenyl]-3,3'-diyl)bis(methylene))bis(oxy))bis(5-chloro-2-hydroxybenzaldehyde) (250 mg, 0.453 mmol) in DMF (2.0 mL) was added cesium carbonate (370 mg, 1.136 mmol), followed by iodomethane (85 μL, 1.365 mmol). The reaction mixture was flushed briefly with $N_2$, securely capped and stirred at room temp overnight. The mixture was diluted with dichloromethane (225 mL) and water (25 mL). The organic layer was washed with water (5×20 mL), brine (1×20 mL), dried over $Na_2SO_4$, filtered and evaporated to dryness. The crude residue was dissolved in dichloromethane (25 mL), applied to the head of a 80 g Teledyne Isco To a reaction vial containing 1-acetylpiperazine (40 mg, 0.312 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min to give the pure title compound: (10.9 mg, 47%). LC/MS Condition E: ret time 1.46 min; m/e=510 (M+H)$^+$; LC/MS Condition F: ret time 1.16 min; m/e=510 (M+H)$^+$.

Example 2002: (R)-1-(3-((3'-(3-(3-(dimethylamino)azetidin-1-yl)propoxy)-2,2'-dimethyl-[1,1'-biphenyl]-3-yl)oxy)propyl)pyrrolidin-3-ol

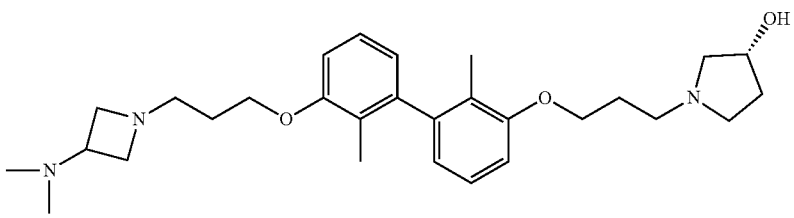 [SMILES: Cc1c(OCCCN2CC(N(C)C)C2)cccc1-c1cccc(OCCCN2CC[C@@H](O)C2)c1C]

To a reaction vial containing 3-(dimethylamino)azetidine dihydrochloride (60 mg, 0.347 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (150 μL, 0.859 mmol). The reaction mixture was briefly flushed with N₂, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (15.5 mg, 74%). LC/MS Condition E: ret time 1.23 min; m/e=482 (M+H)⁺; LC/MS Condition F: ret time 1.1 min; m/e=482 (M+H)⁺.

Example 2003: (3R)-1-(3-((3'-(3-(3-(hydroxymethyl)piperidin-1-yl)propoxy)-2,2'-dimethyl-[1,1'-biphenyl]-3-yl)oxy)propyl)pyrrolidin-3-ol

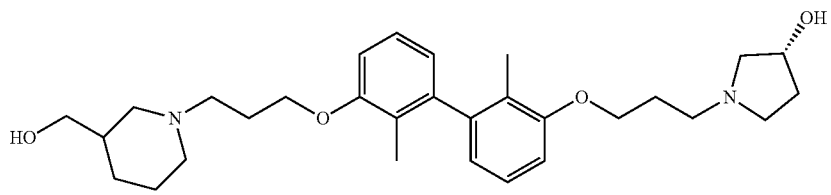 [SMILES: Cc1c(OCCCN2CCCC(CO)C2)cccc1-c1cccc(OCCCN2CC[C@@H](O)C2)c1C]

To a reaction vial containing 3-piperidinemethanol (34.1 μL, 0.304 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with N₂, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound as a mixture of diastereomers: (11.8 mg, 55%). LC/MS Condition E: ret time 1.2 min; m/e=497 (M+H)⁺; LC/MS Condition F: ret time 1.2 min; m/e=497 (M+H)⁺; ¹H NMR (500 MHz, DMSO-d₆) δ 7.18 (t, J=7.9 Hz, 2H), 6.93 (d, J=8.1 Hz, 2H), 6.64 (d, J=7.7 Hz, 2H), 4.22 (br s, 1H), 4.05 (br d, J=8.4 Hz, 4H), 3.29 (br dd, J=10.6, 5.1 Hz, 1H), 3.25-3.19 (m, 1H), 2.93 (br s, 1H), 2.81 (br s, 2H), 2.75-2.62 (m, 3H), 2.60-2.55 (m, 1H), 2.49-2.41 (m, 1H), 2.07-1.88 (m, 8H), 1.83 (s, 6H), 1.79-1.68 (m, 1H), 1.62 (br d, J=9.2 Hz, 4H), 1.46 (br d, J=11.7 Hz, 1H), 0.91 (br d, J=9.9 Hz, 1H).

Example 2004: (R)-1-(3-((3'-(3-(6,7-dimethoxy-3,4-dihydroisoquinolin-2(1H)-yl)propoxy)-2,2'-dimethyl-[1,1'-biphenyl]-3-yl)oxy)propyl)pyrrolidin-3-ol

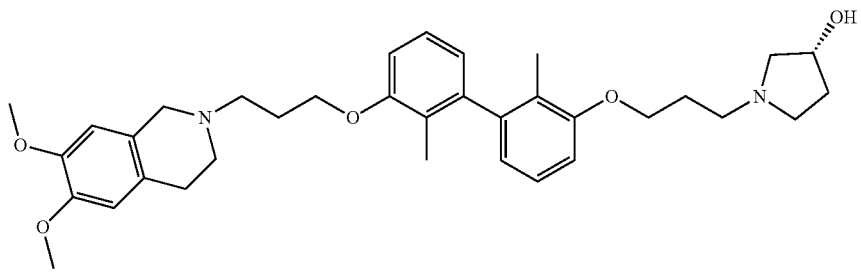 [SMILES: COc1cc2c(cc1OC)CN(CCCOc1cccc(-c3cccc(OCCCN4CC[C@@H](O)C4)c3C)c1C)CC2]

To a reaction vial containing 3-piperidinemethanol (34.1 µL, 0.304 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (100 µL, 0.573 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to give the pure title compound: (23.5 mg, 94%). LC/MS Condition E: ret time 1.64 min; m/e=575 (M+H)$^+$. LC/MS Condition F: ret time 1.31 min; m/e=575 (M+H)$^+$; $^1$H NMR (500 MHz, DMSO-$d_6$) δ 7.17 (td, J=7.7, 4.4 Hz, 2H), 6.94 (dd, J=8.4, 4.4 Hz, 2H), 6.69-6.61 (m, 4H), 4.21 (br s, 1H), 4.13-3.97 (m, 4H), 3.70 (d, J=5.1 Hz, 6H), 3.50 (s, 2H), 2.81-2.69 (m, 3H), 2.69-2.59 (m, 6H), 2.42 (br s, 1H), 2.07-1.97 (m, 3H), 1.96-1.88 (m, 4H), 1.84 (d, J=6.6 Hz, 6H), 1.56 (br s, 1H)

Example 2005: (R)-1-(3-((2,2'-dimethyl-3'-(3-((2-morpholinoethyl)amino)propoxy)-[1,1'-biphenyl]-3-yl)oxy)propyl)pyrrolidin-3-ol

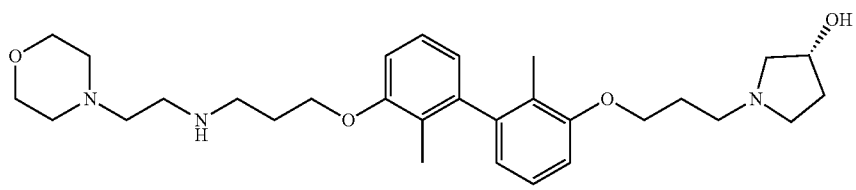 [SMILES: Cc1c(OCCCNCCN2CCOCC2)cccc1-c1cccc(OCCCN2CC[C@@H](O)C2)c1C]

To a reaction vial containing 4-(2-aminoethyl)morpholine (85 µL, 0.646 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the pure title compound: (21.4 mg, 96%). LC/MS Condition E: ret time 1.17 min; m/e=512 (M+H)$^+$. LC/MS Condition F: ret time 1.07 min; m/e=512 (M+H)$^+$.

Example 2006: (R)-1-(3-((2,2'-dimethyl-3'-(3-((pyridin-4-ylmethyl)amino)propoxy)-[1,1'-biphenyl]-3-yl)oxy)propyl)pyrrolidin-3-ol

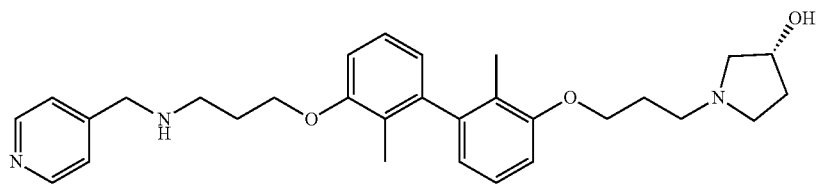 [SMILES: Cc1c(OCCCNCc2ccncc2)cccc1-c1cccc(OCCCN2CC[C@@H](O)C2)c1C]

To a reaction vial containing added pyridin-4-ylmethanamine (66 mg, 0.610 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound: (10.0 mg, 46%). LC/MS Condition E: ret time 1.32 min; m/e=490 (M+H)$^+$. LC/MS Condition F: ret time 1.08 min; m/e=490 (M+H)$^+$.

Example 2007: (R)-1-(3-((3'-(3-((2-(dimethylamino)ethyl)amino)propoxy)-2,2'-dimethyl-[1,1'-biphenyl]-3-yl)oxy)propyl)pyrrolidin-3-ol

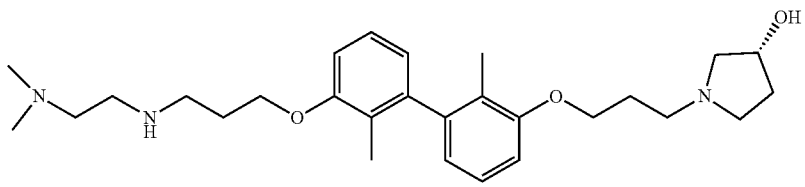 [SMILES: Cc1c(OCCCNCCN(C)C)cccc1-c1cccc(OCCCN2CC[C@@H](O)C2)c1C]

To a reaction vial containing N,N-dimethylethylenediamine (57 μL, 0.522 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (57 μL, 0.522 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min to give the pure title compound: (12.8 mg, 61%). LC/MS Condition E: ret time 1.20 min; m/e=470 (M+H)$^+$. LC/MS Condition F: ret time 1.08 min; m/e=470 (M+H)$^+$.

Example 2008: (R)-1-(3-((3'-(3-((2-(1H-pyrazol-1-yl)ethyl)amino)propoxy)-2,2'-dimethyl-[1,1'-biphenyl]-3-yl)oxy)propyl)pyrrolidin-3-ol

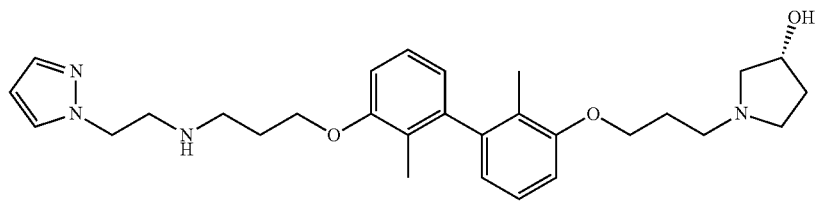 [SMILES: Cc1c(OCCCNCCn2cccn2)cccc1-c1cccc(OCCCN2CC[C@@H](O)C2)c1C]

To a reaction vial containing 2-(1H-pyrazol-1-yl)ethanamine (60 mg, 0.540 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min to give the pure title compound: (12.5 mg, 59%). LC/MS Condition E: ret time 1.29 min; m/e=493 (M+H)$^+$. LC/MS Condition F: ret time 1.23 min; m/e=493 (M+H)$^+$.

Example 2009: (R)-1-(3-((2,2'-dimethyl-3'-(3-((2-(3-methyl-1H-pyrazol-1-yl)ethyl)amino)propoxy)-[1,1'-biphenyl]-3-yl)oxy)propyl)pyrrolidin-3-ol

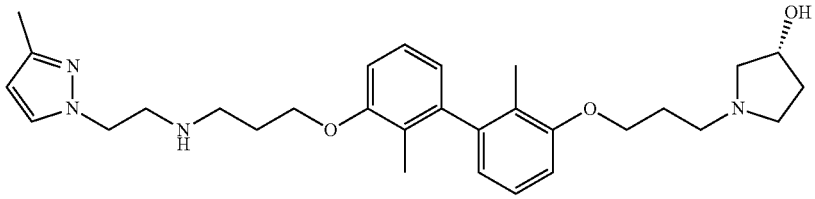 [SMILES: Cc1ccn(CCNCCCOc2cccc(-c3cccc(OCCCN4CC[C@@H](O)C4)c3C)c2C)n1]

To a reaction vial containing 3-(3-methyl-1H-pyrazol-1-yl)propan-1-amine (75 mg, 0.539 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (14.9 mg, 63%). LC/MS Condition E: ret time 1.28 min; m/e=521 (M+H)⁺. LC/MS Condition F: ret time 1.28 min; m/e=521 (M+H)⁺.

Example 2010: (R)-1-(3-((2,2'-dimethyl-3'-(3-((2-(methylsulfonyl)ethyl)amino)propoxy)-[1,1'-biphenyl]-3-yl)oxy)propyl)pyrrolidin-3-ol

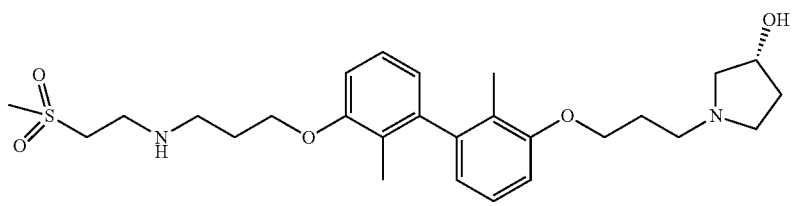 [SMILES: Cc1c(OCCCNCCS(C)(=O)=O)cccc1-c1cccc(OCCCN2CC[C@@H](O)C2)c1C]

To a reaction vial containing 2-(methylsulfonyl)ethanamine, 1.0 HCl (75 mg, 0.470 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (100 μL, 0.573 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (15.9 mg, 48%). LC/MS Condition E: ret time 1.32 min; m/e=505 (M+H)⁺. LC/MS Condition F: ret time 1.14 min; m/e=505 (M+H)⁺; ¹H NMR (500 MHz, DMSO-$d_6$) δ 7.21 (t, J=7.9 Hz, 2H), 6.95 (d, J=8.4 Hz, 2H), 6.66 (d, J=7.3 Hz, 2H), 4.45 (br s, 1H), 4.09 (br dd, J=9.5, 6.2 Hz, 4H), 3.58-3.49 (m, 2H), 3.47-3.32 (m, 9H), 3.27-3.15 (m, 3H), 3.13 (s, 3H), 2.22-2.06 (m, 4H), 1.85 (s, 6H)

Example 2011: (S)-3-((3-((3'-(3-((R)-3-hydroxypyrrolidin-1-yl)propoxy)-2,2'-dimethyl-[1,1'-biphenyl]-3-yl)oxy)propyl)amino)propane-1,2-diol

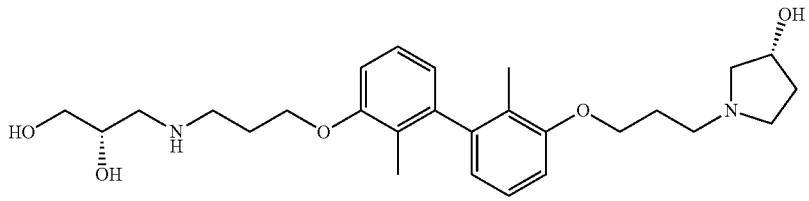 [SMILES: Cc1c(OCCCNC[C@H](O)CO)cccc1-c1cccc(OCCCN2CC[C@@H](O)C2)c1C]

To a reaction vial containing (S)-3-aminopropane-1,2-diol, 1.0 HCl (58 mg, 0.455 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (100 µL, 0.573 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (19.0 mg, 92%). LC/MS Condition E: ret time 1.08 min; m/e=473 (M+H)+. LC/MS Condition F: ret time 1.12 min; m/e=473 (M+H)+. $^1$H NMR (500 MHz, DMSO-$d_6$) δ 7.18 (td, J=7.8, 4.2 Hz, 2H), 6.93 (dd, J=8.1, 3.7 Hz, 2H), 6.64 (t, J=7.3 Hz, 2H), 4.19 (br s, 1H), 4.12-3.99 (m, 4H), 3.61 (br s, 1H), 3.39-3.26 (m, 3H), 2.86 (br t, J=6.8 Hz, 2H), 2.78 (dd, J=12.1, 3.7 Hz, 1H), 2.72 (br dd, J=15.0, 6.2 Hz, 1H), 2.63-2.56 (m, 3H), 2.55 (s, 2H), 2.44 (br d, J=6.6 Hz, 1H), 2.33 (br d, J=6.2 Hz, 1H), 2.03-1.94 (m, 3H), 1.83 (d, J=3.3 Hz, 6H), 1.61-1.47 (m, 1H)

Example 2012: (3-((3'-(3-((R)-3-hydroxypyrrolidin-1-yl)propoxy)-2,2'-dimethyl-[1,1'-biphenyl]-3-yl)oxy)propyl)-L-serine

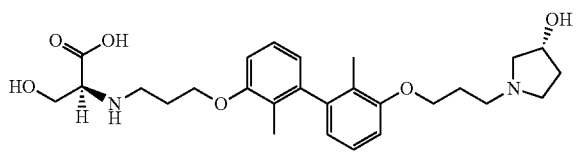 [SMILES: Cc1c(OCCCN[C@@H](CO)C(=O)O)cccc1-c1cccc(OCCCN2CC[C@@H](O)C2)c1C]

To a reaction vial containing L-serine (55 mg, 0.523 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (12.3 mg, 54%). LC/MS Condition E: ret time 1.10 min; m/e=487 (M+H)+. LC/MS Condition F: ret time 1.11 min; m/e=487 (M+H)+.

Example 2013: (S)-3-hydroxy-2-((3-((3'-(3-((R)-3-hydroxypyrrolidin-1-yl)propoxy)-2,2'-dimethyl-[1,1'-biphenyl]-3-yl)oxy)propyl)amino)-2-methylpropanoic acid

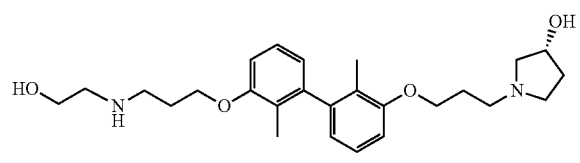 [SMILES: Cc1c(OCCCNCCO)cccc1-c1cccc(OCCCN2CC[C@@H](O)C2)c1C]

To a reaction vial containing 2-methyl-L-serine (62 mg, 0.520 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 minutes, then a 5-minute hold at 100% B; Flow: 20 mL/min to give the pure title compound: (9.0 mg, 40%). LC/MS Condition E: ret time 1.12 min; m/e=501 (M+H)+. LC/MS Condition F: ret time 1.15 min; m/e=501 (M+H)+.

Example 2014: (R)-1-(3-((3'-(3-((2-hydroxyethyl)amino)propoxy)-2,2'-dimethyl-[1,1'-biphenyl]-3-yl)oxy)propyl)pyrrolidin-3-ol To a reaction vial containing ethanolamine (32 mg, 0.524 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C.

sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 minutes, then a 5-minute hold at 100% B; Flow: 20 mL/min to give the pure title compound: (22.4 mg, quantitative yield). LC/MS Condition E: ret time 1.09 min; m/e=443 (M+H)$^+$. LC/MS Condition F: ret time 1.13 min; m/e=443 (M+H)$^+$. $^1$H NMR (500 MHz, DMSO-d$_6$) δ 7.23-7.13 (m, 2H), 6.94 (dd, J=8.3, 3.9 Hz, 2H), 6.64 (t, J=7.9 Hz, 2H), 4.19 (br s, 1H), 4.14-3.98 (m, 4H), 3.53 (t, J=5.3 Hz, 2H), 2.87 (br t, J=7.0 Hz, 2H), 2.80-2.66 (m, 3H), 2.63-2.54 (m, 5H), 2.44 (br d, J=8.1 Hz, 1H), 2.33 (br d, J=6.2 Hz, 1H), 1.98 (br s, 3H), 1.83 (d, J=3.3 Hz, 6H), 1.54 (br d, J=3.7 Hz, 1H)

Example 2015: 3-((3-((3'-(3-((R)-3-hydroxypyrrolidin-1-yl)propoxy)-2,2'-dimethyl-[1,1'-biphenyl]-3-yl)oxy)propyl)(methyl)amino)propane-1,2-diol, 2.0 TFA

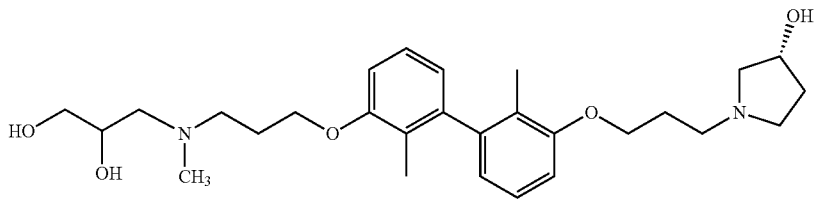 [SMILES: Cc1c(OCCCN(C)CC(O)CO)cccc1-c1cccc(OCCCN2CC[C@@H](O)C2)c1C]

To a reaction vial containing 3-methylamino-1,2-propanediol (30 μl, 0.311 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with N$_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 0.1% TFA; Mobile Phase B: 95:5 acetonitrile: water with 0.1% TFA; Gradient: 15-55% B over 15 minutes, then a 5-minute hold at 100% B; Flow: 20 mL/min to give the pure title compound as a TFA salt and as a mixture of diastereomers: (29.9 mg, 98%). LC/MS Condition E: ret time 1.11 min; m/e=487 (M+H)$^+$. LC/MS Condition F: ret time 1.10 min; m/e=487 (M+H)$^+$.

Example 2016: 2-hydroxy-3-((3-((3'-(3-((R)-3-hydroxypyrrolidin-1-yl)propoxy)-2,2'-dimethyl-[1,1'-biphenyl]-3-yl)oxy)propyl)amino)propanoic acid

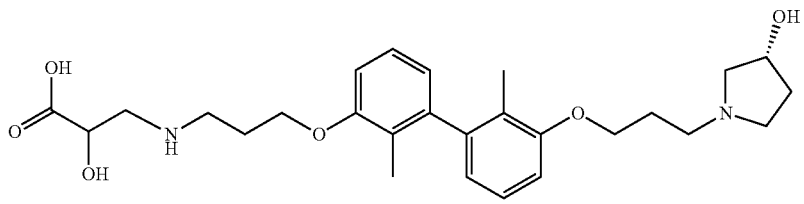 [SMILES: Cc1c(OCCCNCC(O)C(=O)O)cccc1-c1cccc(OCCCN2CC[C@@H](O)C2)c1C]

To a reaction vial containing DL-isoserine (55 mg, 0.523 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (7.3 mg, 34%). LC/MS Condition E: ret time 1.10 min; m/e=487 (M+H)$^+$. LC/MS Condition F: ret time 1.13 min; m/e=487 (M+H)$^+$. $^1$H NMR (500 MHz, DMSO-$d_6$) δ 7.23-7.12 (m, 2H), 6.93 (br d, J=8.1 Hz, 2H), 6.65 (dd, J=12.7, 7.5 Hz, 2H), 4.21 (br s, 1H), 4.06 (br dd, J=17.2, 8.1 Hz, 4H), 3.71 (br t, J=6.6 Hz, 1H), 3.11 (br t, J=7.2 Hz, 2H), 2.97 (br d, J=3.3 Hz, 2H), 2.76 (br dd, J=15.0, 9.5 Hz, 1H), 2.71-2.60 (m, 3H), 2.42 (br d, J=8.8 Hz, 1H), 2.14-2.04 (m, 2H), 2.04-1.97 (m, 1H), 1.95-1.90 (m, 3H), 1.84 (d, J=6.6 Hz, 6H), 1.57 (br s, 1H)

Example 2017: (R)-1-(3-((3'-(3-(((1r,4r)-4-hydroxycyclohexyl)amino)propoxy)-2,2'-dimethyl-[1,1'-biphenyl]-3-yl)oxy)propyl)pyrrolidin-3-ol

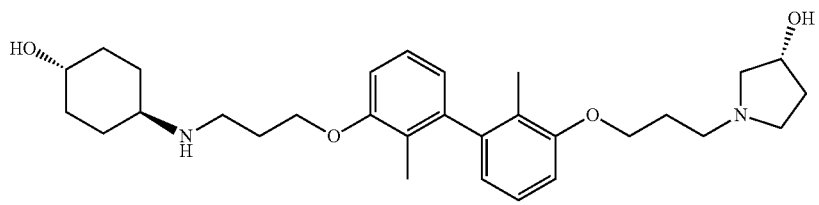 [SMILES: Cc1c(OCCCN[C@H]2CC[C@H](O)CC2)cccc1-c1cccc(OCCCN2CC[C@@H](O)C2)c1C]

To a reaction vial containing trans-4-aminocyclohexanol hydrochloride (80 mg, 0.528 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (125 µL, 0.716 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (15.0 mg, 70%). LC/MS Condition E: ret time 1.13 min; m/e=497 (M+H)$^+$. LC/MS Condition F: ret time 1.16 min; m/e=497 (M+H)$^+$.

Example 2018: N—((R)-1-(3-((3'-(3-((R)-3-hydroxypyrrolidin-1-yl)propoxy)-2,2'-dimethyl-[1,1'-biphenyl]-3-yl)oxy)propyl)pyrrolidin-3-yl)acetamide

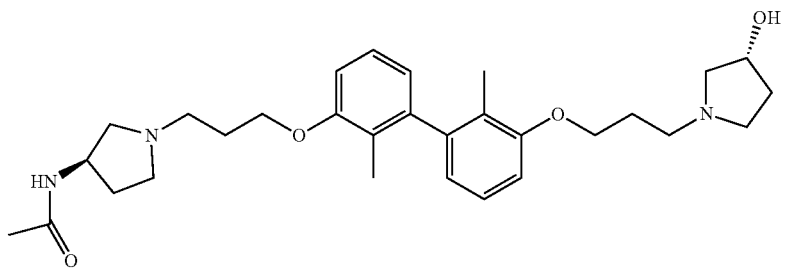 [SMILES: CC(=O)N[C@@H]1CCN(CCCOc2cccc(-c3cccc(OCCCN4CC[C@@H](O)C4)c3C)c2C)C1]

To a reaction vial containing (3R)-(+)-3-acetamidopyrrolidine (40 mg, 0.312 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-55% B over 15 minutes, then a 5-minute hold at 100% B; Flow: 20 mL/min to give the pure title compound: (18.0 mg, 80%). LC/MS Condition E: ret time 1.22 min; m/e=510 (M+H)$^+$. LC/MS Condition F: ret time 1.15 min; m/e=510 (M+H)$^+$.

Example 2019: 1-(3-((3'-(3-((R)-3-hydroxypyrrolidin-1-yl)propoxy)-2,2'-dimethyl-[1,1'-biphenyl]-3-yl)oxy)propyl)piperidine-3-carboxamide

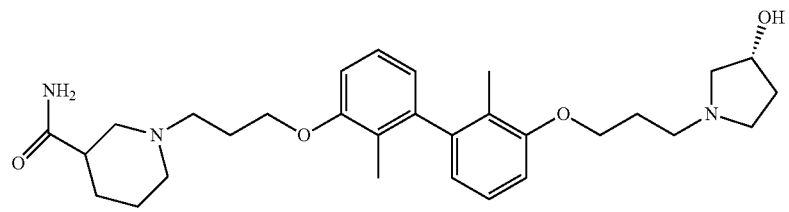 [SMILES: Cc1c(OCCCN2CCCC(C(N)=O)C2)cccc1-c1cccc(OCCCN2CC[C@@H](O)C2)c1C]

To a reaction vial containing nipecotamide (40 mg, 0.312 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 45-85% B over 15 minutes, then a 5-minute hold at 100% B; Flow: 20 mL/min to give the pure title compound: (11.4 mg, 51%). LC/MS Condition E: ret time 1.24 min; m/e=510 (M+H)$^+$. LC/MS Condition F: ret time 1.14 min; m/e=510 (M+H)$^+$.

Example 2020: (R)-1-(3-((3'-(3-((3-(1H-imidazol-1-yl)propyl)amino)propoxy)-2,2'-dimethyl-[1,1'-biphenyl]-3-yl)oxy)propyl)pyrrolidin-3-ol

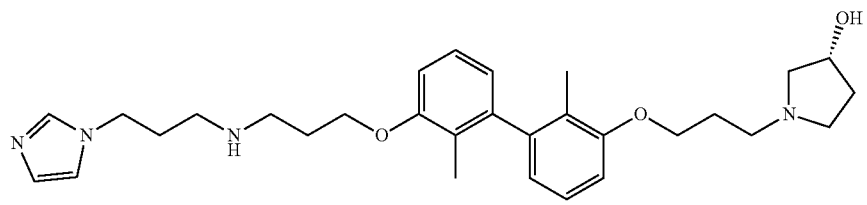 [SMILES: Cc1c(OCCCNCCCn2ccnc2)cccc1-c1cccc(OCCCN2CC[C@@H](O)C2)c1C]

To a reaction vial containing 1-(3-aminopropyl)imidazole (80 µl, 0.670 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound: (19.0 mg, 86%). LC/MS Condition E: ret time 1.15 min; m/e=507 $(M+H)^+$. LC/MS Condition F: ret time 1.07 min; m/e=507 $(M+H)^+$.

Example 2021: (R)-1-(3-((2,2'-dimethyl-3'-(3-((3-morpholinopropyl)amino)propoxy)-[1,1'-biphenyl]-3-yl)oxy)propyl)pyrrolidin-3-ol

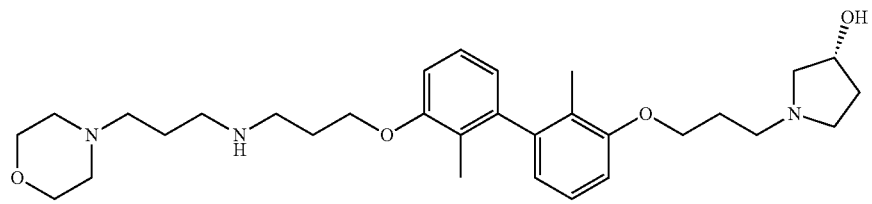 [SMILES: Cc1c(OCCCNCCCN2CCOCC2)cccc1-c1cccc(OCCCN2CC[C@@H](O)C2)c1C]

To a reaction vial containing N-(3-aminopropyl)morpholine (95 µl, 0.646 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound: (21.3 mg, 94%). LC/MS Condition E: ret time 1.17 min; m/e=526 $(M+H)^+$. LC/MS Condition F: ret time 1.07 min; m/e=526 $(M+H)^+$.

Example 2022: (R)-1-(3-((2,2'-dimethyl-3'-(3-((2-(pyridin-3-yl)ethyl)amino)propoxy)-[1,1'-biphenyl]-3-yl)oxy)propyl)pyrrolidin-3-ol

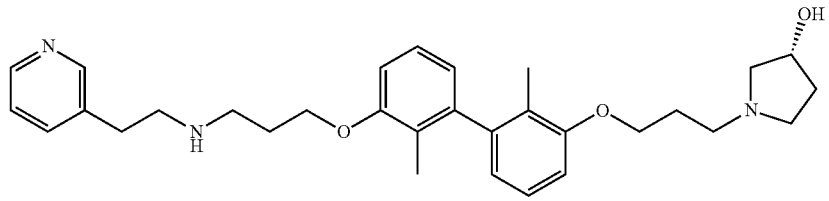 [SMILES: Cc1c(OCCCNCCc2cccnc2)cccc1-c1cccc(OCCCN2CC[C@@H](O)C2)c1C]

To a reaction vial containing 3-(2-aminoethyl)pyridine (76 µl, 0.647 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with N₂, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound: (16.2 mg, 72%). LC/MS Condition E: ret time 1.22 min; m/e=504 (M+H)⁺. LC/MS Condition F: ret time 1.08 min; m/e=504 (M+H)⁺. ¹H NMR (500 MHz, DMSO-d₆) δ 8.47 (s, 1H), 8.43 (d, J=3.7 Hz, 1H), 7.67 (br d, J=8.1 Hz, 1H), 7.32 (dd, J=7.7, 4.8 Hz, 1H), 7.24-7.14 (m, 2H), 6.93 (d, J=8.4 Hz, 2H), 6.64 (dd, J=10.3, 8.1 Hz, 2H), 4.22 (br s, 1H), 4.06 (br dd, J=14.3, 8.1 Hz, 4H), 3.05-2.97 (m, 2H), 2.93 (br t, J=7.0 Hz, 2H), 2.86-2.76 (m, 3H), 2.65 (br s, 3H), 2.44 (br d, J=9.9 Hz, 1H), 2.05-1.96 (m, 3H), 1.96-1.89 (m, 3H), 1.82 (s, 6H), 1.57 (br s, 1H)

Example 2023: N,N-diethyl-1-(3-((3'-(3-((R)-3-hydroxypyrrolidin-1-yl)propoxy)-2,2'-dimethyl-[1,1'-biphenyl]-3-yl)oxy)propyl)piperidine-3-carboxamide To a reaction vial containing N,N-diethylnipecotamide (60 mg, 0.326 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with N₂, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound as a mixture of diastereomers: (19.9 mg, 81%). LC/MS Condition E: ret time 1.42 min; m/e=566 (M+H)⁺. LC/MS Condition F: ret time 1.37 min; m/e=566 (M+H)⁺.

Example 2024: (R)-1-(3-((2,2'-dimethyl-3'-(3-((pyridin-2-ylmethyl)amino)propoxy)-[1,1'-biphenyl]-3-yl)oxy)propyl)pyrrolidin-3-ol

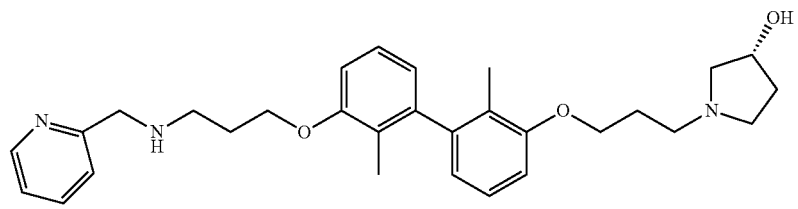

To a reaction vial containing 2-(aminomethyl)pyridine (61 µL, 0.587 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with N₂, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B;

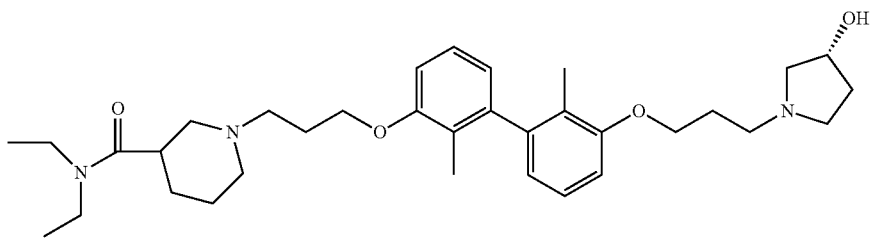 [SMILES: CCN(CC)C(=O)C1CCCN(CCCOc2cccc(-c3cccc(OCCCN4CC[C@@H](O)C4)c3C)c2C)C1]

Flow: 20 mL/min to give the pure title compound: (14.9 mg, 65%). LC/MS Condition E: ret time 1.28 min; m/e=490 (M+H)⁺. LC/MS Condition F: ret time 1.25 min; m/e=490 (M+H)⁺. ¹H NMR (500 MHz, DMSO-d₆) δ 8.52 (d, J=4.4 Hz, 1H), 7.77 (t, J=7.7 Hz, 1H), 7.45 (d, J=7.3 Hz, 1H), 7.33-7.26 (m, 1H), 7.18 (t, J=7.9 Hz, 2H), 6.94 (br d, J=8.8 Hz, 2H), 6.64 (dd, J=7.2, 4.6 Hz, 2H), 4.23 (br s, 1H), 4.15-3.97 (m, 6H), 2.90 (br t, J=7.2 Hz, 2H), 2.81 (br s, 1H), 2.76-2.65 (m, 3H), 2.58 (br s, 1H), 2.07-1.98 (m, 3H), 1.98-1.93 (m, 2H), 1.91 (s, 2H), 1.83 (s, 3H), 1.79 (s, 3H), 1.59 (br s, 1H)

Example 2025: (3R)-1-(3-((3'-(3-(2-(hydroxymethyl)piperidin-1-yl)propoxy)-2,2'-dimethyl-[1,1'-biphenyl]-3-yl)oxy)propyl)pyrrolidin-3-ol

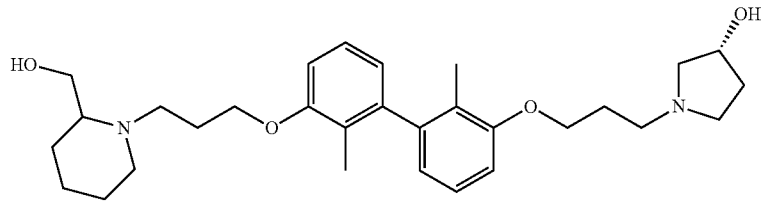 [SMILES: Cc1c(OCCCN2CC[C@@H](O)C2)cccc1-c1cccc(OCCCN2CCCCC2CO)c1C]

To a reaction vial containing 2-piperidinemethanol (35 mg, 0.304 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (50 µL, 0.286 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min to give the pure title compound as a mixture of diastereomers: (28.0 mg, quantitative yield). LC/MS Condition E: ret time 1.22 min; m/e=497 (M+H)$^+$. LC/MS Condition F: ret time 1.24 min; m/e=497 (M+H)$^+$.

Example 2026: ((((2,2'-dimethyl-[1,1'-biphenyl]-3,3'-diyl)bis(oxy))bis(propane-3,1-diyl))bis(piperidine-1,3-diyl))dimethanol, 2.0 TFA

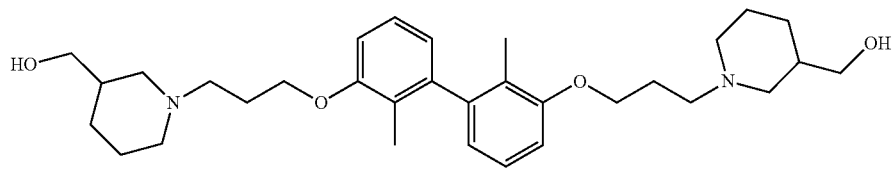 [SMILES: Cc1c(OCCCN2CCCC(CO)C2)cccc1-c1cccc(OCCCN2CCCC(CO)C2)c1C]

To a reaction vial containing 3,3'-bis(3-bromopropoxy)-2,2'-dimethyl-1,1'-biphenyl (20 mg, 0.044 mmol) was added 3-piperidinemethanol (103 µL, 0.920 mmol), DMF (0.5 mL) and MeOH (0.5 mL) and N,N-diisopropylethylamine (35 µL, 0.200 mmol). The reaction mixture was briefly flushed with $N_2$, securely capped, sonicated for 10 sec, and placed in a 65° C. sand bath with shaking for 18 h. The crude material was purified via preparative LC/MS with the following conditions: Column: XBridge C18, 19×200 mm, 5-µm particles; Mobile Phase A: 5:95 acetonitrile:water with 0.1% TFA; Mobile Phase B: 95:5 acetonitrile:water with 0.1% TFA; Gradient: 15-55% B over 15 minutes, then a 5-minute hold at 100% B; Flow: 20 mL/min to give the pure title compound as a TFA salt and as a mixture of diastereomers: (32.0 mg, 96%). LC/MS Condition E: ret time 1.29 min; m/e=525 (M+H)$^+$. LC/MS Condition F: ret time 1.25 min; m/e=525 (M+H)$^+$. $^1$H NMR (500 MHz, DMSO-d$_6$) δ 7.21 (t, J=7.9 Hz, 2H), 6.96 (d, J=8.1 Hz, 2H), 6.66 (d, J=7.7 Hz, 2H), 4.09 (td, J=10.1, 5.1 Hz, 4H), 3.52 (br d, J=10.6 Hz, 4H), 3.33-3.21 (m, 6H), 2.84 (br d, J=11.0 Hz, 2H), 2.73-2.61 (m, 2H), 2.25-2.12 (m, 4H), 1.94-1.81 (m, 10H), 1.76-1.62 (m, 4H), 1.25-1.09 (m, 2H)

Example 2027: 2,2'-((((2,2'-dimethyl-[1,1'-biphenyl]-3,3'-diyl)bis(oxy))bis(propane-3,1-diyl))bis(azanediyl))bis(ethan-1-ol)

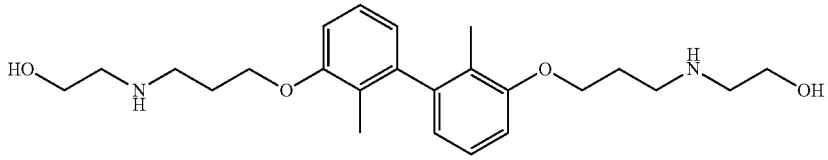 [SMILES: Cc1c(OCCCNCCO)cccc1-c1cccc(OCCCNCCO)c1C]

To a reaction vial containing 3,3'-bis(3-bromopropoxy)-2,2'-dimethyl-1,1'-biphenyl (20 mg, 0.044 mmol) was added ethanolamine (55 mg, 0.900 mmol), DMF (0.5 mL) and MeOH (0.5 mL) and N,N-diisopropylethylamine (31 μL, 0.177 mmol). The reaction mixture was briefly flushed with N$_2$, securely capped, sonicated for 10 sec, and placed in a 65° C. sand bath with shaking for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min to give the pure title compound: (17.9 mg, 98%). LC/MS Condition E: ret time 1.09 min; m/e=417 (M+H)$^+$. LC/MS Condition F: ret time 1.14 min; m/e=417 (M+H)$^+$. $^1$H NMR (500 MHz, DMSO-d$_6$) δ 7.19 (t, J=7.9 Hz, 2H), 6.95 (d, J=8.1 Hz, 2H), 6.65 (d, J=7.3 Hz, 2H), 4.15-4.02 (m, 4H), 3.59 (t, J=5.3 Hz, 4H), 2.99 (br t, J=7.3 Hz, 4H), 2.91-2.86 (m, 4H), 2.10-1.99 (m, 4H), 1.84 (s, 6H)

Example 2028: 3,3'-((2,2'-dimethyl-[1,1'-biphenyl]-3,3'-diyl)bis(oxy))bis(N-(2-(pyridin-4-yl)ethyl)propan-1-amine)

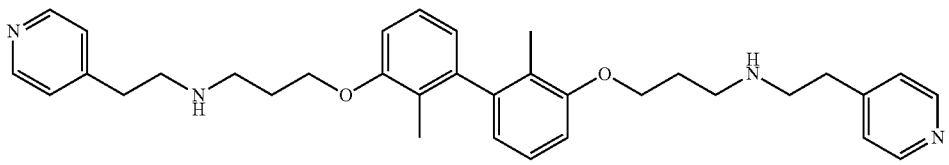 [SMILES: Cc1c(OCCCNCCc2ccncc2)cccc1-c1cccc(OCCCNCCc2ccncc2)c1C]

To a reaction vial containing 3,3'-bis(3-bromopropoxy)-2,2'-dimethyl-1,1'-biphenyl (20 mg, 0.044 mmol) was added 4-(2-aminoethyl)pyridine (106 μl, 0.878 mmol), MeOH (0.5 mL) and N,N-diisopropylethylamine (31 μL, 0.177 mmol). The reaction mixture was briefly flushed with N$_2$, securely capped, sonicated for 10 sec, and placed in a 65° C. sand bath with shaking for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 22 minutes, then a 5-minute hold at 100% B; Flow: 20 mL/min to give the pure title compound: (22.1 mg, 85%). LC/MS Condition E: ret time 1.30 min; m/e=539 (M+H)$^+$. LC/MS Condition F: ret time 1.05 min; m/e=539 (M+H)$^+$. $^1$H NMR (500 MHz, DMSO-d$_6$) δ 8.45 (br d, J=5.1 Hz, 4H), 7.26 (d, J=5.1 Hz, 4H), 7.19 (t, J=7.9 Hz, 2H), 6.93 (d, J=8.1 Hz, 2H), 6.64 (d, J=7.7 Hz, 2H), 4.06 (q, J=6.4 Hz, 4H), 3.00-2.91 (m, 4H), 2.90-2.85 (m, 4H), 2.80 (br t, J=7.5 Hz, 4H), 2.02-1.92 (m, 4H), 1.82 (s, 6H)

Example 2029: 4,4'-((((2,2'-dimethyl-[1,1'-biphenyl]-3,3'-diyl)bis(oxy))bis(propane-3,1-diyl))bis(azanediyl))bis(2-methylbutane-2,3-diol)

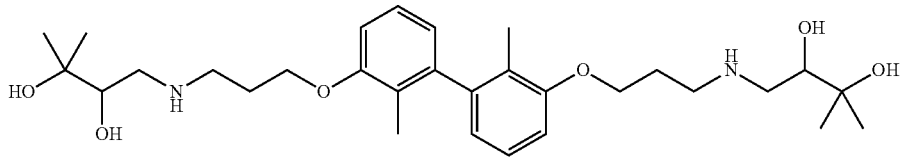 [SMILES: Cc1c(OCCCNCC(O)C(C)(C)O)cccc1-c1cccc(OCCCNCC(O)C(C)(C)O)c1C]

To a reaction vial containing 3,3'-bis(3-bromopropoxy)-2,2'-dimethyl-1,1'-biphenyl (20 mg, 0.044 mmol) was added 1-amino-3-methyl-2,3-butanediol (105 mg, 0.881 mmol), MeOH (1.5 mL) and N,N-diisopropylethylamine (25 µL, 0.143 mmol). The reaction mixture was briefly flushed with N₂, securely capped, sonicated for 10 sec, and placed in a 65° C. sand bath with shaking for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound as a mixture of diastereomers: (22.1 mg, 85%). LC/MS Condition E: ret time 1.11 min; m/e=533 (M+H)⁺. LC/MS Condition F: ret time 1.43 min; m/e=533 (M+H)⁺.

Example 2030: 3,3'-((((2,2'-dimethyl-[1,1'-biphenyl]-3,3'-diyl)bis(oxy))bis(propane-3,1-diyl))bis(methylazanediyl))bis(propan-1-ol)

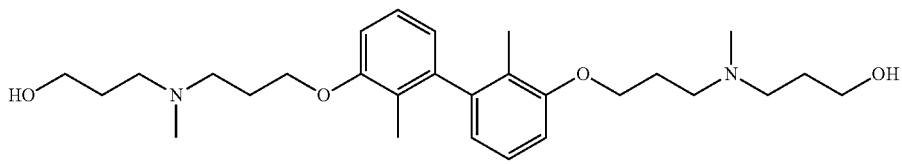 [SMILES: Cc1c(OCCCN(C)CCCO)cccc1-c1cccc(OCCCN(C)CCCO)c1C]

To a reaction vial containing 3,3'-bis(3-bromopropoxy)-2,2'-dimethyl-1,1'-biphenyl (20 mg, 0.044 mmol) was added 3-(methylamino)-1-propanol (80 mg, 0.898 mmol), MeOH (1.5 mL) and N,N-diisopropylethylamine (25 µL, 0.143 mmol). The reaction mixture was briefly flushed with N₂, securely capped, sonicated for 10 sec, and placed in a 65° C. sand bath with shaking for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (20.9 mg, 100%). LC/MS Condition E: ret time 1.15 min; m/e=473 (M+H)⁺. LC/MS Condition F: ret time 1.18 min; m/e=473 (M+H)⁺.

Example 2031: (2S,2'S)-3,3'-((((2,2'-dimethyl-[1,1'-biphenyl]-3,3'-diyl)bis(oxy))bis(propane-3,1-diyl))bis(methylazanediyl))bis(propane-1,2-diol)

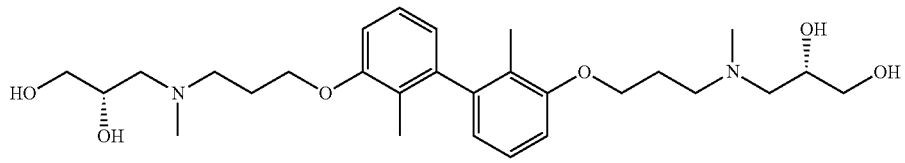 [SMILES: Cc1c(OCCCN(C)C[C@H](O)CO)cccc1-c1cccc(OCCCN(C)C[C@H](O)CO)c1C]

To a reaction vial containing 3,3'-bis(3-bromopropoxy)-2,2'-dimethyl-1,1'-biphenyl (20 mg, 0.044 mmol) was added (S)-3-(methylamino)propane-1,2-diol (100 mg, 0.951 mmol), MeOH (1.5 mL) and N,N-diisopropylethylamine (25 µL, 0.143 mmol). The reaction mixture was briefly flushed with N₂, securely capped, sonicated for 10 sec, and placed in a 65° C. sand bath with shaking for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min to give the pure title compound: (22.5 mg, 100%). LC/MS Condition E: ret time 1.21 min; m/e=505 (M+H)⁺. LC/MS Condition F: ret time 1.03 min; m/e=505 (M+H)⁺.

Example 2032: (R)-1-(3-((3'-(3-((2-(dimethylamino)ethyl)(methyl)amino)propoxy)-2,2'-dimethyl-[1,1'-biphenyl]-3-yl)oxy)propyl)pyrrolidin-3-ol

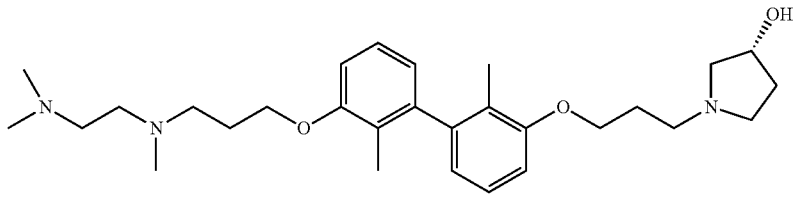 [SMILES: Cc1c(OCCCN(C)CCN(C)C)cccc1-c1cccc(OCCCN2CC[C@@H](O)C2)c1C]

To a reaction vial containing N,N,N'-trimethylethylenediamine (40 μL, 0.313 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 μL, 0.172 mmol). The reaction mixture was briefly flushed with $N_2$, securely capped, sonicated for 10 sec, and placed in a 65° C. sand bath with shaking for 18-36 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to give the pure title compound: (17.5 mg, 84%). LC/MS Condition E: ret time 1.12 min; m/e=484 (M+H)⁺. LC/MS Condition F: ret time 1.06 min; m/e=484 (M+H)⁺.

Example 2033: (3S,4R)-4-(hydroxymethyl)-1-(3-((3'-(3-((R)-3-hydroxypyrrolidin-1-yl)propoxy)-2,2'-dimethyl-[1,1'-biphenyl]-3-yl)oxy)propyl)piperidin-3-ol

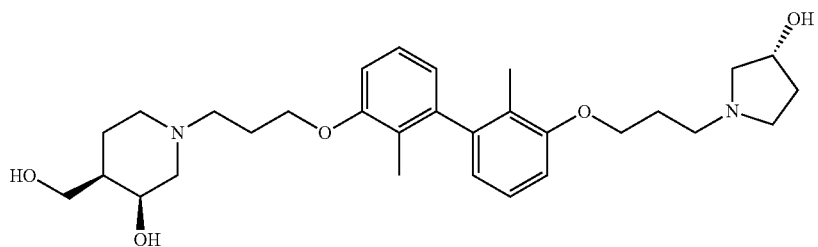 [SMILES: Cc1c(OCCCN2CC[C@@H](O)C2)cccc1-c1cccc(OCCCN2CC[C@H](CO)[C@H](O)C2)c1C]

To a reaction vial containing (3S,4R)-4-(hydroxymethyl)piperidin-3-ol, HCl (58 mg, 0.346 mmol) was added a solution of (R)-1-(3-((3'-(3-bromopropoxy)-2,2'-dimethyl-[1,1'-biphenyl]-3-yl)oxy)propyl)pyrrolidin-3-ol (25 mg, 0.054 mmol) dissolved in methanol (2.0 mL) and N,N-diisopropylethylamine (80 μL, 0.458 mmol). The reaction mixture was briefly flushed with $N_2$, securely capped, sonicated for 10 sec, and placed in a 65° C. sand bath with shaking for 18-48 h. The crude material was purified via preparative LC/MS with the following conditions: Column: XBridge C18, 19×mm, 5-m particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min to give the pure title compound: (20.2 mg, 50%). LC/MS Condition E: ret time 1.07 min; m/e=513 (M+H)⁺. LC/MS Condition F: ret time 1.12 min; m/e=513 (M+H)⁺.

Example 2034: (R)-1-(3-((3'-(3-((2-hydroxyethyl)(methyl)amino)propoxy)-2,2'-dimethyl-[1,1'-biphenyl]-3-yl)oxy)propyl)pyrrolidin-3-ol

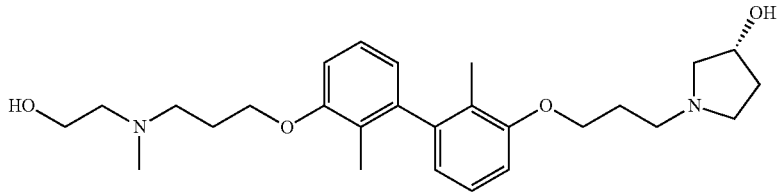 [SMILES: Cc1c(OCCCN(C)CCO)cccc1-c1cccc(OCCCN2CC[C@@H](O)C2)c1C]

To a reaction vial containing 2-(methylamino)ethanol (35 µL, 0.436 mmol) was added a solution of (R)-1-(3-((3'-(3-bromopropoxy)-2,2'-dimethyl-[1,1'-biphenyl]-3-yl)oxy)propyl)pyrrolidin-3-ol (29 mg, 0.063 mmol) dissolved in methanol (2.0 mL). The reaction mixture was briefly flushed with $N_2$, securely capped, sonicated for 10 sec, and placed in a 70° C. sand bath with shaking for 24 h. The crude material was purified via preparative LC/MS with the following conditions: Column: XBridge C18, 19×mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min, to give the pure title compound as a TFA salt: (17.3 mg, 40%). LC/MS Condition E: ret time 1.08 min; m/e=457 (M+H)⁺. LC/MS Condition F: ret time 1.13 min; m/e=457 (M+H)⁺.

Example 2035: (R)-1-(3-((2,2'-dimethyl-3'-(3-((2-(pyridin-4-yl)ethyl)amino)propoxy)-[1,1'-biphenyl]-3-yl)oxy)propyl)pyrrolidin-3-ol

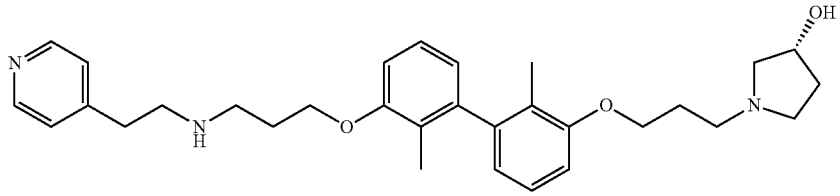 [SMILES: Cc1c(OCCCNCCc2ccncc2)cccc1-c1cccc(OCCCN2CC[C@@H](O)C2)c1C]

To a reaction vial containing 2-(pyridin-4-yl)ethanamine (64.4 mg, 0.527 mmol) was added a solution of (R)-1-(3-((3'-(3-bromopropoxy)-2,2'-dimethyl-[1,1'-biphenyl]-3-yl)oxy)propyl)pyrrolidin-3-ol (29 mg, 0.063 mmol) dissolved in methanol (2.0 mL). The reaction mixture was briefly flushed with $N_2$, securely capped, sonicated for 10 sec, and placed in a 70° C. sand bath with shaking for 72 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min, to give the pure title compound as a TFA salt: (4.9 mg, 10%). LC/MS Condition E: ret time 1.30 min; m/e=504 (M+H)⁺. LC/MS Condition F: ret time 1.12 min; m/e=504 (M+H)⁺.

Example 2036: (R)-4-(3-((3'-(3-(3-hydroxypyrrolidin-1-yl)propoxy)-2,2'-dimethyl-[1,1'-biphenyl]-3-yl)oxy)propyl)-1-methylpiperazin-2-one

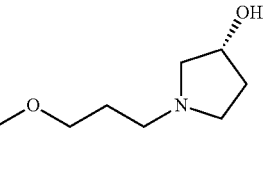

To a reaction vial containing 1-methylpiperazin-2-one, HCl (47.2 mg, 0.313 mmol) was added a solution of (R)-1-(3-((3'-(3-bromopropoxy)-2,2'-dimethyl-[1,1'-biphenyl]-3-yl)oxy)propyl)pyrrolidin-3-ol (25 mg, 0.054 mmol) dissolved in methanol (1 mL). N,N-diisopropylethylamine (80 µL, 0.458 mmol) was added and the reaction mixture was briefly flushed with $N_2$, securely capped, sonicated for 10 sec, and placed in a 70° C. sand bath with shaking for 72 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min, to give the pure title compound as a TFA salt: (4.2 mg, 11%). LC/MS Condition E: ret time 1.36 min; m/e=496 (M+H)⁺. LC/MS Condition F: ret time 1.13 min; m/e=496 (M+H)⁺.

Example 2037: (S)-2-((3-((3'-(3-((R)-3-hydroxypyrrolidin-1-yl)propoxy)-2,2'-dimethyl-[1,1'-biphenyl]-3-yl)oxy)propyl)amino)-3-(pyridin-4-yl)propanoic acid

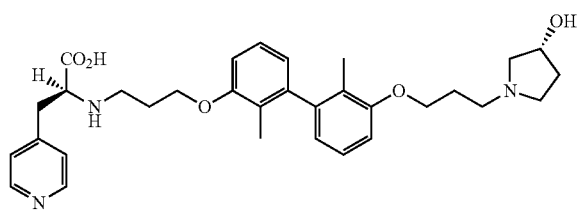 [SMILES: Cc1c(OCCCN[C@@H](Cc2ccncc2)C(=O)O)cccc1-c1cccc(OCCCN2CC[C@@H](O)C2)c1C]

To a reaction vial containing (S)-2-amino-3-(pyridin-4-yl)propanoic acid (65 mg, 0.391 mmol) in MeOH (1.5 mL) was added a solution of (R)-1-(3-((3'-(3-bromopropoxy)-2,2'-dimethyl-[1,1'-biphenyl]-3-yl)oxy)propyl)pyrrolidin-3-ol (29 mg, 0.063 mmol) dissolved in methanol (2.0 mL). N,N-diisopropylethylamine (90 µL, 0.515 mmol) was added followed by DMF (0.2 mL) and water (0.15 mL). The reaction mixture was briefly flushed with $N_2$, securely capped, sonicated for 10 sec, and placed in a 70° C. sand bath with shaking for 72 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min, to give the pure title compound as a TFA salt: (4.3 mg, 8%). LC/MS Condition E: ret time 1.13 min; m/e=548 (M+H)+. LC/MS Condition F: ret time 1.18 min; m/e=548 (M+H)+.

Example 2038: (R)-3-((3-((3'-(3-(3-hydroxypyrrolidin-1-yl)propoxy)-2,2'-dimethyl-[1,1'-biphenyl]-3-yl)oxy)propyl)amino)propanamide To a reaction vial containing 3-aminopropanamide, HCl (55 mg, 0.442 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (90 µL, 0.515 mmol). The reaction mixture was briefly flushed with $N_2$, securely capped, sonicated for 10 sec, and placed in a 65° C. sand bath with shaking for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. to give the pure title compound: (9.7 mg, 48%). LC/MS Condition E: ret time 1.11 min; m/e=470 (M+H)+. LC/MS Condition F: ret time 1.124 min; m/e=470 (M+H)+.

Example 2039: (2S,4R)-4-hydroxy-1-(3-((3'-(3-((R)-3-hydroxypyrrolidin-1-yl)propoxy)-2,2'-dimethyl-[1,1'-biphenyl]-3-yl)oxy)propyl)pyrrolidine-2-carboxylic acid

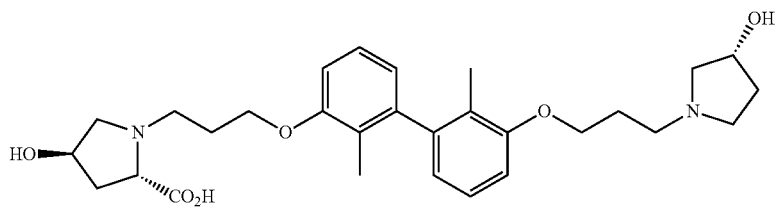

To a reaction vial containing (2S,4R)-4-hydroxypyrrolidine-2-carboxylic acid (35 mg, 0.267 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (65 µL, 0.372 mmol). Then DMF (0.2 mL) and water (0.18 mL) were added to the mixture. The reaction mixture was briefly flushed with $N_2$, securely capped, sonicated for 10 sec, and placed in a 65° C. sand bath with shaking for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. to give the pure title compound: (7.4 mg, 33%). LC/MS Condition E: ret time 1.11 min; m/e=513 (M+H)+. LC/MS Condition F: ret time 1.15 min; m/e=513 (M+H)+.

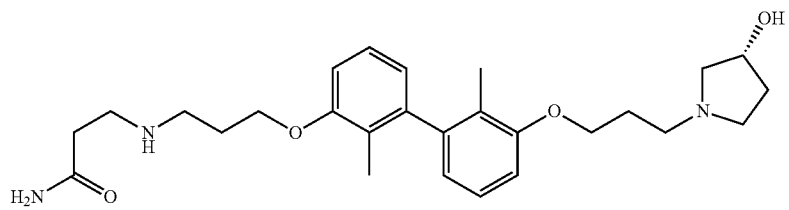 [SMILES: Cc1c(OCCCNCCC(N)=O)cccc1-c1cccc(OCCCN2CC[C@@H](O)C2)c1C]

Example 2040: (3R)-1-(3-((3'-(3-((2-hydroxy-2-(pyridin-3-yl)ethyl)amino)propoxy)-2,2'-dimethyl-[1,1'-biphenyl]-3-yl)oxy)propyl)pyrrolidin-3-ol

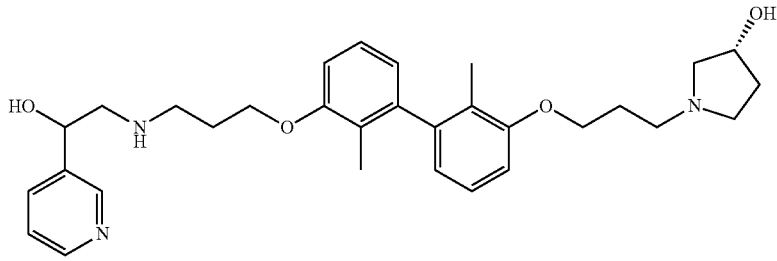 [SMILES: Cc1c(OCCCNCC(O)c2cccnc2)cccc1-c1cccc(OCCCN2CC[C@@H](O)C2)c1C]

To a reaction vial containing 2-amino-1-(pyridin-3-yl)ethanol, oxalic acid salt (70 mg, 0.307 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (120 µL, 0.687 mmol). The reaction mixture was briefly flushed with N₂, securely capped, sonicated for 10 sec, and placed in a 65° C. sand bath with shaking for 24 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-40% B over 20 minutes, then a 5-minute hold at 100% B; Flow: 20 mL/min to give the pure title compound as a TFA salt as a mixture of epimers: (4.1 mg, 10%). LC/MS Condition E: ret time 1.21 min; m/e=520 (M+H)⁺.
LC/MS Condition F: ret time 1.09 min; m/e=520 (M+H)⁺.

Example 2041: (R)-1-(3-((2,2'-dimethyl-3'-(3-(phenethylamino)propoxy)-[1,1'-biphenyl]-3-yl)oxy)propyl)pyrrolidin-3-ol

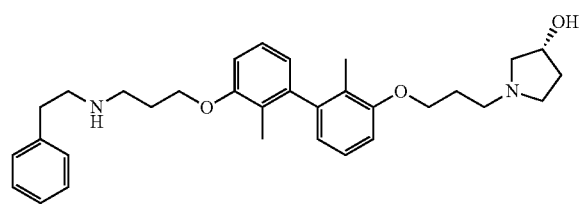 [SMILES: Cc1c(OCCCNCCc2ccccc2)cccc1-c1cccc(OCCCN2CC[C@@H](O)C2)c1C]

To a reaction vial containing 2-phenylethanamine (65 mg, 0.536 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (30 µL, 0.172 mmol). The reaction mixture was briefly flushed with N₂, securely capped, sonicated for 10 sec, and placed in a 65° C. sand bath with shaking for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. to give the pure title compound: (20.7 mg, 93%). LC/MS Condition E: ret time 1.52 min; m/e=503 (M+H)⁺.
LC/MS Condition F: ret time 1.37 min; m/e=503 (M+H)⁺.

Example 2042: (R)-1-(3-((3'-(3-((3-hydroxypropyl)amino)propoxy)-2,2'-dimethyl-[1,1'-biphenyl]-3-yl)oxy)propyl)pyrrolidin-3-ol

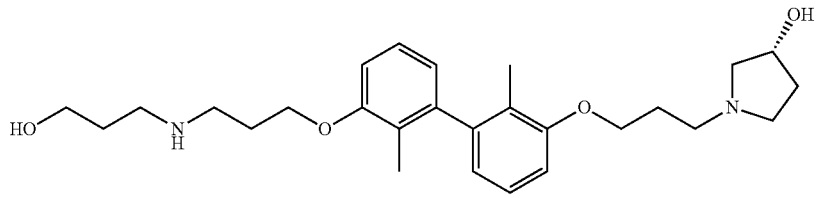 [SMILES: Cc1c(OCCCNCCCO)cccc1-c1cccc(OCCCN2CC[C@@H](O)C2)c1C]

A mixture of 3-aminopropan-1-ol (40 mg, 0.533 mmol), (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (65 µL, 0.372 mmol) was heated at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. to give the pure title compound: (19.6 mg, 99%). LC/MS Condition E: ret time 1.11 min; m/e=457 (M+H)⁺. LC/MS Condition F: ret time 1.16 min; m/e=457 (M+H)⁺.

Example 2043: (R)-1-(3-((2,2'-dimethyl-3'-(3-((2-(1-methyl-1H-imidazol-4-yl)ethyl)amino)propoxy)-[1,1'-biphenyl]-3-yl)oxy)propyl)pyrrolidin-3-ol

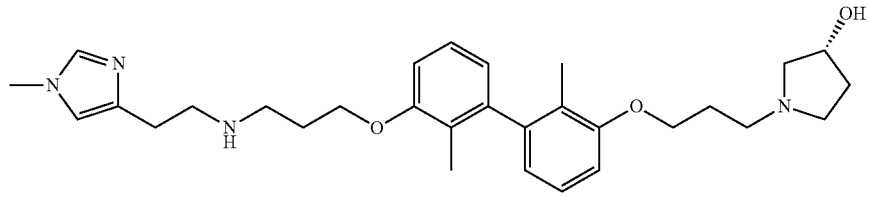 [SMILES: Cc1c(OCCCNCCc2cn(C)cn2)cccc1-c1cccc(OCCCN2CC[C@@H](O)C2)c1C]

A mixture of 2-(1-methyl-1H-imidazol-4-yl)ethanamine (62 mg, 0.495 mmol), and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (60 μL, 0.344 mmol) was heated at 70° C. for 24 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. to give the pure title compound: (20.4 mg, 92%). LC/MS Condition E: ret time 1.16 min; m/e=507 (M+H)$^+$. LC/MS Condition F: ret time 1.08 min; m/e=507 (M+H)$^+$.

Example 2044: (R)-1-(3-((2,2'-dimethyl-3'-(3-(((1-methylpiperidin-4-yl)methyl)amino)propoxy)-[1,1'-biphenyl]-3-yl)oxy)propyl)pyrrolidin-3-ol

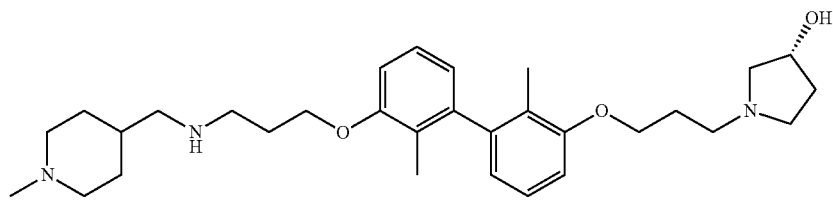 [SMILES: Cc1c(OCCCNCC2CCN(C)CC2)cccc1-c1cccc(OCCCN2CC[C@@H](O)C2)c1C]

A mixture of (1-methylpiperidin-4-yl)methanamine (53.3 mg, 0.416 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (30 μL, 0.172 mmol) was heated at 70° C. for 24 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. to give the pure title compound: (15.8 mg, 70%). LC/MS Condition E: ret time 1.08 min; m/e=510 (M+H)$^+$. LC/MS Condition F: ret time 1.08 min; m/e=510 (M+H)$^+$.

Example 2045: (S)-2-hydroxy-3-((3-((3'-(3-((R)-3-hydroxypyrrolidin-1-yl)propoxy)-2,2'-dimethyl-[1,1'-biphenyl]-3-yl)oxy)propyl)amino)propanoic acid

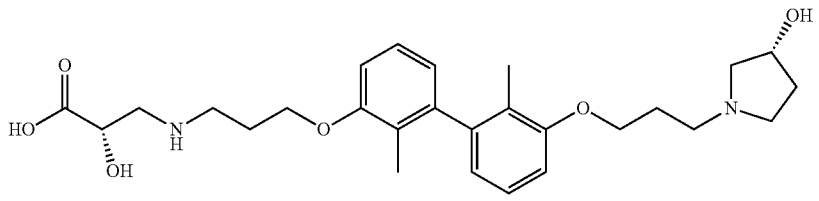 [SMILES: Cc1c(OCCCNC[C@H](O)C(=O)O)cccc1-c1cccc(OCCCN2CC[C@@H](O)C2)c1C]

A mixture of L-Isoserine (50 mg, 0.48 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL), DMF (0.1 mL) and N,N-diisopropylethylamine (90 µL, 0.515 mmol) was heated at 60-70° C. for 48 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. to give the pure title compound: (15.6 mg, 73%). LC/MS Condition E: ret time 1.09 min; m/e=487 (M+H)$^+$. LC/MS Condition F: ret time 1.14 min; m/e=487 (M+H)$^+$.

Example 2046: (R)-1-(3-((3'-(3-((3-hydroxy-2,2-dimethylpropyl)amino)propoxy)-2,2'-dimethyl-[1,1'-biphenyl]-3-yl)oxy)propyl)pyrrolidin-3-ol

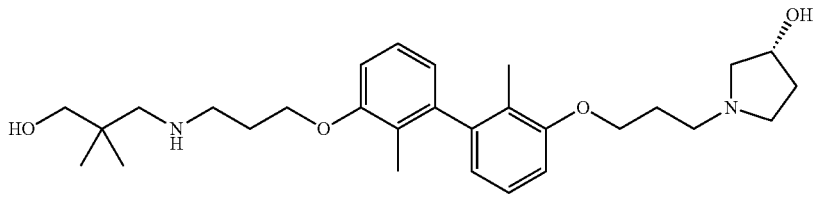 [SMILES: Cc1c(OCCCNCC(C)(C)CO)cccc1-c1cccc(OCCCN2CC[C@@H](O)C2)c1C]

A mixture of 3-amino-2,2-dimethylpropan-1-ol (55 mg, 0.533 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (50 µL, 0.286 mmol) was heated at 70° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. to give the pure title compound: (23 mg, 97%). $^1$H NMR (500 MHz, DMSO-d$_6$) δ 7.26-7.13 (m, 2H), 6.93 (dd, J=8.1, 4.4 Hz, 2H), 6.67-6.60 (m, 2H), 4.21-4.17 (m, 1H), 4.11-4.00 (m, 4H), 3.20 (s, 2H), 2.84-2.68 (m, 3H), 2.63-2.54 (m, 5H), 2.47-2.43 (m, 1H), 2.37-2.33 (m, 1H), 2.03-1.88 (m, 5H), 1.83 (s, 3H), 1.82 (s, 3H), 1.59-1.50 (m, 1H), 0.83 (s, 6H). LC/MS Condition E: ret time 1.21 min; m/e=485 (M+H)$^+$. LC/MS Condition F: ret time 1.22 min; m/e=485 (M+H)$^+$.

Example 2047: (3R)-1-(3-((3'-(3-((2-hydroxy-1-(pyridin-4-yl)ethyl)amino)propoxy)-2,2'-dimethyl-[1,1'-biphenyl]-3-yl)oxy)propyl)pyrrolidin-3-ol

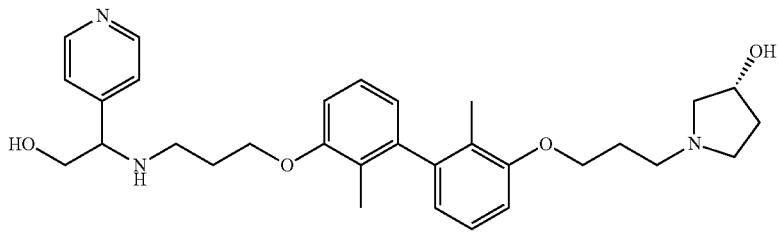 [SMILES: Cc1c(OCCCNC(CO)c2ccncc2)cccc1-c1cccc(OCCCN2CC[C@@H](O)C2)c1C]

A mixture of 2-amino-2-(pyridin-4-yl)ethanol, 2 HCl (77.7 mg, 0.368 mmol) and (R)-1-(3-((3'-(3-bromopropoxy)-2,2'-dimethyl-[1,1'-biphenyl]-3-yl)oxy)propyl) pyrrolidin-3-ol (20 mg, 0.043 mmol) in methanol (1.0 mL) and N,N-diisopropylethylamine (130 µL, 0.744 mmol) was heated at 65-70° C. for 48 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. to give the pure title compound: (5.4 mg, 23%). LC/MS Condition E: ret time 1.44 min; m/e=520 (M+H)$^+$. LC/MS Condition F: ret time 1.05 min; m/e=520 (M+H)$^+$.

Example 2048: (R)—N-(2-((3-((3'-(3-(3-hydroxypyrrolidin-1-yl)propoxy)-2,2'-dimethyl-[1,1'-biphenyl]-3-yl)oxy)propyl)amino)ethyl)acetamide

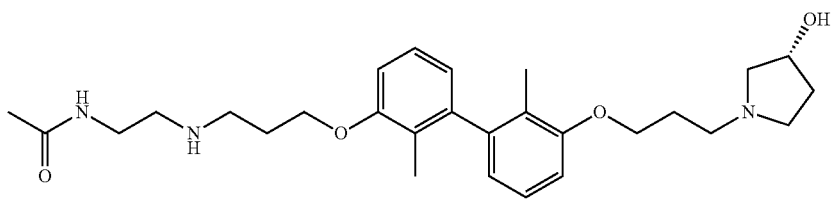 [SMILES: CC(=O)NCCNCCCOc1cccc(-c2cccc(OCCCN3CC[C@@H](O)C3)c2C)c1C]

A mixture of N-(2-aminoethyl)acetamide (56 mg, 0.548 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (40 µL, 0.229 mmol) was heated at 70° C. for 48 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min to give the pure title compound as a TFA salt: (26.1 mg, 85%). LC/MS Condition E: ret time 1.11 min; m/e=484 (M+H)$^+$; LC/MS Condition F: ret time 1.13 min; m/e=484 (M+H)$^+$.

Example 2049: (R)-1-(3-((2,2'-dimethyl-3'-(3-(methyl(pyridin-3-ylmethyl)amino)propoxy)-[1,1'-biphenyl]-3-yl)oxy)propyl)pyrrolidin-3-ol

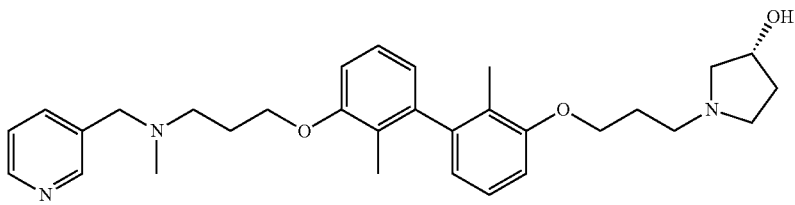 [SMILES: Cc1c(OCCCN(C)Cc2cccnc2)cccc1-c1cccc(OCCCN2CC[C@@H](O)C2)c1C]

A mixture of N-methyl-1-(pyridin-3-yl)methanamine (38 mg, 0.311 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (30 μL, 0.172 mmol) was heated at 70° C. for 48 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min to give the pure title compound as a TFA salt: (15.8 mg, 41.4%). LC/MS Condition E: ret time 1.59 min; m/e=504 (M+H)$^+$. LC/MS Condition F: ret time 1.10 min; m/e=504 (M+H)$^+$.

Example 2050: (R)-1-(3-((2,2'-dimethyl-3'-(3-((pyridin-3-ylmethyl)amino)propoxy)-[1,1'-biphenyl]-3-yl)oxy)propyl)pyrrolidin-3-ol

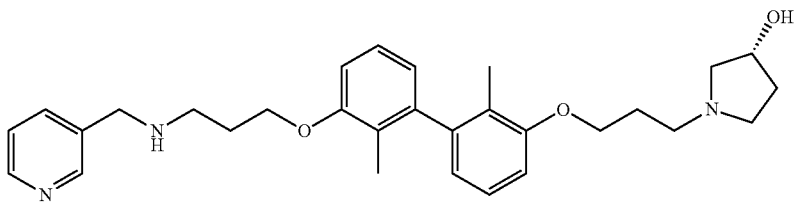 [SMILES: Cc1c(OCCCNCc2cccnc2)cccc1-c1cccc(OCCCN2CC[C@@H](O)C2)c1C]

A mixture of pyridin-3-ylmethanamine (80 mg, 0.740 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (30 μL, 0.172 mmol) was heated at 65-70° C. for 48 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (11.9 mg, 55%). LC/MS Condition E: ret time 1.29 min; m/e=490 (M+H)$^+$. LC/MS Condition F: ret time 1.10 min; m/e=490 (M+H)$^+$.

Example 2051: (2S,4R)-4-hydroxy-1-(3-((3'-(3-((R)-3-hydroxypyrrolidin-1-yl)propoxy)-2,2'-dimethyl-[1,1'-biphenyl]-3-yl)oxy)propyl)pyrrolidine-2-carboxylic acid

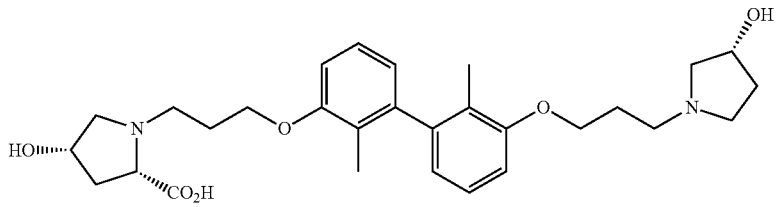 [SMILES: Cc1c(OCCCN2CC[C@@H](O)C2)cccc1-c1cccc(OCCCN2C[C@@H](O)C[C@H]2C(=O)O)c1C]

To a reaction vial containing (2S,4S)-4-hydroxypyrrolidine-2-carboxylic acid (35 mg, 0.267 mmol) was added a solution of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) dissolved in methanol (1.0 mL) and N,N-diisopropylethylamine (65 μL, 0.372 mmol). Then DMF (0.2 mL) and water (0.18 mL) were added to the mixture. The reaction mixture was briefly flushed with $N_2$, securely capped, sonicated for 10 sec, and placed in a 65° C. sand bath with shaking for 24 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. to give the pure title compound: (21.7 mg, 97%). LC/MS Condition E: ret time 1.11 min; m/e=513 $(M+H)^+$; LC/MS Condition F: ret time 1.15 min; m/e=513 $(M+H)^+$.

Example 2052: (R)-3-((3-((3'-(3-((R)-3-hydroxypyrrolidin-1-yl)propoxy)-2,2'-dimethyl-[1,1'-biphenyl]-3-yl)oxy)propyl)amino)propane-1,2-diol

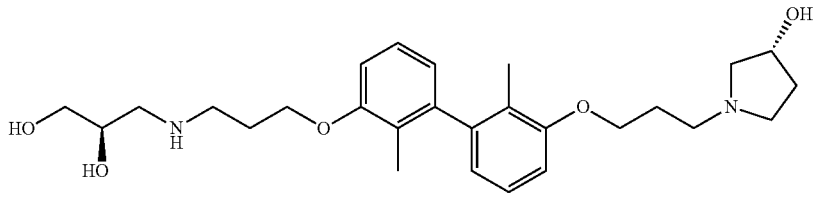 [SMILES: Cc1c(OCCCNC[C@@H](O)CO)cccc1-c1cccc(OCCCN2CC[C@@H](O)C2)c1C]

A mixture of (R)-3-aminopropane-1,2-diol, HCl (62.4 mg, 0.489 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (170 μL, 0.973 mmol) was heated at 65-70° C. for 48 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (20.2 mg, 98%). $^1H$ NMR (500 MHz, DMSO-$d_6$) δ 7.18 (td, J=7.9, 3.3 Hz, 2H), 6.94 (dd, J=7.9, 5.3 Hz, 2H), 6.64 (dd, J=7.3, 5.1 Hz, 2H), 4.21-4.17 (m, 1H), 4.12-3.99 (m, 4H), 3.53-3.34 (m, 6H), 2.96-2.85 (m, 2H), 2.77-2.66 (m, 2H), 2.64-2.56 (m, 3H), 2.49-2.44 (m, 1H), 2.37-2.33 (m, 1H), 2.03-1.93 (m, 3H), 1.83 (s, 3H), 1.82 (s, 3H), 1.57-1.52 (m, 1H). LC/MS Condition E: ret time 1.09 min; m/e=473 $(M+H)^+$. LC/MS Condition F: ret time 1.12 min; m/e=473 $(M+H)^+$.

Example 2053: (R)-1-(3-((3'-(3-((2-hydroxyethyl)(propyl)amino)propoxy)-2,2'-dimethyl-[1,1'-biphenyl]-3-yl)oxy)propyl)pyrrolidin-3-ol

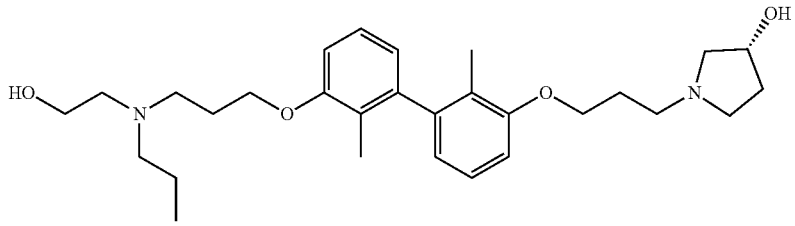 [SMILES: CCCN(CCO)CCCOc1cccc(-c2cccc(OCCCN3CC[C@@H](O)C3)c2C)c1C]

A mixture of 2-(propylamino)ethanol (41 mg, 0.397 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (40 μL, 0.229 mmol) was heated at 65-70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the pure title compound: (12.5 mg, 59%). LC/MS Condition E: ret time 1.27 min; m/e=485 (M+H)+; LC/MS Condition F: ret time 1.22 min; m/e=485 (M+H)+.

Example 2054: (R)-3-((3-((3'-(3-(3-hydroxypyrrolidin-1-yl)propoxy)-2,2'-dimethyl-[1,1'-biphenyl]-3-yl)oxy)propyl)(methyl)amino)propanamide

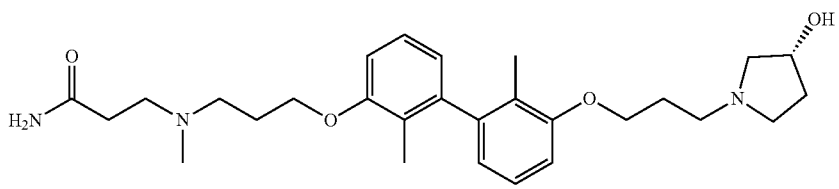 [SMILES: Cc1c(OCCCN(C)CCC(N)=O)cccc1-c1cccc(OCCCN2CC[C@@H](O)C2)c1C]

A mixture of 2-(propylamino)ethanol (41 mg, 0.397 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (40 μL, 0.229 mmol) was heated at 65-70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (10 mg, 47%). LC/MS Condition E: ret time 1.18 min; m/e=484 (M+H)+; LC/MS Condition F: ret time 1.12 min; m/e=484 (M+H)+.

Example 2055: (R)-1-(3-((3'-(3-(((R)-1-hydroxy-3-methylbutan-2-yl)amino)propoxy)-2,2'-dimethyl-[1,1'-biphenyl]-3-yl)oxy)propyl)pyrrolidin-3-ol

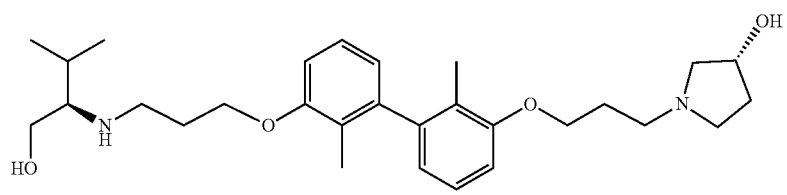 [SMILES: Cc1c(OCCCN[C@@H](CO)C(C)C)cccc1-c1cccc(OCCCN2CC[C@@H](O)C2)c1C]

A mixture of (R)-2-amino-3-methylbutan-1-ol (50 mg, 0.485 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (40 μL, 0.229 mmol) was heated at 65-70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (14.4 mg, 62%). LC/MS Condition E: ret time 1.24 min; m/e=485 (M+H)+; LC/MS Condition F: ret time 1.23 min; m/e=485 (M+H)+.

Example 2056: (R)-1-(3-((3'-(3-(bis(pyridin-2-ylmethyl)amino)propoxy)-2,2'-dimethyl-[1,1'-biphenyl]-3-yl)oxy)propyl)pyrrolidin-3-ol

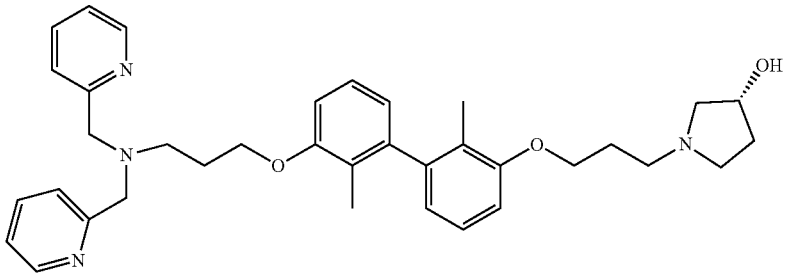 [SMILES: Cc1c(OCCCN(Cc2ccccn2)Cc2ccccn2)cccc1-c1cccc(OCCCN2CC[C@@H](O)C2)c1C]

A mixture of bis(pyridin-2-ylmethyl)amine (52 mg, 0.261 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (40 μL, 0.229 mmol) was heated at 65-70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min to give the pure title compound: (18.4 mg, 66%). LC/MS Condition E: ret time 1.78 min; m/e=581 (M+H)+; LC/MS Condition F: ret time 1.28 min; m/e=581 (M+H)+.

Example 2057: (R)-1-(3-((3'-(3-(((S)-2-hydroxy-1-phenylethyl)amino)propoxy)-2,2'-dimethyl-[1,1'-biphenyl]-3-yl)oxy)propyl)pyrrolidin-3-ol

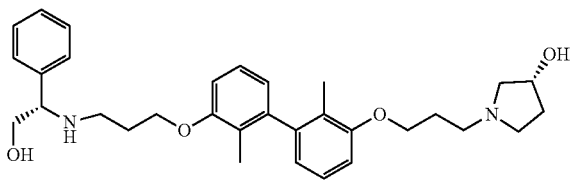 [SMILES: Cc1c(OCCCN[C@H](CO)c2ccccc2)cccc1-c1cccc(OCCCN2CC[C@@H](O)C2)c1C]

A mixture of (S)-2-amino-2-phenylethanol (55 mg, 0.401 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1.0 mL) and N,N-diisopropylethylamine (40 μL, 0.229 mmol) was heated at 70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min to give the pure title compound: (8.3 mg, 34%). LC/MS Condition E: ret time 1.46 min; m/e=519 (M+H)+; LC/MS Condition F: ret time 1.29 min; m/e=519 (M+H)+.

Example 2058: (R)-1-(3-((3'-(3-(((S)-1-hydroxy-3-methylbutan-2-yl)amino)propoxy)-2,2'-dimethyl-[1,1'-biphenyl]-3-yl)oxy)propyl)pyrrolidin-3-ol

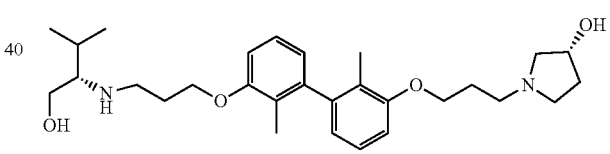

A mixture of (S)-2-amino-3-methylbutan-1-ol (45 mg, 0.436 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (0.8 mL) and N,N-diisopropylethylamine (40 μL, 0.229 mmol) was heated at 70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound: (4.7 mg, 91%). LC/MS Condition E: ret time 1.25 min; m/e=485 (M+H)+; LC/MS Condition F: ret time 1.24 min; m/e=485 (M+H)+.

Example 2059: 3-((3-((3'-(3-((R)-3-hydroxypyrrolidin-1-yl)propoxy)-2,2'-dimethyl-[1,1'-biphenyl]-3-yl)oxy)propyl)amino)propane-1,2-diol

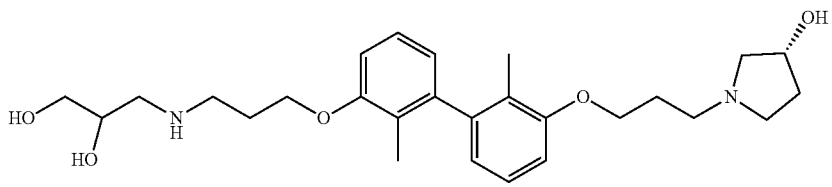 [SMILES: Cc1c(OCCCNCC(O)CO)cccc1-c1cccc(OCCCN2CC[C@@H](O)C2)c1C]

A mixture of 3-aminopropane-1,2-diol (61 mg, 0.670 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (70 µL, 0.401 mmol) was heated at 60-70° C. for 48 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound as a mixture of diastereomers: (19.2 mg, 93%). LC/MS Condition E: ret time 1.09 min; m/e=473 (M+H)$^+$. LC/MS Condition F: ret time 1.11 min; m/e=473 (M+H)$^+$.

Example 2060: (R)-1-(3-((3'-(3-((2-(4-chloro-1H-pyrazol-1-yl)ethyl)amino)propoxy)-2,2'-dimethyl-[1,1'-biphenyl]-3-yl)oxy)propyl)pyrrolidin-3-ol

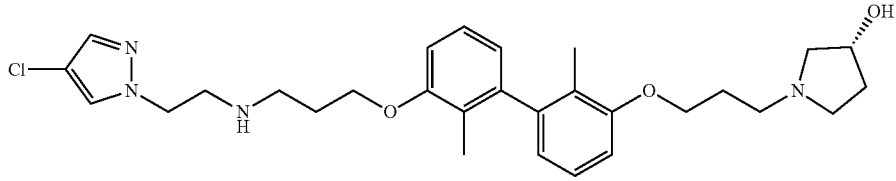 [SMILES: Cc1c(OCCCNCCn2cc(Cl)cn2)cccc1-c1cccc(OCCCN2CC[C@@H](O)C2)c1C]

A mixture of 2-(4-chloro-1H-pyrazol-1-yl)ethanamine, HCl (75 mg, 0.412 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (100 µL, 0.573 mmol) was heated at 70° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min to give the pure title compound: (11 mg, 46%). $^1$H NMR (500 MHz, DMSO-d$_6$) δ 7.96 (s, 1H), 7.51 (s, 1H), 7.18 (t, J=7.9 Hz, 2H), 6.93 (t, J=7.5 Hz, 2H), 6.64 (d, J=7.3 Hz, 2H), 4.27-4.24 (m, 1H), 4.17 (t, J=6.1 Hz, 2H), 4.09-3.99 (m, 4H), 3.43-3.36 (m, 2H), 2.98 (t, J=6.2 Hz, 2H), 2.93-2.65 (m, 7H), 2.62-2.57 (m, 1H), 2.07-1.94 (m, 3H), 1.93-1.86 (m, 2H), 1.83 (s, 3H), 1.82 (s, 3H), 1.67-1.60 (m, 1H).
LC/MS Condition E: ret time 1.48 min; m/e=527 (M+H)$^+$.
LC/MS Condition F: ret time 1.31 min; m/e=527 (M+H)$^+$.

Example 2061: (R)-1-(3-((3'-(3-((2-(4-chloro-1H-pyrazol-1-yl)ethyl)amino)propoxy)-2,2'-dimethyl-[1,1'-biphenyl]-3-yl)oxy)propyl)pyrrolidin-3-ol

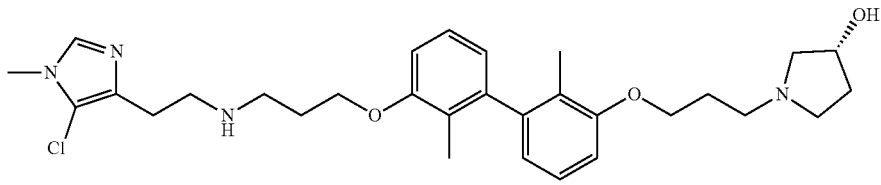 [SMILES: Cc1c(OCCCNCCc2ncn(C)c2Cl)cccc1-c1cccc(OCCCN2CC[C@@H](O)C2)c1C]

A mixture of 2-(5-chloro-1-methyl-1H-imidazol-4-yl)ethanamine, 2 HCl (95 mg, 0.409 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (160 μL, 0.916 mmol) was heated at 70° C. for 48 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound: (4 mg, 17%). $^1$H NMR (500 MHz, DMSO-$d_6$) δ 7.68 (s, 1H), 7.18 (q, J=7.7 Hz, 2H), 6.93 (d, J=7.3 Hz, 2H), 6.64 (dd, J=13.0, 7.5 Hz, 2H), 4.21 (br. s., 1H), 4.12-4.00 (m, 4H), 3.08-2.97 (m, 4H), 2.78 (dd, J=9.4, 5.7 Hz, 1H), 2.74-2.61 (m, 6H), 2.43 (d, J=8.8 Hz, 1H), 2.07-1.97 (m, 3H), 1.95-1.87 (m, 2H), 1.89 (s, 3H), 1.82 (s, 6H), 1.63-1.53 (m, 1H). LC/MS Condition E: ret time 1.27 min; m/e=541 (M+H)$^+$; LC/MS Condition F: ret time 1.12 min; m/e=541 (M+H)$^+$.

Example 2062: (R)-1-(3-((2,2'-dimethyl-3'-(3-(methyl(pyridin-2-ylmethyl)amino)propoxy)-[1,1'-biphenyl]-3-yl)oxy)propyl)pyrrolidin-3-ol

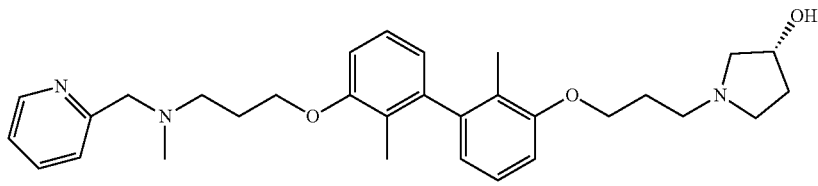 [SMILES: Cc1c(OCCCN(C)Cc2ccccn2)cccc1-c1cccc(OCCCN2CC[C@@H](O)C2)c1C]

A mixture of N-methyl-1-(pyridin-2-yl)methanamine (53.6 mg, 0.439 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 μL, 0.172 mmol) was heated at 70° C. for 48 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound: (18.5 mg, 76%). $^1$H NMR (500 MHz, DMSO-$d_6$) δ 8.44 (d, J=4.8 Hz, 1H), 7.64 (s, 1H), 7.39 (d, J=7.7 Hz, 1H), 7.20-7.15 (m, 3H), 6.93 (dd, J=8.3, 3.9 Hz, 2H), 6.63 (dd, J=11.9, 7.5 Hz, 2H), 4.38-4.25 (m, 1H), 4.12-3.99 (m, 4H), 3.64 (br. s., 2H), 3.12-2.84 (m, 5H), 2.60-2.55 (m, 3H), 2.24 (s, 3H), 2.11-1.92 (m, 5H), 1.83 (s, 3H), 1.71 (s, 3H), 1.71-1.69 (m, 1H). LC/MS Condition E: ret time 1.50 min; m/e=504 (M+H)$^+$. LC/MS Condition F: ret time 1.23 min; m/e=504 (M+H)$^+$.

Example 2063: (R)-1-(3-((3'-(3-(4-(2-hydroxyethyl)piperazin-1-yl)propoxy)-2,2'-dimethyl-[1,1'-biphenyl]-3-yl)oxy)propyl)pyrrolidin-3-ol

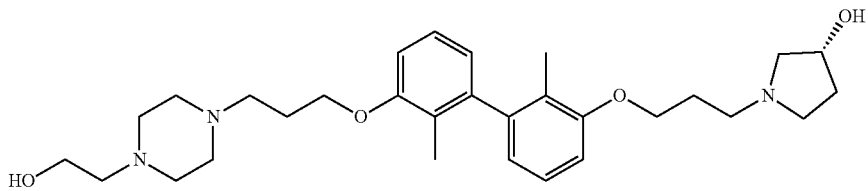 [SMILES: Cc1c(OCCCN2CCN(CCO)CC2)cccc1-c1cccc(OCCCN2CC[C@@H](O)C2)c1C]

A mixture of 2-(piperazin-1-yl)ethanol (45.3 mg, 0.348 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 μL, 0.172 mmol) was heated at 70° C. for 24 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min to give the pure title compound: (20.1 mg, 89%). LC/MS Condition E: ret time 1.21 min; m/e=512 (M+H)$^+$. LC/MS Condition F: ret time 1.07 min; m/e=512 (M+H)$^+$.

Example 2064: (R)-1-(3-((2,2'-dimethyl-3'-(3-(methyl(pyridin-4-ylmethyl)amino)propoxy)-[1,1'-biphenyl]-3-yl)oxy)propyl)pyrrolidin-3-ol

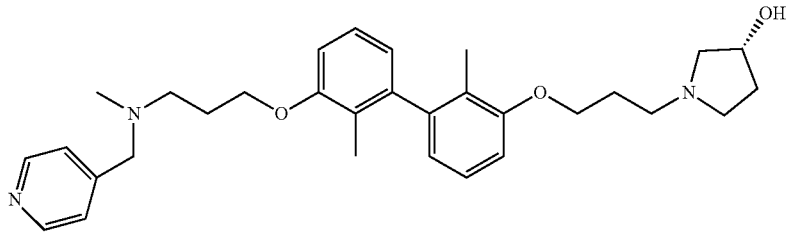 [SMILES: Cc1c(OCCCN(C)Cc2ccncc2)cccc1-c1cccc(OCCCN2CC[C@@H](O)C2)c1C]

A mixture of N-methyl-1-(pyridin-4-yl)methanamine, 2 HCl (39.7 mg, 0.203 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (80 μL, 0.458 mmol) was heated at 70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 60-100% B over 15 minutes, then a 5-minute hold at 100% B; Flow: 20 mL/min to give the pure title compound: (28.8 mg, 40%). LC/MS Condition E: ret time 1.71 min; m/e=504 (M+H)$^+$. LC/MS Condition F: ret time 1.12 min; m/e=504 (M+H)$^+$.

Example 2065: (R)-1-(3-((3'-(3-((4-aminophenethyl)amino)propoxy)-2,2'-dimethyl-[1,1'-biphenyl]-3-yl)oxy)propyl)pyrrolidin-3-ol

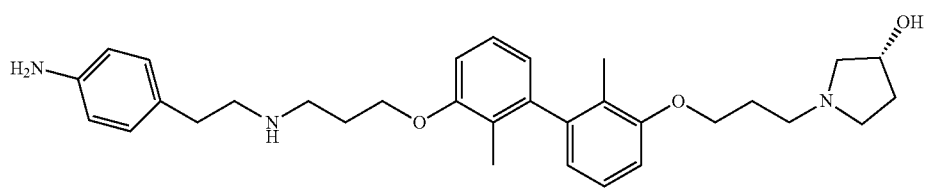 [SMILES: Cc1c(OCCCNCCc2ccc(N)cc2)cccc1-c1cccc(OCCCN2CC[C@@H](O)C2)c1C]

A mixture of 4-(2-aminoethyl)aniline (40.8 mg, 0.300 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 μL, 0.172 mmol) was heated at 70° C. for 48 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min to give the pure title compound: (14.2 mg, 63%). $^1$H NMR (500 MHz, DMSO-d$_6$) δ 7.25-7.13 (m, 2H), 6.94 (d, J=8.4 Hz, 2H), 6.88 (d, J=8.4 Hz, 2H), 6.66 (d, J=7.3 Hz, 1H), 6.63 (d, J=7.7 Hz, 1H), 6.50 (d, J=8.1 Hz, 2H), 4.19 (br. s., 1H), 4.10-4.00 (m, 4H), 3.00-2.87 (m, 4H), 2.78-2.70 (m, 1H), 2.67-2.56 (m, 5H), 2.46 (d, J=7.0 Hz, 1H), 2.37 (br. s., 1H), 2.05-1.96 (m, 3H), 1.93-1.89 (m, 2H), 1.86 (s, 3H), 1.80 (s, 3H), 1.63-1.48 (m, 1H). LC/MS Condition E: ret time 1.2 min; m/e=518 (M+H)$^+$. LC/MS Condition F: ret time 1.14 min; m/e=518 (M+H)$^+$.

Example 2066: (R)-1-(3-((2,2'-dimethyl-3'-(3-((1-methylpiperidin-4-yl)amino)propoxy)-[1,1'-biphenyl]-3-yl)oxy)propyl)pyrrolidin-3-ol

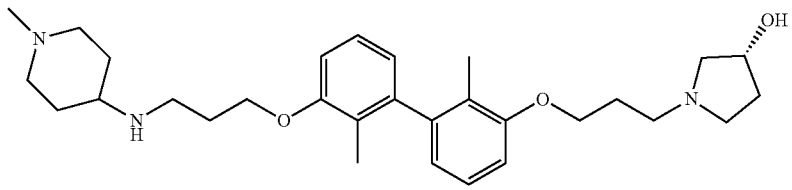 [SMILES: Cc1c(OCCCNC2CCN(C)CC2)cccc1-c1cccc(OCCCN2CC[C@@H](O)C2)c1C]

A mixture of 1-methylpiperidin-4-amine (56.2 mg, 0.492 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 µL, 0.172 mmol) was heated at 65-70° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-85% B over 15 minutes, then a 5-minute hold at 100% B; Flow: 20 mL/min to give the pure title compound: (10.1 mg, 47%). LC/MS Condition E: ret time 1.06 min; m/e=496 (M+H)$^+$. LC/MS Condition F: ret time 1.10 min; m/e=496 (M+H)$^+$.

Example 2067: (R)-1-(3-((3'-(3-((1-(2-hydroxyethyl)piperidin-4-yl)amino)propoxy)-2,2'-dimethyl-[1,1'-biphenyl]-3-yl)oxy)propyl)pyrrolidin-3-ol

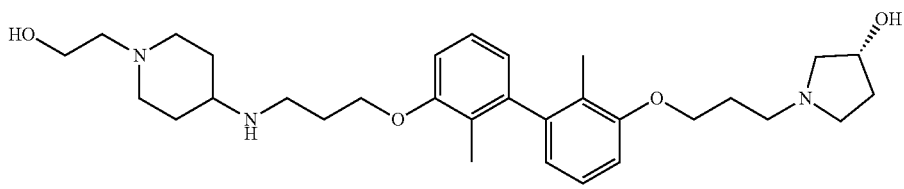 [SMILES: Cc1c(OCCCNC2CCN(CCO)CC2)cccc1-c1cccc(OCCCN2CC[C@@H](O)C2)c1C]

A mixture of 2-(4-aminopiperidin-1-yl)ethanol (82 mg, 0.569 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 µL, 0.172 mmol) was heated at 65° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min to give the pure title compound: (7.7 mg, 34%). LC/MS Condition E: ret time 1.14 min; m/e=526 (M+H)$^+$. LC/MS Condition F: ret time 1.09 min; m/e=526 (M+H)$^+$.

Example 2068: (R)-2,2'-((3-((3'-(3-(3-hydroxypyrrolidin-1-yl)propoxy)-2,2'-dimethyl-[1,1'-biphenyl]-3-yl)oxy)propyl)azanediyl)bis(ethan-1-ol)

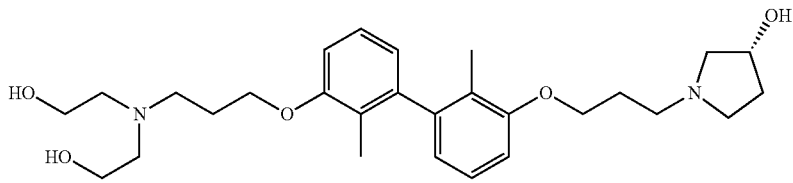 [SMILES: Cc1c(OCCCN(CCO)CCO)cccc1-c1cccc(OCCCN2CC[C@@H](O)C2)c1C]

A mixture of 2,2'-azanediyldiethanol (26 mg, 0.247 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 µL, 0.172 mmol) was heated at 65-70° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound: (10.5 mg, 49%). $^1$H NMR (500 MHz, DMSO-d$_6$) δ 7.19 (td, J=7.8, 4.2 Hz, 2H), 6.94 (d, J=8.4 Hz, 2H), 6.65 (dd, J=13.0, 7.5 Hz, 2H), 4.37-4.33 (m, 1H), 4.13-3.97 (m, 4H), 3.53-3.48 (m, 3H), 3.43-3.37 (m, 3H), 3.17-2.63 (m, 10H), 2.12-2.03 (m, 3H), 1.97-1.92 (m, 2H), 1.84 (s, 3H), 1.83 (s, 3H), 1.79-1.72 (m, 1H). LC/MS Condition E: ret time 1.18 min; m/e=487 (M+H)$^+$. LC/MS Condition F: ret time 1.16 min; m/e=487 (M+H)$^+$.

Example 2069: (R)-1-(3-((3'-(3-(((R)-2-hydroxy-1-phenylethyl)amino)propoxy)-2,2'-dimethyl-[1,1'-biphenyl]-3-yl)oxy)propyl)pyrrolidin-3-ol

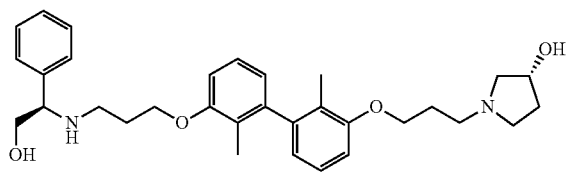 [SMILES: Cc1c(OCCCN[C@@H](CO)c2ccccc2)cccc1-c1cccc(OCCCN2CC[C@@H](O)C2)c1C]

A mixture of (R)-2-amino-2-phenylethanol (58 mg, 0.423 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (40 µL, 0.229 mmol) was heated at 70° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 60-100% B over 15 minutes, then a 5-minute hold at 100% B; Flow: 20 mL/min to give the pure title compound: (11 mg, 47%). LC/MS Condition E: ret time 1.44 min; m/e=519 (M+H)$^+$. LC/MS Condition F: ret time 1.33 min; m/e=519 (M+H)$^+$.

Example 2070: (R)-1-(3-((3'-(3-(4-(dimethylamino)piperidin-1-yl)propoxy)-2,2'-dimethyl-[1,1'-biphenyl]-3-yl)oxy)propyl)pyrrolidin-3-ol

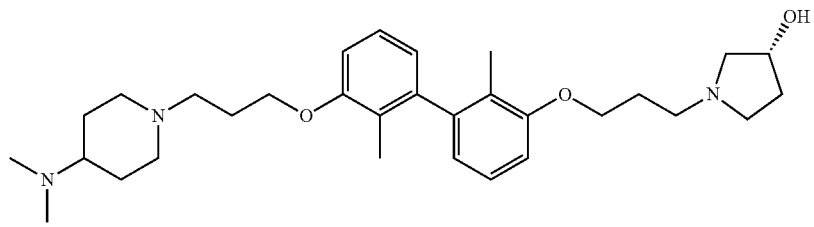 [SMILES: Cc1c(OCCCN2CCC(N(C)C)CC2)cccc1-c1cccc(OCCCN2CC[C@@H](O)C2)c1C]

A mixture of N,N-dimethylpiperidin-4-amine (42 mg, 0.328 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (30 µL, 0.172 mmol) was heated at 70° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min to give the pure title compound: (20.1 mg, 89%). LC/MS Condition E: ret time 1.22 min; m/e=510 (M+H)$^+$. LC/MS Condition F: ret time 1.05 min; m/e=510 (M+H)$^+$.

Example 2071: (R)-1-(3-((3'-(3-(((R)-1-(5-chloro-1-methyl-1H-imidazol-4-yl)-3-hydroxypropan-2-yl)amino)propoxy)-2,2'-dimethyl-[1,1'-biphenyl]-3-yl)oxy)propyl)pyrrolidin-3-ol

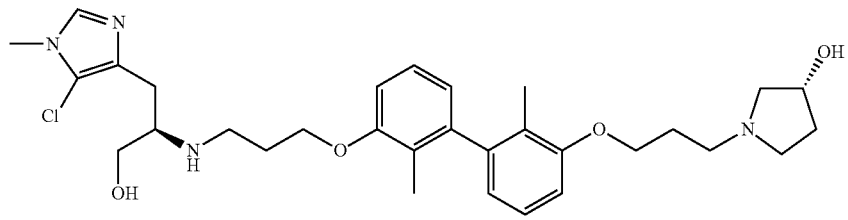 [SMILES: Cc1c(OCCCN[C@@H](CO)Cc2ncn(C)c2Cl)cccc1-c1cccc(OCCCN2CC[C@@H](O)C2)c1C]

A mixture of (R)-2-amino-3-(5-chloro-1-methyl-1H-imidazol-4-yl)propan-1-ol, 2 HCl (110 mg, 0.419 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (150 µL, 0.859 mmol) was heated at 70° C. for 48 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min to give the pure title compound: (9.1 mg, 19%). LC/MS Condition E: ret time 1.35 min; m/e=571 (M+H)$^+$. LC/MS Condition F: ret time 1.13 min; m/e=571 (M+H)$^+$.

Example 2072: (R)-1-(3-((3'-(3-(benzyl(2-hydroxyethyl)amino)propoxy)-2,2'-dimethyl-[1,1'-biphenyl]-3-yl)oxy)propyl)pyrrolidin-3-ol

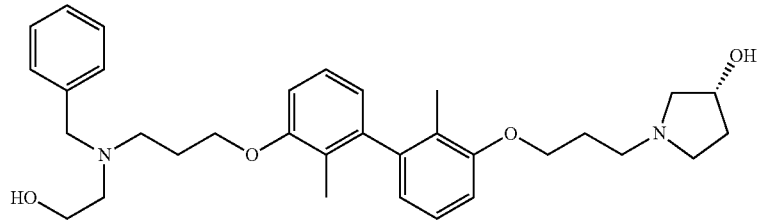 [SMILES: Cc1c(OCCCN(CCO)Cc2ccccc2)cccc1-c1cccc(OCCCN2CC[C@@H](O)C2)c1C]

A mixture of 2-(benzylamino)ethanol (47 mg, 0.311 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (40 µL, 0.229 mmol) was heated at 65-70° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min to give the pure title compound: (12.0 mg, 52%). $^1$H NMR (500 MHz, DMSO-d$_6$) δ 7.34-7.13 (m, 7H), 6.92 (dd, J=16.3, 8.3 Hz, 2H), 6.63 (dd, J=15.0, 7.7 Hz, 2H), 4.30 (br. s., 1H), 4.14-3.96 (m, 4H), 3.62 (s, 2H), 3.52-3.47 (m, 2H), 3.09-2.72 (m, 6H), 2.65-2.61 (m, 2H), 2.57-2.53 (m, 2H), 2.15-2.00 (m, 3H), 1.92-1.88 (m, 2H), 1.83 (s, 3H), 1.73-1.68 (m, 1H), 1.70 (s, 3H). LC/MS Condition E: ret time 1.71 min; m/e=533 (M+H)$^+$. LC/MS Condition F: ret time 1.28 min; m/e=533 (M+H)$^+$.

Example 2073: (R)-1-(3-((3'-(3-((2-hydroxyethyl)(isopentyl)amino)propoxy)-2,2'-dimethyl-[1,1'-biphenyl]-3-yl)oxy)propyl)pyrrolidin-3-ol

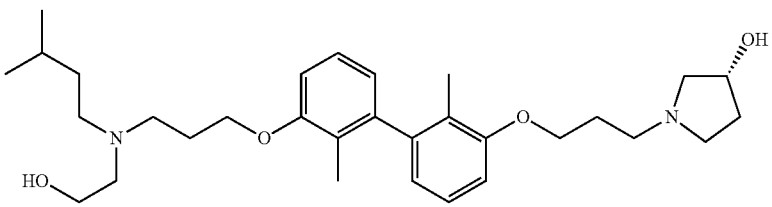 [SMILES: Cc1c(OCCCN(CCO)CCC(C)C)cccc1-c1cccc(OCCCN2CC[C@@H](O)C2)c1C]

A mixture of 2-(isopentylamino)ethanol (44 mg, 0.335 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (50 μL, 0.286 mmol) was heated at 65-70° C. for 120 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min to give the pure title compound: (14.4 mg, 63%). LC/MS Condition E: ret time 1.43 min; m/e=513 (M+H)$^+$. LC/MS Condition F: ret time 1.31 min; m/e=513 (M+H)$^+$.

XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min to give the pure title compound: (1.7 mg, 7%). $^1$H NMR (400 MHz, METHANOL-d$_4$) δ 7.23-7.15 (m, 2H), 6.95 (t, J=8.1 Hz, 2H), 6.69 (dd, J=7.5, 2.8 Hz, 2H), 4.57-4.47 (m, 1H), 4.15 (s, 4H), 3.40-3.15 (m, 12H), 2.68-2.60 (m, 1H), 2.35-2.15 (m, 5H), 2.00-1.90 (m, 4H), 1.92 (s, 3H), 1.90 (s, 3H), 1.86-1.81 (m, 1H). LC/MS Condition E: ret time 1.14 min; m/e=511 (M+H)$^+$. LC/MS Condition F: ret time 1.21 min; m/e=511 (M+H)$^+$.

Example 2075: (R)-1-(3-((3'-(3-(((S)-2-(3-chloro-4-fluorophenyl)-2-hydroxyethyl)amino)propoxy)-2,2'-dimethyl-[1,1'-biphenyl]-3-yl)oxy)propyl)pyrrolidin-3-ol

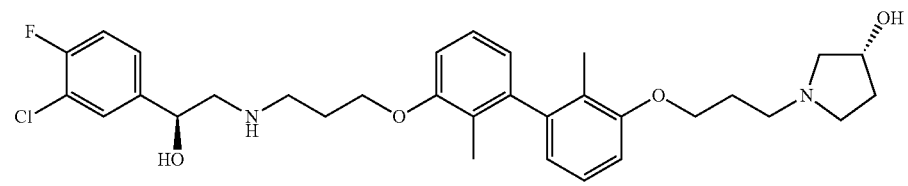

A mixture of (S)-2-amino-1-(3-chloro-4-fluorophenyl)ethanol, HCl (94.2 mg, 0.417 mmol) and (R)-1-(3-((3'-(3-bromopropoxy)-2,2'-dimethyl-[1,1'-biphenyl]-3-yl)oxy)propyl)pyrrolidin-3-ol (20 mg, 0.043 mmol) in methanol (1 mL) and N,N-diisopropylethylamine (100 μL, 0.573 mmol) was heated at 70° C. for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min to give the pure title compound: (15.5 mg, 62%). LC/MS Condition E: ret time 1.48 min; m/e=571 (M+H)$^+$. LC/MS Condition F: ret time 1.43 min; m/e=571 (M+H)$^+$.

Example 2074: (R)-1-(3-((3'-(3-((R)-3-hydroxypyrrolidin-1-yl)propoxy)-2,2'-dimethyl-[1,1'-biphenyl]-3-yl)oxy)propyl)piperidine-3-carboxylic acid

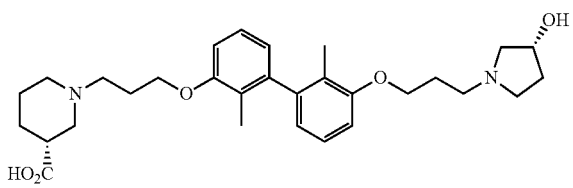 [SMILES: Cc1c(OCCCN2CC[C@@H](O)C2)cccc1-c1cccc(OCCCN2CCC[C@@H](C(=O)O)C2)c1C]

A mixture of (S)-piperidine-3-carboxylic acid (10 mg, 0.07 mmol) and (R)-1-(3-((3'-(3-bromopropoxy)-2,2'-dimethyl-[1,1'-biphenyl]-3-yl)oxy)propyl)pyrrolidin-3-ol (22 mg, 0.047 mmol) in DMF (0.5 mL), methanol (0.5 mL) and N,N-diisopropylethylamine (30 μL, 0.172 mmol) was heated at 70° C. for 24 h. The crude material was purified via preparative LC/MS with the following conditions: Column:

Example 2076: 3,3'-((((2,2'-dimethyl-[1,1'-biphenyl]-3,3'-diyl)bis(oxy))bis(propane-3,1-diyl))bis(methylazanediyl))dipropanamine

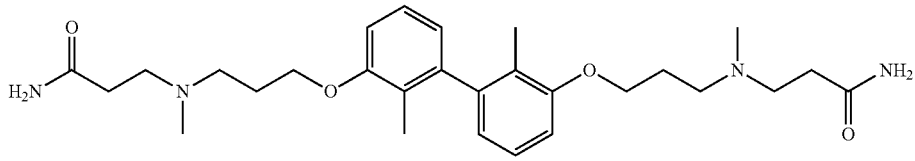 [SMILES: Cc1c(OCCCN(C)CCC(N)=O)cccc1-c1cccc(OCCCN(C)CCC(N)=O)c1C]

A mixture of 3-(methylamino)propanamide (90 mg, 0.88 mmol) and 3,3'-bis(3-bromopropoxy)-2,2'-dimethyl-1,1'-biphenyl (20 mg, 0.044 mmol) in DMF (0.5 mL), methanol (0.5 mL) and N,N-diisopropylethylamine (30 µL, 0.172 mmol) was heated at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 10-40% B over 20 minutes, then a 5-minute hold at 100% B; Flow: 20 mL/min to give the pure title compound: (16.8 mg, 75%). $^1$H NMR (500 MHz, DMSO-$d_6$) δ 7.39 (br. s., 2H), 7.17 (t, J=7.9 Hz, 2H), 6.92 (d, J=8.4 Hz, 2H), 6.78 (br. s., 2H), 6.63 (d, J=7.7 Hz, 2H), 4.09-3.97 (m, 4H), 2.67-2.53 (m, 8H), 2.29-2.19 (m, 10H), 1.94-1.88 (m, 4H), 1.82 (s, 6H). LC/MS Condition E: ret time 1.24 min; m/e=499 (M+H)$^+$. LC/MS Condition F: ret time 1.08 min; m/e=499 (M+H)$^+$.

Example 2077: 2,2',2'',2'''-((((2,2'-dimethyl-[1,1'-biphenyl]-3,3'-diyl)bis(oxy))bis(propane-3,1-diyl))bis(azanetriyl))tetrakis(ethan-1-ol)

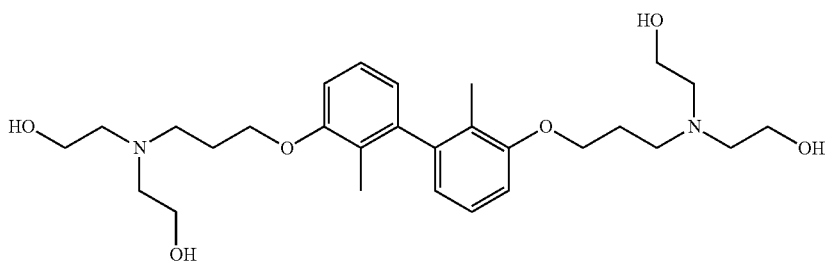 [SMILES: Cc1c(OCCCN(CCO)CCO)cccc1-c1cccc(OCCCN(CCO)CCO)c1C]

A mixture of 2,2'-azanediyldiethanol (80 mg, 0.761 mmol) and 3,3'-bis(3-bromopropoxy)-2,2'-dimethyl-1,1'-biphenyl (20 mg, 0.044 mmol) in methanol (0.5 mL), DMF (0.5 mL) and N,N-diisopropylethylamine (30 µL, 0.172 mmol) was heated at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min to give the pure title compound: (16.5 mg, 89%). LC/MS Condition E: ret time 1.25 min; m/e=505 (M+H)$^+$. LC/MS Condition F: ret time 1.13 min; m/e=505 (M+H)$^+$.

Example 2078: 3,3'-((((2,2'-dimethyl-[1,1'-biphenyl]-3,3'-diyl)bis(oxy))bis(propane-3,1-diyl))bis(methylazanediyl))bis(propane-1,2-diol)

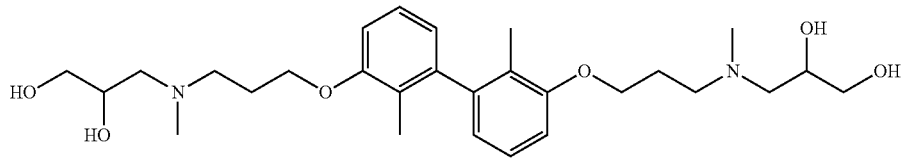 [SMILES: Cc1c(OCCCN(C)CC(O)CO)cccc1-c1cccc(OCCCN(C)CC(O)CO)c1C]

A mixture of 3-(methylamino)propane-1,2-diol (99 mg, 0.942 mmol) and 3,3'-bis(3-bromopropoxy)-2,2'-dimethyl-1,1'-biphenyl (20 mg, 0.044 mmol) in methanol (0.5 mL), THF (0.5 mL) and N,N-diisopropylethylamine (30 µL, 0.172 mmol) was heated at 65° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min to give the pure title compound as a mixture of diastereoisomers: (21.6 mg, 98%). LC/MS Condition E: ret time 1.06 min; m/e=505 (M+H)$^+$. LC/MS Condition F: ret time 1.06 min; m/e=505 (M+H)$^+$.

Example 2079: (2S,2'S)-3,3'-((((2,2'-dimethyl-[1,1'-biphenyl]-3,3'-diyl)bis(oxy))bis(propane-3,1-diyl))bis(azanediyl))bis(propane-1,2-diol)

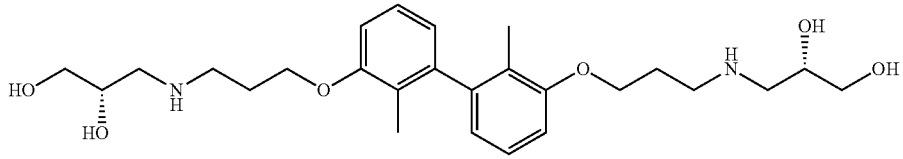 [SMILES: Cc1c(OCCCNC[C@H](O)CO)cccc1-c1cccc(OCCCNC[C@H](O)CO)c1C]

A mixture of (S)-3-aminopropane-1,2-diol (2 g, 21.95 mmol) and 3,3'-bis(3-bromopropoxy)-2,2'-dimethyl-1,1'-biphenyl (500 mg, 1.096 mmol) in methanol (11 mL) and N,N-diisopropylethylamine (600 μL, 3.44 mmol) was heated at 65° C. for 20 h. The crude material was purified via preparative LC/MS with the following conditions: Column: XBridge C18, 30×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 50 mL/min to give the pure title compound: (440 mg, 83%). $^1$H NMR (500 MHz, DMSO-$d_6$) δ 7.19 (t, J=7.9 Hz, 2H), 6.94 (d, J=8.1 Hz, 2H), 6.65 (d, J=7.7 Hz, 2H), 4.16-4.01 (m, 4H), 3.72-3.64 (m, 2H), 3.45-3.28 (m, 4H), 2.95 (t, J=7.2 Hz, 4H), 2.92-2.87 (m, 2H), 2.69 (dd, J=12.1, 8.4 Hz, 2H), 2.08-1.99 (m, 4H), 1.84 (s, 6H). LC/MS Condition E: ret time 1.06 min; m/e=477 (M+H)$^+$. LC/MS Condition F: ret time 1.08 min; m/e=477 (M+H)$^+$.

Example 2080: (S)-3-((3-((3'-(3-((3-hydroxypropyl)amino)propoxy)-2,2'-dimethyl-[1,1'-biphenyl]-3-yl)oxy)propyl)amino)propane-1,2-diol

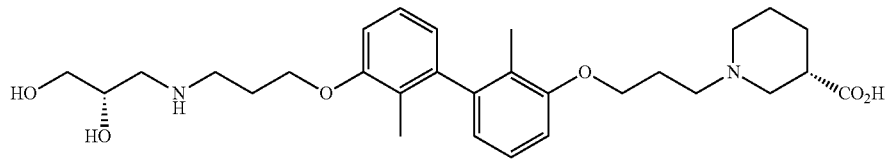

A mixture of (S)-3-aminopropane-1,2-diol (66.7 mg, 0.73 mmol), 3-aminopropan-1-ol (42 mg, 0.56 mmol), and 3,3'-bis(3-bromopropoxy)-2,2'-dimethyl-1,1'-biphenyl (20 mg, 0.044 mmol) in methanol (0.5 mL), DMF (0.5 mL) and N,N-diisopropylethylamine (100 μL, 0.573 mmol) was heated at 65° C. for 24 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-45% B over 20 minutes, then a 5-minute hold at 100% B; Flow: 20 mL/min to give the pure title compound as a TFA salt: (6.8 mg, 22%). $^1$H NMR (500 MHz, DMSO-$d_6$) δ 7.20 (t, J=7.9 Hz, 2H), 6.95 (d, J=8.1 Hz, 2H), 6.65 (d, J=7.7 Hz, 2H), 4.20-4.01 (m, 4H), 3.75 (d, J=5.5 Hz, 1H), 3.49 (t, J=6.1 Hz, 2H), 3.45-3.30 (m, 2H), 3.12-3.03 (m, 5H), 2.98 (t, J=7.5 Hz, 2H), 2.81 (dd, J=12.3, 9.4 Hz, 1H), 2.10 (d, J=5.5 Hz, 4H), 1.85 (s, 6H), 1.78-1.70 (m, 2H). LC/MS Condition E: ret time 1.01 min; m/e=461 (M+H)$^+$. LC/MS Condition F: ret time 1.08 min; m/e=461 (M+H)$^+$.

Example 2081: (S)-1-(3-((3'-(3-(((S)-2,3-dihydroxypropyl)amino)propoxy)-2,2'-dimethyl-[1,1'-biphenyl]-3-yl)oxy)propyl)piperidine-3-carboxylic acid

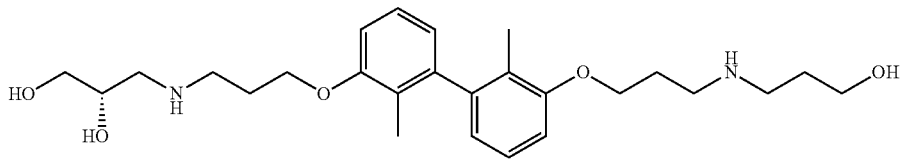 [SMILES: Cc1c(OCCCNCCCO)cccc1-c1cccc(OCCCNC[C@H](O)CO)c1C]

A mixture of (S)-piperidine-3-carboxylic acid (11.2 mg, 0.087 mmol) and 3,3'-bis(3-bromopropoxy)-2,2'-dimethyl-1,1'-biphenyl (20 mg, 0.044 mmol) in methanol (0.5 mL), DMF (0.5 mL) and N,N-diisopropylethylamine (170 μL, 0.975 mmol) was heated at 65° C. for 2 h. Then (S)-3-aminopropane-1,2-diol, HCl (53 mg, 0.415 mmol), N,N-diisopropylethylamine (90 μL, 0.52 mmol), and more (S)-piperidine-3-carboxylic acid (35 mg, 0.27 mmol) were added and the mixture was heated at 65° C. for 24 h. The crude material was purified via preparative LC/MS with the following conditions: Column: XBridge C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 25 minutes, then a 5-minute hold at 100% B; Flow: 20 mL/min. to give the pure title compound as a TFA salt: (8.5 mg, 38%). LC/MS Condition E: ret time 1.11 min; m/e=515 (M+H)$^+$. LC/MS Condition F: ret time 1.18 min; m/e=515 (M+H)$^+$.

Example 2082: (3S,3'S)-1,1'-(((2,2'-dimethyl-[1,1'-biphenyl]-3,3'-diyl)bis(oxy))bis(propane-3,1-diyl))bis(piperidine-3-carboxylic acid)

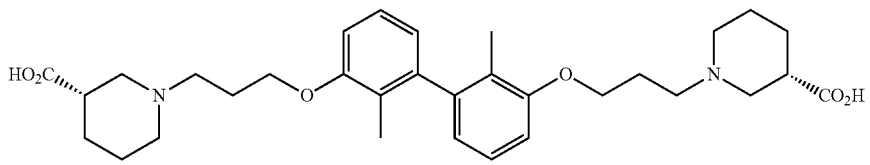 [SMILES: Cc1c(OCCCN2CCC[C@H](C(=O)O)C2)cccc1-c1cccc(OCCCN2CCC[C@H](C(=O)O)C2)c1C]

Isolated from the reaction mixture for Example 2081. The pure title compound was also obtained as a TFA salt: (11.7 mg, 43%). LC/MS Condition E: ret time 1.13 min; m/e=553 (M+H)$^+$. LC/MS Condition F: ret time 1.25 min; m/e=553 (M+H)$^+$.

Example 2083: 3,3'-((((2,2'-dimethyl-[1,1'-biphenyl]-3,3'-diyl)bis(oxy))bis(propane-3,1-diyl))bis(azanediyl))bis(propane-1,2-diol)

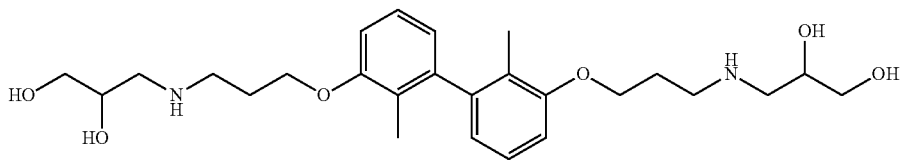

A mixture of 3-aminopropane-1,2-diol (84 mg, 0.922 mmol) and 3,3'-bis(3-bromopropoxy)-2,2'-dimethyl-1,1'-biphenyl (20 mg, 0.044 mmol) in methanol (0.5 mL), THF (0.5 mL) and N,N-diisopropylethylamine (30 µL, 0.172 mmol) was heated at 65° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 2-42% B over 20 minutes, then a 5-minute hold at 100% B; Flow: 20 mL/min to give the pure title compound as a mixture of diastereoisomers: (19.4 mg, 90%). LC/MS Condition E: ret time 1.07 min; m/e=477 (M+H)$^+$. LC/MS Condition F: ret time 1.10 min; m/e=477 (M+H)$^+$.

Example 2084: (3S,3'S,4S,4'S)-1,1'-(((2,2'-dimethyl-[1,1'-biphenyl]-3,3'-diyl)bis(oxy))bis(propane-3,1-diyl))bis(piperidine-3,4-diol)

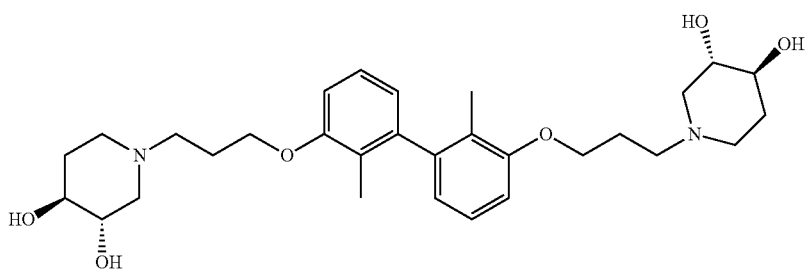 [SMILES: Cc1c(OCCCN2CC[C@H](O)[C@@H](O)C2)cccc1-c1cccc(OCCCN2CC[C@H](O)[C@@H](O)C2)c1C]

A mixture of (3S,4S)-piperidine-3,4-diol, HCl (40 mg, 0.260 mmol) and 3,3'-bis(3-bromopropoxy)-2,2'-dimethyl-1,1'-biphenyl (20 mg, 0.044 mmol) in methanol (1 mL) and N,N-diisopropylethylamine (60 μL, 0.344 mmol) was heated at 65° C. for 24 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound: (9.9 mg, 43%). LC/MS Condition E: ret time 1.27 min; m/e=529 (M+H)+. LC/MS Condition F: ret time 1.07 min; m/e=529 (M+H)+.

Example 2085: 2,2'-((((2,2'-dimethyl-[1,1'-biphenyl]-3,3'-diyl)bis(oxy))bis(propane-3,1-diyl))bis(piperazine-4,1-diyl))bis(ethan-1-ol)

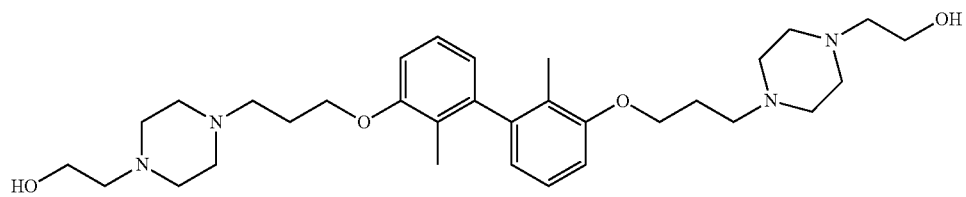 [SMILES: Cc1c(OCCCN2CCN(CCO)CC2)cccc1-c1cccc(OCCCN2CCN(CCO)CC2)c1C]

A mixture of 2-(piperazin-1-yl)ethanol (99 mg, 0.760 mmol) and 3,3'-bis(3-bromopropoxy)-2,2'-dimethyl-1,1'-biphenyl (20 mg, 0.044 mmol) in methanol (1 mL) and N,N-diisopropylethylamine (25 μL, 0.143 mmol) was heated at 65° C. for 72 h. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile:water with 0.1% trifluoroacetic acid; Gradient: 10-50% B over 15 minutes, then a 5-minute hold at 100% B; Flow: 20 mL/min to give the pure title compound as a TFA salt: (45.9 mg, 99%). LC/MS Condition E: ret time 1.28 min; m/e=555 (M+H)+. LC/MS Condition F: ret time 1.05 min; m/e=555 (M+H)+.

Example 2086: 3,3'-((2,2'-dimethyl-[1,1'-biphenyl]-3,3'-diyl)bis(oxy))bis(N-(2-(pyridin-3-yl)ethyl)propan-1-amine)

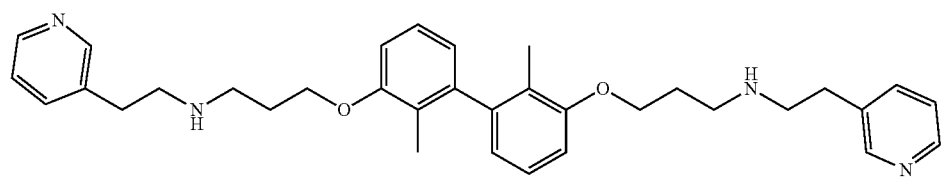 [SMILES: Cc1c(OCCCNCCc2cccnc2)cccc1-c1cccc(OCCCNCCc2cccnc2)c1C]

A mixture of 2-(pyridin-3-yl)ethanamine (100.7 mg, 0.824 mmol) and 3,3'-bis(3-bromopropoxy)-2,2'-dimethyl-1,1'-biphenyl (20 mg, 0.044 mmol) in methanol (1.5 mL) and N,N-diisopropylethylamine (25 μL, 0.143 mmol) was heated at 65° C. for 72 h. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min to give the pure title compound as a TFA salt: (26 mg, 59%). $^1$H NMR (500 MHz, DMSO-$d_6$) δ 8.80 (br. s., 2H), 8.60 (d, J=1.5 Hz, 2H), 8.57 (dd, J=4.8, 1.5 Hz, 2H), 7.91 (d, J=7.7 Hz, 2H), 7.54 (dd, J=7.9, 5.0 Hz, 2H), 7.21 (t, J=7.9 Hz, 2H), 6.96 (d, J=8.1 Hz, 2H), 6.66 (d, J=7.3 Hz, 2H), 4.15-4.07 (m, 4H), 3.33-3.27 (m, 4H), 3.22-3.15 (m, 4H), 3.05-2.99 (m, 4H), 2.16-2.10 (m, 4H), 1.85 (s, 6H). LC/MS Condition E: ret time 1.30 min; m/e=539 (M+H)+. LC/MS Condition F: ret time 1.07 min; m/e=539 (M+H)+.

Example 2087: 1,1'-(((2,2'-dimethyl-[1,1'-biphenyl]-3,3'-diyl)bis(oxy))bis(propane-3,1-diyl))bis(N,N-dimethylazetidin-3-amine)

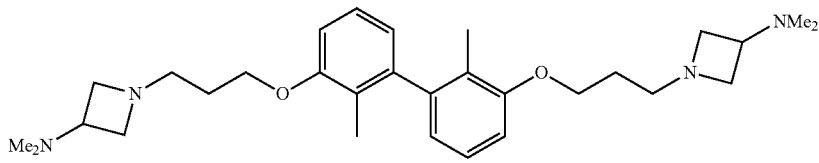 [SMILES: Cc1c(OCCCN2CC(N(C)C)C2)cccc1-c1cccc(OCCCN2CC(N(C)C)C2)c1C]

A mixture of N,N-dimethylazetidin-3-amine, 2 HCl (110 mg, 0.636 mmol) and 3,3'-bis(3-bromopropoxy)-2,2'-dimethyl-1,1'-biphenyl (20 mg, 0.044 mmol) in methanol (3 mL) and N,N-diisopropylethylamine (220 µL, 1.26 mmol) was heated at 65° C. for 48 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the pure title compound: (16.6 mg, 77%). LC/MS Condition E: ret time 1.59 min; m/e=495 (M+H)$^+$. LC/MS Condition F: ret time 1.68 min; m/e=495 (M+H)$^+$.

Example 2088: (1S,1'S,2R,2'R,3R,3'R,5R,5'R)-5,5'-((((2,2'-dimethyl-[1,1'-biphenyl]-3,3'-diyl)bis(oxy))bis(propane-3,1-diyl))bis(azanediyl))bis(3-(hydroxymethyl)cyclopentane-1,2-diol)

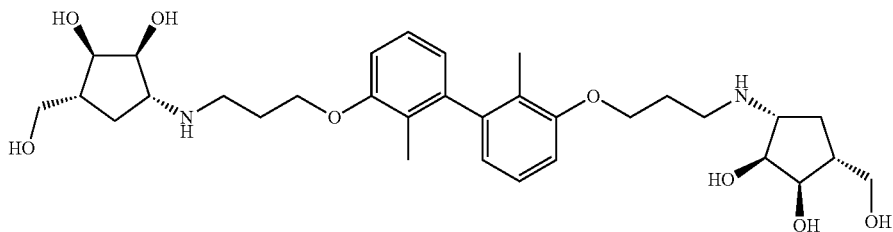 [SMILES: Cc1c(OCCCN[C@@H]2C[C@H](CO)[C@@H](O)[C@H]2O)cccc1-c1cccc(OCCCN[C@@H]2C[C@H](CO)[C@@H](O)[C@H]2O)c1C]

A mixture of (1R,2S,3R,5R)-3-amino-5-(hydroxymethyl)cyclopentane-1,2-diol, HCl (40 mg, 0.218 mmol) and 3,3'-bis(3-bromopropoxy)-2,2'-dimethyl-1,1'-biphenyl (20 mg, 0.044 mmol) in methanol (1 mL) and N,N-diisopropylethylamine (70 µL, 0.40 mmol) was heated at 65° C. for 24 h. Then 2-(pyridin-4-yl)ethanamine (50 mg, 0.409 mmol) was added, and the mixture heated at 65° C. for 48 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 minutes, then a 5-minute hold at 100% B; Flow: 20 mL/min to give the pure title compound: (2.3 mg, 9%). LC/MS Condition E: ret time 1.40 min; m/e=589 (M+H)$^+$. LC/MS Condition F: ret time 1.45 min; m/e=589 (M+H)$^+$.

Example 2089: (1R,2S,3R,5R)-3-((3-((2,2'-dimethyl-3'-(3-((2-(pyridin-4-yl)ethyl)amino)propoxy)-[1,1'-biphenyl]-3-yl)oxy)propyl)amino)-5-(hydroxymethyl)cyclopentane-1,2-diol

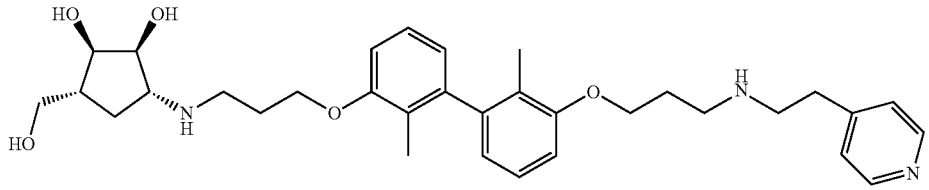 [SMILES: Cc1c(OCCCNCCc2ccncc2)cccc1-c1cccc(OCCCN[C@@H]2C[C@H](CO)[C@@H](O)[C@H]2O)c1C]

From Example 2088: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 minutes, then a 5-minute hold at 100% B; Flow: 20 mL/min. A second purification via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 15 minutes, then a 5-minute hold at 100% B; Flow: 20 mL/min gave the pure title compound as a TFA salt: (3.2 mg, 9%). LC/MS Condition E: ret time 1.52 min; m/e=564 (M+H)$^+$. LC/MS Condition F: ret time 1.43 min; m/e=564 (M+H)$^+$.

Example 2090: 3,3'-((((2,2'-dimethyl-[1,1'-biphenyl]-3,3'-diyl)bis(oxy))bis(propane-3,1-diyl))bis(methylazanediyl))bis(cyclobutan-1-ol)

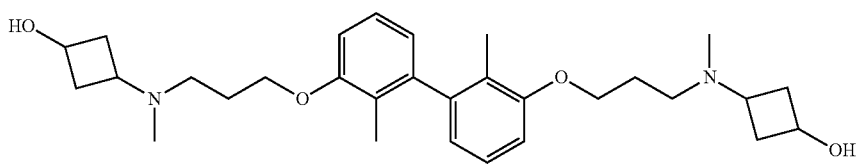 [SMILES: Cc1c(OCCCN(C)C2CC(O)C2)cccc1-c1cccc(OCCCN(C)C2CC(O)C2)c1C]

A mixture of 3-(methylamino)cyclobutanol (73.2 mg, 0.724 mmol) and 3,3'-bis(3-bromopropoxy)-2,2'-dimethyl-1,1'-biphenyl (20 mg, 0.044 mmol) in methanol (1 mL) and N,N-diisopropylethylamine (30 μL, 0.172 mmol) was heated at 65° C. for 24 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min to give the pure title compound: (20.8 mg, 90%). LC/MS Condition E: ret time 1.49 min; m/e=497 (M+H)$^+$. LC/MS Condition F: ret time 1.22 min; m/e=497 (M+H)$^+$.

Example 2091: (2S,3S)-3-((3-((3'-(3-((R)-3-hydroxypyrrolidin-1-yl)propoxy)-2,2'-dimethyl-[1,1'-biphenyl]-3-yl)oxy)propyl)amino)-3-phenylpropane-1,2-diol

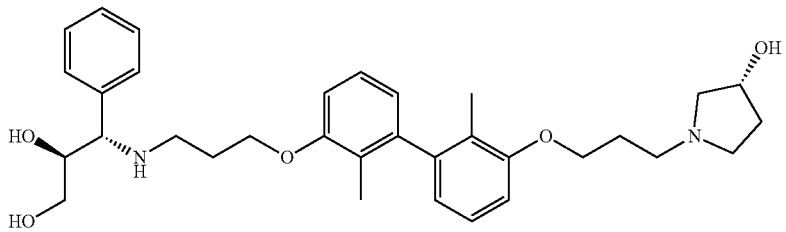 [SMILES: Cc1c(OCCCN[C@@H](c2ccccc2)[C@H](O)CO)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (2S,3S)-3-amino-3-phenylpropane-1,2-diol, HCl (42.8 mg, 0.210 mmol) in methanol (1 mL) and N,N-diisopropylethylamine (60 µL, 0.344 mmol) was heated at 65° C. for 48 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the pure title compound: (9.9 mg, 41%). LC/MS Condition E: ret time 1.79 min; m/e=549 (M+H)+. LC/MS Condition F: ret time 1.66 min; m/e=549 (M+H)+.

Example 2092: (R)-1-(3-((3'-(3-((R)-2-(hydroxymethyl)morpholino)propoxy)-2,2'-dimethyl-[1,1'-biphenyl]-3-yl)oxy)propyl)pyrrolidin-3-ol

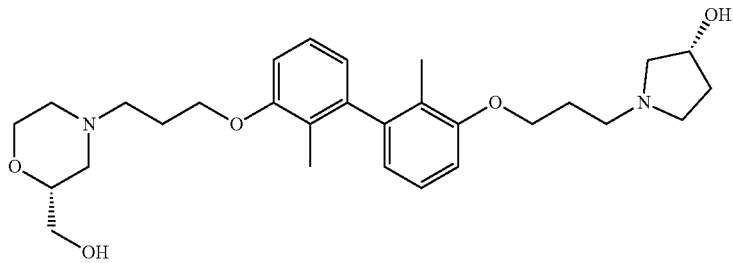 [SMILES: Cc1c(OCCCN2CC[C@@H](O)C2)cccc1-c1cccc(OCCCN2CCO[C@@H](CO)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (R)-morpholin-2-ylmethanol, HCl (39 mg, 0.254 mmol) in methanol (1 mL) and N,N-diisopropylethylamine (60 µL, 0.344 mmol) was heated at 65° C. for 24 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the pure title compound: (19.7 mg, 91%). LC/MS Condition E: ret time 1.71 min; m/e=499 (M+H)+. LC/MS Condition F: ret time 1.51 min; m/e=499 (M+H)+.

Example 2093: (3R,3'R)-1,1'-((((((propane-1,3-diyl-bis(methylazanediyl))bis(propane-3,1-diyl))bis(oxy))bis(2,2'-dimethyl-[1,1'-biphenyl]-3',3-diyl))bis(oxy))bis(propane-3,1-diyl))bis(pyrrolidin-3-ol)

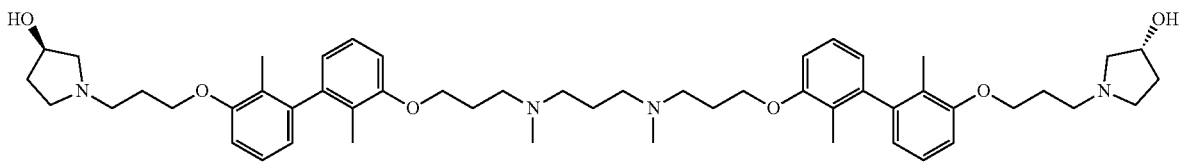 [SMILES: Cc1c(OCCCN(C)CCCN(C)CCCOc2cccc(-c3cccc(OCCCN4CC[C@@H](O)C4)c3C)c2C)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and N1,N3-dimethylpropane-1,3-diamine (2.6 mg, 0.025 mmol) in methanol (3 mL) and N,N-diisopropylethylamine (30 µL, 0.172 mmol) was heated at 65° C. for 72 h. More N1,N3-dimethylpropane-1,3-diamine (7.5 mg, 0.072 mmol) was added, and the mixture heated at 65° C. for 48 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min to give the pure title compound: (1.3 mg, 3%). LC/MS Condition E: ret time 1.99 min; m/e=865 (M+H)+. LC/MS Condition F: ret time 1.69 min; m/e=865 (M+H)+.

Example 2094: 3,3'-(((((2,2'-dimethyl-[1,1'-biphenyl]-3,3'-diyl)bis(oxy))bis(propane-3,1-diyl))bis(azanediyl))bis(1-methoxypropan-2-ol)

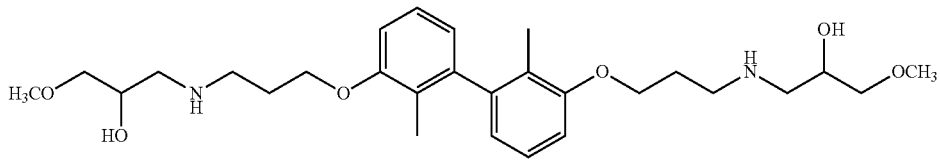 [SMILES: COCC(O)CNCCCOc1cccc(-c2cccc(OCCCNCC(O)COC)c2C)c1C]

A mixture of 1-amino-3-methoxypropan-2-ol (95 mg, 0.904 mmol) and 3,3'-bis(3-bromopropoxy)-2,2'-dimethyl-1,1'-biphenyl (20 mg, 0.044 mmol) in methanol (1 mL) and N,N-diisopropylethylamine (70 µL, 0.401 mmol) was heated at 65° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 18 minutes, then a 5-minute hold at 100% B; Flow: 20 mL/min to give the pure title compound as a mixture of diasteromers: (21.8 mg, 98%). LC/MS Condition E: ret time 1.13 min; m/e=505 (M+H)$^+$. LC/MS Condition F: ret time 1.15 min; m/e=505 (M+H)$^+$.

Example 2095: (3R,3'R)-1,1'-(((((((oxybis(ethane-2,1-diyl))bis(methylazanediyl))bis(propane-3,1-diyl))bis(oxy))bis(2,2'-dimethyl-[1,1'-biphenyl]-3',3-diyl))bis(oxy))bis(propane-3,1-diyl))bis(pyrrolidin-3-ol)

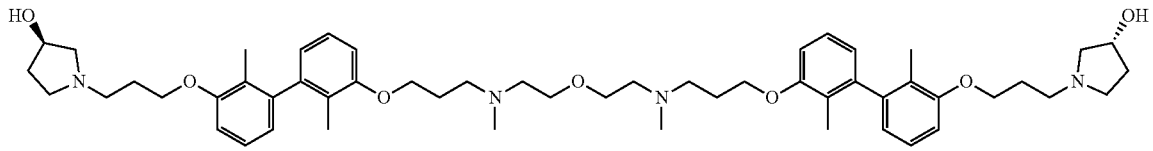 [SMILES: Cc1c(OCCCN(C)CCOCCN(C)CCCOc2cccc(-c3cccc(OCCCN4CC[C@@H](O)C4)c3C)c2C)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and 2,2'-oxybis(N-methylethanamine) (2.7 mg, 0.020 mmol) in methanol (1.5 mL) and N,N-diisopropylethylamine (40 µL, 0.229 mmol) was heated at 65° C. for 72 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min to give the pure title compound: (4.2 mg, 10%). LC/MS Condition E: ret time 1.94 min; m/e=895 (M+H)$^+$. LC/MS Condition F: ret time 1.77 min; m/e=895 (M+H)$^+$.

Example 2096: (R)-1-(3-((2,2'-dimethyl-3'-(3-(methyl(2-(2-(methylamino)ethoxy)ethyl)amino)propoxy)-[1,1'-biphenyl]-3-yl)oxy)propyl)pyrrolidin-3-ol

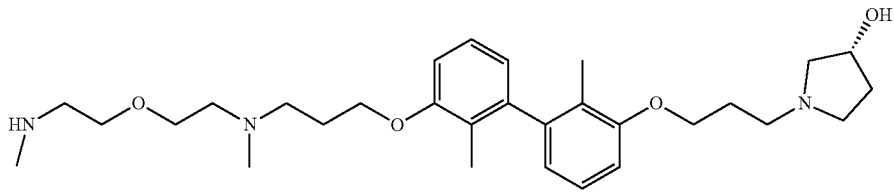 [SMILES: CNCCOCCN(C)CCCOc1cccc(-c2cccc(OCCCN3CC[C@@H](O)C3)c2C)c1C]

From the above describing the preparation of Example 2095, (3R,3'R)-1,1'-(((((((oxybis(ethane-2,1-diyl))bis(methylazanediyl))bis(propane-3,1-diyl))bis(oxy))bis(2,2'-dimethyl-[1,1'-biphenyl]-3',3-diyl))bis(oxy))bis(propane-3,1-diyl))bis(pyrrolidin-3-ol), Example 2096 was also obtained: (5.2 mg, 21%). LC/MS Condition E: ret time 1.60 min; m/e=514 (M+H)⁺. LC/MS Condition F: ret time 1.55 min; m/e=514 (M+H)⁺.

Example 2097: (1R,1'R,2R,2'R)-2,2'-((((2,2'-dimethyl-[1,1'-biphenyl]-3,3'-diylbis)bis(bis(propane-3,1-diyl))bis(azanediyl))bis(1-phenylpropane-1,3-diol)

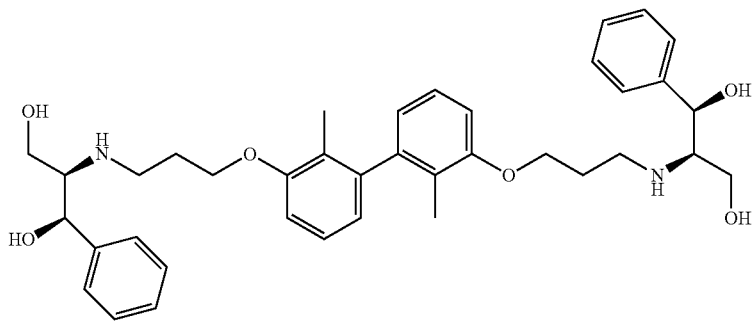 [SMILES: Cc1c(OCCCN[C@H](CO)[C@H](O)c2ccccc2)cccc1-c1cccc(OCCCN[C@H](CO)[C@H](O)c2ccccc2)c1C]

A mixture of (1R,2R)-2-amino-1-phenylpropane-1,3-diol (119 mg, 0.712 mmol) and 3,3'-bis(3-bromopropoxy)-2,2'-dimethyl-1,1'-biphenyl (20 mg, 0.044 mmol) in methanol (1 mL) and N,N-diisopropylethylamine (55 μL, 0.315 mmol) was heated at 65° C. for 24 h. (S)-3-aminopropane-1,2-diol (50 mg, 0.549 mmol) and more N,N-diisopropylethylamine (50 ul) were added, and the mixture was continued heating at 65° C. overnight. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 12-52% B over 25 minutes, then a 5-minute hold at 100% B; Flow: 20 mL/min to give the pure title compound: (15.0 mg, 54%). LC/MS Condition E: ret time 1.95 min; m/e=629 (M+H)⁺. LC/MS Condition F: ret time 1.58 min; m/e=629 (M+H)⁺.

Example 2098: (S)-3-((3-((3'-(3-(((1R,2R)-1,3-dihy-droxy-1-phenylpropan-2-yl)amino)propoxy)-2,2'-dimethyl-[1,1'-biphenyl]-3-yl)oxy)propyl)amino)propane-1,2-diol

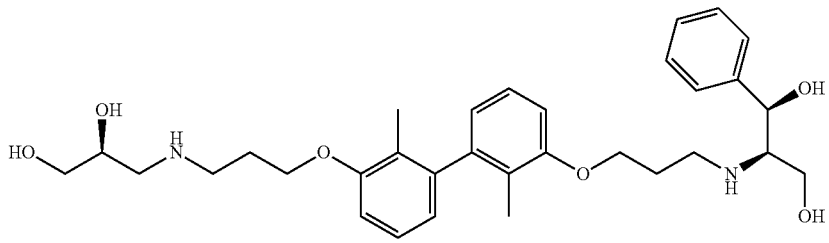 [SMILES: Cc1c(OCCCNC[C@H](O)CO)cccc1-c1cccc(OCCCN[C@H](CO)[C@H](O)c2ccccc2)c1C]

From the above describing the preparation of Example 2097, (1R,1'R,2R,2'R)-2,2'-((((2,2'-dimethyl-[1,1'-biphenyl]-3,3'-diyl)bis(oxy))bis(propane-3,1-diyl))bis(azanediyl))bis(1-phenylpropane-1,3-diol), Example 2098 was also obtained: (4.1 mg, 17%). LC/MS Condition E: ret time 1.67 min; m/e=553 (M+H)$^+$. LC/MS Condition F: ret time 1.42 min; m/e=553 (M+H)$^+$.

Example 2099: 5,5'-(((((2,2'-dimethyl-[1,1'-biphenyl]-3,3'-diyl)bis(oxy))bis(propane-3,1-diyl))bis(((S)-2,3-dihydroxypropyl)azanediyl))bis(methylene))dinicotinonitrile

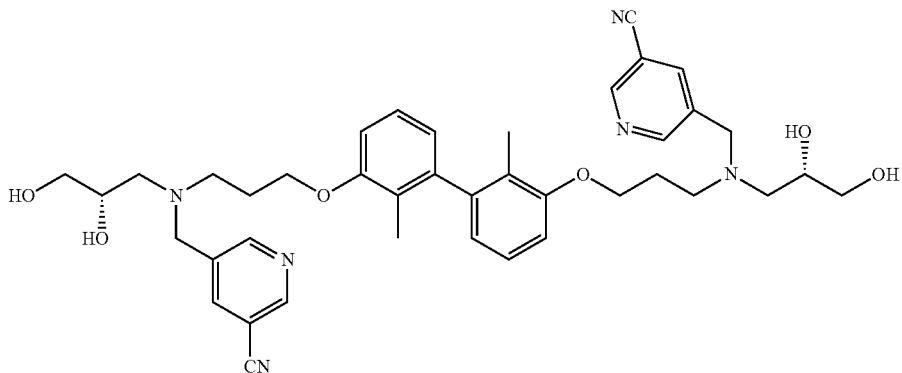 [SMILES: Cc1c(OCCCN(Cc2cncc(C#N)c2)C[C@H](O)CO)cccc1-c1cccc(OCCCN(Cc2cncc(C#N)c2)C[C@H](O)CO)c1C]

A mixture of (2S,2'S)-3,3'-((((2,2'-dimethyl-[1,1'-biphenyl]-3,3'-diyl)bis(oxy))bis(propane-3,1-diyl))bis(azanediyl))bis(propane-1,2-diol) (Example 2079, 20 mg, 0.042 mmol) and 5-(chloromethyl)nicotinonitrile (51 mg, 0.334 mmol) in methanol (1 mL) and N,N-diisopropylethylamine (130 μL, 0.744 mmol) was heated at 65° C. for 24 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 40-80% B over 20 minutes, then a 5-minute hold at 100% B; Flow: 20 mL/min to give the pure title compound: (15.0 mg, 45%). LC/MS Condition E: ret time 2.43 min; m/e=709 (M+H)$^+$. LC/MS Condition F: ret time 1.84 min; m/e=709 (M+H)$^+$.

Example 2100: 2,2'-((((2,2'-dimethyl-[1,1'-biphe-nyl]-3,3'-diyl)bis(oxy))bis(propane-3,1-diyl))bis (((S)-2,3-dihydroxypropyl)azanediyl))diacetonitrile

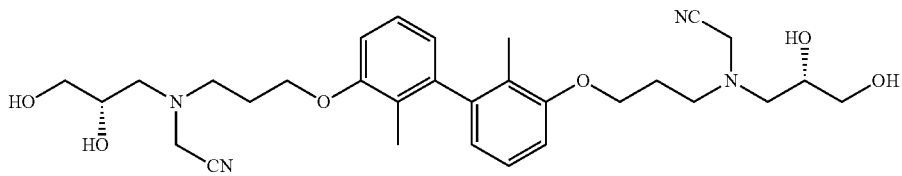 [SMILES: Cc1c(OCCCN(CC#N)C[C@H](O)CO)cccc1-c1cccc(OCCCN(CC#N)C[C@H](O)CO)c1C]

A mixture of (2S,2'S)-3,3'-((((2,2'-dimethyl-[1,1'-biphe-nyl]-3,3'-diyl)bis(oxy))bis(propane-3,1-diyl))bis (azanediyl))bis(propane-1,2-diol) (Example 2079, 20 mg, 0.042 mmol) and 2-iodoacetonitrile (20 μl, 0.276 mmol) in methanol (1 mL) and N,N-diisopropylethylamine (50 μL, 0.286 mmol) was heated at 65° C. for 4 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min to give the pure title compound: (16.1 mg, 64%). LC/MS Condition E: ret time 1.65 min; m/e=555 (M+H)$^+$. LC/MS Condition F: ret time 1.45 min; m/e=555 (M+H)$^+$.

Example 2101: (2S,2'S)-3,3'-((((2,2'-dimethyl-[1,1'-biphenyl]-3,3'-diyl)bis(oxy))bis(propane-3,1-diyl)) bis((2-(pyridin-2-yl)ethyl)azanediyl))bis(propane-1,2-diol)

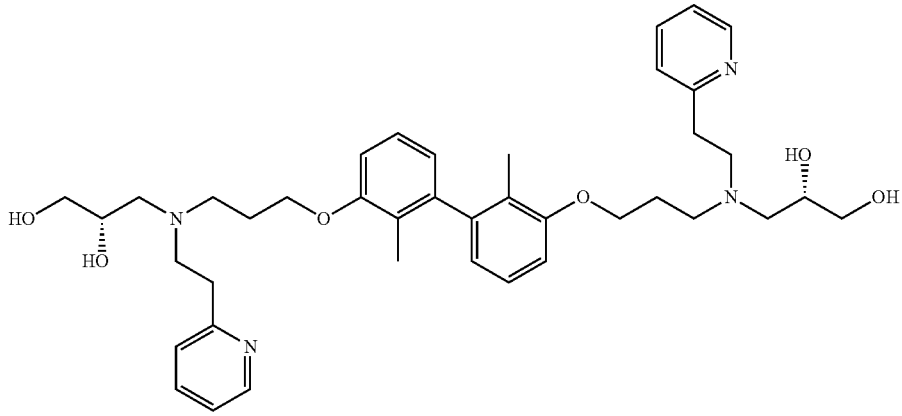 [SMILES: Cc1c(OCCCN(CCc2ccccn2)C[C@H](O)CO)cccc1-c1cccc(OCCCN(CCc2ccccn2)C[C@H](O)CO)c1C]

A solution of (2S,2'S)-3,3'-((((2,2'-dimethyl-[1,1'-biphe-nyl]-3,3'-diyl)bis(oxy))bis(propane-3,1-diyl))bis (azanediyl))bis(propane-1,2-diol) (Example 2079, 22 mg, 0.046 mmol), 2-(2-bromoethyl)pyridine, hydrobromide (151 mg, 0.336 mmol) in NMP (0.9 mL) was treated with N,N-diisopropylethylamine (180 μl, 1.03 mmol), and heated at 80 C for 5.5 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to give the pure title compound: (10.3 mg, 32%). LC/MS Condition E: ret time 1.39 min; m/e=687 (M+H)$^+$. LC/MS Condition F: ret time 1.20 min; m/e=687 (M+H)$^+$.

Example 2102: (2S,2'S)-3,3'-((((2,2'-dimethyl-[1,1'-biphenyl]-3,3'-diyl)bis(oxy))bis(propane-3,1-diyl))bis((2-(pyridin-3-yl)ethyl)azanediyl))bis(propane-1,2-diol)

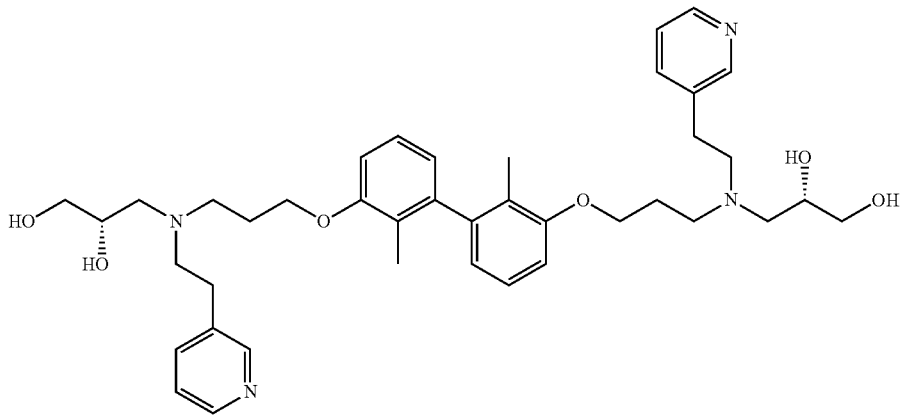 [SMILES: Cc1c(OCCCN(CCc2cccnc2)C[C@H](O)CO)cccc1-c1cccc(OCCCN(CCc2cccnc2)C[C@H](O)CO)c1C]

A solution of (2S,2'S)-3,3'-((((2,2'-dimethyl-[1,1'-biphenyl]-3,3'-diyl)bis(oxy))bis(propane-3,1-diyl))bis(azanediyl))bis(propane-1,2-diol) (Example 2079, 10 mg, 0.021 mmol), 3-(2-bromoethyl)pyridine, hydrobromide (18 mg, 0.067 mmol) in DMF (0.5 mL) was treated with N,N-diisopropylethylamine (30 μl, 0.172 mmol), and placed in a 65-70 C sand bath shaker for 72 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 20 minutes, then a 5-minute hold at 100% B; Flow: 20 mL/min to give the pure title compound: (0.7 mg, 4%). LC/MS Condition E: ret time 1.58 min; m/e=687 (M+H)$^+$. LC/MS Condition F: ret time 0.98 min; m/e=344 (M+2H)$^{2+}$.

Example 2103: (S)-3-((3-((3'-(3-(((S)-2,3-dihydroxypropyl)(2-(pyridin-3-yl)ethyl)amino)propoxy)-2,2'-dimethyl-[1,1'-biphenyl]-3-yl)oxy)propyl)amino)propane-1,2-diol

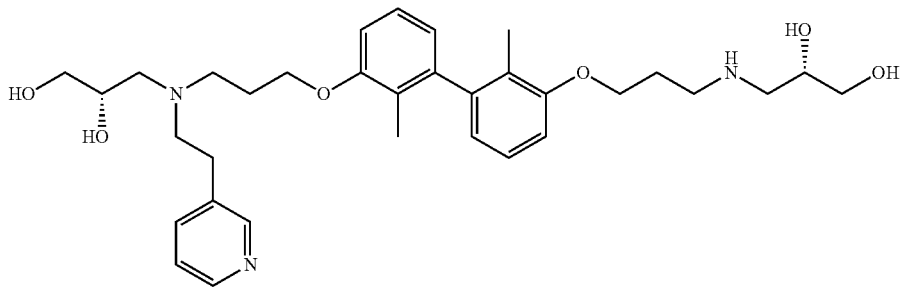 [SMILES: Cc1c(OCCCNC[C@H](O)CO)cccc1-c1cccc(OCCCN(CCc2cccnc2)C[C@H](O)CO)c1C]

From the above describing the purification of Example 2102, (2S,2'S)-3,3'-((((2,2'-dimethyl-[1,1'-biphenyl]-3,3'-diyl)bis(oxy))bis(propane-3,1-diyl))bis((2-(pyridin-3-yl)ethyl)azanediyl))bis(propane-1,2-diol), Example 2103 was also isolated: (3.2 mg, 24%). LC/MS Condition E: ret time 1.33 min; m/e=582 (M+H)$^+$. LC/MS Condition F: ret time 1.04 min; m/e=582 (M+H)$^+$.

Example 2104: 3,3'-((((2,2'-dimethyl-[1,1'-biphenyl]-3,3'-diyl)bis(oxy))bis(propane-3,1-diyl))bis(azanediyl))bis(2-methylpropane-1,2-diol)

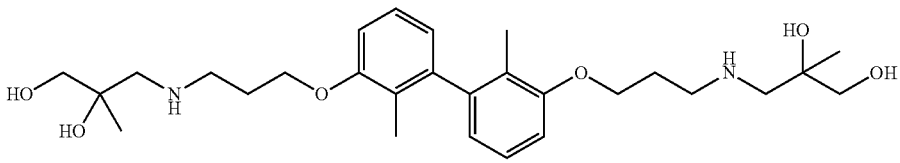 [SMILES: Cc1c(OCCCNCC(C)(O)CO)cccc1-c1cccc(OCCCNCC(C)(O)CO)c1C]

A mixture of 3,3'-bis(3-bromopropoxy)-2,2'-dimethyl-1,1'-biphenyl (20 mg, 0.044 mmol) and 3-amino-2-methylpropane-1,2-diol (60 mg, 0.571 mmol) in methanol (1 mL) and N,N-diisopropylethylamine (30 µL, 0.172 mmol) was heated at 65° C. for 24 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to give the pure title compound as a mixture of diastereomers: (10.3 mg, 32%). LC/MS Condition E: ret time 1.13 min; m/e=505 (M+H)$^+$. LC/MS Condition F: ret time 1.17 min; m/e=505 (M+H)$^+$.

Example 2105: (R)-1-(3-((2,2'-dimethyl-3'-(3-(piperidin-1-yl)propoxy)-[1,1'-biphenyl]-3-yl)oxy)propyl)pyrrolidin-3-ol

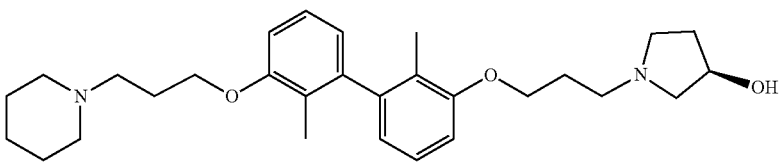 [SMILES: Cc1c(OCCCN2CCCCC2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and piperidine (36.8 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (19.1 mg, 95%). $^1$H NMR (500 MHz, DMSO-d$_6$) δ 7.18 (t, J=7.9 Hz, 2H), 6.94 (d, J=8.1 Hz, 2H), 6.64 (d, J=7.3 Hz, 2H), 4.26 (br. s., 1H), 4.11-3.97 (m, 4H), 3.36 (br. s., 2H), 2.93-2.52 (m, 10H), 1.98 (br. s., 5H), 1.83 (s, 6H), 1.64 (br. s., 1H), 1.55 (br. s., 4H), 1.42 (br. s., 2H). LC/MS Condition E: RT (Retention Time)=1.28 min; m/e=467 (M+H)$^+$.

Example 2106: (R)-1-(3-((3'-(3-(4-(hydroxymethyl)piperidin-1-yl)propoxy)-2,2'-dimethyl-[1,1'-biphenyl]-3-yl)oxy)propyl)pyrrolidin-3-ol

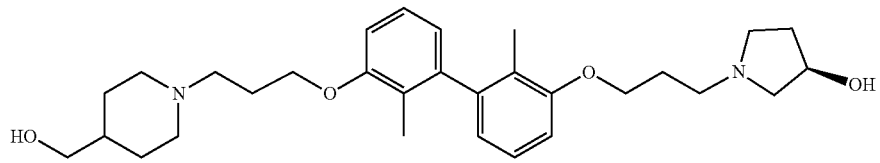 [SMILES: Cc1c(OCCCN2CCC(CO)CC2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and piperidin-4-ylmethanol (49.8 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (19.9 mg, 93%). $^1$H NMR (500 MHz, DMSO-d$_6$) δ 7.18 (t, J=7.9 Hz, 2H), 6.93 (d, J=8.1 Hz, 2H), 6.64 (d, J=7.3 Hz, 2H), 4.22 (br. s., 1H), 4.08-3.94 (m, 4H), 3.37 (br. s., 3H), 3.24 (d, J=5.9 Hz, 2H), 2.94 (br. s., 2H), 2.85-2.63 (m, 4H), 2.55 (s, 2H), 2.06-1.92 (m, 6H), 1.83 (s, 6H), 1.69-1.55 (m, 3H), 1.37 (br. s., 1H), 1.22-1.05 (m, 2H).

LC/MS Condition E: RT=1.15 min; m/e=497 (M+H)$^+$.

Example 2107: N-(1-(3-((3'-(3-((R)-3-hydroxypyrrolidin-1-yl)propoxy)-2,2'-dimethyl-[1,1'-biphenyl]-3-yl)oxy)propyl)pyrrolidin-3-yl)acetamide

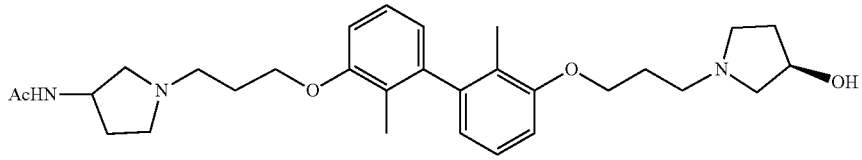 [SMILES: CC(=O)NC1CCN(CCCOc2cccc(-c3cccc(OCCCN4CC[C@@H](O)C4)c3C)c2C)C1]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and N-(pyrrolidin-3-yl)acetamide (55.4 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (18 mg, 77%).
$^1$H NMR (500 MHz, DMSO-d$_6$) δ 7.99 (d, J=6.6 Hz, 1H), 7.18 (t, J=7.9 Hz, 2H), 6.93 (d, J=8.1 Hz, 2H), 6.64 (dd, J=7.3, 4.0 Hz, 2H), 4.25 (br. s., 1H), 4.13 (br. s., 1H), 4.10-3.97 (m, 4H), 2.93-2.73 (m, 4H), 2.71-2.57 (m, 5H), 2.43 (d, J=6.2 Hz, 1H), 2.38-2.32 (m, 1H), 2.14-1.91 (m, 7H), 1.83 (d, J=2.9 Hz, 6H), 1.78 (s, 3H), 1.63 (br. s., 1H), 1.54 (dd, J=13.2, 6.2 Hz, 1H). LC/MS Condition E: RT=1.15 min; m/e=510 (M+H)$^+$.

Example 2108: (R)-1-(3-((2,2'-dimethyl-3'-(3-(4-(pyridin-2-yl)piperazin-1-yl)propoxy)-[1,1'-biphenyl]-3-yl)oxy)propyl)pyrrolidin-3-ol

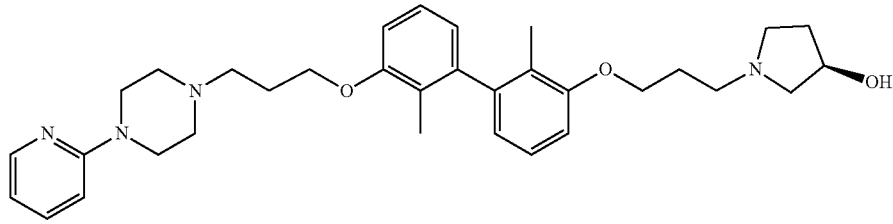 [SMILES: Cc1c(OCCCN2CCN(c3ccccn3)CC2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and 1-(pyridin-2-yl)piperazine (70.6 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (23.5 mg, 97%).
$^1$H NMR (500 MHz, METHANOL-d$_4$) δ 8.11 (d, J=4.8 Hz, 1H), 7.59 (t, J=7.7 Hz, 1H), 7.22-7.13 (m, 2H), 6.94 (d, J=8.1 Hz, 2H), 6.85 (d, J=8.4 Hz, 1H), 6.74-6.63 (m, 3H), 4.52 (br. s., 1H), 4.15 (d, J=5.9 Hz, 4H), 3.57 (d, J=4.8 Hz, 4H), 3.39 (d, J=8.4 Hz, 1H), 3.23 (d, J=4.0 Hz, 3H), 3.20-3.09 (m, 2H), 2.75-2.68 (m, 6H), 2.29-2.19 (m, 3H), 2.15-2.09 (m, 2H), 1.97 (br. s., 1H), 1.91 (d, J=8.4 Hz, 6H). LC/MS Condition E: RT=1.12 min; m/e=545 (M+H)$^+$.

Example 2109: (R)-2-(4-(3-((3'-(3-(3-hydroxypyrrolidin-1-yl)propoxy)-2,2'-dimethyl-[1,1'-biphenyl]-3-yl)oxy)propyl)piperazin-1-yl)-N-isopropylacetamide

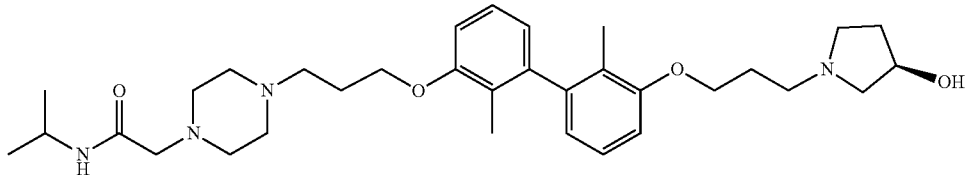 [SMILES: Cc1c(OCCCN2CCN(CC(=O)NC(C)C)CC2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and N-isopropyl-2-(piperazin-1-yl)acetamide (80 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (21.6 mg, 85%). $^1$H NMR (500 MHz, DMSO-$d_6$) δ 7.39 (d, J=8.4 Hz, 1H), 7.18 (t, J=7.7 Hz, 2H), 6.93 (d, J=8.1 Hz, 2H), 6.64 (d, J=8.1 Hz, 2H), 4.22 (br. s., 1H), 4.10-3.99 (m, 4H), 3.88 (dd, J=14.1, 6.8 Hz, 1H), 2.80 (br. s., 1H), 2.75-2.62 (m, 3H), 2.55 (s, 3H), 2.50-2.31 (m, 10H), 2.06-1.87 (m, 6H), 1.83 (s, 6H), 1.58 (br. s., 1H), 1.06 (d, J=6.6 Hz, 6H). LC/MS Condition E: RT=1.20 min; m/e=567 (M+H)⁺.

Example 2110: (R)-1-(3-((2,2'-dimethyl-3'-(3-(methyl(phenethyl)amino)propoxy)-[1,1'-biphenyl]-3-yl)oxy)propyl)pyrrolidin-3-ol

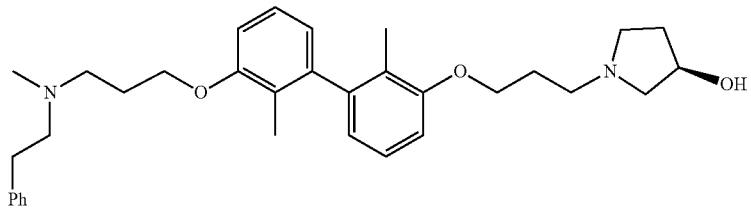 [SMILES: Cc1c(OCCCN(C)CCc2ccccc2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and N-methyl-2-phenylethanamine (58.5 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (12.5 mg, 46%).

$^1$H NMR (500 MHz, DMSO-$d_6$) δ 7.21 (td, J=15.4, 7.3 Hz, 7H), 6.92 (dd, J=17.8, 8.3 Hz, 2H), 6.64 (dd, J=7.2, 5.0 Hz, 2H), 4.33 (br. s., 1H), 4.11-3.95 (m, 4H), 3.16-2.82 (m, 5H), 2.79-2.59 (m, 6H), 2.34 (br. s., 3H), 2.13-1.99 (m, 3H), 1.97-1.88 (m, 2H), 1.83 (s, 6H), 1.73 (br. s., 1H). LC/MS Condition E: RT=1.58 min; m/e=517 (M+H)⁺.

Example 2111: (R)-1-(3-((3'-(3-(4-(2-methoxyphenyl)piperazin-1-yl)propoxy)-2,2'-dimethyl-[1,1'-biphenyl]-3-yl)oxy)propyl)pyrrolidin-3-ol

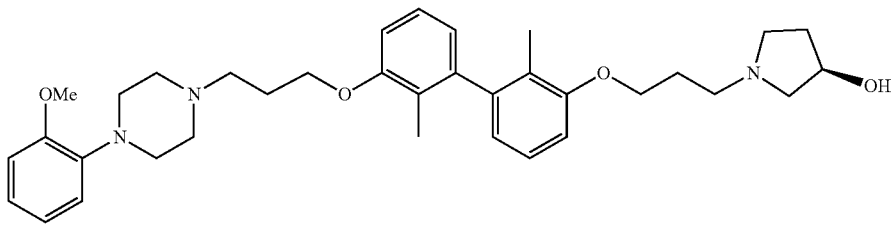 [SMILES: COc1ccccc1N1CCN(CCCOc2cccc(-c3cccc(OCCCN4CC[C@@H](O)C4)c3C)c2C)CC1]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and 1-(2-methoxyphenyl)piperazine (83 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (16.3 mg, 66%).

$^1$H NMR (500 MHz, DMSO-$d_6$) δ 7.18 (t, J=7.9 Hz, 2H), 6.98-6.90 (m, 4H), 6.88 (s, 2H), 6.65 (t, J=7.0 Hz, 2H), 4.26 (br. s., 1H), 4.12-3.99 (m, 4H), 3.77 (s, 3H), 2.97 (br. s., 4H), 2.92-2.75 (m, 4H), 2.55 (s, 8H), 2.08-1.93 (m, 5H), 1.84 (s, 6H), 1.65 (br. s., 1H). LC/MS Condition E: RT=1.39 min; m/e=574 (M+H)$^+$.

Example 2112: (R)-1-(3-((3'-(3-(((R)-2-hydroxy-2-phenylethyl)amino)propoxy)-2,2'-dimethyl-[1,1'-biphenyl]-3-yl)oxy)propyl)pyrrolidin-3-ol

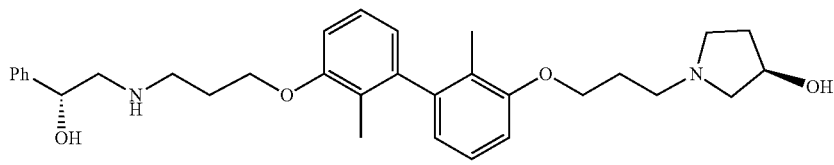 [SMILES: Cc1c(OCCCNC[C@H](O)c2ccccc2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (R)-2-amino-1-phenylethanol (59.3 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (10.7 mg, 47%).

$^1$H NMR (500 MHz, DMSO-$d_6$) δ 7.38-7.30 (m, 4H), 7.27-7.22 (m, 1H), 7.21-7.14 (m, 2H), 6.93 (d, J=8.1 Hz, 2H), 6.64 (t, J=7.9 Hz, 2H), 4.72 (dd, J=8.8, 3.7 Hz, 1H), 4.19 (br. s., 1H), 4.05 (dd, J=13.8, 7.5 Hz, 4H), 2.93-2.69 (m, 5H), 2.67-2.57 (m, 3H), 2.47 (d, J=7.3 Hz, 1H), 2.36 (d, J=8.4 Hz, 1H), 2.04-1.95 (m, 3H), 1.91-1.87 (m, 2H), 1.83 (s, 6H). LC/MS Condition E: RT=1.36 min; m/e=519 (M+H)$^+$.

Example 2113: (R)-1-(3-((3'-(3-(((S)-2-hydroxy-2-phenylethyl)amino)propoxy)-2,2'-dimethyl-[1,1'-biphenyl]-3-yl)oxy)propyl)pyrrolidin-3-ol

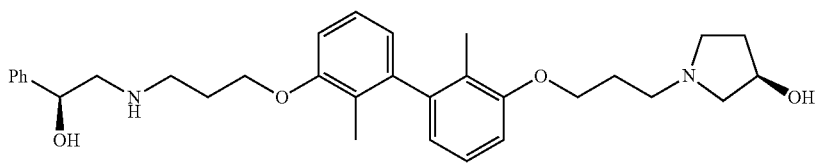 [SMILES: Cc1c(OCCCNC[C@@H](O)c2ccccc2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (S)-2-amino-1-phenylethanol (59.3 mg, 0.433 mmol) was treated with MeOH (1 mL) and Hunig's base (100 μl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (9.0 mg, 37%).
$^1$H NMR (500 MHz, DMSO-d$_6$) δ 7.39-7.28 (m, 7H), 7.25 (d, J=7.0 Hz, 2H), 7.21-7.15 (m, 2H), 6.93 (d, J=8.4 Hz, 2H), 6.64 (t, J=7.3 Hz, 2H), 4.70 (dd, J=8.6, 3.9 Hz, 1H), 4.19 (br. s., 1H), 4.05 (dd, J=12.7, 7.2 Hz, 4H), 2.89-2.71 (m, 5H), 2.64-2.56 (m, 3H), 2.46 (d, J=6.6 Hz, 1H), 2.35 (d, J=7.0 Hz, 1H), 2.04-1.94 (m, 3H), 1.90-1.87 (m, 1H), 1.83 (s, 6H), 1.55 (d, J=3.7 Hz, 1H). $^1$H NMR showed some extra protons in the aromatic region that might came from the sm/amine). LC/MS Condition E: RT=1.34 min; m/e=519 (M+H)$^+$.

Example 2114: (R)-1-(3-((3'-(3-((R)-3-hydroxypyrrolidin-1-yl)propoxy)-2,2'-dimethyl-[1,1'-biphenyl]-3-yl)oxy)propyl)piperidin-3-ol

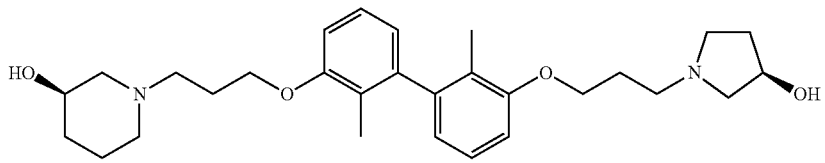 [SMILES: Cc1c(OCCCN2CCC[C@@H](O)C2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (R)-piperidin-3-ol, HCl (59.5 mg, 0.433 mmol) was treated with MeOH (1 mL) and Hunig's base (100 μl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (17.3 mg, 79%).
$^1$H NMR (500 MHz, DMSO-d$_6$) δ 7.18 (t, J=7.9 Hz, 2H), 6.93 (d, J=8.4 Hz, 2H), 6.64 (dd, J=7.2, 3.1 Hz, 2H), 4.23 (br. s., 1H), 4.09-3.96 (m, 4H), 3.48 (br. s., 1H), 2.91-2.56 (m, 8H), 2.05-1.86 (m, 8H), 1.83 (s, 6H), 1.78 (d, J=7.3 Hz, 2H), 1.61 (br. s., 2H), 1.41 (d, J=11.7 Hz, 1H), 1.10 (br. s., 1H). LC/MS Condition E: RT=1.17 min; m/e=483 (M+H)$^+$.

Example 2115: (S)-1-(3-((3'-(3-((R)-3-hydroxypyrrolidin-1-yl)propoxy)-2,2'-dimethyl-[1,1'-biphenyl]-3-yl)oxy)propyl)piperidin-3-ol

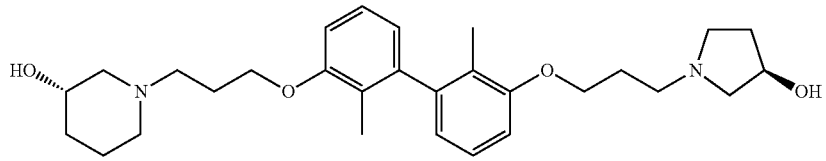 [SMILES: Cc1c(OCCCN2CC[C@@H](O)C2)cccc1-c1cccc(OCCCN2CCC[C@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (S)-piperidin-3-ol, HCl (59.5 mg, 0.433 mmol) was treated with MeOH (1 mL) and Hunig's base (100 μl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (15.9 mg, 71%).

$^1$H NMR (500 MHz, DMSO-d$_6$) δ 7.18 (t, J=7.7 Hz, 2H), 6.93 (d, J=8.1 Hz, 2H), 6.67-6.61 (m, 2H), 4.25 (br. s., 1H), 4.10-3.98 (m, 4H), 3.49 (br. s., 1H), 3.37 (br. s., 2H), 2.95-2.60 (m, 8H), 2.08-1.92 (m, 6H), 1.79 (br. s., 2H), 1.63 (br. s., 2H), 1.42 (d, J=13.2 Hz, 1H), 1.11 (br. s., 1H). LC/MS Condition E: RT=1.22 min; m/e=483 (M+H)$^+$.

Example 2116: (S)-2-((3-((3'-(3-((R)-3-hydroxypyrrolidin-1-yl)propoxy)-2,2'-dimethyl-[1,1'-biphenyl]-3-yl)oxy)propyl)amino)-3-(pyridin-2-yl)propanoic acid

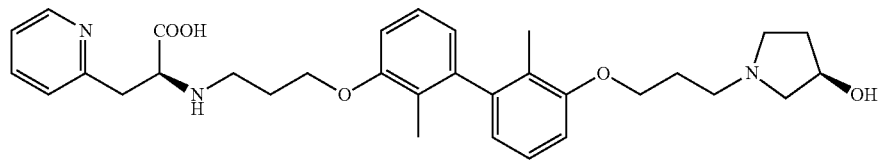 [SMILES: Cc1c(OCCCN[C@@H](Cc2ccccn2)C(=O)O)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (S)-2-amino-3-(pyridin-2-yl)propanoic acid (71.9 mg, 0.433 mmol) was treated with MeOH (1 mL) and Hunig's base (100 µl, 0.573 mmol). The resulting mixture was stirred at 60° C. for 16 h. The reaction mixture was filtered and the filtrate was purified via preparative LC/MS with the following conditions: ColumnX-Bridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (4.8 mg, 20%). $^1$H NMR (500 MHz, DMSO-d$_6$) δ 8.30 (br. s., 1H), 7.69 (t, J=7.5 Hz, 1H), 7.31 (d, J=7.7 Hz, 1H), 7.24-7.15 (m, 3H), 6.92 (t, J=7.5 Hz, 2H), 6.69-6.59 (m, 2H), 4.24 (br. s., 1H), 4.11-3.99 (m, 4H), 3.68 (dd, J=7.2, 5.0 Hz, 1H), 3.28 (dd, J=15.4, 4.4 Hz, 1H), 3.14-2.94 (m, 3H), 2.90-2.58 (m, 5H), 2.55 (s, 1H), 2.15-1.93 (m, 5H), 1.84-1.76 (m, 6H), 1.62 (br. s., 1H).
LC/MS Condition E: RT=1.24 min; m/e=548 (M+H)$^+$.

Example 2117: (S)-2-((3-((3'-(3-((R)-3-hydroxypyrrolidin-1-yl)propoxy)-2,2'-dimethyl-[1,1'-biphenyl]-3-yl)oxy)propyl)amino)-3-(pyridin-3-yl)propanoic acid A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and (S)-2-amino-3-(pyridin-3-yl)propanoic acid, 2 HCl (103 mg, 0.433 mmol) was treated with MeOH (1 mL) and Hunig's Base (100 µl, 0.573 mmol). The resulting mixture was stirred at 60° C. for 16 h. The reaction mixture was filtered and the filtrate was purified via preparative LC/MS with the following conditions: ColumnX-Bridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (7.9 mg, 32%). $^1$H NMR (500 MHz, DMSO-d$_6$) δ 8.45 (s, 1H), 8.39 (d, J=4.8 Hz, 1H), 7.67 (d, J=7.7 Hz, 1H), 7.29-7.23 (m, 1H), 7.18 (t, J=7.7 Hz, 2H), 6.93 (d, J=8.1 Hz, 1H), 6.89 (d, J=8.4 Hz, 1H), 6.64 (t, J=6.8 Hz, 2H), 4.21 (br. s., 1H), 4.09-3.97 (m, 4H), 3.03-2.91 (m, 3H), 2.79 (d, J=7.0 Hz, 2H), 2.66 (br. s., 3H), 2.55 (s, 2H), 2.44 (d, J=8.1 Hz, 1H), 2.04-1.91 (m, 5H), 1.81 (d, J=11.7 Hz, 6H), 1.57 (br. s., 1H).

LC/MS Condition E: RT=1.13 min; m/e=548 (M+H)$^+$.

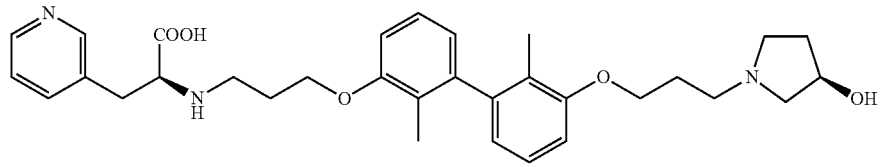 [SMILES: Cc1c(OCCCN[C@@H](Cc2cccnc2)C(=O)O)cccc1-c1cccc(OCCCN2CC[C@@H](O)C2)c1C]

Example 2118: (R)-1-(3-((2,2'-dimethyl-3'-(3-((2-(pyridin-2-yl)ethyl)amino)propoxy)-[1,1'-biphenyl]-3-yl)oxy)propyl)pyrrolidin-3-ol

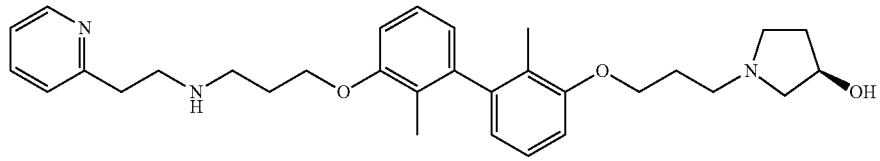 [SMILES: Cc1c(OCCCNCCc2ccccn2)cccc1-c1cccc(OCCCN2CC[C@@H](O)C2)c1C]

A mixture of (R)-1-(3-((3'-(3-bromopropoxy)-2,2'-dimethyl-[1,1'-biphenyl]-3-yl)oxy)propyl)pyrrolidin-3-ol (20 mg, 0.043 mmol) and 2-(pyridin-2-yl)ethanamine, 2 HCl (84 mg, 0.433 mmol) was treated with MeOH (1 mL) and Hunig's Base (100 µl, 0.573 mmol). The resulting mixture was stirred at 60° C. for 16 h. The reaction mixture was filtered and the filtrate was purified via preparative LC/MS with the following conditions: ColumnXBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 10-70% B over 22 minutes, then a 5-minute hold at 100% B; Flow: 20 mL/min. Fractions containing the desired products were combined and dried via centrifugal evaporation to give the pure title compound: (16.5 mg, 73.5%). $^1$H NMR (500 MHz, DMSO-d$_6$) δ 8.46 (d, J=4.4 Hz, 1H), 7.70 (t, J=7.5 Hz, 1H), 7.29 (d, J=7.7 Hz, 1H), 7.24-7.20 (m, 1H), 7.20-7.13 (m, 2H), 6.93 (d, J=8.4 Hz, 2H), 6.64 (dd, J=12.3, 7.5 Hz, 2H), 4.19 (br. s., 1H), 4.12-3.98 (m, 4H), 3.39 (br. s., 5H), 3.13-3.05 (m, 2H), 2.99-2.88 (m, 4H), 2.76-2.68 (m, 1H), 2.66-2.54 (m, 3H), 2.46 (d, J=6.6 Hz, 1H), 2.36 (d, J=8.8 Hz, 1H), 2.04-1.94 (m, 3H), 1.82 (s, 6H), 1.59-1.47 (m, 1H). LC/MS Condition E: RT=1.24 min; m/e=504 (M+H)$^+$.

Example 2119: (2S,2'S)-1,1'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(piperidine-2-carboxylic acid)

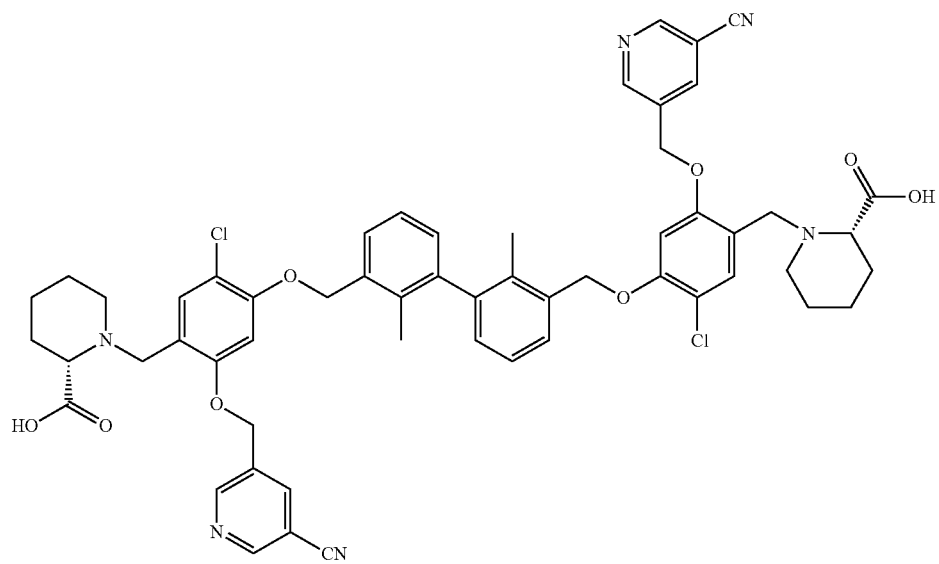 [SMILES: Cc1c(COc2cc(OCc3cncc(C#N)c3)c(CN3CCCC[C@H]3C(=O)O)cc2Cl)cccc1-c1cccc(COc2cc(OCc3cncc(C#N)c3)c(CN3CCCC[C@H]3C(=O)O)cc2Cl)c1C]

To a reaction vial containing 5,5'-((((((2,2'-dimethyl-[1,1'-biphenyl]-3,3'-diyl)bis(methylene))bis(oxy))bis(4-chloro-2-formyl-5,1-phenylene))bis(oxy))bis(methylene))dinicotinonitrile (45 mg, 0.057 mmol), and L-pipecolic acid (70 mg, 0.542 mmol), was added 1,2-dichloroethane (1.13 mL), ethanol (900 µL), acetic acid (12 µL, 0.210 mmol) and activated 4 A mol. sieves. The reaction was stirred at room temperature for 45 min, then treated dropwise with sodium cyanoborohydride, 1.0M in THF (230 µL, 0.230 mmol) over 2-4 h. After the addition is complete, the reaction was stirred at room temperature overnight. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-80% B over 25 minutes, then a 5-minute hold at 100% B; Flow: 20 mL/min to give the pure title compound: (11.5 mg, 20%). $^1$H NMR (500 MHz, DMSO-$d_6$) δ 9.01 (dd, J=5.8, 2.1 Hz, 4H), 8.46 (s, 2H), 7.52 (d, J=7.0 Hz, 2H), 7.43 (s, 2H), 7.31 (t, J=7.5 Hz, 2H), 7.17-7.08 (m, 4H), 5.38-5.32 (m, 4H), 5.31-5.24 (m, 4H), 3.78 (br d, J=13.7 Hz, 2H), 3.61 (br d, J=13.7 Hz, 2H), 3.13 (br dd, J=7.6, 4.3 Hz, 2H), 2.91-2.86 (m, 2H), 2.37-2.21 (m, 2H), 2.03 (s, 6H), 1.79 (br s, 2H), 1.72 (br d, J=9.2 Hz, 2H), 1.48 (br s, 6H), 1.36 (br s, 2H). LC/MS Condition E: ret time 1.76 min; m/e=1009 (M+H)$^+$.

LC/MS Condition F: ret time 1.77 min; m/e=1009 (M+H)$^+$.

Example 2120: (S)-1-(5-chloro-4-((3'-((2-chloro-5-((5-cyanopyridin-3-yl)methoxy)-4-(hydroxymethyl)phenoxy)methyl)-2,2'-dimethyl-[1,1'-biphenyl]-3-yl)methoxy)-2-((5-cyanopyridin-3-yl)methoxy)benzyl)piperidine-2-carboxylic acid

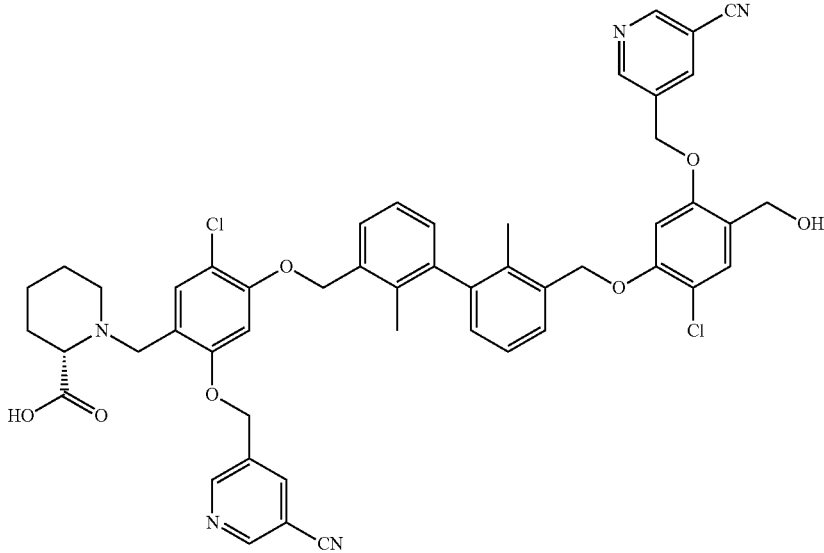 [SMILES: Cc1c(COc2cc(OCc3cncc(C#N)c3)c(CO)cc2Cl)cccc1-c1cccc(COc2cc(OCc3cncc(C#N)c3)c(CN3CCCC[C@H]3C(=O)O)cc2Cl)c1C]

From the reaction mixture for Example 2119, Example 2120 was also isolated: (11.8 mg, 22%). LC/MS Condition E: ret time 2.01 min; m/e=898 (M+H)$^+$. LC/MS Condition F: ret time 2.03 min; m/e=898 (M+H)$^+$.

Example 2121: (2R,2'R)-2,2'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxy-2-methylpropanoic acid)

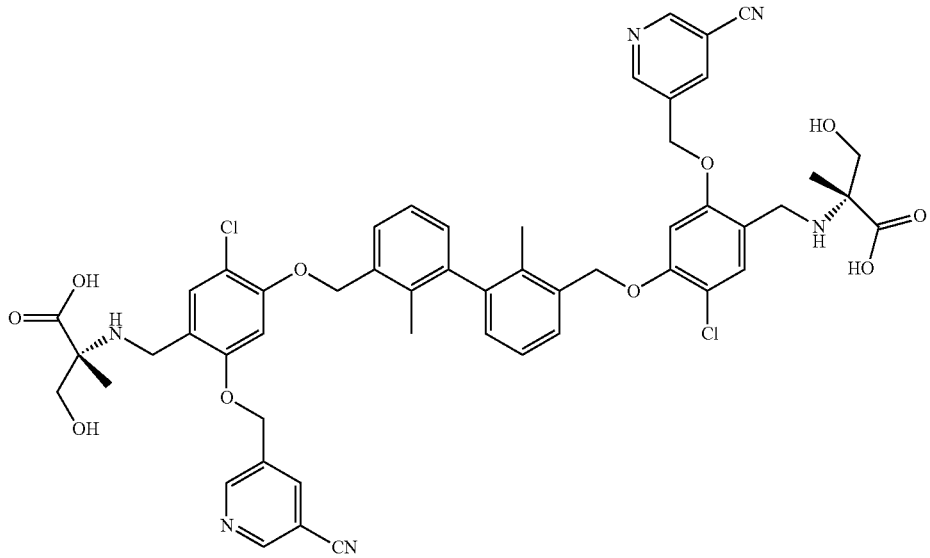 [SMILES: Cc1c(COc2cc(OCc3cncc(C#N)c3)c(CN[C@](C)(CO)C(=O)O)cc2Cl)cccc1-c1cccc(COc2cc(OCc3cncc(C#N)c3)c(CN[C@](C)(CO)C(=O)O)cc2Cl)c1C]

To a reaction vial containing 5,5'-((((((2,2'-dimethyl-[1,1'-biphenyl]-3,3'-diyl)bis(methylene))bis(oxy))bis(4-chloro-2-formyl-5,1-phenylene))bis(oxy))bis(methylene))dinicotinonitrile (45 mg, 0.057 mmol), and 2-methyl-d-serine (66.9 mg, 0.562 mmol), was added 1,2-dichloroethane (2.5 mL), ethanol (2.0 mL), acetic acid (22 µL, 0.384 mmol) and activated 4 A mol. sieves. The reaction was stirred at room temp. for 2 h, then treated dropwise with sodium cyanoborohydride, 1.0M in THF (400 µL, 0.400 mmol) over 3.5 h. After the addition was complete, the reaction was stirred at room temp. for 7 days. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to give the pure title compound: (4.2 mg, 4%). LC/MS Condition E: ret time 1.67 min; m/e=989 (M+H)$^+$. LC/MS Condition F: ret time 1.76 min; m/e=989 (M+H)$^+$.

Example 2122: 2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(propane-1,3-diol)

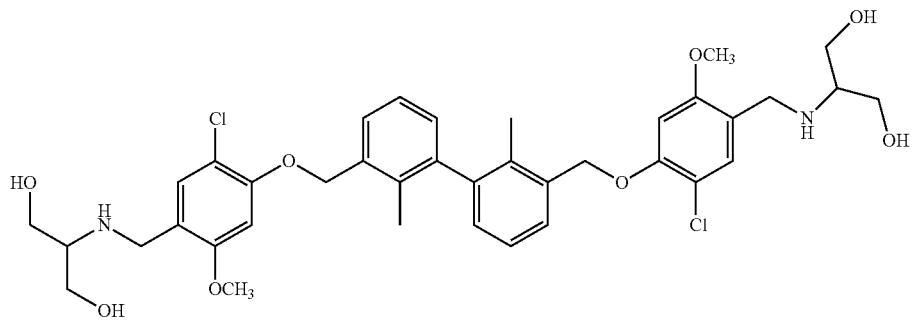 [SMILES: COc1cc(OCc2cccc(-c3cccc(COc4cc(OC)c(CNC(CO)CO)cc4Cl)c3C)c2C)c(Cl)cc1CNC(CO)CO]

To a solution of 4,4'-(((2,2'-dimethyl-[1,1'-biphenyl]-3,3'-diyl)bis(methylene))bis(oxy))bis(5-chloro-2-methoxybenzaldehyde) (35 mg, 0.060 mmol) in a mixture of 1,2-dichloroethane (1.25 mL) and ethanol (1.00 mL) was added 2-amino-1,3-propanediol (55 mg, 0.604 mmol), acetic acid (11.8 µL, 0.206 mmol) and activated 4 A mol sieves. The reaction was stirred at room temp, for 45 min, then treated dropwise with sodium cyanoborohydride, 1.0 M in THF (242 µL, 0.242 mmol) over 90 min. After the addition was complete, the reaction was allowed to stir at room temp overnight. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min to give the pure title compound: (36.2 mg, 82%). LC/MS Condition E: ret time 1.58 min; m/e=729 (M+H)$^+$.

LC/MS Condition F: ret time 1.64 min; m/e=729 (M+H)$^+$.

Example 2123: (2S,2'S)-2,2'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxy-2-methylpropanoic acid)

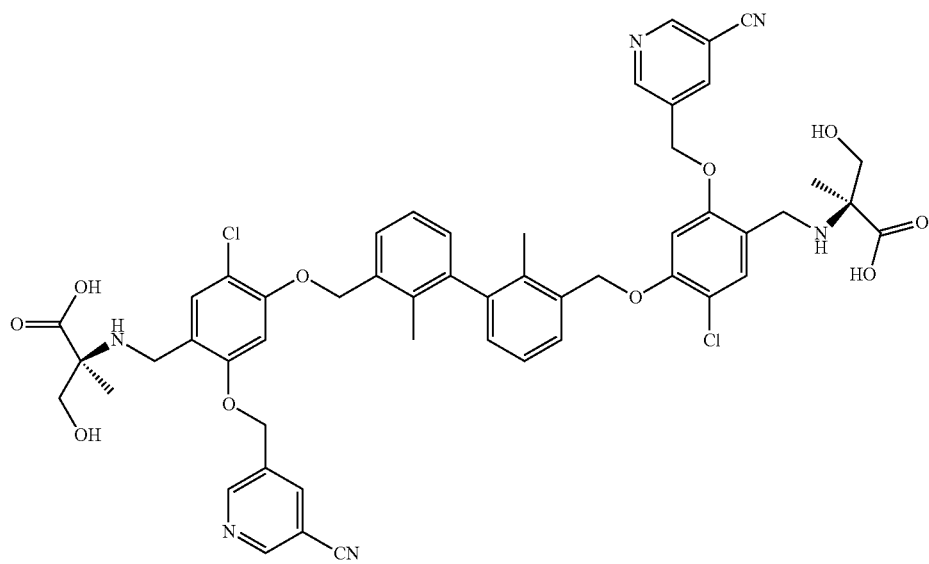 [SMILES: Cc1c(COc2cc(OCc3cncc(C#N)c3)c(CN[C@@](C)(CO)C(=O)O)cc2Cl)cccc1-c1cccc(COc2cc(OCc3cncc(C#N)c3)c(CN[C@@](C)(CO)C(=O)O)cc2Cl)c1C]

To a reaction vial containing 5,5'-((((((2,2'-dimethyl-[1,1'-biphenyl]-3,3'-diyl)bis(methylene))bis(oxy))bis(4-chloro-2-formyl-5,1-phenylene))bis(oxy))bis(methylene)) dinicotinonitrile (78 mg, 0.100 mmol), and 2-methyl-L-serine (66.9 mg, 0.562 mmol), was added 1,2-dichloroethane (2.5 mL), ethanol (2.0 mL), acetic acid (22 μL, 0.384 mmol) and activated 4 A mol. sieves. The reaction was stirred at room temp for 105 min, then treated dropwise with sodium cyanoborohydride, 1.0 M in THF (400 μL, 0.400 mmol) over 2.5 h. After the addition was complete, anhydrous DMF (1.2 mL) was added and the reaction was stirred overnight at room temp. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-80% B over 25 minutes, then a 5-minute hold at 100% B; Flow: 20 mL/min to give the pure title compound: (8.3 mg, 8%). LC/MS Condition E: ret time 1.67 min; m/e=989 (M+H)$^+$. LC/MS Condition F: ret time 1.73 min; m/e=989 (M+H)$^+$. $^1$H NMR (500 MHz, DMSO-d$_6$) δ 9.03 (d, J=1.8 Hz, 2H), 9.01 (d, J=1.8 Hz, 2H), 8.51 (s, 2H), 7.55 (s, 2H), 7.49 (d, J=7.3 Hz, 2H), 7.30 (t, J=7.5 Hz, 2H), 7.14 (s, 2H), 7.12 (d, J=7.3 Hz, 2H), 5.36 (s, 4H), 5.31 (s, 4H), 3.98 (s, 4H), 2.55 (s, 4H), 2.03 (s, 6H), 1.25 (s, 6H).

Example 2124: (S)-2-((5-chloro-4-((3'-((2-chloro-5-((5-cyanopyridin-3-yl)methoxy)-4-(hydroxymethyl)phenoxy)methyl)-2,2'-dimethyl-[1,1'-biphenyl]-3-yl)methoxy)-2-((5-cyanopyridin-3-yl)methoxy)benzyl)amino)-3-hydroxy-2-methylpropanoic acid To a reaction vial containing 5,5'-((((((2,2'-dimethyl-[1,1'-biphenyl]-3,3'-diyl)bis(methylene))bis(oxy))bis(4-chloro-2-formyl-5,1-phenylene))bis(oxy))bis(methylene))dinicotinonitrile (78 mg, 0.100 mmol), and (R)-pyrrolidin-3-ol, HCl (111 mg, 0.898 mmol), was added 1,2-dichloroethane (2.5 mL), ethanol (2.0 mL), acetic acid (22

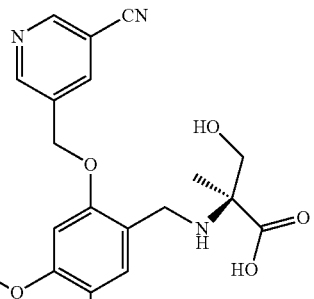
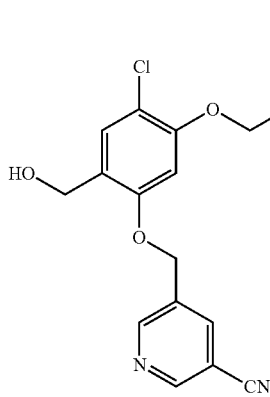

From the reaction mixture for Example 2123, Example 2124 was also isolated (5.9 mg, 6%). LC/MS Condition E: ret time 2.01 min; m/e=888 (M+H)+. LC/MS Condition F: ret time 2.16 min; m/e=888 (M+H)+.

Example 2125: 5,5'-((((((2,2'-dimethyl-[1,1'-biphenyl]-3,3'-diyl)bis(methylene))bis(oxy))bis(4-chloro-6-(((R)-3-hydroxypyrrolidin-1-yl)methyl)-3,1-phenylene))bis(oxy))bis(methylene))dinicotinonitrile μL, 0.384 mmol), N,N-diisopropylethylamine (20 μL, 0.115 mmol) and activated 4 A mol. sieves. The reaction was stirred at room temp. for 70 min, then treated dropwise with sodium cyanoborohydride, 1.0M in THF (400 μL, 0.400 mmol) over 2.5 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-85% B over 25 minutes, then a

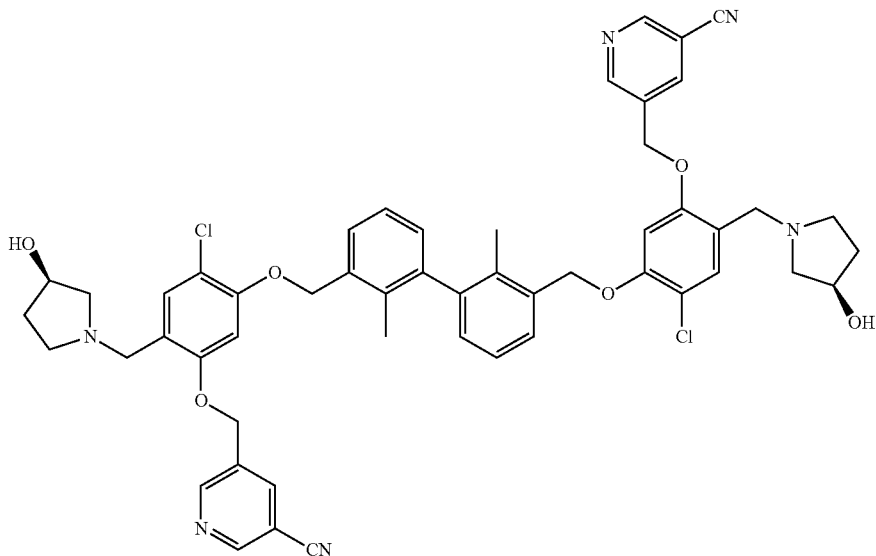 [SMILES: Cc1c(COc2cc(OCc3cncc(C#N)c3)c(CN3CC[C@@H](O)C3)cc2Cl)cccc1-c1cccc(COc2cc(OCc3cncc(C#N)c3)c(CN3CC[C@@H](O)C3)cc2Cl)c1C]

5-minute hold at 100% B; Flow: 20 mL/min to give the pure title compound: (38.4 mg, 38%). $^1$H NMR (500 MHz, DMSO-d$_6$) δ 9.01 (s, 2H), 8.99 (s, 2H), 8.43 (s, 2H), 7.52 (d, J=7.3 Hz, 2H), 7.37-7.27 (m, 4H), 7.16-7.10 (m, 4H), 5.33 (s, 4H), 5.27 (s, 4H), 4.22-4.16 (m, 2H), 3.59-3.49 (m, 4H), 2.67 (dd, J=9.5, 6.2 Hz, 2H), 2.61-2.55 (m, 2H), 2.46-2.39 (m, 2H), 2.31 (dd, J=9.5, 3.7 Hz, 2H), 2.04 (s, 6H), 1.99 (dd, J=13.4, 7.5 Hz, 2H), 1.57-1.51 (m, 2H). LC/MS Condition E: ret time 1.65 min; m/e=925 (M+H)$^+$.

LC/MS Condition F: ret time 1.94 min; m/e=925 (M+H)$^+$.

Example 2126: (R)-5-((4-chloro-5-((3'-((2-chloro-5-((5-cyanopyridin-3-yl)methoxy)-4-((3-hydroxypyrrolidin-1-yl)methyl)phenoxy)methyl)-2,2'-dimethyl-[1,1'-biphenyl]-3-yl)methoxy)-2-(hydroxymethyl)phenoxy)methyl)nicotinonitrile

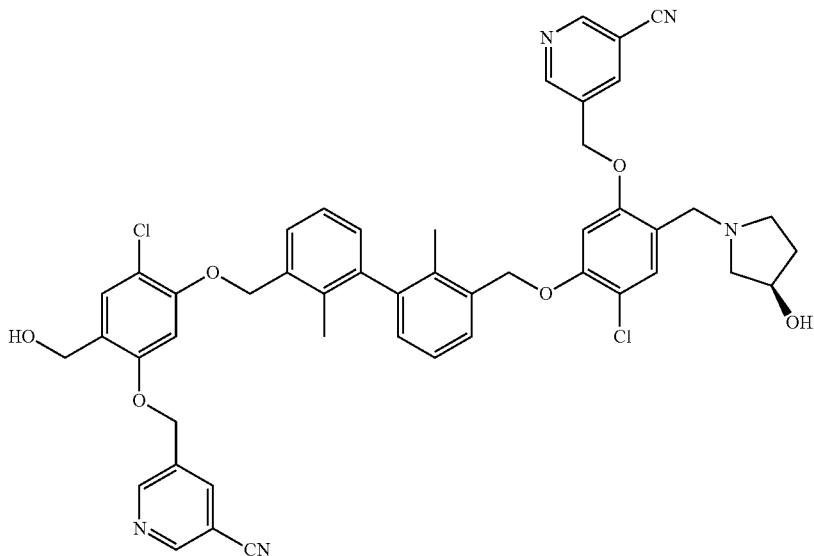 [SMILES: Cc1c(COc2cc(OCc3cncc(C#N)c3)c(CO)cc2Cl)cccc1-c1cccc(COc2cc(OCc3cncc(C#N)c3)c(CN3CC[C@@H](O)C3)cc2Cl)c1C]

From the reaction mixture for Example 2125, Example 2126 was also isolated (7.8 mg, 9%). $^1$H NMR (500 MHz, DMSO-d$_6$) δ 9.02 (s, 2H), 8.98 (d, J=6.2 Hz, 2H), 8.43 (s, 2H), 7.51 (t, J=7.7 Hz, 2H), 7.36 (s, 1H), 7.33 (s, 1H), 7.32-7.26 (m, 2H), 7.15-7.08 (m, 4H), 5.33 (br.s., 4H), 5.27 (br. s., 4H), 4.48 (d, J=3.7 Hz, 2H), 4.21-4.16 (m, 1H), 3.91 (s, 1H), 3.59-3.54 (m, 1H), 3.53-3.48 (m, 1H), 3.39-3.37 (m, 1H), 2.67 (dd, J=9.5, 6.2 Hz, 1H), 2.60-2.56 (m, 1H), 2.44-2.38 (m, 1H), 2.31 (dd, J=9.7, 3.9 Hz, 1H), 2.05 (s, 6H), 1.99 (dd, J=13.0, 6.8 Hz, 1H), 1.58-1.51 (m, 1H). LC/MS Condition E: ret time 2.10 min; m/e=856 (M+H)$^+$. LC/MS Condition F: ret time 1.96 min; m/e=856 (M+H)$^+$.

Example 2127: 5,5'-((((((2,2'-dimethyl-[1,1'-biphenyl]-3,3'-diyl)bis(methylene))bis(oxy))bis(4-chloro-6-((((S)-2,3-dihydroxypropyl)amino)methyl)-3,1-phenylene))bis(oxy))bis(methylene))dinicotinonitrile

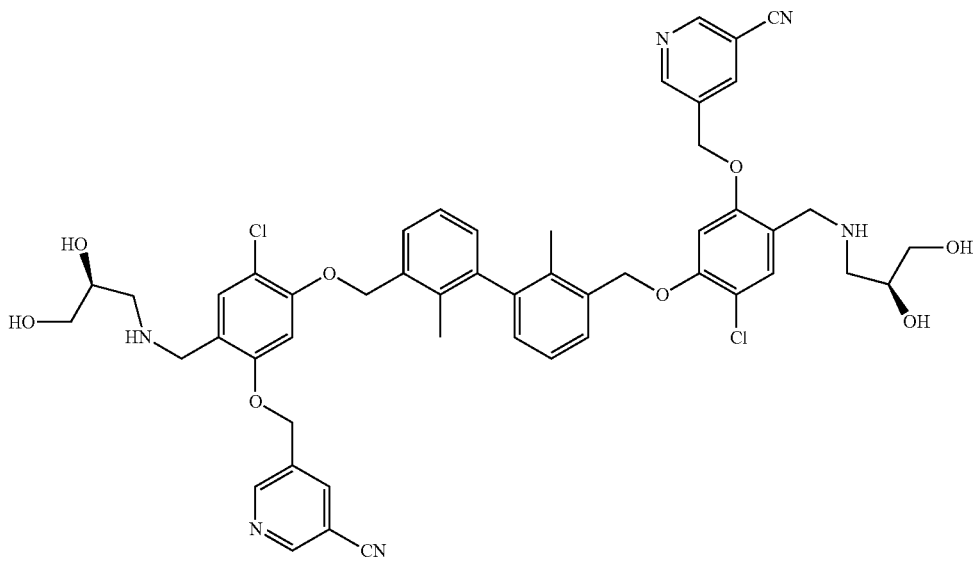 [SMILES: Cc1c(COc2cc(OCc3cncc(C#N)c3)c(CNC[C@H](O)CO)cc2Cl)cccc1-c1cccc(COc2cc(OCc3cncc(C#N)c3)c(CNC[C@H](O)CO)cc2Cl)c1C]

To a reaction vial containing 5,5'-((((((2,2'-dimethyl-[1,1'-biphenyl]-3,3'-diyl)bis(methylene))bis(oxy))bis(4-chloro-2-formyl-5,1-phenylene))bis(oxy))bis(methylene))dinicotinonitrile (78 mg, 0.100 mmol), and (S)-3-aminopropane-1,2-diol, HCl (121 mg, 0.948 mmol), was added 1,2-dichloroethane (2.5 mL), ethanol (2.0 mL), acetic acid (20 µL, 0.349 mmol), N,N-diisopropylethylamine (20 □L, 0.115 mmol) and activated 4 A mol. sieves. The reaction was stirred at room temp. for 70 min, then treated dropwise with sodium cyanoborohydride, 1.0M in THF (400 µL, 0.400 mmol) over 3.5 h. After the addition was complete, the reaction was stirred overnight at room temperature. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-90% B over 25 minutes, then a 5-minute hold at 100% B; Flow: 20 mL/min to give the pure title compound: (32.1 mg, 32%). $^1$H NMR (500 MHz, DMSO-$d_6$) δ 9.02 (d, J=1.8 Hz, 2H), 8.99 (d, J=1.5 Hz, 2H), 8.43 (s, 2H), 7.51 (d, J=7.7 Hz, 2H), 7.38 (s, 2H), 7.30 (t, J=7.7 Hz, 2H), 7.14-7.09 (m, 4H), 5.33 (s, 4H), 5.27 (s, 4H), 3.67 (d, J=4.0 Hz, 4H), 3.58-3.52 (m, 2H), 3.37-3.26 (m, 4H), 2.58 (dd, J=11.7, 4.4 Hz, 2H), 2.43 (dd, J=11.7, 7.3 Hz, 2H), 2.05 (s, 6H). LC/MS Condition E: ret time 1.81 min; m/e=933 (M+H)$^+$.

LC/MS Condition F: ret time 1.66 min; m/e=933 (M+H)$^+$.

Example 2128: 5,5'-((((((2,2'-dimethyl-[1,1'-biphenyl]-3,3'-diyl)bis(methylene))bis(oxy))bis(4-chloro-6-(((1,3-dihydroxypropan-2-yl)amino)methyl)-3,1-phenylene))bis(oxy))bis(methylene))dinicotinonitrile

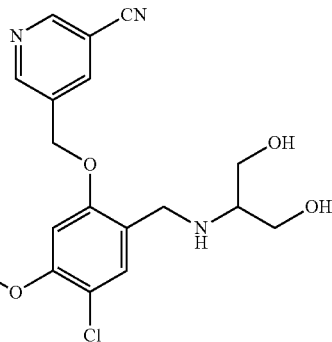
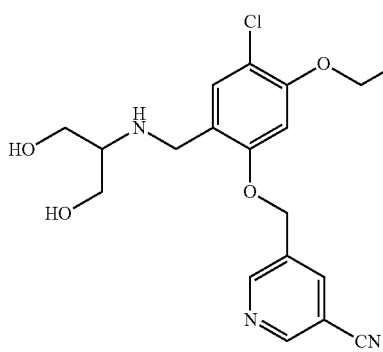

To a reaction vial containing 5,5'-((((((2,2'-dimethyl-[1,1'-biphenyl]-3,3'-diyl)bis(methylene))bis(oxy))bis(4-chloro-2-formyl-5,1-phenylene))bis(oxy))bis(methylene))dinicotinonitrile (63.6 mg, 0.081 mmol), and 2-aminopropane-1,3-diol (110 mg, 1.207 mmol), was added 1,2-dichloroethane (2.1 mL), ethanol (1.75 mL), acetic acid (15 µL, 0.262 mmol), and activated 4 A mol. sieves. The reaction was stirred at room temp for 90 min, then treated dropwise with sodium cyanoborohydride, 1.0M in THF (0.35 mL, 0.350 mmol) over 4 h. The crude material was purified via preparative LC/MS with the following conditions: Column: XBridge C18, 19×200 mm, 5-µm particles;

Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min to give the pure title compound: (49.4 mg, 64%). LC/MS Condition E: ret time 1.84 min; m/e=933 (M+H)+. LC/MS Condition F: ret time 1.82 min; m/e=933 (M+H)+.

Example 2129: 5-((4-chloro-5-((3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)methoxy)-2-(hydroxymethyl)phenoxy)methyl)nicotinonitrile

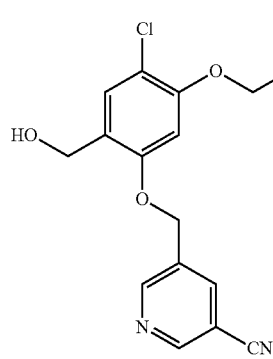

From the reaction mixture for Example 2128, the pure title compound above (Example 2129) (3.5 mg, 5%) was also isolated. LC/MS Condition E: ret time 2.39 min; m/e=860 (M+H)⁺. LC/MS Condition F: ret time 2.27 min; m/e=860 (M+H)⁺.

Example 2131: 5,5'-((((((2,2'-dimethyl-[1,1'-biphenyl]-3,3'-diyl)bis(methylene))bis(oxy))bis(4-chloro-6-(((1,3-dihydroxypropan-2-yl)((S)-2,3-dihydroxypropyl)amino)methyl)-3,1-phenylene))bis(oxy))bis(methylene))dinicotinonitrile

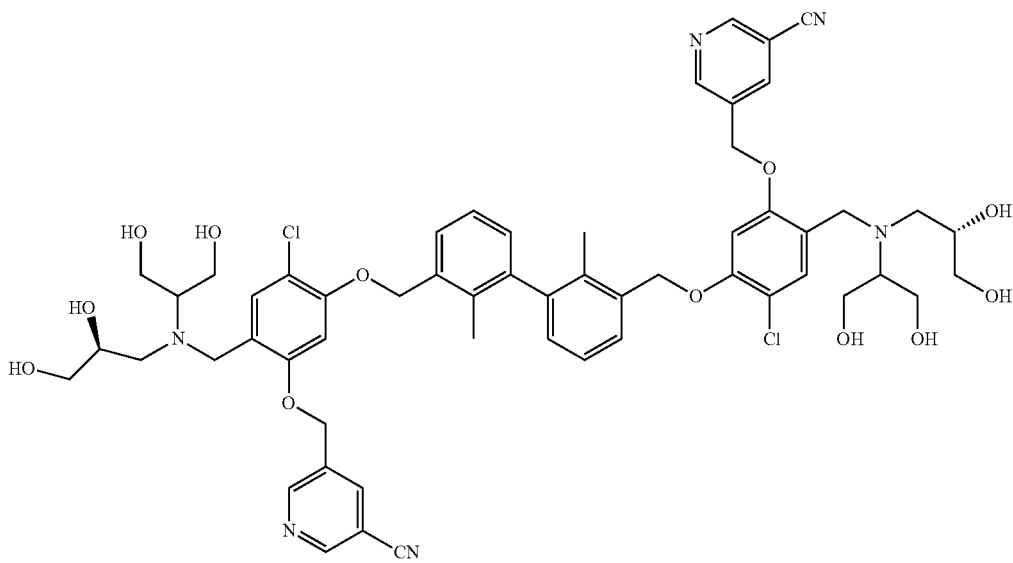 [SMILES: Cc1c(COc2cc(OCc3cncc(C#N)c3)c(CN(C[C@H](O)CO)C(CO)CO)cc2Cl)cccc1-c1cccc(COc2cc(OCc3cncc(C#N)c3)c(CN(C[C@H](O)CO)C(CO)CO)cc2Cl)c1C]

To a solution of 5,5'-((((((2,2'-dimethyl-[1,1'-biphenyl]-3,3'-diyl)bis(methylene))bis(oxy))bis(4-chloro-2-(((1,3-dihydroxypropan-2-yl)amino)methyl)-5,1-phenylene))bis(oxy))bis(methylene))dinicotinonitrile (10 mg, 10.7 µmol) in methanol (500 µL) was added (R)-glycidol (4 mg, 0.054 mmol), and the reaction was allowed to stir overnight at room temp. Additional (R)-glycidol (20 mg, 0.27 mmol) was added and the reaction was heated to 65° C. overnight. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 50-95% B over 25 minutes, then a 5-minute hold at 100% B; Flow: 20 mL/min to give the pure title compound: (1.6 mg, 12%). LC/MS Condition E: ret time 1.73 min; m/e=1081 (M+H)⁺. LC/MS Condition F: ret time 1.53 min; m/e=1081 (M+H)⁺.

Examples 2132 to 2136 were prepared as described below, and the HPLC LC/MS conditions employed for these examples were listed above for the 2001 compound series:

Example 2132: (1R,2S,5R)-3-((3-((3'-(3-(((1R,2S,3R,4R)-2,3-dihydroxy-4-(hydroxymethyl)cyclopentyl)amino)propoxy)-2,2'-dimethyl-[1,1'-biphenyl]-3-yl)oxy)propyl)amino)-5-(hydroxymethyl)cyclopentane-1,2-diol

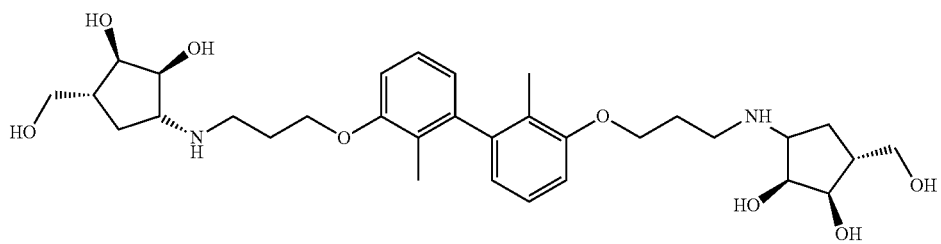

To a solution of 3,3'-bis(3-bromopropoxy)-2,2'-dimethyl-1,1'-biphenyl (20 mg, 0.044 mmol) and (1R,2S,3R,4R)-2,3-dihydroxy-4-(hydroxymethyl)-1-aminocyclopentane hydrochloride (84 mg, 0.457 mmol) in MeOH (1 mL) was added Hunig's Base (135 µl, 0.773 mmol) and the reaction was heated at 65° C. for 18 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-50% B over 15 minutes, then a 5-minute hold at 100% B; Flow: 20 mL/min to give the pure title compound: (16.2 mg, 63%). LC/MS Condition E: ret time 1.07 min; m/e=589 (M+H)+. LC/MS Condition F: ret time 1.06 min; m/e=589 (M+H)+.

Example 2133: 5,5'-((((((2,2'-dimethyl-[1,1'-biphenyl]-3,3'-diyl)bis(methylene))bis(oxy))bis(4-chloro-6-((4-(hydroxymethyl)-2-oxooxazolidin-3-yl)methyl)-3,1-phenylene))bis(oxy))bis(methylene))dinicotinonitrile

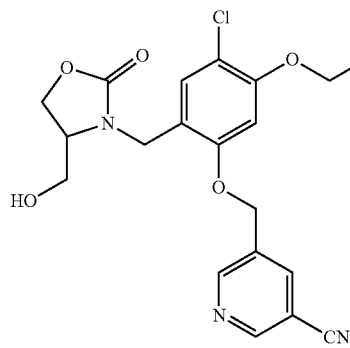

To a solution of 5,5'-((((((2,2'-dimethyl-[1,1'-biphenyl]-3,3'-diyl)bis(methylene))bis(oxy))bis(4-chloro-2-(((1,3-dihydroxypropan-2-yl)amino)methyl)-5,1-phenylene))bis(oxy))bis(methylene))dinicotinonitrile (20 mg, 0.021 mmol) and 1,1'-carbonyldiimidazole (18.9 mg, 0.117 mmol) in anhydrous DMF (0.7 mL) was added Hunig's Base (8 µl, 0.046 mmol) and the reaction was stirred at room temp for 18 h, followed by heating at 65° C. for 6 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 42-82% B over 25 minutes, then a 5-minute hold at 100% B; Flow: 20 mL/min to give the pure title compound (1.3 mg, 6%). LC/MS Condition E: ret time 2.14 min; m/e=985 (M+H)+. LC/MS Condition F: ret time 2.12 min; m/e=985 (M+H)+.

Intermediate: tert-butyl (3-(3-bromo-2-chlorophenoxy)propyl)carbamate

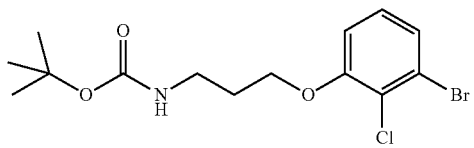 [SMILES: CC(C)(C)OC(=O)NCCCOc1cccc(Br)c1Cl]

To a mixture of tert-butyl (3-bromopropyl)carbamate (4.29 g, 18.02 mmol) and 3-bromo-2-chlorophenol (3.74 g, 18.02 mmol) in anhydrous DMF (25 mL) was added solid potassium carbonate (5 g, 36.2 mmol). The reaction was flushed with argon, stirred at room temp for 5 min, then heated at 50° C. for 19 h. The reaction was cooled to room temp, diluted with EtOAc (600 mL) and the organic layer was washed with water (4×150 mL), sat. aq NaCl (100 mL), dried over anhydrous Na2SO4, filtered and concentrated. The crude product (6.5 g, 94%) was used "as is" without further purification in subsequent reactions. ¹H NMR (500 MHz, CHLOROFORM-d) δ 7.26 (dd, J=8.1, 1.2 Hz, 1H), 7.10 (t, J=8.2 Hz, 1H), 6.88 (dd, J=8.3, 1.1 Hz, 1H), 5.17 (br s, 1H), 4.13 (t, J=5.8 Hz, 2H), 3.40 (q, J=5.8 Hz, 2H), 2.14-2.01 (m, 2H), 1.46 (s, 9H).

Intermediate: tert-butyl (3-(2-chloro-3-(4,4,5,5-tetramethyl-1,3,2-dioxaborolan-2-yl)phenoxy)propyl)carbamate

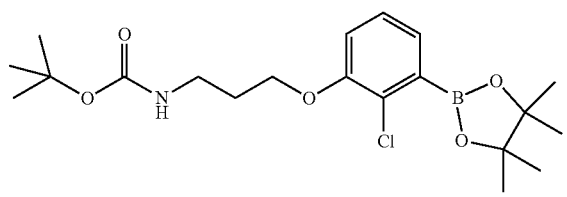 [SMILES: CC(C)(C)OC(=O)NCCCOc1cccc(B2OC(C)(C)C(C)(C)O2)c1Cl]

To a dry 150 mL pressure bottle under N2 was added tert-butyl (3-(3-bromo-2-chlorophenoxy)propyl)carbamate (2.5 g, 6.86 mmol), 4,4,4',4',5,5,5',5'-octamethyl-2,2'-bi(1,3,2-dioxaborolane) (2.96 g, 11.66 mmol), potassium acetate (2.1 g, 21.40 mmol), and anhydrous dioxane (60 mL). The reaction mixture was purged well with argon for 15 min, treated with [1,1'-bis(diphenylphosphino)ferrocene]dichloropalladium(II) (250 mg, 0.342 mmol), purged again with Ar for 15 min. The tube was securely capped and placed into an 80° C. oil bath for 24 h, followed by room temp for 5 days. The reaction mixture was diluted with EtOAc (400 mL) and water (300 mL), and filtered through a pad of celite. The organic layer was washed with brine (1×200 mL), dried over Na₂SO₄ and concentrated. The crude residue was dissolved in dichloromethane, applied to the head of a 120 g Teledyne Isco Silica Flash Column and purified on Biotage using a gradient from 100% hexanes to 100% dichloromethane over 8 column volumes. The fractions containing the product were evaporated in vacuo and then dried on high vacuum to give the pure title compound (2.25 g, 80%). ¹H NMR (500 MHz, CHLOROFORM-d) δ 7.28-7.26 (m, 1H), 7.23-7.19 (m, 1H), 7.00 (dd, J=8.0, 1.4 Hz, 1H), 4.11 (t, J=5.7 Hz, 2H), 3.40 (q, J=5.6 Hz, 2H), 2.07-1.99 (m, 2H), 1.46 (s, 9H), 1.39 (s, 12H).

Intermediate: di-tert-butyl (((2,2'-dichloro-[1,1'-biphenyl]-3,3'-diyl)bis(oxy))bis(propane-3,1-diyl)) dicarbamate

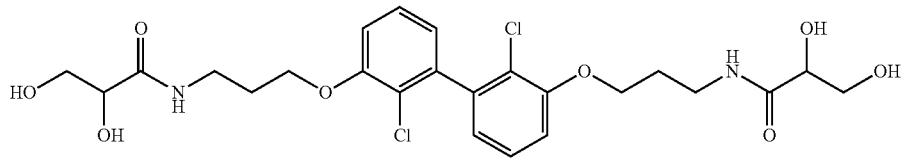

To a solution of tert-butyl (3-(2-chloro-3-(4,4,5,5-tetramethyl-1,3,2-dioxaborolan-2-yl)phenoxy)propyl)carbamate (1.68 g, 4.08 mmol) and tert-butyl (3-(3-bromo-2-chlorophenoxy)propyl)carbamate (1.488 g, 4.08 mmol) in THF (150 mL) was added potassium phosphate tribasic 0.5 M in water (20.5 ml, 10.25 mmol). The reaction mixture was flushed with argon, treated with 2ⁿᵈ generation xphos precatalyst (320 mg, 0.407 mmol), flushed with argon again and stirred at room temp for 66 h. The reaction was diluted with EtOAc (350 mL) and water (150 mL). The water layer was back extracted with additional EtOAc (200 mL). The organic layers were combined, washed with brine (1×75 mL), dried over Na₂SO₄, filtered and concentrated. The crude residue was applied to the head of a 120 g Teledyne Isco Silica Flash Column and purified on Biotage using a gradient from 100% hexanes to 100% CH₂Cl₂ over 5 column volumes, followed by 10-20% EtOAc in CH₂Cl₂. The fractions containing the product were evaporated in vacuo and then dried on high vacuum to give the pure title compound (2.08 g, 85%). ¹H NMR (500 MHz, CHLOROFORM-d) δ 7.31-7.26 (m, 1H), 6.98 (dd, J=8.3, 1.1 Hz, 1H), 6.89 (dd, J=7.6, 1.2 Hz, 1H), 4.25-4.09 (m, 2H), 3.52-3.31 (m, 2H), 2.17-2.07 (m, 2H), 1.45 (s, 9H). LC/MS Condition A: ret time 1.45 min; m/e=591, 593 (M+Na).

Example 2134: 3,3'-((2,2'-dichloro-[1,1'-biphenyl]-3,3'-diyl)bis(oxy))bis(propan-1-amine)

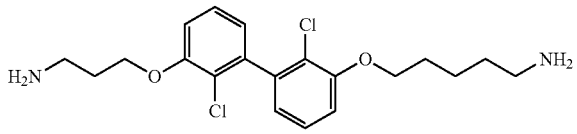

To a solution of di-tert-butyl (((2,2'-dichloro-[1,1'-biphenyl]-3,3'-diyl)bis(oxy))bis(propane-3,1-diyl))dicarbamate (1.28 g, 2.248 mmol) in dichloromethane (50 mL) was added TFA (6 mL, 78 mmol), and the mixture stirred at room temp for 2 h. The solvent was removed in vacuo and the residue was diluted with EtOAc (250 mL), washed with sat'd aq NaHCO₃ (1×50 mL), brine (1×50 mL), dried over Na₂SO₄, filtered and concentrated to give the title compound (388 mg, 47%). LC/MS Condition A: ret time 0.67 min; m/e=369, 371 (M+H)⁺.

Example 2135: N,N'-(((2,2'-dichloro-[1,1'-biphenyl]-3,3'-diyl)bis(oxy))bis(propane-3,1-diyl))bis(2,3-dihydroxypropanamide)

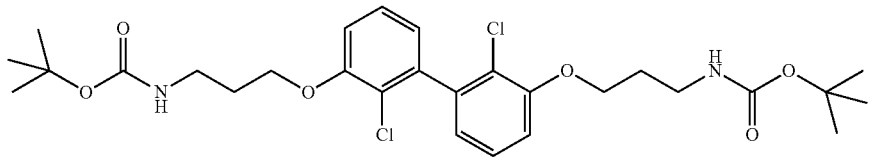 [SMILES: CC(C)(C)OC(=O)NCCCOc1cccc(-c2cccc(OCCCNC(=O)OC(C)(C)C)c2Cl)c1Cl]

To a mixture of 3,3'-((2,2'-dichloro-[1,1'-biphenyl]-3,3'-diyl)bis(oxy))bis(propan-1-amine) (18 mg, 0.049 mmol) and 1-hydroxy-7-azabenzotriazole (6.63 mg, 0.049 mmol) in DMF (0.9 mL) was added 2,3-dihydroxypropanoic acid, 2 M in water (190 µL, 0.380 mmol), N-methylmorpholine (15 µL, 0.136 mmol) and EDC (40 mg, 0.209 mmol). The reaction mixture was capped and allowed to stir at room temp for 18 h. The crude material was purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile:water with 0.1% trifluoroacetic acid; Gradient: 15-55% B over 15 minutes, then a 5-minute hold at 100% B; Flow: 20 mL/min to give the pure title compound (13.6 mg, 50%), as a bis TFA salt.

LC/MS Condition E: ret time 1.22 min; m/e=545, 547 (M+H)⁺. LC/MS Condition F: ret time 1.31 min; m/e=545, 547 (M+H)⁺.

Example 2136: (3R,3'R)-4,4'-((((2,2'-dichloro-[1,1'-biphenyl]-3,3'-diyl)bis(oxy))bis(propane-3,1-diyl))bis(azanediyl))bis(3-hydroxy-4-oxobutanoic acid)

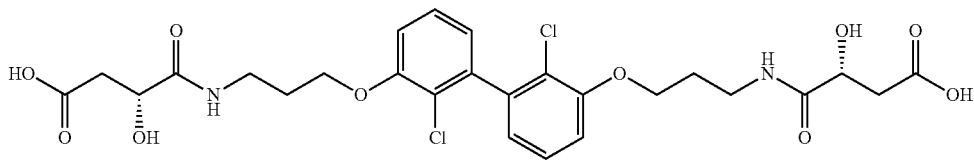 [SMILES: O=C(O)C[C@@H](O)C(=O)NCCCOc1cccc(-c2cccc(OCCCNC(=O)[C@H](O)CC(=O)O)c2Cl)c1Cl]

To a mixture of 3,3'-((2,2'-dichloro-[1,1'-biphenyl]-3,3'-diyl)bis(oxy))bis(propan-1-amine) (15.4 mg, 0.042 mmol), 1-hydroxy-7-azabenzotriazole (5 mg, 0.037 mmol), and D-(+)-malic acid (80 mg, 0.597 mmol) in DMF (0.9 mL) and water (0.2 mL) was added N-methylmorpholine (20 µL, 0.182 mmol), followed by EDC (30 mg, 0.156 mmol). The reaction mixture was capped and allowed to stir at 35° C. for 5 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-45% B over 25 minutes, then a 5-minute hold at 100% B; Flow: 20 mL/min. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile: water with 0.1% trifluoroacetic acid; Gradient: 10-40% B over 18 minutes, then a 3-minute hold at 100% B; Flow: 20 mL/min to give the pure title compound (2.6 mg, 9%) as a bis TFA salt. LC/MS Condition E: ret time 0.96 min; m/e=601, 603 (M+H)$^+$.
LC/MS Condition F: ret time 1.34 min; m/e=601, 603 (M+H)$^+$.

Intermediate: 2,2'-dimethyl-[1,1'-biphenyl]-3,3'-dicarbaldehyde

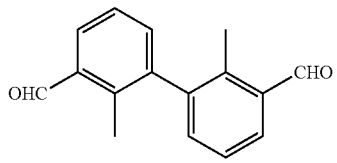 [SMILES: Cc1c(C=O)cccc1-c1cccc(C=O)c1C]

To a dry 150 mL pressure bottle was added (2,2'-dimethyl-[1,1'-biphenyl]-3,3'-diyl)dimethanol (856 mg, 3.53 mmol) and anhydrous CH$_2$Cl$_2$ (100 mL), followed by solid black activated manganese dioxide (4.1 g, 47.2 mmol). The reaction mixture was capped and placed in a 55° C. oil bath for 18 h. The mixture was filtered warm through a pad of Celite and the pad was washed with CH$_2$Cl$_2$ (4×30 mL). The organic layers were combined and the solvent removed in vacuo to give the pure title compound (781 mg, 88%) that was used "as is" without further purification. $^1$H NMR (500 MHz, DMSO-d$_6$) δ 10.35 (s, 2H), 7.91 (dd, J=7.7, 1.4 Hz, 2H), 7.53 (t, J=7.6 Hz, 2H), 7.42 (dd, J=7.5, 1.4 Hz, 2H), 2.30 (s, 6H).

Examples 3001 to 3032 were prepared as described below:

Intermediate: (R)-1-(3-(3-bromo-2-methylphenoxy)propyl)pyrrolidin-3-ol

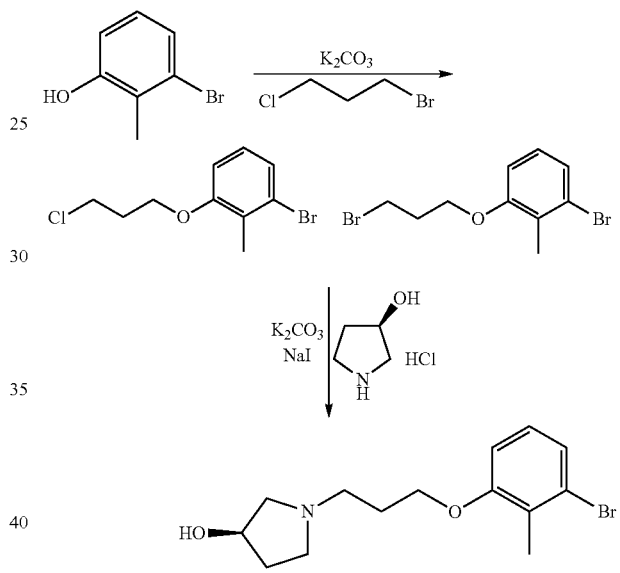

To a solution of 3-bromo-2-methylphenol (2 g, 10.69 mmol, 1 eq) in DMF (30 mL), was added 1-bromo-3-chloropropane (1.052 mL, 10.69 mmol, 1 eq) and K$_2$CO$_3$ (1.773 g, 12.83 mmol, 1.2 eq.). The reaction mixture was stirred at 50° C. for 16 h. The reaction mixture was cooled to room temperature, diluted with EtOAc. The mixture was washed with sat. NaHCO$_3$, water, brine, dried over anhydrous Na$_2$SO$_4$, filtered and concentrated. The crude product was purified on silica gel (220 g Isco cartridge) employing 20 column volumes of 0-20% EtOAc/hexane to give 2.16 g (40%) of the mixture 1-bromo-3-(3-chloropropoxy)-2-methylbenzene and 1-bromo-3-(3-bromopropoxy)-2-methylbenzene as a colorless oil. $^1$H NMR (400 MHz, CDCl$_3$) δ 7.20-7.15 (m, 1H), 7.01 (m, 1H), 6.80 (m, 1H), 4.12 (m, 2H), 3.77 (t, J=6.2 Hz, 1.70H), 3.63 (t, J=6.2 Hz, 0.30H), 2.36-2.23 (m, 5H).

To a sealed tube was added (R)-3-hydroxypyrrolidine HCl (1.153 g, 9.33 mmol, 1.5 eq), DMF (20 mL), the mixture of 1-bromo-3-(3-chloropropoxy)-2-methylbenzene and 1-bromo-3-(3-bromopropoxy)-2-methylbenzene (2.05 g, 6.22 mmol), sodium iodide (1.399 g, 9.33 mmol, 1.5 eq) and K$_2$CO$_3$ (2.150 g, 15.56 mmol, 2.5 eq). The vessel was sealed and the mixture stirred overnight at 50° C. The mixture was cooled to room temperature and evaporated to a paste. The mixture was taken up in 30 mL of DCM, washed with 10 mL water×3, brine, dried over anhydrous Na₂SO₄, filtered and concentrated. The resulting residue was diluted with 10 mL of methanol and then pushed through a Waters 5 g MCX cartridge. The cartridge was flushed with 20 mL of methanol and the product eluted with 20 mL of 2M ammonia in methanol. Evaporation of the 2M ammonia solution gave 1.15 g (59%) of (R)-1-(3-(3-bromo-2-methylphenoxy)propyl)pyrrolidin-3-ol as a light yellow powder.

The LC/MS data was obtained on a Shimadzu analytical LC/Micromass Platform LC (ESI+) at 220 nm using the following set of conditions: Phenomenex Luna 3 □m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt (Retention time)=1.328 min., m/z 316.2 (M+H). ¹H NMR (500 MHz, DMSO-d₆) δ7.22-7.17 (m, 1H), 7.12 (t, J=8.1 Hz, 1H), 6.99 (d, J=8.1 Hz, 1H), 5.51 (d, J=3.8 Hz, 1H), 4.46-4.37 (m, 1H), 4.08 (t, J=6.0 Hz, 2H), 3.32-3.24 (m, 5H), 3.17 (d, J=4.4 Hz, 1H), 2.26 (s, 3H), 2.22-2.13 (m, 3H), 1.90 (m, 1H).

The following intermediates were synthesized in an analogous fashion as described above.

Intermediate: (R)-1-(4-(3-bromo-2-methylphenoxy)butyl)pyrrolidin-3-ol

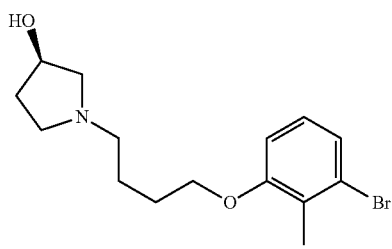 [SMILES: Cc1c(Br)cccc1OCCCCN1CC[C@@H](O)C1]

The intermediate was obtained in 59% yield as a light tan oil with a purity of 98%. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.342 min., m/z 328.15 & 330.05 (M+H). ¹H NMR (500 MHz, CDCl₃) δ 7.14 (dd, J=8.0, 0.6 Hz, 1H), 7.03-6.96 (m, 1H), 6.76 (d, J=8.2 Hz, 1H), 4.35 (m, 1H), 3.98 (t, J=6.2 Hz, 2H), 2.89 (m, 1H), 2.73-2.66 (m, 1H), 2.57-2.49 (m, 3H), 2.38-2.26 (m, 4H), 2.19 (m, 1H), 1.91-1.82 (m, 2H), 1.79-1.61 (m, 3H).

Intermediate: (R)-1-(5-(3-bromo-2-methylphenoxy)pentyl)pyrrolidin-3-ol

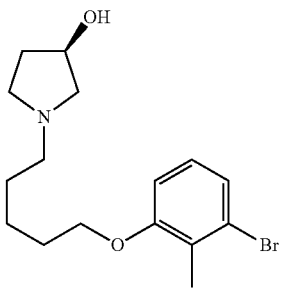 [SMILES: Cc1c(Br)cccc1OCCCCCN1CC[C@@H](O)C1]

The intermediate was obtained in 66% yield as a light tan oil with a purity of 99%. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.392 min., m/z 342.05 & 344.15 (M+H). ¹H NMR (500 MHz, CDCl₃) δ 7.14 (d, J=7.9 Hz, 1H), 6.99 (t, J=8.1 Hz, 1H), 6.76 (d, J=8.2 Hz, 1H), 4.34 (m, 1H), 3.96 (t, J=6.4 Hz, 2H), 2.87 (m, 1H), 2.68 (d, J=9.9 Hz, 1H), 2.52 (dd, J=9.9, 5.2 Hz, 1H), 2.50-2.43 (m, 2H), 2.36-2.25 (m, 4H), 2.25-2.13 (m, 1H), 1.83 (quin, J=6.9 Hz, 2H), 1.79-1.70 (m, 1H), 1.65-1.46 (m, 4H).

Intermediate: (R)-1-(3-(4-bromo-3-methylphenoxy)propyl)pyrrolidin-3-ol

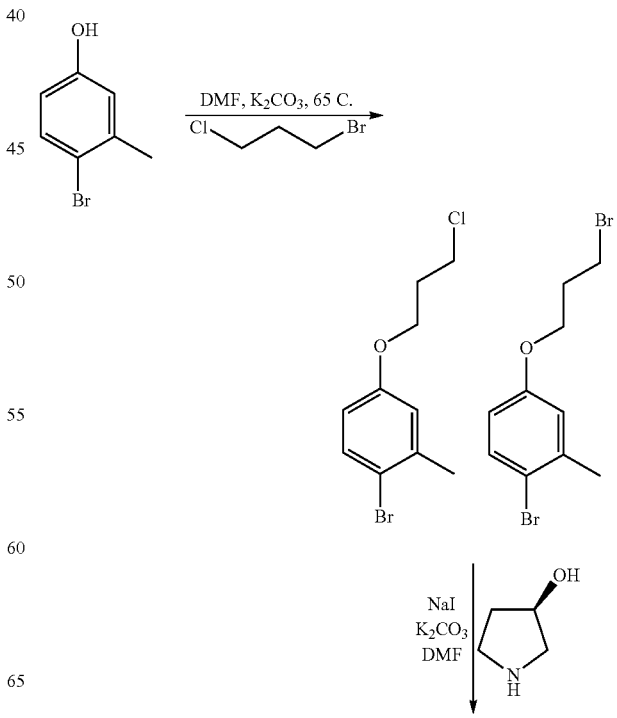

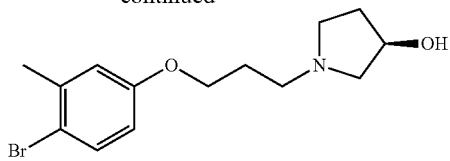

(R)-1-(3-(4-Bromo-3-methylphenoxy)propyl)pyrrolidin-3-ol was synthesized in a similar fashion. First to obtain 1.01 g (57% yield, 80% purity) of a 4:1 mixture of 1-bromo-4-(3-chloropropoxy)-2-methylbenzene and 1-bromo-4-(3-bromopropoxy)-2-methylbenzene as a colorless oil. $^1$H NMR (500 MHz, CDCl$_3$) δ 7.41 (m, 1H), 6.81 (m, 1H), 6.67-6.60 (m, 1H), 4.15-4.01 (m, 2H), 3.74 (t, J=6.3 Hz, 1.6H), 3.60 (t, J=6.3 Hz, 0.4H), 2.37 (s, 3H), 2.36-2.18 (m, 2H).

(R)-1-(3-(4-Bromo-3-methylphenoxy) propyl)pyrrolidin-3-ol was then obtained (685 mg, 90% yield, 95% purity) as a tan oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.192 min., m/z 316.1 (M+H). $^1$H NMR (500 MHz, CDCl$_3$) δ 7.39 (d, J=8.7 Hz, 1H), 6.80 (d, J=2.8 Hz, 1H), 6.61 (dd, J=8.7, 2.8 Hz, 1H), 4.39-4.29 (m, 1H), 4.04-3.91 (m, 2H), 2.91 (m, 1H), 2.71 (d, J=10.2 Hz, 1H), 2.62 (t, J=7.3 Hz, 2H), 2.53 (m, 1H), 2.44 (t, J=7.3 Hz, 1H), 2.36 (s, 3H), 2.30 (m, 1H), 2.24-2.15 (m, 1H), 2.02-1.90 (m, 1H), 1.75 (m, 1H).

Intermediate: 3-(3-bromo-2-methylphenoxy)-N,N-dimethylpropan-1-amine

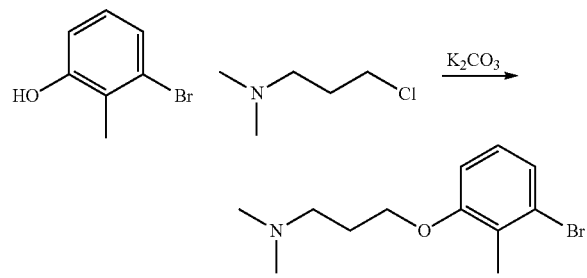

To a small sealed tube was added DMF (5 mL), 3-bromo-2-methylphenol (100 mg, 0.535 mmol), 3-chloro-N,N-dimethylpropan-1-amine (65.0 mg, 0.535 mmol), and potassium carbonate (89 mg, 0.642 mmol). The vessel was sealed and the mixture stirred over night at 65° C. The mixture was cooled, diluted with DCM (15 mL), washed with water, brine, dried over sodium sulfate, filtered and evaporated to give 126 mg (78% yield, 90% purity) of 3-(3-bromo-2-methylphenoxy)-N,N-dimethylpropan-1-amine as a tan oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.320 min., m/z 272.20 & 274.15 (M+H). $^1$H NMR (500 MHz, CDCl$_3$) δ 7.14 (dd, J=8.0, 0.6 Hz, 1H), 7.02-6.96 (m, 1H), 6.78 (d, J=8.0 Hz, 1H), 4.01 (t, J=6.3 Hz, 2H), 2.50-2.44 (m, 2H), 2.32 (s, 3H), 2.27 (s, 6H), 1.98 (m, 2H).

Intermediates (R)-3-bromo-N-(4-(3-hydroxypyrrolidin-1-yl)butyl)-2-methylbenzamide, (R)-3-bromo-N-(3-(3-hydroxypyrrolidin-1-yl)propyl)-2-methylbenzamide, and (R)-3-bromo-N-(2-(3-hydroxypyrrolidin-1-yl)ethyl)-2-methylbenzamide were synthesized in the following manner:

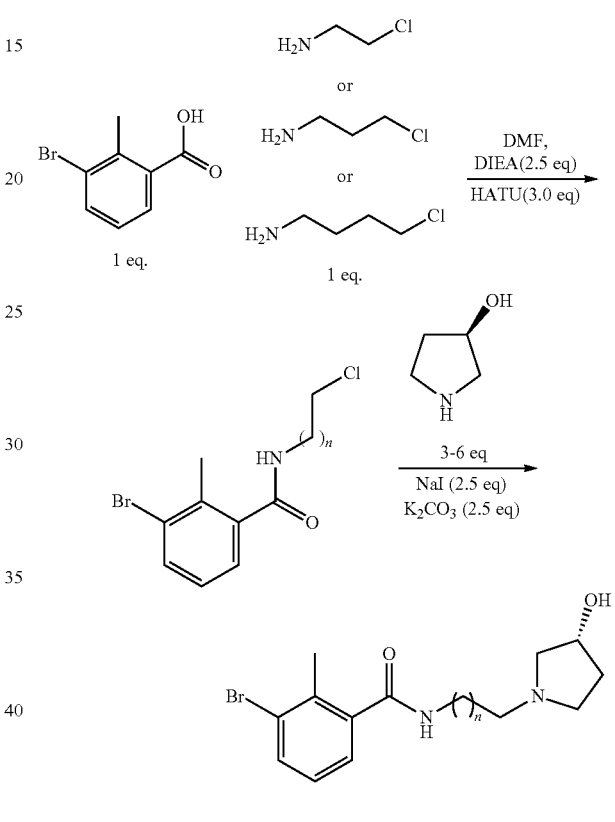

Intermediate: (R)-3-bromo-N-(3-(3-hydroxypyrrolidin-1-yl)propyl)-2-methylbenzamide To a scintillation vial was added 3-bromo-2-methylbenzoic acid (250 mg, 1.163 mmol) in DMF (10 mL) along with Hunig's base (0.508 mL, 2.91 mmol), 3-chloropropan-1-amine, HCl (151 mg, 1.163 mmol), and HATU (1.326 g, 3.49 mmol). The vial was capped and the mixture shaken at room temperature for 2 hours. The resulting crude mixture in DMF was diluted with 10 mL of water and pulled through two 1 g of Waters HLB resin extraction cartridges. The resin was flushed with 20 mL of water, and the product eluted with 20 mL of methanol which was then evaporated to give 468 mg of 3-bromo-N-(3-chloropropyl)-2-methylbenzamide (99% yield, 85% purity) as an orange solid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.633 min., m/z 292.0 & 294.2 (M+H). $^1$H NMR (500 MHz, CDCl$_3$) δ 7.60 (dd, J=8.0, 1.0 Hz, 1H), 7.25 (dd, J=8.0, 1.0 Hz, 1H), 7.10-7.04 (m, 1H), 3.69-3.58 (m, 4H), 2.46 (s, 3H), 2.17-2.09 (m, 2H).

To 3-bromo-N-(3-chloropropyl)-2-methylbenzamide (460 mg, 1.346 mmol) in DMF (20 mL) was added (R)-pyrrolidin-3-ol hydrochloride (3 eq, 499 mg, 4.04 mmol), sodium iodide (504 mg, 3.36 mmol) and potassium carbonate (465 mg, 3.36 mmol). The mixture was heated overnight at 50° C. The mixture was cooled, diluted with 50 mL of DCM, washed with 4 mL of water, dried over sodium sulfate, filtered and evaporated. The crude oil was taken up in 10 mL of methanol and pushed through a Waters 6 g MCX resin cartridge. The resin was flushed with 30 mL of methanol and the product eluted with 50 mL of 2M ammonia in methanol. Upon evaporation, 266.1 mg of (R)-3-bromo-N-(3-(3-hydroxypyrrolidin-1-yl)propyl)-2-methylbenzamide was obtained as a tan oil (43% yield, 98% purity). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.373 min., m/z 341.0 & 343.1 (M+H). $^1$H NMR (500 MHz, CDCl$_3$) δ 7.58 (d, J=8.0, 1H), 7.29-7.25 (m, 1H), 7.08-7.03 (m, 1H), 4.27 (m, 1H), 3.58-3.50 (m, 2H), 2.88 (m, 1H), 2.70-2.61 (m, 3H), 2.55-2.47 (m, 5H), 2.15-2.05 (m, 1H), 1.87-1.72 (m, 2H), 1.66-1.57 (m, 1H).

Intermediate: (R)-3-bromo-N-(4-(3-hydroxypyrrolidin-1-yl)butyl)-2-methylbenzamide 387 mg of 3-bromo-N-(4-chlorobutyl)-2-methylbenzamide was obtained (82% yield, 85% purity) in a similar fashion employing 1 eq of 4-chlorobutan-1-amine hydrochloride. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.707 min., m/z 306.0 & 308.0 (M+H). $^1$H NMR (500 MHz, CDCl$_3$) δ 7.59 (dd, J=8.0, 1.0 Hz, 1H), 7.25 (dd, J=7.6, 0.9 Hz, 1H), 7.08-7.02 (m, 1H), 3.60 (t, J=6.4 Hz, 2H), 3.48 (q, J=6.9 Hz, 2H), 2.46 (s, 3H), 1.93-1.84 (m, 2H), 1.82-1.73 (m, 2H).

227.4 mg of (R)-3-bromo-N-(4-(3-hydroxypyrrolidin-1-yl)butyl)-2-methylbenzamide was obtained (46% yield, 90% purity) as a tan oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.147 min., m/z 355.15 & 357.15 (M+H). $^1$H NMR (500 MHz, CDCl$_3$) δ 7.61-7.55 (m, 1H), 7.26-7.23 (m, 1H), 7.08-7.02 (m, 1H), 4.20 (m, 1H), 3.47-3.38 (m, 2H), 2.75 (m, 1H), 2.63-2.55 (m, 1H), 2.53-2.43 (m, 7H), 2.32-2.22 (m, 1H), 2.04-1.93 (m, 1H), 1.78-1.50 (m, 4H).

Intermediate: (R)-3-bromo-N-(2-(3-hydroxypyrrolidin-1-yl)ethyl)-2-methylbenzamide 425.8 mg of 3-bromo-N-(2-chloroethyl)-2-methylbenzamide was obtained (99% yield, 90% purity) in a similar fashion employing 1 eq of 2-chloroethanamine hydrochloride. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.537 min., m/z 276.05 & 278.05 (M+H). $^1$H NMR (400 MHz, CDCl$_3$) δ 7.63 (d, J=8.0 Hz, 1H), 7.32 (d, J=7.5 Hz, 1H), 7.17-7.03 (m, 1H), 6.17 (br. s., 1H), 3.92-3.67 (m, 4H), 2.49 (s, 3H).

120 mg of (R)-3-bromo-N-(2-(3-hydroxypyrrolidin-1-yl)ethyl)-2-methylbenzamide was obtained (26% yield, 99% purity) as a tan oil. The LC/MS data was obtained on a Shimadzu analytical LC/Micromass Platform LC (ESI+) at 220 nm using the following set of conditions: Phenomenex Luna 3 Dm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=0.935 min., m/z 326.90 & 328.95 (M+H). $^1$H NMR (500 MHz, CDCl$_3$) δ 7.64 (d, J=8.0 Hz, 1H), 7.33-7.28 (m, 1H), 7.11-7.01 (m, 1H), 4.76-4.61 (m, 1H), 4.09-3.78 (m, 3H), 3.66-3.50 (m, 1H), 3.50-3.27 (m, 2H), 3.20 (d, J=12.5 Hz, 1H), 3.13-2.99 (m, 1H), 2.51-2.38 (m, 4H), 2.29-2.11 (m, 1H).

Intermediate (R)-1-(3-(2-methyl-3-(4,4,5,5-tetramethyl-1,3,2-dioxaborolan-2-yl)phenoxy)propyl)pyrrolidin-3-ol was synthesized in the following manner:

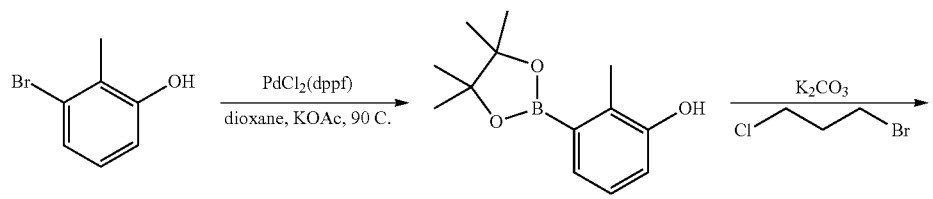

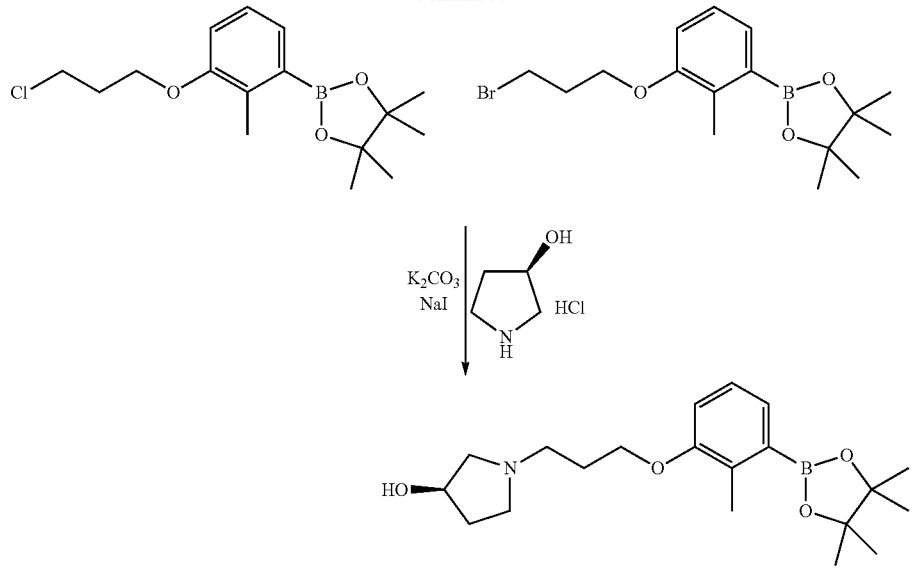

To a sealed tube was added 3-bromo-2-methylphenol (501 mg, 2.68 mmol) in dioxane (15.0 ml) along with potassium acetate (789 mg, 8.04 mmol), bis(pinacolato)diboron (1089 mg, 4.29 mmol) and [1,1'-bis(diphenylphosphino)ferrocene] dichloropalladium(II) (255 mg, 0.348 mmol). The vessel was sealed, the contents evacuated/flushed three times with nitrogen and then heated for 24 hours at 90° C. The volatiles were removed under a stream of nitrogen. The reaction mixture was then diluted with 50 mL of ethyl acetate and pushed through diatomaceous earth (Celite®), and the bed then washed with 2×10 mL of ethyl acetate. The combined filtrates were washed with water, saturated sodium bicarbonate and brine, dried over sodium sulfate, and then evaporated to a dark oily solid. The compound was purified using a 40 g silica gel cartridge emplying 20 column volumes of 0-9% MeOH/DCM to give 707 mg (96% yield) of 2-methyl-3-(4,4,5,5-tetramethyl-1,3,2-dioxaborolan-2-yl) phenol. The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.650 min., m/z 235.2 (M+H). $^1$H NMR (500 MHz, DMSO-$d_6$) δ 9.19 (s, 1H), 7.06 (d, J=7.3 Hz, 1H), 6.97 (t, J=7.3 Hz, 1H), 6.87 (d, J=7.3 Hz, 1H), 2.29 (s, 3H), 1.33-1.25 (m, 12H).

To 2-methyl-3-(4,4,5,5-tetramethyl-1,3,2-dioxaborolan-2-yl)phenol (707 mg, 2.57 mmol) in DMF (8 mL) was added potassium carbonate (426 mg, 3.08 mmol) and 1-bromo-3-chloropropane (0.253 mL, 2.57 mmol). The mixture was stirred for 18 hours at room temperature. To the mixture was added 1 eq of 1-bromo-3-chloropropane (0.253 mL, 2.57 mmol) and 0.5 eq (178 mgs, 1.29 mmol) of potassium carbonate. The mixture was stirred an additional 18 hours at room temperature. The resulting product was diluted with 50 mL of DCM, washed with 5 mL of water, brine, dried over sodium sulfate, filtered and evaporated under a stream of nitrogen. The crude product was purified with a 40 g silica gel cartridge employing 0 to 20% EtOAc/Hexane to give 574.7 mg of a 2:1 mixture of 2-(3-(3-chloropropoxy)-2-methylphenyl)-4,4,5,5-tetramethyl-1,3,2-dioxaborolane and 2-(3-(3-bromopropoxy)-2-methylphenyl)-4,4,5,5-tetramethyl-1,3,2-dioxaborolane (54% yield) as a colorless oil. $^1$H NMR (500 MHz, CDCl$_3$) δ 7.37 (dd, J=7.5, 1.0 Hz, 1H), 7.18-7.06 (m, 1H), 6.96-6.85 (m, 1H), 4.14-4.08 (m, 2H), 3.82-3.60 (m, 2H), 2.43 (s, 3H), 2.27 (m, 2H), 1.36 (s, 12H).

To a sealed flask was added (R)-3-hydroxypyrrolidine hydrochloride (223 mg, 1.804 mmol), 2-(3-(3-chloropropoxy)-2-methylphenyl)-4,4,5,5-tetramethyl-1,3,2-dioxaborolane (574.7 mg, 1.388 mmol, the 2:1 mixture prepared above was used), DMF (8 mL), sodium iodide (312 mg, 2.081 mmol), and potassium carbonate (479 mg, 3.47 mmol). The flask was sealed and the mixture stirred for 40 hours at 50° C. The crude mixture was diluted with 75 mL of DCM, washed with water, brine, dried over sodium sulfate, filtered and evaporated. The resulting crude oil was taken up in 20 mL of methanol and pushed through SCX Bondesil resin. The resin was washed with 60 mL of additional methanol. The desired product was then eluted with 60 mL of 2M NH$_3$ in methanol. The volatiles were evaporated to give 319.5 mg (60% yield) of (R)-1-(3-(2-methyl-3-(4,4,5,5-tetramethyl-1,3,2-dioxaborolan-2-yl)phenoxy)propyl)pyrrolidin-3-ol as a waxy solid. The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.338 min., m/z 362.3 (M+H). $^1$H NMR (500 MHz, CDCl$_3$) δ 7.34 (dd, J=7.5, 1.0 Hz, 1H), 7.17-7.11 (t, J=7.5 Hz, 1H), 6.91 (dd, J=7.5, 1.0 Hz, 1H), 4.38-4.29 (m, 1H), 4.05-3.97 (m, 2H), 2.91 (m, 1H), 2.75-2.63 (m, 2H), 2.58-2.45 (m, 2H), 2.43 (s, 3H), 2.35-2.28 (m, 1H), 2.24-2.15 (m, 1H), 2.08-1.95 (m, 2H), 1.81-1.69 (m, 1H), 1.35 (s, 12H).

Intermediate (R)-1-(3-(3-methyl-4-(4,4,5,5-tetramethyl-1,3,2-dioxaborolan-2-yl)phenoxy)propyl)pyrrolidin-3-ol was synthesized in the following manner:

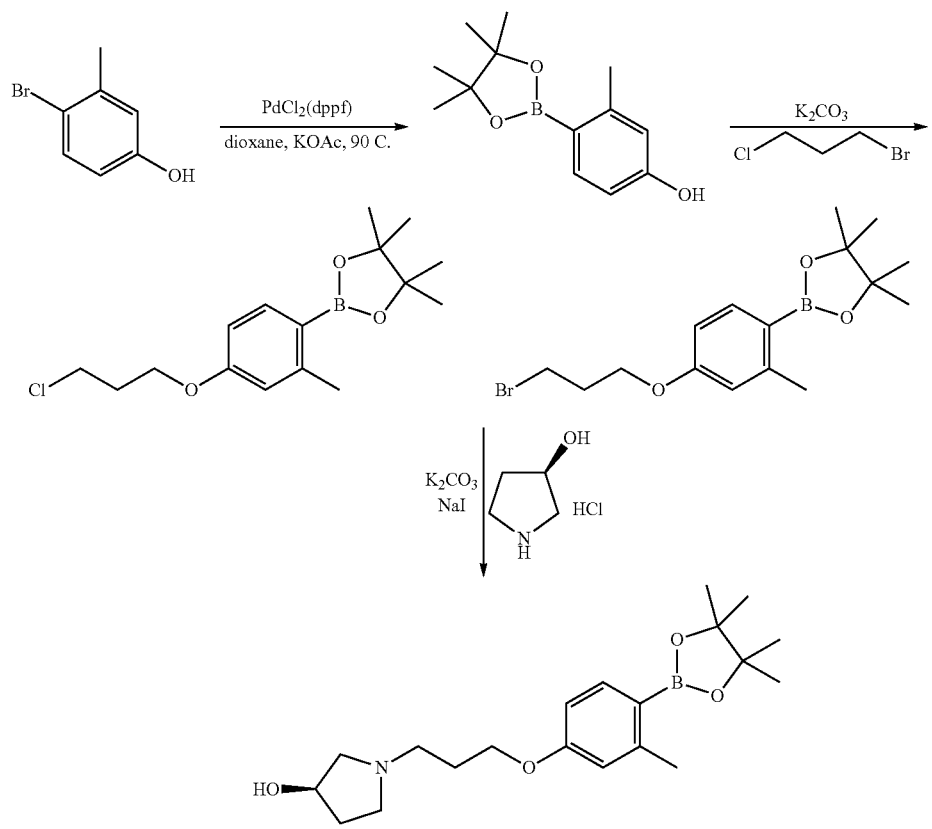

3-Methyl-4-(4,4,5,5-tetramethyl-1,3,2-dioxaborolan-2-yl)phenol was obtained (99% yield, 90% purity) as a tan foam. The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.727 min., m/z 235.3 (M+H). $^1$H NMR (500 MHz, CDCl$_3$) δ 7.68 (d, J=7.9 Hz, 1H), 6.64 (m, 2H), 5.14 (br. s., 1H), 2.50 (s, 3H), 1.33 (m, 12H).

2-(4-(3-Chloropropoxy)-2-methylphenyl)-4,4,5,5-tetramethyl-1,3,2-dioxaborolane and 2-(4-(3-bromopropoxy)-2-methylphenyl)-4,4,5,5-tetramethyl-1,3,2-dioxaborolane (mixture) was obtained (61% yield, 85% purity) as a light tan oil. $^1$H NMR (500 MHz, CDCl$_3$) δ 7.72 (d, J=7.9 Hz, 1H), 6.81-6.63 (m, 2H), 4.19-4.01 (m, 2H), 3.75 (t, J=6.3 Hz, 1.5H), 3.60 (t, J=6.3 Hz, 0.5H), 2.53 (m, 3H), 2.32 (quin, J=6.1 Hz, 0.5H), 2.24 (quin, J=6.1 Hz, 1.5H), 1.34 (s, 12H).

(R)-1-(3-(3-methyl-4-(4,4,5,5-tetramethyl-1,3,2-dioxaborolan-2-yl)phenoxy)propyl)pyrrolidin-3-ol was obtained (40% yield, 90% purity) as a light tan oil. The LC/MS data was obtained on a Shimadzu analytical LC/Micromass Platform LC (ESI+) at 220 nm using the following set of conditions: Phenomenex Luna 3 µm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.437 min., m/z 362.25 (M+H). $^1$H NMR (500 MHz, CDCl$_3$) δ 7.71 (d, J=7.9 Hz, 1H), 6.74-6.66 (m, 2H), 4.41-4.27 (m, 1H), 4.04 (t, J=6.4 Hz, 2H), 2.98-2.82 (m, 1H), 2.74-2.69 (m, 1H), 2.63 (t, J=7.3 Hz, 2H), 2.56-2.50 (s, 3H), 2.35-2.27 (m, 1H), 2.24-2.15 (m, 1H), 2.03-1.91 (m, 3H), 1.80-1.71 (m, 1H), 1.33 (s, 12H).

Intermediate: 3-bromo-N-(3-(dimethylamino)propyl)-2-methylbenzenesulfonamide

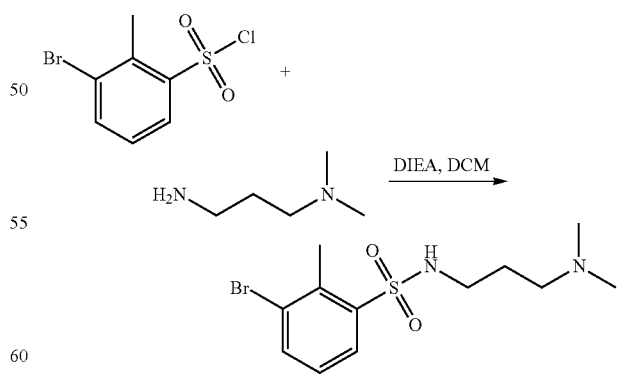

To a screw capped vial was added DCM (5 mL), N,N-dimethyl-1,3-propanediamine (37.9 mg, 0.371 mmol), Hunig's base (0.065 mL, 0.371 mmol), and finally 3-bromo-2-methylbenzene-1-sulfonyl chloride (100 mg, 0.371 mmol). The vial was capped and the mixture shaken for 2 hours. The reaction mixture was further diluted with 5 mL of DCM, washed with water, brine, dried over sodium sulfate, filtered, and evaporated to give 115.9 mg (89% yield, 95% purity) of 3-bromo-N-(3-(dimethylamino)propyl)-2-methylbenzenesulfonamide as a clear colorless oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.100 min., m/z 337.1 (M+H). $^1$H NMR (500 MHz, CDCl$_3$) δ 7.97 (dd, J=7.9, 1.1 Hz, 1H), 7.76 (dd, J=8.0, 1.1 Hz, 1H), 7.22-7.10 (m, 1H), 3.08-2.97 (m, 2H), 2.74 (s, 3H), 2.46-2.37 (m, 2H), 2.25 (s, 6H), 1.71-1.59 (m, 2H).

Intermediate: tert-Butyl 3-(3-bromo-2-methylphenylsulfonamido)propanoate

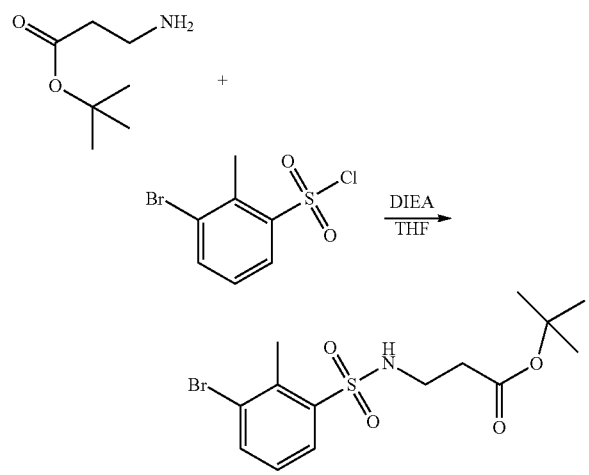

To a small RBF (round-bottomed flask) was added THF (5 mL), tert-butyl 3-aminopropanoate, HCl (162 mg, 0.890 mmol), Hunig's base (0.272 mL, 1.558 mmol), and finally 3-bromo-2-methylbenzene-1-sulfonyl chloride (120 mg, 0.445 mmol). The flask was sealed and the mixture stirred for 6 hours under nitrogen. The solvent was removed, and the crude oil diluted with 30 mL of DCM, washed with water, brine, dried over sodium sulfate, filtered, and evaporated to give 160 mg of tert-butyl 3-(3-bromo-2-methylphenyl sulfonamido)propanoate (100% yield, 80% purity) as a yellow oil. The LC/MS data was obtained on a Shimadzu analytical LC/Micromass Platform LC (ESI+/−) at 220 nm using the following set of conditions: Phenomenex Luna 3 μm C18, 2×30 mm column, with a gradient of 0-100% B (B=95% HPLC grade acetonitrile/10 Mm ammonium acetate/5% HPLC grade water), (A=95% HPLC grade water/10 Mm ammonium acetate/5% HPLC grade acetonitrile), in 2 minutes with a 1 minute hold at a rate of 1 mL/minute. LCMS Rt=1.737 min., m/z 376.18 & 378.18 (M−H).

$^1$H NMR (500 MHz, CDCl$_3$) δ 7.96 (d, J=7.9 Hz, 1H), 7.75 (d, J=8.0 Hz, 1H), 7.17 (t, J=8.0 Hz, 1H), 3.68-3.63 (m, 2H), 2.74 (s, 3H), 2.41 (t, J=6.0 Hz, 2H), 1.41 (s, 9H).

Intermediate: (R)-3-bromo-N-(2-(3-hydroxypyrrolidin-1-yl)ethyl)-2-methylbenzenesulfonamide

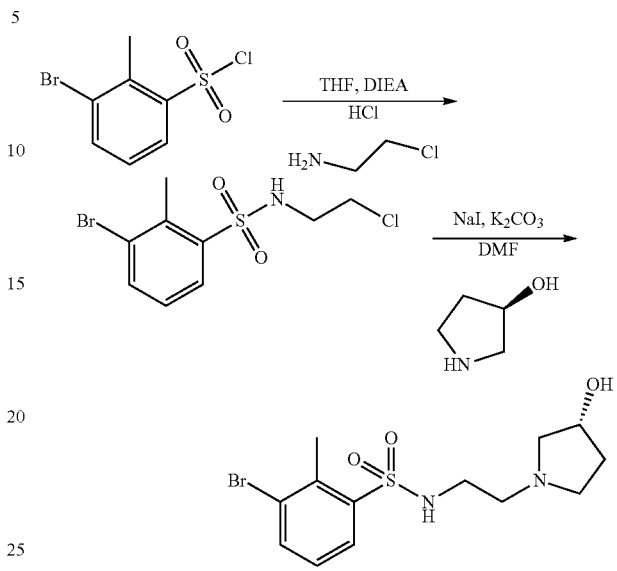

To a small RBF was added THF (5 mL), N-ethyl-N-isopropylpropan-2-amine (0.233 mL, 1.336 mmol), 2-chloroethanamine hydrochloride (51.6 mg, 0.445 mmol), and finally 3-bromo-2-methylbenzene-1-sulfonyl chloride (120 mg, 0.445 mmol). The flask was sealed and the mixture stirred for 6 hours under nitrogen. The solvent was removed, and the crude oil diluted with 30 mL of DCM, washed with water, brine, dried over sodium sulfate, filtered, and evaporated to give 140 mg of 3-bromo-N-(2-chloroethyl)-2-methylbenzenesulfonamide (100% yield, 80% purity) as a white foam. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/ 10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.573 min., m/z 314.1 (M+H). $^1$H NMR (500 MHz, CDCl$_3$) δ 7.96 (dd, J=8.0, 1.0 Hz, 1H), 7.76 (dd, J=8.0, 1.0 Hz, 1H), 7.22-7.13 (m, 1H), 3.56 (t, J=6.1 Hz, 2H), 3.30 (t, J=6.1 Hz, 2H), 2.76 (s, 3H).

To a sealed tube was added (R)-pyrrolidin-3-ol hydrochloride (308 mg, 2.50 mmol), DMF (17 mL), potassium carbonate (287 mg, 2.079 mmol), sodium iodide (312 mg, 2.079 mmol), and 3-bromo-N-(2-chloroethyl)-2-methylbenzenesulfonamide (260 mg, 0.832 mmol). The vessel was sealed and the mixture stirred overnight at 65° C. The mixture was cooled, diluted with 40 mL DCM, washed with water, brine, dried over sodium sulfate, filtered, and evaporated to give a crude oil. The crude oil was taken up in 10 mL of methanol and pushed through a 5 g Biotage SCX-2 resin cartridge. The resin was flushed with additional 50 mL of methanol, and the product then eluted with 50 mL of 2M ammonia in methanol. Evaporation of the volatiles gave 138.9 mg of (R)-3-bromo-N-(2-(3-hydroxypyrrolidin-1-yl) ethyl)-2-methylbenzenesulfonamide (39% yield, 85% purity) as a tan oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.009 min., m/z 363.00 & 365.00 (M+H). $^1$H NMR (500 MHz, CDCl$_3$) δ 8.00 (dd, J=8.0, 1.0 Hz, 1H), 7.78 (dd, J=8.0, 1.0 Hz, 1H), 7.24-7.13 (t, J=8.0 Hz, 1H), 4.36 (m, 1H), 3.01 (t, J=5.8 Hz, 2H), 2.77 (s, 3H), 2.76-2.69 (m, 1H), 2.56-2.47 (m, 4H), 2.24 (m, 1H), 2.20-2.13 (m, 1H), 1.79-1.69 (m, 1H).

Intermediate:
5-((3-bromo-2-methylphenoxy)methyl)nicotinonitrile

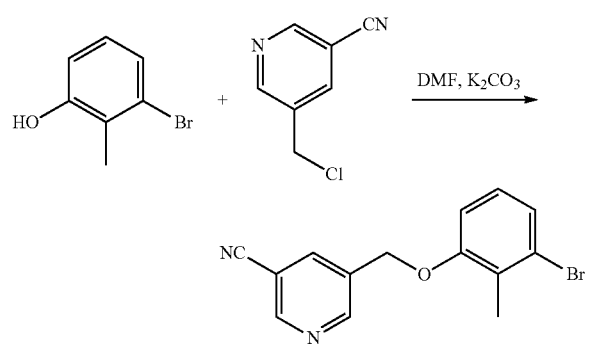

To a sealed tube was added DMF (5 mL), potassium carbonate (247 mg, 1.785 mmol), 3-bromo-2-methylphenol (278 mg, 1.488 mmol), and 5-(chloromethyl)nicotinonitrile (227 mg, 1.488 mmol). The vessel was sealed and the mixture stirred overnight at 65° C. The reaction mixture was cooled, taken up in 50 mL DCM, washed with water, brine, dried over sodium sulfate, filtered, and evaporated to give 463.1 mg of 5-((3-bromo-2-methylphenoxy)methyl)nicotinonitrile as a light tan solid (92% yield, 90% purity). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.772 min., m/z 303.0 (M+H). $^1$H NMR (500 MHz, CDCl$_3$) δ 8.91 (m, 2H), 8.09 (m, 1H), 7.27 (dd, J=8.0, 0.6 Hz, 1H), 7.09-7.03 (m, 1H), 6.84 (d, J=8.0 Hz, 1H), 5.16 (s, 2H), 2.40 (s, 3H).

Intermediate:
3-((3-bromo-2-methylphenoxy)methyl)benzonitrile was synthesized in a similar fashion

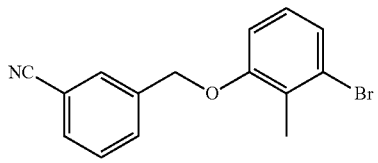 [SMILES: Cc1c(Br)cccc1OCc1cccc(C#N)c1]

441.4 mgs of 3-((3-bromo-2-methylphenoxy)methyl)benzonitrile (97% yield, 100% purity) was obtained as a white solid. $^1$H NMR (500 MHz, DMSO-d$_6$) δ 7.90 (s, 1H), 7.80 (m, 2H), 7.65-7.59 (m, 1H), 7.19 (dd, J=8.0, 0.8 Hz, 1H), 7.10 (t, J=8.0 Hz, 1H), 7.07-7.01 (m, 1H), 5.19 (s, 2H), 2.28 (s, 3H).

Intermediate: (R)—N-(3-bromo-2-methylphenyl)-3-(3-hydroxypyrrolidin-1-yl)propanamide

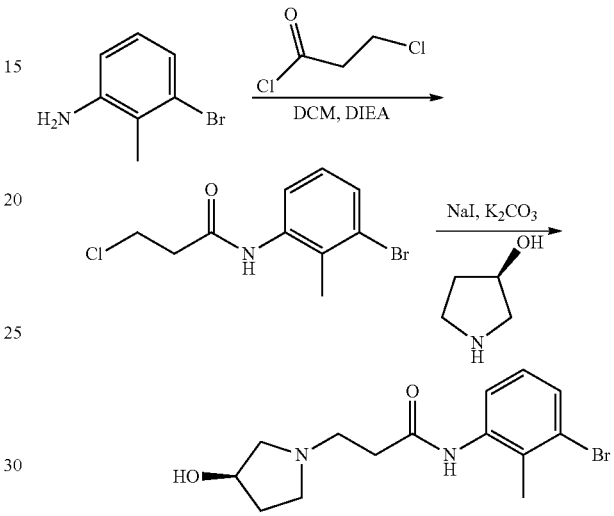

To a RBF at room temperature under nitrogen, was added 3-bromo-2-methylaniline (1.00 g, 5.37 mmol) in DCM (15 mL) along with Hunig's base (0.939 mL, 5.37 mmol). To this solution was then added 3-chloropropionyl chloride (0.516 mL, 5.37 mmol) dropwise. Stirring was continued overnight at room temperature. The product was further diluted with DCM (30 mL), washed with water, brine, dried over magnesium sulfate, filtered and evaporated to give 1.54 g (62% yield, 70% purity) of N-(3-bromo-2-methylphenyl)-3-chloropropanamide as a yellow solid. $^1$H NMR (500 MHz, CDCl$_3$) δ 7.63 (d, J=8.0 Hz, 1H), 7.43 (d, J=7.9 Hz, 1H), 7.17-7.02 (m, 1H), 3.91 (t, J=6.2 Hz, 2H), 2.95-2.79 (m, 2H), 2.38 (s, 3H).

To a RBF was added (R)-pyrrolidin-3-ol hydrochloride (670 mg, 5.42 mmol), DMF (40 mL), N-(3-bromo-2-methylphenyl)-3-chloropropanamide (500 mg, 1.81 mmol), sodium iodide (678 mg, 4.52 mmol), and potassium carbonate (625 mg, 4.52 mmol). The mixture was stirred overnight at 65° C. The mixture was cooled, diluted with 30 mL of DCM, washed with 5 mL water, brine, dried over sodium sulfate, filtered and evaporated to a crude oil. The crude oily mixture was taken up in 10 mL of methanol and pushed through a 5 g Biotage SCX resin cartridge. The resin was flushed with 20 mL of additional methanol and then the product was eluted with 30 mL of 2M ammonia in methanol. Evaporation of the volatiles gave 554 mg of (R)—N-(3-bromo-2-methylphenyl)-3-(3-hydroxypyrrolidin-1-yl)propanamide (84% yield, 90% purity) as a tan oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10%

HPLC grade acetonitrile), in 2 minutes with a 1 minute hold at a rate of 1 mL/minute. LCMS Rt=1.022 min., m/z 327.2 & 330.1 (M+H). ¹H NMR (500 MHz, CDCl₃) δ 10.57 (br. s., 1H), 7.95 (d, J=8.0 Hz, 1H), 7.38-7.30 (m, 1H), 7.05 (t, J=8.0 Hz, 1H), 4.57-4.47 (m, 1H), 3.03-2.95 (m, 1H), 2.95-2.81 (m, 3H), 2.77 (dd, J=10.5, 2.6 Hz, 1H), 2.64-2.55 (m, 3H), 2.38 (s, 3H), 2.30-2.17 (m, 1H), 1.90-1.79 (m, 1H).

Intermediate: (R)-1-(3-((3-bromo-2-methylphenyl)amino)propyl)pyrrolidin-3-ol

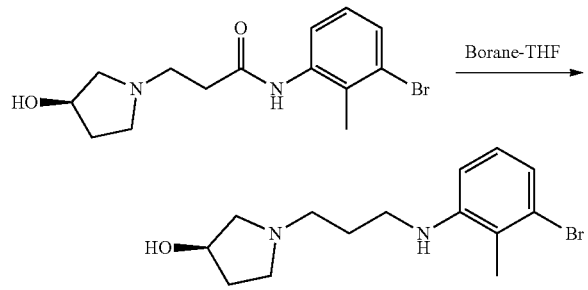

To (R)—N-(3-bromo-2-methylphenyl)-3-(3-hydroxypyrrolidin-1-yl)propanamide (50 mg, 0.153 mmol) in THF (2 mL) under nitrogen at room temperature was added 1M borane-tetrahydrofuran complex (0.458 mL, 0.458 mmol). The mixture was stirred overnight under nitrogen. The reaction mixture was cooled to 0° C. and 5 mL of methanol was added dropwise. The mixture was stirred for 8 hours slowly reaching room temperature and then evaporated to dryness. An additional 5 mL of methanol was added and the product solution was again evaporated to give 45 mg (98% yield, 70% purity) of (R)-1-(3-((3-bromo-2-methylphenyl)amino)propyl)pyrrolidin-3-ol as a glass. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.032 min., m/z 313.05 & 315.05 (M+H).
¹H NMR (500 MHz, CDCl₃) δ 6.95 (m, 2H), 6.52 (t, J=4.7 Hz, 1H), 4.65 (m, 1H), 3.42 (m, 1H), 3.26 (m, 1H), 3.17 (m, 1H), 3.06 (m, 1H), 2.83 (m, 2H), 2.55 (m, 2H), 2.26 (s, 3H), 2.22 (m, 2H), 1.88 (m, 2H).

Intermediate: (R)-1-(3-bromo-2-methylphenyl)-3-(2-(3-hydroxypyrrolidin-1-yl)ethyl)urea

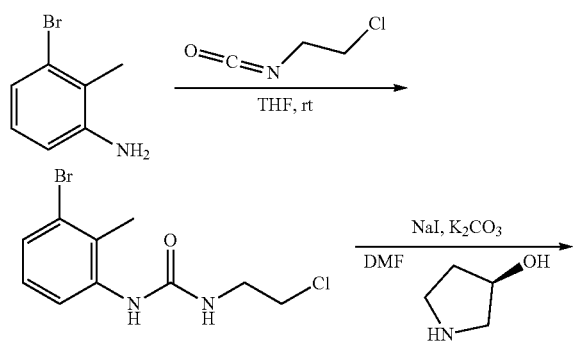

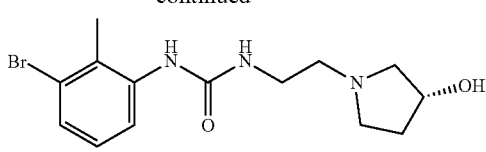

To a solution of 3-bromo-2-methylaniline (500 mg, 2.69 mmol) in THF (17 mL), under nitrogen, was added 2-chloroethyl isocyanate (0.229 mL, 2.69 mmol). The mixture was stirred at room temperature overnight. To the reaction mixture was added an additional 1 eq of 2-chloroethyl isocyanate (0.229 mL, 2.69 mmol). The solution was stirred for 24 hours at room temperature.

The white heterogeneous reaction mixture was cooled to 0° C. and the resulting white solid was filtered to give 683 mg (87% yield, 100% purity) of 1-(3-bromo-2-methylphenyl)-3-(2-chloroethyl)urea as a fluffy white solid. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.415 min., m/z 293.1 & 295.0 (M+H). ¹H NMR (400 MHz, DMSO-d₆) δ 8.05 (br.s., 1H), 7.72 (d, J=7.8 Hz, 1H), 7.26 (d, J=7.8 Hz, 1H), 7.11-7.00 (t, J=7.8 Hz, 1H), 6.84 (t, J=5.5 Hz, 1H), 3.66 (t, J=5.9 Hz, 2H), 3.42 (q, J=5.9 Hz, 3H), 2.27 (s, 3H).

To a sealed tube was added 1-(3-bromo-2-methylphenyl)-3-(2-chloroethyl)urea (200 mg, 0.686 mmol), DMF (10 mL), (R)-pyrrolidin-3-ol hydrochloride (848 mg, 6.86 mmol), potassium carbonate (379 mg, 2.74 mmol) and sodium iodide (206 mg, 1.372 mmol). The vessel was sealed and the mixture stirred overnight at 50° C. The mixture was cooled, diluted with water (10 mL) and pushed through two 1 g Waters HLB extraction cartridges. The resin was flushed with additional water (20 mL), and the product eluted with 20 mL of methanol. The product contained in the methanol solution was then pushed through a Biotage 5 g SCX-2 resin cartridge. The resin cartridge was flushed with additional methanol, and the product eluted with 50 mL of 2M ammonia in methanol. The volatiles were removed to give (R)-1-(3-bromo-2-methylphenyl)-3-(2-(3-hydroxypyrrolidin-1-yl)ethyl)urea (115 mg, 49% yield, 95% purity) as a tan glass. The LC/MS data was obtained on a Shimadzu analytical UPLC/Micromass Platform LC (ESI+) at 220 nm using the following set of conditions: Waters Aquity 1.7 μm C18, 2.1×50 mm column, with a gradient of 0-100% B (B=100% HPLC grade acetonitrile/0.05% trifluoroacetic acid), (A=100% HPLC grade water/0.1% trifluoroacetic acid), in 1.5 minutes with a 0.5 minute hold at a rate of 0.8 mL/minute. LCMS Rt=1.009 min., m/z 341.80 & 343.80 (M+H). ¹H NMR (500 MHz, CDCl₃) δ 7.43 (d, J=8.0 Hz, 1H), 7.24 (d, J=8.0 Hz, 1H), 7.03 (t, J=8.0 Hz, 1H), 5.60 (m, 1H), 4.35-4.27 (m, 1H), 3.40-3.30 (m, 2H), 2.98-2.91 (m, 1H), 2.75 (m, 1H), 2.63 (m, 2H), 2.49 (m, 1H), 2.35 (s, 3H), 2.30-2.25 (m, 1H), 2.20-2.10 (m, 1H), 1.77-1.66 (m, 1H).

Intermediate (3R,3'R)-1,1'-(((4-bromo-1,2-phenylene)bis(oxy))bis(propane-3,1-diyl))bis(pyrrolidin-3-ol) was synthesized in the following manner.

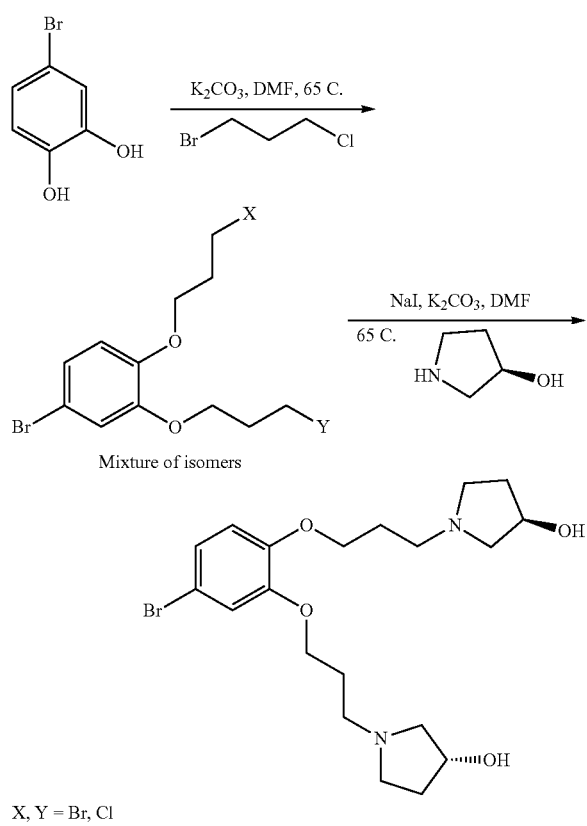

X, Y = Br, Cl

To a sealed tube was added DMF (10 mL), potassium carbonate (877 mg, 6.35 mmol), 1-bromo-3-chloropropane (0.458 mL, 4.66 mmol), and 4-bromocatechol (400 mg, 2.116 mmol). The vessel was sealed and the mixture stirred overnight at 65° C. The reaction mixture was cooled, diluted with 20 mL of water and pushed through two 1 g Waters HLB resin extraction cartridges. The resin was flushed with 2×20 mL of water. The product was eluted with 3×20 mL of methanol. Evaporation of the volatiles gave 556 mg of a mixture of 4-bromo-1,2-bis(3-chloropropoxy)benzene, 4-bromo-1-(3-bromopropoxy)-2-(3-chloropropoxy)benzene, 4-bromo-2-(3-bromopropoxy)-1-(3-chloropropoxy)benzene, and 4-bromo-1,2-bis(3-bromopropoxy)benzene as a crude red oil.

To a sealed tube was added the above isolated red oil (556 mg, 1.625 mmol) in DMF (30 mL) along with (R)-pyrrolidin-3-ol hydrochloride (442 mg, 3.58 mmol), sodium iodide (609 mg, 4.06 mmol), and potassium carbonate (674 mg, 4.88 mmol). The vessel was sealed and the mixture stirred overnight at 65° C. The reaction mixture was cooled, diluted with 20 mL of water and pushed through a 5 g Waters HLB resin extraction cartridge. The cartridge flushed with an additional 30 mL of water. The product was eluted with 50 mL of methanol. The methanol solution was pushed through a Biotage SCX-2 ion exchange cartridge (5 g), and the cartridge flushed with 50 mL of additional methanol. The desired basic product was eluted with 75 mL of 2M ammonia in methanol. Evaporation of the volatiles gave 385 mg of a dark oil. The crude product mixture was taken up in methanol and purified using a Shimadzu preparative HPLC employing methanol/water/TFA where solvent A was 10% MeOH/90% H$_2$O/0.1% trifluoroacetic acid and solvent B was 10% H$_2$O/90% MeOH/0.1% trifluoroacetic acid with a Waters Sunfire 5 μm C18 19×100 mm column at a gradient of 20-100% B and a flow rate of 30 mL/min. over 15 minutes with a 3 minute hold. Evaporation of solvent gave 201.8 mg of (3R,3'R)-1,1'-(((4-bromo-1,2-phenylene)bis(oxy))bis (propane-3,1-diyl))bis(pyrrolidin-3-ol), 2 TFA (20% yield, 100% purity) as a light tan oil. The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/ 0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.397 min., m/z 443.15 & 445.10 (M+H). $^1$H NMR (500 MHz, CDCl$_3$) δ 7.12-7.01 (m, 1H), 6.96 (s, 1H), 6.79-6.66 (m, 1H), 4.24 (m, 2H), 4.05 (d, J=5.4 Hz, 4H), 3.33 (m, 2H), 3.22 (m, 1H), 3.06 (m, 1H), 2.92 (m, 4H), 2.42 (m, 2H), 2.28 (m, 6H), 2.18 (m, 4H).

Example 3001: (3R,3'R)-1,1'-(((2,2'-dimethyl-[1,1'-biphenyl]-3,3'-diyl)bis(oxy))bis(propane-3,1-diyl)) bis(pyrrolidin-3-ol)

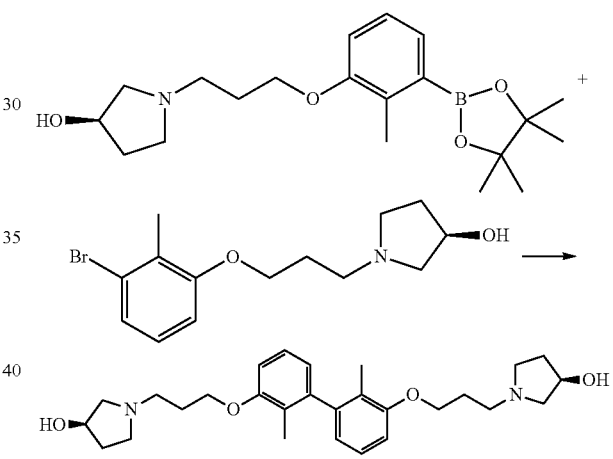

To a sealed tube was added (R)-1-(3-(2-methyl-3-(4,4,5, 5-tetramethyl-1,3,2-dioxaborolan-2-yl)phenoxy)propyl)pyrrolidin-3-ol (20 mg, 0.055 mmol), (R)-1-(3-(3-bromo-2-methyl phenoxy)propyl)pyrrolidin-3-ol (17.39 mg, 0.055 mmol), THF (2.0 mL), water (0.67 mL), potassium phosphate, tribasic (23.50 mg, 0.111 mmol), and second generation X-Phos precatalyst (2.178 mg, 2.77 μmol). The flask was sealed, the mixture de-gassed/flushed with nitrogen and then heated overnight at 80° C. The reaction mixture was cooled, diluted with DCM (20 mL), extracted, washed with water, brine, dried over sodium sulfate, filtered, and evaporated to give a yellow oil. The crude oil was taken up in methanol and was purified via preparative LC/MS using the following conditions: Waters XBridge 5 μm C18, 19×200 mm where mobile phase A was 5:95 acetonitrile: water with 0.1% TFA and mobile phase B was 95:5 acetonitrile:water with 0.1% TFA at a gradient of 10-50% B over 20 minutes with a 5-minute hold at a flow rate of 20 mL/minute. Fractions containing the desired product were combined and dried via centrifugal evaporation. The yield of the product was 26.3 mg (100%) as the bis-TFA salt, and its estimated purity by LCMS analysis was 100%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.218 min; ESI-MS(+) m/z=469.1 (M+H). Analysis condition 2: Retention time=1.158 min; ESI-MS (+) m/z=469.1 (M+H). $^1$H NMR (500 MHz, DMSO-$d_6$) δ 7.20 (t, J=7.7 Hz, 2H), 6.95 (d, J=7.7 Hz, 2H), 6.66 (d, J=7.7 Hz, 2H), 5.43 (br. s., 2H), 4.42 (br. s., 2H), 4.20-3.94 (m, 4H), 3.51-3.02 (m, 6H), 2.74 (m, 2H), 2.55 (m, 4H), 2.27-2.02 (m, 6H), 1.85 (m, 8H).

The following Examples were synthesized in an analogous fashion.

Example 3002: (R)-1-(3-((3'-(4-((R)-3-hydroxypyrrolidin-1-yl)butoxy)-2,2'-dimethyl-[1,1'-biphenyl]-3-yl)oxy)propyl) pyrrolidin-3-ol

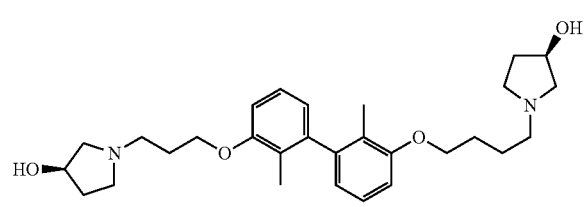 [SMILES: Cc1c(OCCCCN2CC[C@@H](O)C2)cccc1-c1cccc(OCCCN2CC[C@@H](O)C2)c1C]

The crude material was purified via preparative LC/MS using the following conditions: Waters XBridge 5 μm C18, 19×200 mm where mobile phase A was 5:95 methanol:water with 10 mM ammonium acetate and mobile phase B was 95:5 methanol:water 10 mM ammonium acetate at a gradient of 20-60% B over 20 minutes with a 5-minute hold at a flow rate of 20 mL/minute. Fractions containing the desired product were combined and dried via centrifugal evaporation. The yield of the product was 8.6 mg (30%), and its estimated purity by LCMS analysis was 94%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.131 min; ESI-MS(+) m/z=483.2 (M+H); Analysis condition 2: Retention time=1.209 min; ESI-MS (+) m/z=483.2 (M+H); $^1$H NMR (500 MHz, DMSO-$d_6$) δ 7.16 (t, J=7.9 Hz, 2H), 6.92 (d, J=8.4 Hz, 2H), 6.62 (d, J=7.7 Hz, 2H), 4.18 (m, 2H), 4.07-3.94 (m, 4H), 2.76-2.70 (m, 2H), 2.65-2.55 (m, 4H), 2.49-2.43 (m, 3H), 2.39-2.33 (m, 2H), 2.02-1.91 (m, 3H), 1.90 (m, 2H), 1.81 (s, 6H), 1.79-1.73 (m, 2H), 1.66-1.59 (m, 2H), 1.54 (m, 2H).

Example 3003: (R)-1-(3-((3'-((5-((R)-3-hydroxypyrrolidin-1-yl)pentyl)oxy)-2,2'-dimethyl-[1,1'-biphenyl]-3-yl)oxy)propyl)pyrrolidin-3-ol

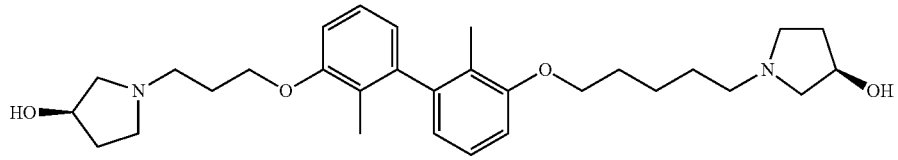 [SMILES: Cc1c(OCCCCCN2CC[C@@H](O)C2)cccc1-c1cccc(OCCCN2CC[C@@H](O)C2)c1C]

The crude material was purified via preparative LC/MS using the following conditions: Waters XBridge 5 μm C18, 19×200 mm where mobile phase A was 5:95 methanol:water with 10 mM ammonium acetate and mobile phase B was 95:5 methanol:water 10 mM ammonium acetate at a gradient of 20-60% B over 25 minutes with a 5-minute hold at a flow rate of 20 mL/minute. Fractions containing the desired product were combined and dried via centrifugal evaporation. The yield of the product was 10.3 mg (37%), and its estimated purity by LCMS analysis was 97%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.368 min; ESI-MS(+) m/z=497.2 (M+H); Analysis condition 2: Retention time=1.302 min; ESI-MS (+) m/z=497.2 (M+H); $^1$H NMR (500 MHz, CDCl$_3$) δ 7.16 (t, J=7.8 Hz, 2H), 6.82 (d, J=8.2 Hz, 2H), 6.73 (t, J=7.4 Hz, 2H), 4.49-4.39 (m, 2H), 4.15-3.97 (m, 4H), 3.42-3.34 (m, 1H), 3.29-3.19 (m, 2H), 3.13-3.05 (m, 1H), 2.88-2.84 (m, 2H), 2.83-2.67 (m, 4H), 2.65-2.49 (m, 2H), 2.32-2.20 (m, 2H), 2.14 (m, 2H), 1.92 (m, 8H), 1.90-1.83 (m, 2H), 1.80-1.70 (m, 2H), 1.64-1.52 (m, 2H).

Example 3004: (R)-1-(3-((3'-(4-((R)-3-hydroxypyrrolidin-1-yl)butoxy)-2,2'-dimethyl-[1,1'-biphenyl]-4-yl)oxy)propyl) pyrrolidin-3-ol

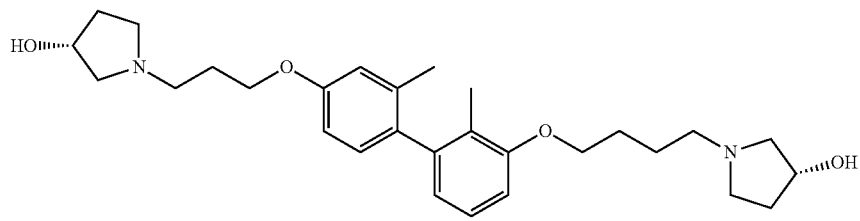 [SMILES: Cc1cc(OCCCN2CC[C@@H](O)C2)ccc1-c1cccc(OCCCCN2CC[C@@H](O)C2)c1C]

The crude material was purified via preparative LC/MS using the following conditions: Waters XBridge 5 μm C18, 19×200 mm where mobile phase A was 5:95 methanol:water with 10 mM ammonium acetate and mobile phase B was 95:5 methanol:water 10 mM ammonium acetate at a gradient of 5-45% B over 20 minutes with a 5-minute hold at a flow rate of 20 mL/minute. Fractions containing the desired product were combined and dried via centrifugal evaporation. The yield of the product was 19.6 mg (70%), and its estimated purity by LCMS analysis was 96%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.212 min; ESI-MS(+) m/z=483.1 (M+H); Analysis condition 2: Retention time=1.252 min; ESI-MS (+) m/z=483.2 (M+H); $^1$H NMR (500 MHz, DMSO-d$_6$) δ 7.15 (t, J=7.9 Hz, 1H), 6.92 (t, J=7.5 Hz, 2H), 6.84 (s, 1H), 6.78-6.75 (m, 1H), 6.62 (d, J=7.3 Hz, 1H), 4.19 (m, 2H), 4.04-3.96 (m, 4H), 3.33 (m, 2H), 2.73 (m, 2H), 2.63 (m, 2H), 2.61-2.53 (m, 4H), 2.38 (m, 2H), 2.02-1.93 (m, 5H), 1.89-1.85 (m, 2H), 1.83 (s, 3H), 1.81-1.73 (m, 2H), 1.65-1.58 (m, 2H), 1.55 (m, 2H).

Example 3005: (R)-1-(3-((3'-((5-((R)-3-hydroxypyrrolidin-1-yl)pentyl)oxy)-2,2'-dimethyl-[1,1'-biphenyl]-4-yl)oxy)propyl)pyrrolidin-3-ol

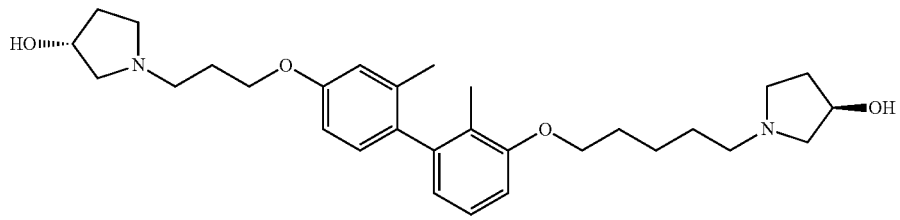 [SMILES: Cc1cc(OCCCN2CC[C@@H](O)C2)ccc1-c1cccc(OCCCCCN2CC[C@@H](O)C2)c1C]

The crude material was purified via preparative LC/MS using the following conditions: Waters XBridge 5 μm C18, 19×200 mm where mobile phase A was 5:95 methanol:water with 10 mM ammonium acetate and mobile phase B was 95:5 methanol:water 10 mM ammonium acetate at a gradient of 5-45% B over 20 minutes with a 5-minute hold at a flow rate of 20 mL/minute. Fractions containing the desired product were combined and dried via centrifugal evaporation. The yield of the product was 9.3 mg (33%), and its estimated purity by LCMS analysis was 98%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50°

C. at a gradient of 0-100% B over 3 minutes with a 0.75-minute hold at 100% B at a flow rate of 1.0 mL/minute at a UV wavelength of 220 nm. Analysis condition 1: Retention time=1.297 min; ESI-MS(+) m/z=497.2 (M+H); Analysis condition 2: Retention time=1.327 min; ESI-MS (+) m/z=497.2 (M+H); $^1$H NMR (500 MHz, DMSO-d$_6$) δ 7.19-7.13 (m, 1H), 6.92 (t, J=7.9 Hz, 2H), 6.85 (m, 1H), 6.78 (dd, J=8.4, 1.0 Hz, 1H), 6.63 (d, J=7.3 Hz, 1H), 4.21 (m, 2H), 4.06-3.96 (m, 4H), 3.39 (m, 2H), 2.85-2.68 (m, 3H), 2.68-2.54 (m, 5H), 2.41 (m, 2H), 2.05-1.97 (m, 2H), 1.95 (s, 3H), 1.92-1.86 (m, 2H), 1.83 (s, 3H), 1.80-1.72 (m, 2H), 1.63-1.43 (m, 6H).

Example 3006: (3R,3'R)-1,1'-(((2,2'-dimethyl-[1,1'-biphenyl]-3,4'-diyl)bis(oxy))bis(propane-3,1-diyl))bis(pyrrolidin-3-ol)

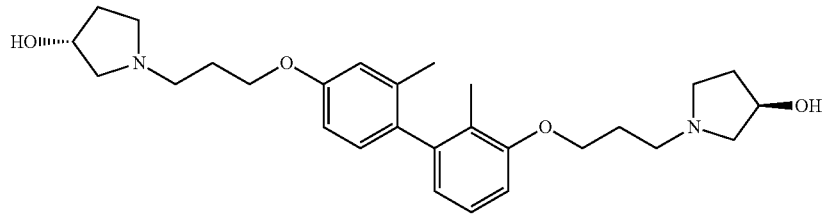 [SMILES: Cc1cc(OCCCN2CC[C@@H](O)C2)ccc1-c1cccc(OCCCN2CC[C@@H](O)C2)c1C]

The crude material was purified via preparative LC/MS using the following conditions: Waters XBridge 5 μm C18, 19×200 mm where mobile phase A was 5:95 methanol:water with 10 mM ammonium acetate and mobile phase B was 95:5 methanol:water 10 mM ammonium acetate at a gradient of 5-45% B over 20 minutes with a 5-minute hold at a flow rate of 20 mL/minute. Fractions containing the desired product were combined and dried via centrifugal evaporation. The yield of the product was 16.7 mg (64%), and its estimated purity by LCMS analysis was 100%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.148 min; ESI-MS(+) m/z=469.1 (M+H); Analysis condition 2: Retention time=1.190 min; ESI-MS (+) m/z=469.1 (M+H); $^1$H NMR (500 MHz, DMSO-d$_6$) δ 7.16 (t, J=7.9 Hz, 1H), 6.92 (m, 2H), 6.85 (m, 1H), 6.82-6.73 (m, 1H), 6.63 (d, J=7.3 Hz, 1H), 4.19 (m, 2H), 4.08-3.98 (m, 4H), 2.78-2.70 (m, 2H), 2.68-2.56 (m, 5H), 2.48 (m, 2H), 2.37 (m, 2H), 2.05-1.97 (m, 2H), 1.95 (s, 3H), 1.94-1.85 (m, 5H), 1.83 (s, 3H), 1.61-1.49 (m, 2H).

Example 3007: (R)-1-(3-((3'-(3-(dimethylamino)propoxy)-2,2'-dimethyl-[1,1'-biphenyl]-3-yl)oxy)propyl)pyrrolidin-3-ol

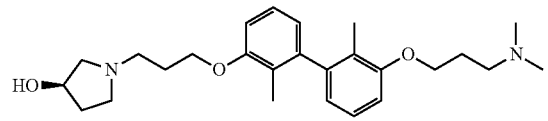 [SMILES: Cc1c(OCCCN(C)C)cccc1-c1cccc(OCCCN2CC[C@@H](O)C2)c1C]

The crude material was purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 10-50% B over 20 minutes with a 5-minute hold at a flow rate of 20 mL/minute. Fractions containing the desired product were combined and dried via centrifugal evaporation. The yield of the product was 55.6 mg (56%), and its estimated purity by LCMS analysis was 97%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.131 min; ESI-MS(+) m/z=427.1 (M+H); Analysis condition 2: Retention time=1.127 min; ESI-MS (+) m/z=427.3 (M+H); $^1$H NMR (500 MHz, DMSO-d$_6$) δ 7.19 (t, J=7.9 Hz, 2H), 6.94 (d, J=8.1 Hz, 2H), 6.65 (d, J=7.3 Hz, 2H), 4.43 (br. s., 1H), 4.11-4.01 (m, 4H), 3.43 (m, 4H), 3.32 (m, 2H), 3.28-3.09 (m, 2H), 2.81 (s, 6H), 2.21-2.07 (m, 5H), 1.84 (m, 7H).

Example 3008: N-(4-((R)-3-hydroxypyrrolidin-1-yl)butyl)-3'-(3-((R)-3-hydroxypyrrolidin-1-yl)propoxy)-2,2'-dimethyl-[1,1'-biphenyl]-3-carboxamide

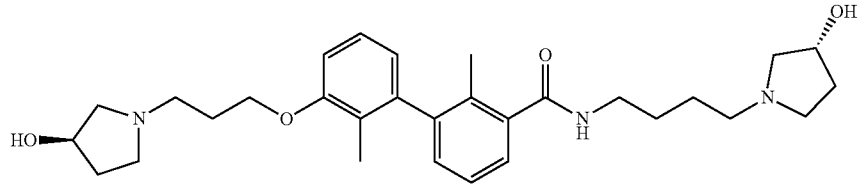 [SMILES: Cc1c(OCCCN2CC[C@@H](O)C2)cccc1-c1cccc(C(=O)NCCCCN2CC[C@@H](O)C2)c1C]

The crude material was purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 10-50% B over 20 minutes with a 5-minute hold at a flow rate of 20 mL/minute. Fractions containing the desired product were combined and dried via centrifugal evaporation. The yield of the product was 63.2 mg (58.4%), and its estimated purity by LCMS analysis was 100%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.023 min; ESI-MS(+) m/z=510.2 (M+H); Analysis condition 2: Retention time=1.032 min; ESI-MS (+) m/z=510.2 (M+H); $^1$H NMR (500 MHz, DMSO-$d_6$) δ 8.38 (br. s., 1H), 7.28 (m, 2H), 7.22 (t, J=7.9 Hz, 1H), 7.14-7.06 (m, 1H), 6.96 (d, J=8.4 Hz, 1H), 6.65 (d, J=7.7 Hz, 1H), 4.43 (br. s., 2H), 4.08 (m, 2H), 3.59 (m, 1H), 3.44 (m, 4H), 3.33 (m, 2H), 3.24 (m, 3H), 3.16 (m, 2H), 3.07 (m, 1H), 2.15 (m, 4H), 1.96 (m, 4H), 1.85 (m, 5H), 1.68 (m, 2H), 1.53 (m, 2H).

Example 3009: 3'-(3-((R)-3-hydroxypyrrolidin-1-yl)propoxy)-N-(3-((R)-3-hydroxypyrrolidin-1-yl)propyl)-2,2'-dimethyl-[1,1'-biphenyl]-3-carboxamide

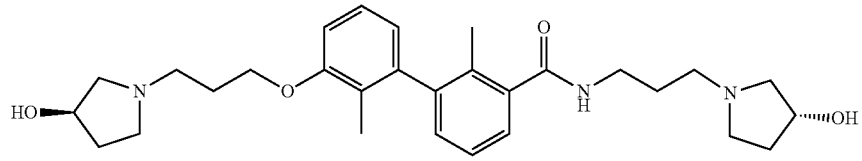 [SMILES: Cc1c(OCCCN2CC[C@@H](O)C2)cccc1-c1cccc(C(=O)NCCCN2CC[C@@H](O)C2)c1C]

The crude material was purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 5-45% B over 20 minutes with a 5-minute hold at a flow rate of 20 mL/minute. Fractions containing the desired product were combined and dried via centrifugal evaporation. The yield of the product was 62.1 mg (58%), and its estimated purity by LCMS analysis was 99%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=0.903 min; ESI-MS(+) m/z=496.2 (M+H); Analysis condition 2: Retention time=0.953 min; ESI-MS (+) m/z=496.2 (M+H); $^1$H NMR (500 MHz, DMSO-d$_6$) δ 8.51-8.41 (m, 1H), 7.37-7.27 (m, 2H), 7.23 (t, J=7.9 Hz, 1H), 7.11 (d, J=7.3 Hz, 1H), 6.97 (d, J=8.1 Hz, 1H), 6.66 (d, J=7.7 Hz, 1H), 4.44 (br. s., 2H), 4.15-4.02 (m, 2H), 3.65 (m, 1H), 3.42 (m, 5H), 3.29 (m, 4H), 3.25 (m, 4H), 2.26 (m, 1H), 2.16 (m, 2H), 1.98 (m, 4H), 1.95-1.79 (m, 7H).

Example 3010: (R)—N-(3-(dimethylamino)propyl)-3'-(3-(3-hydroxypyrrolidin-1-yl)propoxy)-2,2'-dimethyl-[1,1'-biphenyl]-3-sulfonamide

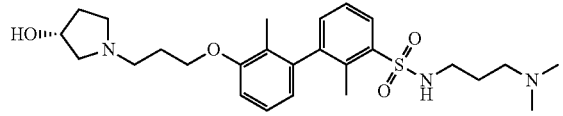 [SMILES: Cc1c(OCCCN2CC[C@@H](O)C2)cccc1-c1cccc(S(=O)(=O)NCCCN(C)C)c1C]

The crude material was purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 10-50% B over 20 minutes with a 5-minute hold at a flow rate of 20 mL/minute. Fractions containing the desired product were combined and dried via centrifugal evaporation. The yield of the product was 68.9 mg (65%), and its estimated purity by LCMS analysis was 99%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=0.991 min; ESI-MS(+) m/z=490.1 (M+H); Analysis condition 2: Retention time=1.036 min; ESI-MS (+) m/z=490.1 (M+H); $^1$H NMR (500 MHz, DMSO-d$_6$) δ 7.86 (d, J=7.7 Hz, 1H), 7.46 (t, J=7.7 Hz, 1H), 7.33 (d, J=7.3 Hz, 1H), 7.26 (t, J=7.7 Hz, 1H), 7.01 (d, J=8.4 Hz, 1H), 6.70 (d, J=7.7 Hz, 1H), 4.44 (br. s., 1H), 4.16-4.04 (m, 2H), 3.41-3.30 (m, 4H), 3.34 (m, 1H), 3.25 (m, 1H), 3.06 (m, 2H), 2.91 (m, 2H), 2.75 (s, 6H), 2.25 (s, 3H), 2.16 (m, 3H), 1.91 (m, 1H), 1.83 (s, 3H), 1.78 (m, 2H).

Example 3011: (R)-5-(((3'-(3-(3-hydroxypyrrolidin-1-yl)propoxy)-2,2'-dimethyl-[1,1'-biphenyl]-3-yl)oxy)methylnicotinonitrile

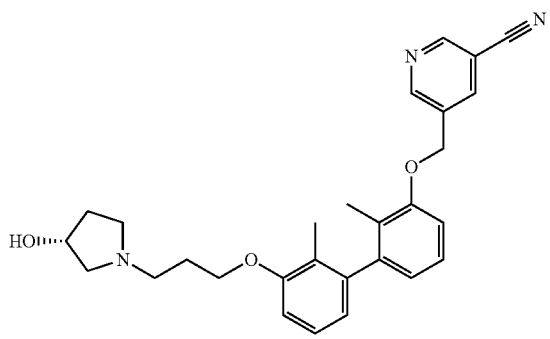 [SMILES: Cc1c(OCCCN2CC[C@@H](O)C2)cccc1-c1cccc(OCc2cncc(C#N)c2)c1C]

The crude material was purified via preparative LC/MS using the following conditions: Waters XBridge 5 μm C18, 19×200 mm where mobile phase A was 5:95 acetonitrile:water with 10-mM ammonium acetate and mobile phase B was 95:5 acetonitrile:water with 10-mM ammonium acetate at a gradient of 20-60% B over 20 minutes with a 5-minute hold at a flow rate of 20 mL/minute. Fractions containing the desired product were combined and dried via centrifugal evaporation. The yield of the product was 22.8 mg (37%), and its estimated purity by LCMS analysis was 98%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=2.051 min; ESI-MS(+) m/z=458.1 (M+H); Analysis condition 2: Retention time=1.986 min; ESI-MS (+) m/z=458.1 (M+H); $^1$H NMR (500 MHz, DMSO-d$_6$) δ 9.00 (m, 2H), 8.43 (t, J=2.0 Hz, 1H), 7.26-7.14 (m, 2H), 7.07 (d, J=8.2 Hz, 1H), 6.93 (d, J=7.9 Hz, 1H), 6.71 (d, J=7.3 Hz, 1H), 6.64 (d, J=7.3 Hz, 1H), 5.31-5.19 (m, 2H), 4.23-4.13 (m, 1H), 4.10-3.97 (m, 2H), 2.73-2.66 (m, 1H), 2.62-2.52 (m, 3H), 2.43 (m, 1H), 2.32 (m, 1H), 1.97 (m, 1H), 1.90 (m, 2H), 1.86 (s, 3H), 1.82 (s, 3H), 1.53 (m, 1H).

Example 3012: (3R,3'R)-1,1'-(((2,2'-dimethyl-[1,1'-biphenyl]-4,4'-diyl)bis(oxy))bis(propane-3,1-diyl))bis(pyrrolidin-3-ol)

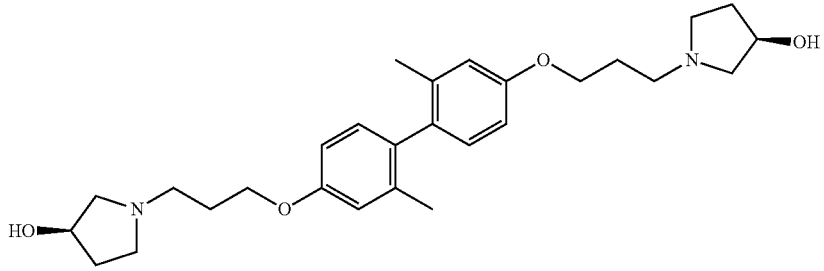 [SMILES: Cc1cc(OCCCN2CC[C@@H](O)C2)ccc1-c1ccc(OCCCN2CC[C@@H](O)C2)cc1C]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 methanol:water with 10 mM ammonium acetate at a gradient of 3-38% B over 30 minutes with a 5-minute hold at a flow rate of 20 mL/minute. Fractions containing the desired product were combined and dried via centrifugal evaporation. The yield of the product was 18.1 mg (35%), and its estimated purity by LCMS analysis was 100%.

Two analytical LC/MS injections were used to determine the final purity.
Injection 1 Conditions:
Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 Conditions:
Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.479 min; ESI-MS(+) m/z=469.2 (M+H); Analysis condition 2: Retention time=1.816 min; ESI-MS (+) m/z=469.1 (M+H); $^1$H NMR (500 MHz, DMSO-$d_6$) δ 6.93 (d, J=8.2 Hz, 2H), 6.85 (d, J=2.4 Hz, 2H), 6.78 (dd, J=8.2, 2.4 Hz, 2H), 5.02 (br. s., 2H), 4.29 (m, 2H), 4.04 (t, J=6.3 Hz, 4H), 2.96 (m, 4H), 2.85 (m, 6H), 2.71 (m, 2H), 2.06 (m, 2H), 2.01-1.97 (m, 2H), 1.96 (m, 10H), 1.68 (m, 2H).

Example 3013: 3-((R)-3-hydroxypyrrolidin-1-yl)-N-(3'-(3-((R)-3-hydroxypyrrolidin-1-yl)propoxy)-2,2'-dimethyl-[1,1'-biphenyl]-3-yl)propanamide

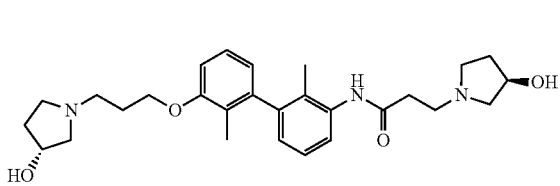 [SMILES: Cc1c(NC(=O)CCN2CC[C@@H](O)C2)cccc1-c1cccc(OCCCN2CC[C@@H](O)C2)c1C]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 methanol:water with 10 mM ammonium acetate at a gradient of 3-43% B over 30 minutes with a 5-minute hold at a flow rate of 20 mL/minute. Fractions containing the desired product were combined and dried via centrifugal evaporation. The yield of the product was 29.8 mg (53.6%), and its estimated purity by LCMS analysis was 96%.

Two analytical LC/MS injections were used to determine the final purity.
Injection 1 Conditions:
Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 Conditions:
Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.422 min; ESI-MS(+) m/z=482.1 (M+H); Analysis condition 2: Retention time=1.446 min; ESI-MS (+) m/z=482.1 (M+H); $^1$H NMR (500 MHz, DMSO-$d_6$) δ 10.02 (s, 1H), 7.66 (d, J=8.1 Hz, 1H), 7.18 (t, J=7.9 Hz, 2H), 6.93 (d, J=8.1 Hz, 1H), 6.83 (d, J=7.7 Hz, 1H), 6.63 (d, J=7.7 Hz, 1H), 4.19 (m, 2H), 4.09-3.99 (m, 2H), 2.79-2.66 (m, 5H), 2.66-2.55 (m, 3H), 2.49 (m, 4H), 2.43 (m, 1H), 2.37 (m, 1H), 1.98 (m, 2H), 1.93-1.91 (m, 2H), 1.87 (s, 3H), 1.81 (s, 3H), 1.60-1.48 (m, 2H).

Example 3014: (R)-3-(3-(3'-(3-(3-hydroxypyrrolidin-1-yl)propoxy)-2,2'-dimethyl-[1,1'-biphenyl]-3-yl)ureido)propanoic acid

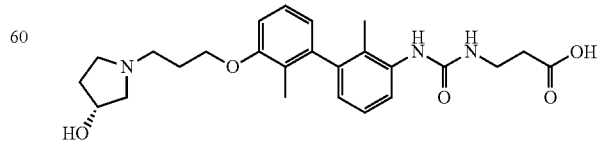

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 5-45% B over 15 minutes with a 5-minute hold at a flow rate of 20 mL/minute. Fractions containing the desired product were combined and dried via centrifugal evaporation. The yield of the product was 12.7 mg (25%), and its estimated purity by LCMS analysis was 100%.

Two analytical LC/MS injections were used to determine the final purity.
Injection 1 Conditions:
Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 Conditions:
Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=0.967 min; ESI-MS(+) m/z=456.2 (M+H); Analysis condition 2: Retention time=1.290 min; ESI-MS (+) m/z=456.4 (M+H); $^1$H NMR (500 MHz, DMSO-d$_6$) δ 7.81 (d, J=8.1 Hz, 1H), 7.78 (br. s., 1H), 7.18 (t, J=7.9 Hz, 1H), 7.12 (t, J=7.9 Hz, 1H), 6.93 (d, J=8.1 Hz, 1H), 6.72-6.61 (m, 3H), 4.21 (br. s., 1H), 4.10-3.99 (m, 2H), 2.77 (d, J=7.7 Hz, 1H), 2.70-2.59 (m, 3H), 2.55 (m, 3H), 2.43 (m, 3H), 1.94 (m, 3H), 1.83 (m, 6H), 1.57 (d, J=4.0 Hz, 1H).

Example 3015: N-(2-((R)-3-hydroxypyrrolidin-1-yl)ethyl)-3'-(3-((R)-3-hydroxypyrrolidin-1-yl)propoxy)-2,2'-dimethyl-[1,1'-biphenyl]-3-carboxamide

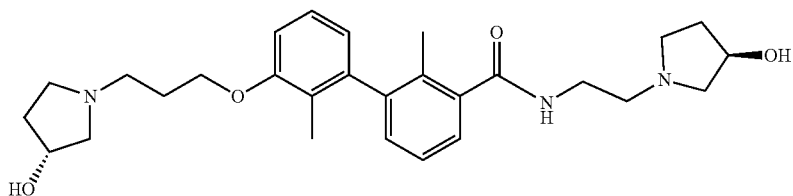 [SMILES: Cc1c(OCCCN2CC[C@@H](O)C2)cccc1-c1cccc(C(=O)NCCN2CC[C@@H](O)C2)c1C]

The crude material was purified via preparative LC/MS using the following conditions: Waters XBridge 5 μm C18, 19×200 mm where mobile phase A was 5:95 methanol:water with 10-mM ammonium acetate and mobile phase B was 95:5 methanol:water with 10-mM ammonium acetate at a gradient of 30-70% B over 15 minutes with a 5-minute hold at a flow rate of 20 mL/minute. Fractions containing the desired product were combined and dried via centrifugal evaporation. The yield of the product was 22.4 mg (42%), and its estimated purity by LCMS analysis was 100%.

Two analytical LC/MS injections were used to determine the final purity.
Injection 1 Conditions:
Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 Conditions:
Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.335 min; ESI-MS(+) m/z=482.1 (M+H); Analysis condition 2: Retention time=1.136 min; ESI-MS (+) m/z=482.1 (M+H); $^1$H NMR (500 MHz, DMSO-d$_6$) δ 8.24 (t, J=5.5 Hz, 1H), 7.27 (m, 2H), 7.20 (t, J=8.1 Hz, 1H), 7.10 (t, J=7.7 Hz, 1H), 6.95 (d, J=8.1 Hz, 1H), 6.64 (d, J=7.7 Hz, 1H), 4.20 (m, 2H), 4.12-4.00 (m, 2H), 2.78 (m, 2H), 2.65 (m, 4H), 2.62-2.54 (m, 4H), 2.50 (m, 2H), 2.46 (m, 1H), 2.38 (m, 1H), 2.06-1.93 (m, 7H), 1.84 (s, 3H), 1.56 (m, 2H).

Example 3016: N-(2-((R)-3-hydroxypyrrolidin-1-yl)ethyl)-3'-(3-((R)-3-hydroxypyrrolidin-1-yl)propoxy)-2,2'-dimethyl-[1,1'-biphenyl]-3-sulfonamide

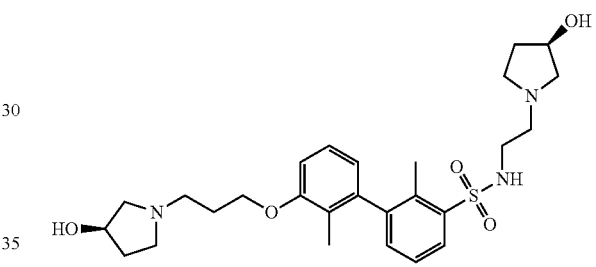

The crude material was purified via preparative LC/MS using the following conditions: Waters XBridge 5 μm C18, 19×200 mm where mobile phase A was 5:95 acetonitrile:water with 10-mM ammonium acetate and mobile phase B was 95:5 acetonitrile:water with 10-mM ammonium acetate at a gradient of 5-45% B over 30 minutes with a 5-minute hold at a flow rate of 20 mL/minute. Fractions containing the desired product were combined and dried via centrifugal evaporation. The material was further purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 10-100% B over 15 minutes with a 5-minute hold at a flow rate of 20 mL/minute. Fractions containing the desired product were combined and dried via centrifugal evaporation. The yield of the product was 18.7 mg (33%), and its estimated purity by LCMS analysis was 100%.

Two analytical LC/MS injections were used to determine the final purity.
Injection 1 Conditions:

Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 µm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.077 min; ESI-MS(+) m/z=518.2 (M+H); Analysis condition 2: Retention time=1.029 min; ESI-MS (+) m/z=518.2 (M+H); $^1$H NMR (500 MHz, DMSO-d$_6$) δ 7.87 (d, J=7.7 Hz, 1H), 7.47 (t, J=7.7 Hz, 1H), 7.34 (d, J=7.0 Hz, 1H), 7.25 (t, J=7.0 Hz, 1H), 7.00 (d, J=7.7 Hz, 1H), 6.70 (d, J=7.0 Hz, 1H), 4.48-4.37 (m, 2H), 4.09 (m, 2H), 3.37 (m, 5H), 3.16 (m, 1H), 2.69 (m, 2H), 2.54 (m, 2H), 2.49 (m, 3H), 2.24 (s, 3H), 2.16 (m, 5H), 1.88 (m, 2H), 1.82 (s, 3H).

Example 3017: 1-(2-((R)-3-hydroxypyrrolidin-1-yl)ethyl)-3-(3'-(3-((R)-3-hydroxypyrrolidin-1-yl)propoxy)-2,2'-dimethyl-[1,1'-biphenyl]-3-yl)urea

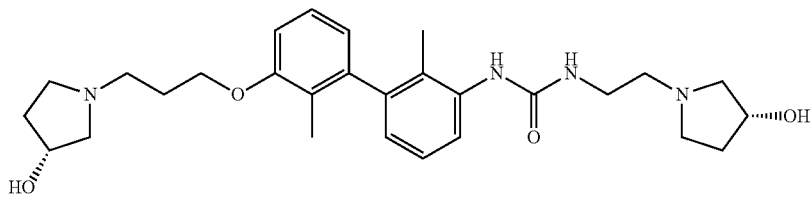 [SMILES: Cc1c(NC(=O)NCCN2CC[C@@H](O)C2)cccc1-c1cccc(OCCCN2CC[C@@H](O)C2)c1C]

The crude material was purified via preparative LC/MS using the following conditions: Waters XBridge 5 µm C18, 19×200 mm where mobile phase A was 5:95 acetonitrile:water with 10 mM ammonium acetate and mobile phase B was 95:5 acetonitrile:water with 10 mM ammonium acetate at a gradient of 0-30% B over 25 minutes with a 5-minute hold at a flow rate of 20 mL/minute. Fractions containing the desired product were combined and dried via centrifugal evaporation.

The compound was further purified via preparative LC/MS using the following conditions: Waters XBridge 5 µm C18, 19×200 mm where mobile phase A was 5:95 acetonitrile:water with 0.1% TFA and mobile phase B was 95:5 acetonitrile:water with 0.1% TFA at a gradient of 0-40% B over 20 minutes with a 5-minute hold at a flow rate of 20 mL/minute. Fractions containing the desired product were combined and dried via centrifugal evaporation. The yield of the product was 12.5 mg (10%), and its estimated purity by LCMS analysis was 99%.

Two analytical LC/MS injections were used to determine the final purity.

Injection 1 Conditions:

Waters Acquity UPLC BEH 1.7 µm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 µm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.032 min; ESI-MS(+) m/z=497.2 (M+H); Analysis condition 2: Retention time=1.075 min; ESI-MS (+) m/z=497.2 (M+H); $^1$H NMR (500 MHz, DMSO-d$_6$) δ 7.99 (br. s., 1H), 7.74 (d, J=8.2 Hz, 1H), 7.24-7.11 (m, 2H), 6.94 (d, J=8.2 Hz, 1H), 6.88 (t, J=5.8 Hz, 1H), 6.72 (d, J=7.0 Hz, 1H), 6.66 (d, J=7.6 Hz, 1H), 4.43 (m, 2H), 4.17-4.02 (m, 2H), 3.74-3.54 (m, 2H), 3.48-3.41 (m, 4H), 3.3 (m, 4H), 3.26 (m, 2H), 3.16 (m, 2H), 2.15 (m, 4H), 1.94-1.76 (m, 8H).

Example 3018: (R)-1-(3-((3'-(3-((R)-3-hydroxypyrrolidin-1-yl)propoxy)-2,2'-dimethyl-[1,1'-biphenyl]-3-yl)amino)propyl)pyrrolidin-3-ol

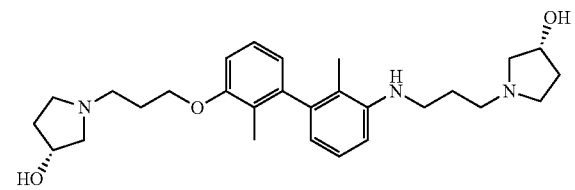 [SMILES: Cc1c(NCCCN2CC[C@@H](O)C2)cccc1-c1cccc(OCCCN2CC[C@@H](O)C2)c1C]

The crude material was purified via preparative LC/MS using the following conditions: Waters XBridge 5 µm C18, 19×200 mm where mobile phase A was 5:95 acetonitrile:water with 10 mM ammonium acetate and mobile phase B was 95:5 acetonitrile:water with 10 mM ammonium acetate at a gradient of 5-50% B over 25 minutes with a 5-minute hold at a flow rate of 20 mL/minute. Fractions containing the desired product were combined and dried via centrifugal evaporation. The yield of the product was 3.5 mg (6%), and its estimated purity by LCMS analysis was 98%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.130 min; ESI-MS(+) m/z=468.2 (M+H); Analysis condition 2: Retention time=1.023 min; ESI-MS (+) m/z=468.2 (M+H); $^1$H NMR (500 MHz, DMSO-$d_6$) δ 7.15 (t, J=7.9 Hz, 1H), 7.04 (t, J=7.3 Hz, 1H), 6.90 (d, J=7.9 Hz, 1H), 6.62 (d, J=7.3 Hz, 1H), 6.52 (d, J=7.9 Hz, 1H), 6.30 (d, J=7.3 Hz, 1H), 4.21 (m, 2H), 4.09-3.98 (m, 2H), 3.15 (m, 2H), 2.83-2.73 (m, 2H), 2.73-2.56 (m, 6H), 2.50 (m, 2H), 2.41 (m, 2H), 2.05-1.93 (m, 2H), 1.93-1.86 (m, 2H), 1.85-1.75 (m, 5H), 1.72 (s, 3H), 1.63-1.51 (m, 2H).

Example 3019: (R)-3-(((3'-(3-(3-hydroxypyrrolidin-1-yl)propoxy)-2,2'-dimethyl-[1,1'-biphenyl]-3-yl)oxy)methyl)benzonitrile

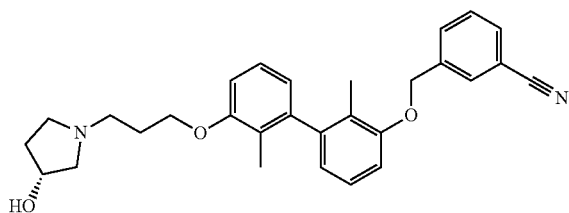 [SMILES: Cc1c(OCCCN2CC[C@@H](O)C2)cccc1-c1cccc(OCc2cccc(C#N)c2)c1C]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 28-68% B over 22 minutes with a 5-minute hold at a flow rate of 20 mL/minute. Fractions containing the desired product were combined and dried via centrifugal evaporation. The yield of the product was 37.4 mg (74%), and its estimated purity by LCMS analysis was 100%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.990 min; ESI-MS(+) m/z=457.1 (M+H); Analysis condition 2: Retention time=1.844 min; ESI-MS (+) m/z=457.1 (M+H); $^1$H NMR (500 MHz, DMSO-$d_6$) δ 7.92 (s, 1H), 7.83 (m, 2H), 7.68-7.61 (m, 1H), 7.19 (m, 2H), 7.04 (d, J=8.1 Hz, 1H), 6.93 (d, J=8.1 Hz, 1H), 6.69 (d, J=7.3 Hz, 1H), 6.64 (d, J=7.3 Hz, 1H), 5.21 (m, 2H), 4.18 (m, 1H), 4.10-3.98 (m, 2H), 2.77-2.68 (m, 1H), 2.66-2.53 (m, 3H), 2.49-2.42 (m, 1H), 2.34 (dd, J=9.9, 3.3 Hz, 1H), 2.05-1.92 (m, 1H), 1.92-1.86 (m, 5H), 1.82 (s, 3H), 1.60-1.47 (m, 1H).

Example 3020: (R)-3-(3'-(3-(3-hydroxypyrrolidin-1-yl)propoxy)-2,2'-dimethyl-[1,1'-biphenyl]-3-ylsulfonamido)propanoic acid

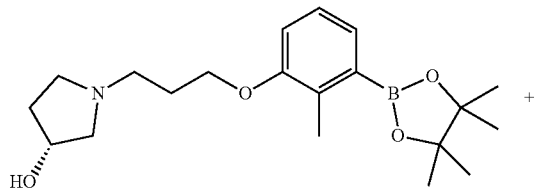

+

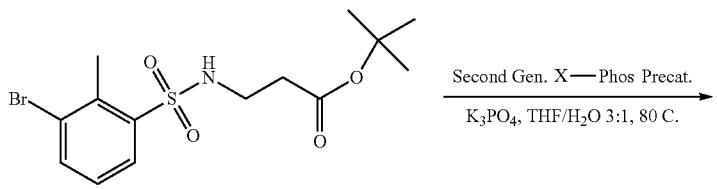

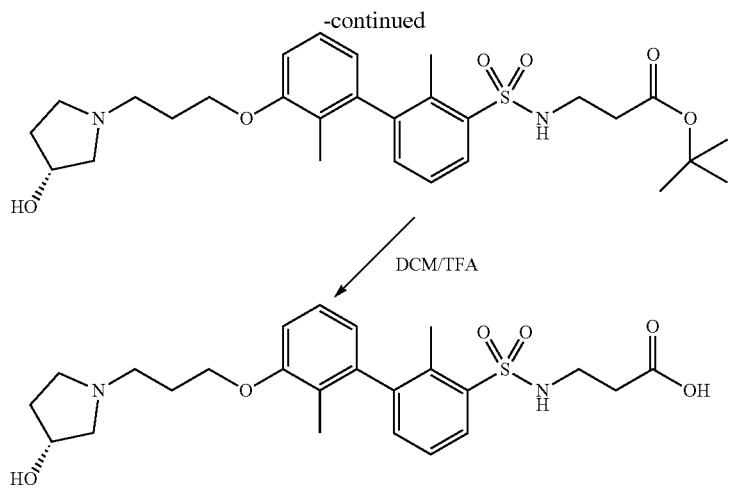

To a small sealed tube was added THF (6.0 mL), water (2.0 mL), (R)-1-(3-(2-methyl-3-(4,4,5,5-tetramethyl-1,3,2-dioxaborolan-2-yl)phenoxy)propyl)pyrrolidin-3-ol (40 mg, 0.111 mmol), tert-butyl 3-(3-bromo-2-methylphenylsulfonamido)propanoate (52.4 mg, 0.111 mmol), tribasic potassium phosphate (47.0 mg, 0.221 mmol), and second generation X-Phos precatalyst (4.36 mg, 5.54 μmol). The vessel was sealed, the mixture de-gassed/flushed with nitrogen and then heated overnight at 80° C. The reaction mixture was cooled and the product concentrated to an oil. The oil was diluted with 10 mL of DCM, washed with water, brine, dried over sodium sulfate, filtered, and evaporated. The crude intermediate was taken up in 4 mL of DCM. To this solution was then added 1 mL of TFA dropwise. The mixture was stirred for 30 minutes and then evaporated to an oil. The crude material was purified via preparative LC/MS using the following conditions: Waters XBridge 5 μm C18, 19×200 mm where mobile phase A was 5:95 methanol:water with 10-mM ammonium acetate and mobile phase B was 95:5 methanol:water with 10-mM ammonium acetate at a gradient of 30-70% B over 20 minutes with a 5-minute hold at a flow rate of 20 mL/minute. Fractions containing the desired product were combined and dried via centrifugal evaporation. The yield of the product was 3.0 mg (6%), and its estimated purity by LCMS analysis was 98%.

Two analytical LC/MS injections were used to determine the final purity.
Injection 1 Conditions:
Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 Conditions:
Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.419 min; ESI-MS(+) m/z=477.0 (M+H); Analysis condition 2: Retention time=1.452 min; ESI-MS (+) m/z=477.0 (M+H); $^1$H NMR (500 MHz, DMSO-$d_6$) δ 7.89 (dd, J=7.7, 1.1 Hz, 1H), 7.45 (t, J=7.7 Hz, 1H), 7.32 (d, J=7.7 Hz, 1H), 7.25 (t, J=8.1 Hz, 1H), 7.00 (d, J=8.1 Hz, 1H), 6.72 (d, J=7.7 Hz, 1H), 4.48-4.38 (m, 1H), 4.18-4.01 (m, 2H), 3.39-3.22 (m, 4H), 3.09-3.00 (m, 2H), 2.55 (m, 2H), 2.36 (td, J=7.1, 2.0 Hz, 2H), 2.24 (s, 3H), 2.15 (m, 3H), 1.83 (m, 4H).

Example 3021: (3S,3'S)-1,1'-(((2'-methyl-[1,1'-biphenyl]-3,4-diyl)bis(oxy))bis(propane-3,1-diyl))bis(pyrrolidin-3-ol)

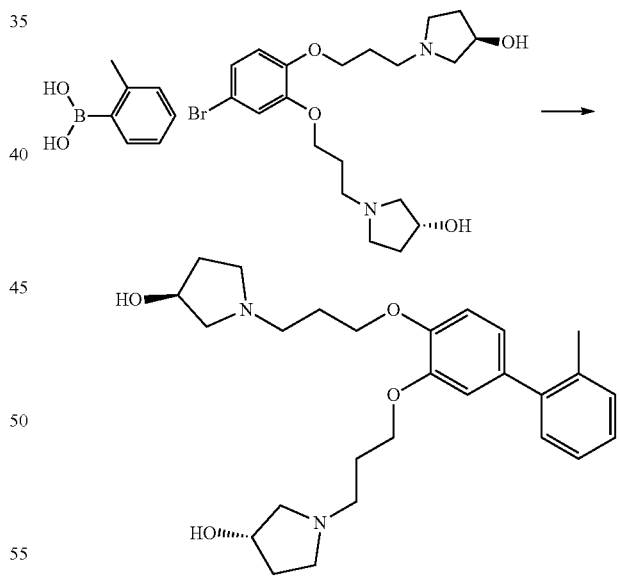

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-55% B over 15 minutes with a 5-minute hold at a flow rate of 20 mL/minute. Fractions containing the desired product were combined and dried via centrifugal evaporation. The yield of the product was 11.8 mg (33.5%), and its estimated purity by LCMS analysis was 96%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.228 min; ESI-MS(+) m/z=455.1 (M+H); Analysis condition 2: Retention time=1.232 min; ESI-MS (+) m/z=455.1 (M+H); $^1$H NMR (500 MHz, DMSO-$d_6$) δ 7.30-7.16 (m, 4H), 7.01 (d, J=8.2 Hz, 1H), 6.89 (d, J=1.8 Hz, 1H), 6.83 (dd, J=8.1, 2.0 Hz, 1H), 4.26-4.18 (m, 2H), 4.04 (q, J=6.3 Hz, 4H), 2.85-2.77 (m, 2H), 2.77-2.63 (m, 6H), 2.63-2.54 (m, 2H), 2.49-2.43 (m, 2H), 2.24 (s, 3H), 2.06-1.94 (m, 2H), 1.94-1.86 (m, 4H), 1.59 (m, 2H).

Example 3022: (3S,3'S)-1,1'-(((3'-(3-((R)-3-hydroxypyrrolidin-1-yl)propoxy)-2'-methyl-[1,1'-biphenyl]-3,4-diyl)bis(oxy))bis(propane-3,1-diyl))bis(pyrrolidin-3-ol)

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 5-40% B over 15 minutes with a 5-minute hold at a flow rate of 20 mL/minute. Fractions containing the desired product were combined and dried via centrifugal evaporation. The yield of the product was 18.8 mg (42%), and its estimated purity by LCMS analysis was 99%.

Two analytical LC/MS injections were used to determine the final purity.

Injection 1 Conditions:

Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 Conditions:

Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=0.994 min; ESI-MS(+) m/z=598.3 (M+H); Analysis condition 2: Retention time=0.954 min; ESI-MS (+) m/z=598.3 (M+H); $^1$H NMR (500 MHz, DMSO-$d_6$) δ

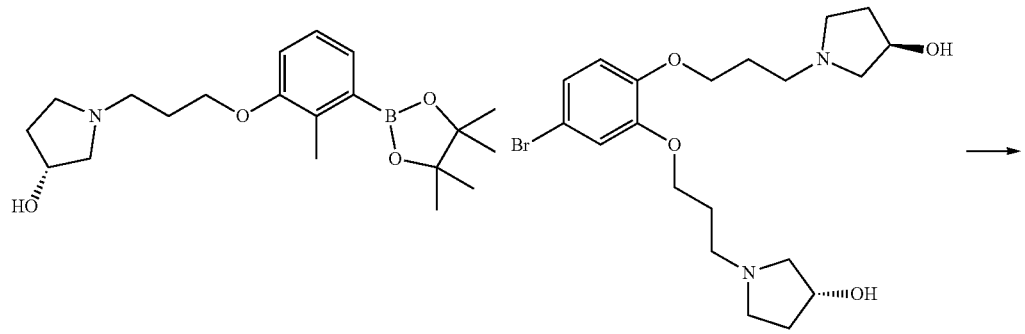

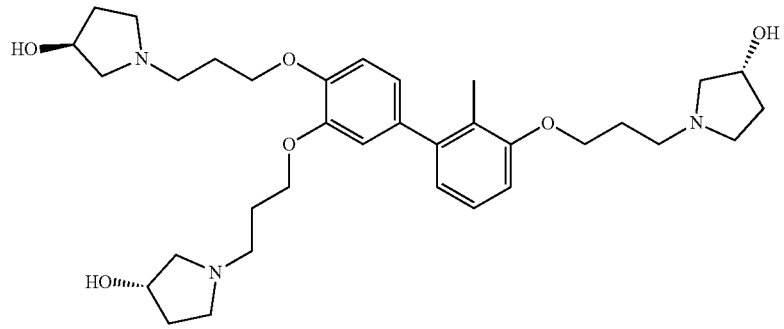

7.19-7.13 (m, 1H), 7.00 (d, J=8.2 Hz, 1H), 6.91 (d, J=8.2 Hz, 1H), 6.85 (d, J=1.8 Hz, 1H), 6.81-6.75 (m, 2H), 4.25-4.16 (m, 3H), 4.08-3.98 (m, 6H), 2.79-2.73 (m, 3H), 2.70-2.57 (m, 9H), 2.50 (m, 3H), 2.44-2.35 (m, 3H), 2.05-1.93 (m, 3H), 1.93-1.83 (m, 9H), 1.57 (m, 3H).

Intermediate: 2-methyl-3-(4,4,5,5-tetramethyl-1,3,2-dioxaborolan-2-yl)phenol

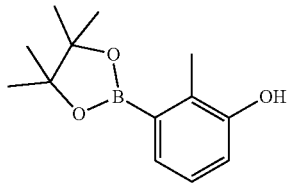 [SMILES: Cc1c(O)cccc1B1OC(C)(C)C(C)(C)O1]

To a sealed tube was added 3-bromo-2-methylphenol (1000 mg, 5.35 mmol) in dioxane (15.0 ml) along with potassium acetate (1574 mg, 16.04 mmol), bis(pinacolato)diboron (2172 mg, 8.55 mmol) and [1,1'-bis(diphenylphosphino)ferrocene]dichloropalladium(II) (509 mg, 0.695 mmol). The vessel was sealed, the contents evacuated/flushed with nitrogen three times, and the mixture then heated for 24 hours at 90° C. The solvent was removed, The residue was purified by silica gel column chromatography (Biotage 25 m, MeOH/CH$_2$Cl$_2$=0 to 15%) to give 1350 mg (108%) of the product.
$^1$H NMR (400 MHz, CHLOROFORM-d) δ 7.37 (d, J=7.5 Hz, 1H), 7.10 (t, J=7.7 Hz, 1H), 6.88 (d, J=7.8 Hz, 1H), 4.66 (s, 1H), 2.47 (s, 3H), 1.36 (s, 12H).

Intermediates: 2-(3-(3-chloropropoxy)-2-methylphenyl)-4,4,5,5-tetramethyl-1,3,2-dioxaborolane and 2-(3-(3-bromopropoxy)-2-methylphenyl)-4,4,5,5-tetramethyl-1,3,2-dioxaborolane

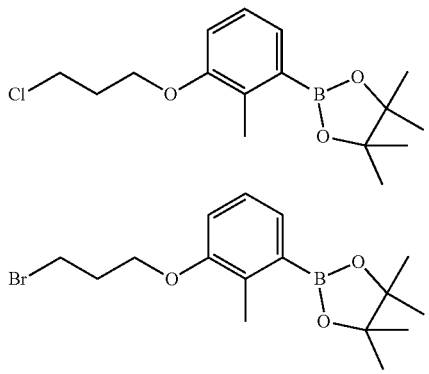

To 2-methyl-3-(4,4,5,5-tetramethyl-1,3,2-dioxaborolan-2-yl)phenol (1300 mg, 5.55 mmol) in DMF (15 mL) was added potassium carbonate (921 mg, 6.66 mmol) and 1-bromo-3-chloropropane (0.546 mL, 5.55 mmol). The mixture was stirred for 23 hrs at 50° C. The solid was removed by filtration. The solvent was removed, and the residue was purified by silica gel column chromatography (Biotage 25m, EtOAc/Hexane=20%) to give 1.015 g (59%) of a mixture of 3-chloropropoxy and 3-bromopropoxy compounds as an oil. Based on $^1$H NMR: 3-chloropropoxy was 77% and 3-bromopropoxy was 23%.

$^1$H NMR (500 MHz, CHLOROFORM-d) δ 7.40 (d, J=7.3 Hz, 1H), 7.21-7.16 (m, 1H), 6.96 (d, J=8.0 Hz, 1H), 4.16-4.10 (m, 2H), 3.81 (t, J=6.3 Hz, 1.55H), 3.67 (t, J=6.5 Hz, 0.45H), 2.47 (s, 3H), 2.37 (quin J=6.1 Hz, 0.45H), 2.29 (quin, J=6.0 Hz, 1.55H), 1.39 (s, 12H).

Intermediate: (R)-1-(3-(2-methyl-3-(4,4,5,5-tetramethyl-1,3,2-dioxaborolan-2-yl)phenoxy)propyl)pyrrolidin-3-ol

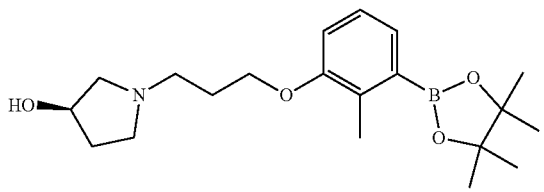 [SMILES: Cc1c(OCCCN2CC[C@@H](O)C2)cccc1B1OC(C)(C)C(C)(C)O1]

The mixture of (R)-3-hydroxypyrrolidine hydrochloride (606 mg, 4.90 mmol), 2-(3-(3-chloropropoxy)-2-methylphenyl)-4,4,5,5-tetramethyl-1,3,2-dioxaborolane (1015 mg, 3.27 mmol, the mixture of chloro- and bromopropoxy prepared above was used and mmol based on the chloro compound), sodium iodide (490 mg, 3.27 mmol), and potassium carbonate (1129 mg, 8.17 mmol) in DMF (50 mL) was stirred for 48 hrs at 50° C. The solid was removed by filtration. The solvent was removed. The residue was purified by silica gel column chromatography (Biotage 25s, NH$_3$/Methanol/CH$_2$Cl$_2$=0:0:100 to 1:19:80) to give 650 mg (55%) of target compound as an oil. $^1$H NMR (500 MHz, CHLOROFORM-d) δ 7.37-7.34 (m, 1H), 7.18-7.13 (m, 1H), 6.94-6.91 (m, 1H), 4.38 (ddt, J=7.1, 4.8, 2.3 Hz, 1H), 4.04 (t, J=6.1 Hz, 2H), 2.97 (td, J=8.7, 5.5 Hz, 1H), 2.79-2.70 (m, 3H), 2.63 (dd, J=10.0, 5.0 Hz, 1H), 2.45 (s, 3H), 2.48-2.36 (m, 1H), 2.22 (dddd, J=13.9, 8.6, 7.0, 5.5 Hz, 1H), 2.10-2.02 (m, 2H), 1.84-1.76 (m, 1H), 1.37 (m, 12H).

Intermediate: 1-bromo-3-(3-chloropropoxy)benzene and 1-bromo-3-(3-bromopropoxy)benzene

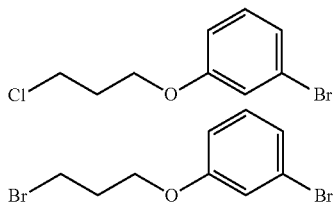

The mixture (410 mg, 57%) of 1-bromo-3-(3-chloropropoxy)benzene and 1-bromo-3-(3-bromopropoxy)benzene was obtained from 3-bromophenol and 1-bromo-3-chloropropane using the procedure described for 2-(3-(3-chloropropoxy)-2-methylphenyl)-4,4,5,5-tetramethyl-1,3,2-dioxaborolane and 2-(3-(3-bromopropoxy)-2-methylphenyl)-4,4,5,5-tetramethyl-1,3,2-dioxaborolane
Base on $^1$H NMR and: 3-chloropropoxy was 80% and 3-bromopropoxy was 20%. $^1$H NMR (400 MHz, CHLOROFORM-d) δ 7.21-7.08 (m, 3H), 6.87 (ddd, J=8.0, 2.4, 1.1 Hz, 1H), 4.16-4.09 (m, 2H), 3.76 (t, J=6.3 Hz, 1.6H), 3.62 (t, J=6.4 Hz, 0.4H), 2.34 (quin, J=6.1 Hz, 0.4H), 2.26 (quin, J=6.0 Hz, 1.6H).

Intermediate:
1-bromo-2-chloro-3-(3-chloropropoxy)benzene

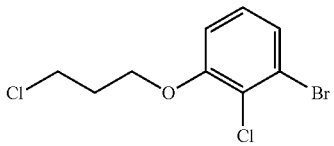 [SMILES: ClCCCOc1cccc(Br)c1Cl]

1-Bromo-2-chloro-3-(3-chloropropoxy)benzene (1.29 g, crude) was obtained from 3-bromo-2-chlorophenol and 1-bromo-3-chloropropane using the procedure described for 2-(3-(3-chloropropoxy)-2-methylphenyl)-4,4,5,5-tetramethyl-1,3,2-dioxaborolane.

Intermediate: (R)-1-(3-(3-bromophenoxy)propyl)pyrrolidin-3-ol

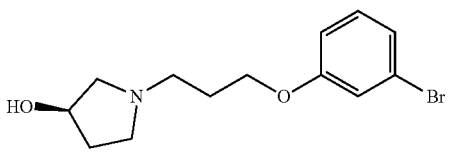 [SMILES: O[C@@H]1CCN(CCCOc2cccc(Br)c2)C1]

(R)-1-(3-(3-Bromophenoxy)propyl)pyrrolidin-3-ol (210 mg, 50%) was obtained from (R)-3-hydroxypyrrolidine hydrochloride and 1-bromo-3-(3-chloropropoxy)benzene (the mixture of chloro- and bromopropoxy prepared above was used) using the procedure described for (R)-1-(3-(2-methyl-3-(4,4,5,5-tetramethyl-1,3,2-dioxaborolan-2-yl)phenoxy)propyl)pyrrolidin-3-ol. $^1$H NMR (400 MHz, METHANOL-$d_4$) δ 7.26-7.19 (m, 1H), 7.19-7.11 (m, 2H), 6.96 (dd, J=8.3, 2.3 Hz, 1H), 4.60 (br. s., 1H), 4.17-4.11 (m, 2H), 3.69 (d, J=6.0 Hz, 1H), 3.53-3.39 (m, 5H), 2.41-2.20 (m, 3H), 2.09 (d, J=5.8 Hz, 1H).

Intermediate: (R)-1-(3-(3-bromo-2-chlorophenoxy)propyl)pyrrolidin-3-ol

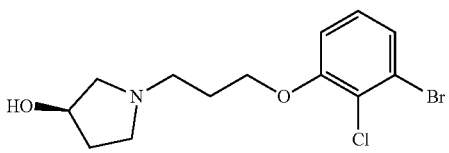 [SMILES: O[C@@H]1CCN(CCCOc2cccc(Br)c2Cl)C1]

(R)-1-(3-(3-Bromo-2-chlorophenoxy)propyl)pyrrolidin-3-ol (1.78 g, 110%) was obtained from (R)-3-hydroxypyrrolidine hydrochloride and 1-bromo-2-chloro-3-(3-chloropropoxy)benzene using the procedure described for (R)-1-(3-(2-methyl-3-(4,4,5,5-tetramethyl-1,3,2-dioxaborolan-2-yl)phenoxy)propyl)pyrrolidin-3-ol. $^1$H NMR (500 MHz, CHLOROFORM-d) δ 7.25 (dd, J=8.0, 1.3 Hz, 1H), 7.09 (t, J=8.2 Hz, 1H), 6.90 (dd, J=8.4, 1.3 Hz, 1H), 4.42 (ddt, J=6.9, 4.7, 2.2 Hz, 1H), 4.14 (t, J=6.1 Hz, 2H), 3.04 (td, J=8.7, 5.9 Hz, 1H), 2.87-2.79 (m, 3H), 2.72 (dd, J=10.2, 4.9 Hz, 1H), 2.52 (br. s., 1H), 2.24 (dddd, J=14.0, 8.5, 6.8, 5.8 Hz, 1H), 2.17-2.09 (m, 2H), 1.84 (td, J=6.9, 0.9 Hz, 1H).

Intermediate: (R)-2-bromo-6-(3-(3-hydroxypyrrolidin-1-yl)propoxy)benzonitrile

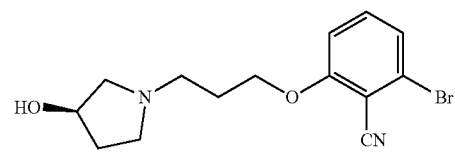 [SMILES: N#Cc1c(Br)cccc1OCCCN1CC[C@@H](O)C1]

(R)-2-Bromo-6-(3-(3-hydroxypyrrolidin-1-yl)propoxy)benzonitrile (1.01 g, 74%) was obtained from (R)-3-hydroxypyrrolidine hydrochloride and 2-bromo-6-(3-chloropropoxy)benzonitrile using the procedure described for (R)-1-(3-(2-methyl-3-(4,4,5,5-tetramethyl-1,3,2-dioxaborolan-2-yl)phenoxy)propyl)pyrrolidin-3-ol. $^1$H NMR (500 MHz, CHLOROFORM-d) δ 7.41-7.35 (m, 1H), 7.24 (d, J=8.0 Hz, 1H), 6.96 (d, J=8.5 Hz, 1H), 4.39 (ddt, J=6.9, 4.7, 2.2 Hz, 1H), 4.20 (t, J=6.1 Hz, 2H), 2.99 (td, J=8.7, 5.5 Hz, 1H), 2.83-2.73 (m, 3H), 2.63 (dd, J=10.2, 5.0 Hz, 1H), 2.46-2.39 (m, 1H), 2.26-2.18 (m, 1H), 2.11 (quin, J=6.6 Hz, 2H), 1.85-1.76 (m, 1H).

Example 3023: (3R,3'R)-1,1'-(((2-methyl-[1,1'-biphenyl]-3,3'-diyl)bis(oxy))bis(propane-3,1-diyl))bis(pyrrolidin-3-ol)

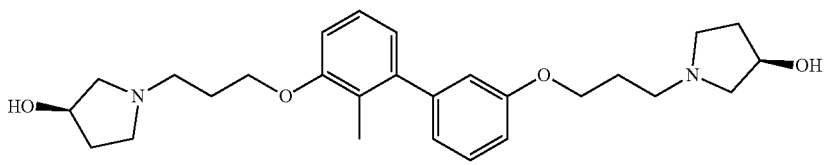 [SMILES: Cc1c(OCCCN2CC[C@@H](O)C2)cccc1-c1cccc(OCCCN2CC[C@@H](O)C2)c1]

A mixture of (R)-1-(3-(2-methyl-3-(4,4,5,5-tetramethyl-1,3,2-dioxaborolan-2-yl)phenoxy)propyl)pyrrolidin-3-ol (20 mg, 0.055 mmol), (R)-1-(3-(3-bromophenoxy)propyl)pyrrolidin-3-ol (16.62 mg, 0.055 mmol), THF (3 mL), and water (1.0 mL), potassium phosphate, tribasic (23.50 mg, 0.111 mmol), and second generation X-Phos precatalyst (2.178 mg, 2.77 µmol) was de-gassed/flushed with nitrogen, and then heated overnight at 80° C. The solvent was removed. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 15 minutes, then a 5-minute hold at 100% B; Flow: 20 mL/min. Fractions containing the desired product were combined and dried via centrifugal evaporation. The yield of the product was 11.9 mg (31%). $^1$H NMR (500 MHz, DMSO-$d_6$) δ 7.33 (t, J=7.9 Hz, 1H), 7.19 (t, J=7.9 Hz, 1H), 6.93 (dd, J=15.4, 8.1 Hz, 2H), 6.84 (d, J=7.3 Hz, 1H), 6.82-6.76 (m, 2H), 4.19 (br. s., 2H), 4.08-3.99 (m, 4H), 2.78-2.68 (m, 2H), 2.68-2.53 (m, 6H), 2.48 (br. s., 2H), 2.37 (br. s., 2H), 2.05 (s, 3H), 2.02-1.82 (m, 6H), 1.60-1.49 (m, 2H).

Two analytical LC/MS injections were used to determine the final purity.

Injection 1 Conditions:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.194 min, ESI m/z 455 (M+1); LCMS (Injection 2 condition) Rt=1.122 min, ESI m/z 455 (M+1).

Example 3024: (3R,3'R)-1,1'-(((2-chloro-2'-methyl-[1,1'-biphenyl]-3,3'-diyl)bis(oxy))bis(propane-3,1-diyl))bis(pyrrolidin-3-ol)

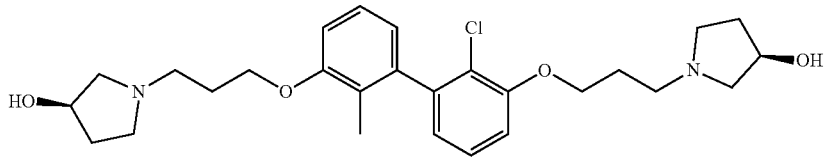 [SMILES: Cc1c(OCCCN2CC[C@@H](O)C2)cccc1-c1cccc(OCCCN2CC[C@@H](O)C2)c1Cl]

(3R,3'R)-1,1'-(((2-Chloro-2'-methyl-[1,1'-biphenyl]-3,3'-diyl)bis(oxy))bis(propane-3,1-diyl))bis(pyrrolidin-3-ol) (18.3 mg, 44.3%)) was obtained from (R)-1-(3-(2-methyl-3-(4,4,5,5-tetramethyl-1,3,2-dioxaborolan-2-yl)phenoxy)propyl)pyrrolidin-3-ol and (R)-1-(3-(3-bromo-2-chlorophenoxy)propyl)pyrrolidin-3-ol using the procedure described for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. ¹H NMR (500 MHz, DMSO-d₆) δ 7.33 (t, J=7.9 Hz, 1H), 7.20 (t, J=8.1 Hz, 1H), 7.15 (d, J=8.1 Hz, 1H), 6.96 (d, J=8.1 Hz, 1H), 6.81 (d, J=7.7 Hz, 1H), 6.67 (d, J=7.7 Hz, 1H), 4.21 (br. s., 2H), 4.14 (m, 2H), 4.05 (m, 2H), 2.76 (br. s., 2H), 2.64 (br. s., 6H), 2.57-2.48 (m, 2H), 2.43 (br. s., 2H), 2.05-1.89 (m, 6H), 1.86 (s, 3H), 1.57 (br. s., 2H).

Two analytical LC/MS injections were used to determine the final purity.

Injection 1 Conditions:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

LCMS (Injection 1 condition) Rt=1.068 min, ESI m/z 489 (M+1).

LCMS (Injection 2 condition) Rt=1.098 min, ESI m/z 489 (M+1).

Example 3025: 3,3'-bis(3-((R)-3-hydroxypyrrolidin-1-yl)propoxy)-2'-methyl-[1,1'-biphenyl]-2-carbonitrile

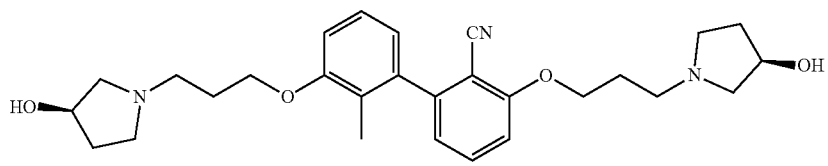 [SMILES: Cc1c(OCCCN2CC[C@@H](O)C2)cccc1-c1cccc(OCCCN2CC[C@@H](O)C2)c1C#N]

3,3'-Bis(3-((R)-3-hydroxypyrrolidin-1-yl)propoxy)-2'-methyl-[1,1'-biphenyl]-2-carbonitrile (18.7 mg, 46%) was obtained from (R)-1-(3-(2-methyl-3-(4,4,5,5-tetramethyl-1,3,2-dioxaborolan-2-yl)phenoxy)propyl)pyrrolidin-3-ol and (R)-2-bromo-6-(3-(3-hydroxypyrrolidin-1-yl)propoxy)benzonitrile using the procedure described for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile: water with 10-mM ammonium acetate; Gradient: 0-40% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.67 (t, J=8.1 Hz, 1H), 7.28-7.21 (m, 2H), 7.03 (d, J=8.4 Hz, 1H), 6.94 (d, J=7.7 Hz, 1H), 6.77 (d, J=7.7 Hz, 1H), 4.26-4.16 (m, 4H), 4.12-4.01 (m, 2H), 2.77-2.69 (m, 2H), 2.67-2.55 (m, 6H), 2.49-2.42 (m, 2H), 2.40-2.32 (m, 2H), 2.05-1.89 (m, 9H), 1.55 (br. s., 2H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.128 min, ESI m/z 480 (M+1); LCMS (Injection 2 condition) Rt=1.080 min, ESI m/z 480 (M+1).

Example 3026: (3R,3'R)-1,1'-(((2-methyl-2'-(trifluoromethyl)-[1,1'-biphenyl]-3,3'-diyl)bis(oxy))bis(propane-3,1-diyl))bis(pyrrolidin-3-ol), 2 TFA

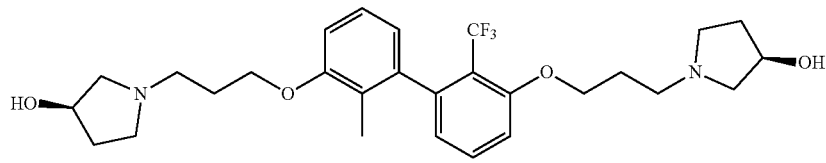 [SMILES: Cc1c(OCCCN2CC[C@@H](O)C2)cccc1-c1cccc(OCCCN2CC[C@@H](O)C2)c1C(F)(F)F]

(3R,3'R)-1,1'-(((2-Methyl-2'-(trifluoromethyl)-[1,1'-biphenyl]-3,3'-diyl)bis(oxy))bis(propane-3,1-diyl))bis(pyrrolidin-3-ol), 2 TFA (8.2 mg, 19%) was obtained from (R)-1-(3-(2-methyl-3-(4,4,5,5-tetramethyl-1,3,2-dioxaborolan-2-yl)phenoxy)propyl)pyrrolidin-3-ol and (R)-1-(3-(3-bromo-2-(trifluoromethyl)phenoxy)propyl)pyrrolidin-3-ol using the procedure described for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.62 (t, J=8.1 Hz, 1H), 7.29 (d, J=8.4 Hz, 1H), 7.18 (t, J=8.1 Hz, 1H), 6.95 (d, J=8.1 Hz, 1H), 6.75 (d, J=7.7 Hz, 1H), 6.66 (d, J=7.3 Hz, 1H), 4.44 (br. s., 2H), 4.22 (br. s., 2H), 4.15-4.02 (m, 2H), 3.80-3.90 (m, 12H), 2.36-2.10 (m, 5H), 2.03-1.78 (m, 3H), 1.85 (s, 3H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.134 min, ESI m/z 523 (M+1). LCMS (Injection 2 condition) Rt=1.261 min, ESI m/z 523 (M+1).

Intermediate: 1-bromo-3-(3-phenylpropoxy)benzene

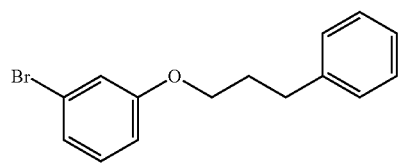 [SMILES: Brc1cccc(OCCCc2ccccc2)c1]

1-Bromo-3-(3-phenylpropoxy)benzene (481 mg, 66%) was obtained from 1-bromo-3-phenylpropane and 3-bromophenol using the procedure described for 2-(3-(3-chloropropoxy)-2-methylphenyl)-4,4,5,5-tetramethyl-1,3,2-dioxaborolane. $^1$H NMR (500 MHz, CHLOROFORM-d) δ 7.36-7.30 (m, 2H), 7.27-7.21 (m, 3H), 7.18-7.13 (m, 1H), 7.12-7.06 (m, 2H), 6.85 (ddd, J=8.2, 2.4, 1.0 Hz, 1H), 3.97 (t, J=6.2 Hz, 2H), 2.83 (t, J=7.6 Hz, 2H), 2.17-2.09 (m, 2H).

Intermediate: 1-(3-(3-bromo-2-methylphenoxy)propyl)-3-phenylpyrrolidin-3-ol

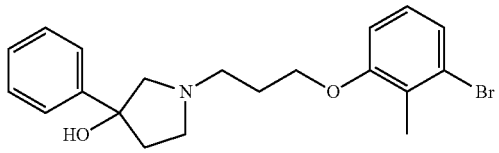 [SMILES: Cc1c(Br)cccc1OCCCN1CCC(O)(c2ccccc2)C1]

1-(3-(3-Bromo-2-methylphenoxy)propyl)-3-phenylpyrrolidin-3-ol (246 mg, 77%) was obtained from 1-bromo-3-(3-chloropropoxy)-2-methylbenzene (a mixture of chloro- and bromopropoxy was used) and 3-phenylpyrrolidin-3-ol using the procedure described for 2-(3-(3-chloropropoxy)-2-methylphenyl)-4,4,5,5-tetramethyl-1,3,2-dioxaborolane. $^1$H NMR (500 MHz, CHLOROFORM-d) δ 7.54-7.50 (m, 1.48H), 7.49-7.44 (m, 0.52H), 7.41-7.33 (m, 2H), 7.29-7.24 (m, 1H), 7.18-7.14 (m, 1H), 7.00 (t, J=8.1 Hz, 1H), 6.78 (d, J=8.2 Hz, 1H), 4.03 (t, J=6.1 Hz, 2H), 3.87-3.78 (m, 1H), 3.75-3.67 (m, 1H), 3.67-3.56 (m, 1H), 3.24-3.18 (m, 1H), 3.08 (d, J=9.9 Hz, 1H), 2.42-2.32 (m, 4H), 2.30-2.18 (m, 2H), 2.05 (quin, J=6.7 Hz, 2H).

Example 3027: (R)-1-(3-((2-methyl-3'-(3-phenylpropoxy)-[1,1'-biphenyl]-3-yl)oxy)propyl)pyrrolidin-3-ol

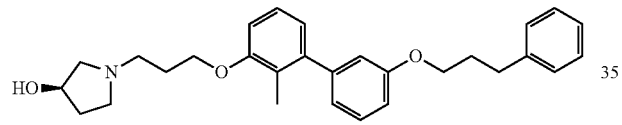

(R)-1-(3-((2-Methyl-3'-(3-phenylpropoxy)-[1,1'-biphenyl]-3-yl)oxy)propyl)pyrrolidin-3-ol (7.2 mg, 19%) was obtained from (R)-1-(3-(2-methyl-3-(4,4,5,5-tetramethyl-1,3,2-dioxaborolan-2-yl)phenoxy)propyl)pyrrolidin-3-ol and 1-bromo-3-(3-phenylpropoxy)benzene using the procedure described for for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 20 minutes, then a 5-minute hold at 100% B; Flow: 20 mL/min. Fractions containing the desired product were combined and dried via centrifugal evaporation. $^1$H NMR (500 MHz, DMSO-d$_6$) δ 7.33 (t, J=7.9 Hz, 1H), 7.31-7.26 (m, 2H), 7.25-7.22 (m, 2H), 7.22-7.16 (m, 2H), 6.97-6.90 (m, 2H), 6.84 (d, J=7.7 Hz, 1H), 6.82-6.77 (m, 2H), 4.25 (br. s., 1H), 4.05 (t, J=6.1 Hz, 2H), 4.00 (t, J=6.4 Hz, 2H), 3.35 (br. s., 1H), 2.90-2.70 (m, 6H), 2.68 (br. s., 1H), 2.56 (br. s., 1H), 2.08-1.93 (m, 7H), 1.63 (br. s., 1H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm LCMS (Injection 1 condition) Rt=2.190 min, ESI m/z 446 (M+1). LCMS (Injection 2 condition) Rt=2.112 min, ESI m/z 446 (M+1).

Example 3028: 1-(3-((3'-(3-((R)-3-hydroxypyrrolidin-1-yl)propoxy)-2,2'-dimethyl-[1,1'-biphenyl]-3-yl)oxy)propyl)-3-phenylpyrrolidin-3-ol, 2 TFA

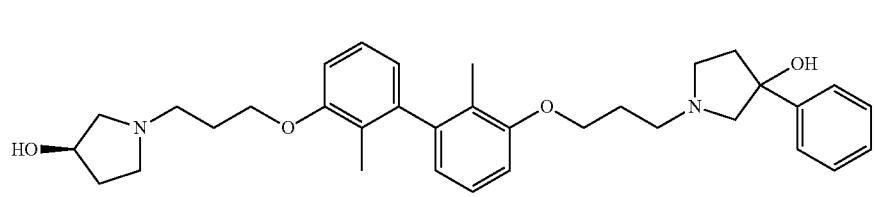 [SMILES: Cc1c(OCCCN2CC[C@@H](O)C2)cccc1-c1cccc(OCCCN2CCC(O)(c3ccccc3)C2)c1C]

1-(3-((3'-(3-((R)-3-Hydroxypyrrolidin-1-yl)propoxy)-2,2'-dimethyl-[1,1'-biphenyl]-3-yl)oxy)propyl)-3-phenylpyrrolidin-3-ol (16.9 mg, 56%) 2 TFA was obtained from (R)-1-(3-(2-methyl-3-(4,4,5,5-tetramethyl-1,3,2-dioxaborolan-2-yl)phenoxy)propyl)pyrrolidin-3-ol and 1-(3-(3-bromo-2-methylphenoxy)propyl)-3-phenylpyrrolidin-3-ol using the procedure described for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.58 (d, J=8.1 Hz, 1.48H), 7.51 (br. s., 0.52H), 7.42 (t, J=7.5 Hz, 2H), 7.35 (d, J=7.3 Hz, 1H), 7.21 (t, J=7.9 Hz, 2H), 6.96 (t, J=7.9 Hz, 2H), 6.66 (d, J=7.7 Hz, 2H), 4.51-4.37 (m, 1H), 4.09 (br. s., 4H), 3.89-3.77 (m, 1H), 3.71 (d, J=10.6 Hz, 2H), 3.46 (br. s., 4H), 3.39-3.33 (m, 3H) 3.16 (d, J=12.1 Hz, 2H), 2.55-2.48 (m, 1H), 2.40-2.10 (m, 6H), 2.07-1.90 (m, 1H), 1.86 (d, J=6.2 Hz, 6H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm LCMS (Injection 1 condition) Rt=1.506 min, ESI m/z 545 (M+1).

LCMS (Injection 2 condition) Rt=1.302 min, ESI m/z 545 (M+1).

Intermediate: 3-((3-bromo-2-methylphenoxy)methyl)-1-methylpiperidine

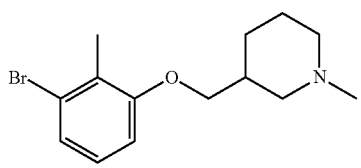 [SMILES: Cc1c(Br)cccc1OCC1CCCN(C)C1]

To a solution of 3-bromo-2-methylphenol (500 mg, 2.67 mmol) in DMF (15 mL) was added 3-(chloromethyl)-1-methylpiperidine, HCl (492 mg, 2.67 mmol) and K$_2$CO$_3$ (813 mg, 5.88 mmol). The reaction mixture was stirred at 80° C. for for 19 h. The solvent was removed, and the residue was purified by silica gel column chromatography (Biotage 25s, MeOH/CH$_2$Cl$_2$=0 to 10%) to afford 284 mg of the target compound. $^1$H NMR (500 MHz, CHLOROFORM-d) δ 7.15 (dd, J=8.0, 0.6 Hz, 1H), 7.02-6.97 (m, 1H), 6.76 (d, J=8.2 Hz, 1H), 3.88-3.83 (m, 1H), 3.83-3.78 (m, 1H), 3.00 (d, J=10.2 Hz, 1H), 2.81 (d, J=11.0 Hz, 1H), 2.33 (s, 3H), 2.32 (s, 3H), 2.25-2.14 (m, 1H), 1.99 (td, J=11.2, 2.7 Hz, 1H), 1.93-1.63 (m, 4H), 1.16 (qd, J=11.8, 4.2 Hz, 1H).

Example 3029: (3R)-1-(3-((2,2'-dimethyl-3'-((1-methylpiperidin-3-yl)methoxy)-[1,1'-biphenyl]-3-yl)oxy)propyl)pyrrolidin-3-ol

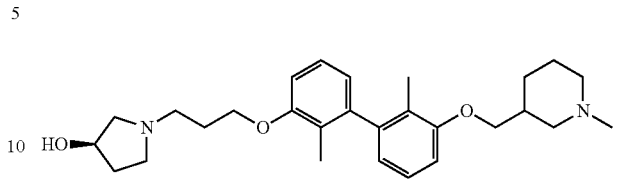

(3R)-1-(3-((2,2'-Dimethyl-3'-((1-methylpiperidin-3-yl)methoxy)-[1,1'-biphenyl]-3-yl)oxy)propyl)pyrrolidin-3-ol (32.7 mg, 75%) was obtained from (R)-1-(3-(2-methyl-3-(4,4,5,5-tetramethyl-1,3,2-dioxaborolan-2-yl)phenoxy)propyl)pyrrolidin-3-ol, and 3-((3-bromo-2-methylphenoxy)methyl)-1-methylpiperidine using the procedure described for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.17 (t, J=7.9 Hz, 2H), 6.95-6.89 (m, 2H), 6.64 (d, J=7.7 Hz, 2H), 4.19 (br. s., 1H), 4.09-3.99 (m, 2H), 3.94-3.81 (m, 2H), 3.46 (br. s., 2H), 2.83 (br. s., 1H), 2.75-2.67 (m, 1H), 2.65 (br. s., 1H), 2.62-2.54 (m, 3H), 2.45 (br. s., 1H), 2.33 (d, J=5.9 Hz, 1H), 2.16 (s, 3H), 2.09-1.94 (m, 2H), 1.94-1.84 (m, 2H) 1.83 (d, J=3.7 Hz, 6H), 1.75 (d, J=11.0 Hz, 1H), 1.64 (br. s., 1H), 1.53 (d, J=8.4 Hz, 2H), 1.11 (d, J=10.3 Hz, 1H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.224 min, ESI m/z 453 (M+1). LCMS (Injection 2 condition) Rt=1.302 min, ESI m/z 453 (M+1).

Intermediates: (3R)-1-(2-(7-bromo-2,3-dihydrobenzo[b][1,4]dioxin-2-yl)ethyl)pyrrolidin-3-ol (Isomer-1), and (3R)-1-(2-(7-bromo-2,3-dihydrobenzo[b][1,4]dioxin-2-yl)ethyl)pyrrolidin-3-ol (Isomer-2)

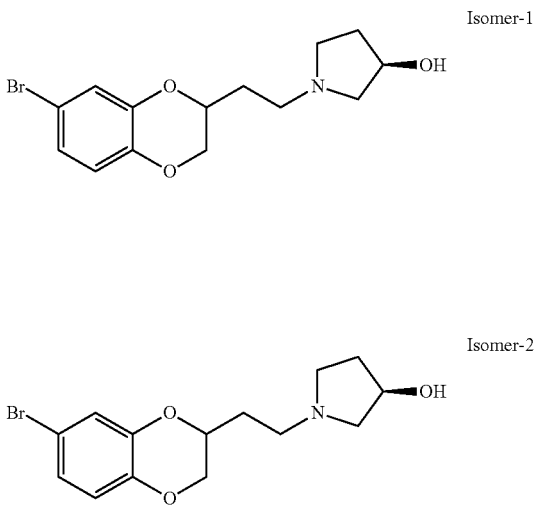

A mixture of 2-(7-bromo-2,3-dihydrobenzo[b][1,4]dioxin-2-yl)acetaldehyde (1 g, 3.89 mmol), (R)-3-hydroxypyrrolidine hydrochloride (1.442 g, 11.67 mmol), and sodium triacetoxyborohydride (2.56 g, 12.06 mmol) in DMF (10 mL) was stirred at rt for 19 hrs. The Solvent was removed, and residue was purified by silica gel column chromatography (Biotage 25m, MeOH/CH$_2$Cl$_2$=0 to 50%) to obtain the two pure diastereomers and a mixture of both isomers. Isomer-1 was obtained in 78 mg: 1H NMR (500 MHz, CHLOROFORM-d) δ 7.02 (dd, J=2.2, 1.4 Hz, 1H), 6.97 (dd, J=8.6, 2.3 Hz, 1H), 6.77 (d, J=8.7 Hz, 1H), 4.66 (br. s., 1H), 4.34-4.25 (m, 2H), 3.91 (d, J=7.4 Hz, 1H), 3.74-3.62 (m, 1H), 3.54 (d, J=11.3 Hz, 1H), 3.48-3.25 (m, 3H), 2.34 (br. s., 2H), 2.13 (br. s., 1H), 2.18-2.07 (m, 2H). Isomer-2 was obtained in 130 mg: 1H NMR (500 MHz, CHLOROFORM-d) δ 6.97 (d, J=2.2 Hz, 1H), 6.90 (dd, J=8.7, 2.2 Hz, 1H), 6.71 (d, J=8.7 Hz, 1H), 4.42 (t, J=5.8 Hz, 1H), 4.25-4.14 (m, 2H), 3.86 (dd, J=11.2, 7.3 Hz, 1H), 3.28-3.19 (m, 1H), 3.05 (d, J=10.9 Hz, 1H), 3.02-2.83 (m, 3H), 2.78-2.68 (m, 1H), 2.21 (ddt, J=13.8, 8.5, 6.8 Hz, 1H), 2.01-1.86 (m, 3H).
In addition, a mixture of Isomer-1 and Isomer-2 was also obtained in 570 mg.

Example 3030: (3R)-1-(3-(3-(3-(2-((R)-3-hydroxypyrrolidin-1-yl)ethyl)-2,3-dihydrobenzo[b][1,4]dioxin-6-yl)-2-methylphenoxy)propyl)pyrrolidin-3-ol (3R)-1-(3-(3-(3-(2-((R)-3-Hydroxypyrrolidin-1-yl)ethyl)-2,3-dihydrobenzo[b][1,4]dioxin-6-yl)-2-methylphenoxy)propyl)pyrrolidin-3-ol (13.1 mg, 48%) was obtained from (R)-1-(3-(2-methyl-3-(4,4,5,5-tetramethyl-1,3,2-dioxaborolan-2-yl)phenoxy)propyl)pyrrolidin-3-ol and (3R)-1-(2-(7-bromo-2,3-dihydrobenzo[b][1,4]dioxin-2-yl)ethyl)pyrrolidin-3-ol (Isomer-1) using the procedure described for (3R, 3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. 1H NMR (500 MHz, DMSO-d$_6$) δ 7.16 (t, J=7.9 Hz, 1H), 6.93-6.88 (m, 2H), 6.78-6.71 (m, 3H), 4.37 (d, J=11.4 Hz, 1H), 4.29-4.23 (m, 1H), 4.22-4.15 (m, 2H), 4.03 (t, J=6.2 Hz, 2H), 3.95 (dd, J=11.0, 8.4 Hz, 1H), 2.76-2.66 (m, 2H), 2.66-2.54 (m, 6H), 2.47 (d, J=7.3 Hz, 2H), 2.36 (d, J=9.5 Hz, 2H), 2.05 (s, 3H), 1.98 (dd, J=12.8, 7.0 Hz, 2H), 1.94-1.87 (m, 2H), 1.78 (q, J=6.6 Hz, 2H), 1.55 (d, J=3.7 Hz, 2H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.080 min, ESI m/z 483 (M+1). LCMS (Injection 2 condition) Rt=1.074 min, ESI m/z 483 (M+1).

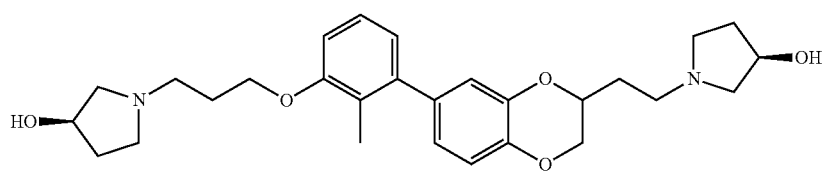 [SMILES: Cc1c(OCCCN2CC[C@@H](O)C2)cccc1-c1ccc2c(c1)OC(CCN1CC[C@@H](O)C1)CO2]

Example 3031: (3R)-1-(3-(3-(3-(2-((R)-3-hydroxy-pyrrolidin-1-yl)ethyl)-2,3-dihydrobenzo[b][1,4]di-oxin-6-yl)-2-methylphenoxy)propyl)pyrrolidin-3-ol

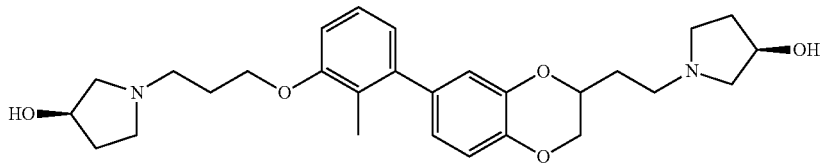 [SMILES: Cc1c(OCCCN2CC[C@@H](O)C2)cccc1-c1ccc2c(c1)OC(CCN1CC[C@@H](O)C1)CO2]

(3R)-1-(3-(3-(3-(2-((R)-3-Hydroxypyrrolidin-1-yl)ethyl)-2,3-dihydrobenzo[b][1,4]dioxin-6-yl)-2-methylphenoxy) propyl)pyrrolidin-3-ol (27.8 mg, 92%) was obtained from (R)-1-(3-(2-methyl-3-(4,4,5,5-tetramethyl-1,3,2-dioxaborolan-2-yl)phenoxy)propyl)pyrrolidin-3-ol and (3R)-1-(2-(7-bromo-2,3-dihydrobenzo[b][1,4]dioxin-2-yl)ethyl)pyrrolidin-3-ol (Isomer-2) using the procedure described for (3R, 3'R)-1,1'-(((2-methyl-[1,1'-biphenyl]-3,3'-diyl)bis(oxy))bis (propane-3,1-diyl))bis(pyrrolidin-3-ol). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. $^1$H NMR (500 MHz, DMSO-$d_6$) δ 7.16 (t, J=7.7 Hz, 1H), 6.91 (d, J=8.1 Hz, 2H), 6.78-6.71 (m, 3H), 4.35 (dd, J=16.0, 11.6 Hz, 1H), 4.30-4.16 (m, 3H), 4.03 (t, J=6.1 Hz, 2H), 3.99-3.89 (m, 1H), 2.88-2.58 (m, 8H), 2.55-2.48 (m, 2H), 2.48-2.38 (m, 2H), 2.05 (s, 3H), 2.04-1.92 (m, 4H), 1.85-1.74 (m, 2H), 1.66-1.51 (m, 2H).

Two analytical LC/MS injections were used to determine the final purity.
Injection 1 Conditions:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.
Injection 2 Conditions:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.542 min, ESI m/z 483 (M+1). LCMS (Injection 2 condition) Rt=1.566 min, ESI m/z 483 (M+1).

Intermediate: (3R)-1-(2-(7-(4,4,5,5-tetramethyl-1,3, 2-dioxaborolan-2-yl)-2,3-dihydrobenzo[b][1,4]di-oxin-2-yl)ethyl)pyrrolidin-3-ol

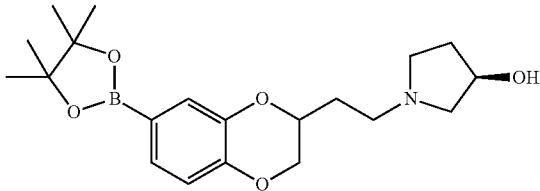 [SMILES: CC1(C)OB(c2ccc3c(c2)OC(CCN2CC[C@@H](O)C2)CO3)OC1(C)C]

To a sealed tube was added (3R)-1-(2-(7-bromo-2,3-dihydrobenzo[b][1,4]dioxin-2-yl)ethyl)pyrrolidin-3-ol (200 mg, 0.609 mmol) (mixture of Isomer-1 and Isomer-2) in dioxane (7 mL) along with bis(pinacolato)diboron (542 mg, 2.133 mmol), triethylamine (0.255 mL, 1.828 mmol) and bis-(triphenylphosphino)-palladous chloride (20.31 mg, 0.030 mmol). The vessel was sealed, the mixture flushed with nitrogen three times and then stirred at 120° C. for 20 hours. The solvent was removed. The resulting residue was purified by silica gel column chromatography (Biotage 25S, MeOH/CH$_2$CL$_2$=0 to 50%) to give 151 mg of the target compound. $^1$H NMR (500 MHz, CHLOROFORM-d) δ 7.34-7.23 (m, 2H), 6.85-6.79 (m, 1H), 4.62 (br. s., 1H), 4.29-4.20 (m, 2H), 3.95-3.87 (m, 1H), 3.64-3.31 (m, 6H), 2.36-2.17 (m, 3H), 2.17-2.06 (m, 1H), 1.29 (s, 12H).

Example 3032: (3R,3'R)-1,1'-((2,2',3,3'-tetrahydro-[6,6'-bibenzo[b][1,4]dioxine]-3,3'-diyl)bis(ethane-2, 1-diyl))bis(pyrrolidin-3-ol)

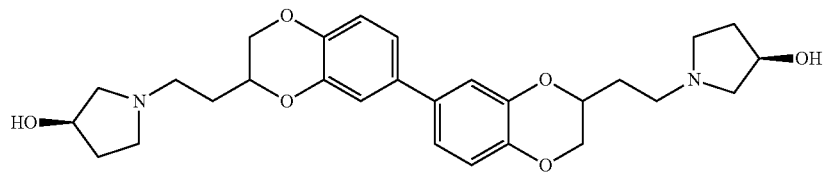 [SMILES: O[C@@H]1CCN(CCC2COc3ccc(-c4ccc5c(c4)OC(CCN4CC[C@@H](O)C4)CO5)cc3O2)C1]

(3R,3'R)-1,1'-((2,2',3,3'-Tetrahydro-[6,6'-bibenzo[b][1,4]dioxine]-3,3'-diyl)bis(ethane-2,1-diyl))bis(pyrrolidin-3-ol) (1.2 mg, 3%) was obtained from (3R)-1-(2-(7-(4,4,5,5-tetramethyl-1,3,2-dioxaborolan-2-yl)-2,3-dihydrobenzo[b][1,4]dioxin-2-yl)ethyl)pyrrolidin-3-ol (prepared as described above) and (3R)-1-(2-(7-bromo-2,3-dihydrobenzo[b][1,4]dioxin-2-yl)ethyl)pyrrolidin-3-ol (Isomer-1) using the procedure described for (3R,3'R)-1,1'-(((2-methyl-[1,1'-biphenyl]-3,3'-diyl)bis(oxy))bis(propane-3,1-diyl))bis(pyrrolidin-3-ol). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 18 minutes, then a 3-minute hold at 100% B; Flow: 20 mL/min. Fractions containing the desired product were combined and dried via centrifugal evaporation. $^1$H NMR (500 MHz, DMSO-$d_6$) δ 7.09-7.01 (m, 4H), 6.88 (d, J=8.8 Hz, 2H), 4.35 (d, J=11.4 Hz, 2H), 4.24 (d, J=6.6 Hz, 2H), 4.18 (br. s., 2H), 3.97-3.89 (m, 2H), 2.75-2.66 (m, 2H), 2.65-2.54 (m, 6H), 2.49-2.39 (m, 2H), 2.39-2.30 (m, 2H), 2.04-1.93 (m, 2H), 1.82-1.73 (m, 4H), 1.55 (br. s., 2H).

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS (Injection 1 condition) Rt=1.194 min, ESI m/z 497 (M+1). LCMS (Injection 2 condition) Rt=1.080 min, ESI m/z 497 (M+1).

Examples 3033 to 3035 were prepared in a similar manner as described for the 3001 compound series:

Example 3033: (R)-1-(3-((3'-((3-aminobenzyl)oxy)-2,2'-dimethyl-[1,1'-biphenyl]-3-yl)oxy)propyl)pyrrolidin-3-ol

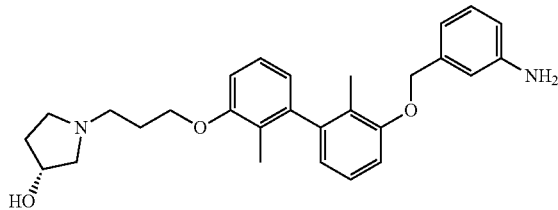 [SMILES: Cc1c(OCCCN2CC[C@@H](O)C2)cccc1-c1cccc(OCc2cccc(N)c2)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 13.9 mg (36%), and its estimated purity by LCMS analysis was 97%.

Two analytical LC/MS injections were used to determine the final purity.

Injection 1 Conditions:

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Injection 2 Conditions:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Analysis condition 1: Retention time=1.735 min; ESI-MS (+) m/z=447.2 (M+H)

Analysis condition 2: Retention time=1.339 min; ESI-MS (+) m/z=447.2 (M+H)

$^1$H NMR (500 MHz, DMSO-$d_6$) δ 7.18 (t, J=7.9 Hz, 2H), 7.06-6.99 (m, 2H), 6.93 (d, J=8.2 Hz, 1H), 6.70-6.63 (m, 3H), 6.61 (d, J=7.6 Hz, 1H), 6.52 (d, J=7.9 Hz, 1H), 5.09 (br. s., 2H), 4.99 (d, J=4.3 Hz, 2H), 4.18 (m, 1H), 4.09-3.98 (m, 2H), 2.75-2.66 (m, 1H), 2.62-2.53 (m, 3H), 2.48-2.40 (m, 1H), 2.37-2.30 (m, 1H), 2.02-1.81 (m, 9H), 1.60-1.50 (m, 1H).

Example 3035: (R)-1-(3-((3'-(3-((R)-3-fluoropyrrolidin-1-yl)propoxy)-2,2'-dimethyl-[1,1'-biphenyl]-3-yl)oxy)propyl)pyrrolidin-3-ol

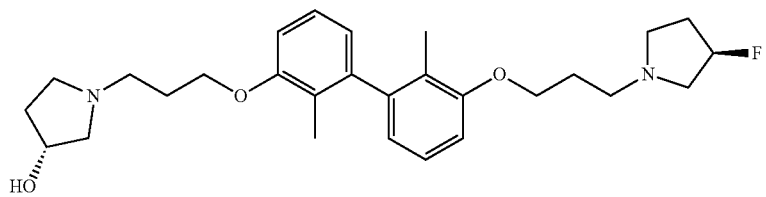 [SMILES: Cc1c(OCCCN2CC[C@@H](O)C2)cccc1-c1cccc(OCCCN2CC[C@@H](F)C2)c1C]

The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile: water 10 mM ammonium acetate at a gradient of 10-50% B over 22 minutes with a 5-minute hold at a flow rate of 20 mL/minute. Fractions containing the desired product were combined and dried via centrifugal evaporation. The yield of the product was 20.1 mg (47%), and its estimated purity by LCMS analysis was 98%.

Two analytical LC/MS injections were used to determine the final purity.
Injection 1 Conditions:
Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 Conditions:
Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.380 min; ESI-MS (+) m/z=471.3 (M+H)

Analysis condition 2: Retention time=1.169 min; ESI-MS (+) m/z=471.2 (M+H)

$^1$H NMR (500 MHz, DMSO-d$_6$) δ 7.18 (t, J=7.9 Hz, 2H), 6.93 (d, J=7.9 Hz, 2H), 6.64 (d, J=7.9 Hz, 2H), 5.25-5.13 (m, 1H), 4.76 (br. s., 1H), 4.21 (br. s., 1H), 4.04 (m, 4H), 2.89-2.71 (m, 3H), 2.70-2.56 (m, 6H), 2.42 (m, 1H), 2.30 (m, 1H), 2.21-2.06 (m, 1H), 2.04-1.85 (m, 7H), 1.83 (s, 6H), 1.57 (m, 1H).

Examples 5001-5039 were prepared in a manner analogous to those described above

Example 5001: 2,2'-(((((2,2'-dimethyl-[1,1'-biphenyl]-3,3'-diyl)bis(methylene))bis(oxy))bis(2,5-dimethyl-4,1-phenylene))bis(methylene))bis(azanediyl))bis(2-methylpropane-1,3-diol)

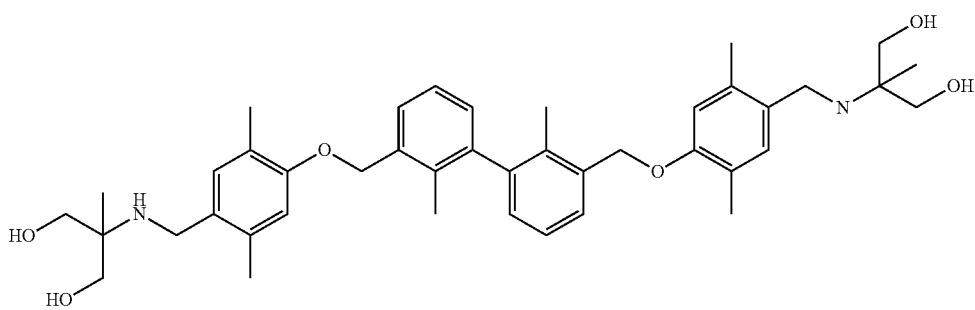

Example 5001

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 35-75% B over 16 minutes, then a 5-minute hold at 100% B; Flow: 20 mL/min. Fractions containing the desired product were combined and dried via centrifugal evaporation, and its estimated purity by LCMS analysis was 100%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 685.44; Retention Time: 1.6 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 685.33; Retention Time: 1.64 min.

Example 5002: (2S,2'S)-1,1'-(((((2,2'-dimethyl-[1,1'-biphenyl]-3,3'-diyl)bis(methylene))bis(oxy))bis(2,5-dimethyl-4,1-phenylene))bis(methylene))bis(piperidine-2-carboxylic acid)

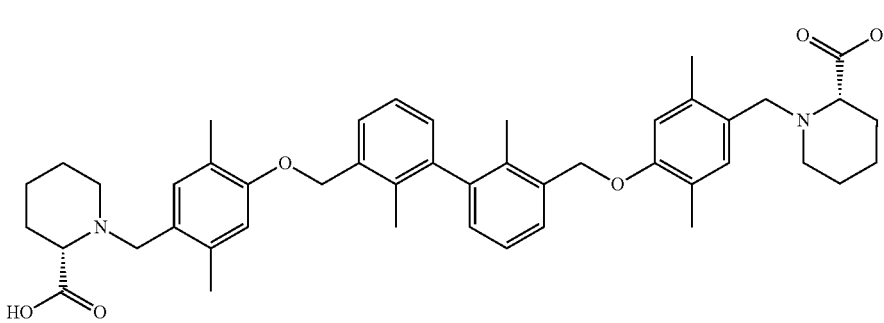

Example 5002

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 30-70% B over 19 minutes, then a 4-minute hold at 100% B; Flow: 20 mL/min. Fractions containing the desired product were combined and dried via centrifugal evaporation, and its estimated purity by LCMS analysis was 100%. Analytical LC/MS was used to determine the final purity.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 367.28; Retention Time: 1.74 min.

Example 5003: 2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(propane-1,3-diol)

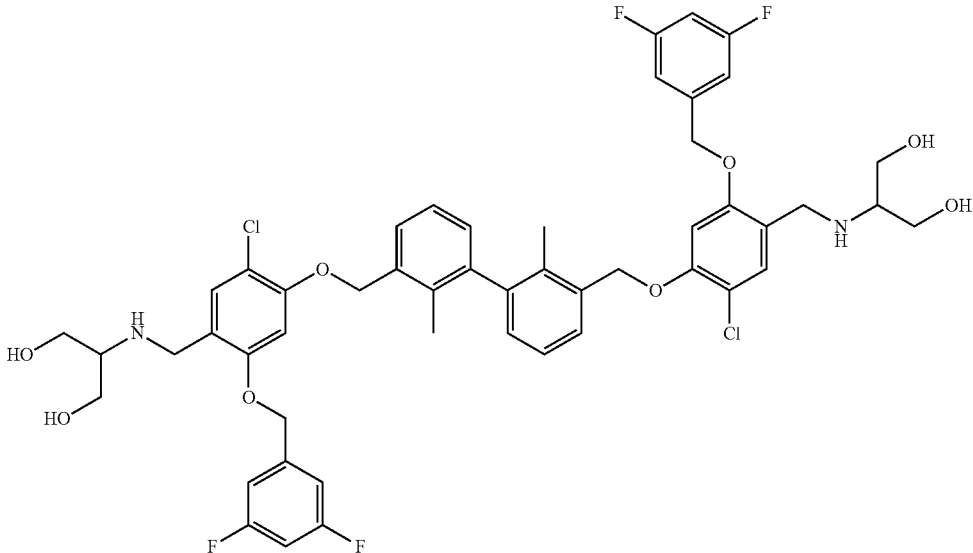

Example 5003

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 733.34; Retention Time: 1.69 min.

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 47-87% B over 19 minutes, then a 4-minute hold at 100% B; Flow: 20 mL/min. Fractions containing the desired product were combined and dried via centrifugal evaporation, and its estimated purity by LCMS analysis was 99%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 952.97; Retention Time: 2.48 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 477.98; Retention Time: 2 min.

Example 5004: 2,2'-((((((2,2'-dimethyl-[1,1'-biphenyl]-3,3'-diyl)bis(methylene))bis(oxy))bis(2,5-dimethyl-4,1-phenylene))bis(methylene))bis(azanediyl)) bis(propane-1,3-diol)

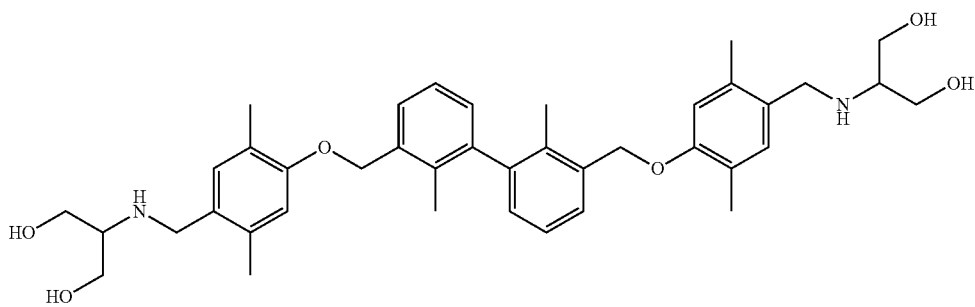

Example 5004

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 28-68% B over 22 minutes, then a 4-minute hold at 100% B; Flow: 20 mL/min. Fractions containing the desired product were combined and dried via centrifugal evaporation, and its estimated purity by LCMS analysis was 99%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 657.22; Retention Time: 1.92 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 657.2; Retention Time: 1.68 min.

Example 5005: 2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(propane-1,3-diol)

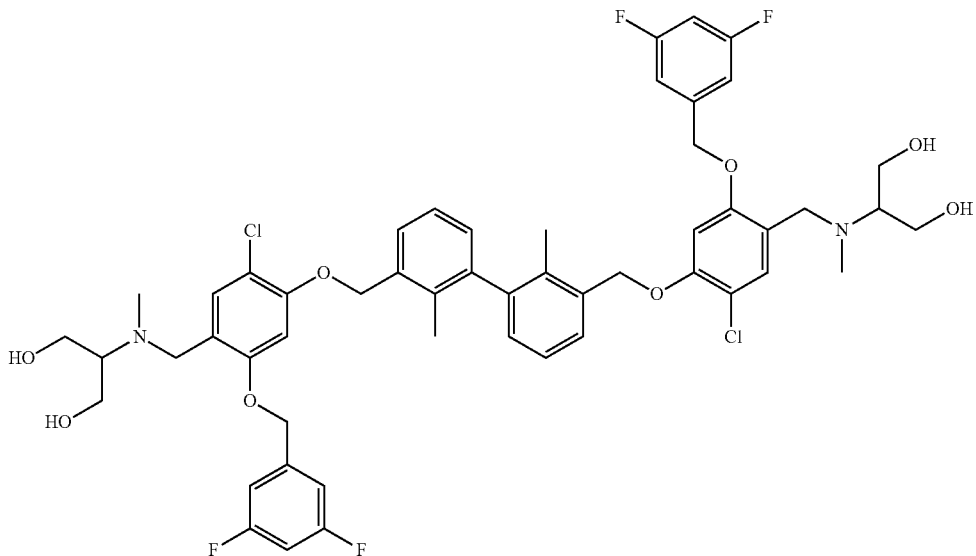

Example 5005

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 50-100% B over 19 minutes, then a 4-minute hold at 100% B; Flow: 20 mL/min. Fractions containing the desired product were combined and dried via centrifugal evaporation, and its estimated purity by LCMS analysis was 94%. Analytical LC/MS was used to determine the final purity.

Injection 1 Conditions:

Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.0%; Observed Mass: 981.03; Retention Time: 2.79 min.

Injection 2 Conditions:

Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.8%; Observed Mass: 981.04; Retention Time: 2.1 min.

Example 5006: (2S,2'S)-1,1'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(piperidine-2-carboxylic acid)

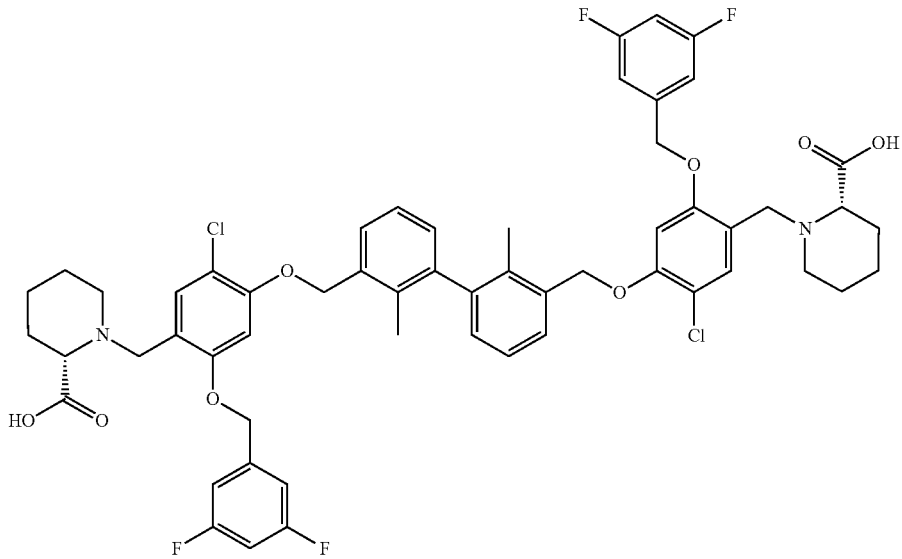

Example 5006

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 38-78% B over 19 minutes, then a 4-minute hold at 100% B; Flow: 20 mL/min. Fractions containing the desired product were combined and dried via centrifugal evaporation, and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1029.26; Retention Time: 2.4 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1029.26; Retention Time: 2.41 min.

Example 5007: 2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(2-methylpropane-1,3-diol)

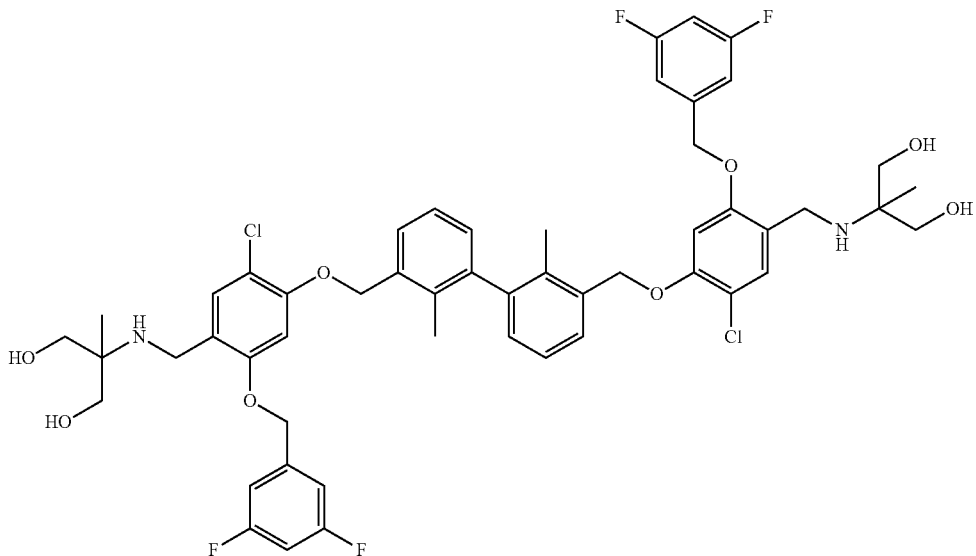

Example 5007

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 42-82% B over 19 minutes, then a 4-minute hold at 100% B; Flow: 20 mL/min. Fractions containing the desired product were combined and dried via centrifugal evaporation, and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 981.2; Retention Time: 2.73 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 981.24; Retention Time: 2.28 min.

Example 5008: (2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(3-hydroxypropanoic acid)

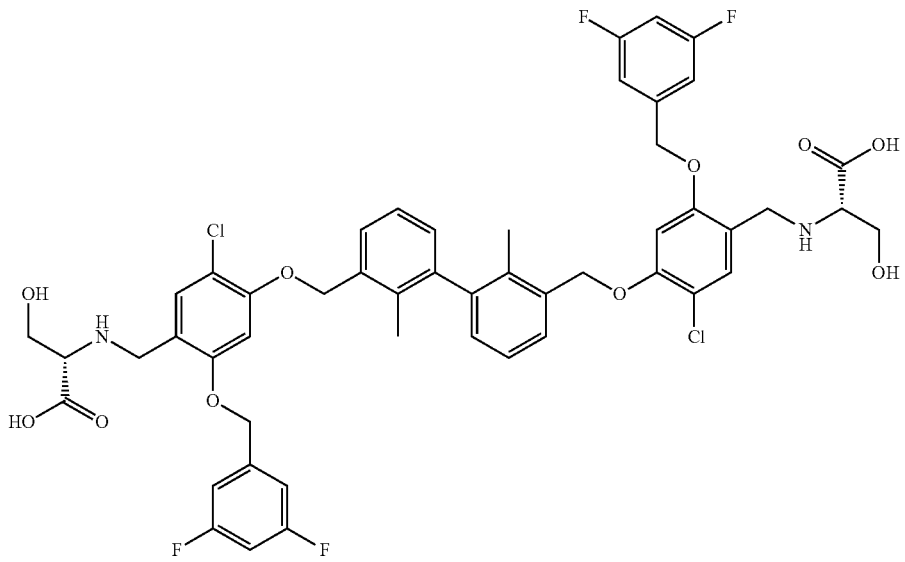

Example 5008

The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation., and its estimated purity by LCMS analysis was 96%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.7%; Observed Mass: 981.13; Retention Time: 2.23 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.9%; Observed Mass: 981.19; Retention Time: 2.23 min.

Example 5009: (2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(3-hydroxy-2-methylpropanoic acid)

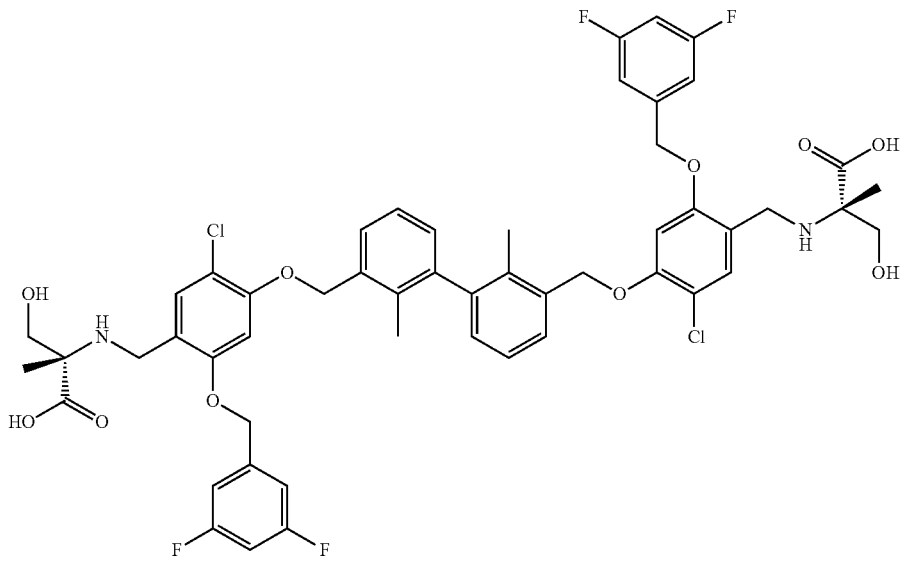

Example 5009

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation, and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 1009.13; Retention Time: 2.27 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1009.19; Retention Time: 2.28 min.

Example 5012: 2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(2-methylpropane-1,3-diol)

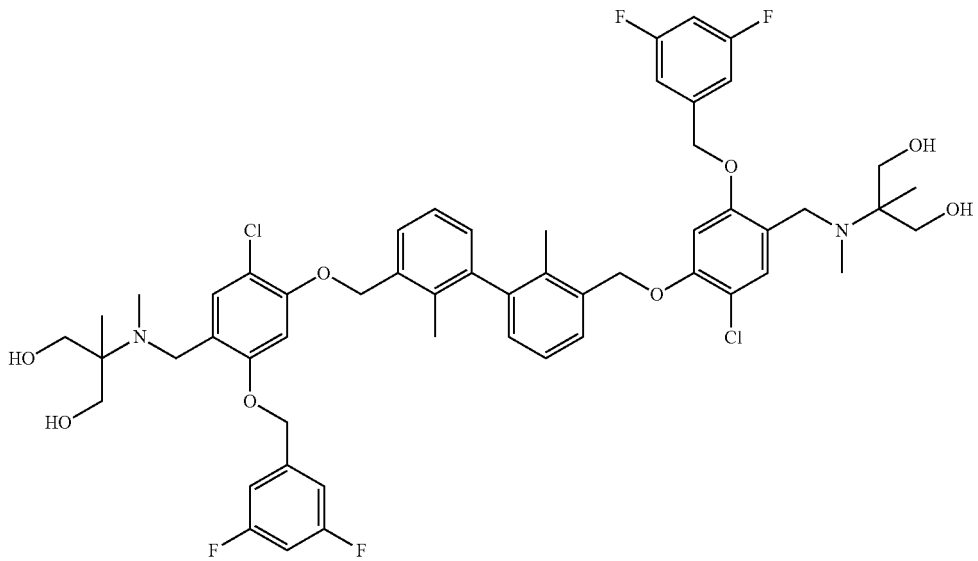

Example 5012

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 50-100% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1009.26; Retention Time: 2 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 1009.24; Retention Time: 2.27 min.

Example 5013: (2S,2'S)-2,2'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(3-hydroxypropanoic acid)

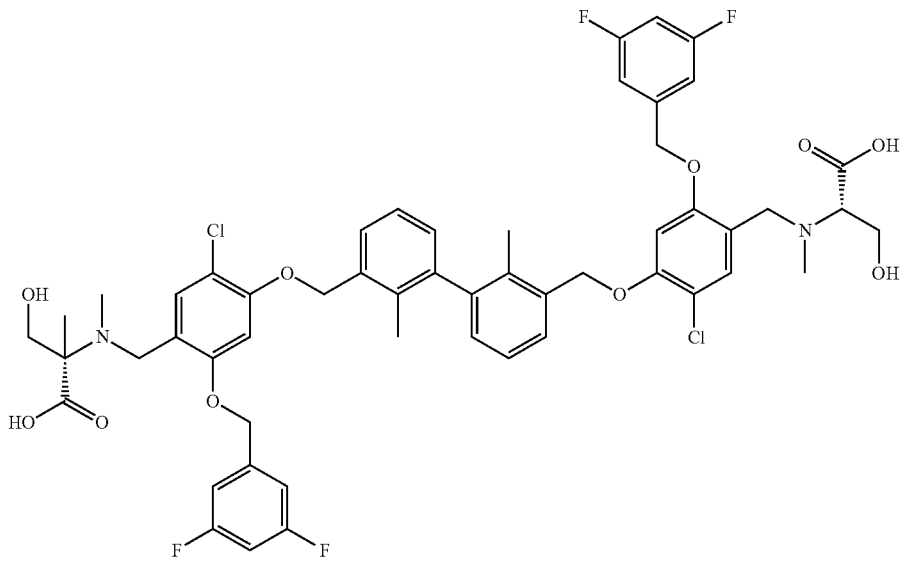

Example 5013

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 35-75% B over 20 minutes, then a 5-minute hold at 100% B; Flow: 20 mL/min. Fractions containing the desired product were combined and dried via centrifugal evaporation. and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1009.22; Retention Time: 1.96 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1009.2; Retention Time: 1. 96 min.

Example 5014: (2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(3-hydroxy-2-methylpropanoic acid)

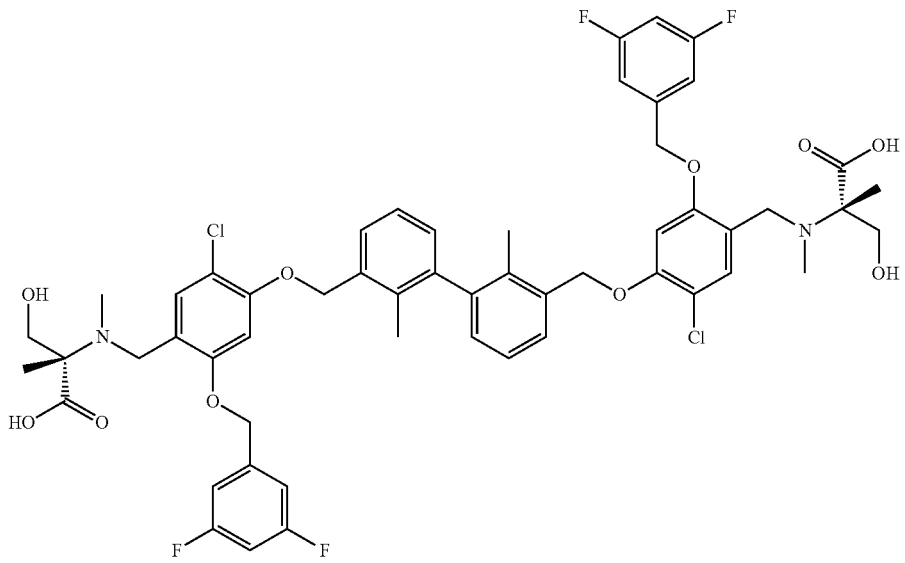

Example 5014

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 38-78% B over 19 minutes, then a 4-minute hold at 100% B; Flow: 20 mL/min. Fractions containing the desired product were combined and dried via centrifugal evaporation and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1037.21; Retention Time: 2 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1037.22; Retention Time: 2.01 min.

Example 5015: (2S,2'S)-2,2'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(3-methylbutanoic acid)

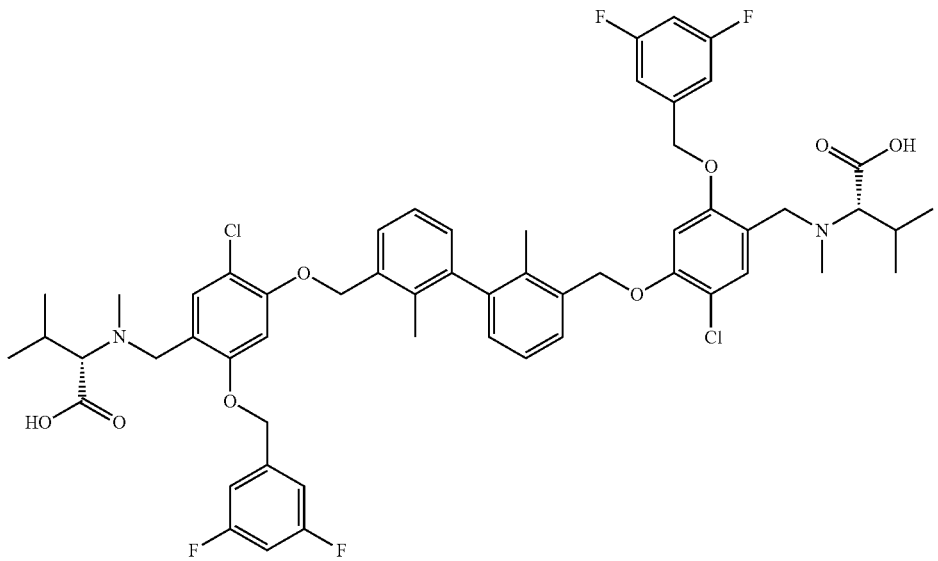

Example 5015

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 40-90% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1033.25; Retention Time: 2.12 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 1033.28; Retention Time: 2.24 min.

Example 5016: (2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))dipentanoic acid

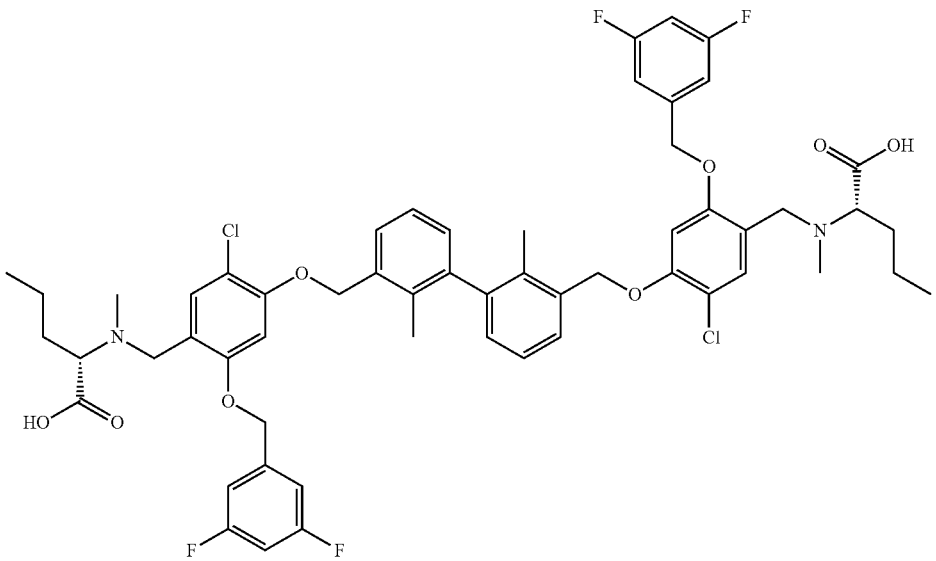

Example 5016

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 42-82% B over 19 minutes, then a 4-minute hold at 100% B; Flow: 20 mL/min. Fractions containing the desired product were combined and dried via centrifugal evaporation and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1033.3; Retention Time: 2.2 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1033.33; Retention Time: 2.16 min.

Example 5017: (2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(4-methylpentanoic acid)

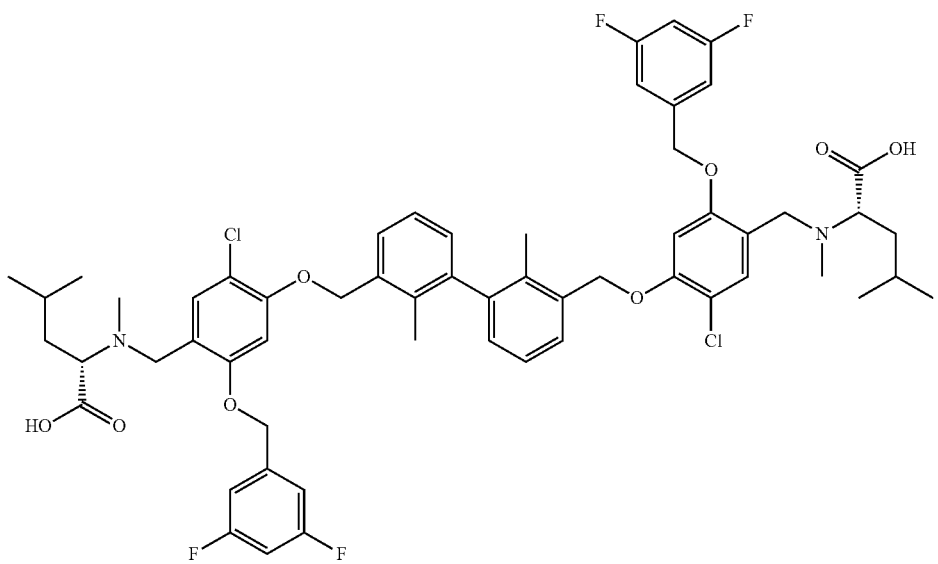

Example 5017

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 40-90% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 532.14; Retention Time: 2.45 min.

Example 5018: (2S,2'S,3R,3'R)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(3-hydroxybutanoic acid)

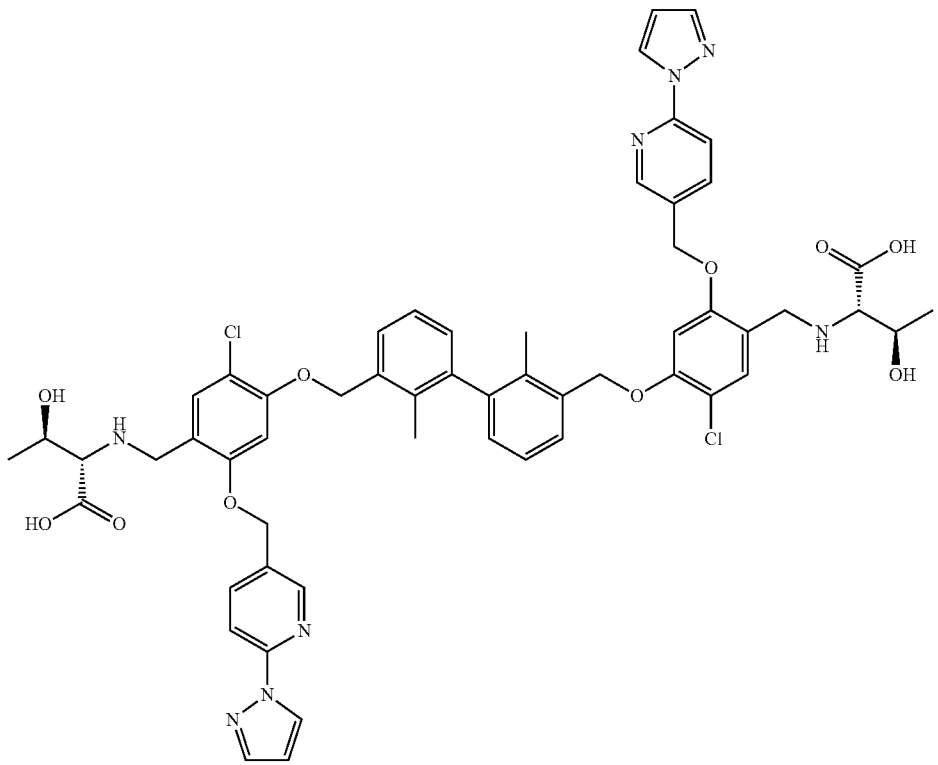

Example 5018

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 20-100% B over 20 minutes, then a 5-minute hold at 100% B; Flow: 20 mL/min. Fractions containing the desired product were combined and dried via centrifugal evaporation and its estimated purity by LCMS analysis was 94%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.4%; Observed Mass: 1071.22; Retention Time: 1.84 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 1071.27; Retention Time: 1.78 min.

Example 5019: 2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(propane-1,3-diol)

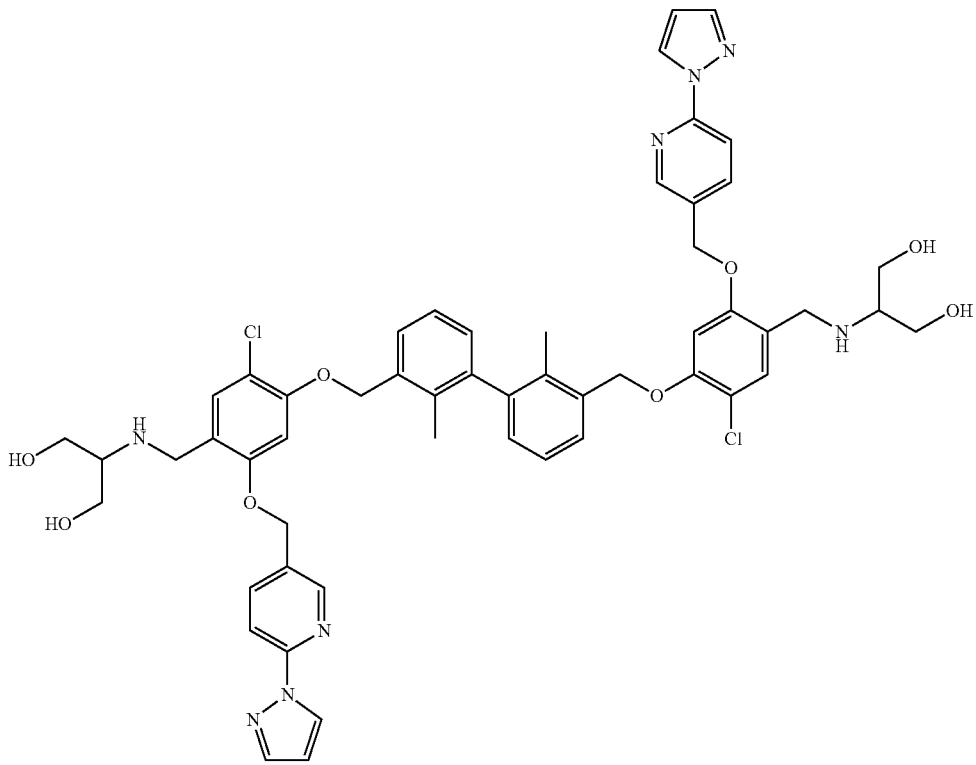

Example 5019

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 40-80% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1015.28; Retention Time: 1.94 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.6%; Observed Mass: 1015.28; Retention Time: 1.79 min.

Example 5020: 2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(2-methylpropane-1,3-diol)

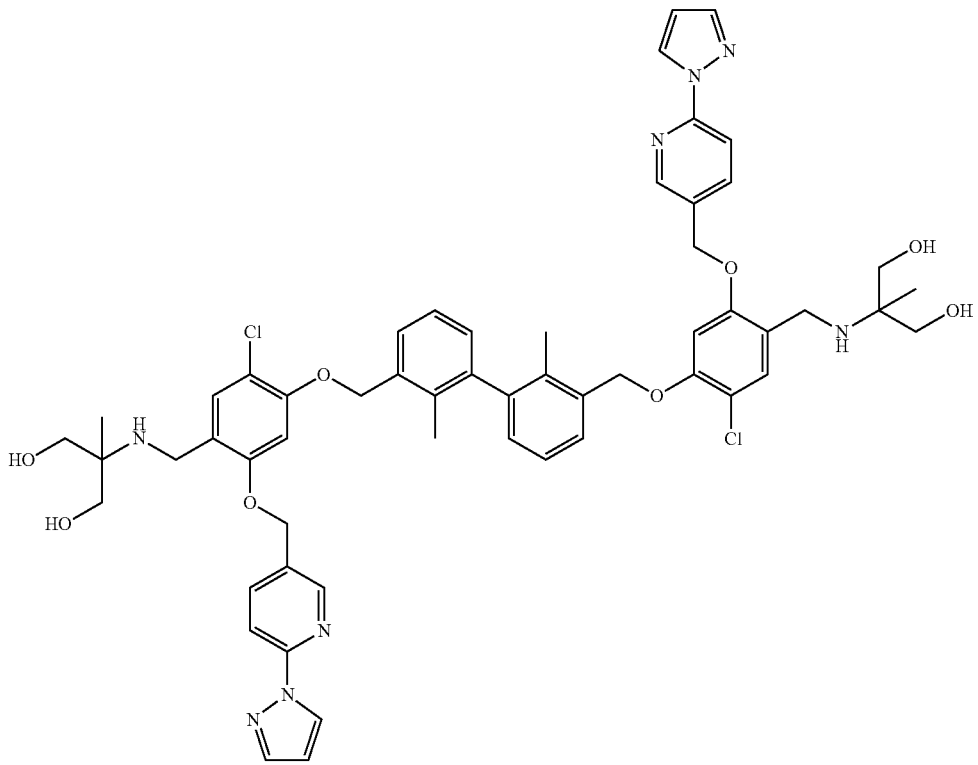

Example 5020

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 42-82% B over 20 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1043.31; Retention Time: 1.93 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: 1043.32; Retention Time: 1.83 min.

Example 5021: (2S,2'S)-1,1'-(((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(piperidine-2-carboxylic acid)

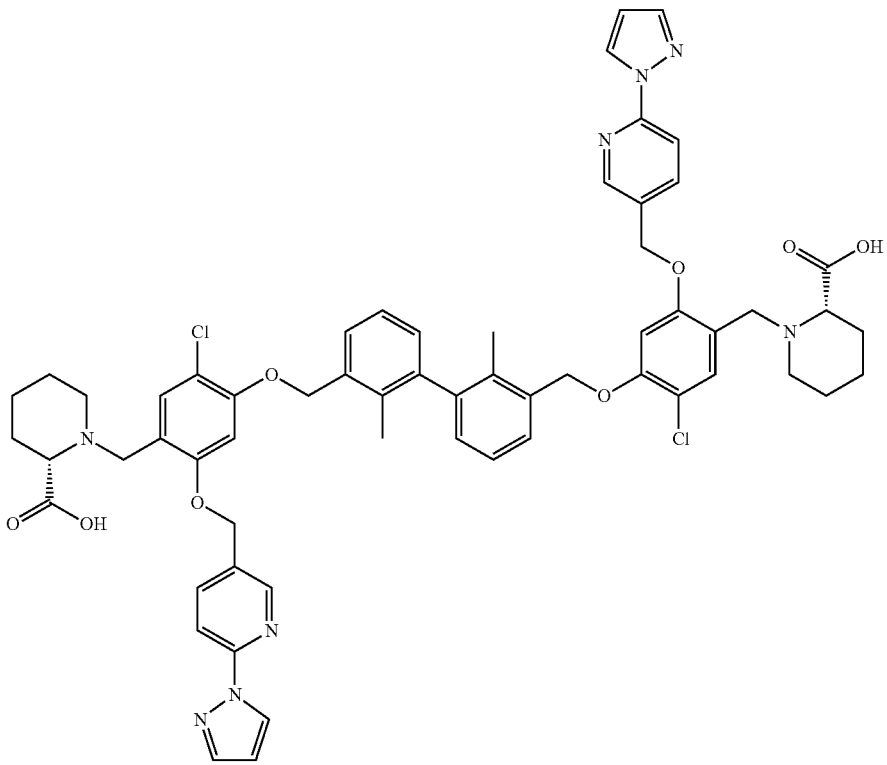

Example 5021

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 35-85% B over 27 minutes, then a 4-minute hold at 100% B; Flow: 20 mL/min. Fractions containing the desired product were combined and dried via centrifugal evaporation and its estimated purity by LCMS analysis was 100%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1091.34; Retention Time: 1.97 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1091.29; Retention Time: 1.99 min.

Example 5022: (2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(3-hydroxy-2-methylpropanoic acid)

Example 5022

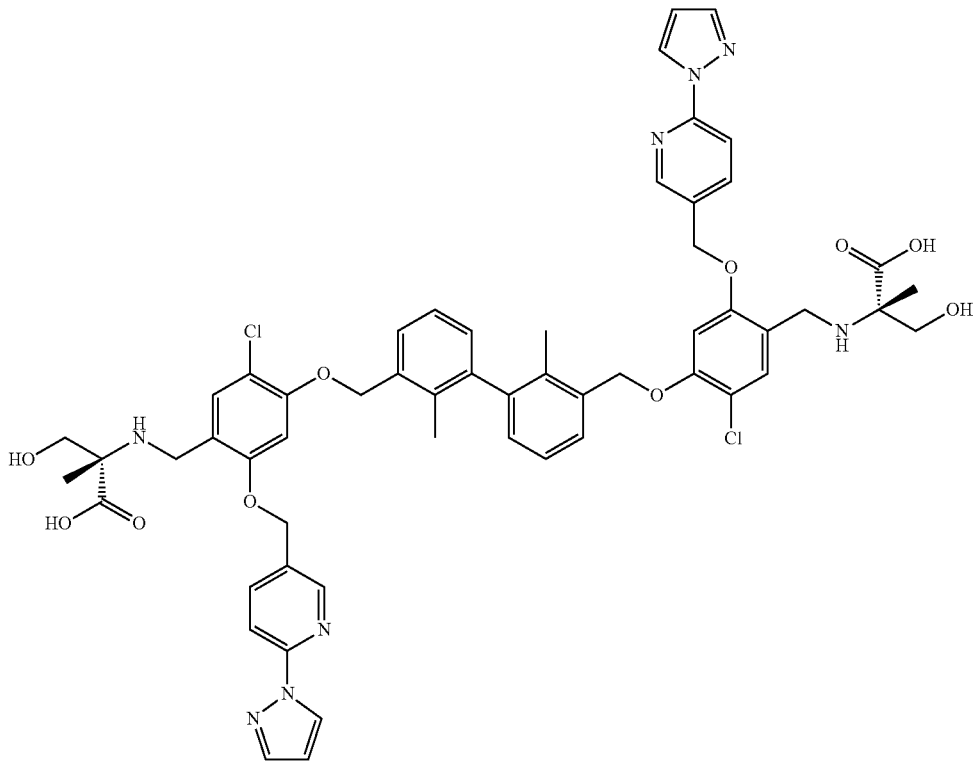

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 35-75% B over 20 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 1071.27; Retention Time: 1.86 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1071.35; Retention Time: 1.91 min.

Example 5023: 2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(2-methylpropane-1,3-diol)

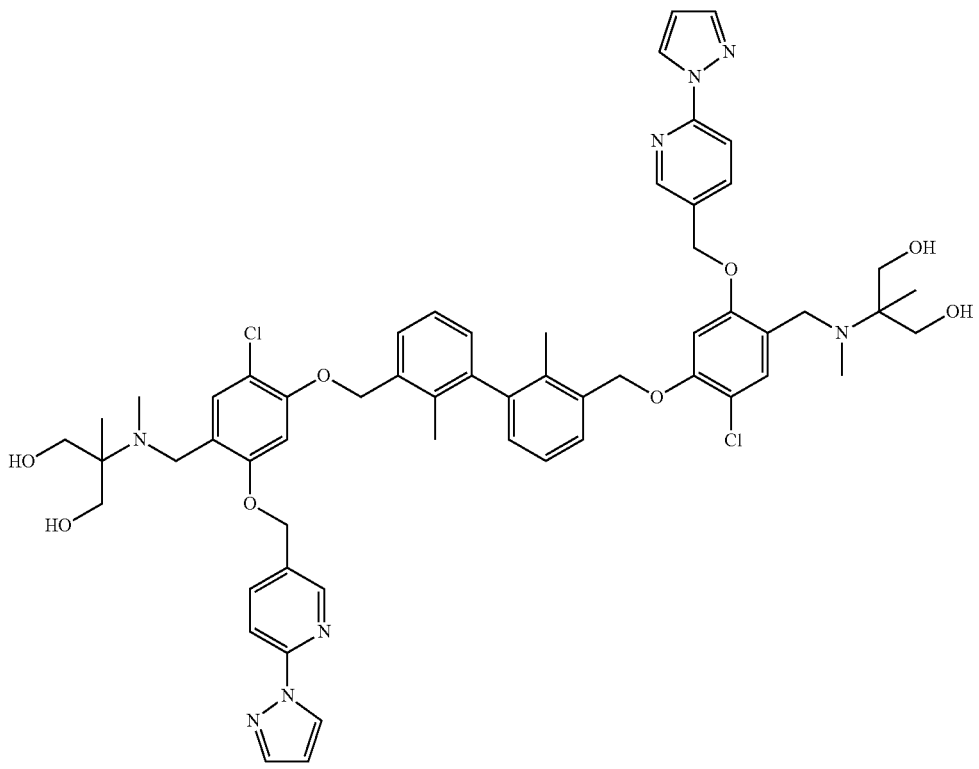

Example 5023

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 45-85% B over 20 minutes, then a 4-minute hold at 100% B; Flow: 20 mL/min. Fractions containing the desired product were combined and dried via centrifugal evaporation and its estimated purity by LCMS analysis was 99%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 1071.2; Retention Time: 1.93 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 537.08; Retention Time: 2.18 min.

Example 5024: 2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(2-methylpropanoic acid)

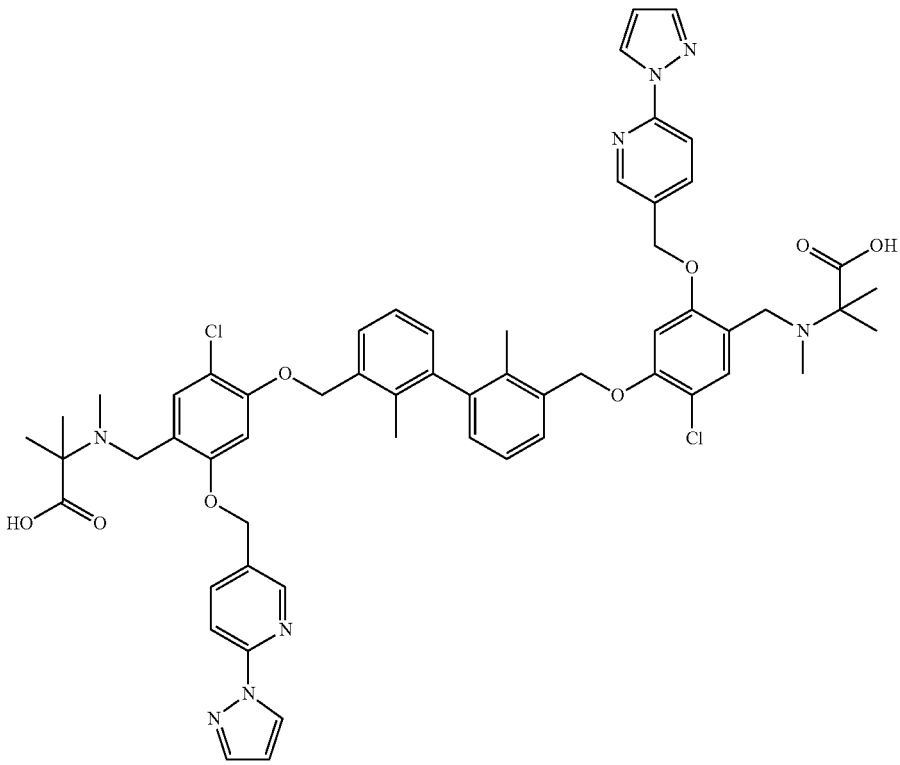

Example 5024

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 35-90% B over 20 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 1067.19; Retention Time: 1.98 min.

Injection 2 Conditions:

Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 535; Retention Time: 1.99 min.

Example 5025: (2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(4-hydroxybutanoic acid)

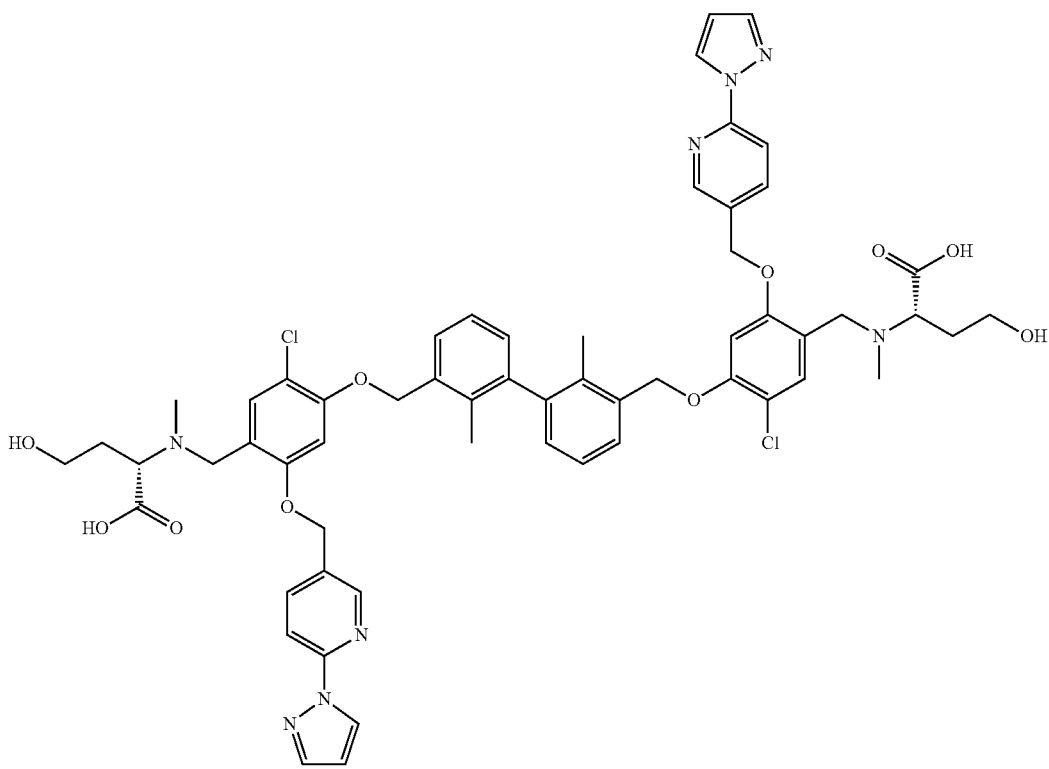

Example 5025

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 32-72% B over 22 minutes, then a 4-minute hold at 100% B; Flow: 20 mL/min. Fractions containing the desired product were combined and dried via centrifugal evaporation and its estimated purity by LCMS analysis was 98%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1099.38; Retention Time: 1.86 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.3%; Observed Mass: 551.07; Retention Time: 1.9 min.

Example 5026: (2S,2'S)-2,2'-(((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))dipentanoic acid

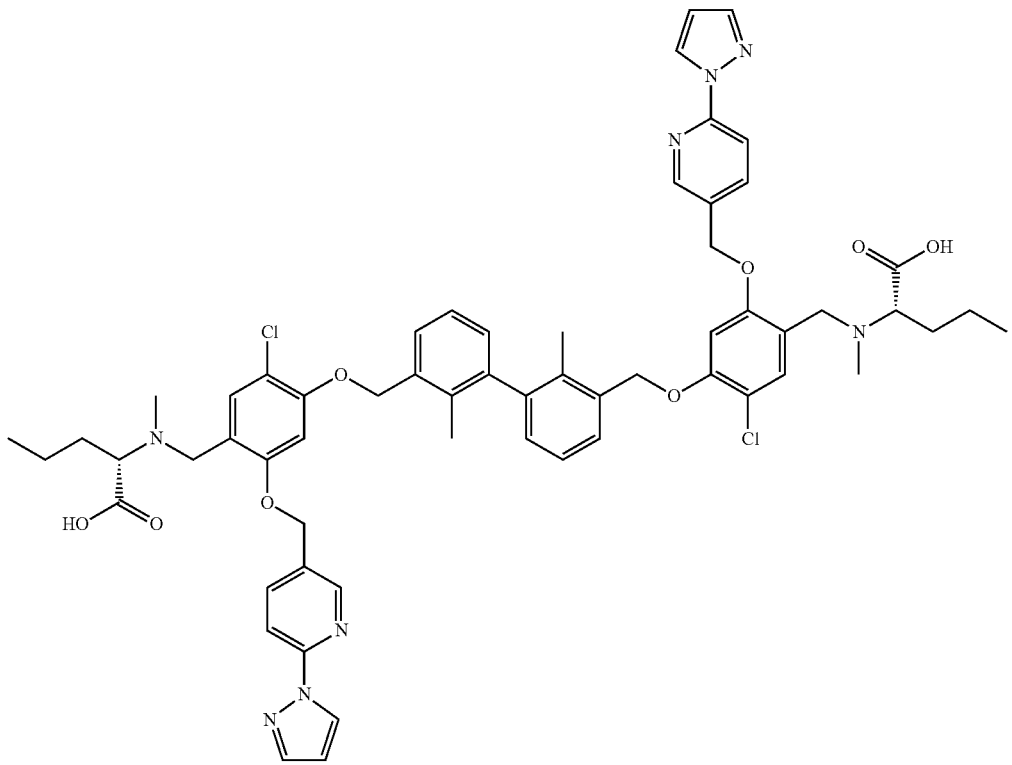

Example 5026

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 42-82% B over 20 minutes, then a 4-minute hold at 100% B; Flow: 20 mL/min. Fractions containing the desired product were combined and dried via centrifugal evaporation and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 1095.37; Retention Time: 2.1 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1095.36; Retention Time: 2.11 min.

Example 5027: (2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(3-hydroxy-2-methylpropanoic acid)

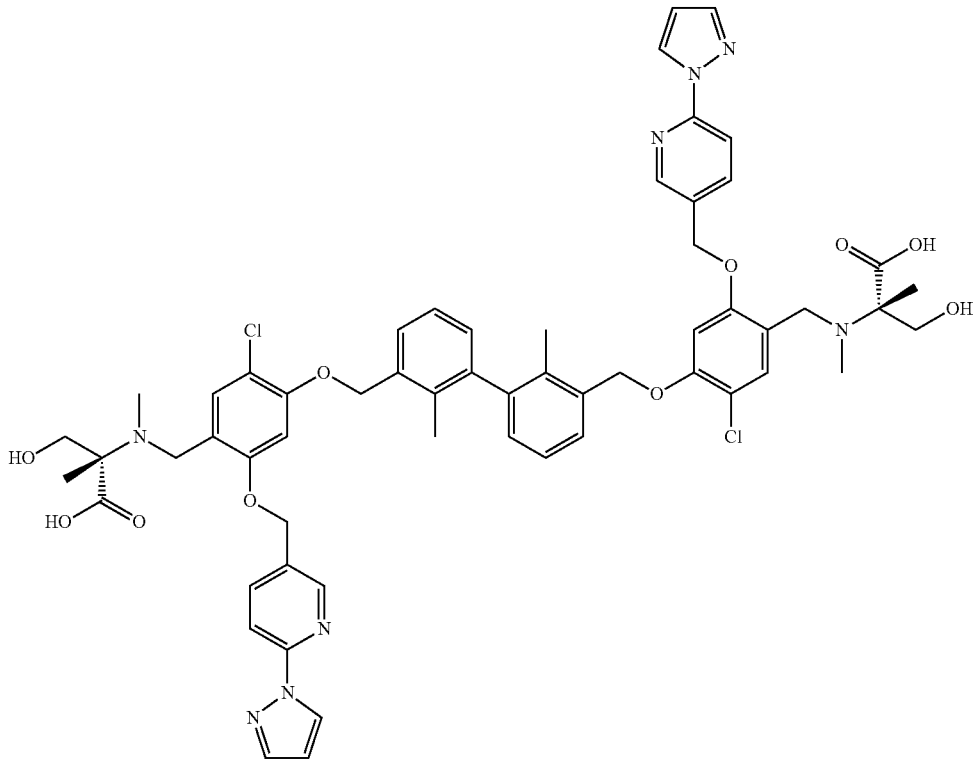

Example 5027

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 38-78% B over 19 minutes, then a 4-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 1099.23; Retention Time: 1.93 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1099.04; Retention Time: 1.96 min.

Example 5028: 2,2'-(((((((2,2'-dimethyl-[1,1'-biphe-nyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(propane-1,3-diol)

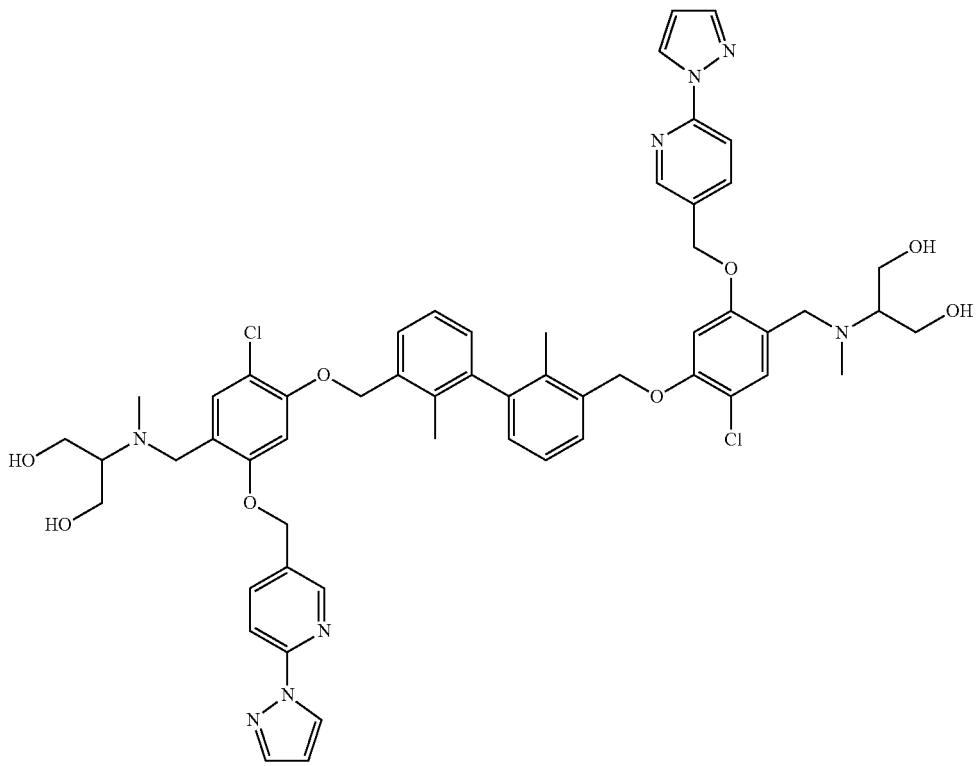

Example 5028

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 47-87% B over 19 minutes, then a 4-minute hold at 100% B; Flow: 20 mL/min. Fractions containing the desired product were combined and dried via centrifugal evaporation and its estimated purity by LCMS analysis was 96%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.3%; Observed Mass: 1043.34; Retention Time: 2.27 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.6%; Observed Mass: 1043.35; Retention Time: 1.9 min.

Example 5029: (2S,2'S,3R,3'R)-2,2'-(((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(3-hydroxybutanoic acid)

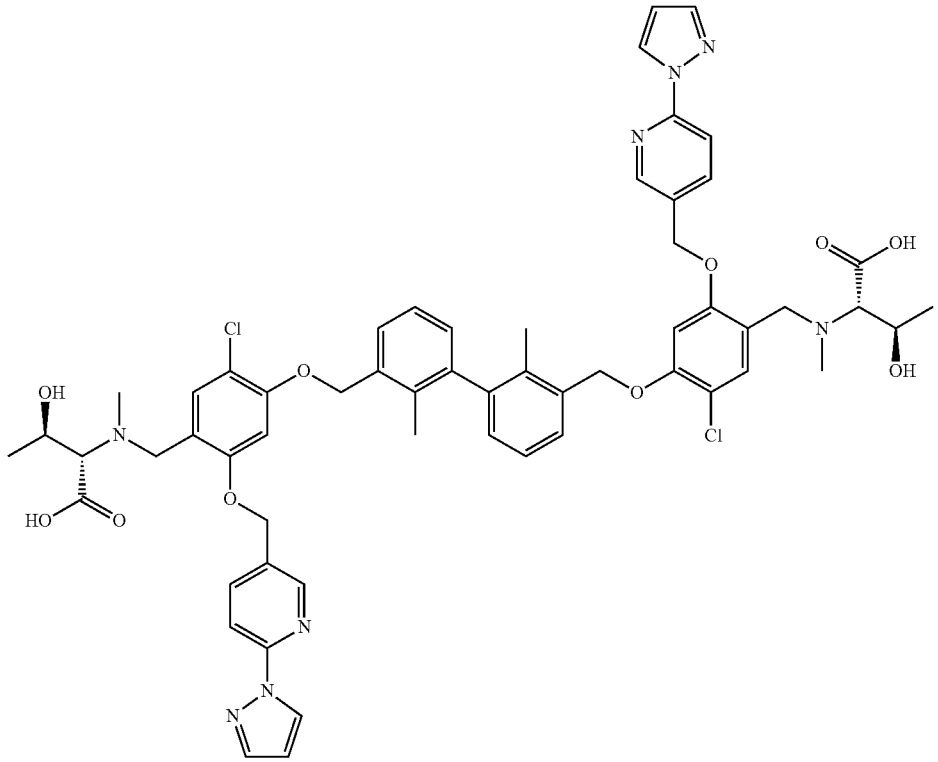

Example 5029

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 25-80% B over 25 minutes, then a 5-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 1099.29; Retention Time: 1.88 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 1099.18; Retention Time: 1.95 min.

Example 5030: N-(4-((3'-((4-((((S)-1-carboxy-3-hydroxypropyl)(methyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methoxybenzyl)-N-methyl-L-homoserine

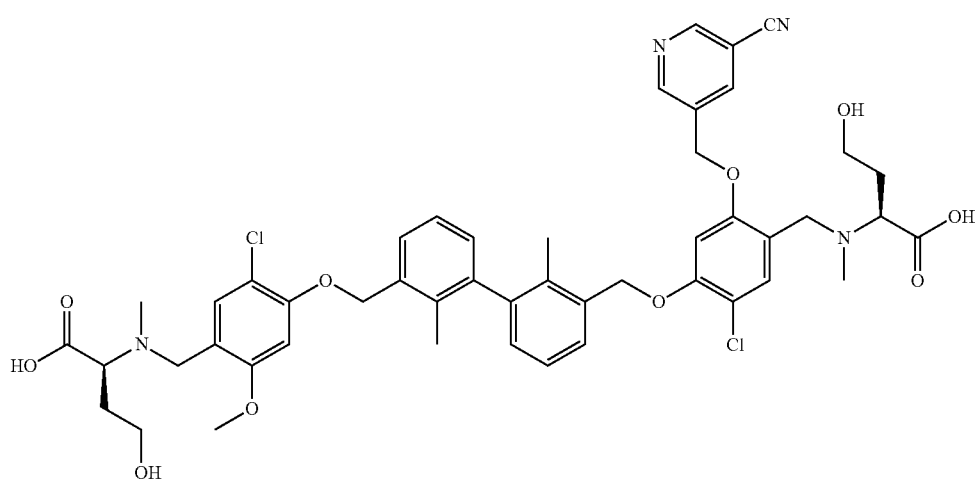

Example 5030

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 16-56% B over 22 minutes, then a 6-minute hold at 100% B; Flow: 20 mL/min. Fractions containing the desired product were combined and dried via centrifugal evaporation and its estimated purity by LCMS analysis was 98%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 915.25; Retention Time: 1.59 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.5%; Observed Mass: 915.26; Retention Time: 1.61 min.

Example 5031: 3-((4-((3'-((4-(((2-carboxyethyl)(methyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methoxybenzyl)(methyl)amino)propanoic acid

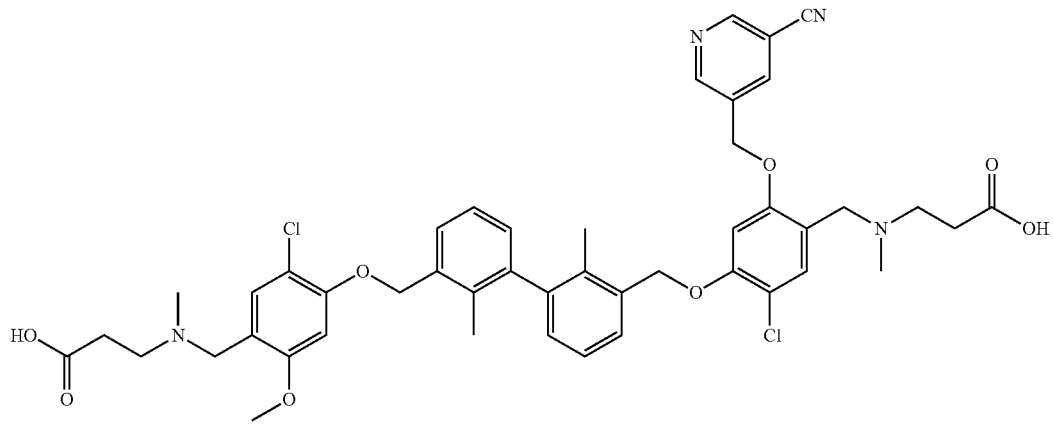

Example 5031

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 19-59% B over 20 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.5%; Observed Mass: 855.15; Retention Time: 1.65 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.3%; Observed Mass: 855.22; Retention Time: 1.61 min.

Example 5032: 1,1'-((((2,2'-dimethyl-[1,1'-biphenyl]-3,3'-diyl)bis(methylene))bis(oxy))bis(5-chloro-2-methoxy-4,1-phenylene))bis(N-((1H-pyrazol-3-yl)methyl)methanamine)

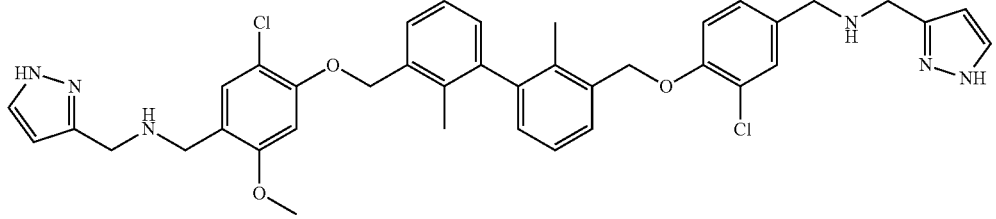

Example 5032

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 26-66% B over 22 minutes, then a 6-minute hold at 100% B; Flow: 20 mL/min. Fractions containing the desired product were combined and dried via centrifugal evaporation and its estimated purity by LCMS analysis was 93%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.3%; Observed Mass: 741.14; Retention Time: 1.67 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 741.21; Retention Time: 1.93 min.

Example 5033: 1,1'-((((2,2'-dimethyl-[1,1'-biphenyl]-3,3'-diyl)bis(methylene))bis(oxy))bis(5-chloro-2-methoxy-4,1-phenylene))bis(N-(pyrimidin-5-ylmethyl)methanamine)

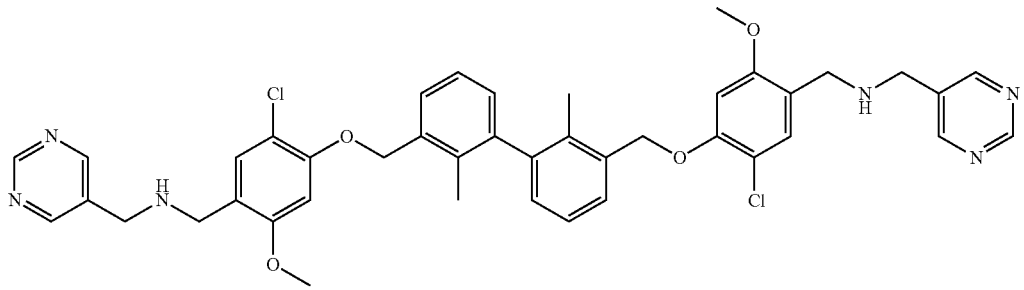

Example 5033

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 40-80% B over 20 minutes, then a 6-minute hold at 100% B; Flow: 20 mL/min. Fractions containing the desired product were combined and dried via centrifugal evaporation and its estimated purity by LCMS analysis was 88%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 88.2%; Observed Mass: 765.26; Retention Time: 1.61 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.0%; Observed Mass: 765.22; Retention Time: 2.25 min.

Example 5034: 1,1'-((((2,2'-dimethyl-[1,1'-biphenyl]-3,3'-diyl)bis(methylene))bis(oxy))bis(5-chloro-2-methoxy-4,1-phenylene))bis(N-(thiazol-5-ylmethyl)methanamine)

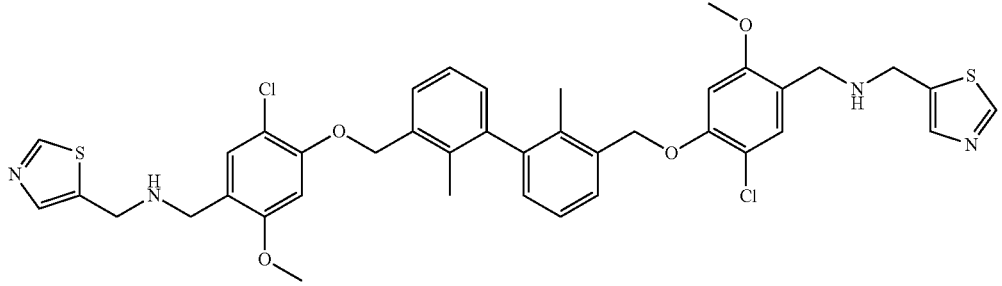

Example 5034

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 40-80% B over 23 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 775.05; Retention Time: 2.51 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.5%; Observed Mass: 775.11; Retention Time: 1.68 min.

Example 5035: 3,3'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))dipropionic acid

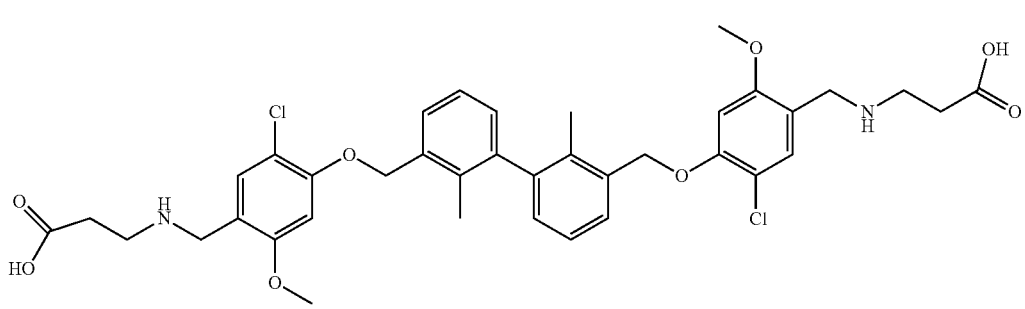

Example 5035

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 15-55% B over 22 minutes, then a 6-minute hold at 100% B; Flow: 20 mL/min. Fractions containing the desired product were combined and dried via centrifugal evaporation and its estimated purity by LCMS analysis was 100%. Analytical LC/MS was used to determine the final purity.

Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 725.17; Retention Time: 1.55 min.

Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 725.16; Retention Time: 1.65 min.

Example 5036: (2S,2'S)-2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(4-hydroxybutanoic acid)

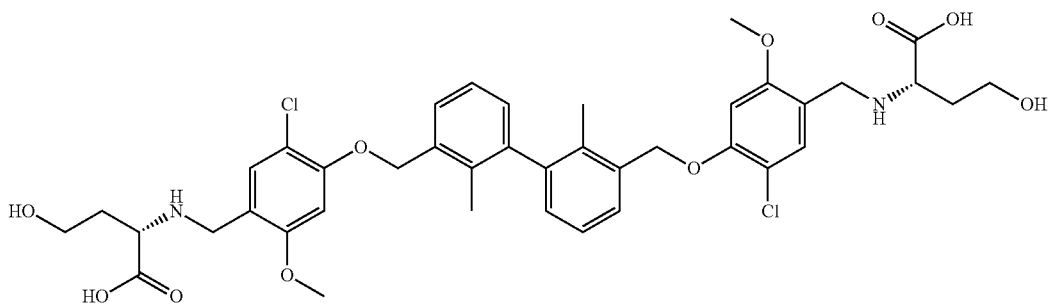

Example 5036

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 20-60% B over 20 minutes, then a 6-minute hold at 100% B; Flow: 20 mL/min. Fractions containing the desired product were combined and dried via centrifugal evaporation and its estimated purity by LCMS analysis was 96%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 785.24; Retention Time: 1.61 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1%; Observed Mass: 785.24; Retention Time: 1.52 min.

Example 5037: 1,1'-((((2,2'-dimethyl-[1,1'-biphenyl]-3,3'-diyl)bis(methylene))bis(oxy))bis(5-chloro-2-methoxy-4,1-phenylene))bis(N-((1H-pyrazol-3-yl)methyl)-N-methylmethanamine)

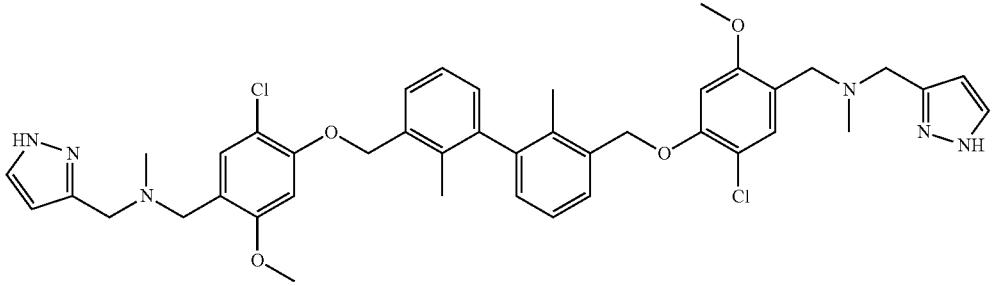

Example 5037

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 34-74% B over 22 minutes, then a 6-minute hold at 100% B; Flow: 20 mL/min. Fractions containing the desired product were combined and dried via centrifugal evaporation and its estimated purity by LCMS analysis was 95%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.2%; Observed Mass: 769.25; Retention Time: 1.71 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.4%; Observed Mass: 769.19; Retention Time: 2.23 min.

Example 5038: 1,1'-((((2,2'-dimethyl-[1,1'-biphe-nyl]-3,3'-diyl)bis(methylene))bis(oxy))bis(5-chloro-2-methoxy-4,1-phenylene))bis(N-methyl-N-(pyrimi-din-5-ylmethyl)methanamine)

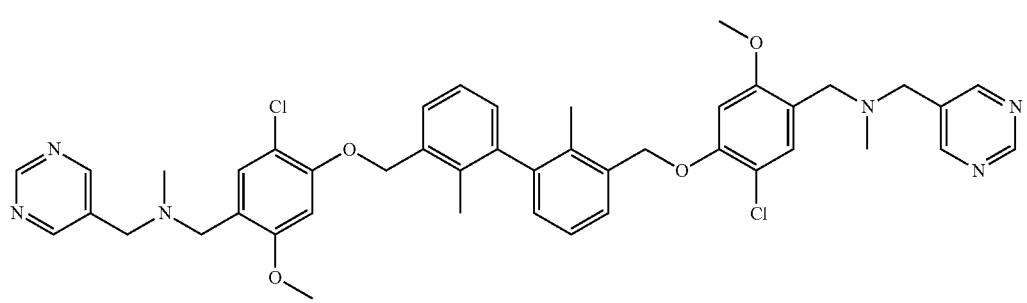

Example 5038

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 56-96% B over 20 minutes, then a 6-minute hold at 100% B; Flow: 20 mL/min. Fractions containing the desired product were combined and dried via centrifugal evaporation and its estimated purity by LCMS analysis was 99%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 793.21; Retention Time: 2.7 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 793.18; Retention Time: 1.63 min.

Example 5039: 1,1'-((((2,2'-dimethyl-[1,1'-biphe-nyl]-3,3'-diyl)bis(methylene))bis(oxy))bis(5-chloro-2-methoxy-4,1-phenylene))bis(N-methyl-N-(thiazol-5-ylmethyl)methanamine)

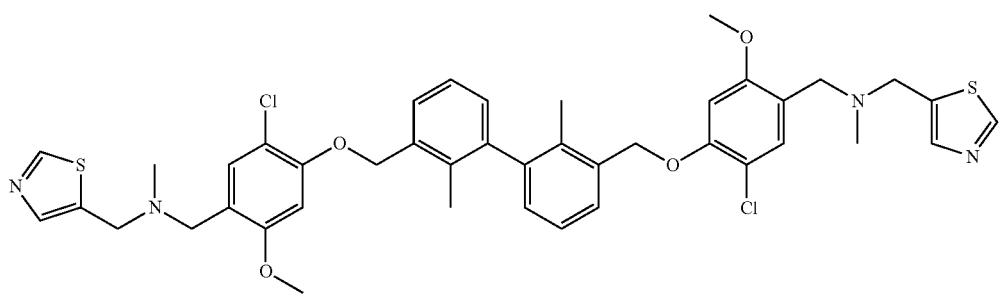

Example 5039

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 63-100% B over 20 minutes, then a 8-minute hold at 100% B; Flow: 20 mL/min. Fractions containing the desired product were combined and dried via centrifugal evaporation and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 803.17; Retention Time: 2.93 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 803.15; Retention Time: 1.71 min.

Intermediate: 5-chloro-4-hydroxy-2-methylbenzaldehyde (A) and 3-chloro-4-hydroxy-2-methylbenzaldehyde (B)

A

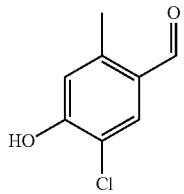

B

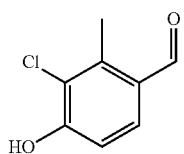

NCS (1.177 g, 8.81 mmol) was added to a stirring solution of 4-hydroxy-2-methylbenzaldehyde (1 g, 7.34 mmol) in DCM (24.48 ml) and acetonitrile (12.24 mL) at rt for 16 h. The solvent was removed under vacuum and the crude residue was purified by flash silica gel chromatography using DCM. The product fractions were collected and the solvent removed under vacuum to give a mixture of regioisomers 5-chloro-4-hydroxy-2-methylbenzaldehyde (A) and 3-chloro-4-hydroxy-2-methylbenzaldehyde (B) (923 mg, 74% yield) which were not separated. LCMS (M+H)= 171.03, 172.94.

Intermediate: 5-chloro-2-methyl-4-((2-methyl-3-(4,4,5,5-tetramethyl-1,3,2-dioxaborolan-2-yl)benzyl)oxy)benzaldehyde (A) and 3-chloro-2-methyl-4-((2-methyl-3-(4,4,5,5-tetramethyl-1,3,2-dioxaborolan-2-yl)benzyl)oxy)benzaldehyde (B)

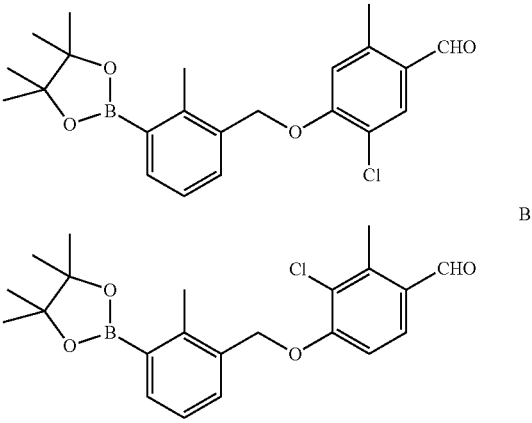

A solution of diisopropyl azodicarboxylate (334 μl, 1.612 mmol) in THF (3053 μl) was added dropwise to the solution of (2-methyl-3-(4,4,5,5-tetramethyl-1,3,2-dioxaborolan-2-yl)phenyl)methanol (364 mg, 1.465 mmol), a mixture of regio-isomers 5-chloro-4-hydroxy-2-methylbenzaldehyde and 3-chloro-4-hydroxy-2-methylbenzaldehyde (250 mg, 1.465 mmol), and triphenylphosphine (423 mg, 1.612 mmol) in THF (6106 μL) at 0° C. The resulting yellow solution was allowed to warm to rt and stirred for 16 h. The solvent was removed under vacuum. The crude material was purified by silica gel chromatography using 5-50% EtOAc/Hex. The product fractions were collected and the solvent removed under vacuum to give: 5-chloro-2-methyl-4-((2-methyl-3-(4,4,5,5-tetramethyl-1,3,2-dioxaborolan-2-yl)benzyl)oxy)benzaldehyde (A) and 3-chloro-2-methyl-4-((2-methyl-3-(4,4,5,5-tetramethyl-1,3,2-dioxaborolan-2-yl)benzyl)oxy)benzaldehyde (B). The regio isomers were then separated by SFC chromatography.

Experimental Details for SFC chromatography:
Column: ChiralCel OD-H, 30×250 mm, 5 μm
Mobile Phase: 15% MeOH/85% C02
Pressure: 150 bar
Temperature: 35° C.
Flow Rate: 80 mL/min
UV: 220 nm
Injection: 0.5 mL (~30 mg/mL in MeOH:CHCl$_3$, 1:1)

Peak 1 and Peak 2 were concentrated under vacuum. Peak 1 corresponds to the acetal of 5-chloro-2-methyl-4-((2-methyl-3-(4,4,5,5-tetramethyl-1,3,2-dioxaborolan-2-yl)benzyl)oxy)benzaldehyde (A) by NMR formed under SFC conditions. The aldehyde was reformed by dissolving Peak 1 in 2 mL DCM and adding 1 mL water and 1 mL TFA. The mixture was stirred for 30 min. The organic layer was collected and washed with bicarbonate and brine, dried over sodium sulfate and concentrated to give 5-chloro-2-methyl-4-((2-methyl-3-(4,4,5,5-tetramethyl-1,3,2-dioxaborolan-2-yl)benzyl)oxy)benzaldehyde (70 mg, 12% yield). LCMS (M+H)=400.97. $^1$H NMR (400 MHz, DMSO-d$_6$) δ 10.07 (s, 1H), 8.31 (s, 1H), 7.86 (s, 1H), 7.64 (dd, J=7.5, 1.5 Hz, 1H), 7.60-7.55 (m, 1H), 7.32 (s, 1H), 7.23 (t, J=7.4 Hz, 1H), 5.30

(s, 2H), 2.63 (s, 3H), 1.31 (s, 11H). The same procedure was followed for Peak 2 3-chloro-2-methyl-4-((2-methyl-3-(4,4,5,5-tetramethyl-1,3,2-dioxaborolan-2-yl)benzyl)oxy)benzaldehyde (B) (100 mg, 17% yield). LCMS (M+H)=400.97.

Intermediate: 4-((3-bromo-2-methylbenzyl)oxy)-5-chloro-2-methylbenzaldehyde (A) and 4-((3-bromo-2-methylbenzyl)oxy)-3-chloro-2-methylbenzaldehyde (B)

A
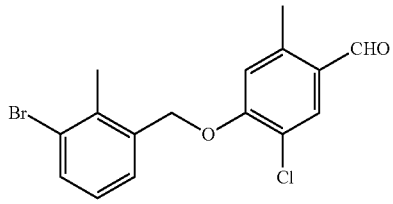

B
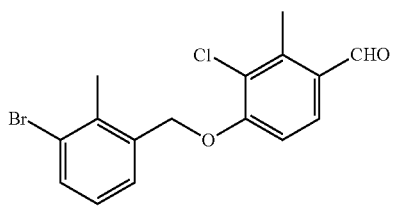

A solution of diisopropyl azodicarboxylate (2.67 ml, 12.90 mmol) in THF (24.42 ml) was added dropwise to the solution of (3-bromo-2-methylphenyl)methanol (2.357 g, 11.72 mmol), a mixture of regio-isomers 5-chloro-4-hydroxy-2-methylbenzaldehyde and 3-chloro-4-hydroxy-2-methylbenzaldehyde (2 g, 11.72 mmol), and triphenylphosphine (3.38 g, 12.90 mmol) in THF (48.8 ml) at 0° C. The resulting yellow solution was allowed to warm to rt and stirred overnight. The solvent was removed under vacuum. The crude material was purified by silica gel chromatography using 5-50% EtOAc/Hex. The product fractions were collected and the solvent removed under vacuum to give: 4-((3-bromo-2-methylbenzyl)oxy)-5-chloro-2-methylbenzaldehyde (A) and 4-((3-bromo-2-methylbenzyl)oxy)-3-chloro-2-methylbenzaldehyde (B) (1.1 g, 27% yield). The regio isomers were then separated by SFC chromatography. Experimental Details for SFC chromatography:
Column: ChiralCel OD-H, 5×25 cm, 5 μm
Mobile Phase: 38% MeOH/62% C02
Pressure: 100 bar
Temperature: 35° C.
Flow Rate: 300 mL/min
UV: 220 nm
Injection: 3.5 mL (~13.6 mg/mL in MeOH:CHCl$_3$, 1:1)

Peak 1 and Peak 2 were concentrated under vacuum. Peak 1 corresponds to the acetal of 4-((3-bromo-2-methylbenzyl)oxy)-5-chloro-2-methylbenzaldehyde (A) by NMR formed under SFC conditions. The aldehyde was reformed by dissolving Peak 1 in 2 mL DCM and adding 1 mL water and 1 mL TFA. The mixture was stirred for 30 min. The organic layer was collected and washed with bicarbonate and brine, dried over sodium sulfate and concentrated to give 4-((3-bromo-2-methylbenzyl)oxy)-5-chloro-2-methylbenzaldehyde (140 mg). $^1$H NMR (400 MHz, CHLOROFORM-d) δ 10.12 (s, 1H), 7.86 (s, 1H), 7.60 (d, J=7.3 Hz, 1H), 7.44 (d, J=7.5 Hz, 1H), 7.12 (t, J=7.8 Hz, 1H), 6.85 (s, 1H), 5.20 (s, 2H), 2.67 (s, 3H), 2.47 (s, 3H).

Example 5500 to Example 5507 were prepared in a manner analogous to those described above.

Example 5500: (2S,2'S)-1,1'-(((((2,2'-dimethyl-[1,1'-biphenyl]-3,3'-diyl)bis(methylene))bis(oxy))bis(3-methyl-4,1-phenylene))bis(methylene))bis(piperidine-2-carboxylic acid)

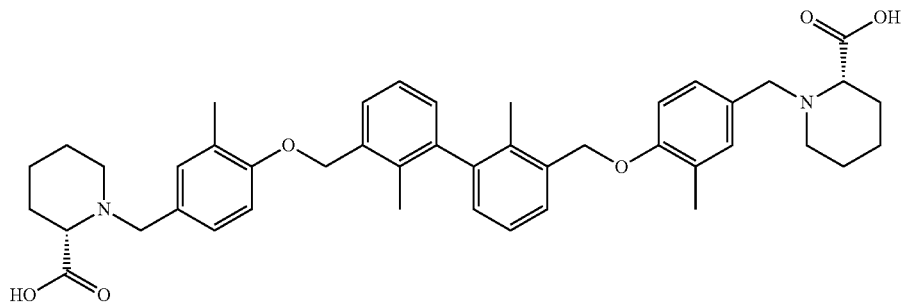 [SMILES: Cc1cc(CN2CCCC[C@H]2C(=O)O)ccc1OCc1cccc(-c2cccc(COc3ccc(CN4CCCC[C@H]4C(=O)O)cc3C)c2C)c1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 13.9 mg, and its estimated purity by LCMS analysis was 98%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100%; Observed Mass: ESI-MS (+) m/z 705.1; Retention Time: 1.75 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.6%; Observed Mass: ESI-MS(+) m/z 705.1; Retention Time: 1.70 min.

Example 5501: (2S,2'S)-1,1'-(((((2,2'-dimethyl-[1,1'-biphenyl]-3,3'-diyl)bis(methylene))bis(oxy))bis(5-chloro-2-methyl-4,1-phenylene))bis(methylene))bis(piperidine-2-carboxylic acid)

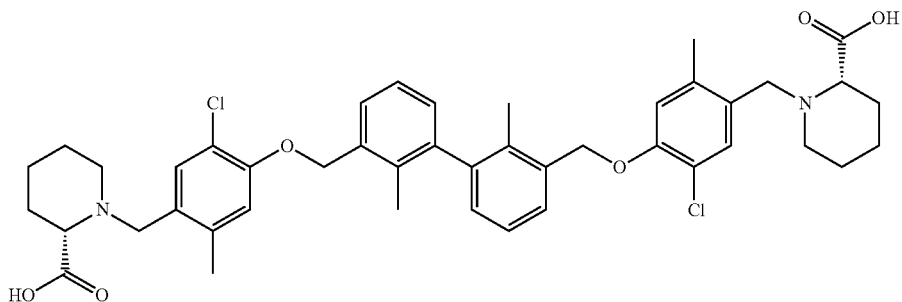 [SMILES: Cc1cc(OCc2cccc(-c3cccc(COc4cc(C)c(CN5CCCC[C@H]5C(=O)O)cc4Cl)c3C)c2C)c(Cl)cc1CN1CCCC[C@H]1C(=O)O]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 18-63% B over 23 minutes, then a 6-minute hold at 100% B; Flow: 20 mL/min. Fractions containing the desired product were combined and dried via centrifugal evaporation. The yield of the product was 2.8 mg, and its estimated purity by LCMS analysis was 100%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: ESI-MS(+) m/z 773.2; Retention Time: 1.71 min.

Injection 2 Conditions:

Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: ESI-MS(+) m/z 773.21; Retention Time: 1.66 min.

Example 5502: 3,3'-(((((2,2'-dimethyl-[1,1'-biphenyl]-3,3'-diyl)bis(methylene))bis(oxy))bis(5-chloro-2-methyl-4,1-phenylene))bis(methylene))bis(azanediyl))dipropionic acid

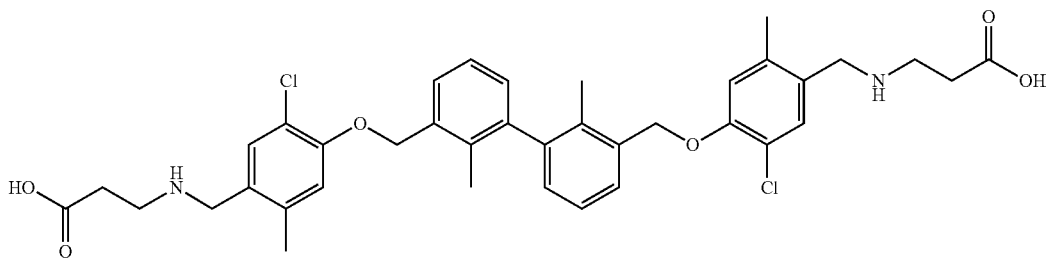 [SMILES: Cc1cc(OCc2cccc(-c3cccc(COc4cc(C)c(CNCCC(=O)O)cc4Cl)c3C)c2C)c(Cl)cc1CNCCC(=O)O]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 14-59% B over 22 minutes, then a 6-minute hold at 100% B; Flow: 20 mL/min. Fractions containing the desired product were combined and dried via centrifugal evaporation. The yield of the product was 1.7 mg, and its estimated purity by LCMS analysis was 95%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.0%; Observed Mass: ESI-MS(+) m/z 693.13; Retention Time: 1.54 min.
Injection 2 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.8%; Observed Mass: ESI-MS(+) m/z 693.14; Retention Time: 1.61 min.

Example 5503: (S)-1-(4-((3'-((4-(((S)-2-carboxypiperidin-1-yl)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)piperidine-2-carboxylic acid

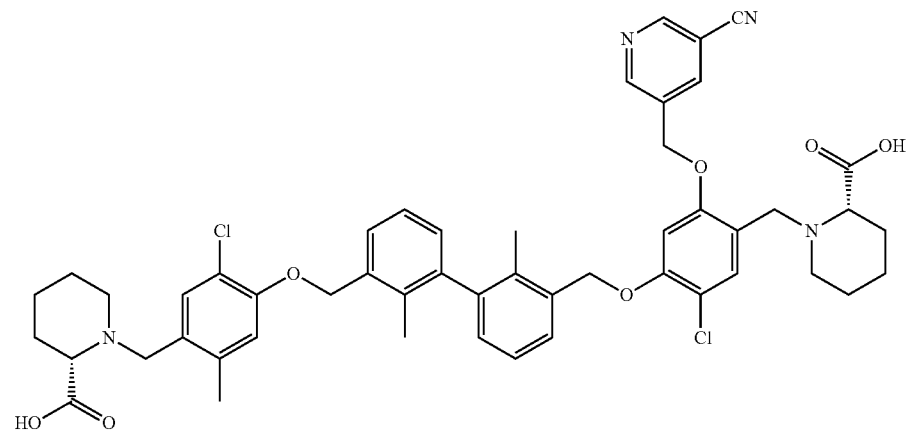 [SMILES: Cc1cc(OCc2cccc(-c3cccc(COc4cc(OCc5cncc(C#N)c5)c(CN5CCCC[C@H]5C(=O)O)cc4Cl)c3C)c2C)c(Cl)cc1CN1CCCC[C@H]1C(=O)O]

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 19-63% B over 23 minutes, then a 6-minute hold at 100% B; Flow: 20 mL/min. Fractions containing the desired product were combined and dried via centrifugal evaporation. The yield of the product was 4.4 mg, and its estimated purity by LCMS analysis was 95%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: ESI-MS(+) m/z 891.21; Retention Time: 1.72 min.
Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: ESI-MS(+) m/z 891.22; Retention Time: 1.67 min.

Example 5504: 3-((4-((3'-((4-(((2-carboxyethyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)amino)propanoic acid

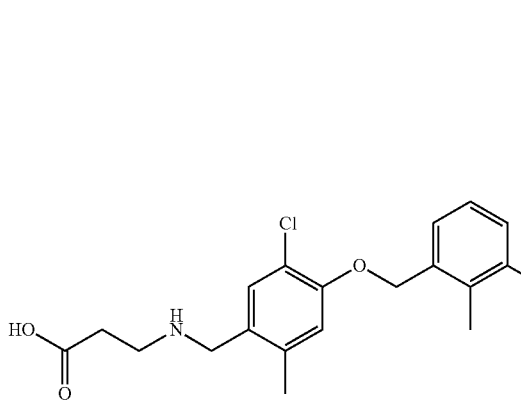

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 15-57% B over 23 minutes, then a 6-minute hold at 100% B; Flow: 20 mL/min. Fractions containing the desired product were combined and dried via centrifugal evaporation. The yield of the product was 5.0 mg, and its estimated purity by LCMS analysis was 97%. Analytical LC/MS was used to determine the final purity.
Injection 1 Conditions:
Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.2%; Observed Mass: ESI-MS (+) m/z 811.2; Retention Time: 1.63 min.

Injection 2 Conditions:
Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.5%; Observed Mass: ESI-MS(+) m/z 811.2; Retention Time: 1.57 min.

Example 5505: N-(4-((3'-((4-((((S)-1-carboxy-3-hydroxypropyl)(methyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)-N-methyl-L-homoserine

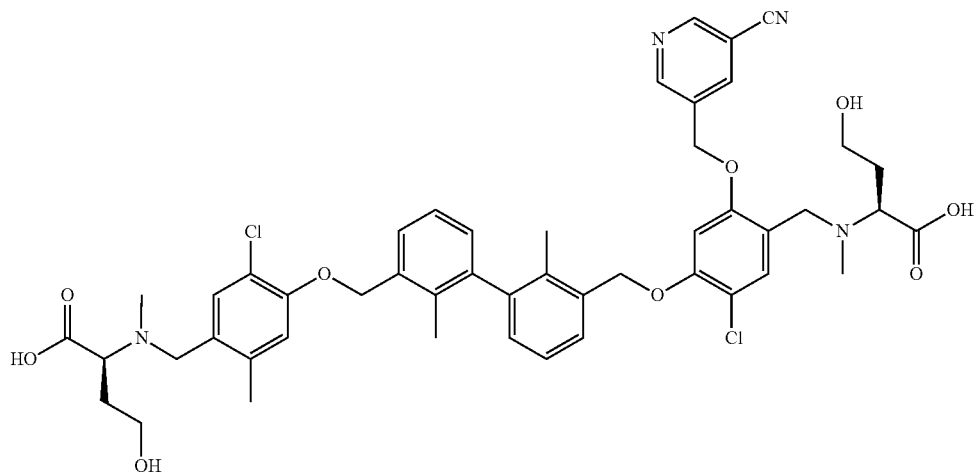 [SMILES: Cc1cc(OCc2cccc(-c3cccc(COc4cc(OCc5cncc(C#N)c5)c(CN(C)[C@@H](CCO)C(=O)O)cc4Cl)c3C)c2C)c(Cl)cc1CN(C)[C@@H](CCO)C(=O)O]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 20-60% B over 20 minutes, then a 6-minute hold at 100% B; Flow: 20 mL/min. Fractions containing the desired product were combined and dried via centrifugal evaporation. The yield of the product was 7.0 mg, and its estimated purity by LCMS analysis was 97%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.6%; Observed Mass: ESI-MS(+) m/z 899.19; Retention Time: 1.63 min.

Injection 2 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.2%; Observed Mass: ESI-MS(+) m/z 899.22; Retention Time: 1.67 min.

Example 5507: (S)-2-((4-((3'-((4-((((S)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)amino)-3-hydroxy-2-methylpropanoic acid

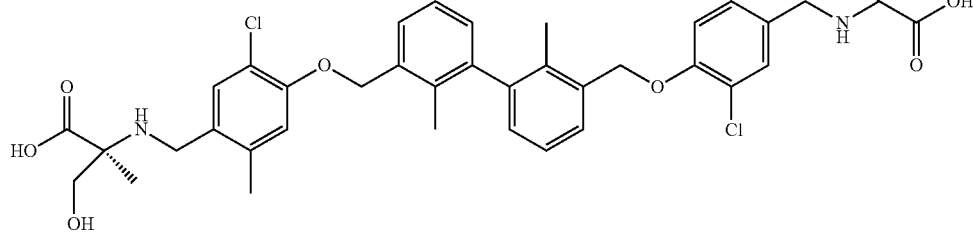

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 18-61% B over 28 minutes, then a 6-minute hold at 100% B; Flow: 20 mL/min. Fractions containing the desired product were combined and dried via centrifugal evaporation. The yield of the product was 3.2 mg, and its estimated purity by LCMS analysis was 97%. Analytical LC/MS was used to determine the final purity.

Injection 1 Conditions:

Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.4%; Observed Mass: ESI-MS(+) m/z 871.16; Retention Time: 1.72 min.

Injection 2 Conditions:

Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.9%; Observed Mass: ESI-MS(+) m/z 871.18; Retention Time: 1.58 min.

Analytical LC-MS Methods USED to Identify the Structures in Table 40000 to Table 90000:

| LC Condition A | |
| --- | --- |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Temperature | 40° C. |
| Column | Phenomenex LUNA C18, 30 × 2, 3u |

| LC Condition B | |
| --- | --- |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 4 min |
| Flow Rate | 0.8 mL/min |
| Wavelength | 220 |
| Temperature | 40° C. |
| Column | PHENOMENEX-LUNA 2.0 × 50 mm 3 um |

| LC Condition C | |
| --- | --- |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |

-continued

| | |
|---|---|
| Flow Rate | 1 mL/min |
| Wavelength | 220 |
| Temperature | 40° C. |
| Column | Acquity BEH C18 2.1 × 50 mm; 1.7 um |
| | LC Condition D |
| Solvent A | 95% Water-5% ACN-0.1% TFA |
| Solvent B | 5% Water-95% ACN-0.1% TFA |
| Start % B | 0 |
| Final % B | 100 |
| Gradient Time | 3 min |
| Flow Rate | 0.8 mL/min |
| Wavelength | 220 |
| Temperature | 40° C. |
| Column | Acquity BEH C18 2.1 × 50 mm; 1.7 um |
| | LC Condition E |
| Solvent A | 5% ACN:95% Water:10 mM Ammonium Actetate |
| Solvent B | 95% ACN:5% Water:10 mM Ammonium Actetate |
| Start % B | 30 |
| Final % B | 100 |
| Gradient Time | 2 min |
| Flow Rate | 1 mL/min |
| Temperature | 40° C. |
| Solvent Pair | ACN:Water:Ammonium Actetate |
| Column | Phenomenex LUNA C18, 30 × 2, 3u |
| | LC Condition F |
| Solvent A | 5% ACN:95% Water:10 mM Ammonium Actetate |
| Solvent B | 95% ACN:5% Water:10 mM Ammonium Actetate |
| Start % B | 50 |
| Final % B | 100 |
| Gradient Time | 2 min |
| Flow Rate | 1 mL/min |
| Wavelength | 220 |
| Temperature | 40° C. |
| Column | Phenomenex LUNA C18, 30 × 2, 3u |
| | LC Condition G |
| Solvent A | 90% Water-10% Methanol-0.1% TFA |
| Solvent B | 10% Water-90% Methanol-0.1% TFA |
| Start % B | 20 |
| Final % B | 100 |
| Gradient Time | 4 min |
| Flow Rate | 0.8 mL/min |
| Wavelength | 220 |
| Temperature | 40° C. |
| Column | PHENOMENEX-LUNA 2.0 × 50 mm 3 um |
| | LC Condition H |
| Solvent A | 90% Water-10% Methanol-0.1% TFA |
| Solvent B | 10% Water-90% Methanol-0.1% TFA |
| Start % B | 40 |
| Final % B | 100 |
| Gradient Time | 4 min |
| Flow Rate | 0.8 mL/min |
| Wavelength | 220 |
| Temperature | 40° C. |
| Column | PHENOMENEX-LUNA 2.0 × 50 mm 3 um |
| | LC Condition I |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Temperature | 40° C. |
| Column | PHENOMENEX-LUNA 2.0 × 50 mm 3 um |
| | LC Condition J |
| Solvent A | 5% ACN:95% Water:10 mM Ammonium Actetate |
| Solvent B | 95% ACN:5% Water:10 mM Ammonium Actetate |
| Start % B | 20 |
| Final % B | 100 |
| Gradient Time | 4 min |
| Flow Rate | 0.8 mL/min |
| Wavelength | 220 |

-continued

| | |
|---|---|
| Temperature | 40° C. |
| Column | Phenomenex LUNA C18, 50 × 2, 3u |
| | LC Condition K |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Temperature | 40° C. |
| Column | Phenomenex LUNA C18, 50 × 2, 3u |
| | LC Condition L |
| Solvent A | 5% ACN:95% Water:10 mM Ammonium Actetate |
| Solvent B | 95% ACN:5% Water:10 mM Ammonium Actetate |
| Start % B | 50 |
| Final % B | 100 |
| Gradient Time | 4 min |
| Flow Rate | 0.8 mL/min |
| Temperature | 40° C. |
| Solvent Pair | ACN:Water:Ammonium Actetate |
| Column | Phenomenex LUNA C18, 50 × 2, 3u |
| | LC Condition M |
| Solvent A | 5:95 acetonitrile:water with 0.1% trifluoroacetic acid |
| Solvent B | 95:5 acetonitrile:water with 0.1% trifluoroacetic acid |
| Start % B | 0 |
| Final % B | 100 |
| Gradient Time | 3 min |
| Flow Rate | 1 mL/min |
| Wavelength | 220 |
| Temperature | 50° C. |
| Column | Waters XBridge C18, 2.1 mm × 50 mm, 1.7 μm particles |
| | LC Condition N |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 1 mL/min |
| Wavelength | 220 |
| Temperature | 50° C. |
| Column | Waters XBridge C18, 2.1 mm × 50 mm, 1.7 μm particles |
| | LC Condition O |
| Solvent A | 5:95 acetonitrile:water with 0.1% trifluoroacetic acid |
| Solvent B | 95:5 acetonitrile:water with 0.1% trifluoroacetic acid |
| Start % B | 0 |
| Final % B | 100 |
| Gradient Time | 3 min |
| Flow Rate | 0.75 mL/min |
| Wavelength | 220 |
| Temperature | 70° C. |
| Column | Waters CSH C18, 2.1 mm × 50 mm, 1.7 μm particles |
| | LC Condition P |
| Solvent A | 5:95 acetonitrile:water with 0.1% trifluoroacetic acid |
| Solvent B | 95:5 acetonitrile:water with 0.1% trifluoroacetic acid |
| Start % B | 0 |
| Final % B | 100 |
| Gradient Time | 3 min |
| Flow Rate | 1 mL/min |
| Wavelength | 220 |

299
-continued

| Temperature | 70° C. |
| Column | Waters XBridge C18, 2.1 mm × 50 mm, 1.7 μm particles |

General Procedure for the Preparation of the Structures in Tables 40000 to 70000:

300

A mixture of aldehyde intermediate (1 eq.), amine (1-20 eq.), Et$_3$N (1-20 eq.) and acetic acid (2-40 eq.) in CH$_2$Cl$_2$/EtOH/DMF (1:1:2) was stirred at room for 2 hours. To the mixture was added NaCN(BH$_3$) (1-20 eq.) slowly by small portion within 3 hours. Then the mixture was stirred at room temperature for 16 hours. After all the solvents were removed under vacuum, the residue was purified by the preparative HPLC to give the compounds in Table 40000 to Table 70000.

TABLE 40000

| Cmpd # | Structure | LC-MS Method | R$_f$ (min) | MS (M + H)$^+$ Calcd. | MS (M + H)$^+$ Observ. |
|---|---|---|---|---|---|
| 40010 | 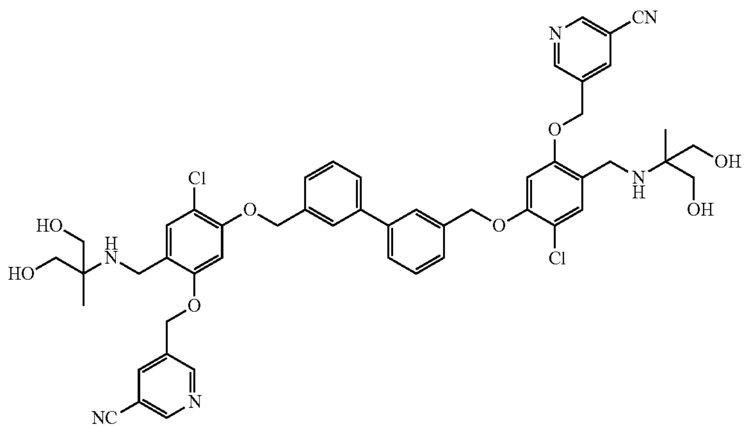 [SMILES: CC(CO)(CO)NCc1cc(Cl)c(OCc2cccc(-c3cccc(COc4cc(OCc5cncc(C#N)c5)c(CNC(C)(CO)CO)cc4Cl)c3)c2)cc1OCc1cncc(C#N)c1] | C | 1.73 | 933.3 | 933.2 |
| 40040 | 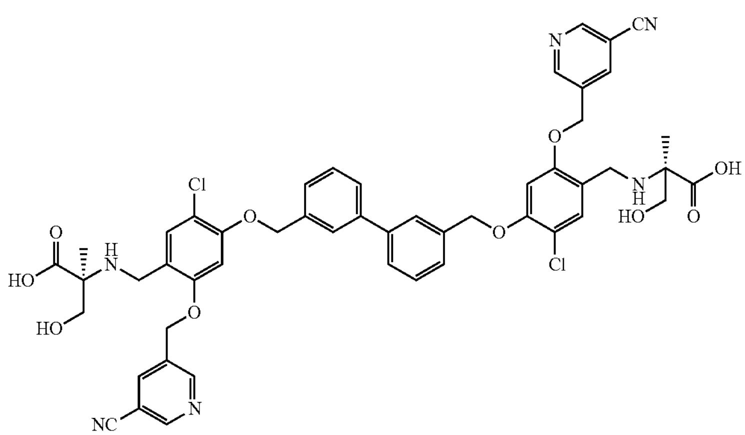 [SMILES: C[C@](CO)(NCc1cc(Cl)c(OCc2cccc(-c3cccc(COc4cc(OCc5cncc(C#N)c5)c(CN[C@@](C)(CO)C(=O)O)cc4Cl)c3)c2)cc1OCc1cncc(C#N)c1)C(=O)O] | C | 1.60 | 961.3 | 961.1 |

TABLE 40000-continued

| Cmpd # | Structure | LC-MS Method | $R_f$ (min) | MS (M+H)+ Calcd. | MS (M+H)+ Observ. |
|---|---|---|---|---|---|
| 40050 | 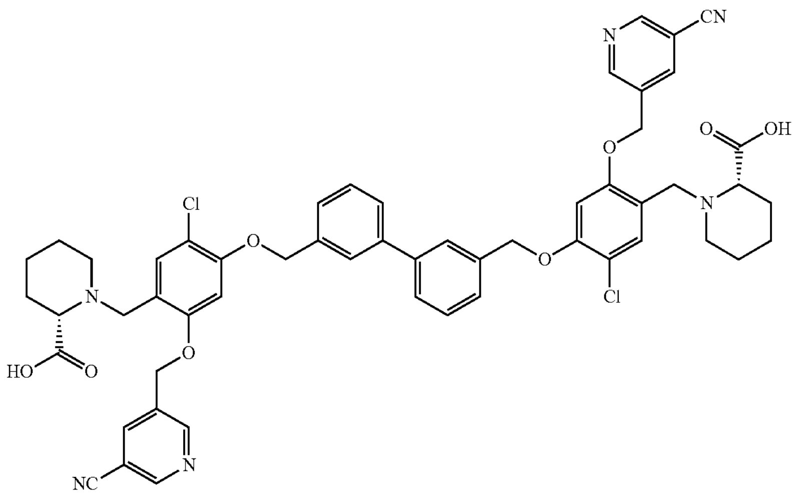 [SMILES: N#Cc1cncc(COc2cc(OCc3cccc(-c4cccc(COc5cc(OCc6cncc(C#N)c6)c(CN6CCCC[C@H]6C(=O)O)cc5Cl)c4)c3)c(Cl)cc2CN2CCCC[C@H]2C(=O)O)c1] | D | 1.72 | 981.3 | 981.1 |
| 40060 | 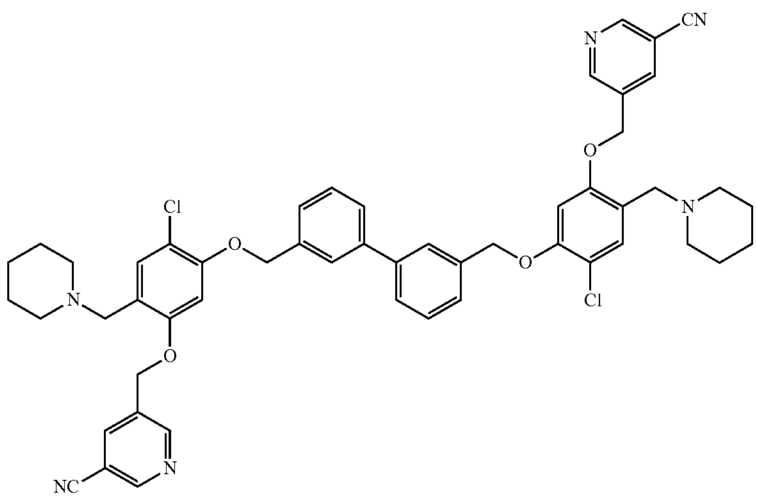 [SMILES: N#Cc1cncc(COc2cc(OCc3cccc(-c4cccc(COc5cc(OCc6cncc(C#N)c6)c(CN6CCCCC6)cc5Cl)c4)c3)c(Cl)cc2CN2CCCCC2)c1] | D | 2.57 | 893.3 | 893.3 |
| 40070 | 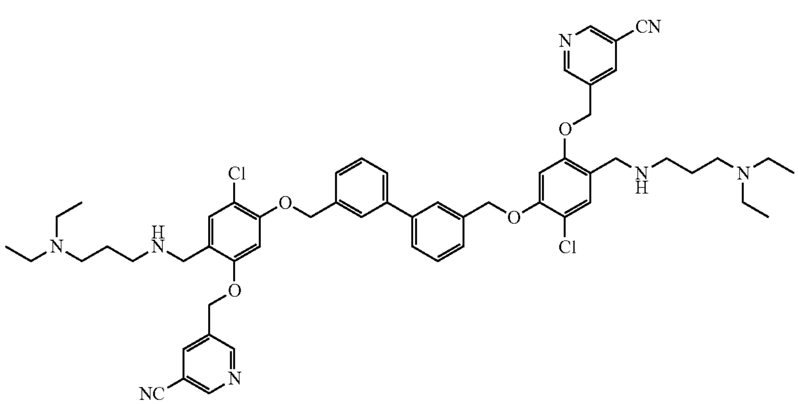 [SMILES: CCN(CC)CCCNCc1cc(Cl)c(OCc2cccc(-c3cccc(COc4cc(OCc5cncc(C#N)c5)c(CNCCCN(CC)CC)cc4Cl)c3)c2)cc1OCc1cncc(C#N)c1] | D | 1.47 | 983.5 | 983.3 |

TABLE 40000-continued

| Cmpd # | Structure | LC-MS Method | $R_f$ (min) | MS (M+H)+ Calcd. | MS (M+H)+ Observ. |
|---|---|---|---|---|---|
| 40090 | 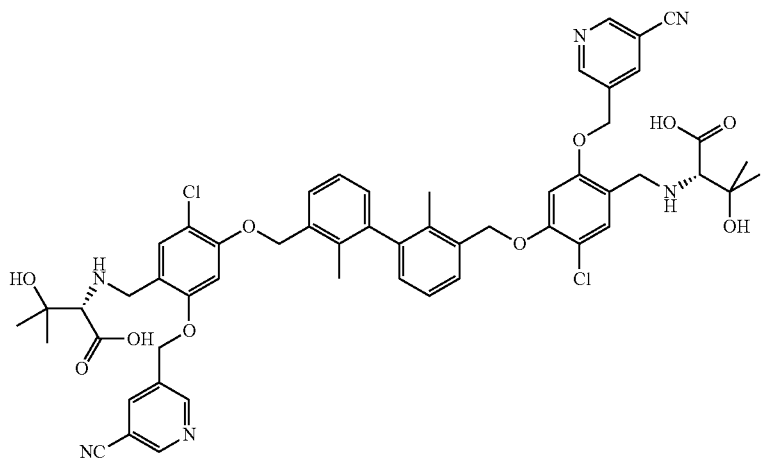 [SMILES: Cc1c(COc2cc(OCc3cncc(C#N)c3)c(CN[C@H](C(=O)O)C(C)(C)O)cc2Cl)cccc1-c1cccc(COc2cc(OCc3cncc(C#N)c3)c(CN[C@H](C(=O)O)C(C)(C)O)cc2Cl)c1C] | D | 1.64 | 1017.3 | 1017.2 |
| 40100 | 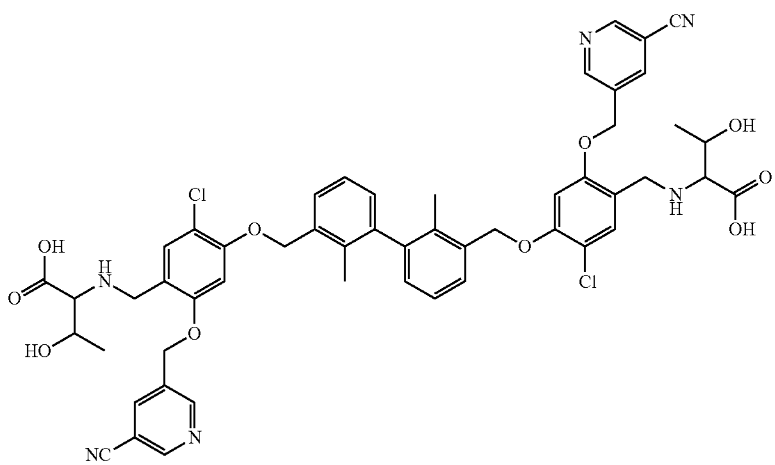 [SMILES: Cc1c(COc2cc(OCc3cncc(C#N)c3)c(CNC(C(=O)O)C(C)O)cc2Cl)cccc1-c1cccc(COc2cc(OCc3cncc(C#N)c3)c(CNC(C(=O)O)C(C)O)cc2Cl)c1C] | D | 1.62 | 989.3 | 989.2 |
| 40110 | 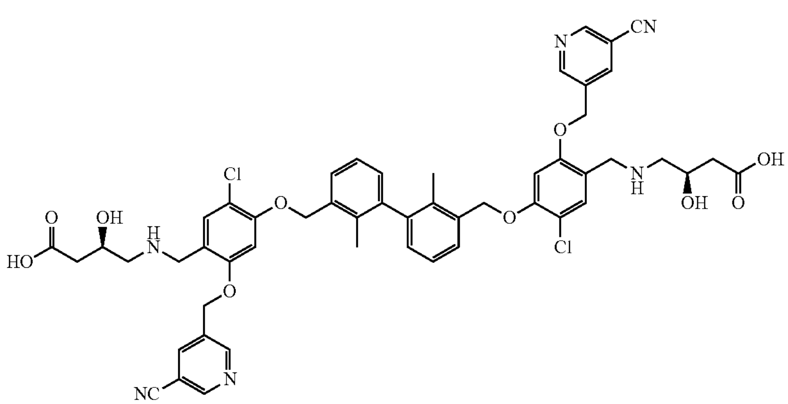 [SMILES: Cc1c(COc2cc(OCc3cncc(C#N)c3)c(CNC[C@H](O)CC(=O)O)cc2Cl)cccc1-c1cccc(COc2cc(OCc3cncc(C#N)c3)c(CNC[C@H](O)CC(=O)O)cc2Cl)c1C] | D | 1.60 | 989.3 | 989.2 |

TABLE 40000-continued

| Cmpd # | Structure | LC-MS Method | R_f (min) | MS (M+H)+ Calcd. | MS (M+H)+ Observ. |
|---|---|---|---|---|---|
| 40130 | 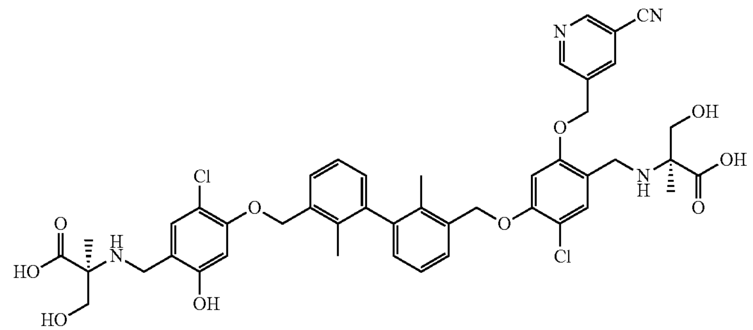 [SMILES: Cc1c(COc2cc(O)c(CN[C@@](C)(CO)C(=O)O)cc2Cl)cccc1-c1cccc(COc2cc(OCc3cncc(C#N)c3)c(CN[C@@](C)(CO)C(=O)O)cc2Cl)c1C] | D | 1.39 | 873.3 | 873.1 |
| 40140 | 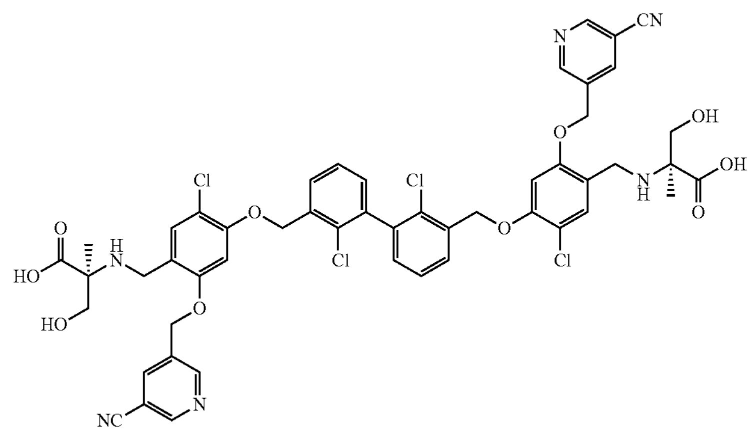 [SMILES: C[C@@](CO)(NCc1cc(Cl)c(OCc2cccc(-c3cccc(COc4cc(OCc5cncc(C#N)c5)c(CN[C@@](C)(CO)C(=O)O)cc4Cl)c3Cl)c2Cl)cc1OCc1cncc(C#N)c1)C(=O)O] | C | 1.60 | 1029.2 | 1029.1 |
| 40150 | 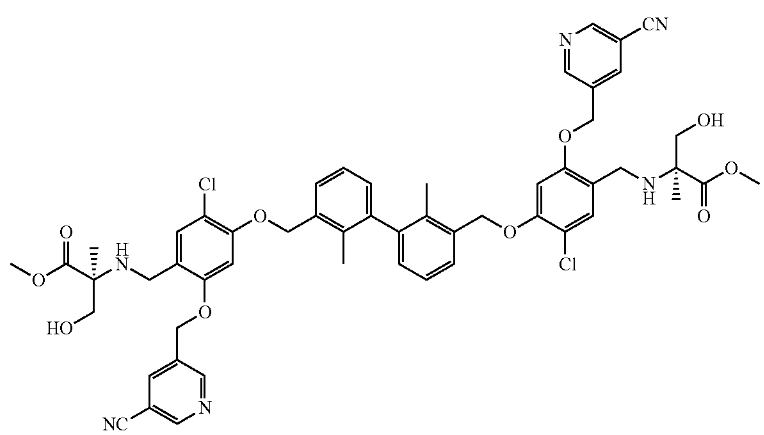 | C | 2.41 | 1017.3 | 1017.2 |
| 40160 | 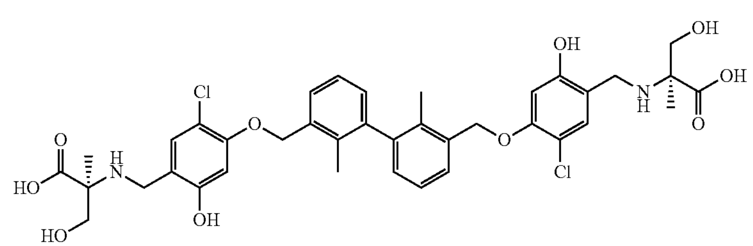 [SMILES: Cc1c(COc2cc(O)c(CN[C@@](C)(CO)C(=O)O)cc2Cl)cccc1-c1cccc(COc2cc(O)c(CN[C@@](C)(CO)C(=O)O)cc2Cl)c1C] | C | 1.48 | 757.2 | 757.2 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40170 | 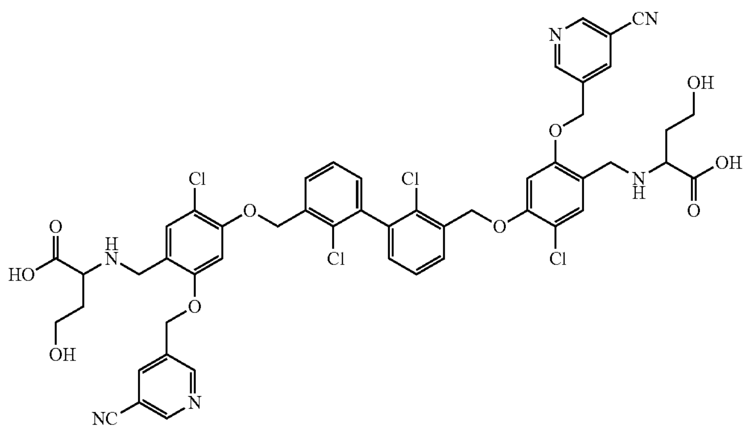 [SMILES: N#Cc1cncc(COc2cc(OCc3cccc(-c4cccc(COc5cc(OCc6cncc(C#N)c6)c(CNC(CCO)C(=O)O)cc5Cl)c4Cl)c3Cl)c(Cl)cc2CNC(CCO)C(=O)O)c1] | C | 1.60 | 1029.2 | 1029.2 |
| 40180 | 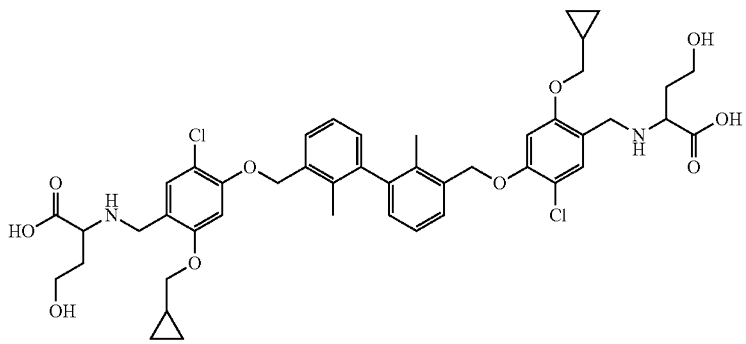 [SMILES: Cc1c(COc2cc(OCC3CC3)c(CNC(CCO)C(=O)O)cc2Cl)cccc1-c1cccc(COc2cc(OCC3CC3)c(CNC(CCO)C(=O)O)cc2Cl)c1C] | C | 1.79 | 865.3 | 865.3 |
| 40190 | 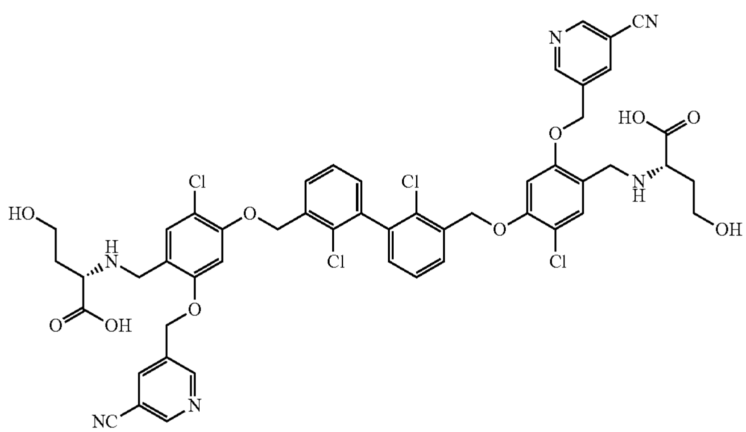 [SMILES: N#Cc1cncc(COc2cc(OCc3cccc(-c4cccc(COc5cc(OCc6cncc(C#N)c6)c(CN[C@@H](CCO)C(=O)O)cc5Cl)c4Cl)c3Cl)c(Cl)cc2CN[C@@H](CCO)C(=O)O)c1] | C | 1.64 | 1029.2 | 1029.1 |
| 40200 | 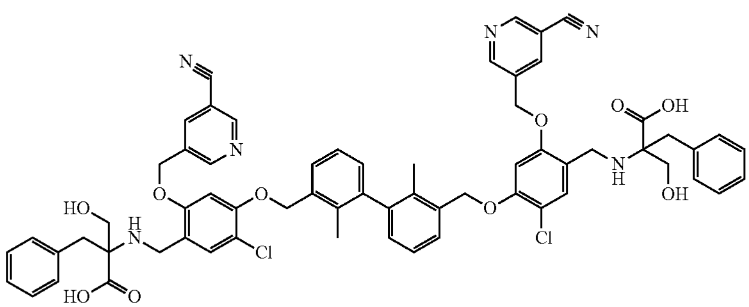 [SMILES: Cc1c(COc2cc(OCc3cncc(C#N)c3)c(CNC(CO)(Cc3ccccc3)C(=O)O)cc2Cl)cccc1-c1cccc(COc2cc(OCc3cncc(C#N)c3)c(CNC(CO)(Cc3ccccc3)C(=O)O)cc2Cl)c1C] | C | 1.84 | 1141.4 | 1141.1 |

TABLE 40000-continued

| Cmpd # | Structure | LC-MS Method | $R_f$ (min) | MS (M+H)+ Calcd. | MS (M+H)+ Observ. |
|---|---|---|---|---|---|
| 40210 | 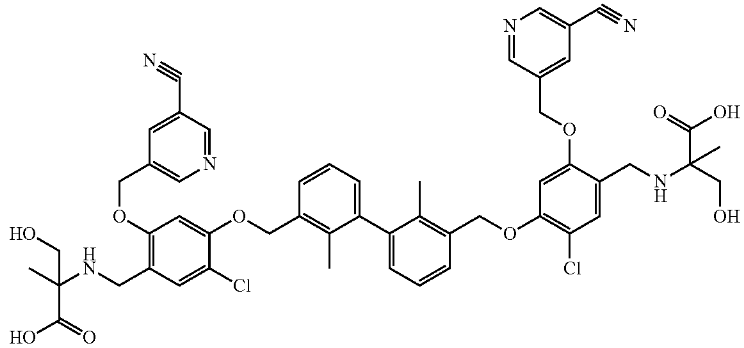 [SMILES: Cc1c(COc2cc(OCc3cncc(C#N)c3)c(CNC(C)(CO)C(=O)O)cc2Cl)cccc1-c1cccc(COc2cc(OCc3cncc(C#N)c3)c(CNC(C)(CO)C(=O)O)cc2Cl)c1C] | G | 3.52 | 989.3 | 989.3 |
| 40220 | 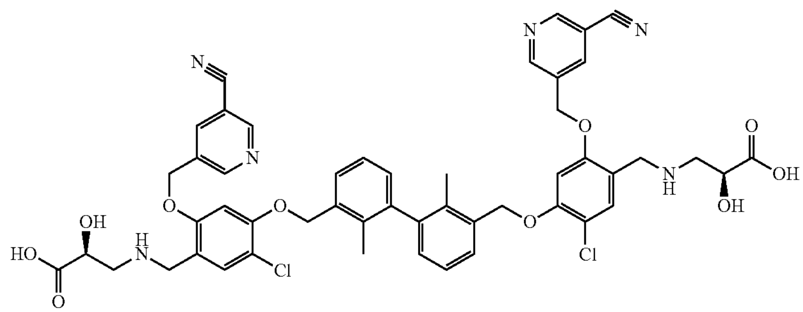 [SMILES: Cc1c(COc2cc(OCc3cncc(C#N)c3)c(CNC[C@H](O)C(=O)O)cc2Cl)cccc1-c1cccc(COc2cc(OCc3cncc(C#N)c3)c(CNC[C@H](O)C(=O)O)cc2Cl)c1C] | G | 3.42 | 961.3 | 961.4 |
| 40230 | 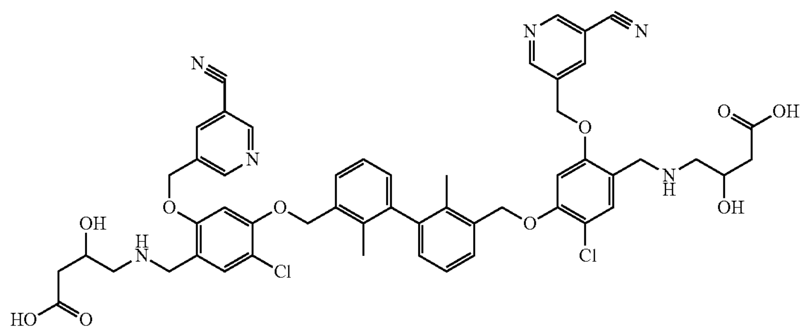 [SMILES: Cc1c(COc2cc(OCc3cncc(C#N)c3)c(CNCC(O)CC(=O)O)cc2Cl)cccc1-c1cccc(COc2cc(OCc3cncc(C#N)c3)c(CNCC(O)CC(=O)O)cc2Cl)c1C] | G | 3.23 | 989.3 | 989.4 |
| 40240 | 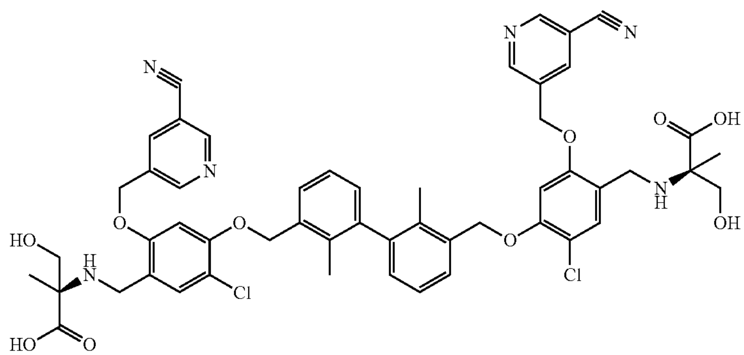 [SMILES: Cc1c(COc2cc(OCc3cncc(C#N)c3)c(CN[C@@](C)(CO)C(=O)O)cc2Cl)cccc1-c1cccc(COc2cc(OCc3cncc(C#N)c3)c(CN[C@@](C)(CO)C(=O)O)cc2Cl)c1C] | H | 2.80 | 989.3 | 989.5 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40250 | 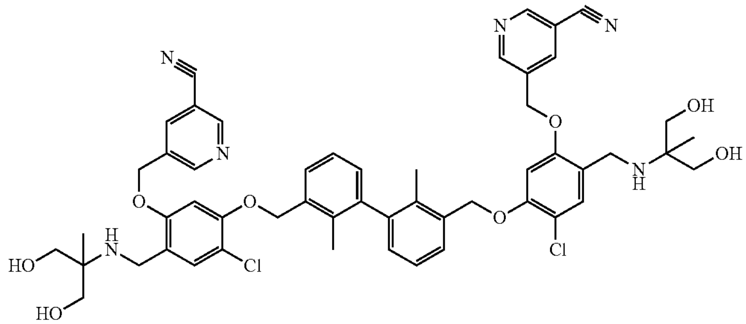 [SMILES: Cc1c(COc2cc(OCc3cncc(C#N)c3)c(CNC(C)(CO)CO)cc2Cl)cccc1-c1cccc(COc2cc(OCc3cncc(C#N)c3)c(CNC(C)(CO)CO)cc2Cl)c1C] | G | 3.24 | 961.3 | 961.4 |
| 40260 | 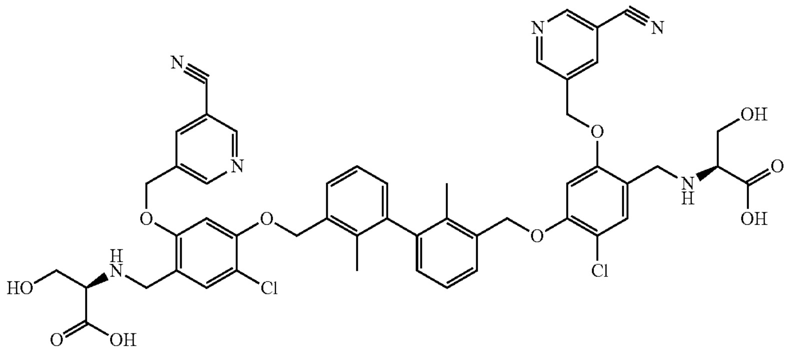 [SMILES: Cc1c(COc2cc(OCc3cncc(C#N)c3)c(CN[C@@H](CO)C(=O)O)cc2Cl)cccc1-c1cccc(COc2cc(OCc3cncc(C#N)c3)c(CN[C@H](CO)C(=O)O)cc2Cl)c1C] | G | 3.33 | 961.3 | 961.4 |
| 40270 | 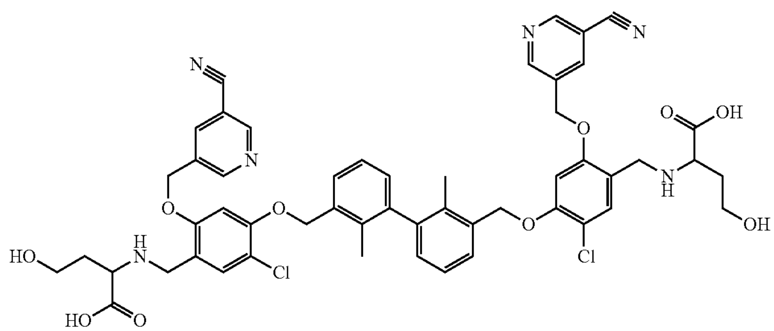 | G | 3.30 | 989.3 | 989.4 |
| 40280 | 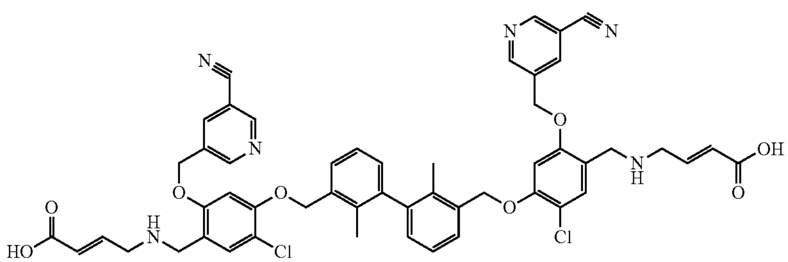 [SMILES: Cc1c(COc2cc(OCc3cncc(C#N)c3)c(CNC/C=C/C(=O)O)cc2Cl)cccc1-c1cccc(COc2cc(OCc3cncc(C#N)c3)c(CNC/C=C/C(=O)O)cc2Cl)c1C] | G | 4.08 | 953.3 | 953.4 |

TABLE 40000-continued

| Cmpd # | Structure | LC-MS Method | $R_f$ (min) | MS (M+H)+ Calcd. | MS (M+H)+ Observ. |
|---|---|---|---|---|---|
| 40300 | 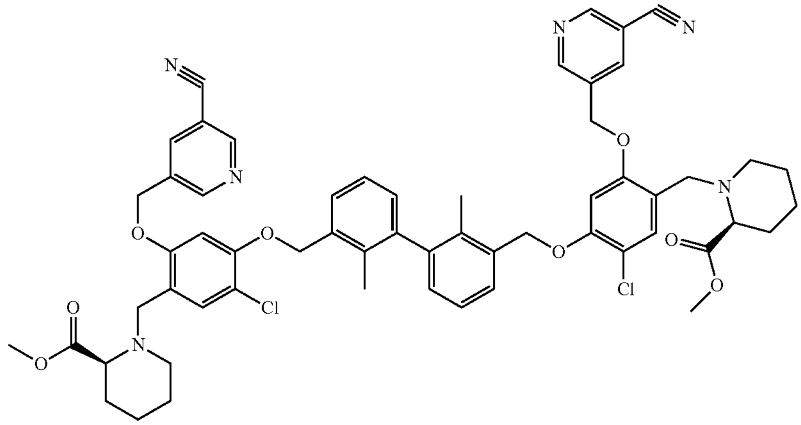 [SMILES: COC(=O)[C@@H]1CCCCN1Cc1cc(Cl)c(OCc2cccc(-c3cccc(COc4cc(OCc5cncc(C#N)c5)c(CN5CCCC[C@H]5C(=O)OC)cc4Cl)c3C)c2C)cc1OCc1cncc(C#N)c1] | I | 3.60 | 1037.4 | 1037.6 |
| 40310 | 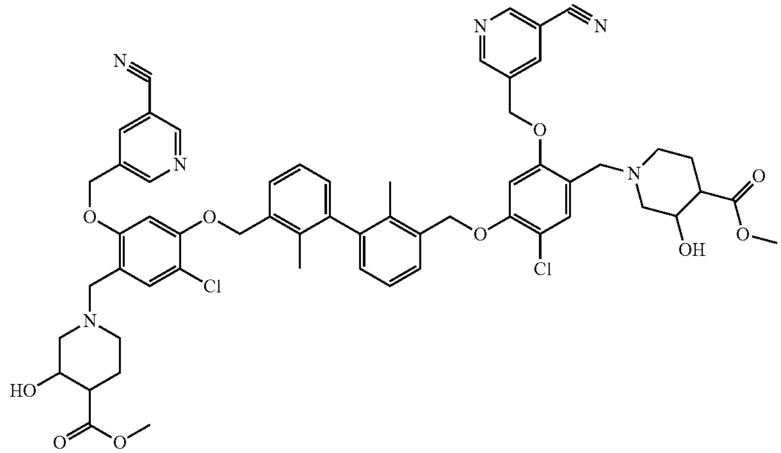 [SMILES: COC(=O)C1CCN(Cc2cc(Cl)c(OCc3cccc(-c4cccc(COc5cc(OCc6cncc(C#N)c6)c(CN6CCC(C(=O)OC)C(O)C6)cc5Cl)c4C)c3C)cc2OCc2cncc(C#N)c2)CC1O] | K | 3.60 | 1069.4 | 1069.4 |
| 40340 | 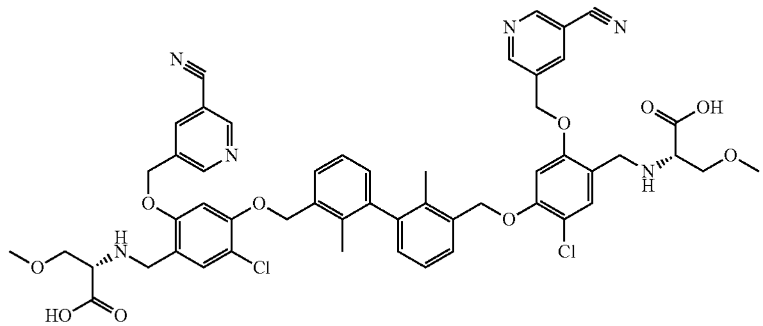 | H | 3.33 | 989.3 | 989.4 |
| 40350 | 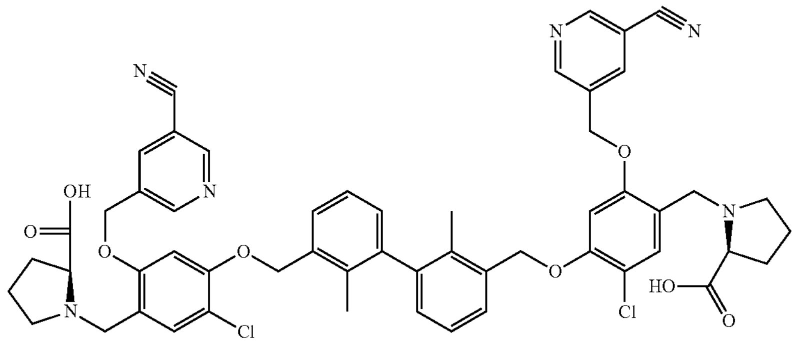 [SMILES: Cc1c(COc2cc(OCc3cncc(C#N)c3)c(CN3CCC[C@H]3C(=O)O)cc2Cl)cccc1-c1cccc(COc2cc(OCc3cncc(C#N)c3)c(CN3CCC[C@H]3C(=O)O)cc2Cl)c1C] | H | 3.19 | 981.3 | 981.4 |

TABLE 40000-continued
| Cmpd # | Structure | LC-MS Method | $R_f$ (min) | MS (M + H)+ Calcd. | MS (M + H)+ Observ. |
|---|---|---|---|---|---|
| 40360 | 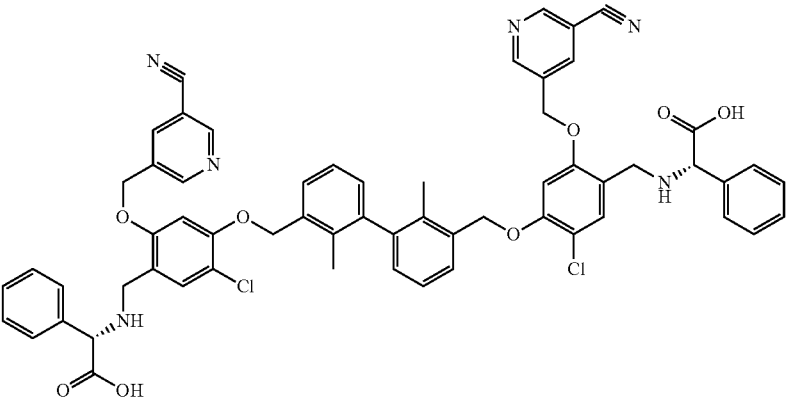 [SMILES: Cc1c(COc2cc(OCc3cncc(C#N)c3)c(CN[C@H](C(=O)O)c3ccccc3)cc2Cl)cccc1-c1cccc(COc2cc(OCc3cncc(C#N)c3)c(CN[C@H](C(=O)O)c3ccccc3)cc2Cl)c1C] | J | 2.46 | 1053.3 | 1053.5 |
| 40370 | 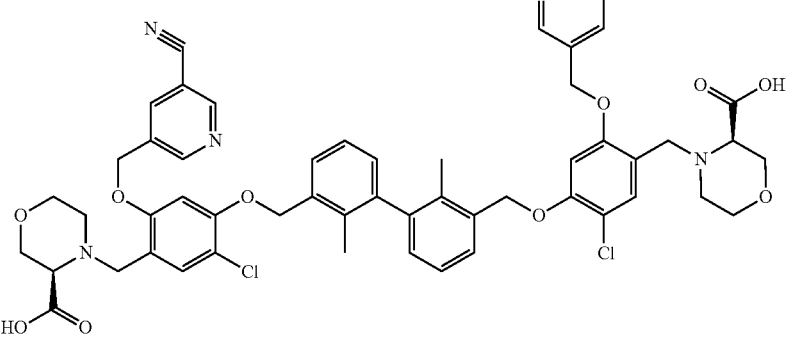 | J | 2.11 | 1013.3 | 1013.4 |
| 40380 | 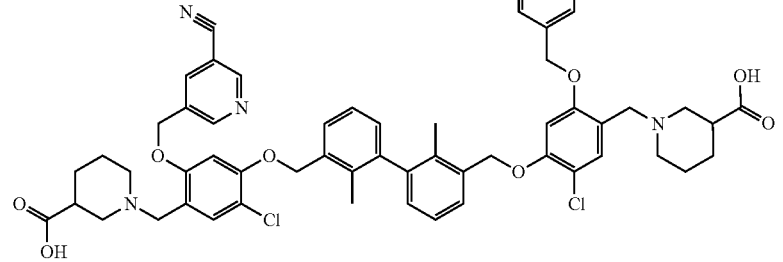 | G | 3.51 | 1009.3 | 1009.5 |
| 40390 | 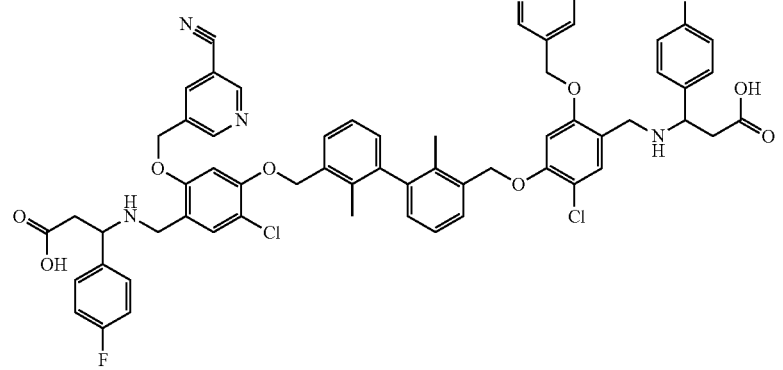 | G | 3.87 | 1117.3 | 1117.5 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40400 | 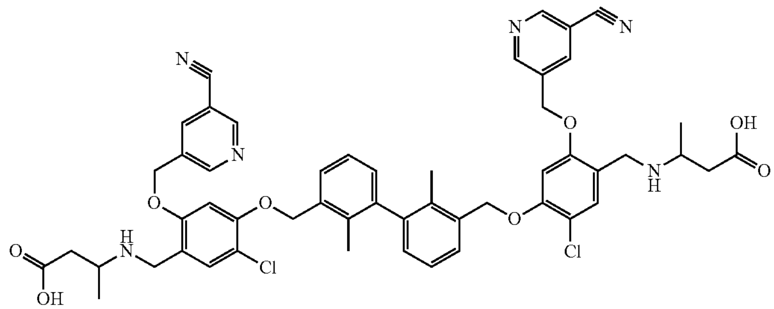 [SMILES: Cc1c(COc2cc(OCc3cncc(C#N)c3)c(CNC(C)CC(=O)O)cc2Cl)cccc1-c1cccc(COc2cc(OCc3cncc(C#N)c3)c(CNC(C)CC(=O)O)cc2Cl)c1C] | G | 3.53 | 957.3 | 957.5 |
| 40410 | 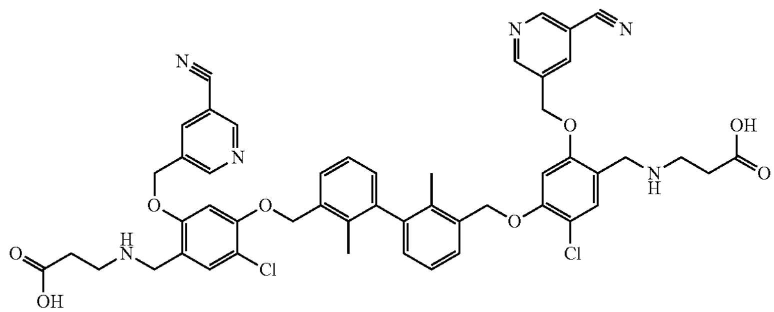 [SMILES: Cc1c(COc2cc(OCc3cncc(C#N)c3)c(CNCCC(=O)O)cc2Cl)cccc1-c1cccc(COc2cc(OCc3cncc(C#N)c3)c(CNCCC(=O)O)cc2Cl)c1C] | G | 3.51 | 929.3 | 929.4 |
| 40420 | 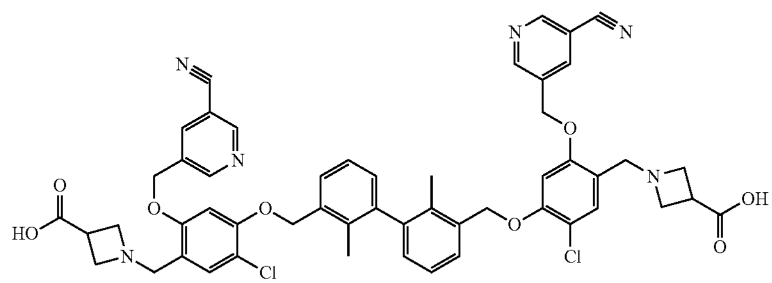 [SMILES: Cc1c(COc2cc(OCc3cncc(C#N)c3)c(CN3CC(C(=O)O)C3)cc2Cl)cccc1-c1cccc(COc2cc(OCc3cncc(C#N)c3)c(CN3CC(C(=O)O)C3)cc2Cl)c1C] | J | 2.10 | 953.3 | 953.4 |
| 40430 | 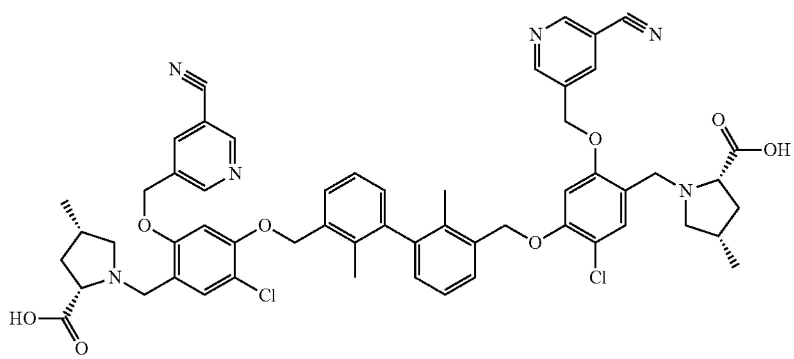 [SMILES: Cc1c(COc2cc(OCc3cncc(C#N)c3)c(CN3C[C@@H](C)C[C@H]3C(=O)O)cc2Cl)cccc1-c1cccc(COc2cc(OCc3cncc(C#N)c3)c(CN3C[C@@H](C)C[C@H]3C(=O)O)cc2Cl)c1C] | G | 3.66 | 1009.3 | 1009.5 |

TABLE 40000-continued

| Cmpd # | Structure | LC-MS Method | $R_f$ (min) | MS (M+H)+ Calcd. | MS (M+H)+ Observ. |
|---|---|---|---|---|---|
| 40440 | 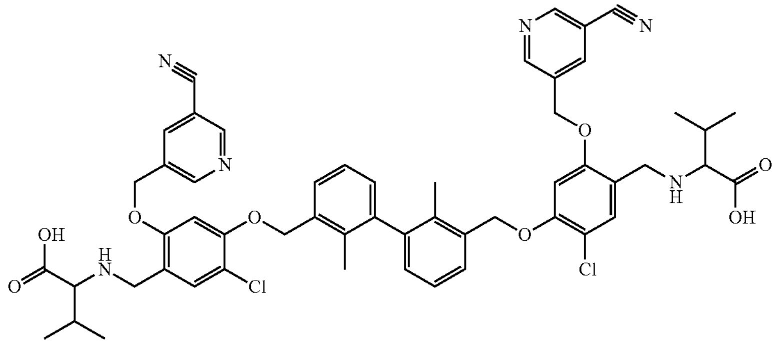 [SMILES: Cc1c(COc2cc(OCc3cncc(C#N)c3)c(CNC(C(=O)O)C(C)C)cc2Cl)cccc1-c1cccc(COc2cc(OCc3cncc(C#N)c3)c(CNC(C(=O)O)C(C)C)cc2Cl)c1C] | G | 3.68 | 985.3 | 985.5 |
| 40450 | 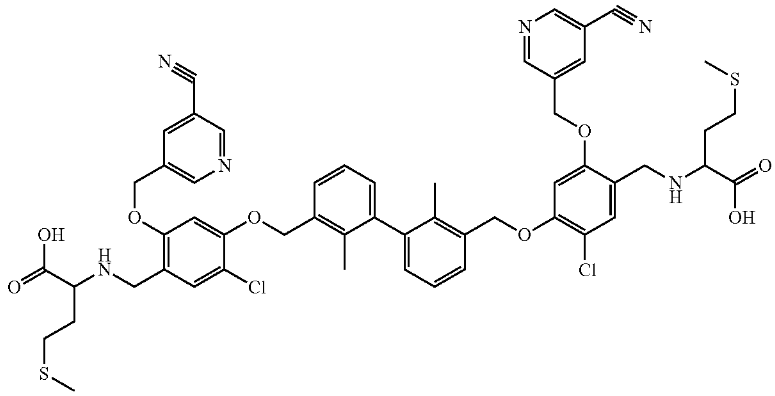 [SMILES: CSCCC(NCc1cc(Cl)c(OCc2cccc(-c3cccc(COc4cc(OCc5cncc(C#N)c5)c(CNC(CCSC)C(=O)O)cc4Cl)c3C)c2C)cc1OCc1cncc(C#N)c1)C(=O)O] | J | 2.28 | 1049.3 | 1049.4 |
| 40460 | 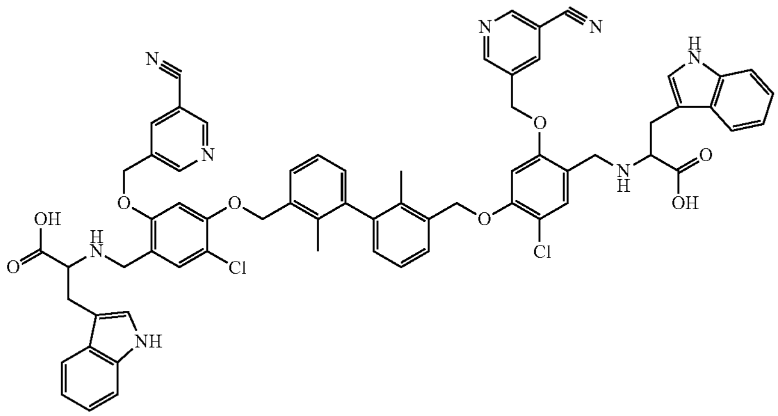 [SMILES: Cc1c(COc2cc(OCc3cncc(C#N)c3)c(CNC(Cc3c[nH]c4ccccc34)C(=O)O)cc2Cl)cccc1-c1cccc(COc2cc(OCc3cncc(C#N)c3)c(CNC(Cc3c[nH]c4ccccc34)C(=O)O)cc2Cl)c1C] | G | 3.91 | 1159.4 | 1159.6 |
| 40470 | 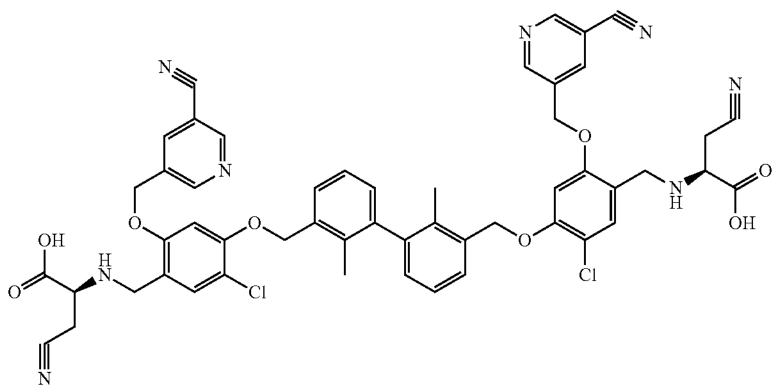 [SMILES: Cc1c(COc2cc(OCc3cncc(C#N)c3)c(CN[C@@H](CC#N)C(=O)O)cc2Cl)cccc1-c1cccc(COc2cc(OCc3cncc(C#N)c3)c(CN[C@@H](CC#N)C(=O)O)cc2Cl)c1C] | G | 3.72 | 979.3 | 979.4 |

TABLE 40000-continued

| Cmpd # | Structure | LC-MS Method | R$_f$ (min) | MS (M + H)$^+$ Calcd. | MS (M + H)$^+$ Observ. |
|---|---|---|---|---|---|
| 40480 | 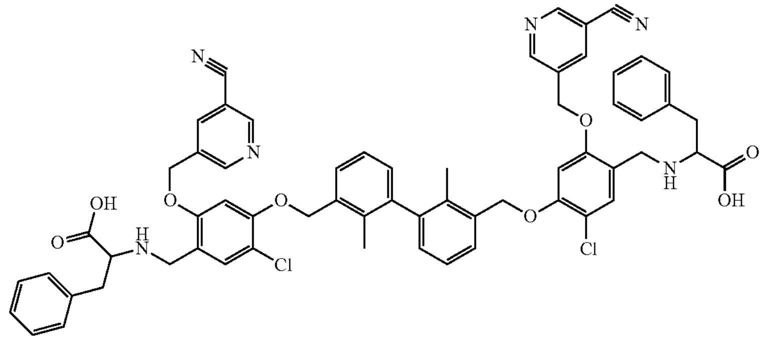 [SMILES: Cc1c(COc2cc(OCc3cncc(C#N)c3)c(CNC(Cc3ccccc3)C(=O)O)cc2Cl)cccc1-c1cccc(COc2cc(OCc3cncc(C#N)c3)c(CNC(Cc3ccccc3)C(=O)O)cc2Cl)c1C] | G | 3.86 | 1081.3 | 1081.5 |
| 40490 | 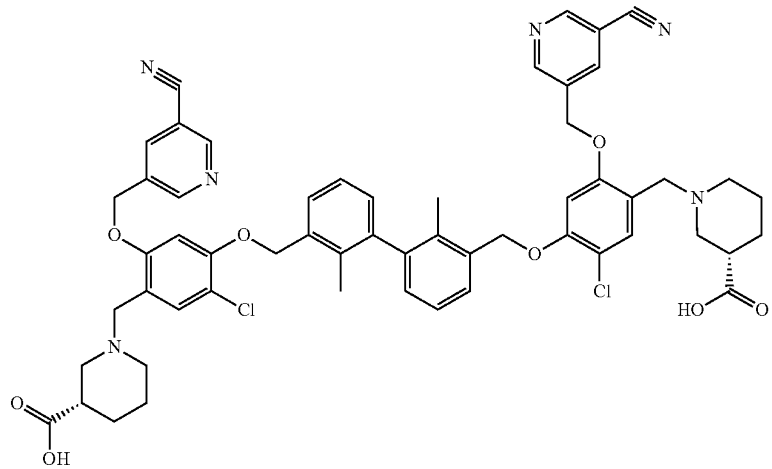 [SMILES: Cc1c(COc2cc(OCc3cncc(C#N)c3)c(CN3CCC[C@H](C(=O)O)C3)cc2Cl)cccc1-c1cccc(COc2cc(OCc3cncc(C#N)c3)c(CN3CCC[C@H](C(=O)O)C3)cc2Cl)c1C] | C | 1.73 | 1009.3 | 1009.1 |
| 40500 | 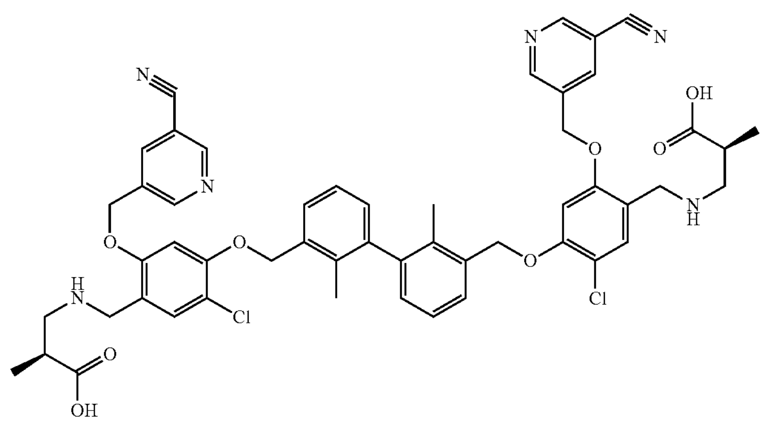 [SMILES: Cc1c(COc2cc(OCc3cncc(C#N)c3)c(CNC[C@H](C)C(=O)O)cc2Cl)cccc1-c1cccc(COc2cc(OCc3cncc(C#N)c3)c(CNC[C@H](C)C(=O)O)cc2Cl)c1C] | G | 3.52 | 957.3 | 957.5 |

TABLE 40000-continued

| Cmpd # | Structure | LC-MS Method | R$_f$ (min) | MS (M + H)$^+$ Calcd. | MS (M + H)$^+$ Observ. |
|---|---|---|---|---|---|
| 40510 | 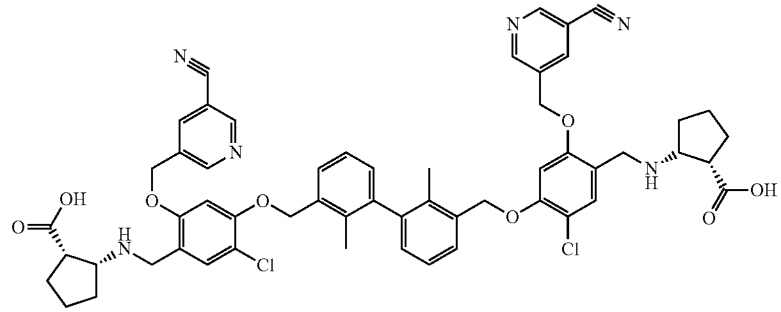 | G | 3.58 | 1009.3 | 1009.5 |
| 40520 | 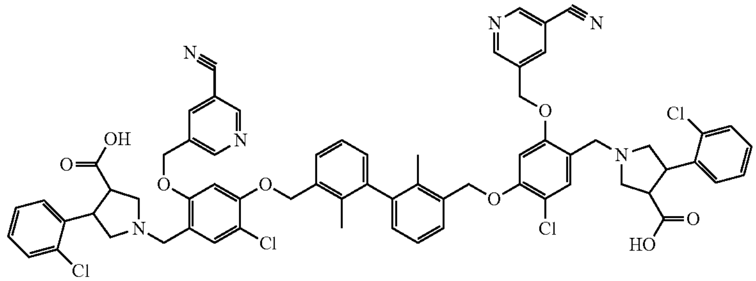 [SMILES: Cc1c(COc2cc(OCc3cncc(C#N)c3)c(CN3CC(C(=O)O)C(c4ccccc4Cl)C3)cc2Cl)cccc1-c1cccc(COc2cc(OCc3cncc(C#N)c3)c(CN3CC(C(=O)O)C(c4ccccc4Cl)C3)cc2Cl)c1C] | J | 2.76 | 1201.3 | 1201.5 |
| 40530 | 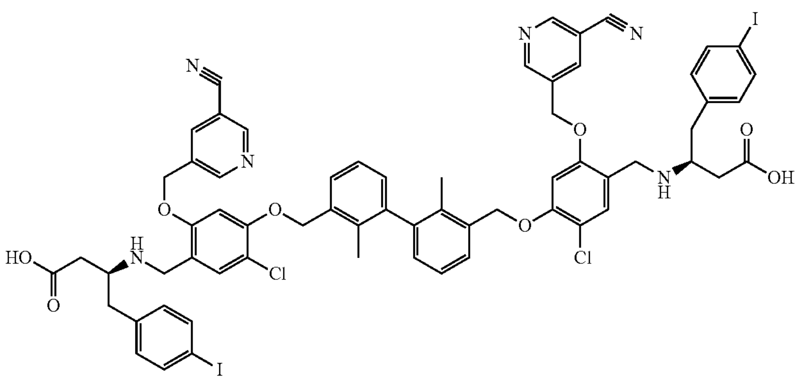 [SMILES: Cc1c(COc2cc(OCc3cncc(C#N)c3)c(CN[C@H](CC(=O)O)Cc3ccc(I)cc3)cc2Cl)cccc1-c1cccc(COc2cc(OCc3cncc(C#N)c3)c(CN[C@H](CC(=O)O)Cc3ccc(I)cc3)cc2Cl)c1C] | G | 4.11 | 1361.2 | 1361.5 |
| 40550 | 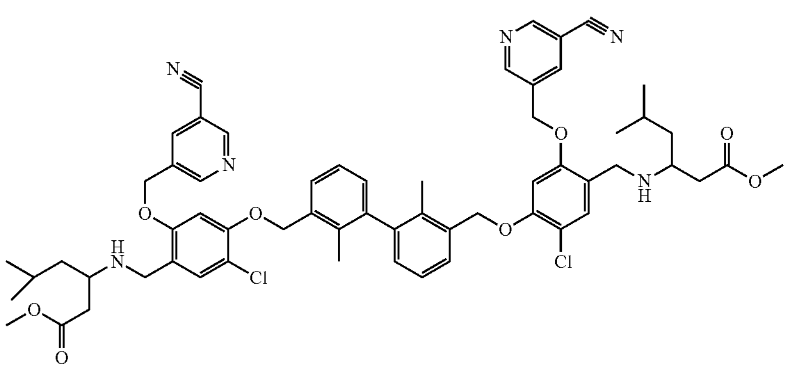 [SMILES: COC(=O)CC(CC(C)C)NCc1cc(Cl)c(OCc2cccc(-c3cccc(COc4cc(OCc5cncc(C#N)c5)c(CNC(CC(=O)OC)CC(C)C)cc4Cl)c3C)c2C)cc1OCc1cncc(C#N)c1] | G | 3.95 | 1069.4 | 1069.6 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40590 | 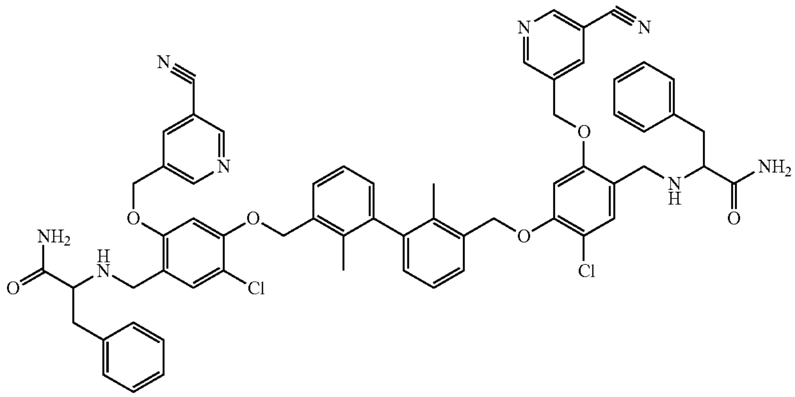 [SMILES: Cc1c(COc2cc(OCc3cncc(C#N)c3)c(CNC(Cc3ccccc3)C(N)=O)cc2Cl)cccc1-c1cccc(COc2cc(OCc3cncc(C#N)c3)c(CNC(Cc3ccccc3)C(N)=O)cc2Cl)c1C] | J | 3.51 | 1079.4 | 1079.5 |
| 40620 | 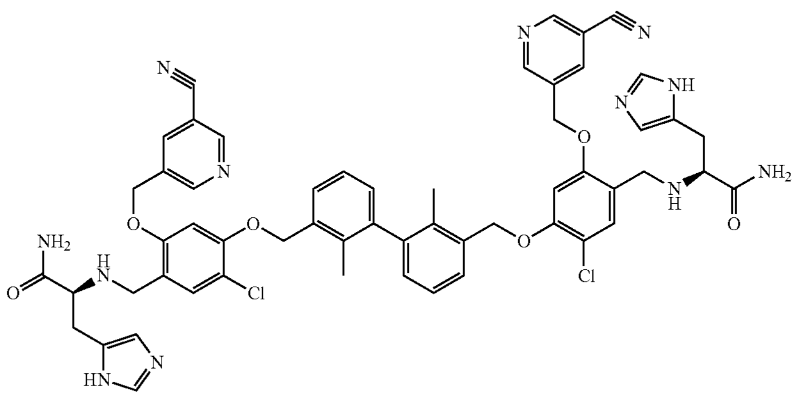 [SMILES: Cc1c(COc2cc(OCc3cncc(C#N)c3)c(CN[C@@H](Cc3cnc[nH]3)C(N)=O)cc2Cl)cccc1-c1cccc(COc2cc(OCc3cncc(C#N)c3)c(CN[C@@H](Cc3cnc[nH]3)C(N)=O)cc2Cl)c1C] | G | 3.12 | 1059.4 | 1059.5 |
| 40670 | 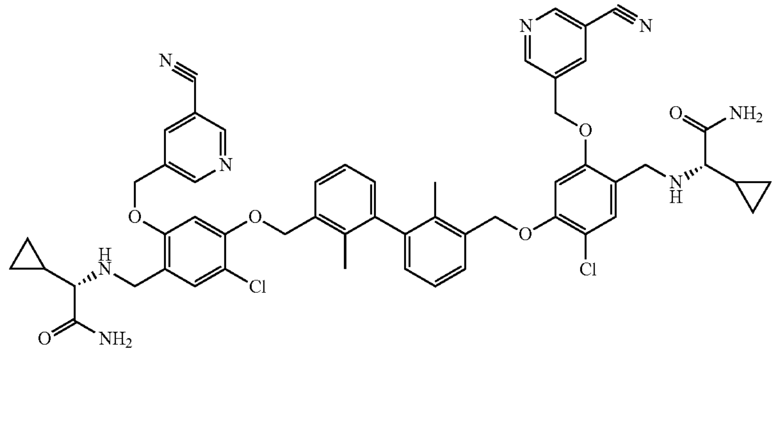 [SMILES: Cc1c(COc2cc(OCc3cncc(C#N)c3)c(CN[C@H](C(N)=O)C3CC3)cc2Cl)cccc1-c1cccc(COc2cc(OCc3cncc(C#N)c3)c(CN[C@H](C(N)=O)C3CC3)cc2Cl)c1C] | G | 3.41 | 979.3 | 979.5 |

TABLE 40000-continued
| Cmpd # | Structure | LC-MS Method | $R_f$ (min) | MS (M + H)+ Calcd. | MS (M + H)+ Observ. |
|---|---|---|---|---|---|
| 40680 | 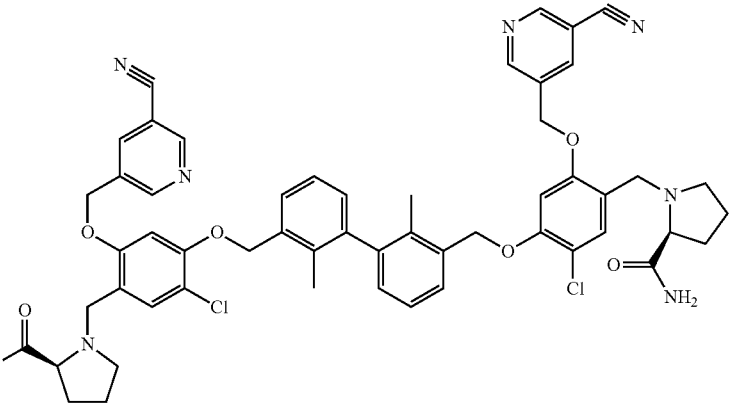 | G | 3.35 | 979.3 | 979.5 |
| 40690 | 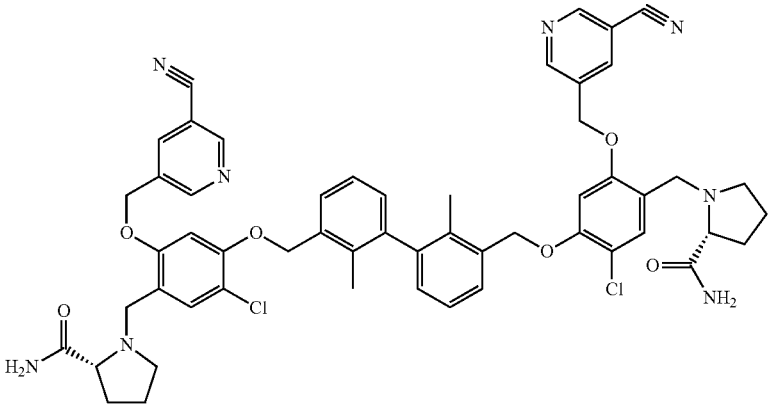 [SMILES: Cc1c(COc2cc(OCc3cncc(C#N)c3)c(CN3CCC[C@@H]3C(N)=O)cc2Cl)cccc1-c1cccc(COc2cc(OCc3cncc(C#N)c3)c(CN3CCC[C@@H]3C(N)=O)cc2Cl)c1C] | G | 3.36 | 979.3 | 979.5 |
| 40700 | 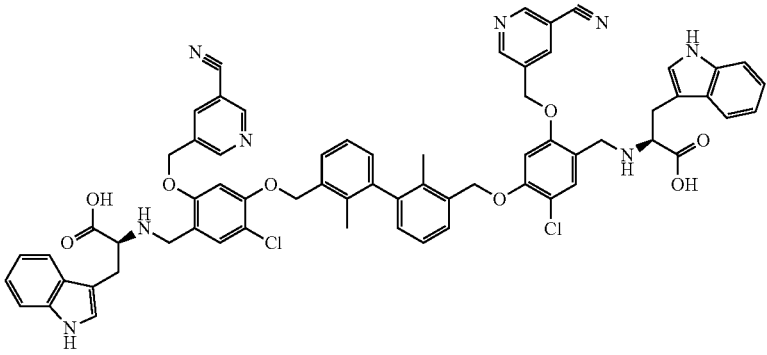 [SMILES: Cc1c(COc2cc(OCc3cncc(C#N)c3)c(CN[C@@H](Cc3c[nH]c4ccccc34)C(=O)O)cc2Cl)cccc1-c1cccc(COc2cc(OCc3cncc(C#N)c3)c(CN[C@@H](Cc3c[nH]c4ccccc34)C(=O)O)cc2Cl)c1C] | C | 1.85 | 1159.4 | 1159.1 |
| 40710 | 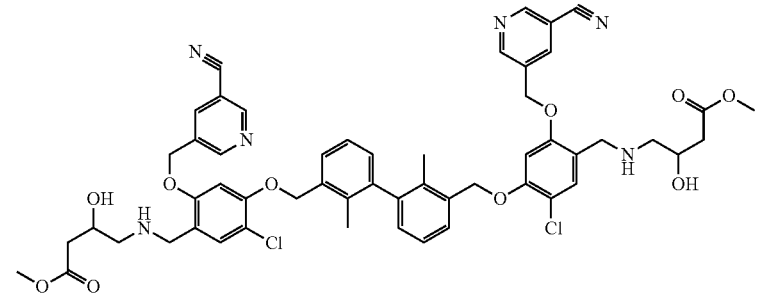 | G | 3.19 | 1017.3 | 1017.5 |

TABLE 40000-continued

| Cmpd # | Structure | LC-MS Method | $R_f$ (min) | MS (M+H)$^+$ Calcd. | MS (M+H)$^+$ Observ. |
|---|---|---|---|---|---|
| 40720 | 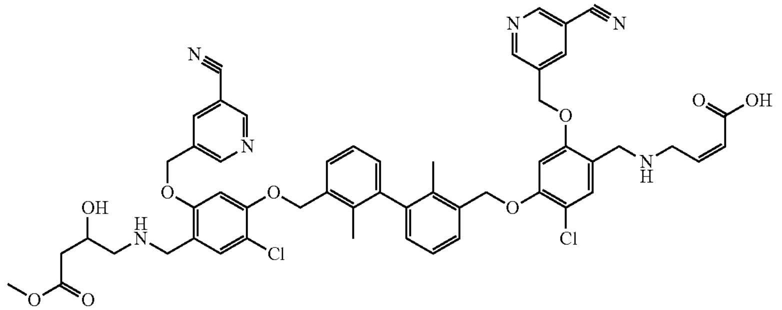 [SMILES: COC(=O)CC(O)CNCc1cc(Cl)c(OCc2cccc(-c3cccc(COc4cc(OCc5cncc(C#N)c5)c(CNC/C=C\C(=O)O)cc4Cl)c3C)c2C)cc1OCc1cncc(C#N)c1] | G | 3.52 | 985.3 | 985.5 |
| 40730 | 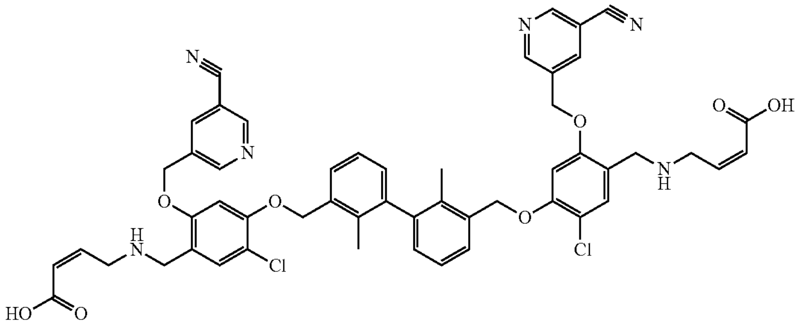 [SMILES: Cc1c(COc2cc(OCc3cncc(C#N)c3)c(CNC/C=C\C(=O)O)cc2Cl)cccc1-c1cccc(COc2cc(OCc3cncc(C#N)c3)c(CNC/C=C\C(=O)O)cc2Cl)c1C] | G | 3.92 | 953.3 | 953.4 |
| 40740 | 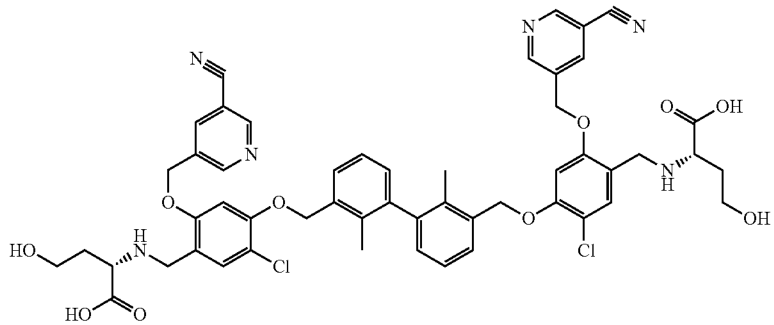 [SMILES: Cc1c(COc2cc(OCc3cncc(C#N)c3)c(CN[C@@H](CCO)C(=O)O)cc2Cl)cccc1-c1cccc(COc2cc(OCc3cncc(C#N)c3)c(CN[C@@H](CCO)C(=O)O)cc2Cl)c1C] | J | 1.98 | 989.3 | 989.4 |
| 40750 | 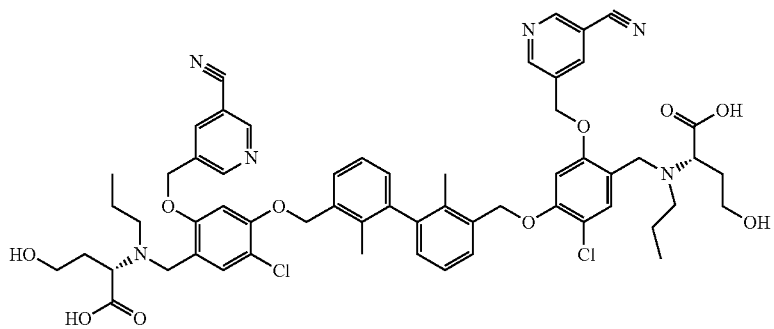 [SMILES: CCCN(Cc1cc(Cl)c(OCc2cccc(-c3cccc(COc4cc(OCc5cncc(C#N)c5)c(CN(CCC)[C@@H](CCO)C(=O)O)cc4Cl)c3C)c2C)cc1OCc1cncc(C#N)c1)[C@@H](CCO)C(=O)O] | J | 2.12 | 1073.4 | 1073.6 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40760 | 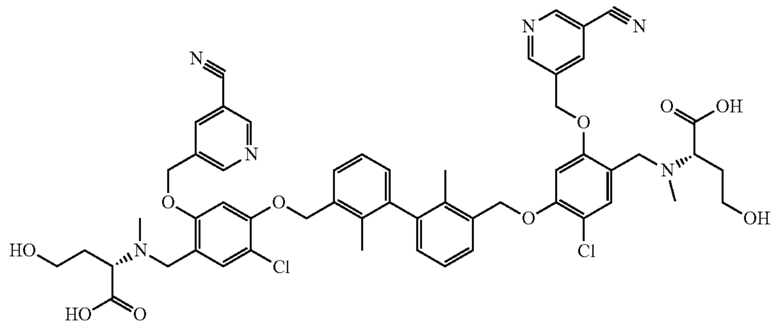 | G | 3.21 | 1017.3 | 1017.4 |
| 40770 | 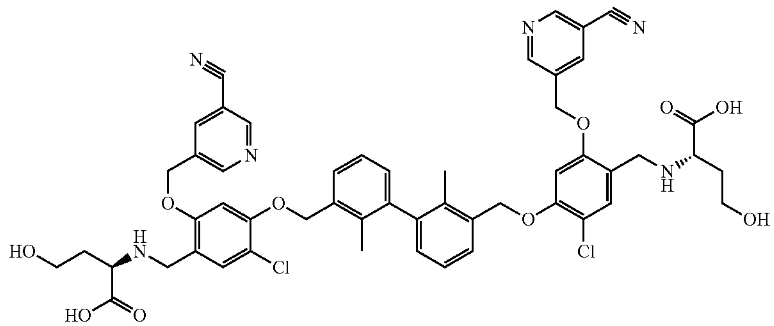 [SMILES: Cc1c(COc2cc(OCc3cncc(C#N)c3)c(CN[C@@H](CCO)C(=O)O)cc2Cl)cccc1-c1cccc(COc2cc(OCc3cncc(C#N)c3)c(CN[C@H](CCO)C(=O)O)cc2Cl)c1C] | G | 3.58 | 989.3 | 989.4 |
| 40780 | 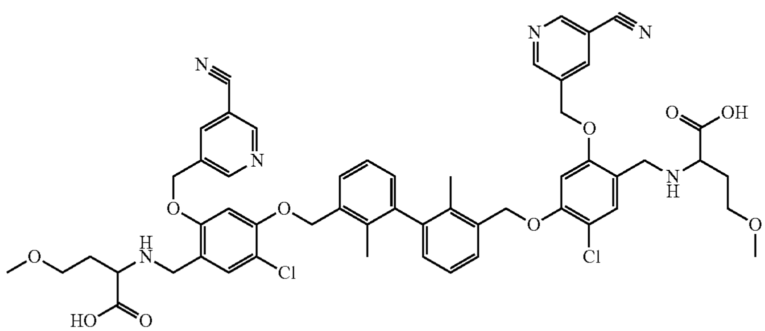 | C | 1.77 | 1017.3 | 1017.2 |
| 40800 | 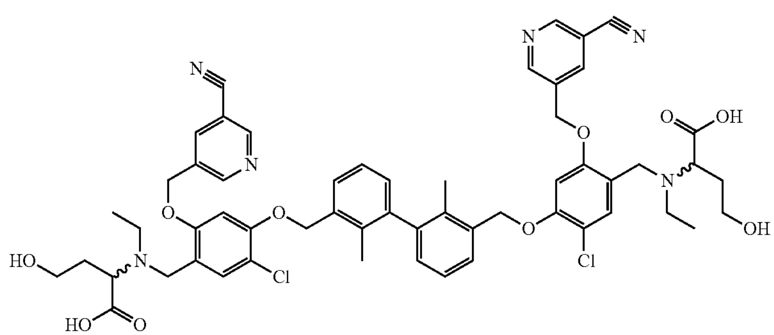 [SMILES: CCN(Cc1cc(Cl)c(OCc2cccc(-c3cccc(COc4cc(OCc5cncc(C#N)c5)c(CN(CC)C(CCO)C(=O)O)cc4Cl)c3C)c2C)cc1OCc1cncc(C#N)c1)C(CCO)C(=O)O] | J | 1.92 | 1045.4 | 1045.4 |

TABLE 40000-continued

| Cmpd # | Structure | LC-MS Method | $R_f$ (min) | MS (M + H)+ Calcd. | MS (M + H)+ Observ. |
|---|---|---|---|---|---|
| 40810 | 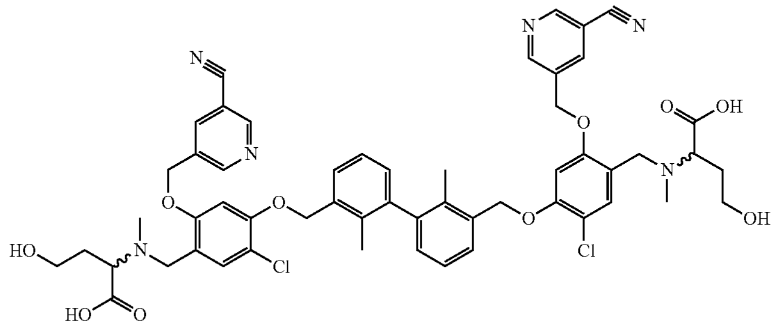 [SMILES: Cc1c(COc2cc(OCc3cncc(C#N)c3)c(CN(C)C(CCO)C(=O)O)cc2Cl)cccc1-c1cccc(COc2cc(OCc3cncc(C#N)c3)c(CN(C)C(CCO)C(=O)O)cc2Cl)c1C] | J | 1.83 | 1017.3 | 1017.3 |
| 40820 | 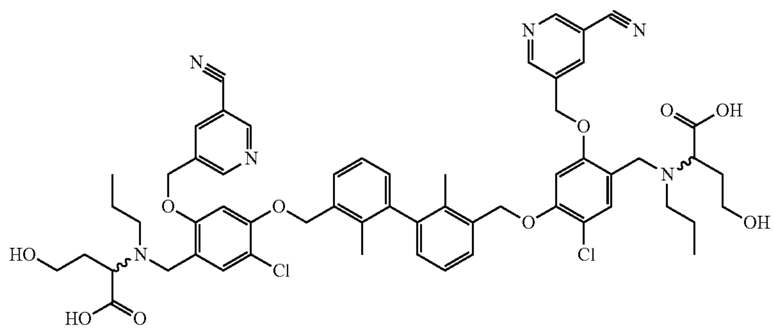 [SMILES: CCCN(Cc1cc(Cl)c(OCc2cccc(-c3cccc(COc4cc(OCc5cncc(C#N)c5)c(CN(CCC)C(CCO)C(=O)O)cc4Cl)c3C)c2C)cc1OCc1cncc(C#N)c1)C(CCO)C(=O)O] | J | 2.05 | 1073.4 | 1073.3 |
| 40830 | 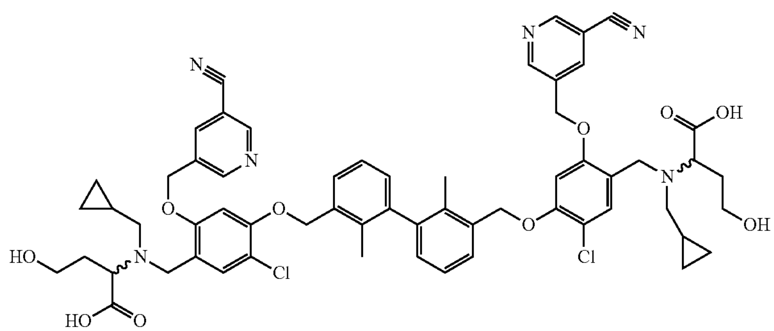 [SMILES: Cc1c(COc2cc(OCc3cncc(C#N)c3)c(CN(CC3CC3)C(CCO)C(=O)O)cc2Cl)cccc1-c1cccc(COc2cc(OCc3cncc(C#N)c3)c(CN(CC3CC3)C(CCO)C(=O)O)cc2Cl)c1C] | K | 2.66 | 1097.4 | 1097.2 |
| 40840 | 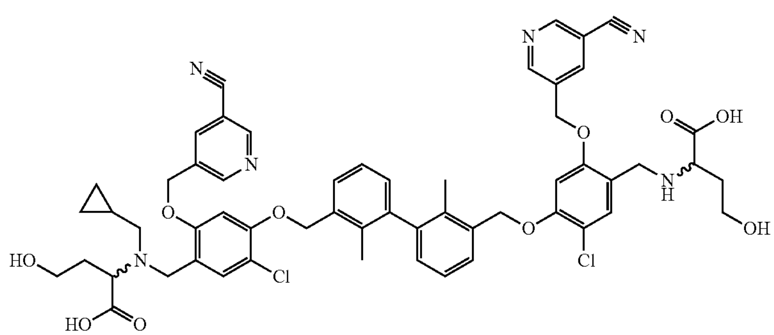 [SMILES: Cc1c(COc2cc(OCc3cncc(C#N)c3)c(CNC(CCO)C(=O)O)cc2Cl)cccc1-c1cccc(COc2cc(OCc3cncc(C#N)c3)c(CN(CC3CC3)C(CCO)C(=O)O)cc2Cl)c1C] | J | 1.92 | 1043.3 | 1043.2 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40850 | 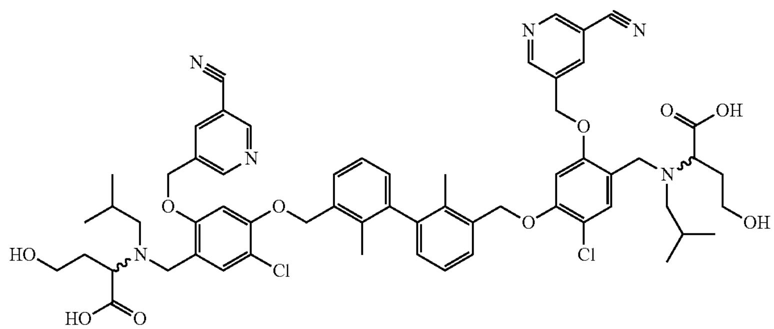 [SMILES: Cc1c(COc2cc(OCc3cncc(C#N)c3)c(CN(CC(C)C)C(CCO)C(=O)O)cc2Cl)cccc1-c1cccc(COc2cc(OCc3cncc(C#N)c3)c(CN(CC(C)C)C(CCO)C(=O)O)cc2Cl)c1C] | J | 2.49 | 1101.4 | 1101.3 |
| 40870 | 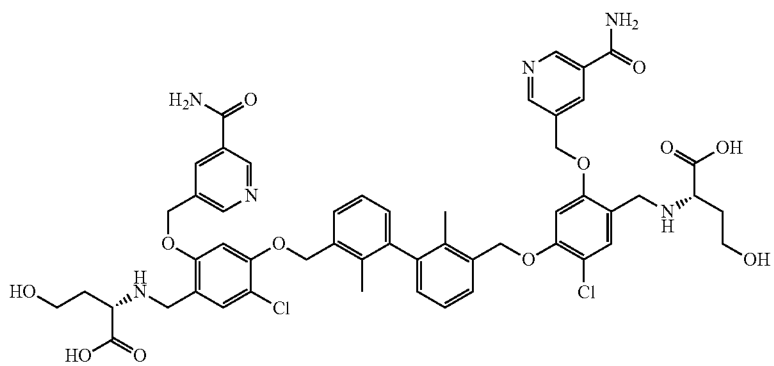 [SMILES: Cc1c(COc2cc(OCc3cncc(C(N)=O)c3)c(CN[C@@H](CCO)C(=O)O)cc2Cl)cccc1-c1cccc(COc2cc(OCc3cncc(C(N)=O)c3)c(CN[C@@H](CCO)C(=O)O)cc2Cl)c1C] | J | 1.75 | 1025.3 | 1025.0 |
| 40880 | 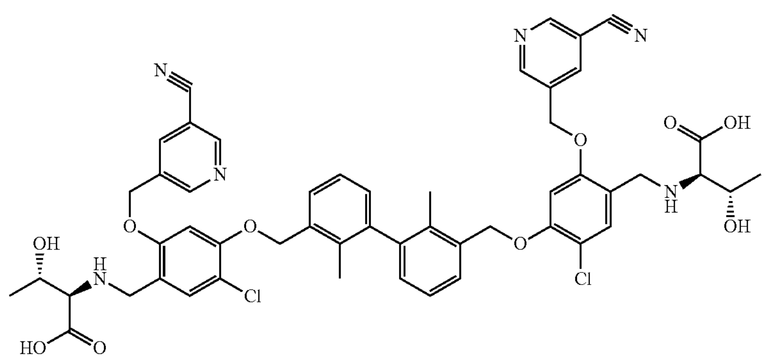 [SMILES: Cc1c(COc2cc(OCc3cncc(C#N)c3)c(CN[C@@H](C(=O)O)[C@H](C)O)cc2Cl)cccc1-c1cccc(COc2cc(OCc3cncc(C#N)c3)c(CN[C@@H](C(=O)O)[C@H](C)O)cc2Cl)c1C] | J | 2.07 | 989.3 | 989.3 |
| 40890 | 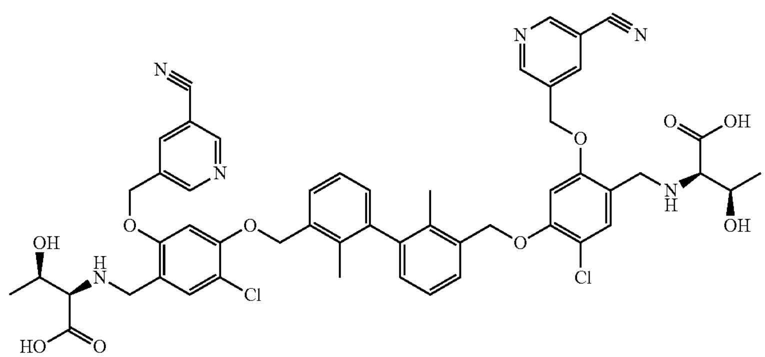 [SMILES: Cc1c(COc2cc(OCc3cncc(C#N)c3)c(CN[C@@H](C(=O)O)[C@@H](C)O)cc2Cl)cccc1-c1cccc(COc2cc(OCc3cncc(C#N)c3)c(CN[C@@H](C(=O)O)[C@@H](C)O)cc2Cl)c1C] | J | 2.06 | 989.3 | 989.1 |

TABLE 40000-continued

| Cmpd # | Structure | LC-MS Method | $R_f$ (min) | MS (M + H)$^+$ Calcd. | MS (M + H)$^+$ Observ. |
|---|---|---|---|---|---|
| 40900 | 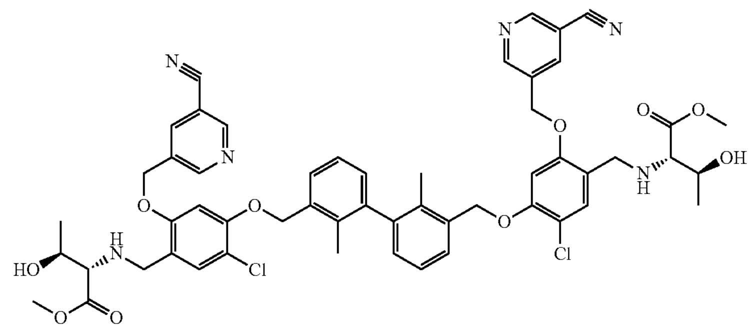 [SMILES: COC(=O)[C@@H](NCc1cc(Cl)c(OCc2cccc(-c3cccc(COc4cc(OCc5cncc(C#N)c5)c(CN[C@H](C(=O)OC)[C@H](C)O)cc4Cl)c3C)c2C)cc1OCc1cncc(C#N)c1)[C@H](C)O] | J | 3.50 | 1017.3 | 1017.1 |
| 40910 | 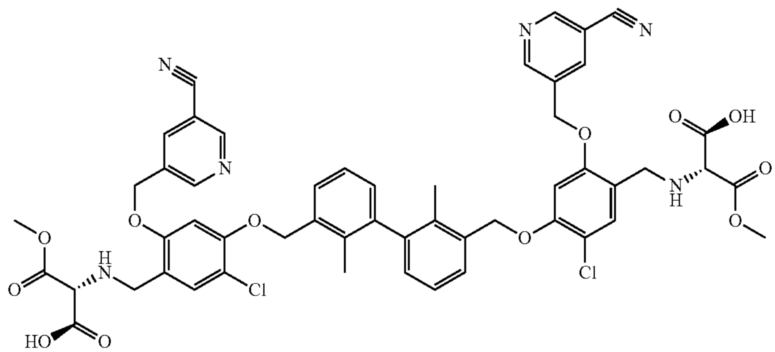 | J | 3.47 | 1017.3 | 1017.1 |
| 40930 | 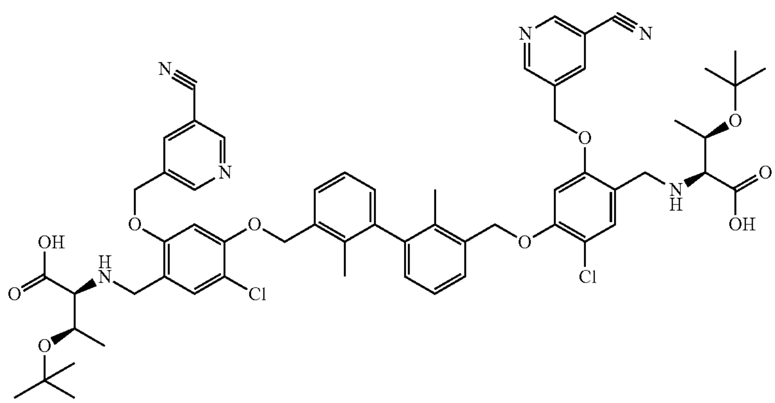 [SMILES: Cc1c(COc2cc(OCc3cncc(C#N)c3)c(CN[C@H](C(=O)O)[C@@H](C)OC(C)(C)C)cc2Cl)cccc1-c1cccc(COc2cc(OCc3cncc(C#N)c3)c(CN[C@H](C(=O)O)[C@@H](C)OC(C)(C)C)cc2Cl)c1C] | G | 3.73 | 1101.4 | 1101.4 |
| 40940 | 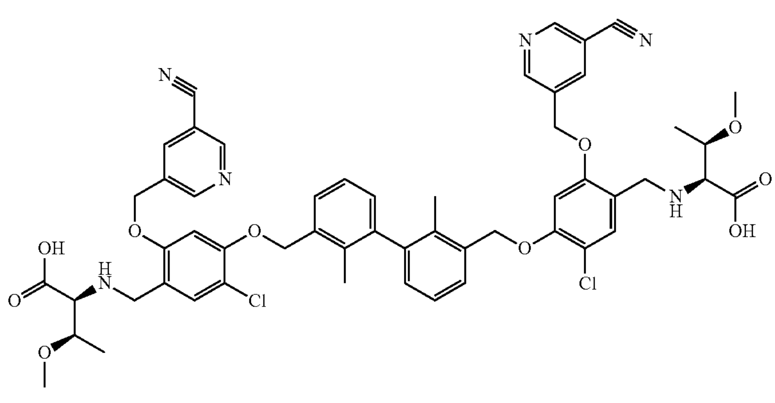 [SMILES: CO[C@H](C)[C@H](NCc1cc(Cl)c(OCc2cccc(-c3cccc(COc4cc(OCc5cncc(C#N)c5)c(CN[C@H](C(=O)O)[C@@H](C)OC)cc4Cl)c3C)c2C)cc1OCc1cncc(C#N)c1)C(=O)O] | J | 2.25 | 1017.3 | 1017.2 |

| Cmpd # | Structure | LC-MS Method | $R_f$ (min) | MS (M + H)+ Calcd. | MS (M + H)+ Observ. |
|---|---|---|---|---|---|
| 40950 | 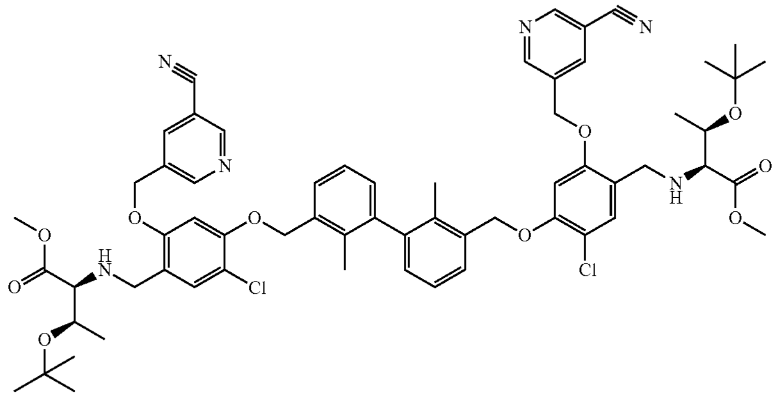 [SMILES: COC(=O)[C@@H](NCc1cc(Cl)c(OCc2cccc(-c3cccc(COc4cc(OCc5cncc(C#N)c5)c(CN[C@H](C(=O)OC)[C@@H](C)OC(C)(C)C)cc4Cl)c3C)c2C)cc1OCc1cncc(C#N)c1)[C@@H](C)OC(C)(C)C] | G | 3.72 | 1129.5 | 1129.5 |
| 40960 | 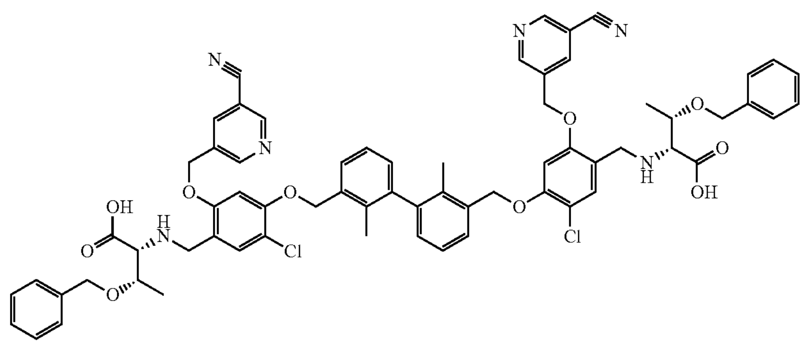 [SMILES: Cc1c(COc2cc(OCc3cncc(C#N)c3)c(CN[C@@H](C(=O)O)[C@H](C)OCc3ccccc3)cc2Cl)cccc1-c1cccc(COc2cc(OCc3cncc(C#N)c3)c(CN[C@@H](C(=O)O)[C@H](C)OCc3ccccc3)cc2Cl)c1C] | J | 2.83 | 1169.4 | 1169.2 |
| 40990 | 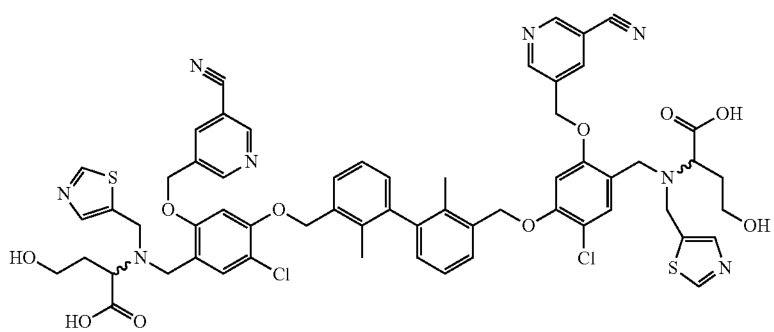 [SMILES: Cc1c(COc2cc(OCc3cncc(C#N)c3)c(CN(Cc3cncs3)C(CCO)C(=O)O)cc2Cl)cccc1-c1cccc(COc2cc(OCc3cncc(C#N)c3)c(CN(Cc3cncs3)C(CCO)C(=O)O)cc2Cl)c1C] | G | 4.20 | 1183.3 | 1183.3 |
| 41010 | 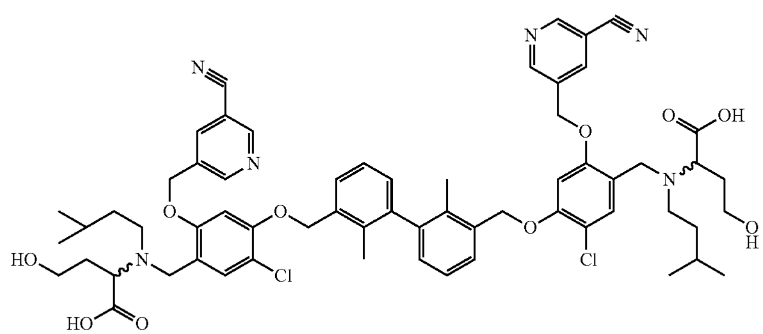 [SMILES: Cc1c(COc2cc(OCc3cncc(C#N)c3)c(CN(CCC(C)C)C(CCO)C(=O)O)cc2Cl)cccc1-c1cccc(COc2cc(OCc3cncc(C#N)c3)c(CN(CCC(C)C)C(CCO)C(=O)O)cc2Cl)c1C] | G | 3.79 | 1129.5 | 1129.6 |

TABLE 40000-continued

| Cmpd # | Structure | LC-MS Method | $R_f$ (min) | MS (M+H)$^+$ Calcd. | MS (M+H)$^+$ Observ. |
|---|---|---|---|---|---|
| 41020 | 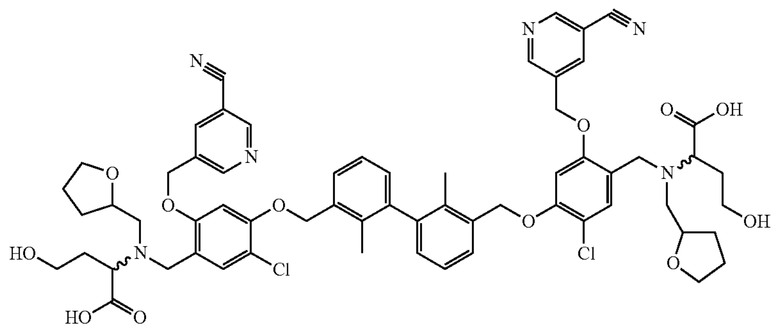 [SMILES: Cc1c(COc2cc(OCc3cncc(C#N)c3)c(CN(CC3CCCO3)C(CCO)C(=O)O)cc2Cl)cccc1-c1cccc(COc2cc(OCc3cncc(C#N)c3)c(CN(CC3CCCO3)C(CCO)C(=O)O)cc2Cl)c1C] | K | 2.41 | 1157.4 | 1157.5 |
| 41030 | 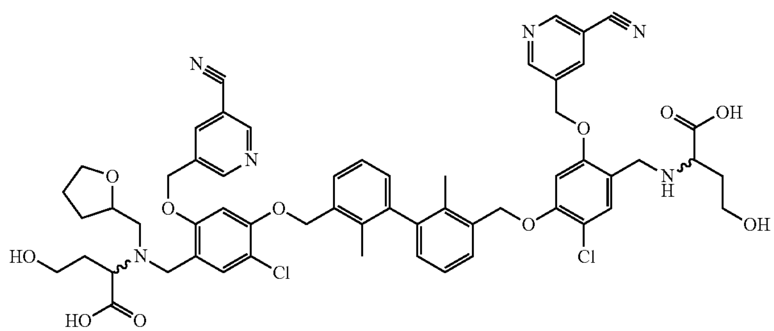 [SMILES: Cc1c(COc2cc(OCc3cncc(C#N)c3)c(CNC(CCO)C(=O)O)cc2Cl)cccc1-c1cccc(COc2cc(OCc3cncc(C#N)c3)c(CN(CC3CCCO3)C(CCO)C(=O)O)cc2Cl)c1C] | G | 3.54 | 1073.4 | 1073.5 |
| 41050 | 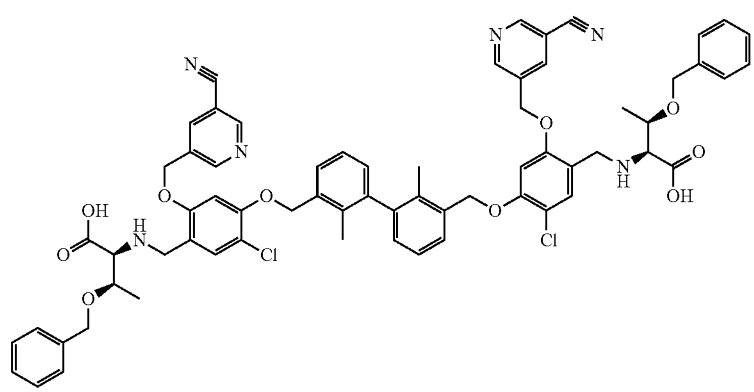 [SMILES: Cc1c(COc2cc(OCc3cncc(C#N)c3)c(CN[C@H](C(=O)O)[C@@H](C)OCc3ccccc3)cc2Cl)cccc1-c1cccc(COc2cc(OCc3cncc(C#N)c3)c(CN[C@H](C(=O)O)[C@@H](C)OCc3ccccc3)cc2Cl)c1C] | J | 2.64 | 1169.4 | 1169.6 |
| 41070 | 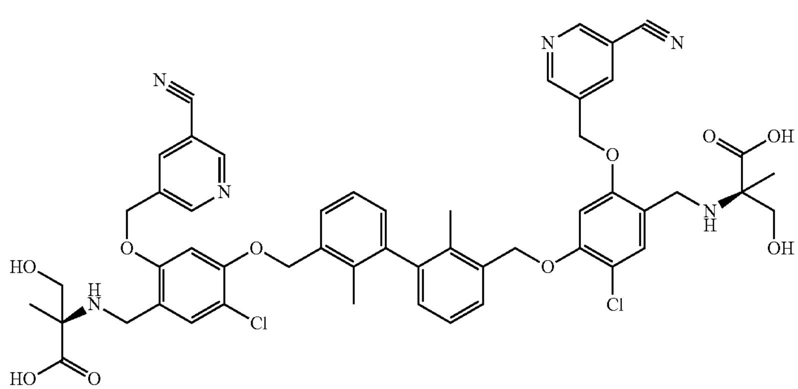 [SMILES: Cc1c(COc2cc(OCc3cncc(C#N)c3)c(CN[C@@](C)(CO)C(=O)O)cc2Cl)cccc1-c1cccc(COc2cc(OCc3cncc(C#N)c3)c(CN[C@@](C)(CO)C(=O)O)cc2Cl)c1C] | C | 2.80 | 989.3 | 989.5 |

TABLE 40000-continued

| Cmpd # | Structure | LC-MS Method | $R_f$ (min) | MS (M+H)$^+$ Calcd. | MS (M+H)$^+$ Observ. |
|---|---|---|---|---|---|
| 41090 | 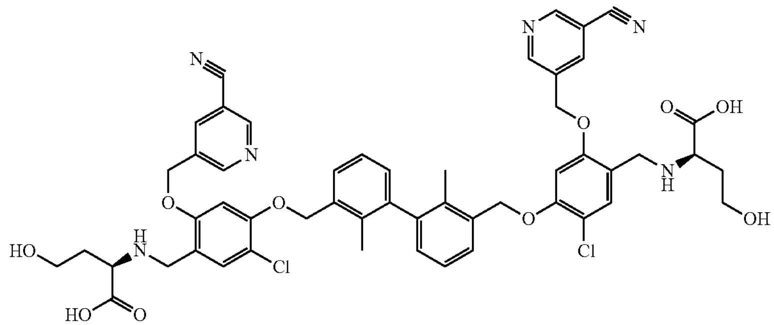 [SMILES: Cc1c(COc2cc(OCc3cncc(C#N)c3)c(CN[C@H](CCO)C(=O)O)cc2Cl)cccc1-c1cccc(COc2cc(OCc3cncc(C#N)c3)c(CN[C@H](CCO)C(=O)O)cc2Cl)c1C] | C | 1.70 | 989.3 | 989.2 |
| 41100 | 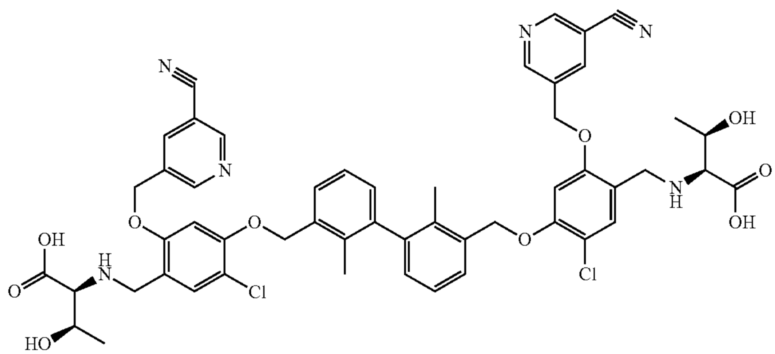 [SMILES: Cc1c(COc2cc(OCc3cncc(C#N)c3)c(CN[C@H](C(=O)O)[C@@H](C)O)cc2Cl)cccc1-c1cccc(COc2cc(OCc3cncc(C#N)c3)c(CN[C@H](C(=O)O)[C@@H](C)O)cc2Cl)c1C] | I | 2.90 | 989.3 | 989.4 |
| 41110 | 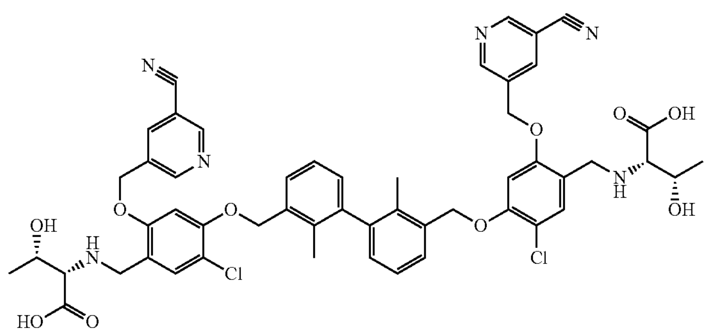 [SMILES: Cc1c(COc2cc(OCc3cncc(C#N)c3)c(CN[C@H](C(=O)O)[C@H](C)O)cc2Cl)cccc1-c1cccc(COc2cc(OCc3cncc(C#N)c3)c(CN[C@H](C(=O)O)[C@H](C)O)cc2Cl)c1C] | C | 1.68 | 989.3 | 989.2 |
| 41120 | 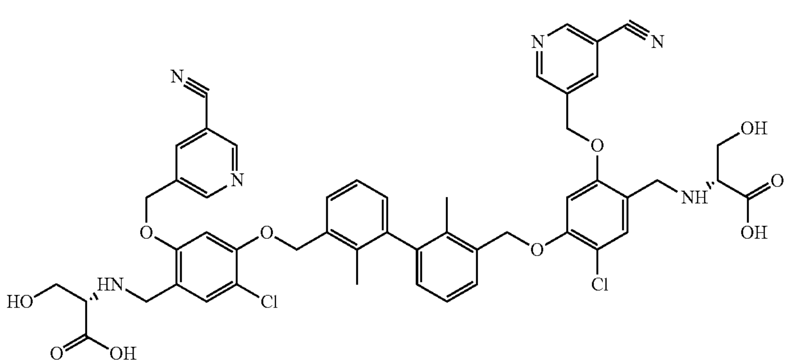 [SMILES: Cc1c(COc2cc(OCc3cncc(C#N)c3)c(CN[C@@H](CO)C(=O)O)cc2Cl)cccc1-c1cccc(COc2cc(OCc3cncc(C#N)c3)c(CN[C@H](CO)C(=O)O)cc2Cl)c1C] | I | 3.58 | 961.3 | 961.3 |

TABLE 40000-continued

| Cmpd # | Structure | LC-MS Method | $R_f$ (min) | MS (M + H)+ Calcd. | MS (M + H)+ Observ. |
|---|---|---|---|---|---|
| 41130 | 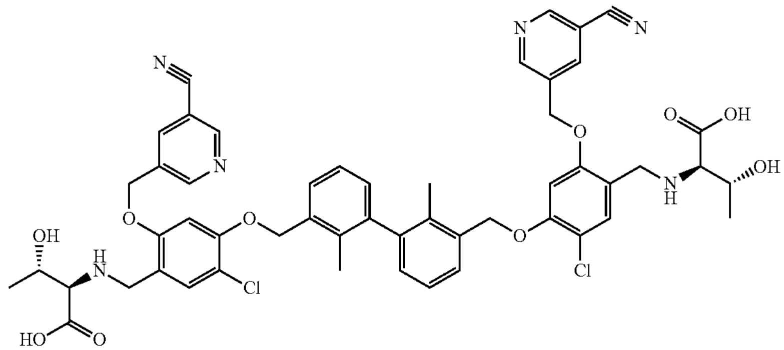 [SMILES: Cc1c(COc2cc(OCc3cncc(C#N)c3)c(CN[C@@H](C(=O)O)[C@H](C)O)cc2Cl)cccc1-c1cccc(COc2cc(OCc3cncc(C#N)c3)c(CN[C@@H](C(=O)O)[C@@H](C)O)cc2Cl)c1C] | I | 3.61 | 989.3 | 989.4 |
| 41140 | 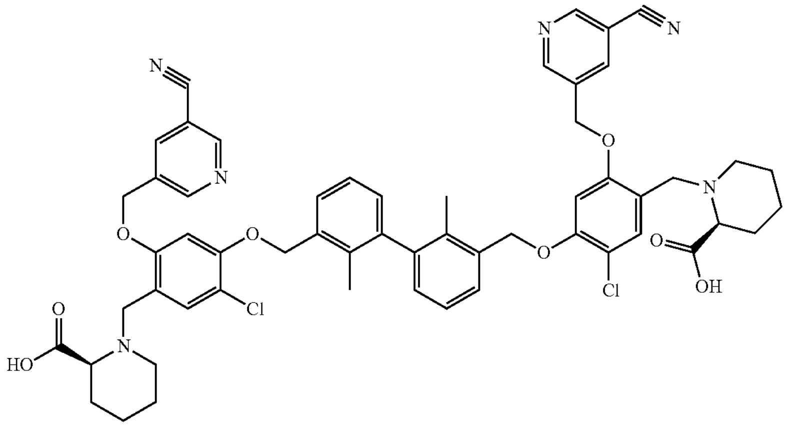 [SMILES: Cc1c(COc2cc(OCc3cncc(C#N)c3)c(CN3CCCC[C@H]3C(=O)O)cc2Cl)cccc1-c1cccc(COc2cc(OCc3cncc(C#N)c3)c(CN3CCCC[C@H]3C(=O)O)cc2Cl)c1C] | I | 3.62 | 1009.3 | 1009.5 |
| 41170 | 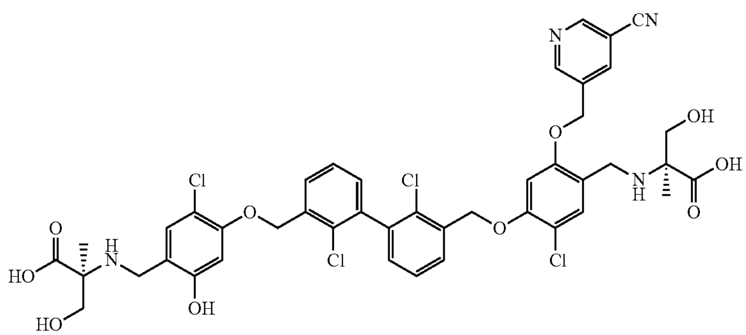 [SMILES: C[C@@](CO)(NCc1cc(Cl)c(OCc2cccc(-c3cccc(COc4cc(OCc5cncc(C#N)c5)c(CN[C@@](C)(CO)C(=O)O)cc4Cl)c3Cl)c2Cl)cc1O)C(=O)O] | C | 1.53 | 913.2 | 913.1 |
| 41180 | 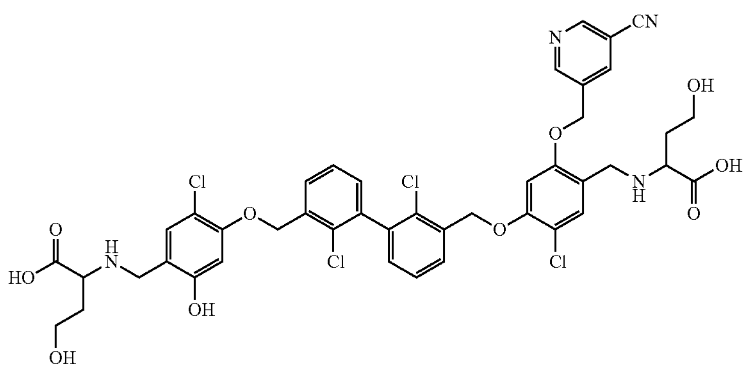 [SMILES: N#Cc1cncc(COc2cc(OCc3cccc(-c4cccc(COc5cc(O)c(CNC(CCO)C(=O)O)cc5Cl)c4Cl)c3Cl)c(Cl)cc2CNC(CCO)C(=O)O)c1] | C | 1.52 | 913.2 | 913.1 |

TABLE 40000-continued

| Cmpd # | Structure | LC-MS Method | R$_f$ (min) | MS (M + H)$^+$ Calcd. | MS (M + H)$^+$ Observ. |
|---|---|---|---|---|---|
| 41190 | 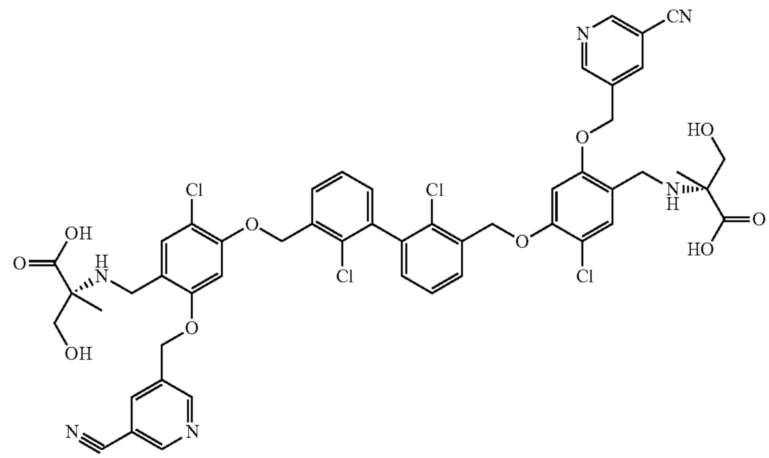 [SMILES: C[C@](CO)(NCc1cc(Cl)c(OCc2cccc(-c3cccc(COc4cc(OCc5cncc(C#N)c5)c(CN[C@](C)(CO)C(=O)O)cc4Cl)c3Cl)c2Cl)cc1OCc1cncc(C#N)c1)C(=O)O] | K | 2.64 | 1029.2 | 1029.2 |
| 41200 | 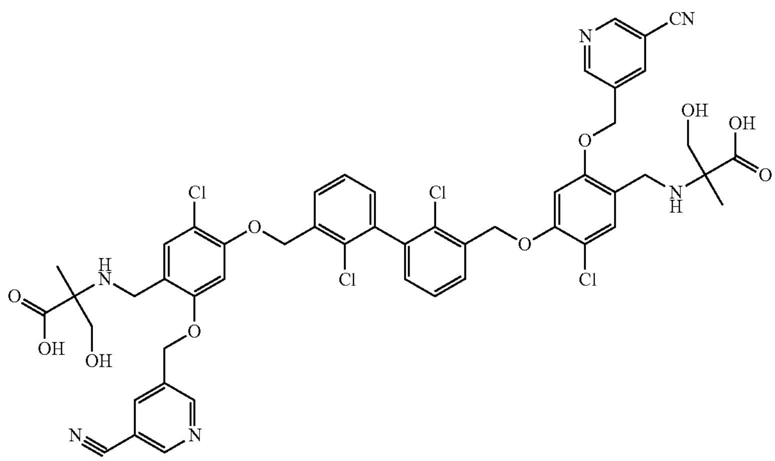 [SMILES: CC(CO)(NCc1cc(Cl)c(OCc2cccc(-c3cccc(COc4cc(OCc5cncc(C#N)c5)c(CNC(C)(CO)C(=O)O)cc4Cl)c3Cl)c2Cl)cc1OCc1cncc(C#N)c1)C(=O)O] | K | 2.63 | 1029.2 | 1029.2 |
| 41210 | 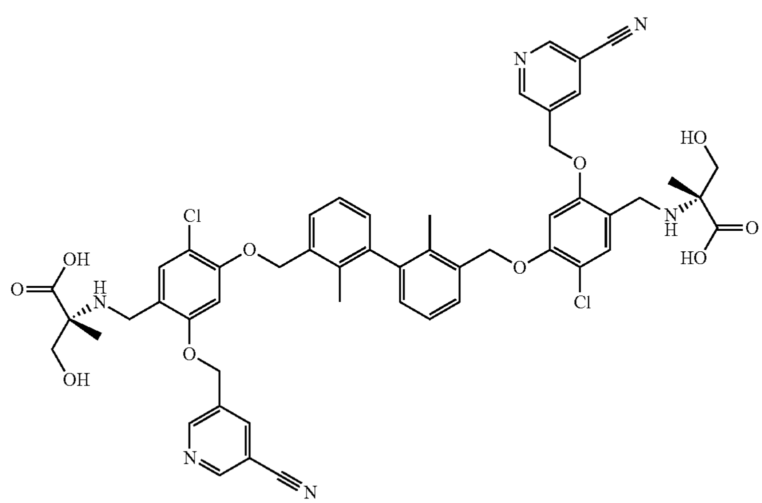 [SMILES: Cc1c(COc2cc(OCc3cncc(C#N)c3)c(CN[C@](C)(CO)C(=O)O)cc2Cl)cccc1-c1cccc(COc2cc(OCc3cncc(C#N)c3)c(CN[C@](C)(CO)C(=O)O)cc2Cl)c1C] | L | 0.59 | 989.3 | 989.4 |

TABLE 40000-continued

| Cmpd # | Structure | LC-MS Method | $R_f$ (min) | MS (M + H)+ Calcd. | MS (M + H)+ Observ. |
|---|---|---|---|---|---|
| 41220 | 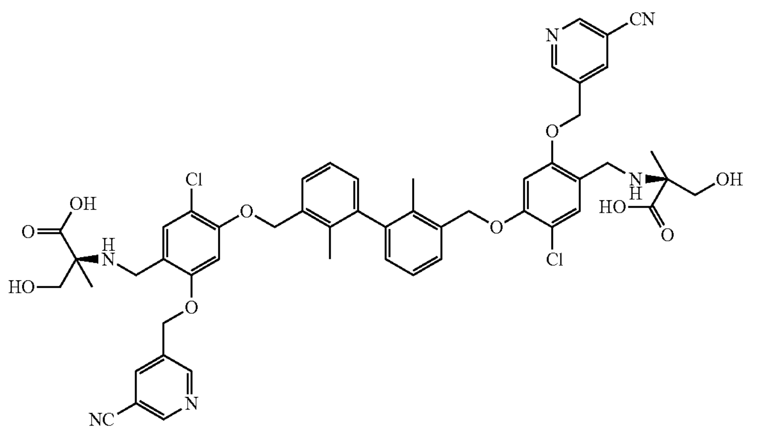 [SMILES: Cc1c(COc2cc(OCc3cncc(C#N)c3)c(CN[C@@](C)(CO)C(=O)O)cc2Cl)cccc1-c1cccc(COc2cc(OCc3cncc(C#N)c3)c(CN[C@@](C)(CO)C(=O)O)cc2Cl)c1C] | M | 1.65 | 989.3 | 989.2 |
| 41230 | 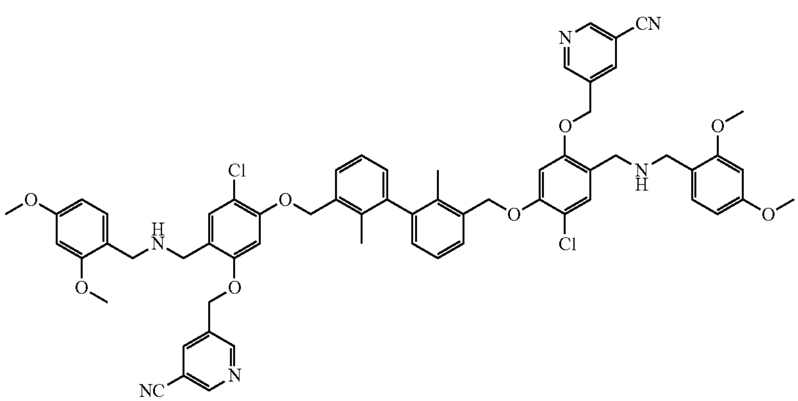 | N | 2.41 | 1085.4 | 1085.3 |

TABLE 50000

| Cmpd # | Structure | LC-MS Method | $R_f$ (min) | MS (M + H)+ Calcd. | MS (M + H)+ Observ. |
|---|---|---|---|---|---|
| 50020 | 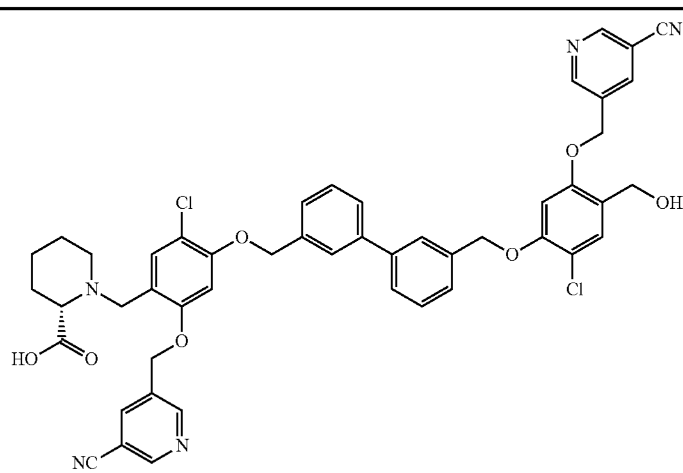 | D | 1.97 | 870.3 | 870.1 |

TABLE 50000-continued

| Cmpd # | Structure | LC-MS Method | $R_f$ (min) | MS (M+H)+ Calcd. | MS (M+H)+ Observ. |
|---|---|---|---|---|---|
| 50040 | 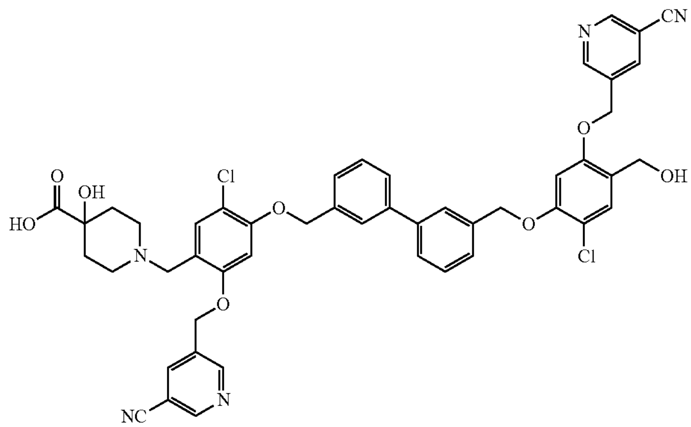 [SMILES: N#Cc1cncc(COc2cc(OCc3cccc(-c4cccc(COc5cc(OCc6cncc(C#N)c6)c(CN6CCC(O)(C(=O)O)CC6)cc5Cl)c4)c3)c(Cl)cc2CO)c1] | D | 2.23 | 886.2 | 886.1 |
| 50060 | 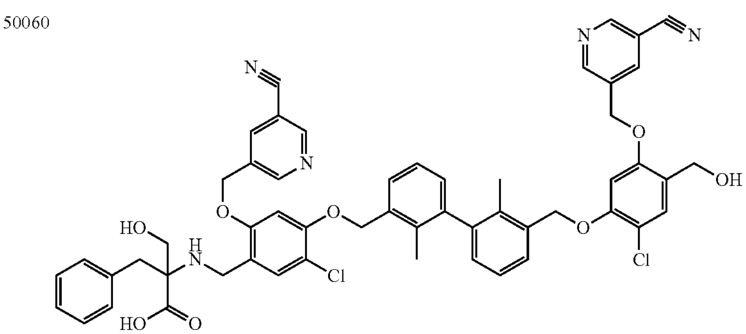 | I | 4.28 | 964.3 | 964.3 |
| 50070 | 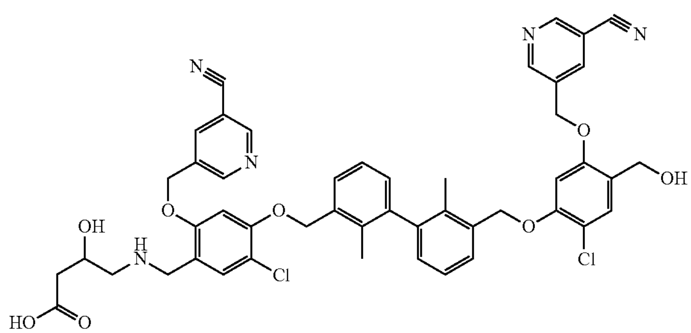 [SMILES: Cc1c(COc2cc(OCc3cncc(C#N)c3)c(CO)cc2Cl)cccc1-c1cccc(COc2cc(OCc3cncc(C#N)c3)c(CNCC(O)CC(=O)O)cc2Cl)c1C] | G | 3.75 | 888.3 | 888.3 |
| 50080 | 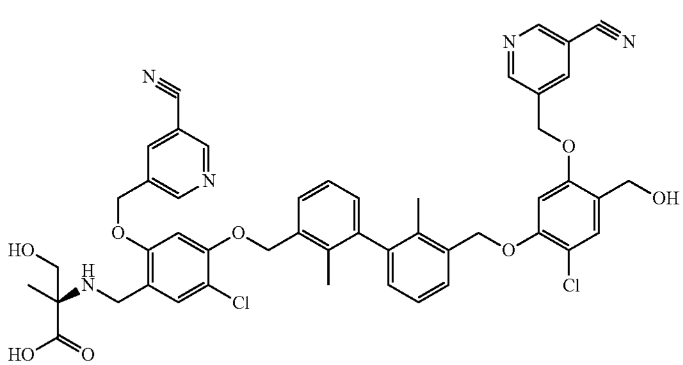 [SMILES: Cc1c(COc2cc(OCc3cncc(C#N)c3)c(CO)cc2Cl)cccc1-c1cccc(COc2cc(OCc3cncc(C#N)c3)c(CN[C@@](C)(CO)C(=O)O)cc2Cl)c1C] | H | 3.32 | 888.2 | 888.3 |

TABLE 50000-continued

| Cmpd # | Structure | LC-MS Method | $R_f$ (min) | MS (M+H)$^+$ Calcd. | MS (M+H)$^+$ Observ. |
|---|---|---|---|---|---|
| 50100 | 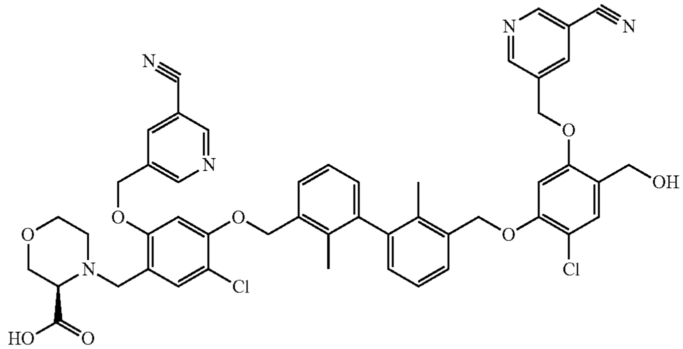 [SMILES: Cc1c(COc2cc(OCc3cncc(C#N)c3)c(CO)cc2Cl)cccc1-c1cccc(COc2cc(OCc3cncc(C#N)c3)c(CN3CCOC[C@@H]3C(=O)O)cc2Cl)c1C] | G | 4.06 | 900.2 | 900.3 |
| 50110 | 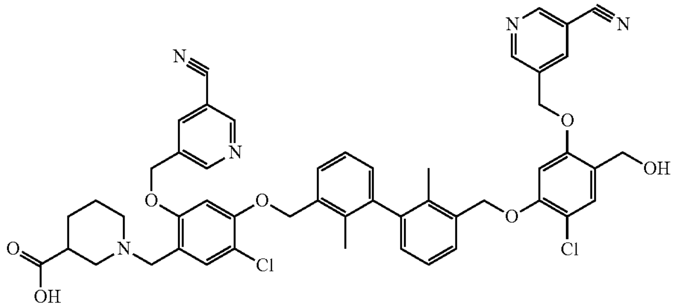 [SMILES: Cc1c(COc2cc(OCc3cncc(C#N)c3)c(CO)cc2Cl)cccc1-c1cccc(COc2cc(OCc3cncc(C#N)c3)c(CN3CCCC(C(=O)O)C3)cc2Cl)c1C] | G | 3.93 | 898.3 | 898.4 |
| 50120 | 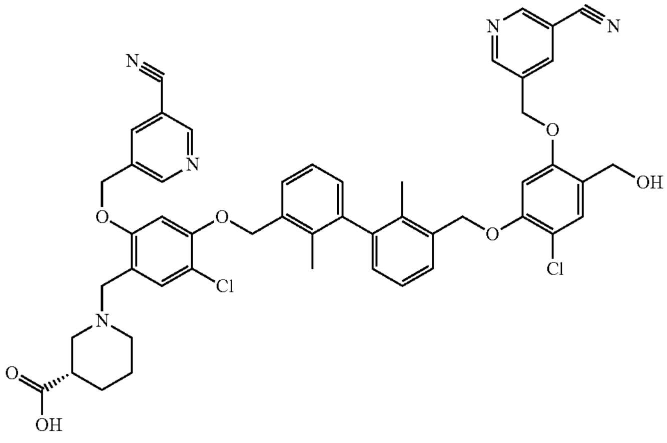 [SMILES: Cc1c(COc2cc(OCc3cncc(C#N)c3)c(CO)cc2Cl)cccc1-c1cccc(COc2cc(OCc3cncc(C#N)c3)c(CN3CCC[C@H](C(=O)O)C3)cc2Cl)c1C] | G | 3.91 | 898.3 | 898.4 |
| 50150 | 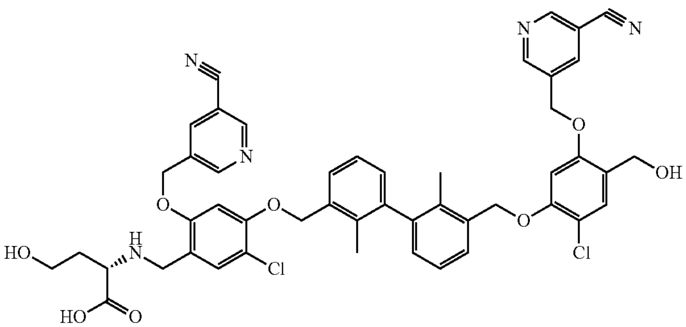 [SMILES: Cc1c(COc2cc(OCc3cncc(C#N)c3)c(CO)cc2Cl)cccc1-c1cccc(COc2cc(OCc3cncc(C#N)c3)c(CN[C@@H](CCO)C(=O)O)cc2Cl)c1C] | G | 3.90 | 888.2 | 888.3 |

TABLE 50000-continued

| Cmpd # | Structure | LC-MS Method | $R_f$ (min) | MS (M+H)+ Calcd. | MS (M+H)+ Observ. |
|---|---|---|---|---|---|
| 50170 | 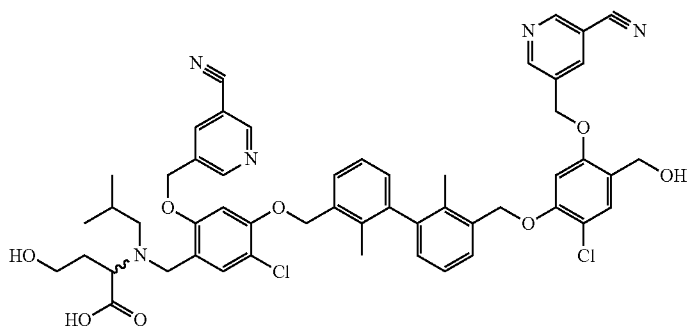 [SMILES: Cc1c(COc2cc(OCc3cncc(C#N)c3)c(CO)cc2Cl)cccc1-c1cccc(COc2cc(OCc3cncc(C#N)c3)c(CN(CC(C)C)C(CCO)C(=O)O)cc2Cl)c1C] | J | 2.92 | 944.3 | 944.3 |
| 50180 | 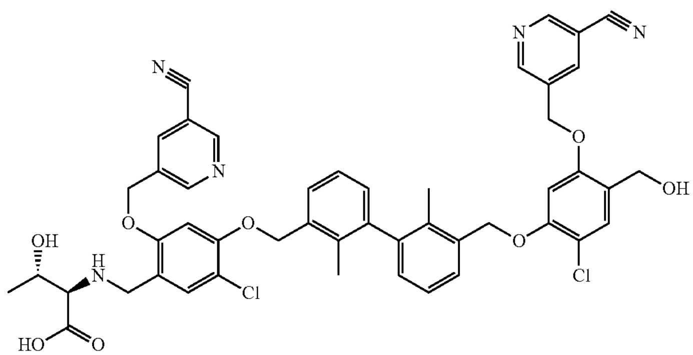 [SMILES: Cc1c(COc2cc(OCc3cncc(C#N)c3)c(CO)cc2Cl)cccc1-c1cccc(COc2cc(OCc3cncc(C#N)c3)c(CN[C@@H](C(=O)O)[C@H](C)O)cc2Cl)c1C] | C | 2.02 | 888.2 | 888.2 |
| 50190 | 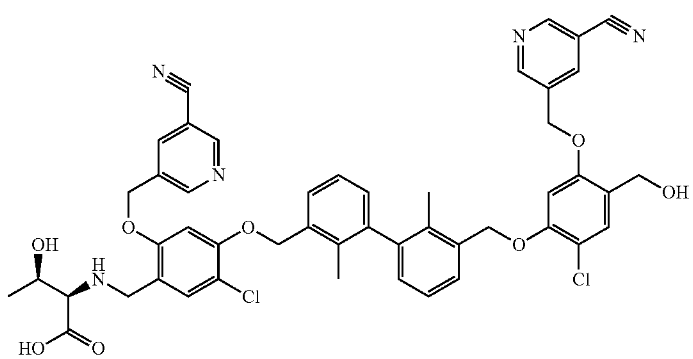 [SMILES: Cc1c(COc2cc(OCc3cncc(C#N)c3)c(CO)cc2Cl)cccc1-c1cccc(COc2cc(OCc3cncc(C#N)c3)c(CN[C@@H](C(=O)O)[C@@H](C)O)cc2Cl)c1C] | J | 2.59 | 888.2 | 888.1 |
| 50200 | 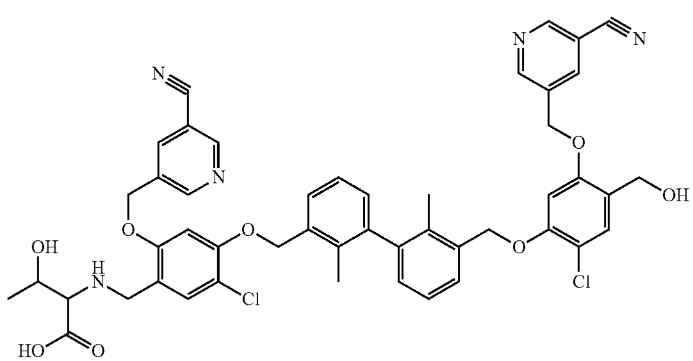 [SMILES: Cc1c(COc2cc(OCc3cncc(C#N)c3)c(CO)cc2Cl)cccc1-c1cccc(COc2cc(OCc3cncc(C#N)c3)c(CNC(C(=O)O)C(C)O)cc2Cl)c1C] | J | 2.62 | 888.2 | 888.1 |

TABLE 50000-continued

| Cmpd # | Structure | LC-MS Method | $R_f$ (min) | MS (M+H)+ Calcd. | MS (M+H)+ Observ. |
|---|---|---|---|---|---|
| 50210 | 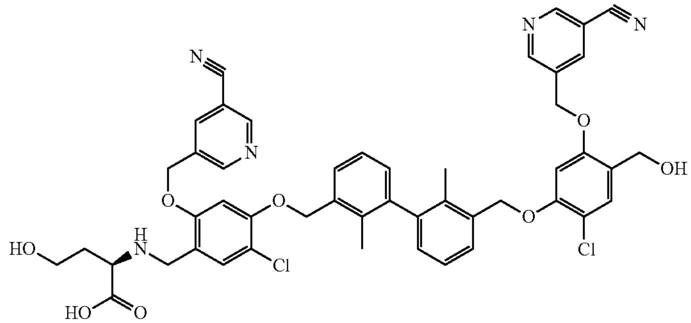 [SMILES: Cc1c(COc2cc(OCc3cncc(C#N)c3)c(CO)cc2Cl)cccc1-c1cccc(COc2cc(OCc3cncc(C#N)c3)c(CN[C@H](CCO)C(=O)O)cc2Cl)c1C] | C | 2.03 | 888.2 | 888.2 |
| 50220 | 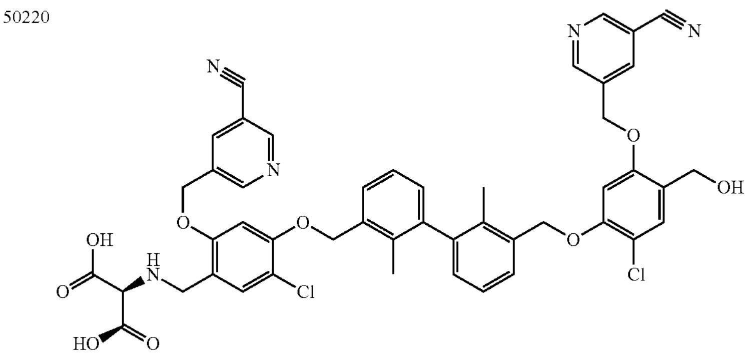 | K | 3.17 | 888.2 | 888.6 |
| 50230 | 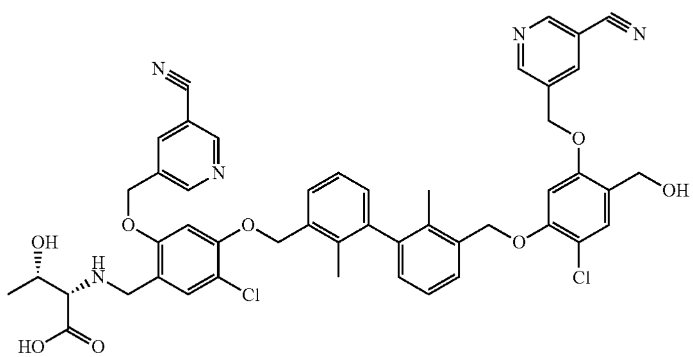 [SMILES: Cc1c(COc2cc(OCc3cncc(C#N)c3)c(CO)cc2Cl)cccc1-c1cccc(COc2cc(OCc3cncc(C#N)c3)c(CN[C@H](C(=O)O)[C@H](C)O)cc2Cl)c1C] | C | 2.00 | 888.2 | 888.2 |
| 50240 | 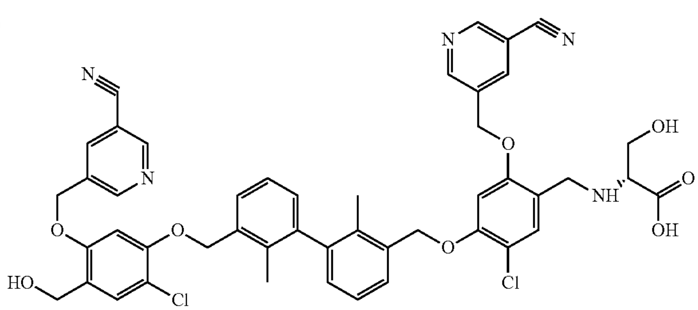 [SMILES: Cc1c(COc2cc(OCc3cncc(C#N)c3)c(CO)cc2Cl)cccc1-c1cccc(COc2cc(OCc3cncc(C#N)c3)c(CN[C@H](CO)C(=O)O)cc2Cl)c1C] | I | 4.05 | 874.2 | 874.3 |

TABLE 50000-continued

| Cmpd # | Structure | LC-MS Method | $R_f$ (min) | MS (M + H)$^+$ Calcd. | MS (M + H)$^+$ Observ. |
|---|---|---|---|---|---|
| 50250 | 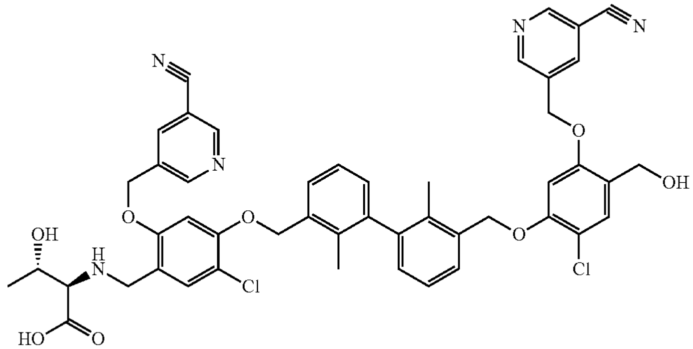 [SMILES: Cc1c(COc2cc(OCc3cncc(C#N)c3)c(CO)cc2Cl)cccc1-c1cccc(COc2cc(OCc3cncc(C#N)c3)c(CN[C@@H](C(=O)O)[C@H](C)O)cc2Cl)c1C] | I | 4.07 | 888.2 | 888.3 |
| 50260 | 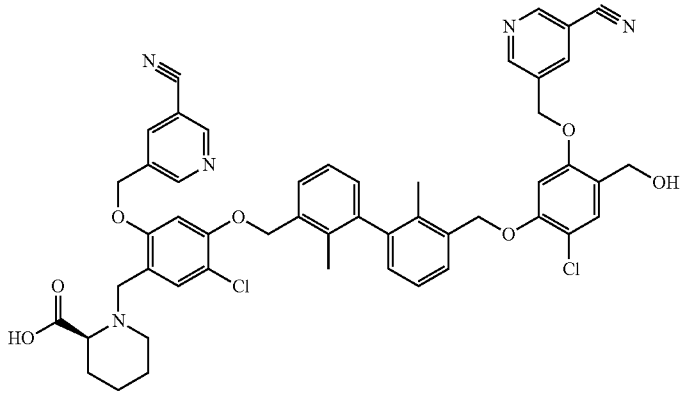 [SMILES: Cc1c(COc2cc(OCc3cncc(C#N)c3)c(CO)cc2Cl)cccc1-c1cccc(COc2cc(OCc3cncc(C#N)c3)c(CN3CCCC[C@H]3C(=O)O)cc2Cl)c1C] | I | 3.94 | 898.3 | 898.4 |
| 50270 | 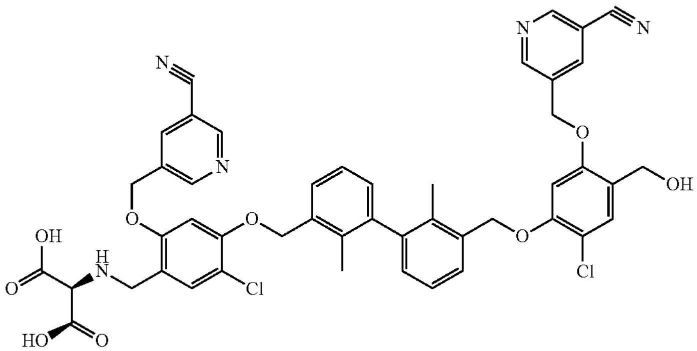 | C | 2.03 | 888.2 | 888.1 |
| 50280 | 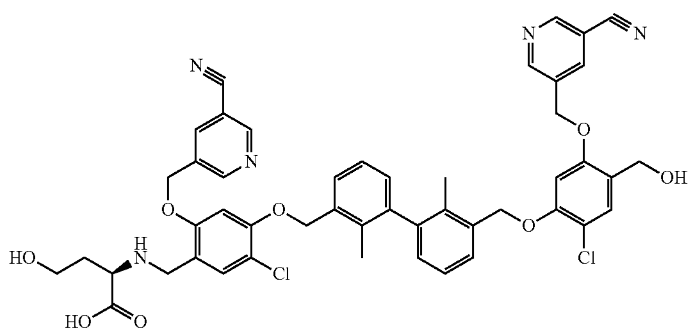 [SMILES: Cc1c(COc2cc(OCc3cncc(C#N)c3)c(CO)cc2Cl)cccc1-c1cccc(COc2cc(OCc3cncc(C#N)c3)c(CN[C@H](CCO)C(=O)O)cc2Cl)c1C] | G | 3.79 | 888.2 | 888.3 |

TABLE 50000-continued

| Cmpd # | Structure | LC-MS Method | R_f (min) | MS (M + H)+ Calcd. | MS (M + H)+ Observ. |
|---|---|---|---|---|---|
| 50300 | 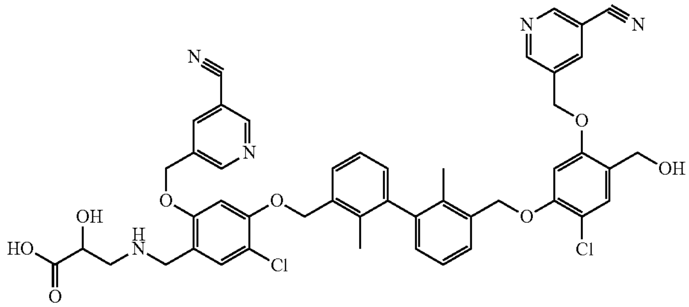 [SMILES: Cc1c(COc2cc(OCc3cncc(C#N)c3)c(CO)cc2Cl)cccc1-c1cccc(COc2cc(OCc3cncc(C#N)c3)c(CNCC(O)C(=O)O)cc2Cl)c1C] | G | 3.76 | 874.2 | 874.3 |
| 50310 | 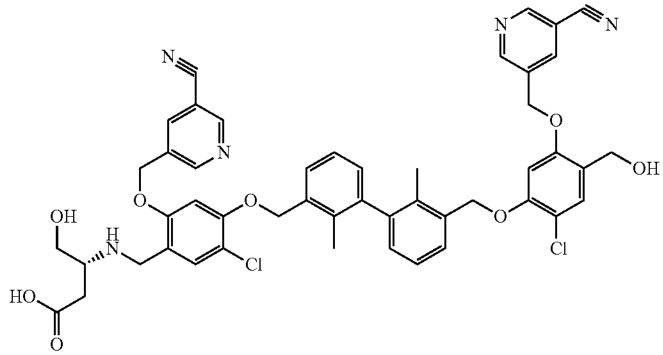 [SMILES: Cc1c(COc2cc(OCc3cncc(C#N)c3)c(CO)cc2Cl)cccc1-c1cccc(COc2cc(OCc3cncc(C#N)c3)c(CN[C@@H](CO)CC(=O)O)cc2Cl)c1C] | G | 3.93 | 888.2 | 888.3 |
| 50330 | 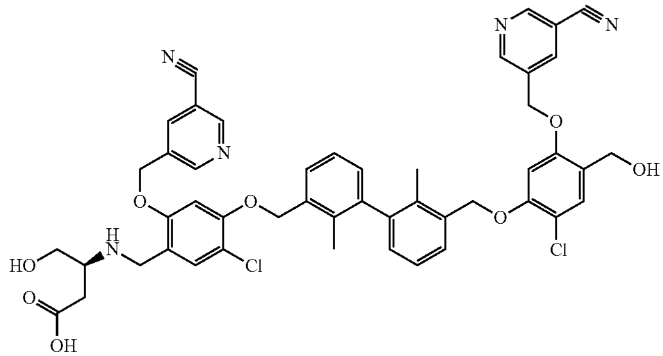 [SMILES: Cc1c(COc2cc(OCc3cncc(C#N)c3)c(CO)cc2Cl)cccc1-c1cccc(COc2cc(OCc3cncc(C#N)c3)c(CN[C@H](CO)CC(=O)O)cc2Cl)c1C] | C | 1.95 | 888.2 | 888.2 |
| 50340 | 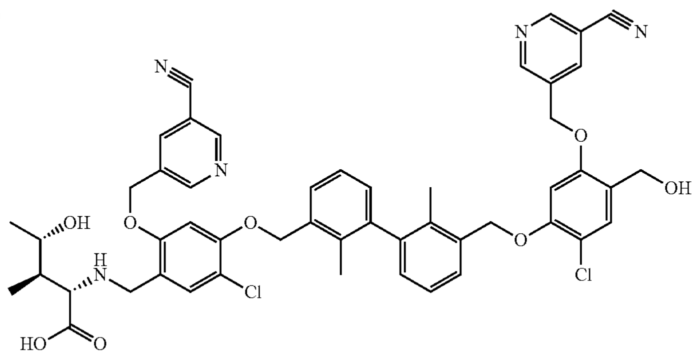 [SMILES: Cc1c(COc2cc(OCc3cncc(C#N)c3)c(CO)cc2Cl)cccc1-c1cccc(COc2cc(OCc3cncc(C#N)c3)c(CN[C@H](C(=O)O)[C@@H](C)[C@H](C)O)cc2Cl)c1C] | C | 3.42 | 916.3 | 916.3 |

TABLE 50000-continued

| Cmpd # | Structure | LC-MS Method | $R_f$ (min) | MS (M + H)+ Calcd. | MS (M + H)+ Observ. |
|---|---|---|---|---|---|
| 50360 | 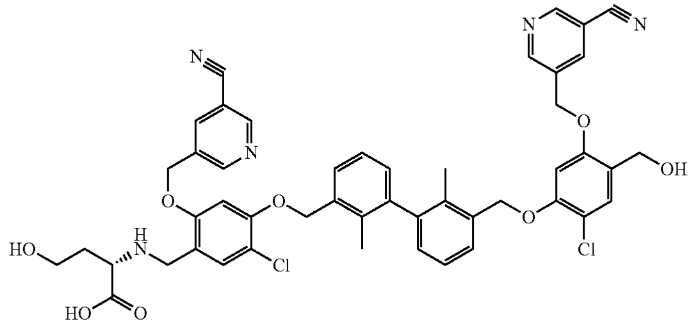 [SMILES: Cc1c(COc2cc(OCc3cncc(C#N)c3)c(CO)cc2Cl)cccc1-c1cccc(COc2cc(OCc3cncc(C#N)c3)c(CN[C@@H](CCO)C(=O)O)cc2Cl)c1C] | G | 3.78 | 888.2 | 888.3 |
| 50380 | 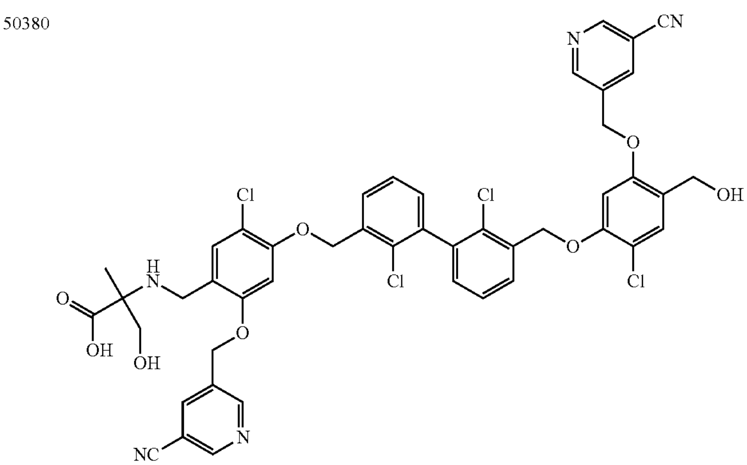 | M | 1.97 | 928.2 | 928.1 |
| 50390 | 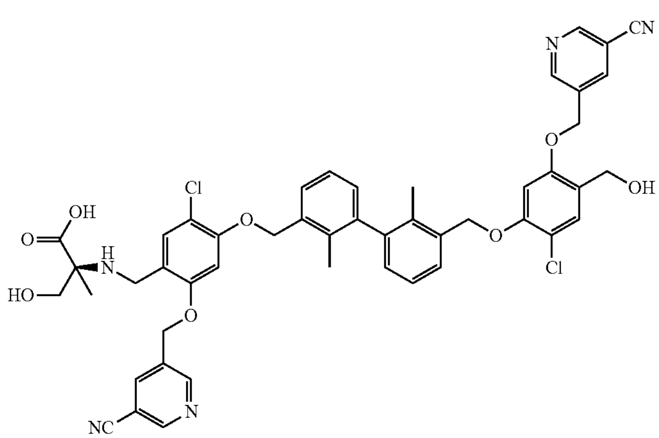 [SMILES: Cc1c(COc2cc(OCc3cncc(C#N)c3)c(CO)cc2Cl)cccc1-c1cccc(COc2cc(OCc3cncc(C#N)c3)c(CN[C@@](C)(CO)C(=O)O)cc2Cl)c1C] | M | 1.98 | 888.3 | 888.2 |

TABLE 50000-continued

| Cmpd # | Structure | LC-MS Method | $R_f$ (min) | MS (M+H)$^+$ Calcd. | MS (M+H)$^+$ Observ. |
|---|---|---|---|---|---|
| 50400 | 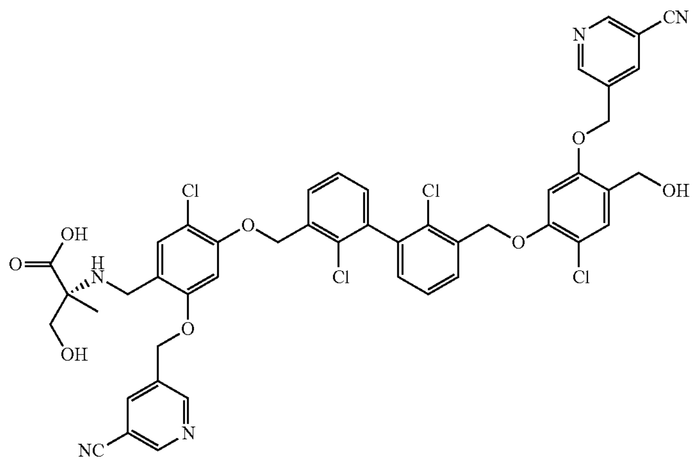 [SMILES: C[C@](CO)(NCc1cc(Cl)c(OCc2cccc(-c3cccc(COc4cc(OCc5cncc(C#N)c5)c(CO)cc4Cl)c3Cl)c2Cl)cc1OCc1cncc(C#N)c1)C(=O)O] | M | 2.07 | 928.2 | 928.1 |

TABLE 60000

| Cmpd# | Structure | LC-MS Method | $R_f$ (min) | MS (M+H)$^+$ Calcd. | MS (M+H)$^+$ Observ. |
|---|---|---|---|---|---|
| 60010 | 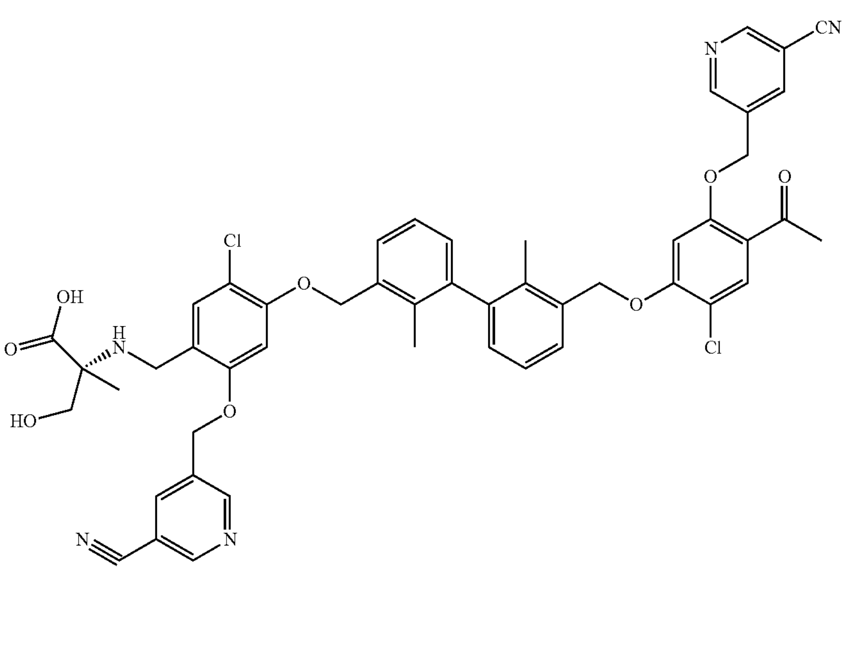 [SMILES: CC(=O)c1cc(Cl)c(OCc2cccc(-c3cccc(COc4cc(OCc5cncc(C#N)c5)c(CN[C@](C)(CO)C(=O)O)cc4Cl)c3C)c2C)cc1OCc1cncc(C#N)c1] | K | 3.25 | 900.3 | 900.3 |

TABLE 60000-continued

| Cmpd# | Structure | LC-MS Method | R$_f$ (min) | MS (M + H)$^+$ Calcd. | MS (M + H)$^+$ Observ. |
|---|---|---|---|---|---|
| 60020 | 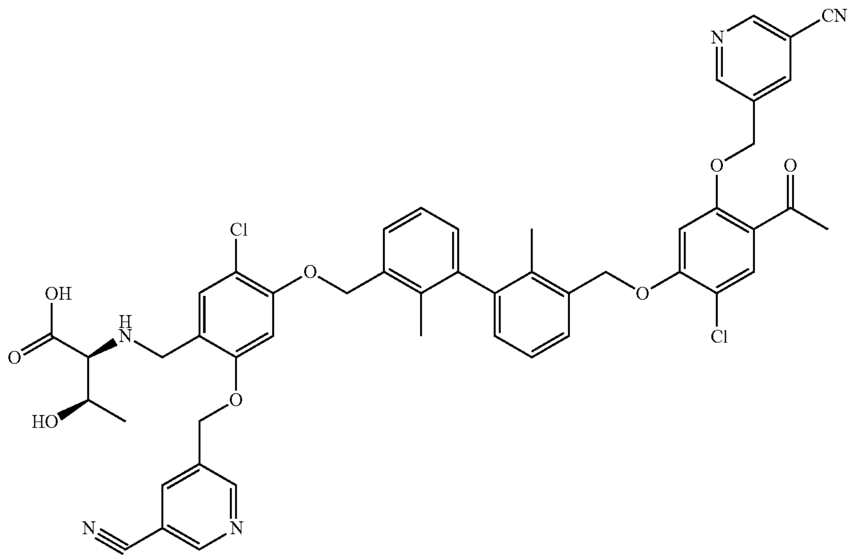 [SMILES: CC(=O)c1cc(Cl)c(OCc2cccc(-c3cccc(COc4cc(OCc5cncc(C#N)c5)c(CN[C@H](C(=O)O)[C@@H](C)O)cc4Cl)c3C)c2C)cc1OCc1cncc(C#N)c1] | K | 3.25 | 900.3 | 900.2 |
| 60030 | 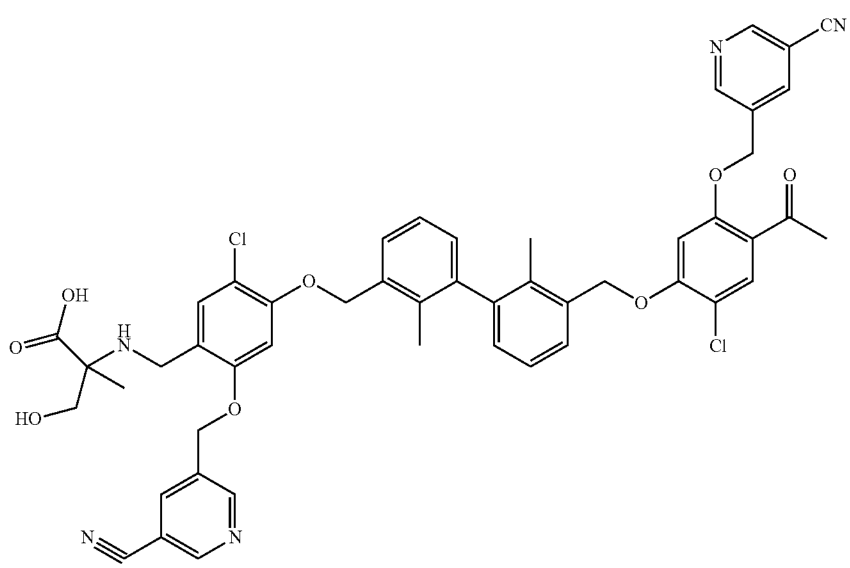 [SMILES: CC(=O)c1cc(Cl)c(OCc2cccc(-c3cccc(COc4cc(OCc5cncc(C#N)c5)c(CNC(C)(CO)C(=O)O)cc4Cl)c3C)c2C)cc1OCc1cncc(C#N)c1] | L | 1.39 | 900.3 | 900.3 |

TABLE 60000-continued

| Cmpd# | Structure | LC-MS Method | $R_f$ (min) | MS (M + H)$^+$ Calcd. | MS (M + H)$^+$ Observ. |
|---|---|---|---|---|---|
| 60040 | 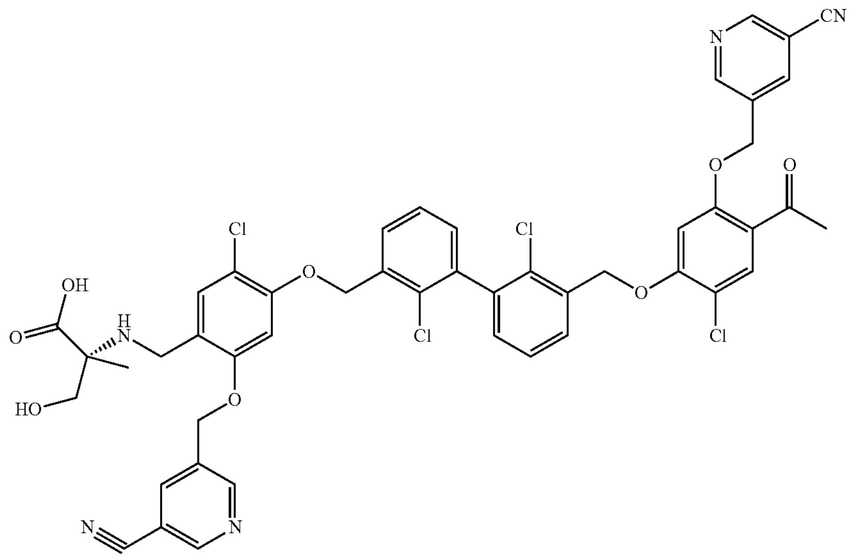 [SMILES: CC(=O)c1cc(Cl)c(OCc2cccc(-c3cccc(COc4cc(OCc5cncc(C#N)c5)c(CN[C@](C)(CO)C(=O)O)cc4Cl)c3Cl)c2Cl)cc1OCc1cncc(C#N)c1] | M | 2.23 | 940.2 | 940.0 |
| 60050 | 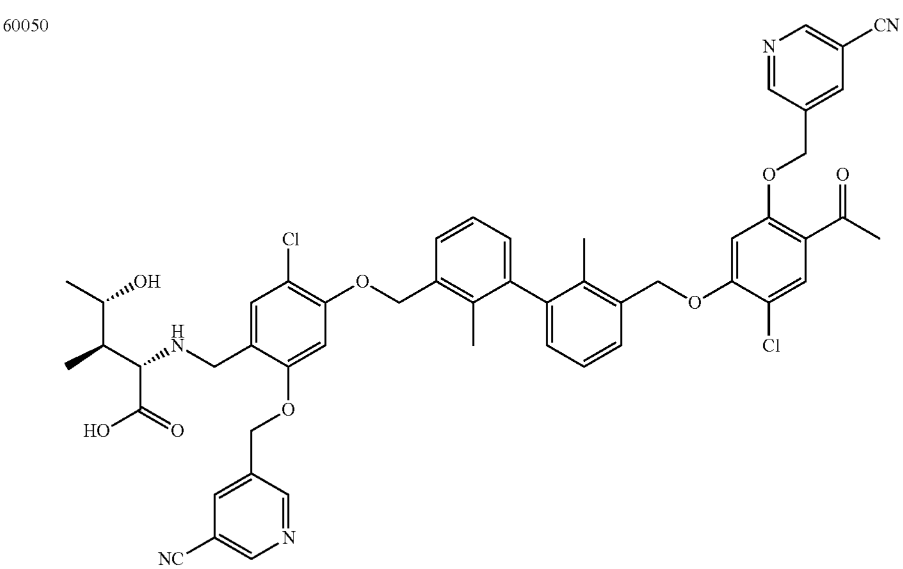 | M | 2.15 | 928.3 | 928.2 |

TABLE 60000-continued

| Cmpd# | Structure | LC-MS Method | R$_f$ (min) | MS (M + H)$^+$ Calcd. | MS (M + H)$^+$ Observ. |
|---|---|---|---|---|---|
| 60060 | 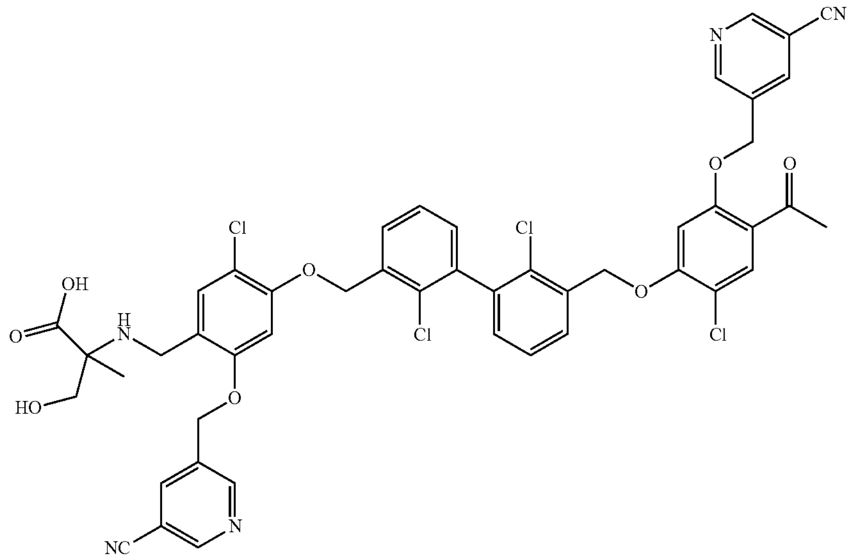 [SMILES: CC(=O)c1cc(Cl)c(OCc2cccc(-c3cccc(COc4cc(OCc5cncc(C#N)c5)c(CNC(C)(CO)C(=O)O)cc4Cl)c3Cl)c2Cl)cc1OCc1cncc(C#N)c1] | M | 2.23 | 940.1 | 940.0 |
| 60070 | 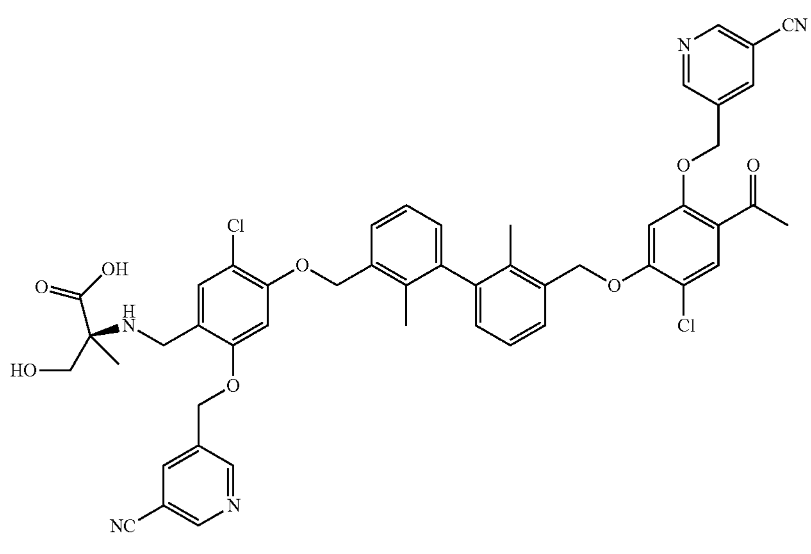 [SMILES: CC(=O)c1cc(Cl)c(OCc2cccc(-c3cccc(COc4cc(OCc5cncc(C#N)c5)c(CN[C@@](C)(CO)C(=O)O)cc4Cl)c3C)c2C)cc1OCc1cncc(C#N)c1] | M | 2.15 | 900.3 | 900.2 |

TABLE 60000-continued
| Cmpd# | Structure | LC-MS Method | $R_f$ (min) | MS (M + H)+ Calcd. | MS (M + H)+ Observ. |
|---|---|---|---|---|---|
| 60080 | 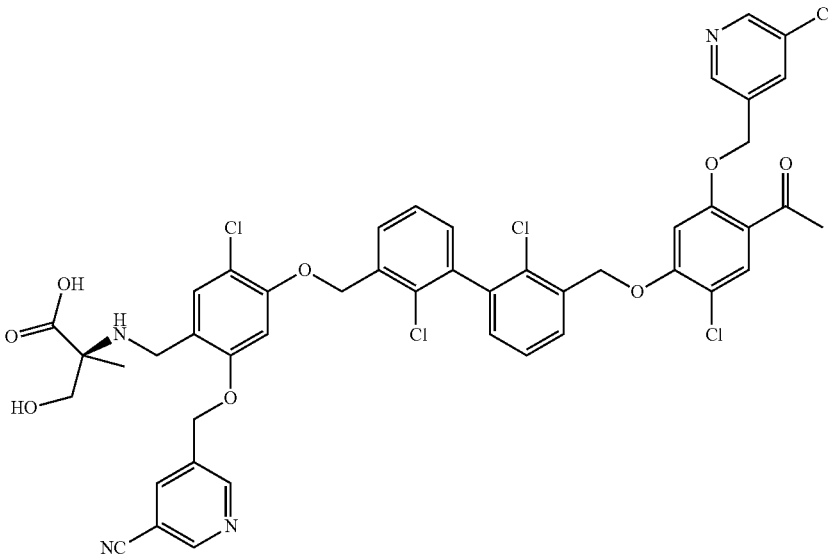 | M | 2.23 | 940.2 | 940.2 |
| 60090 | 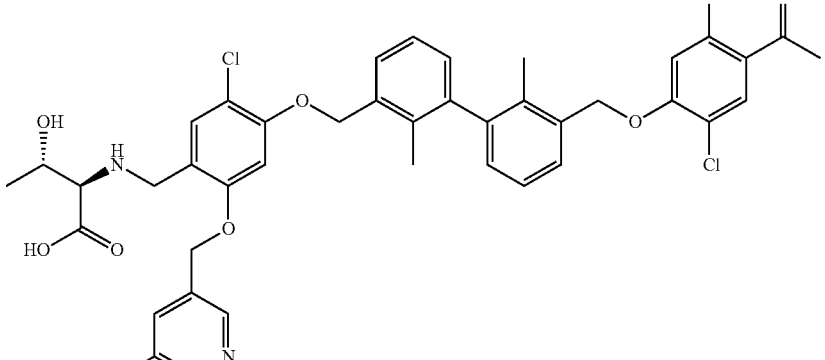 | M | 2.13 | 900.3 | 900.1 |

TABLE 70000

| Cmpd# | Structure | LC-MS Method | $R_f$ (min) | MS (M + H)$^+$ Calcd. | MS (M + H)$^+$ Observ. |
|---|---|---|---|---|---|
| 70010 | 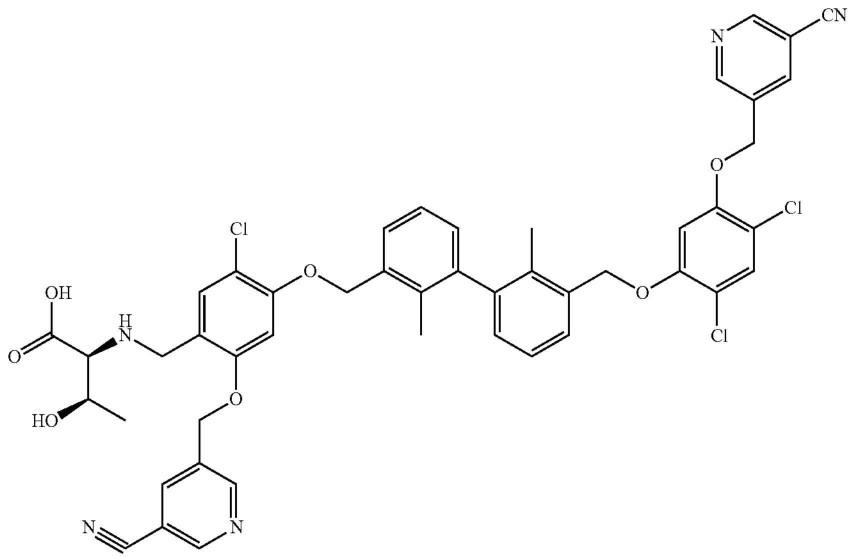 [SMILES: Cc1c(COc2cc(OCc3cncc(C#N)c3)c(Cl)cc2Cl)cccc1-c1cccc(COc2cc(OCc3cncc(C#N)c3)c(CN[C@H](C(=O)O)[C@@H](C)O)cc2Cl)c1C] | M | 2.30 | 892.2 | 892.1 |
| 70020 | 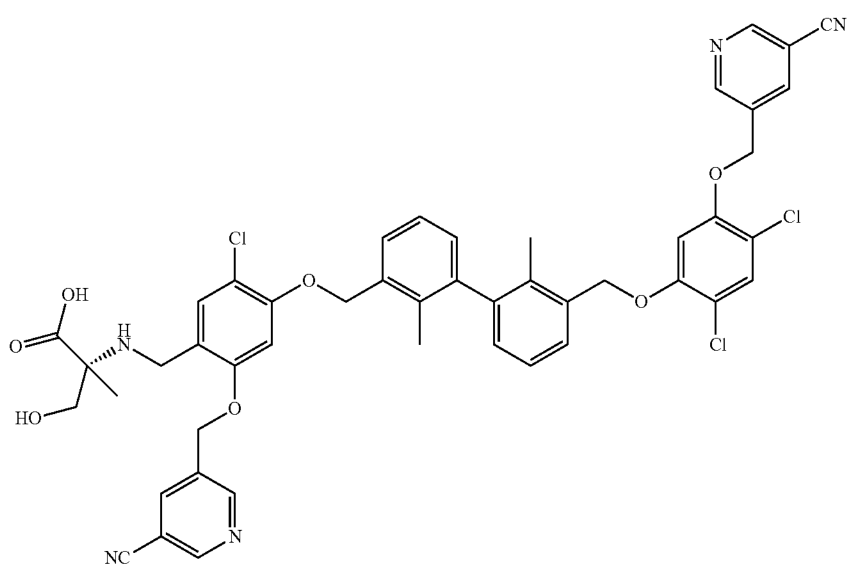 [SMILES: Cc1c(COc2cc(OCc3cncc(C#N)c3)c(Cl)cc2Cl)cccc1-c1cccc(COc2cc(OCc3cncc(C#N)c3)c(CN[C@](C)(CO)C(=O)O)cc2Cl)c1C] | M | 2.32 | 892.2 | 892.1 |

TABLE 70000-continued

| Cmpd# | Structure | LC-MS Method | R_f (min) | MS (M + H)+ Calcd. | MS (M + H)+ Observ. |
|---|---|---|---|---|---|
| 70030 | 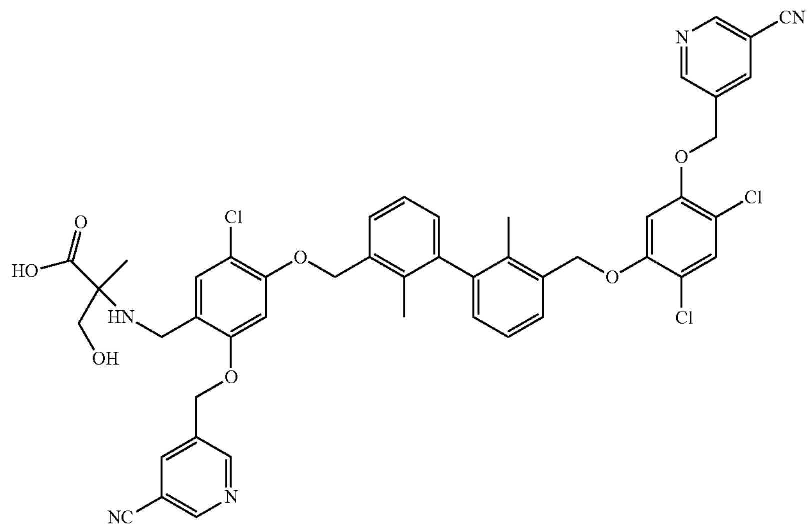 [SMILES: Cc1c(COc2cc(OCc3cncc(C#N)c3)c(Cl)cc2Cl)cccc1-c1cccc(COc2cc(OCc3cncc(C#N)c3)c(CNC(C)(CO)C(=O)O)cc2Cl)c1C] | M | 2.31 | 892.2 | 892.1 |
| 70040 | 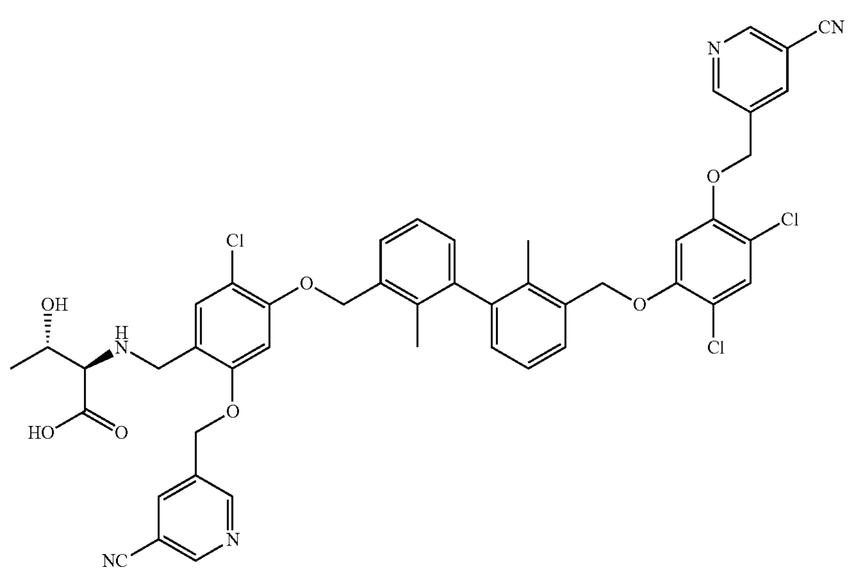 [SMILES: Cc1c(COc2cc(OCc3cncc(C#N)c3)c(Cl)cc2Cl)cccc1-c1cccc(COc2cc(OCc3cncc(C#N)c3)c(CN[C@@H](C(=O)O)[C@H](C)O)cc2Cl)c1C] | M | 2.31 | 892.2 | 892.1 |

TABLE 70000-continued

| Cmpd# | Structure | LC-MS Method | $R_f$ (min) | MS (M + H)+ Calcd. | MS (M + H)+ Observ. |
|---|---|---|---|---|---|
| 70050 | 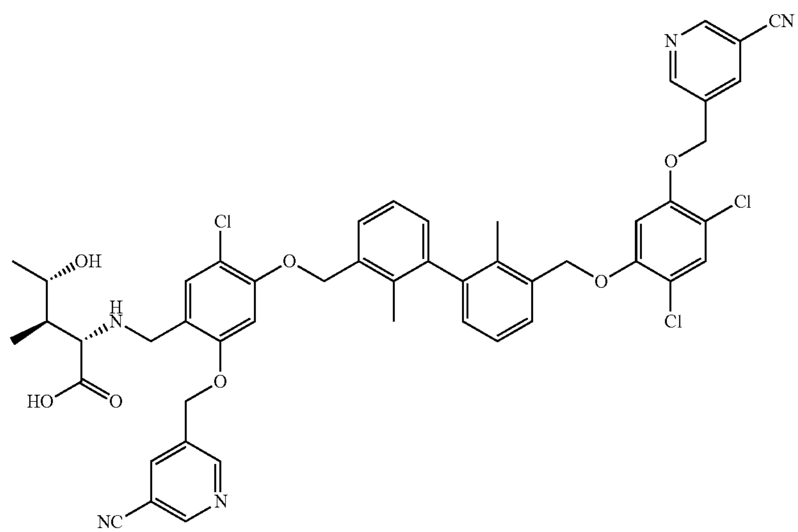 [SMILES: Cc1c(COc2cc(OCc3cncc(C#N)c3)c(Cl)cc2Cl)cccc1-c1cccc(COc2cc(OCc3cncc(C#N)c3)c(CN[C@H](C(=O)O)[C@@H](C)[C@H](C)O)cc2Cl)c1C] | N | 2.35 | 920.2 | 920.1 |
| 70060 | 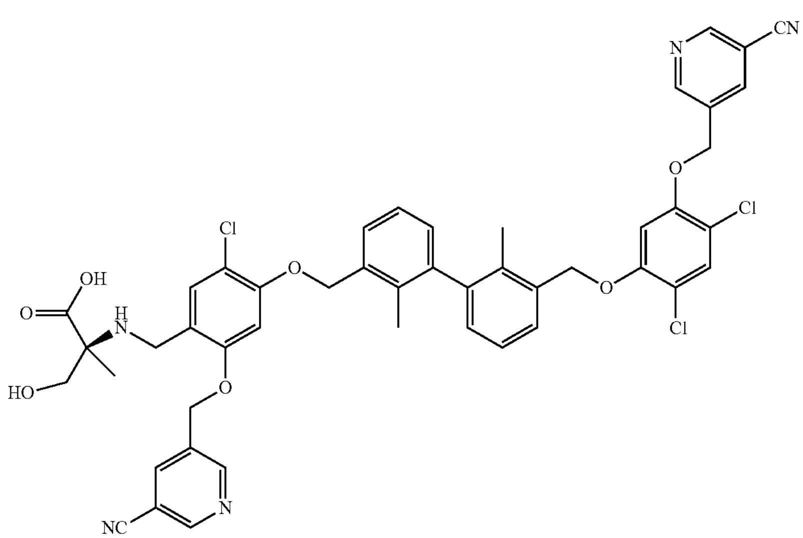 [SMILES: Cc1c(COc2cc(OCc3cncc(C#N)c3)c(Cl)cc2Cl)cccc1-c1cccc(COc2cc(OCc3cncc(C#N)c3)c(CN[C@@](C)(CO)C(=O)O)cc2Cl)c1C] | M | 2.32 | 892.2 | 892.1 |

Intermediates Used in Synthesizing the Structures in Table 80000 and Table 90000:

Diacid I

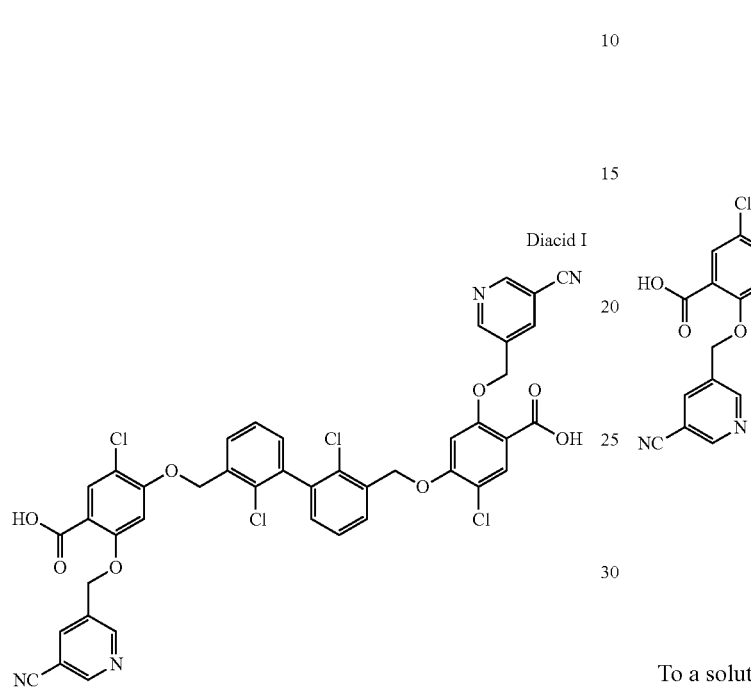

Diacid I

To a solution of 5,5'-((((((2,2'-dichloro-[1,1'-biphenyl]-3,3'-diyl)bis(methylene)) bis(oxy))bis(4-chloro-6-formyl-3,1-phenylene))bis(oxy))bis(methylene))dinicotinonitrile (800 mg, 0.970 mmol) in THF (20 mL)/water (5 mL) was added sodium chlorite (263 mg, 2.91 mmol) and sulfamic acid (283 mg, 2.91 mmol) at 5° C. The mixture was stirred at 5° C. for 5 minutes and then room temperature for 20 minutes. The reaction mixture was diluted with EtOAc and washed with water. The precipitate was collected by filtration to give 4,4'-(((2,2'-dichloro-[1,1'-biphenyl]-3,3'-diyl)bis(methylene))bis(oxy))bis(5-chloro-2-((5-cyanopyridin-3-yl)methoxy)benzoic acid) (700 mg, 0.817 mmol, 84% yield). $^1$H NMR (500 MHz, DMSO-$d_6$) δ 9.00 (br d, J=14.0 Hz, 4H), 8.49 (br s, 2H), 7.76 (s, 4H), 7.54 (t, J=7.5 Hz, 2H), 7.41 (br d, J=7.0 Hz, 2H), 7.13 (br s, 2H), 5.41 (br s, 4H), 5.37 (br s, 4H). LCMS (M+H)=855.4

Diacid II

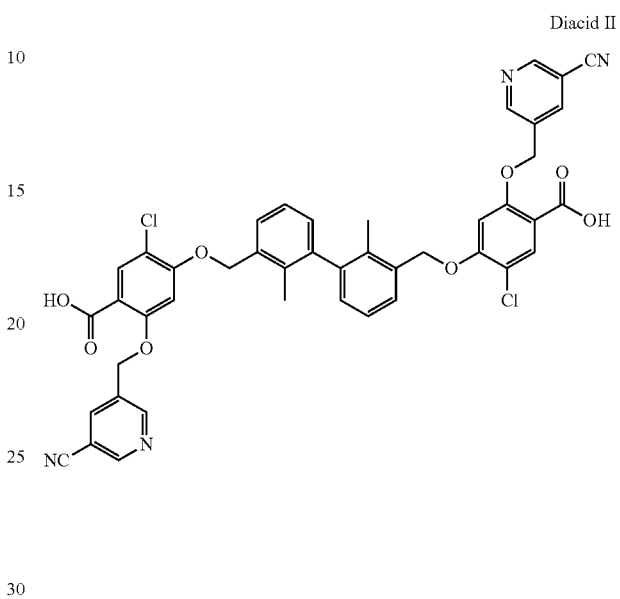

Diacid II

To a solution of 5,5'-((((((2,2'-dimethyl-[1,1'-biphenyl]-3,3'-diyl)bis(methylene)) bis(oxy))bis(4-chloro-6-formyl-3,1-phenylene))bis(oxy))bis(methylene))dinicotinonitrile (400 mg, 0.510 mmol) in THF (10 mL)/water (3 mL) was added sodium chlorite (138 mg, 1.531 mmol) and sulfamic acid (149 mg, 1.531 mmol) at 5° C. The mixture was stirred at 5° C. for 5 minutes and then room temperature for 20 minutes. The reaction mixture was diluted with EtOAc and washed with water. The precipitate was collected by filtration to give 4,4'-(((2,2'-dimethyl-[1,1'-biphenyl]-3,3'-diyl)bis(methylene))bis(oxy))bis(5-chloro-2-((5-cyanopyridin-3-yl)methoxy)benzoic acid) (300 mg, 0.357 mmol, 70.0% yield). $^1$H NMR (500 MHz, DMSO-$d_6$) δ 9.01 (br d, J=8.2 Hz, 4H), 8.48 (s, 2H), 7.78 (s, 2H), 7.55 (br d, J=7.3 Hz, 2H), 7.32 (br t, J=7.6 Hz, 2H), 7.20 (s, 2H), 7.14 (br d, J=7.0 Hz, 2H), 5.48-5.34 (m, 8H), 2.11-2.00 (m, 6H). LCMS (M+H)=815.2

General Procedure for the Preparation of the Structures in Tables 80000 to 90000:

Et$_3$N or iPr$_2$NEt (1-200 eq.) was added into a solution of diacid I or II (1 eq.), amine (1-10 eq.), HCTU or HATU or HOBt (1-20 eq.) in DMF or THF or dioxane or DME. The mixture was stirred at room temperature to 100° C. for 0.5 to 72 hours, before the reaction was quenched with methanol or water. After all the solvents were removed under vacuum, the residue was purified by the preparative HPLC to give the compounds of in Table 80000 and Table 90000.

TABLE 80000
| Cmpd# | Structure | LC-MS Method | R$_f$ (min) | MS (M + H)$^+$ Calcd. | MS (M + H)$^+$ Observ. |
|---|---|---|---|---|---|
| 80010 | 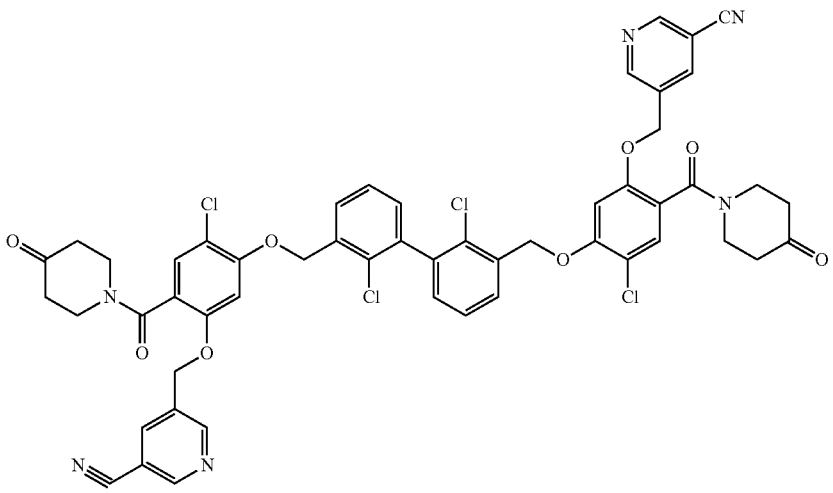 [SMILES: N#Cc1cncc(COc2cc(OCc3cccc(-c4cccc(COc5cc(OCc6cncc(C#N)c6)c(C(=O)N6CCC(=O)CC6)cc5Cl)c4Cl)c3Cl)c(Cl)cc2C(=O)N2CCC(=O)CC2)c1] | M | 2.15 | 1017.2 | 1017.3 |
| 80020 | 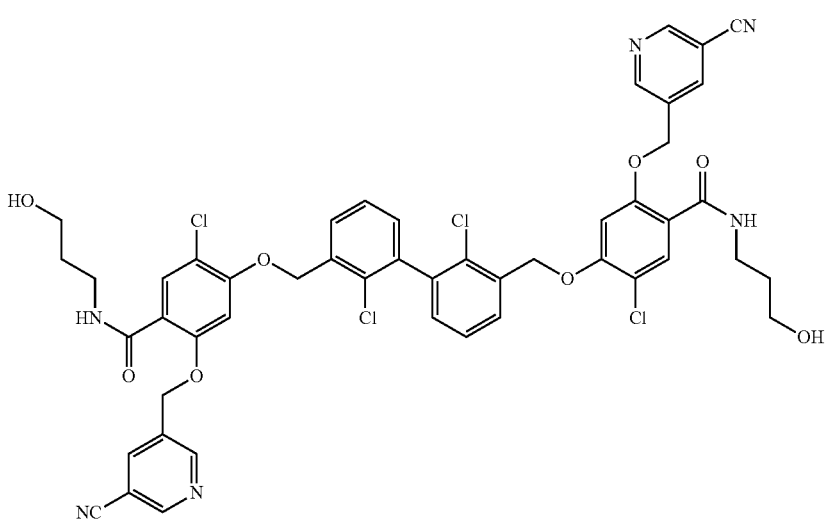 [SMILES: N#Cc1cncc(COc2cc(OCc3cccc(-c4cccc(COc5cc(OCc6cncc(C#N)c6)c(C(=O)NCCCO)cc5Cl)c4Cl)c3Cl)c(Cl)cc2C(=O)NCCCO)c1] | N | 2.03 | 969.2 | 969.2 |
| 80030 | 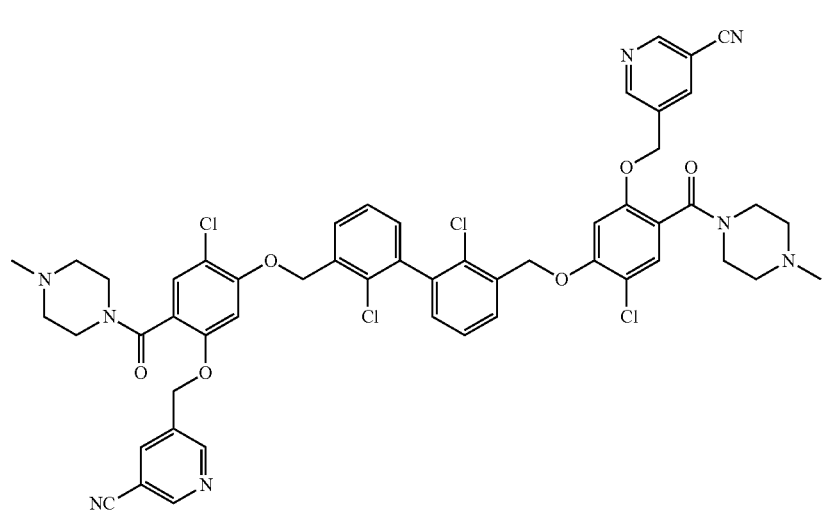 | M | 1.61 | 1019.2 | 1019.2 |

TABLE 80000-continued

| Cmpd# | Structure | LC-MS Method | $R_f$ (min) | MS (M+H)+ Calcd. | MS (M+H)+ Observ. |
|---|---|---|---|---|---|
| 80040 | 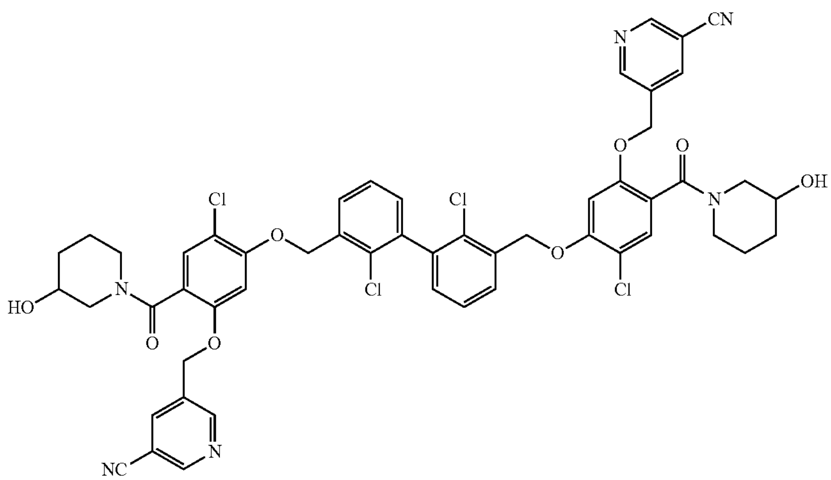 [SMILES: N#Cc1cncc(COc2cc(OCc3cccc(-c4cccc(COc5cc(OCc6cncc(C#N)c6)c(C(=O)N6CCCC(O)C6)cc5Cl)c4Cl)c3Cl)c(Cl)cc2C(=O)N2CCCC(O)C2)c1] | M | 2.08 | 1021.2 | 1021.1 |
| 80050 | 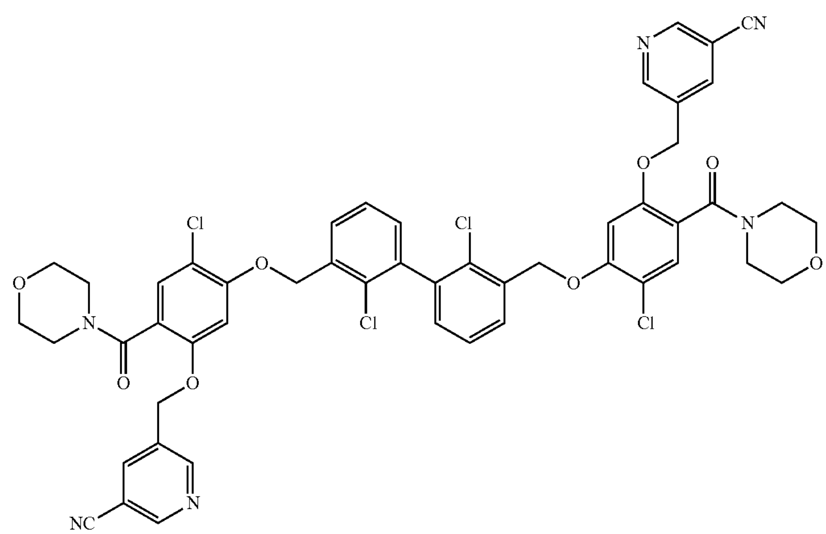 [SMILES: N#Cc1cncc(COc2cc(OCc3cccc(-c4cccc(COc5cc(OCc6cncc(C#N)c6)c(C(=O)N6CCOCC6)cc5Cl)c4Cl)c3Cl)c(Cl)cc2C(=O)N2CCOCC2)c1] | M | 2.27 | 993.2 | 993.3 |
| 80060 | 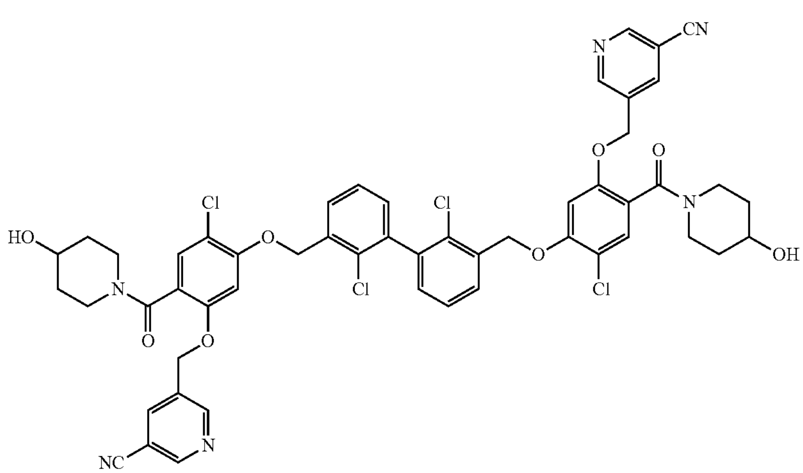 [SMILES: N#Cc1cncc(COc2cc(OCc3cccc(-c4cccc(COc5cc(OCc6cncc(C#N)c6)c(C(=O)N6CCC(O)CC6)cc5Cl)c4Cl)c3Cl)c(Cl)cc2C(=O)N2CCC(O)CC2)c1] | M | 2.03 | 1021.2 | 1021.1 |

TABLE 80000-continued

| Cmpd# | Structure | LC-MS Method | $R_f$ (min) | MS (M + H)+ Calcd. | MS (M + H)+ Observ. |
|---|---|---|---|---|---|
| 80090 | 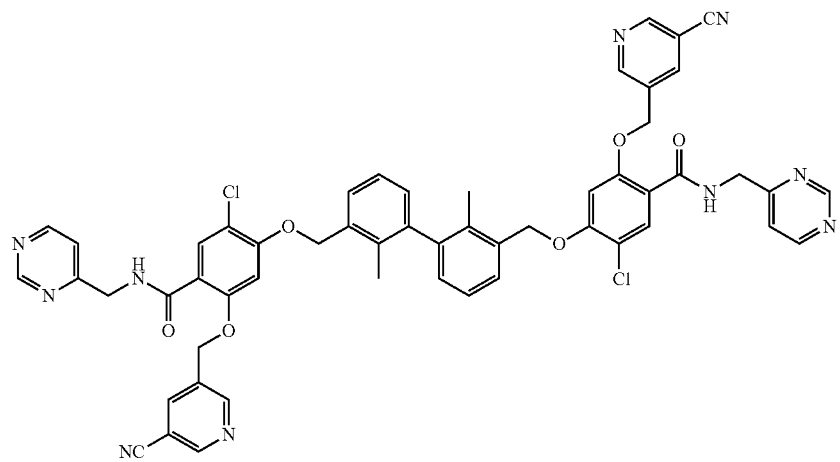 [SMILES: Cc1c(COc2cc(OCc3cncc(C#N)c3)c(C(=O)NCc3ccncn3)cc2Cl)cccc1-c1cccc(COc2cc(OCc3cncc(C#N)c3)c(C(=O)NCc3ccncn3)cc2Cl)c1C] | M | 2.11 | 997.3 | 997.2 |
| 80100 | 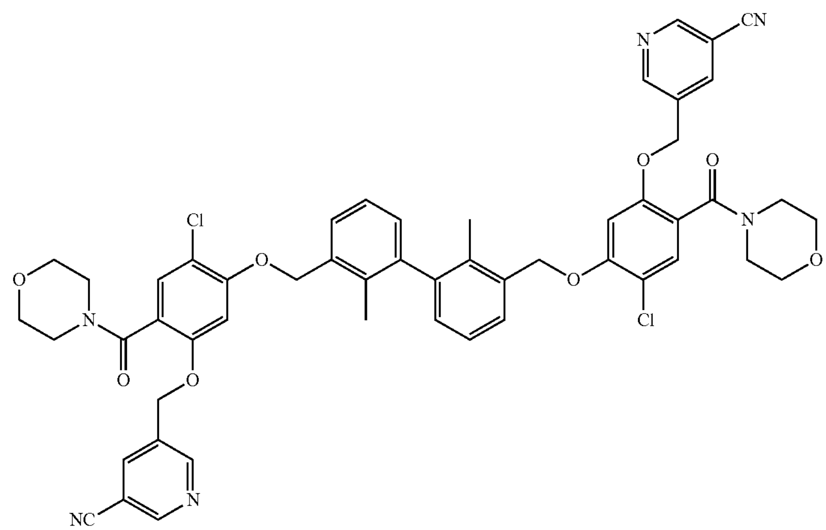 [SMILES: Cc1c(COc2cc(OCc3cncc(C#N)c3)c(C(=O)N3CCOCC3)cc2Cl)cccc1-c1cccc(COc2cc(OCc3cncc(C#N)c3)c(C(=O)N3CCOCC3)cc2Cl)c1C] | M | 2.27 | 953.3 | 953.2 |
| 80120 | 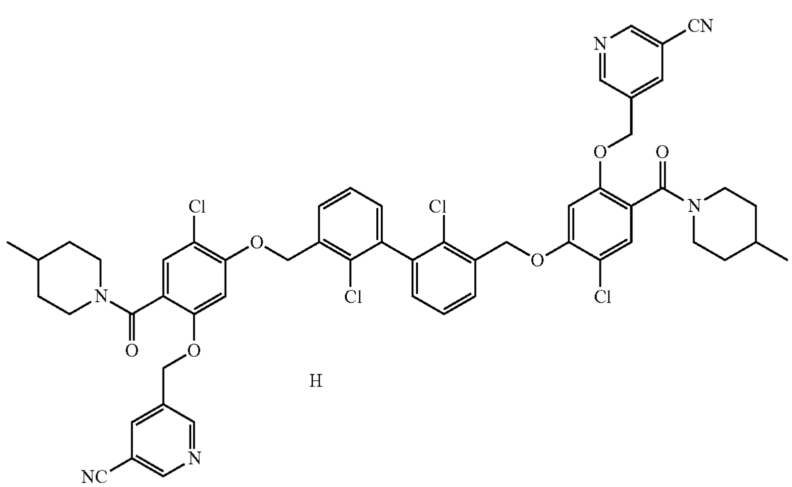 | M | 2.8 | 1017.3 | 1017.2 |

TABLE 80000-continued

| Cmpd# | Structure | LC-MS Method | $R_f$ (min) | MS (M+H)$^+$ Calcd. | MS (M+H)$^+$ Observ. |
|---|---|---|---|---|---|
| 80140 | 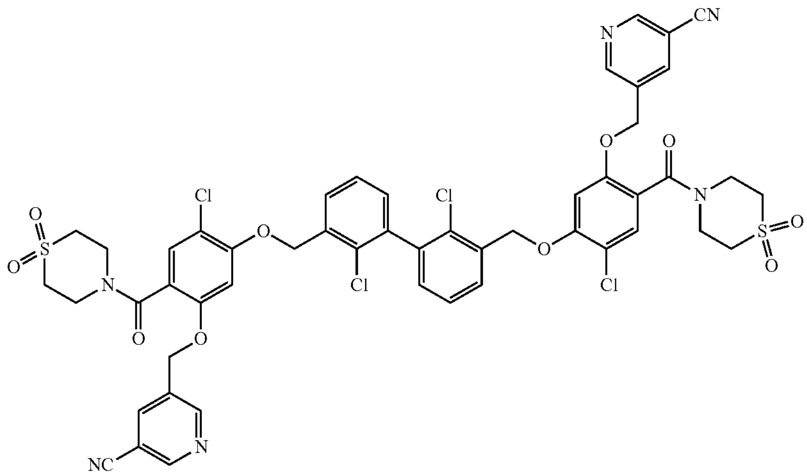 [SMILES: N#Cc1cncc(COc2cc(OCc3cccc(-c4cccc(COc5cc(OCc6cncc(C#N)c6)c(C(=O)N6CCS(=O)(=O)CC6)cc5Cl)c4Cl)c3Cl)c(Cl)cc2C(=O)N2CCS(=O)(=O)CC2)c1] | M | 2.08 | 1089.1 | 1089.0 |
| 80160 | 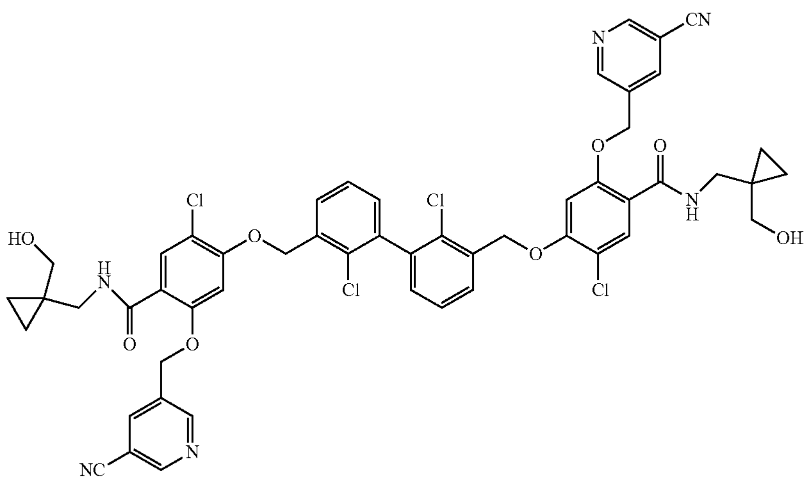 [SMILES: N#Cc1cncc(COc2cc(OCc3cccc(-c4cccc(COc5cc(OCc6cncc(C#N)c6)c(C(=O)NCC6(CO)CC6)cc5Cl)c4Cl)c3Cl)c(Cl)cc2C(=O)NCC2(CO)CC2)c1] | M | 2.18 | 1021.2 | 1021.3 |
| 80180 | 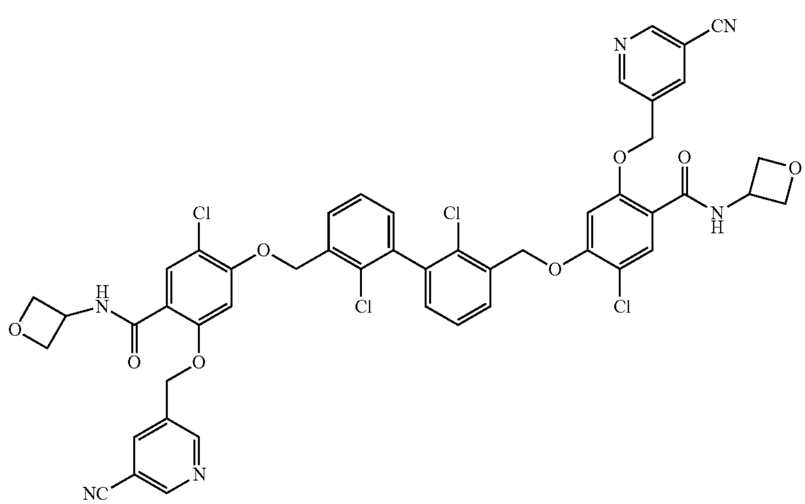 [SMILES: N#Cc1cncc(COc2cc(OCc3cccc(-c4cccc(COc5cc(OCc6cncc(C#N)c6)c(C(=O)NC6COC6)cc5Cl)c4Cl)c3Cl)c(Cl)cc2C(=O)NC2COC2)c1] | N | 3.01 | 965.1 | 965.1 |

TABLE 80000-continued
| Cmpd# | Structure | LC-MS Method | $R_f$ (min) | MS (M + H)$^+$ Calcd. | MS (M + H)$^+$ Observ. |
|---|---|---|---|---|---|
| 80200 | 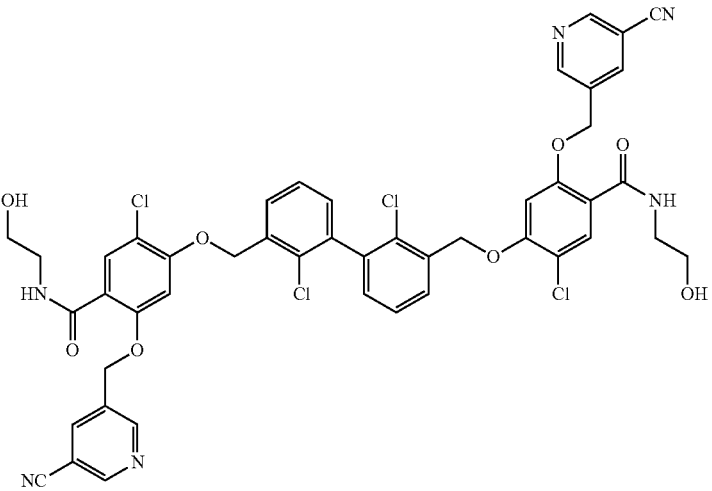 [SMILES: N#Cc1cncc(COc2cc(OCc3cccc(-c4cccc(COc5cc(OCc6cncc(C#N)c6)c(C(=O)NCCO)cc5Cl)c4Cl)c3Cl)c(Cl)cc2C(=O)NCCO)c1] | N | 2.86 | 941.1 | 941.1 |
| 80220 | 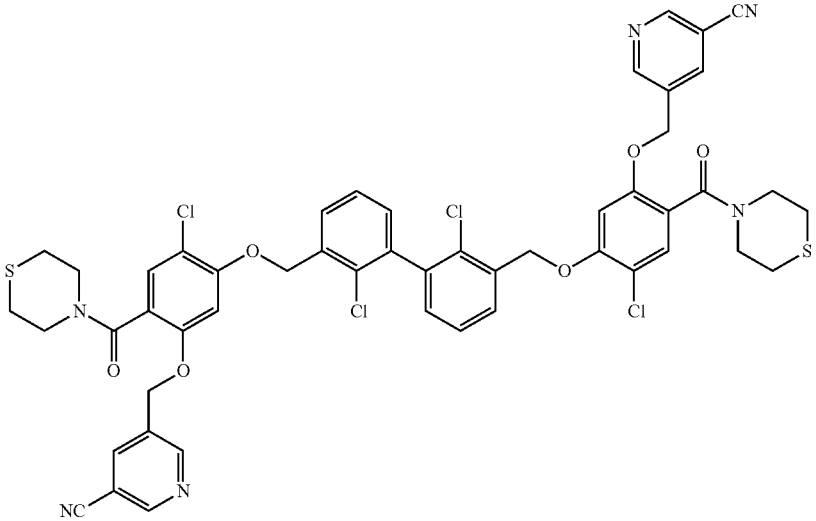 [SMILES: N#Cc1cncc(COc2cc(OCc3cccc(-c4cccc(COc5cc(OCc6cncc(C#N)c6)c(C(=O)N6CCSCC6)cc5Cl)c4Cl)c3Cl)c(Cl)cc2C(=O)N2CCSCC2)c1] | M | 2.46 | 1025.1 | 1025.1 |
| 80230 | 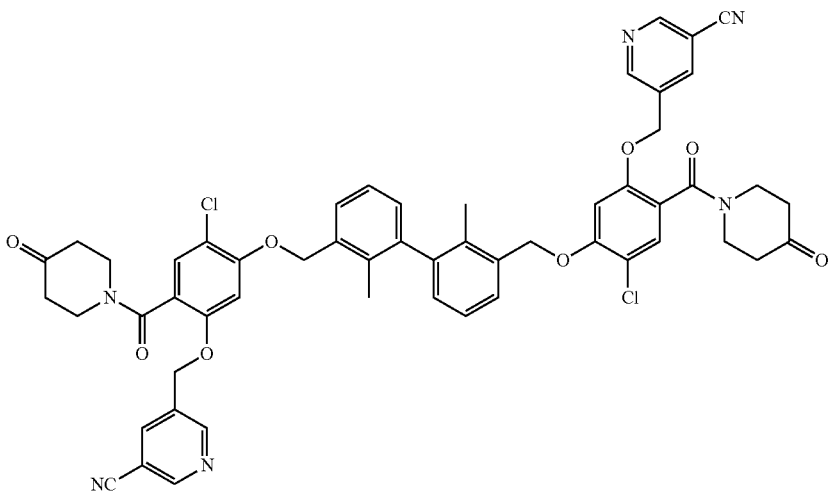 [SMILES: Cc1c(COc2cc(OCc3cncc(C#N)c3)c(C(=O)N3CCC(=O)CC3)cc2Cl)cccc1-c1cccc(COc2cc(OCc3cncc(C#N)c3)c(C(=O)N3CCC(=O)CC3)cc2Cl)c1C] | M | 2.17 | 977.3 | 977.2 |

TABLE 90000
| Cmpd# | Structure | LC-MS Method | $R_f$ (min) | MS (M+H)+ Calcd. | MS (M+H)+ Observ. |
|---|---|---|---|---|---|
| 90010 | 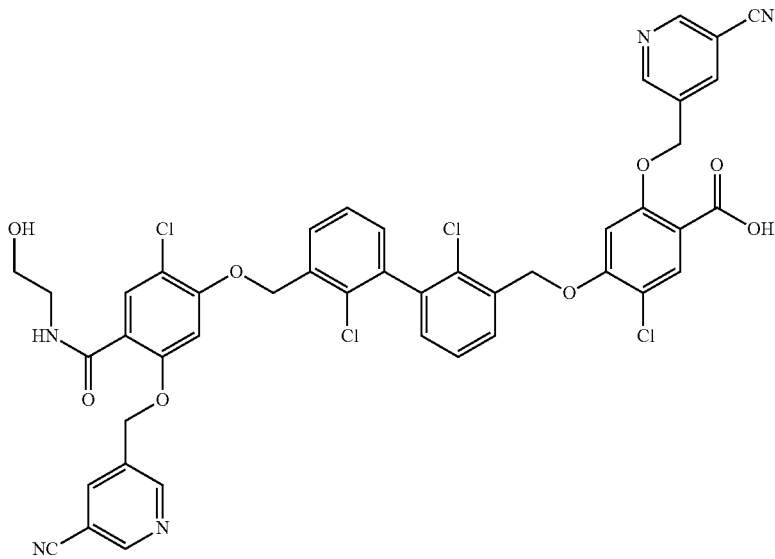 [SMILES: N#Cc1cncc(COc2cc(OCc3cccc(-c4cccc(COc5cc(OCc6cncc(C#N)c6)c(C(=O)NCCO)cc5Cl)c4Cl)c3Cl)c(Cl)cc2C(=O)O)c1] | N | 2.59 | 898.1 | 898.0 |
| 90020 | 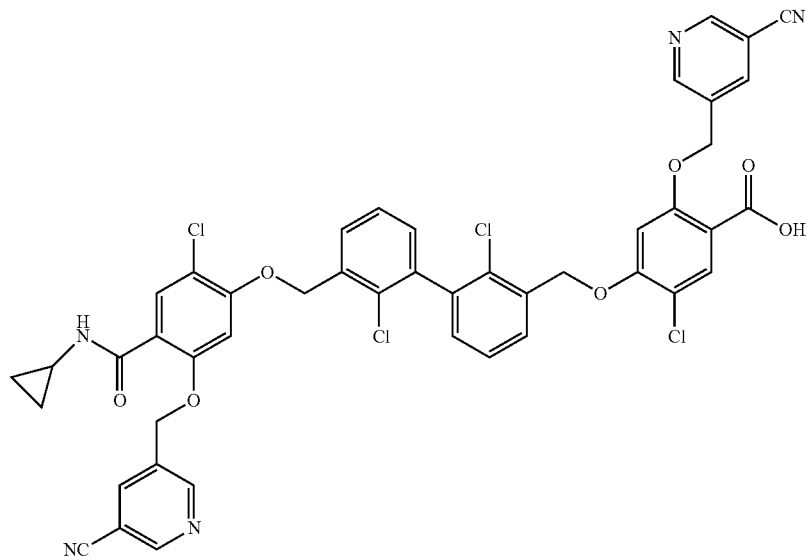 [SMILES: N#Cc1cncc(COc2cc(OCc3cccc(-c4cccc(COc5cc(OCc6cncc(C#N)c6)c(C(=O)NC6CC6)cc5Cl)c4Cl)c3Cl)c(Cl)cc2C(=O)O)c1] | M | 3.19 | 894.1 | 893.9 |

TABLE 90000-continued
| Cmpd# | Structure | LC-MS Method | $R_f$ (min) | MS (M + H)$^+$ Calcd. | MS (M + H)$^+$ Observ. |
|---|---|---|---|---|---|
| 90030 | 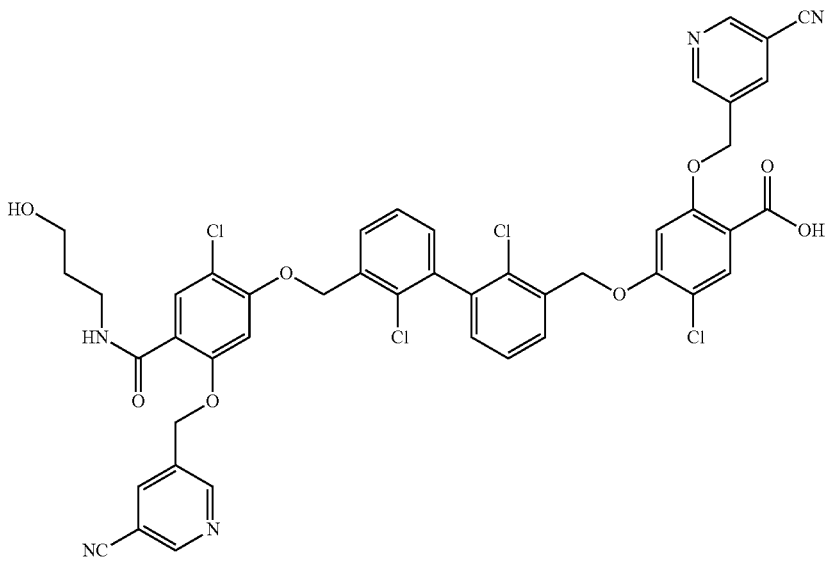 [SMILES: N#Cc1cncc(COc2cc(OCc3cccc(-c4cccc(COc5cc(OCc6cncc(C#N)c6)c(C(=O)NCCCO)cc5Cl)c4Cl)c3Cl)c(Cl)cc2C(=O)O)c1] | M | 2.14 | 912.1 | 912.1 |
| 90040 | 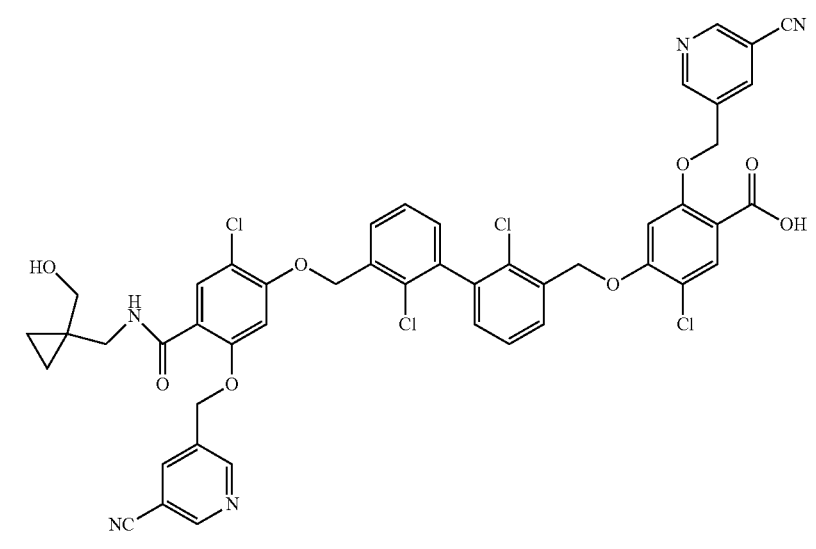 [SMILES: N#Cc1cncc(COc2cc(OCc3cccc(-c4cccc(COc5cc(OCc6cncc(C#N)c6)c(C(=O)NCC6(CO)CC6)cc5Cl)c4Cl)c3Cl)c(Cl)cc2C(=O)O)c1] | M | 2.22 | 938.1 | 938.2 |

TABLE 90000-continued

| Cmpd# | Structure | LC-MS Method | R_f (min) | MS (M+H)+ Calcd. | MS (M+H)+ Observ. |
|---|---|---|---|---|---|
| 90050 | 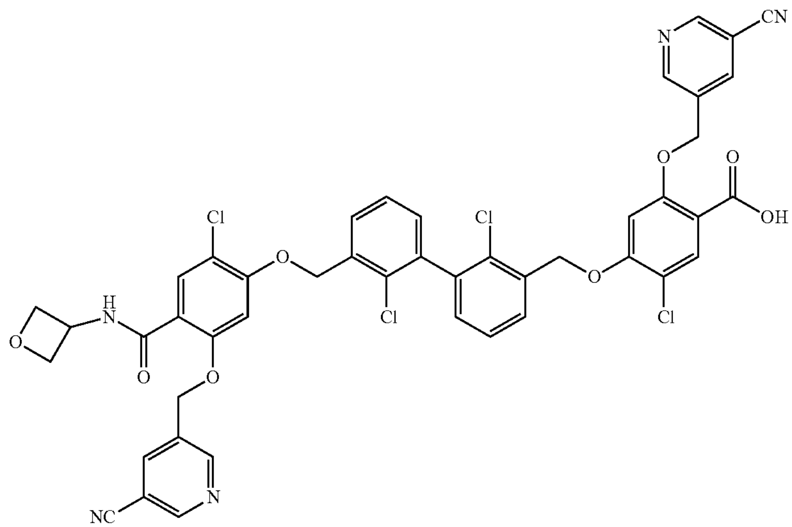 [SMILES: N#Cc1cncc(COc2cc(OCc3cccc(-c4cccc(COc5cc(OCc6cncc(C#N)c6)c(C(=O)NC6COC6)cc5Cl)c4Cl)c3Cl)c(Cl)cc2C(=O)O)c1] | N | 2.68 | 910.1 | 910.1 |
| 90060 | 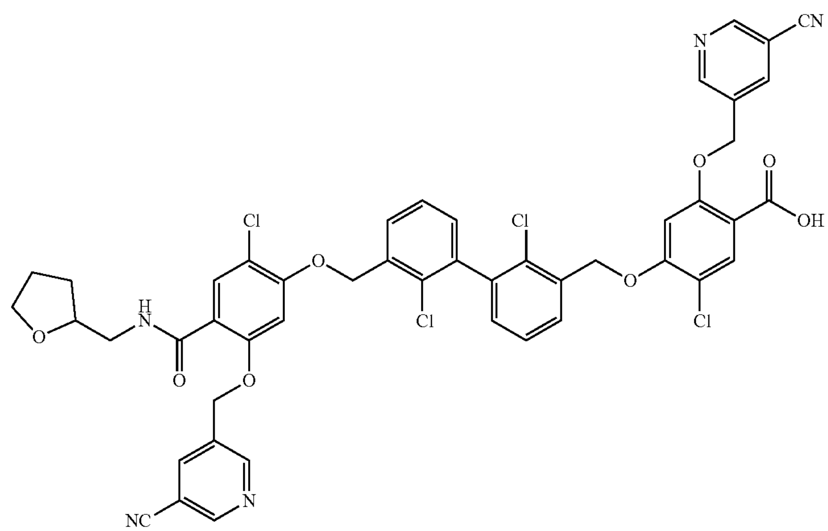 [SMILES: N#Cc1cncc(COc2cc(OCc3cccc(-c4cccc(COc5cc(OCc6cncc(C#N)c6)c(C(=O)NCC6CCCO6)cc5Cl)c4Cl)c3Cl)c(Cl)cc2C(=O)O)c1] | M | 2.51 | 938.1 | 938.1 |

Biological Assay

The ability of the compounds of formula (I) to bind to PD-L1 was investigated using a PD-1/PD-L1 Homogenous Time-Resolved Fluorescence (HTRF) binding assay.

Homogenous Time-Resolved Fluorescence (HTRF) Binding Assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 µl of assay buffer, followed by addition of PD-1-Ig (20 nM final) in 1 µl of assay buffer and further incubation for 15 m. HTRF detection was achieved using europium crypate-labeled anti-Ig (1 nM final) and allophycocyanin (APC) labeled anti-His (20 nM final). Antibodies were diluted in HTRF detection buffer and 5 µl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and CD80-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-239)-TVMV-His] were expressed in HEK293T cells and purified sequentially by ProteinA affinity chromatography and size exclusion chromatography. Human PD-L2-His and CD80-His was obtained through commercial sources.

Sequence of Recombinant Human PD-1-Ig

```
hPD1(25-167)-3S-IG
                                                       (SEQ ID NO: 1)
  1    LDSPDRPWNP PTFSPALLVV TEGDNATFTC SFSNTSESPV LNWYRMSPSN

51    QTDKLAAFPE DRSQPGQDCR FRVTQLPNGR DFHMSVVRAR RNDSGTYLCG

101    AISLAPKAQI KESLRAELRV TERRAEVPTA HPSPSPRPAG QFQGSPGGGG

151    GREPKSSDKT HTGPPSPAPE LLGGSSVFLF PPKPDKTLMI SRTPEVTCVV

201    VDVSHEDPEV KFNWYVDGVE VHNAKTKPRE EQYNSTYPVV SVLTVLHQDW

251    LNGKEYKCKV SNKALPAPIE KTISKAKGQP REPQVYTLPP SRDELTKNQV

301    SLTCLVKGFY PSDIAVEWES NGQPENNYKT TPPVLDSDGS FFLYSKLTVD

351    KSPMQQGNVF SCSVMHEALH NHYTQKSLSL SPGK
```

Sequence of Recombinant Human PD-L1-his

```
hPDL1(18-239)-TVMV-His
                                                       (SEQ ID NO: 2)
  1    AFTVTVPKDL YVVEYGSNMT IECKFPVEKQ LDLAALIVYW EMEDKNIIQF

51    VHGEEDLKVQ HSSYRQRAPL LKDQLSLGNA ALQITDVKLQ DAGVYRCMIS

101    YGGADYKRIT VKVNAPYNKI NQRILVVDPV TSEHELTCQA EGYPKAEVIW

151    TSSDHQVLSG KTTTTNSKRE EKLFNVTSTL RINTTTNEIF YCTFRRLDPE

201    ENHTAELVIP ELPLAHPPNE RTGSSETVRF QGHHHHHH
```

The table below lists the IC$_{50}$ values for representative examples of this disclosure measured in the PD-1/PD-L1 Homogenous Time-Resolved Fluorescence (HTRF) binding assay. Ranges are as follows: A=0.00004 μM–0.0200 μM; B=0.0201 μM–0.0900 μM; C=0.0901 μM–1.000 μM; D=1.001 μM–10.00 μM; E=>10 μM.

| Example Number | Range or IC50 (μM) |
|---|---|
| 1001 | B |
| 1002 | A |
| 1003 | E |
| 1004 | D |
| 2001 | B |
| 2002 | 0.099 |
| 2003 | B |
| 2004 | B |
| 2005 | B |
| 2006 | C |
| 2007 | C |
| 2008 | C |
| 2009 | B |
| 2010 | B |
| 2011 | B |
| 2012 | C |
| 2013 | C |
| 2014 | B |
| 2015 | B |
| 2016 | B |
| 2017 | B |
| 2018 | 0.069 |
| 2019 | A |
| 2020 | A |
| 2021 | B |
| 2022 | A |
| 2023 | B |
| 2024 | B |
| 2025 | B |

-continued

| Example Number | Range or IC50 (μM) |
|---|---|
| 2026 | A |
| 2027 | B |
| 2028 | A |
| 2029 | A |
| 2030 | A |
| 2031 | A |
| 2032 | B |
| 2033 | A |
| 2034 | B |
| 2035 | A |
| 2036 | C |
| 2037 | C |
| 2038 | C |
| 2039 | D |
| 2040 | B |
| 2041 | C |
| 2042 | B |
| 2043 | C |
| 2044 | C |
| 2045 | C |
| 2046 | B |
| 2047 | C |
| 2048 | B |
| 2049 | C |
| 2050 | D |
| 2051 | D |
| 2052 | C |
| 2053 | C |
| 2054 | B |
| 2055 | C |
| 2056 | 3.177 |
| 2057 | C |
| 2058 | C |
| 2059 | A |
| 2060 | B |
| 2061 | B |

| Example Number | Range or IC50 (μM) |
|---|---|
| 2062 | B |
| 2063 | B |
| 2064 | B |
| 2065 | B |
| 2066 | C |
| 2067 | B |
| 2068 | C |
| 2069 | C |
| 2070 | C |
| 2071 | C |
| 2072 | C |
| 2073 | B |
| 2074 | C |
| 2075 | B |
| 2076 | B |
| 2077 | B |
| 2078 | A |
| 2079 | A |
| 2080 | A |
| 2081 | B |
| 2082 | C |
| 2083 | A |
| 2084 | B |
| 2085 | C |
| 2086 | A |
| 2087 | C |
| 2088 | A |
| 2089 | 0.0071 |
| 2090 | B |
| 2091 | B |
| 2092 | B |
| 2093 | B |
| 2094 | A |
| 2095 | B |
| 2096 | B |
| 2097 | C |
| 2098 | A |
| 2099 | 1.248 |
| 2100 | B |
| 2101 | B |
| 2102 | B |
| 2103 | A |
| 2104 | A |
| 2105 | B |
| 2106 | B |
| 2107 | B |
| 2108 | C |
| 2109 | C |
| 2110 | C |
| 2111 | B |
| 2112 | 0.081 |
| 2113 | B |
| 2114 | C |
| 2115 | B |
| 2116 | C |
| 2117 | C |
| 2118 | B |
| 2119 | A |
| 2120 | A |
| 2121 | A |
| 2122 | A |
| 2123 | A |
| 2124 | A |
| 2125 | A |
| 2126 | B |
| 2127 | A |
| 2128 | A |
| 2129 | C |
| 2131 | A |
| 3001 | A |
| 3002 | A |
| 3003 | A |
| 3004 | D |
| 3005 | D |
| 3006 | D |
| 3007 | A |
| 3008 | D |
| 3009 | D |
| 3010 | 10.00 |
| 3011 | B |
| 3012 | E |
| 3013 | D |
| 3014 | E |
| 3015 | E |
| 3016 | E |
| 3017 | D |
| 3018 | C |
| 3019 | 0.106 |
| 3020 | D |
| 3021 | E |
| 3022 | E |
| 3023 | C |
| 3024 | 0.012 |
| 3025 | C |
| 3026 | C |
| 3027 | D |
| 3028 | B |
| 3029 | A |
| 3030 | A |
| 3031 | A |
| 3032 | B |
| 2132 | A |
| 2133 | C |
| 2134 | C |
| 2135 | D |
| 2136 | 3.453 |
| 3033 | D |
| 3035 | A |
| 5001 | A |
| 5002 | B |
| 5003 | C |
| 5004 | A |
| 5005 | C |
| 5006 | A |
| 5007 | A |
| 5008 | B |
| 5009 | A |
| 5012 | B |
| 5013 | B |
| 5014 | B |
| 5015 | B |
| 5016 | 0.031 |
| 5017 | A |
| 5018 | A |
| 5019 | B |
| 5020 | A |
| 5021 | A |
| 5022 | A |
| 5023 | B |
| 5024 | A |
| 5025 | A |
| 5026 | A |
| 5027 | A |
| 5028 | C |
| 5029 | B |
| 5030 | A |
| 5031 | A |
| 5032 | A |
| 5033 | A |
| 5034 | B |
| 5035 | A |
| 5036 | A |
| 5037 | B |
| 5038 | C |
| 5039 | C |
| 5500 | C |
| 5501 | A |
| 5502 | A |
| 5503 | A |
| 5504 | A |
| 5505 | A |
| 5507 | A |

| Example Number | Range or IC50 (μM) |
|---|---|
| 40010 | A |
| 40040 | A |
| 40050 | A |
| 40060 | B |
| 40070 | A |
| 40090 | A |
| 40100 | A |
| 40110 | A |
| 40130 | A |
| 40140 | A |
| 40150 | B |
| 40160 | A |
| 40170 | A |
| 40180 | A |
| 40190 | A |
| 40200 | A |
| 40210 | 0.0011 |
| 40220 | A |
| 40230 | A |
| 40240 | A |
| 40250 | A |
| 40260 | A |
| 40270 | A |
| 40280 | A |
| 40300 | C |
| 40310 | B |
| 40340 | A |
| 40350 | A |
| 40360 | A |
| 40370 | A |
| 40380 | A |
| 40390 | B |
| 40400 | A |
| 40410 | A |
| 40420 | A |
| 40430 | A |
| 40440 | A |
| 40450 | A |
| 40460 | A |
| 40470 | A |
| 40480 | A |
| 40490 | A |
| 40500 | A |
| 40510 | A |
| 40520 | C |
| 40530 | C |
| 40550 | 9.22 |
| 40590 | C |
| 40620 | B |
| 40670 | B |
| 40680 | C |
| 40690 | C |
| 40700 | A |
| 40710 | A |
| 40720 | B |
| 40730 | 0.022 |
| 40740 | A |
| 40750 | A |
| 40760 | A |
| 40770 | 0.00004 |
| 40780 | A |
| 40800 | A |
| 40810 | B |
| 40820 | A |
| 40830 | A |
| 40840 | A |
| 40850 | A |
| 40870 | A |
| 40880 | A |
| 40890 | A |
| 40900 | D |
| 40910 | D |
| 40930 | A |
| 40940 | A |
| 40950 | 0.168 |
| 40960 | B |
| 40990 | A |
| 41010 | A |
| 41020 | A |
| 41030 | A |
| 41050 | B |
| 41070 | A |
| 41090 | A |
| 41100 | A |
| 41110 | A |
| 41120 | A |
| 41130 | A |
| 41140 | A |
| 41170 | A |
| 41180 | A |
| 41190 | A |
| 41200 | A |
| 41210 | A |
| 41220 | A |
| 41230 | B |
| 50020 | B |
| 50040 | 0.115 |
| 50060 | A |
| 50070 | A |
| 50080 | A |
| 50100 | A |
| 50110 | A |
| 50120 | A |
| 50150 | A |
| 50170 | A |
| 50180 | A |
| 50190 | A |
| 50200 | A |
| 50210 | A |
| 50220 | A |
| 50230 | A |
| 50240 | A |
| 50250 | A |
| 50260 | A |
| 50270 | 0.023 |
| 50280 | A |
| 50300 | A |
| 50310 | B |
| 50330 | A |
| 50340 | A |
| 50360 | A |
| 50380 | A |
| 50390 | A |
| 50400 | A |
| 60010 | A |
| 60020 | A |
| 60030 | 0.006 |
| 60040 | A |
| 60050 | A |
| 60060 | A |
| 60070 | A |
| 60080 | A |
| 60090 | B |
| 70010 | C |
| 70020 | A |
| 70030 | B |
| 70040 | 1.05 |
| 70050 | C |
| 70060 | B |
| 80010 | B |
| 80020 | C |
| 80030 | A |
| 80040 | B |
| 80050 | B |
| 80060 | A |
| 80090 | C |
| 80100 | A |

-continued

| Example Number | Range or IC50 (μM) |
|---|---|
| 80120 | 0.105 |
| 80140 | A |
| 80160 | D |
| 80180 | D |
| 80200 | C |
| 80220 | D |
| 80230 | B |
| 90010 | A |
| 90020 | B |
| 90030 | B |
| 90040 | C |

-continued

| Example Number | Range or IC50 (μM) |
|---|---|
| 90050 | C |
| 90060 | D |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, Hepatitis A, B, C, or D and cancer.

The invention claimed is:
1. A compound of formula (I)

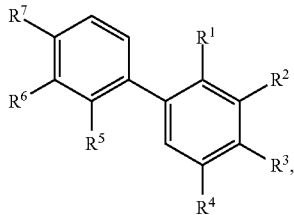

or a pharmaceutically acceptable salt thereof, wherein:
$R^1$ and $R^5$ are independently selected from hydrogen, —$CH_3$, cyano, halo, halomethyl, dihalomethyl, and trihalomethyl;
$R^2$ and $R^3$ are independently selected from hydrogen, —O(CH$_2$)$_m$Ph, —(CH$_2$)$_m$OPh, —O(CH$_2$)$_n$NR$^a$R$^b$, —(CH$_2$)$_m$Ph, -(alkenylene)Ph, —S(O)$_2$NH(CH$_2$)$_n$NR$^a$R$^b$, —S(O)$_2$NH(CH$_2$)$_n$CO$_2$H, —O(CH$_2$)piperidinyl, —O(CH$_2$)$_m$pyridinyl, —(CH$_2$)$_m$NH(CH$_2$)$_n$NR$^a$R$^b$, —NH(CH$_2$)$_n$NR$^a$R$^b$, —C(O)NH(CH$_2$)$_n$NR$^a$R$^b$, —NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H; wherein each piperidinyl group is optionally substituted with a $C_1$-$C_3$alkyl group; and wherein the pyridinyl group is optionally substituted with a cyano group; and wherein each Ph group is optionally substituted with one, two, or three groups independently selected from $C_1$-$C_3$alkoxy, $C_1$-$C_3$alkyl, $C_1$-$C_3$alkylcarbonyl, amino, carboxy, ($C_3$-$C_6$cycloalkyl)alkoxy, cyano, halo, hydroxy, hydroxymethyl, —CHO, —C(O)NR$^a$R$^b$, —(CH$_2$)$_m$NR$^a$R$^b$; —OCH$_2$phenyl wherein the phenyl is optionally substituted with one or two halo groups, and —OCH$_2$pyridinyl optionally substituted with a cyano group, aminocarbonyl group, or a pyrazole ring; or
$R^2$ and $R^3$, together with the atoms to which they are attached, form a 1,4-dioxane ring optionally substituted with —O(CH$_2$)$_n$NR$^a$R$^b$;
$R^4$ is selected from hydrogen, —O(CH$_2$)$_m$Ph, —(CH$_2$)$_m$OPh, —O(CH$_2$)$_n$NR$^a$R$^b$, —(CH$_2$)$_m$Ph, -(alkenylene)Ph, —S(O)$_2$NH(CH$_2$)$_n$NR$^a$R$^b$, —S(O)$_2$NH(CH$_2$)$_n$CO$_2$H, —O(CH$_2$)piperidinyl, —O(CH$_2$)$_m$pyridinyl, —NH(CH$_2$)$_n$NR$^a$R$^b$, —C(O)NH(CH$_2$)$_n$NR$^a$R$^b$, NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H, wherein each piperidinyl group is optionally substituted with a $C_1$-$C_3$alkyl group; and wherein the pyridinyl group is optionally substituted with a cyano group; and wherein each Ph group is optionally substituted with one, two, or three groups independently selected from $C_1$-$C_3$alkoxy, $C_1$-$C_3$alkyl, $C_1$-$C_3$alkylcarbonyl, amino, carboxy, cyano, ($C_3$-$C_6$cycloalkyl)alkoxy, halo, hydroxy, hydroxymethyl, —C(O)NR$^a$R$^b$, —(CH$_2$)$_m$NR$^a$R$^b$; —OCH$_2$phenyl wherein the phenyl is optionally substituted with one or two halo groups, and —OCH$_2$pyridinyl optionally substituted with a cyano group, aminocarbonyl group, or a pyrazole ring;
$R^6$ and $R^7$ are independently selected from hydrogen; —O(CH$_2$)$_m$Ph, —(CH$_2$)$_m$OPh, —O(CH$_2$)$_n$NR$^a$R$^b$, —(CH$_2$)$_m$Ph, -(alkenylene)Ph, —S(O)$_2$NH(CH$_2$)$_n$NR$^a$R$^b$, —S(O)$_2$NH(CH$_2$)$_n$CO$_2$H, —O(CH$_2$)piperidinyl, —O(CH$_2$)$_m$pyridinyl, —(CH$_2$)$_m$NH(CH$_2$)$_n$NR$^a$R$^b$, —NH(CH$_2$)$_n$NR$^a$R$^b$, —C(O)NH(CH$_2$)$_n$NR$^a$R$^b$, NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H, wherein the piperidinyl group is optionally substituted with a $C_1$-$C_3$alkyl group; and wherein the pyridinyl group is optionally substituted with a cyano group; and wherein each Ph group is optionally substituted with one, two, or three groups independently selected from $C_1$-$C_3$alkoxy, $C_1$-$C_3$alkyl, $C_1$-$C_3$alkylcarbonyl, amino, carboxy, cyano, ($C_3$-$C_6$cycloalkyl)alkoxy, halo, hydroxy, hydroxymethyl, —C(O)NR$^a$R$^b$, —(CH$_2$)$_m$NR$^a$R$^b$; —OCH$_2$phenyl wherein the phenyl is optionally substituted with one or two halo groups; and —OCH$_2$pyridinyl optionally substituted with a cyano group, aminocarbonyl group, or a pyrazole ring; or
$R^6$ and $R^7$, together with the atoms to which they are attached, form a 1,4-dioxane ring optionally substituted with —O(CH$_2$)$_n$NR$^a$R$^b$;
provided that at least two of $R^2$, $R^3$, $R^4$, $R^6$, and $R^7$ are other than hydrogen; and
provided that when $R^2$ is —(CH$_2$)$_m$OPh, —(CH$_2$)$_m$Ph, or -(alkenylene)Ph then $R^6$ is selected from —(CH$_2$)$_m$OPh, —(CH$_2$)$_m$Ph, and -(alkenylene)Ph;
m is 1, 2, or 3;
n is 2, 3, 4, 5;
$R^a$ and $R^b$ are independently selected from hydrogen, $C_1$-$C_3$alkyl, $C_1$-$C_3$alkylsulfonyl$C_1$-$C_3$alkyl, aminocarbonyl$C_1$-$C_6$alkyl, carboxy$C_2$-$C_6$alkenyl, carboxy$C_1$-$C_6$alkyl, (carboxy$C_1$-$C_3$alkyl)carbonyl, cyano$C_1$-$C_3$alkyl, ($C_3$-$C_6$cycloalkyl)$C_1$-$C_3$alkyl, $C_3$-$C_6$cycloalkyl, halo$C_1$-$C_3$alkyl, hydroxy$C_1$-$C_6$alkyl, (hydroxy$C_1$-$C_6$alkyl)carbonyl, imidazolyl$C_1$-$C_3$alkyl, morpholinyl$C_1$-$C_3$alkyl, oxeranyl, phenyl, phenyl$C_1$-$C_3$alkyl, piperidinyl, piperidinyl$C_1$-$C_3$alkyl, pyridinyl$C_1$-$C_3$alkyl, pyrimidinyl$C_1$-$C_3$alkyl, pyrazolyl$C_1$-$C_3$alkyl, tetrahydrofuryl$C_1$-$C_3$alkyl, thiazolyl, thiazolyl$C_1$-$C_3$alkyl, (NR$^c$R$^d$)$C_1$-$C_3$alkyl,

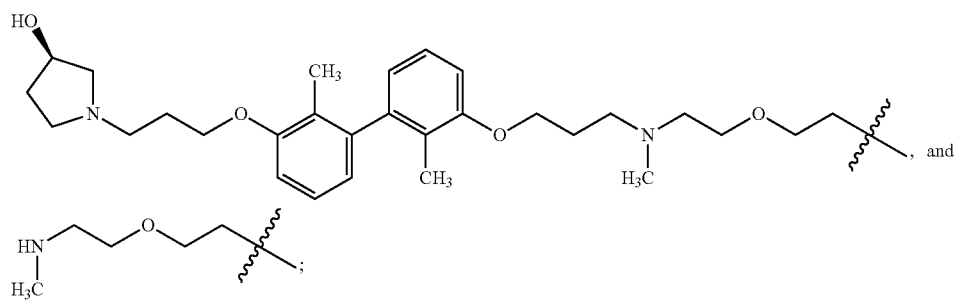

wherein the alkyl part of the carboxyC$_1$-C$_3$alkyl is further optionally substituted with one or two groups selected from C$_1$-C$_3$alkoxy, C$_1$-C$_3$alkylsulfanyl, cyano, hydroxy, indolyl, phenylC$_1$-C$_3$alkoxy, phenyl optionally substituted with one halo, and pyridinyl; and wherein the alkyl part of the (C$_3$-C$_6$cycloalkyl)C$_1$-C$_3$alkyl, the haloC$_1$-C$_3$alkyl, the imidazolylC$_1$-C$_3$alkyl, and the phenylC$_1$-C$_3$alkyl is optionally substituted with a aminocarbonyl or carboxy group;

wherein the alkyl part of, the is optionally substituted with an aminocarbonyl group;

wherein the C$_3$-C$_6$cycloalkyl and the cycloalkyl part of the (C$_3$-C$_6$cycloalkyl)C$_1$-C$_3$alkyl is optionally substituted with one, two, or three groups independently selected from hydroxy and hydroxyC$_1$-C$_3$alkyl; and wherein the alkyl part of the hydroxyC$_1$-C$_6$alkyl is further optionally substituted with one group selected from C$_1$-C$_3$alkoxy, C$_1$-C$_6$alkoxycarbonyl, C$_3$-C$_6$cycloalkyl, phenylC$_1$-C$_3$alkoxycarbonyl, tetrahydrofuryl, imidazolyl optionally substituted with one or two groups independently selected from C$_1$-C$_3$alkyl and halo, pyridinyl, phenyl optionally substituted with two halo groups, and thiazolyl; and wherein the imidazolyl part of the imidazolylC$_1$-C$_3$alkyl, the piperidinyl, the piperidinyl part of the piperidinylC$_1$-C$_3$alkyl, the pyrazolyl part of the pyrazolylC$_1$-C$_3$alkyl, and the pyridinyl part of the pyridinylC$_1$-C$_3$alkyl are optionally substituted with one, two, or three groups independently selected from C$_1$-C$_3$alkyl, cyano, halo, and hydroxyC$_1$-C$_3$alkyl; and wherein the phenyl and the phenyl part of the phenylC$_1$-C$_3$alkyl is optionally substituted with one or two groups independently selected from C$_1$-C$_3$alkoxy, amino and halo; or R$^a$ and R$^b$, together with the nitrogen atom to which they are attached, form a four-, five-, or six-membered ring optionally containing one additional heteroatom selected from nitrogen, oxygen, and sulfur; wherein the ring is optionally fused to a phenyl group to form a bicyclic structure and wherein the ring and bicyclic structure are optionally substituted with one or two groups selected from C$_1$-C$_3$alkoxy, C$_1$-C$_3$alkoxycarbonyl, C$_1$-C$_3$alkyl, C$_1$-C$_3$alkylcarbonyl, aminocarbonyl, carboxy, carboxyC$_1$-C$_3$alkyl, halo, hydroxy, hydroxyC$_1$-C$_3$alkyl, —NR$^c$R$^d$, (NR$^c$R$^d$)carbonyl, (NR$^c$R$^d$)carbonylC$_1$-C$_3$alkyl, oxo, pyridinyl, and phenyl optionally substituted with a halo or methoxy group; and R$^c$ and R$^d$ are independently selected from hydrogen, C$_1$-C$_3$alkyl, C$_1$-C$_3$alkylcarbonyl; and

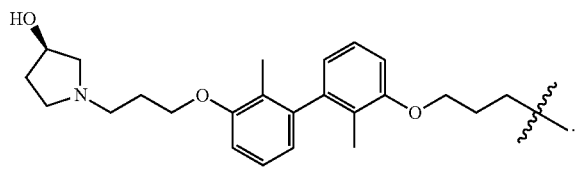 [SMILES: *CCCOc1cccc(-c2cccc(OCCCN3CC[C@@H](O)C3)c2C)c1C]

2. A compound of claim 1 wherein R$^4$ is hydrogen.

3. A compound of claim 2 wherein R$^1$ and R$^5$ are selected from —CH$_3$ and halo.

4. A compound of claim 3, or a pharmaceutically acceptable salt thereof, wherein:
one of R$^2$ and R$^3$ is hydrogen and the other is selected from —O(CH$_2$)$_m$Ph, —(CH$_2$)$_m$OPh, —O(CH$_2$)$_n$NR$^a$R$^b$, —S(O)$_2$NH(CH$_2$)$_n$NR$^a$R$^b$, —S(O)$_2$NH(CH$_2$)$_n$CO$_2$H, —O(CH$_2$)$_m$pyridinyl, —(CH$_2$)$_m$NH(CH$_2$)$_n$NR$^a$R$^b$, —C(O)NH(CH$_2$)$_n$NR$^a$R$^b$, —NHC(O)(CH$_2$)$_n$NR$^a$R$^b$, —NHC(O)NH(CH$_2$)$_n$NR$^a$R$^b$; and —NHC(O)NH(CH$_2$)$_n$CO$_2$H; wherein each piperidinyl group is optionally substituted with a C$_1$-C$_3$alkyl group; and wherein the pyridinyl group is optionally substituted with a cyano group; and wherein each Ph group is optionally substituted with one, two, or three groups independently selected from C$_1$-C$_3$alkoxy, C$_1$-C$_3$alkyl, C$_1$-C$_3$alkylcarbonyl, amino, carboxy, (C$_3$-C$_6$cycloalkyl)alkoxy, cyano, halo, hydroxy, hydroxymethyl, —CHO, —C(O)NR$^a$R$^b$, —(CH$_2$)$_m$NR$^a$R$^b$, —OCH$_2$phenyl wherein the phenyl is optionally substituted with one or two halo groups, and —OCH$_2$pyridinyl optionally substituted with a cyano group, aminocarbonyl group, or a pyrazole ring; and one of R$^6$ and R$^7$ is hydrogen and the other is selected from —O(CH$_2$)$_m$Ph, —(CH$_2$)$_m$OPh, —O(CH$_2$)$_n$NR$^a$R$^b$, —S(O)$_2$NH(CH$_2$)$_n$NR$^a$R$^b$, —S(O)$_2$NH(CH$_2$)$_n$CO$_2$H, —O(CH$_2$)$_m$pyridinyl, —(CH$_2$)$_m$NH(CH$_2$)$_n$NR$^a$R$^b$, —C(O)NH(CH$_2$)$_n$NR$^a$R$^b$, —NHC(O)(CH$_2$)$_n$NR$^a$R$^b$, —NHC(O)NH(CH$_2$)$_n$NR$^a$R$^b$, and —NHC(O)NH(CH$_2$)$_n$CO$_2$H, wherein the pyridinyl group is optionally substituted with a cyano group; and wherein each Ph group is optionally substituted with one, two, or three groups independently selected from C$_1$-C$_3$alkoxy, C$_1$-C$_3$alkyl, C$_1$-C$_3$alkylcarbonyl, amino, carboxy, cyano, (C$_3$-C$_6$cycloalkyl)alkoxy, halo, hydroxy, hydroxymethyl, —C(O)NR$^a$R$^b$, —(CH$_2$)$_m$NR$^a$R$^b$; —OCH$_2$phenyl wherein the phenyl is optionally substituted with one or two halo groups; and —OCH$_2$pyridinyl optionally substituted with a cyano group, aminocarbonyl group, or a pyrazole ring.

5. A compound selected from
2,2'-((((2-chloro-2'-methyl-[1,1'-biphenyl]-3,3'-diyl)bis(oxy))bis(propane-3,1-diyl))bis(3-hydroxypyrrolidine-1,3-diyl))diacetic acid;
1,1'-(((2-chloro-2'-methyl-[1,1'-biphenyl]-3,3'-diyl)bis(oxy))bis(propane-3,1-diyl))bis(4-hydroxypiperidine-4-carboxylic acid);
(2S,2'S,4R,4'R)-1,1'-(((2-chloro-2'-methyl-[1,1'-biphenyl]-3,3'-diyl)bis(oxy))bis(propane-3,1-diyl))bis(4-hydroxypyrrolidine-2-carboxylic acid);
(3R,3'R)-1,1'-(((2,6'-dimethyl-[1,1'-biphenyl]-3,3'-diyl)bis(oxy))bis(propane-3,1-diyl))bis(pyrrolidin-3-ol);
(R)-1-(4-(3-((3'-(3-(3-hydroxypyrrolidin-1-yl)propoxy)-2,2'-dimethyl-[1,1'-biphenyl]-3-yl)oxy)propyl)piperazin-1-yl)ethan-1-one;
(R)-1-(3-((3'-(3-(3-(dimethylamino)azetidin-1-yl)propoxy)-2,2'-dimethyl-[1,1'-biphenyl]-3-yl)oxy)propyl)pyrrolidin-3-ol;
(3R)-1-(3-((3'-(3-(3-(hydroxymethyl)piperidin-1-yl)propoxy)-2,2'-dimethyl-[1,1'-biphenyl]-3-yl)oxy)propyl)pyrrolidin-3-ol;
(R)-1-(3-((3'-(3-(6,7-dimethoxy-3,4-dihydroisoquinolin-2(1H)-yl)propoxy)-2,2'-dimethyl-[1,1'-biphenyl]-3-yl)oxy)propyl)pyrrolidin-3-ol;
(R)-1-(3-((2,2'-dimethyl-3'-(3-((2-morpholinoethyl)amino)propoxy)-[1,1'-biphenyl]-3-yl)oxy)propyl)pyrrolidin-3-ol;
(R)-1-(3-((2,2'-dimethyl-3'-(3-((pyridin-4-ylmethyl)amino)propoxy)-[1,1'-biphenyl]-3-yl)oxy)propyl)pyrrolidin-3-ol;
(R)-1-(3-((3'-(3-(2-(dimethylamino)ethyl)amino)propoxy)-2,2'-dimethyl-[1,1'-biphenyl]-3-yl)oxy)propyl)pyrrolidin-3-ol;

(R)-1-(3-((3'-(3-((2-(1H-pyrazol-1-yl)ethyl)amino)
propoxy)-2,2'-dimethyl-[1,1'-biphenyl]-3-yl)oxy)pro-
pyl)pyrrolidin-3-ol;
(R)-1-(3-((2,2'-dimethyl-3'-(3-((2-(3-methyl-1H-pyrazol-
1-yl)ethyl)amino)propoxy)-[1,1'-biphenyl]-3-yl)oxy)
propyl)pyrrolidin-3-ol;
(R)-1-(3-((2,2'-dimethyl-3'-(3-((2-(methylsulfonyl)ethyl)
amino)propoxy)-[1,1'-biphenyl]-3-yl)oxy)propyl)pyr-
rolidin-3-ol;
(S)-3-((3-((3'-(3-((R)-3-hydroxypyrrolidin-1-yl)
propoxy)-2,2'-dimethyl-[1,1'-biphenyl]-3-yl)oxy)pro-
pyl)amino)propane-1,2-diol;
(3-((3'-(3-((R)-3-hydroxypyrrolidin-1-yl)propoxy)-2,2'-
dimethyl-[1,1'-biphenyl]-3-yl)oxy)propyl)-L-serine;
(S)-3-hydroxy-2-((3-((3'-(3-((R)-3-hydroxypyrrolidin-1-
yl)propoxy)-2,2'-dimethyl-[1,1'-biphenyl]-3-yl)oxy)
propyl)amino)-2-methylpropanoic acid;
(R)-1-(3-((3'-(3-((2-hydroxyethyl)amino)propoxy)-2,2'-
dimethyl-[1,1'-biphenyl]-3-yl)oxy)propyl)pyrrolidin-
3-ol;
3-((3'-(3-((R)-3-hydroxypyrrolidin-1-yl)propoxy)-2,
2'-dimethyl-[1,1'-biphenyl]-3-yl)oxy)propyl)(methyl)
amino)propane-1,2-diol, 2.0 TFA;
2-hydroxy-3-((3-((3'-(3-((R)-3-hydroxypyrrolidin-1-yl)
propoxy)-2,2'-dimethyl-[1,1'-biphenyl]-3-yl)oxy)pro-
pyl)amino)propanoic acid;
(R)-1-(3-((3'-(3-(((1r,4r)-4-hydroxycyclohexyl)amino)
propoxy)-2,2'-dimethyl-[1,1'-biphenyl]-3-yl)oxy)pro-
pyl)pyrrolidin-3-ol;
N—((R)-1-(3-((3'-(3-((R)-3-hydroxypyrrolidin-1-yl)
propoxy)-2,2'-dimethyl-[1,1'-biphenyl]-3-yl)oxy)pro-
pyl)pyrrolidin-3-yl)acetamide;
1-(3-((3'-(3-((R)-3-hydroxypyrrolidin-1-yl)propoxy)-2,
2'-dimethyl-[1,1'-biphenyl]-3-yl)oxy)propyl)piperi-
dine-3-carboxamide;
(R)-1-(3-((3'-(3-((3-(1H-imidazol-1-yl)propyl)amino)
propoxy)-2,2'-dimethyl-[1,1'-biphenyl]-3-yl)oxy)pro-
pyl)pyrrolidin-3-ol;
(R)-1-(3-((2,2'-dimethyl-3'-(3-((3-morpholinopropyl)
amino)propoxy)-[1,1'-biphenyl]-3-yl)oxy)propyl)pyr-
rolidin-3-ol;
(R)-1-(3-((2,2'-dimethyl-3'-(3-((2-(pyridin-3-yl)ethyl)
amino)propoxy)-[1,1'-biphenyl]-3-yl)oxy)propyl)pyr-
rolidin-3-ol;
N,N-diethyl-1-(3-((3'-(3-((R)-3-hydroxypyrrolidin-1-yl)
propoxy)-2,2'-dimethyl-[1,1'-biphenyl]-3-yl)oxy)pro-
pyl)piperidine-3-carboxamide;
(R)-1-(3-((2,2'-dimethyl-3'-(3-((pyridin-2-ylmethyl)
amino)propoxy)-[1,1'-biphenyl]-3-yl)oxy)propyl)pyr-
rolidin-3-ol;
(3R)-1-(3-((3'-(3-(2-(hydroxymethyl)piperidin-1-yl)
propoxy)-2,2'-dimethyl-[1,1'-biphenyl]-3-yl)oxy)pro-
pyl)pyrrolidin-3-ol;
((((2,2'-dimethyl-[1,1'-biphenyl]-3,3'-diyl)bis(oxy))bis
(propane-3,1-diyl))bis(piperidine-1,3-diyl))dimetha-
nol, 2.0 TFA;
2,2'-((((2,2'-dimethyl-[1,1'-biphenyl]-3,3'-diyl)bis(oxy))
bis(propane-3,1-diyl))bis(azanediyl))bis(ethan-1-ol);
3,3'-((2,2'-dimethyl-[1,1'-biphenyl]-3,3'-diyl)bis(oxy))bis
(N-(2-(pyridin-4-yl)ethyl)propan-1-amine);
4,4'-((((2,2'-dimethyl-[1,1'-biphenyl]-3,3'-diyl)bis(oxy))
bis(propane-3,1-diyl))bis(azanediyl))bis(2-methylbu-
tane-2,3-diol);
3,3'-((((2,2'-dimethyl-[1,1'-biphenyl]-3,3'-diyl)bis(oxy))
bis(propane-3,1-diyl))bis(methylazanediyl))bis(pro-
pan-1-ol);
(2S,2'S)-3,3'-((((2,2'-dimethyl-[1,1'-biphenyl]-3,3'-diyl)
bis(oxy))bis(propane-3,1-diyl))bis(methylazanediyl))
bis(propane-1,2-diol);
(R)-1-(3-((3'-(3-((2-(dimethylamino)ethyl)(methyl)
amino)propoxy)-2,2'-dimethyl-[1,1'-biphenyl]-3-yl)
oxy)propyl)pyrrolidin-3-ol;
(3S,4R)-4-(hydroxymethyl)-1-(3-((3'-(3-((R)-3-hydroxy-
pyrrolidin-1-yl)propoxy)-2,2'-dimethyl-[1,1'-biphe-
nyl]-3-yl)oxy)propyl)piperidin-3-ol;
(R)-1-(3-((3'-(3-((2-hydroxyethyl)(methyl)amino)
propoxy)-2,2'-dimethyl-[1,1'-biphenyl]-3-yl)oxy)pro-
pyl)pyrrolidin-3-ol;
(R)-1-(3-((2,2'-dimethyl-3'-(3-((2-(pyridin-4-yl)ethyl)
amino)propoxy)-[1,1'-biphenyl]-3-yl)oxy)propyl)pyr-
rolidin-3-ol;
(R)-4-(3-((3'-(3-(3-hydroxypyrrolidin-1-yl)propoxy)-2,
2'-dimethyl-[1,1'-biphenyl]-3-yl)oxy)propyl)-1-meth-
ylpiperazin-2-one;
(S)-2-((3-((3'-(3-((R)-3-hydroxypyrrolidin-1-yl)
propoxy)-2,2'-dimethyl-[1,1'-biphenyl]-3-yl)oxy)pro-
pyl)amino)-3-(pyridin-4-yl)propanoic acid;
(R)-3-((3-((3'-(3-(3-hydroxypyrrolidin-1-yl)propoxy)-2,
2'-dimethyl-[1,1'-biphenyl]-3-yl)oxy)propyl)amino)
propanamide;
(2S,4R)-4-hydroxy-1-(3-((3'-(3-((R)-3-hydroxypyrroli-
din-1-yl)propoxy)-2,2'-dimethyl-[1,1'-biphenyl]-3-yl)
oxy)propyl)pyrrolidine-2-carboxylic acid;
(3R)-1-(3-((3'-(3-((2-hydroxy-2-(pyridin-3-yl)ethyl)
amino)propoxy)-2,2'-dimethyl-[1,1'-biphenyl]-3-yl)
oxy)propyl)pyrrolidin-3-ol;
(R)-1-(3-((2,2'-dimethyl-3'-(3-(phenethylamino)
propoxy)-[1,1'-biphenyl]-3-yl)oxy)propyl)pyrrolidin-
3-ol;
(R)-1-(3-((3'-(3-((3-hydroxypropyl)amino)propoxy)-2,2'-
dimethyl-[1,1'-biphenyl]-3-yl)oxy)propyl)pyrrolidin-
3-ol;
(R)-1-(3-((2,2'-dimethyl-3'-(3-((2-(1-methyl-1H-imida-
zol-4-yl)ethyl)amino)propoxy)-[1,1'-biphenyl]-3-yl)
oxy)propyl)pyrrolidin-3-ol;
(R)-1-(3-((2,2'-dimethyl-3'-(3-(((1-methylpiperidin-4-yl)
methyl)amino)propoxy)-[1,1'-biphenyl]-3-yl)oxy)pro-
pyl)pyrrolidin-3-ol;
(S)-2-hydroxy-3-((3-((3'-(3-((R)-3-hydroxypyrrolidin-1-
yl)propoxy)-2,2'-dimethyl-[1,1'-biphenyl]-3-yl)oxy)
propyl)amino)propanoic acid;
(R)-1-(3-((3'-(3-((3-hydroxy-2,2-dimethylpropyl)amino)
propoxy)-2,2'-dimethyl-[1,1'-biphenyl]-3-yl)oxy)pro-
pyl)pyrrolidin-3-ol;
(3R)-1-(3-((3'-(3-((2-hydroxy-1-(pyridin-4-yl)ethyl)
amino)propoxy)-2,2'-dimethyl-[1,1'-biphenyl]-3-yl)
oxy)propyl)pyrrolidin-3-ol;
(R)—N-(2-((3-((3'-(3-(3-hydroxypyrrolidin-1-yl)
propoxy)-2,2'-dimethyl-[1,1'-biphenyl]-3-yl)oxy)pro-
pyl)amino)ethyl)acetamide;
(R)-1-(3-((2,2'-dimethyl-3'-(3-(methyl(pyridin-3-ylm-
ethyl)amino)propoxy)-[1,1'-biphenyl]-3-yl)oxy)pro-
pyl)pyrrolidin-3-ol;
(R)-1-(3-((2,2'-dimethyl-3'-(3-((pyridin-3-ylmethyl)
amino)propoxy)-[1,1'-biphenyl]-3-yl)oxy)propyl)pyr-
rolidin-3-ol;
(2S,4R)-4-hydroxy-1-(3-((3'-(3-((R)-3-hydroxypyrroli-
din-1-yl)propoxy)-2,2'-dimethyl-[1,1'-biphenyl]-3-yl)
oxy)propyl)pyrrolidine-2-carboxylic acid;
(R)-3-((3-((3'-(3-((R)-3-hydroxypyrrolidin-1-yl)
propoxy)-2,2'-dimethyl-[1,1'-biphenyl]-3-yl)oxy)pro-
pyl)amino)propane-1,2-diol;

(R)-1-(3-((3'-(3-((2-hydroxyethyl)(propyl)amino)propoxy)-2,2'-dimethyl-[1,1'-biphenyl]-3-yl)oxy)propyl)pyrrolidin-3-ol;

(R)-3-((3-(3'-(3-(3-hydroxypyrrolidin-1-yl)propoxy)-2,2'-dimethyl-[1,1'-biphenyl]-3-yl)oxy)propyl)(methyl)amino)propanamide;

(R)-1-(3-((3'-(3-(((R)-1-hydroxy-3-methylbutan-2-yl)amino)propoxy)-2,2'-dimethyl-[1,1'-biphenyl]-3-yl)oxy)propyl)pyrrolidin-3-ol;

(R)-1-(3-((3'-(3-(bis(pyridin-2-ylmethyl)amino)propoxy)-2,2'-dimethyl-[1,1'-biphenyl]-3-yl)oxy)propyl)pyrrolidin-3-ol;

(R)-1-(3-((3'-(3-(((S)-2-hydroxy-1-phenylethyl)amino)propoxy)-2,2'-dimethyl-[1,1'-biphenyl]-3-yl)oxy)propyl)pyrrolidin-3-ol;

(R)-1-(3-((3'-(3-(((S)-1-hydroxy-3-methylbutan-2-yl)amino)propoxy)-2,2'-dimethyl-[1,1'-biphenyl]-3-yl)oxy)propyl)pyrrolidin-3-ol;

3-((3-((3'-(3-((R)-3-hydroxypyrrolidin-1-yl)propoxy)-2,2'-dimethyl-[1,1'-biphenyl]-3-yl)oxy)propyl)amino)propane-1,2-diol;

(R)-1-(3-((3'-(3-((2-(4-chloro-1H-pyrazol-1-yl)ethyl)amino)propoxy)-2,2'-dimethyl-[1,1'-biphenyl]-3-yl)oxy)propyl)pyrrolidin-3-ol;

(R)-1-(3-((3'-(3-((2-(4-chloro-1H-pyrazol-1-yl)ethyl)amino)propoxy)-2,2'-dimethyl-[1,1'-biphenyl]-3-yl)oxy)propyl)pyrrolidin-3-ol;

(R)-1-(3-((2,2'-dimethyl-3'-(3-(methyl(pyridin-2-ylmethyl)amino)propoxy)-[1,1'-biphenyl]-3-yl)oxy)propyl)pyrrolidin-3-ol;

(R)-1-(3-((3'-(3-(4-(2-hydroxyethyl)piperazin-1-yl)propoxy)-2,2'-dimethyl-[1,1'-biphenyl]-3-yl)oxy)propyl)pyrrolidin-3-ol;

(R)-1-(3-((2,2'-dimethyl-3'-(3-(methyl(pyridin-4-ylmethyl)amino)propoxy)-[1,1'-biphenyl]-3-yl)oxy)propyl)pyrrolidin-3-ol;

(R)-1-(3-((3'-(3-((4-aminophenethyl)amino)propoxy)-2,2'-dimethyl-[1,1'-biphenyl]-3-yl)oxy)propyl)pyrrolidin-3-ol;

(R)-1-(3-((2,2'-dimethyl-3'-(3-((1-methylpiperidin-4-yl)amino)propoxy)-[1,1'-biphenyl]-3-yl)oxy)propyl)pyrrolidin-3-ol;

(R)-1-(3-((3'-(3-((1-(2-hydroxyethyl)piperidin-4-yl)amino)propoxy)-2,2'-dimethyl-[1,1'-biphenyl]-3-yl)oxy)propyl)pyrrolidin-3-ol;

(R)-2,2'-((3-((3'-(3-(3-hydroxypyrrolidin-1-yl)propoxy)-2,2'-dimethyl-[1,1'-biphenyl]-3-yl)oxy)propyl)azanediyl)bis(ethan-1-ol);

(R)-1-(3-((3'-(3-(((R)-2-hydroxy-1-phenylethyl)amino)propoxy)-2,2'-dimethyl-[1,1'-biphenyl]-3-yl)oxy)propyl)pyrrolidin-3-ol;

(R)-1-(3-((3'-(3-(4-(dimethylamino)piperidin-1-yl)propoxy)-2,2'-dimethyl-[1,1'-biphenyl]-3-yl)oxy)propyl)pyrrolidin-3-ol;

(R)-1-(3-((3'-(3-(((R)-1-(5-chloro-1-methyl-1H-imidazol-4-yl)-3-hydroxypropan-2-yl)amino)propoxy)-2,2'-dimethyl-[1,1'-biphenyl]-3-yl)oxy)propyl)pyrrolidin-3-ol;

(R)-1-(3-((3'-(3-(benzyl(2-hydroxyethyl)amino)propoxy)-2,2'-dimethyl-[1,1'-biphenyl]-3-yl)oxy)propyl)pyrrolidin-3-ol;

(R)-1-(3-((3'-(3-((2-hydroxyethyl)(isopentyl)amino)propoxy)-2,2'-dimethyl-[1,1'-biphenyl]-3-yl)oxy)propyl)pyrrolidin-3-ol;

(R)-1-(3-((3'-(3-((R)-3-hydroxypyrrolidin-1-yl)propoxy)-2,2'-dimethyl-[1,1'-biphenyl]-3-yl)oxy)propyl)piperidine-3-carboxylic acid;

(R)-1-(3-((3'-(3-(((S)-2-(3-chloro-4-fluorophenyl)-2-hydroxyethyl)amino)propoxy)-2,2'-dimethyl-[1,1'-biphenyl]-3-yl)oxy)propyl)pyrrolidin-3-ol;

3,3'-((((2,2'-dimethyl-[1,1'-biphenyl]-3,3'-diyl)bis(oxy))bis(propane-3,1-diyl))bis(methylazanediyl))dipropanamide;

2,2',2''',2''''-((((2,2'-dimethyl-[1,1'-biphenyl]-3,3'-diyl)bis(oxy))bis(propane-3,1-diyl))bis(azanetriyl))tetrakis(ethan-1-ol);

3,3'-((((2,2'-dimethyl-[1,1'-biphenyl]-3,3'-diyl)bis(oxy))bis(propane-3,1-diyl))bis(methylazanediyl))bis(propane-1,2-diol);

(2S,2'S)-3,3'-((((2,2'-dimethyl-[1,1'-biphenyl]-3,3'-diyl)bis(oxy))bis(propane-3,1-diyl))bis(azanediyl))bis(propane-1,2-diol);

(S)-3-((3-((3'-(3-((3-hydroxypropyl)amino)propoxy)-2,2'-dimethyl-[1,1'-biphenyl]-3-yl)oxy)propyl)amino)propane-1,2-diol;

(S)-1-(3-((3'-(3-(((S)-2,3-dihydroxypropyl)amino)propoxy)-2,2'-dimethyl-[1,1'-biphenyl]-3-yl)oxy)propyl)piperidine-3-carboxylic acid;

(3S,3'S)-1,1'-(((2,2'-dimethyl-[1,1'-biphenyl]-3,3'-diyl)bis(oxy))bis(propane-3,1-diyl))bis(piperidine-3-carboxylic acid);

3,3'-((((2,2'-dimethyl-[1,1'-biphenyl]-3,3'-diyl)bis(oxy))bis(propane-3,1-diyl))bis(azanediyl))bis(propane-1,2-diol);

(3S,3'S,4S,4'S)-1,1'-(((2,2'-dimethyl-[1,1'-biphenyl]-3,3'-diyl)bis(oxy))bis(propane-3,1-diyl))bis(piperidine-3,4-diol);

2,2'-((((2,2'-dimethyl-[1,1'-biphenyl]-3,3'-diyl)bis(oxy))bis(propane-3,1-diyl))bis(piperazine-4,1-diyl))bis(ethan-1-ol);

3,3'-((2,2'-dimethyl-[1,1'-biphenyl]-3,3'-diyl)bis(oxy))bis(N-(2-(pyridin-3-yl)ethyl)propan-1-amine);

1,1'-(((2,2'-dimethyl-[1,1'-biphenyl]-3,3'-diyl)bis(oxy))bis(propane-3,1-diyl))bis(N,N-dimethylazetidin-3-amine);

(1S,1'S,2R,2'R,3R,3'R,5R,5'R)-5,5'-((((2,2'-dimethyl-[1,1'-biphenyl]-3,3'-diyl)bis(oxy))bis(propane-3,1-diyl))bis(azanediyl))bis(3-(hydroxymethyl)cyclopentane-1,2-diol);

(1R,2S,3R,5R)-3-((3-((2,2'-dimethyl-3'-(3-((2-(pyridin-4-yl)ethyl)amino)propoxy)-[1,1'-biphenyl]-3-yl)oxy)propyl)amino)-5-(hydroxymethyl)cyclopentane-1,2-diol;

3,3'-((((2,2'-dimethyl-[1,1'-biphenyl]-3,3'-diyl)bis(oxy))bis(propane-3,1-diyl))bis(methylazanediyl))bis(cyclobutan-1-ol);

(2S,3S)-3-((3-((3'-(3-((R)-3-hydroxypyrrolidin-1-yl)propoxy)-2,2'-dimethyl-[1,1'-biphenyl]-3-yl)oxy)propyl)amino)-3-phenylpropane-1,2-diol;

(R)-1-(3-((3'-(3-((R)-2-(hydroxymethyl)morpholino)propoxy)-2,2'-dimethyl-[1,1'-biphenyl]-3-yl)oxy)propyl)pyrrolidin-3-ol;

(3R,3'R)-1,1'-((((((propane-1,3-diylbis(methylazanediyl))bis(propane-3,1-diyl))bis(oxy))bis(2,2'-dimethyl-[1,1'-biphenyl]-3',3-diyl))bis(oxy))bis(propane-3,1-diyl))bis(pyrrolidin-3-ol);

3,3'-((((2,2'-dimethyl-[1,1'-biphenyl]-3,3'-diyl)bis(oxy))bis(propane-3,1-diyl))bis(azanediyl))bis(1-methoxypropan-2-ol);

(3R,3'R)-1,1'-(((((((oxybis(ethane-2,1-diyl))bis(methylazanediyl))bis(propane-3,1-diyl))bis(oxy))bis(2,2'-dimethyl-[1,1'-biphenyl]-3',3-diyl))bis(oxy))bis(propane-3,1-diyl))bis(pyrrolidin-3-ol);

(R)-1-(3-((2,2'-dimethyl-3'-(3-(methyl(2-(2-(methylamino)ethoxy)ethyl)amino)propoxy)-[1,1'-biphenyl]-3-yl)oxy)propyl)pyrrolidin-3-ol;

(1R,1'R,2R,2'R)-2,2'-((((2,2'-dimethyl-[1,1'-biphenyl]-3,3'-diyl)bis(oxy))bis(propane-3,1-diyl))bis(azanediyl))bis(1-phenylpropane-1,3-diol);

(S)-3-((3-((3'-(3-(((1R,2R)-1,3-dihydroxy-1-phenylpropan-2-yl)amino)propoxy)-2,2'-dimethyl-[1,1'-biphenyl]-3-yl)oxy)propyl)amino)propane-1,2-diol;

5,5'-(((((2,2'-dimethyl-[1,1'-biphenyl]-3,3'-diyl)bis(oxy))bis(propane-3,1-diyl))bis(((S)-2,3-dihydroxypropyl)azanediyl))bis(methylene))dinicotinonitrile;

2,2'-((((2,2'-dimethyl-[1,1'-biphenyl]-3,3'-diyl)bis(oxy))bis(propane-3,1-diyl))bis(((S)-2,3-dihydroxypropyl)azanediyl))diacetonitrile;

(2S,2'S)-3,3'-((((2,2'-dimethyl-[1,1'-biphenyl]-3,3'-diyl)bis(oxy))bis(propane-3,1-diyl))bis((2-(pyridin-2-yl)ethyl)azanediyl))bis(propane-1,2-diol);

(2S,2'S)-3,3'-((((2,2'-dimethyl-[1,1'-biphenyl]-3,3'-diyl)bis(oxy))bis(propane-3,1-diyl))bis((2-(pyridin-3-yl)ethyl)azanediyl))bis(propane-1,2-diol);

(S)-3-((3-((3'-(3-(((S)-2,3-dihydroxypropyl)(2-(pyridin-3-yl)ethyl)amino)propoxy)-2,2'-dimethyl-[1,1'-biphenyl]-3-yl)oxy)propyl)amino)propane-1,2-diol;

3,3'-((((2,2'-dimethyl-[1,1'-biphenyl]-3,3'-diyl)bis(oxy))bis(propane-3,1-diyl))bis(azanediyl))bis(2-methylpropane-1,2-diol);

(R)-1-(3-((2,2'-dimethyl-3'-(3-(piperidin-1-yl)propoxy)-[1,1'-biphenyl]-3-yl)oxy)propyl)pyrrolidin-3-ol;

(R)-1-(3-((3'-(3-(4-(hydroxymethyl)piperidin-1-yl)propoxy)-2,2'-dimethyl-[1,1'-biphenyl]-3-yl)oxy)propyl)pyrrolidin-3-ol;

N-(1-(3-((3'-(3-((R)-3-hydroxypyrrolidin-1-yl)propoxy)-2,2'-dimethyl-[1,1'-biphenyl]-3-yl)oxy)propyl)pyrrolidin-3-yl)acetamide;

(R)-1-(3-((2,2'-dimethyl-3'-(3-(4-(pyridin-2-yl)piperazin-1-yl)propoxy)-[1,1'-biphenyl]-3-yl)oxy)propyl)pyrrolidin-3-ol;

(R)-2-(4-(3-((3'-(3-(3-hydroxypyrrolidin-1-yl)propoxy)-2,2'-dimethyl-[1,1'-biphenyl]-3-yl)oxy)propyl)piperazin-1-yl)-N-isopropylacetamide;

(R)-1-(3-((2,2'-dimethyl-3'-(3-(methyl(phenethyl)amino)propoxy)-[1,1'-biphenyl]-3-yl)oxy)propyl)pyrrolidin-3-ol;

(R)-1-(3-((3'-(3-(4-(2-methoxyphenyl)piperazin-1-yl)propoxy)-2,2'-dimethyl-[1,1'-biphenyl]-3-yl)oxy)propyl)pyrrolidin-3-ol;

(R)-1-(3-((3'-(3-(((R)-2-hydroxy-2-phenylethyl)amino)propoxy)-2,2'-dimethyl-[1,1'-biphenyl]-3-yl)oxy)propyl)pyrrolidin-3-ol;

(R)-1-(3-((3'-(3-(((S)-2-hydroxy-2-phenylethyl)amino)propoxy)-2,2'-dimethyl-[1,1'-biphenyl]-3-yl)oxy)propyl)pyrrolidin-3-ol;

(R)-1-(3-((3'-(3-((R)-3-hydroxypyrrolidin-1-yl)propoxy)-2,2'-dimethyl-[1,1'-biphenyl]-3-yl)oxy)propyl)piperidin-3-ol;

(S)-1-(3-((3'-(3-((R)-3-hydroxypyrrolidin-1-yl)propoxy)-2,2'-dimethyl-[1,1'-biphenyl]-3-yl)oxy)propyl)piperidin-3-ol;

(S)-2-((3-((3'-(3-((R)-3-hydroxypyrrolidin-1-yl)propoxy)-2,2'-dimethyl-[1,1'-biphenyl]-3-yl)oxy)propyl)amino)-3-(pyridin-2-yl)propanoic acid;

(S)-2-((3-((3'-(3-((R)-3-hydroxypyrrolidin-1-yl)propoxy)-2,2'-dimethyl-[1,1'-biphenyl]-3-yl)oxy)propyl)amino)-3-(pyridin-3-yl)propanoic acid;

(R)-1-(3-((2,2'-dimethyl-3'-(3-((2-(pyridin-2-yl)ethyl)amino)propoxy)-[1,1'-biphenyl]-3-yl)oxy)propyl)pyrrolidin-3-ol;

(2S,2'S)-1,1'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(piperidine-2-carboxylic acid);

(S)-1-(5-chloro-4-((3'-((2-chloro-5-((5-cyanopyridin-3-yl)methoxy)-4-(hydroxymethyl)phenoxy)methyl)-2,2'-dimethyl-[1,1'-biphenyl]-3-yl)methoxy)-2-((5-cyanopyridin-3-yl)methoxy)benzyl)piperidine-2-carboxylic acid;

(2R,2'R)-2,2'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxy-2-methylpropanoic acid);

2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(propane-1,3-diol);

(2S,2'S)-2,2'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxy-2-methylpropanoic acid);

(S)-2-((5-chloro-4-((3'-((2-chloro-5-((5-cyanopyridin-3-yl)methoxy)-4-(hydroxymethyl)phenoxy)methyl)-2,2'-dimethyl-[1,1'-biphenyl]-3-yl)methoxy)-2-((5-cyanopyridin-3-yl)methoxy)benzyl)amino)-3-hydroxy-2-methylpropanoic acid;

5,5'-((((((2,2'-dimethyl-[1,1'-biphenyl]-3,3'-diyl)bis(methylene))bis(oxy))bis(4-chloro-6-(((R)-3-hydroxypyrrolidin-1-yl)methyl)-3,1-phenylene))bis(oxy))bis(methylene))dinicotinonitrile;

(R)-5-((4-chloro-5-((3'-((2-chloro-5-((5-cyanopyridin-3-yl)methoxy)-4-((3-hydroxypyrrolidin-1-yl)methyl)phenoxy)methyl)-2,2'-dimethyl-[1,1'-biphenyl]-3-yl)methoxy)-2-(hydroxymethyl)phenoxy)methyl)nicotinonitrile;

5,5'-((((((2,2'-dimethyl-[1,1'-biphenyl]-3,3'-diyl)bis(methylene))bis(oxy))bis(4-chloro-6-((((S)-2,3-dihydroxypropyl)amino)methyl)-3,1-phenylene))bis(oxy))bis(methylene))dinicotinonitrile;

5,5'-((((((2,2'-dimethyl-[1,1'-biphenyl]-3,3'-diyl)bis(methylene))bis(oxy))bis(4-chloro-6-(((1,3-dihydroxypropan-2-yl)amino)methyl)-3,1-phenylene))bis(oxy))bis(methylene))dinicotinonitrile;

5-((4-chloro-5-((3'-((2-chloro-5-((5-cyanopyridin-3-yl)methoxy)-4-(((1,3-dihydroxypropan-2-yl)amino)methyl)phenoxy)methyl)-2,2'-dimethyl-[1,1'-biphenyl]-3-yl)methoxy)-2-(hydroxymethyl)phenoxy)methyl)nicotinonitrile;

5,5'-((((((2,2'-dimethyl-[1,1'-biphenyl]-3,3'-diyl)bis(methylene))bis(oxy))bis(4-chloro-6-(((1,3-dihydroxypropan-2-yl)((S)-2,3-dihydroxypropyl)amino)methyl)-3,1-phenylene))bis(oxy))bis(methylene))dinicotinonitrile;

(3R,3'R)-1,1'-(((2,2'-dimethyl-[1,1'-biphenyl]-3,3'-diyl)bis(oxy))bis(propane-3,1-diyl))bis(pyrrolidin-3-ol);

(R)-1-(3-((3'-(4-((R)-3-hydroxypyrrolidin-1-yl)butoxy)-2,2'-dimethyl-[1,1'-biphenyl]-3-yl)oxy)propyl) pyrrolidin-3-ol;

(R)-1-(3-((3'-((5-((R)-3-hydroxypyrrolidin-1-yl)pentyl)oxy)-2,2'-dimethyl-[1,1'-biphenyl]-3-yl)oxy)propyl)pyrrolidin-3-ol;

(R)-1-(3-((3'-(4-((R)-3-hydroxypyrrolidin-1-yl)butoxy)-2,2'-dimethyl-[1,1'-biphenyl]-4-yl)oxy)propyl) pyrrolidin-3-ol;

(R)-1-(3-((3'-((5-((R)-3-hydroxypyrrolidin-1-yl)pentyl)oxy)-2,2'-dimethyl-[1,1'-biphenyl]-4-yl)oxy)propyl) pyrrolidin-3-ol;

(3R,3'R)-1,1'-(((2,2'-dimethyl-[1,1'-biphenyl]-3,4'-diyl)bis(oxy))bis(propane-3,1-diyl))bis(pyrrolidin-3-ol);

(R)-1-(3-((3'-(3-(dimethylamino)propoxy)-2,2'-dimethyl-[1,1'-biphenyl]-3-yl)oxy)propyl)pyrrolidin-3-ol;

N-(4-((R)-3-hydroxypyrrolidin-1-yl)butyl)-3'-(3-((R)-3-hydroxypyrrolidin-1-yl)propoxy)-2,2'-dimethyl-[1,1'-biphenyl]-3-carboxamide;

3'-(3-((R)-3-hydroxypyrrolidin-1-yl)propoxy)-N-(3-((R)-3-hydroxypyrrolidin-1-yl)propyl)-2,2'-dimethyl-[1,1'-biphenyl]-3-carboxamide;

(R)—N-(3-(dimethylamino)propyl)-3'-(3-(3-hydroxypyrrolidin-1-yl)propoxy)-2,2'-dimethyl-[1,1'-biphenyl]-3-sulfonamide;

(R)-5-(((3'-(3-(3-hydroxypyrrolidin-1-yl)propoxy)-2,2'-dimethyl-[1,1'-biphenyl]-3-yl)oxy)methylnicotinonitrile;

(3R,3'R)-1,1'-(((2,2'-dimethyl-[1,1'-biphenyl]-4,4'-diyl)bis(oxy))bis(propane-3,1-diyl))bis(pyrrolidin-3-ol);

3-((R)-3-hydroxypyrrolidin-1-yl)-N-(3'-(3-((R)-3-hydroxypyrrolidin-1-yl)propoxy)-2,2'-dimethyl-[1,1'-biphenyl]-3-yl)propanamide;

(R)-3-(3-(3'-(3-(3-hydroxypyrrolidin-1-yl)propoxy)-2,2'-dimethyl-[1,1'-biphenyl]-3-yl)ureido)propanoic acid;

N-(2-((R)-3-hydroxypyrrolidin-1-yl)ethyl)-3'-(3-((R)-3-hydroxypyrrolidin-1-yl)propoxy)-2,2'-dimethyl-[1,1'-biphenyl]-3-carboxamide;

N-(2-((R)-3-hydroxypyrrolidin-1-yl)ethyl)-3'-(3-((R)-3-hydroxypyrrolidin-1-yl)propoxy)-2,2'-dimethyl-[1,1'-biphenyl]-3-sulfonamide;

1-(2-((R)-3-hydroxypyrrolidin-1-yl)ethyl)-3-(3'-(3-((R)-3-hydroxypyrrolidin-1-yl)propoxy)-2,2'-dimethyl-[1,1'-biphenyl]-3-yl)urea;

(R)-1-(3-((3'-(3-((R)-3-hydroxypyrrolidin-1-yl)propoxy)-2,2'-dimethyl-[1,1'-biphenyl]-3-yl)amino)propyl)pyrrolidin-3-ol;

(R)-3-(((3'-(3-(3-hydroxypyrrolidin-1-yl)propoxy)-2,2'-dimethyl-[1,1'-biphenyl]-3-yl)oxy)methyl)benzonitrile;

(R)-3-(3'-(3-(3-hydroxypyrrolidin-1-yl)propoxy)-2,2'-dimethyl-[1,1'-biphenyl]-3-ylsulfonamido)propanoic acid;

(3S,3'S)-1,1'-(((2'-methyl-[1,1'-biphenyl]-3,4-diyl)bis(oxy))bis(propane-3,1-diyl))bis(pyrrolidin-3-ol);

(3S,3'S)-1,1'-(((3'-(3-((R)-3-hydroxypyrrolidin-1-yl)propoxy)-2'-methyl-[1,1'-biphenyl]-3,4-diyl)bis(oxy))bis(propane-3,1-diyl))bis(pyrrolidin-3-ol);

(3R,3'R)-1,1'-(((2-methyl-[1,1'-biphenyl]-3,3'-diyl)bis(oxy))bis(propane-3,1-diyl))bis(pyrrolidin-3-ol);

(3R,3'R)-1,1'-(((2-chloro-2'-methyl-[1,1'-biphenyl]-3,3'-diyl)bis(oxy))bis(propane-3,1-diyl))bis(pyrrolidin-3-ol);

3,3'-bis(3-((R)-3-hydroxypyrrolidin-1-yl)propoxy)-2'-methyl-[1,1'-biphenyl]-2-carbonitrile;

(3R,3'R)-1,1'-(((2-methyl-2'-(trifluoromethyl)-[1,1'-biphenyl]-3,3'-diyl)bis(oxy))bis(propane-3,1-diyl))bis(pyrrolidin-3-ol), 2 TFA;

(R)-1-(3-((2-methyl-3'-(3-phenylpropoxy)-[1,1'-biphenyl]-3-yl)oxy)propyl)pyrrolidin-3-ol;

1-(3-((3'-(3-((R)-3-hydroxypyrrolidin-1-yl)propoxy)-2,2'-dimethyl-[1,1'-biphenyl]-3-yl)oxy)propyl)-3-phenylpyrrolidin-3-ol, 2 TFA;

(3R)-1-(3-((2,2'-dimethyl-3'-((1-methylpiperidin-3-yl)methoxy)-[1,1'-biphenyl]-3-yl)oxy)propyl)pyrrolidin-3-ol;

(3R)-1-(3-(3-(3-(2-((R)-3-hydroxypyrrolidin-1-yl)ethyl)-2,3-dihydrobenzo[b][1,4]dioxin-6-yl)-2-methylphenoxy)propyl)pyrrolidin-3-ol;

(3R)-1-(3-(3-(3-(2-((R)-3-hydroxypyrrolidin-1-yl)ethyl)-2,3-dihydrobenzo[b][1,4]dioxin-6-yl)-2-methylphenoxy)propyl)pyrrolidin-3-ol; and (3R,3'R)-1,1'-((2,2',3,3'-tetrahydro-[6,6'-bibenzo[b][1,4]dioxine]-3,3'-diyl)bis(ethane-2,1-diyl))bis(pyrrolidin-3-ol);

or a pharmaceutically acceptable salt thereof.

6. A compound selected from (1R,2S,5R)-3-((3-((3'-(3-(((1R,2S,3R,4R)-2,3-dihydroxy-4-(hydroxymethyl)cyclopentyl)amino)propoxy)-2,2'-dimethyl-[1,1'-biphenyl]-3-yl)oxy)propyl)amino)-5-(hydroxymethyl)cyclopentane-1,2-diol;

5,5'-((((((2,2'-dimethyl-[1,1'-biphenyl]-3,3'-diyl)bis(methylene))bis(oxy))bis(4-chloro-6-((4-(hydroxymethyl)-2-oxooxazolidin-3-yl)methyl)-3,1-phenylene))bis(oxy))bis(methylene))dinicotinonitrile;

3,3'-((2,2'-dichloro-[1,1'-biphenyl]-3,3'-diyl)bis(oxy))bis(propan-1-amine);

N,N'-(((2,2'-dichloro-[1,1'-biphenyl]-3,3'-diyl)bis(oxy))bis(propane-3,1-diyl))bis(2,3-dihydroxypropanamide);

(3R,3'R)-4,4'-(((((2,2'-dichloro-[1,1'-biphenyl]-3,3'-diyl)bis(oxy))bis(propane-3,1-diyl))bis(azanediyl))bis(3-hydroxy-4-oxobutanoic acid);

(R)-1-(3-((3'-((3-aminobenzyl)oxy)-2,2'-dimethyl-[1,1'-biphenyl]-3-yl)oxy)propyl)pyrrolidin-3-ol;

(R)-1-(3-((3'-(3-((R)-3-fluoropyrrolidin-1-yl)propoxy)-2,2'-dimethyl-[1,1'-biphenyl]-3-yl)oxy)propyl)pyrrolidin-3-ol;

2,2'-(((((2,2'-dimethyl-[1,1'-biphenyl]-3,3'-diyl)bis(methylene))bis(oxy))bis(2,5-dimethyl-4,1-phenylene))bis(methylene))bis(azanediyl))bis(2-methylpropane-1,3-diol;

(2S,2'S)-1,1'-(((((2,2'-dimethyl-[1,1'-biphenyl]-3,3'-diyl)bis(methylene))bis(oxy))bis(2,5-dimethyl-4,1-phenylene))bis(methylene))bis(piperidine-2-carboxylic acid);

2,2'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene)bis(azanediyl))bis(propane-1,3-diol);

2,2'-(((((2,2'-dimethyl-[1,1'-biphenyl]-3,3'-diyl)bis(methylene))bis(oxy))bis(2,5-dimethyl-4,1-phenylene))bis(methylene))bis(azanediyl))bis(propane-1,3-diol);

2,2'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(propane-1,3-diol);

(2S,2'S)-1,1'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(piperidine-2-carboxylic acid);

2,2'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(2-methylpropane-1,3-diol);

(2S,2'S)-2,2'-(((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(3-hydroxypropanoic acid);

(2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(azanediyl))bis(3-hydroxy-2-methylpropanoic acid);

2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(2-methylpropane-1,3-diol);

(2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(3-hydroxypropanoic acid);

(2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(3-hydroxy-2-methylpropanoic acid);

(2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(3-methylbutanoic acid);

(2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))dipentanoic acid;

(2S,2'S)-2,2'-((((((2,2'-dimethyl-[1,1'-biphenyl]-3,3'-diyl)bis(methylene))bis(oxy))bis(5-chloro-2-((3,5-difluorobenzyl)oxy)-4,1-phenylene))bis(methylene))bis(methylazanediyl))bis(4-methylpentanoic acid);

(2S,2'S,3R,3'R)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(3-hydroxybutanoic acid);

2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(propane-1,3-diol);

2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(2-methylpropane-1,3-diol;

(2S,2'S)-1,1'-(((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(piperidine-2-carboxylic acid);

(2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(azanediyl))bis(3-hydroxy-2-methylpropanoic acid);

2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(2-methylpropane-1,3-diol);

2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(2-methylpropanoic acid);

(2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(4-hydroxybutanoic acid);

(2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))dipentanoic acid;

(2S,2'S)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(3-hydroxy-2-methylpropanoic acid);

2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(propane-1,3-diol);

(2S,2'S,3R,3'R)-2,2'-((((((2,2'-dimethyl-[1,1'-biphenyl]-3,3'-diyl)bis(methylene))bis(oxy))bis(2-((6-(1H-pyrazol-1-yl)pyridin-3-yl)methoxy)-5-chloro-4,1-phenylene))bis(methylene))bis(methylazanediyl))bis(3-hydroxybutanoic acid);

N-(4-((3'-((((S)-1-carboxy-3-hydroxypropyl)(methyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methoxybenzyl)-N-methyl-L-homoserine;

3-((4-((3'-((4-(((2-carboxyethyl)(methyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methoxybenzyl)(methyl)amino)propanoic acid;

1,1'-(((2,2'-dimethyl-[1,1'-biphenyl]-3,3'-diyl)bis(methylene))bis(oxy))bis(5-chloro-2-methoxy-4,1-phenylene))bis(N-((1H-pyrazol-3-yl)methyl)methanamine);

1,1'-(((2,2'-dimethyl-[1,1'-biphenyl]-3,3'-diyl)bis(methylene))bis(oxy))bis(5-chloro-2-methoxy-4,1-phenylene))bis(N-(pyrimidin-5-ylmethyl)methanamine);

1,1'-(((2,2'-dimethyl-[1,1'-biphenyl]-3,3'-diyl)bis(methylene))bis(oxy))bis(5-chloro-2-methoxy-4,1-phenylene))bis(N-(thiazol-5-ylmethyl)methanamine);

3,3'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))dipropionic acid;

(2S,2'S)-2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(4-hydroxybutanoic acid);

1,1'-(((2,2'-dimethyl-[1,1'-biphenyl]-3,3'-diyl)bis(methylene))bis(oxy))bis(5-chloro-2-methoxy-4,1-phenylene))bis(N-((1H-pyrazol-3-yl)methyl)-N-methylmethanamine);

1,1'-(((2,2'-dimethyl-[1,1'-biphenyl]-3,3'-diyl)bis(methylene))bis(oxy))bis(5-chloro-2-methoxy-4,1-phenylene))bis(N-methyl-N-(pyrimidin-5-ylmethyl)methanamine);

1,1'-(((2,2'-dimethyl-[1,1'-biphenyl]-3,3'-diyl)bis(methylene))bis(oxy))bis(5-chloro-2-methoxy-4,1-phenylene))bis(N-methyl-N-(thiazol-5-ylmethyl)methanamine);

(2S,2'S)-1,1'-(((((2,2'-dimethyl-[1,1'-biphenyl]-3,3'-diyl)bis(methylene))bis(oxy))bis(3-methyl-4,1-phenylene))bis(methylene))bis(piperidine-2-carboxylic acid);

(2S,2'S)-1,1'-(((((2,2'-dimethyl-[1,1'-biphenyl]-3,3'-diyl)bis(methylene))bis(oxy))bis(5-chloro-2-methyl-4,1-phenylene))bis(methylene))bis(piperidine-2-carboxylic acid);

3,3'-((((((2,2'-dimethyl-[1,1'-biphenyl]-3,3'-diyl)bis (methylene))bis(oxy))bis(5-chloro-2-methyl-4,1-phenylene))bis(methylene))bis(azanediyl))dipropionic acid;

(S)-1-(4-((3'-((4-(((S)-2-carboxypiperidin-1-yl)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)piperidine-2-carboxylic acid;

3-((4-((3'-((4-(((2-carboxyethyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)amino)propanoic acid;

N-(4-((3'-((4-((((S)-1-carboxy-3-hydroxypropyl)(methyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)-N-methyl-L-homoserine; and (S)-2-((4-((3'-((4-((((S)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methylbenzyl)amino)-3-hydroxy-2-methylpropanoic acid;

or a pharmaceutically acceptable salt thereof.

7. A compound selected from

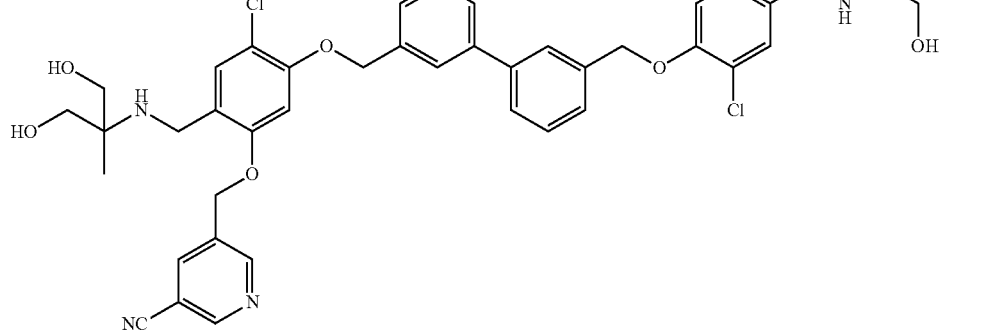

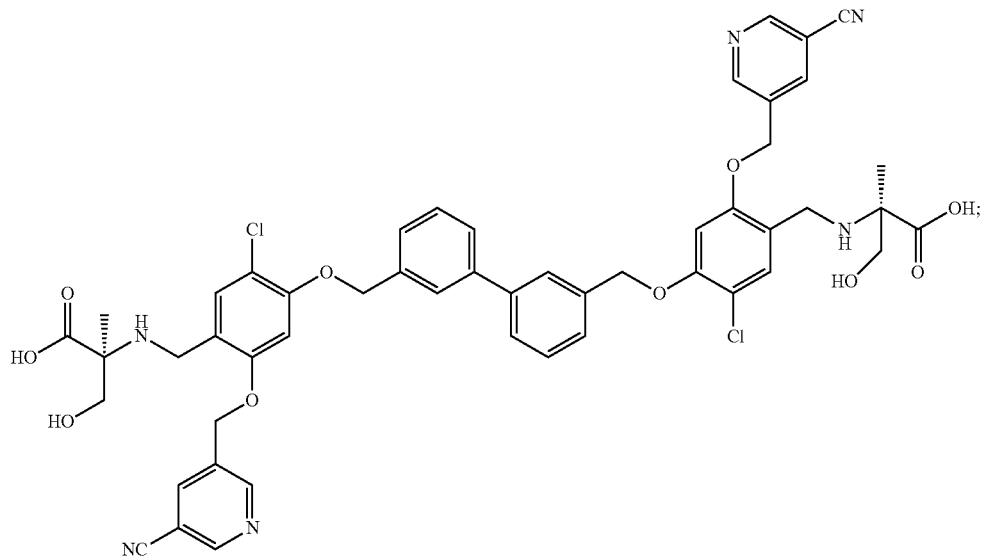

425
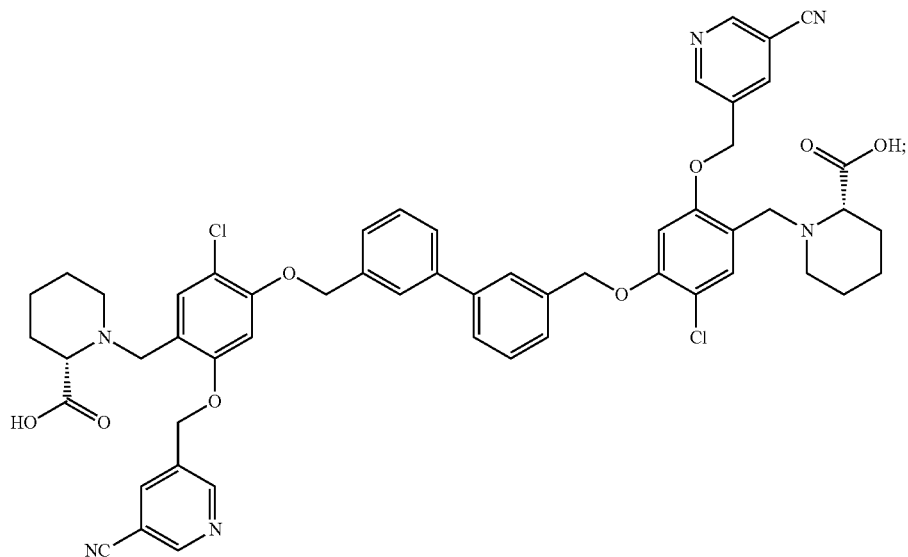
426
-continued
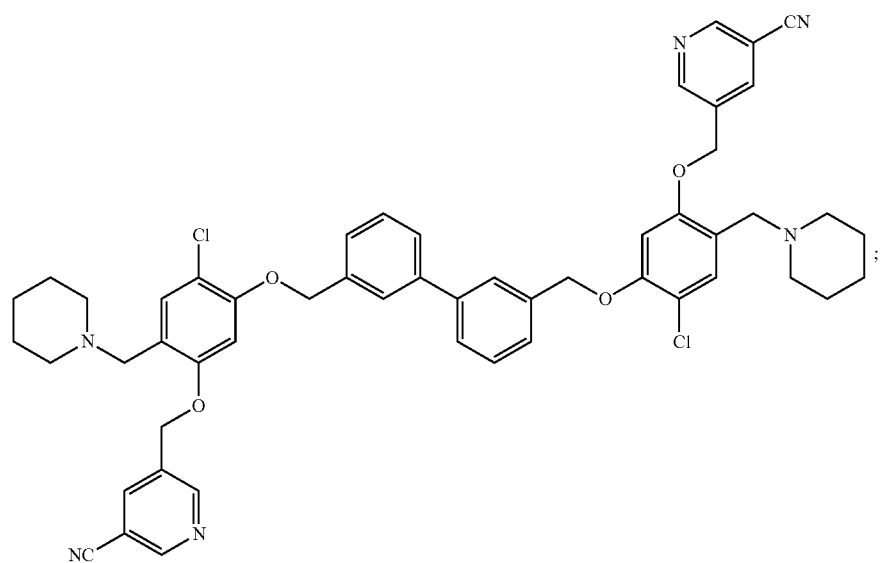
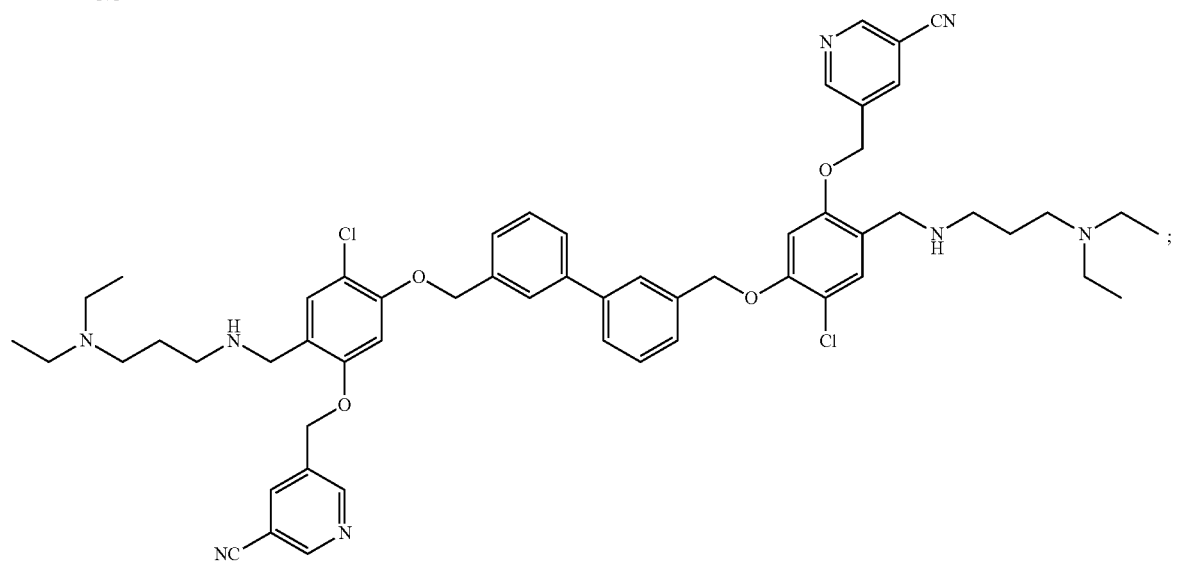

-continued
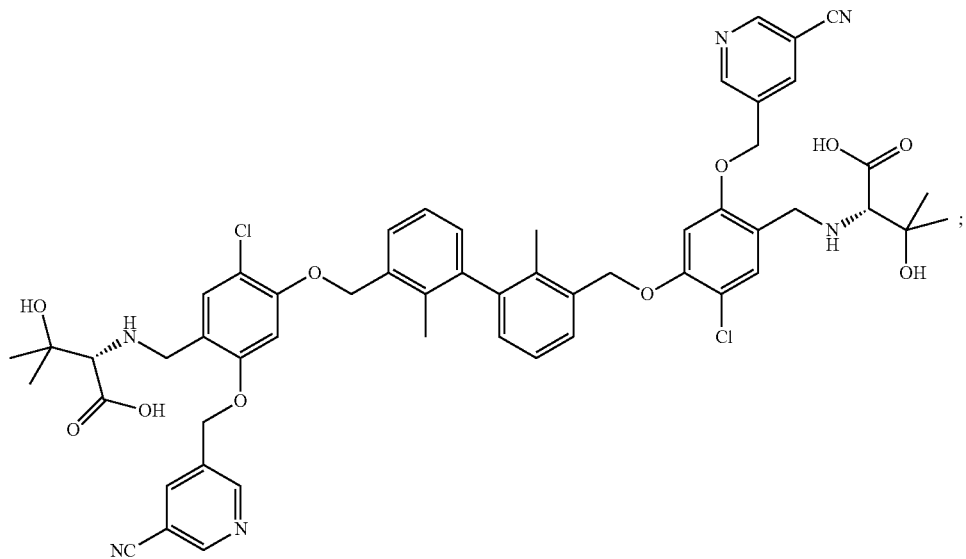
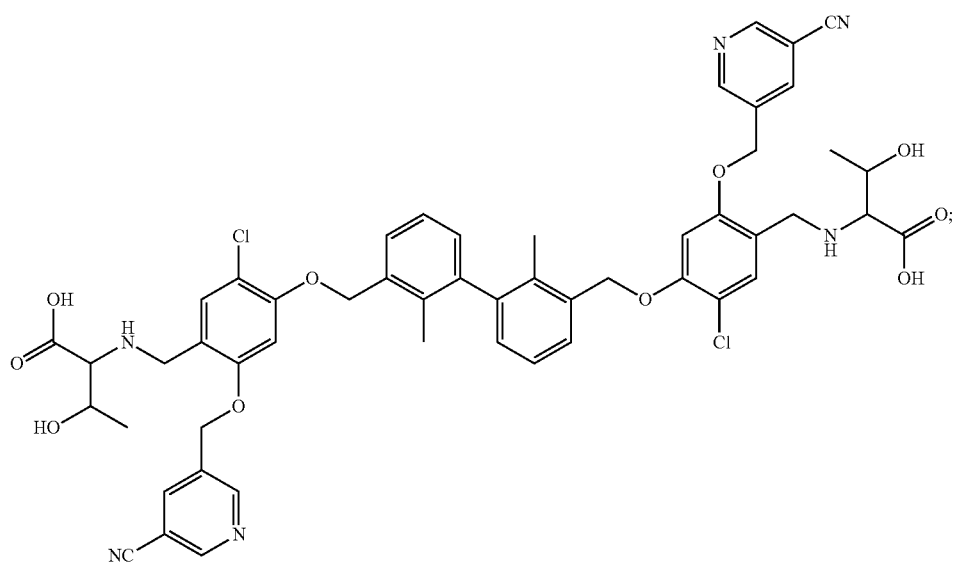
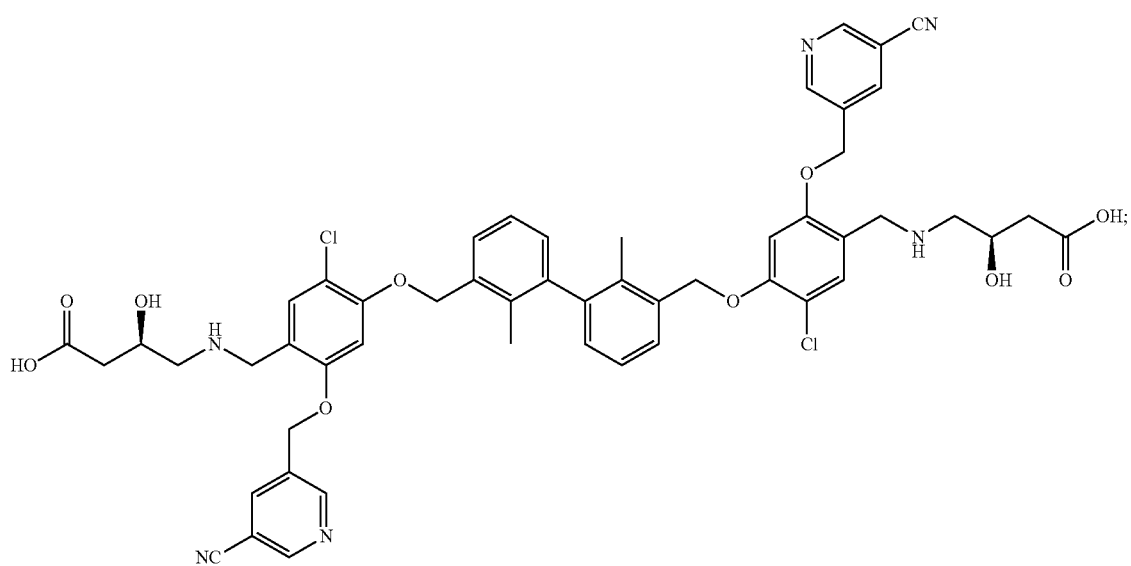

429
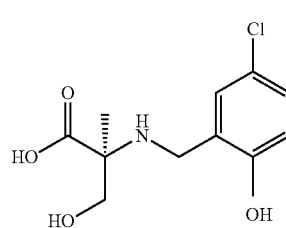
430
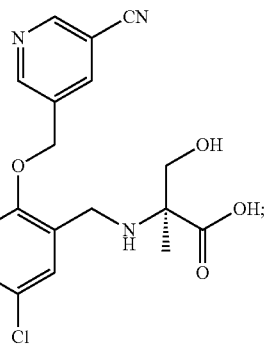
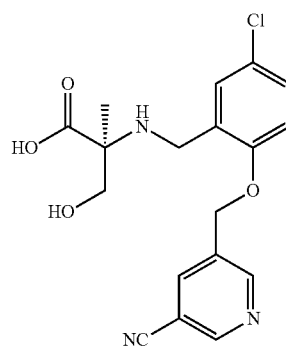
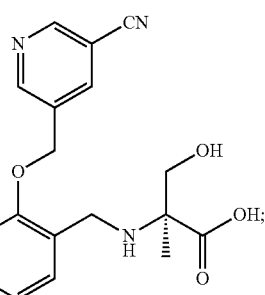
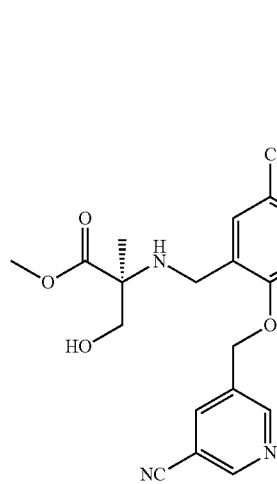
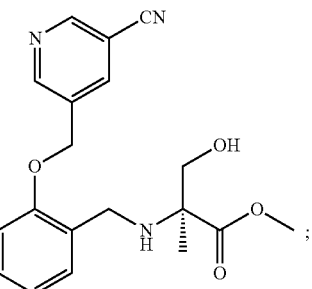

431 432
-continued
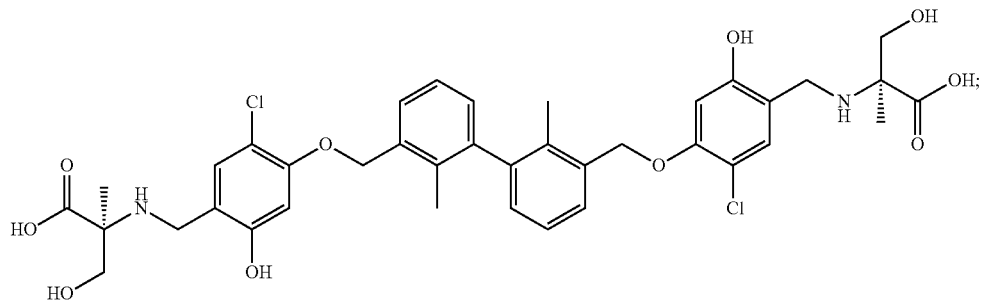
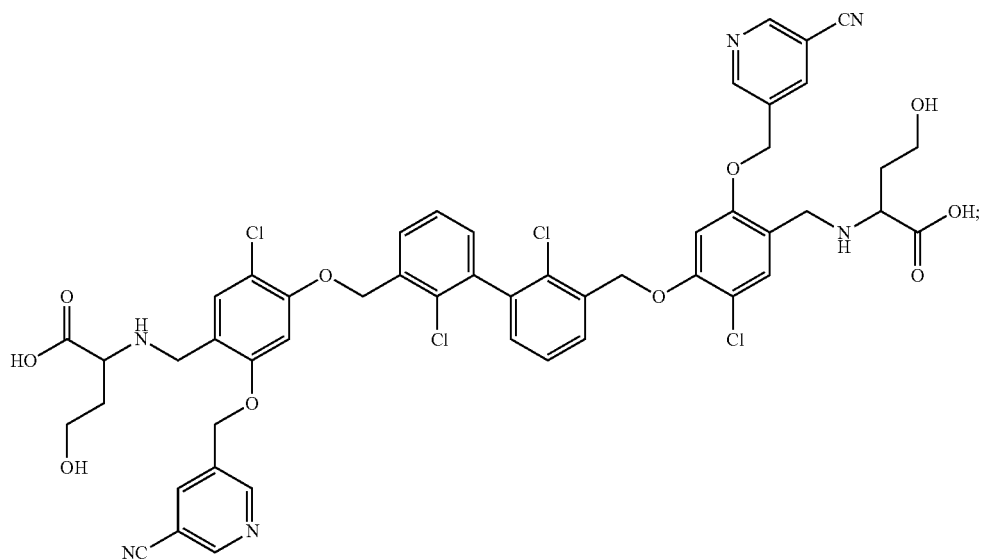
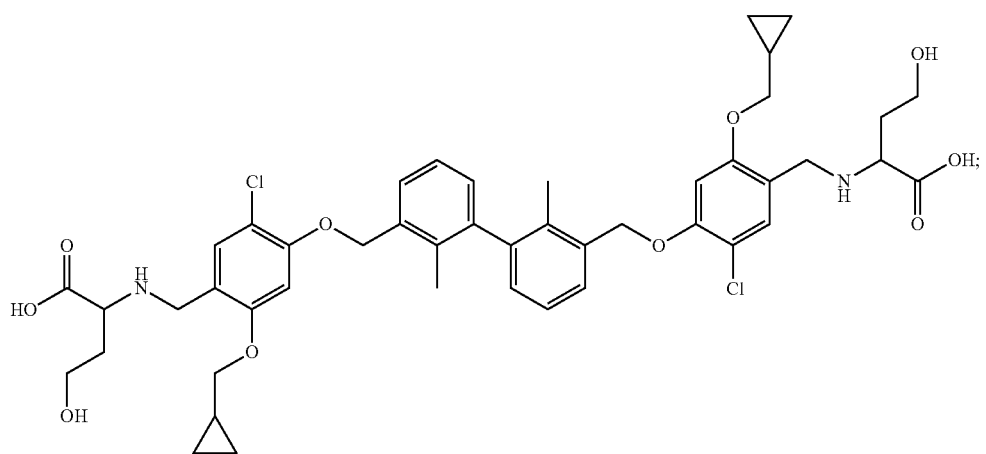

433                                              434
-continued
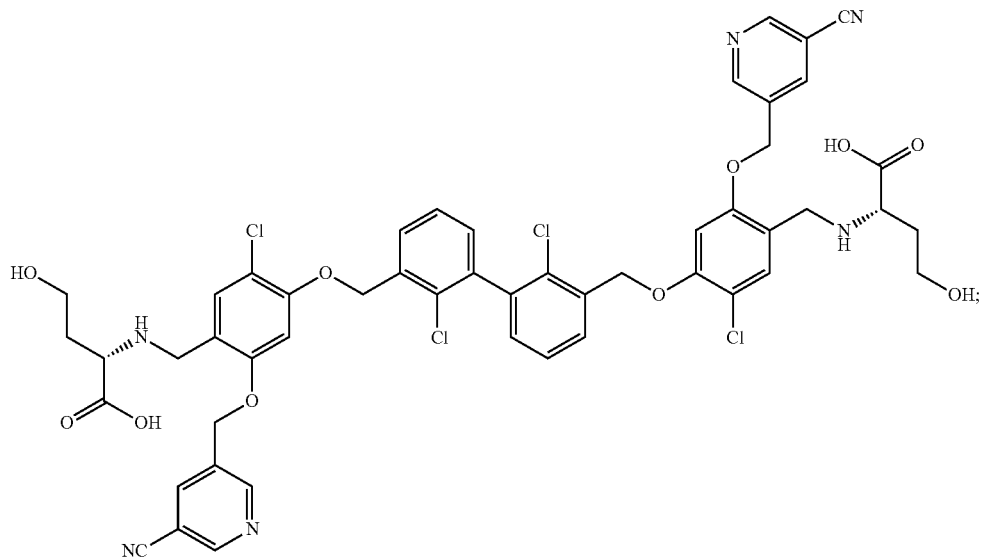
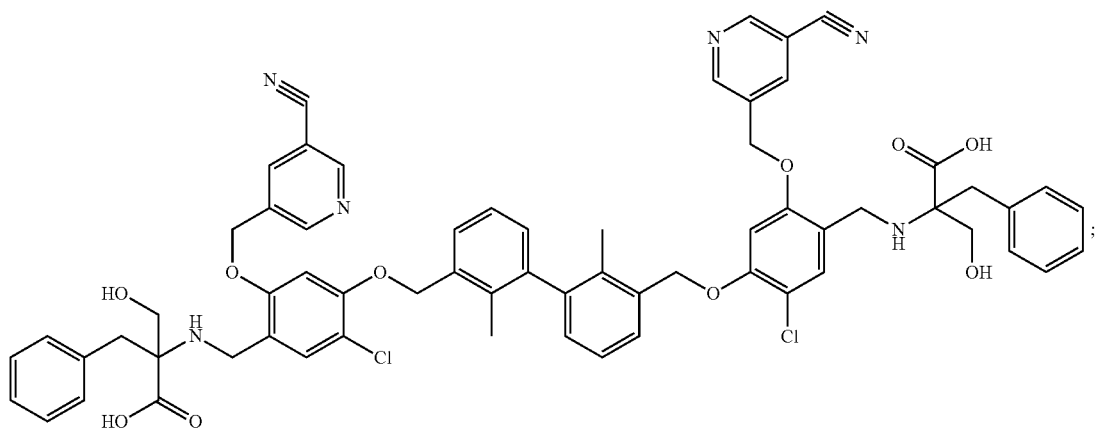
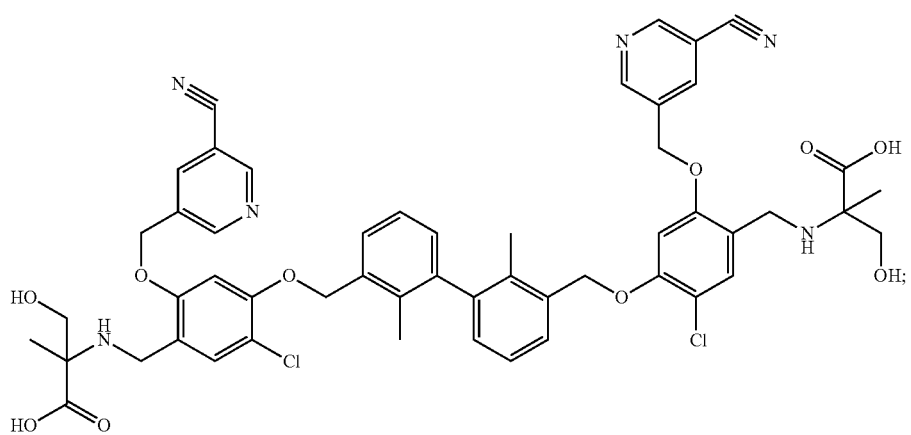

435
436
-continued
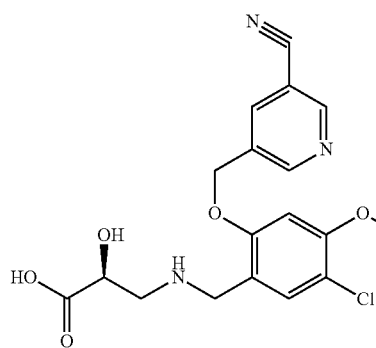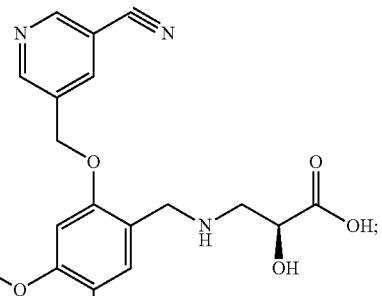
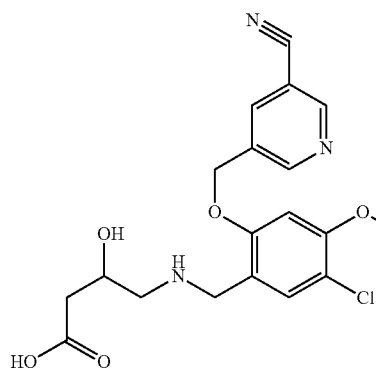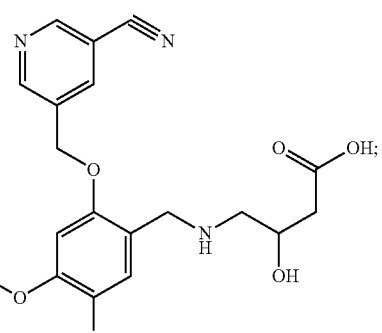
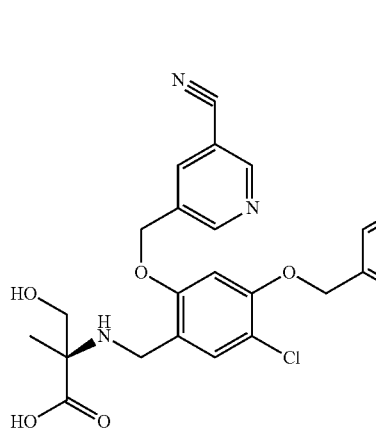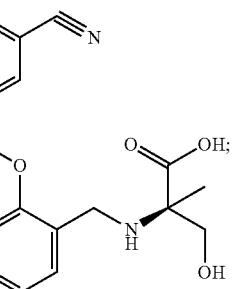
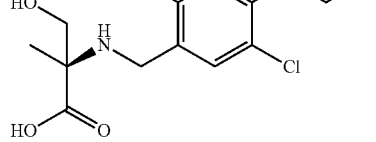
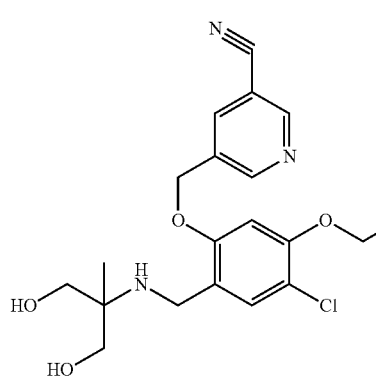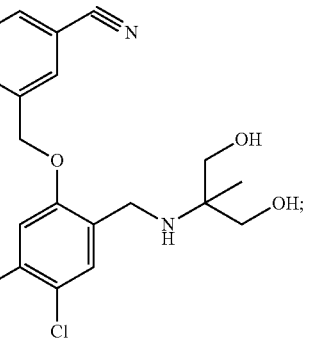

-continued
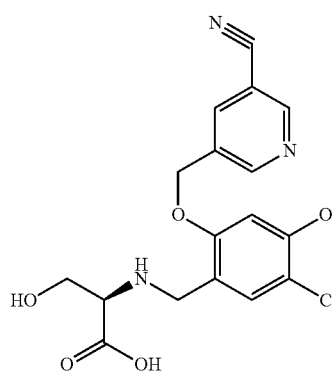
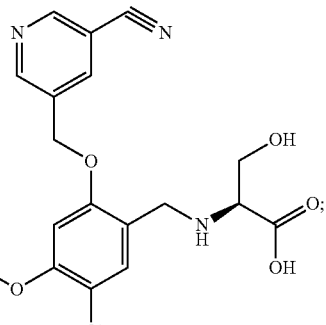
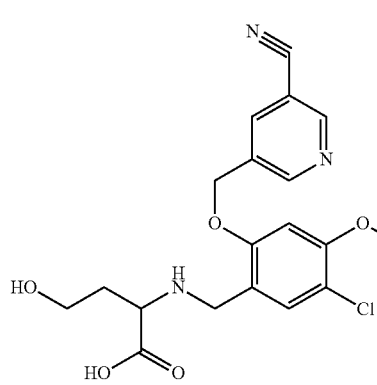
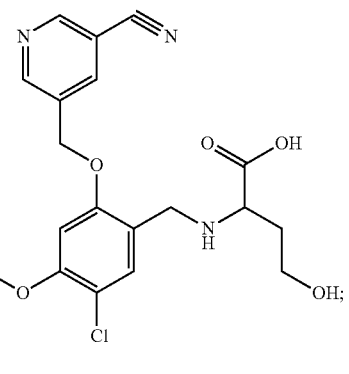
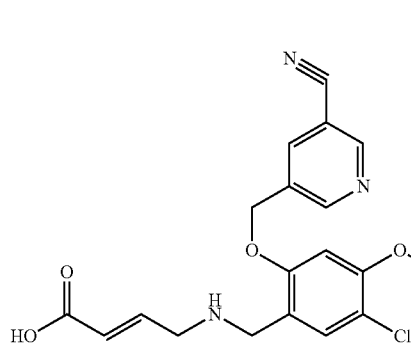
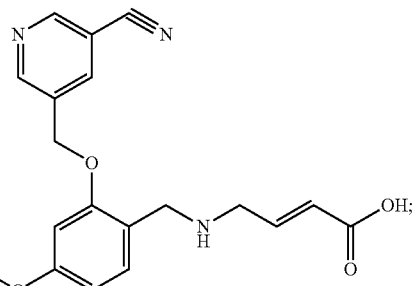
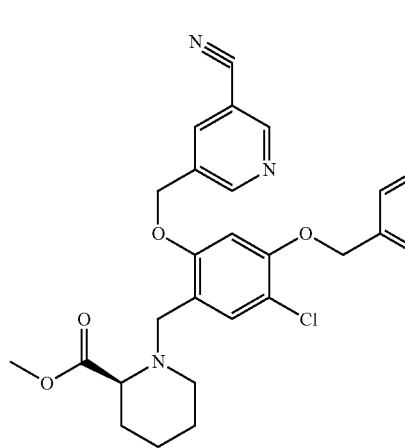
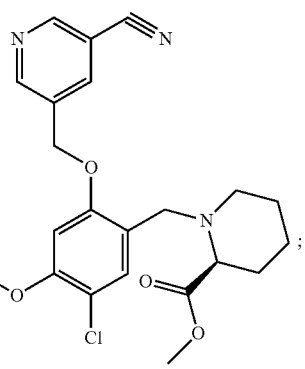

-continued
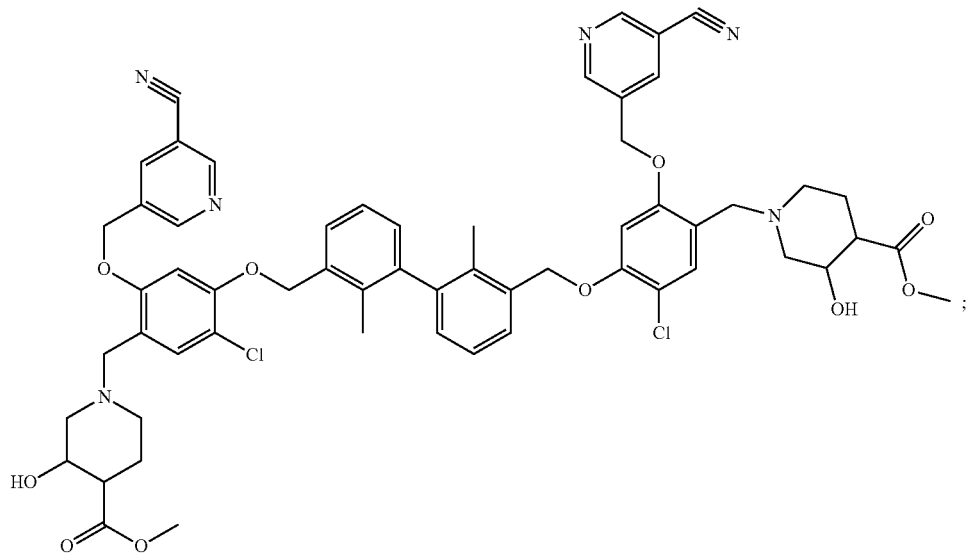
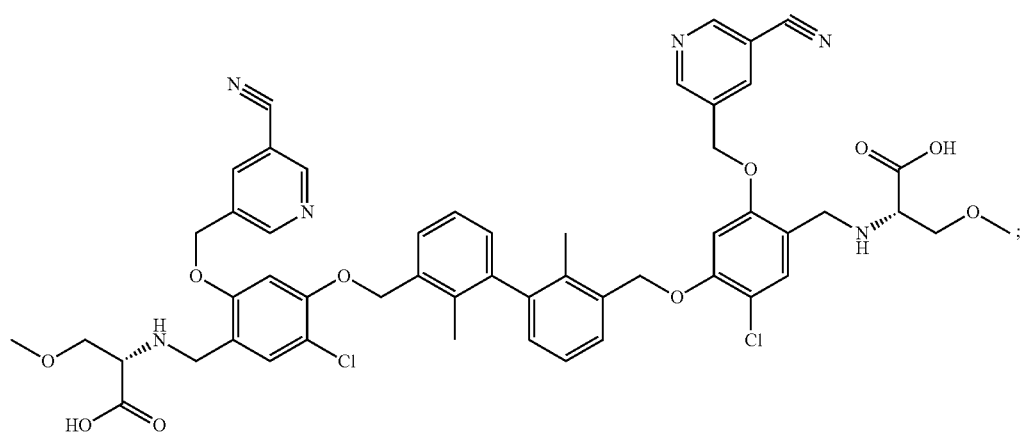
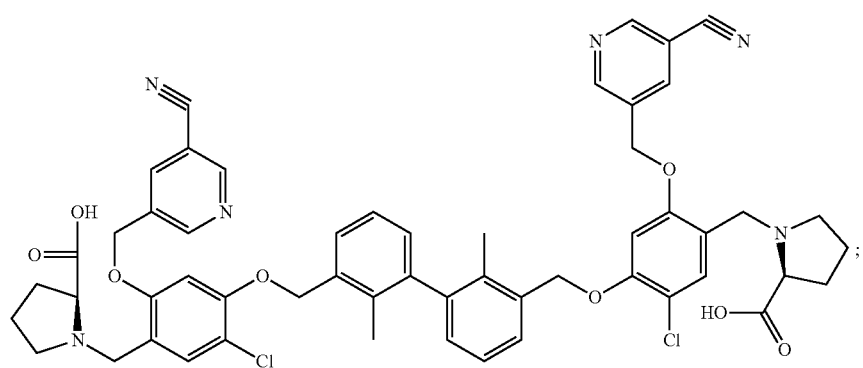

441
442
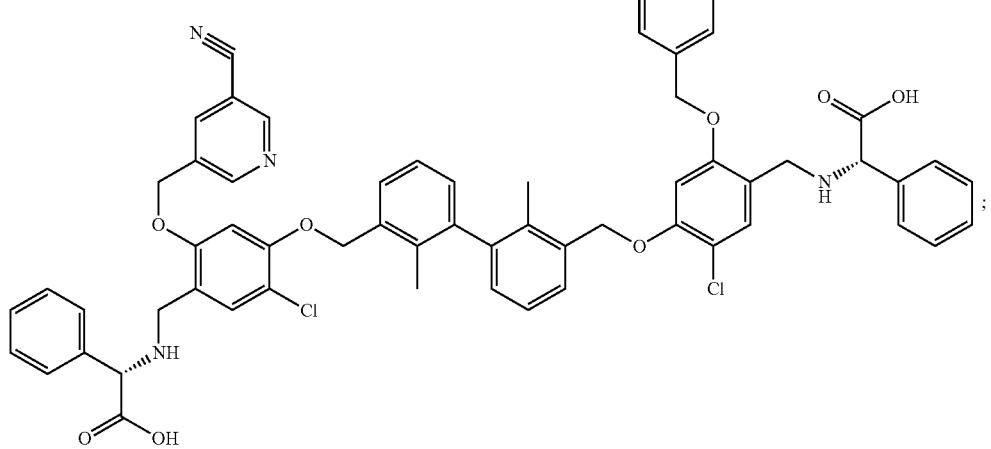
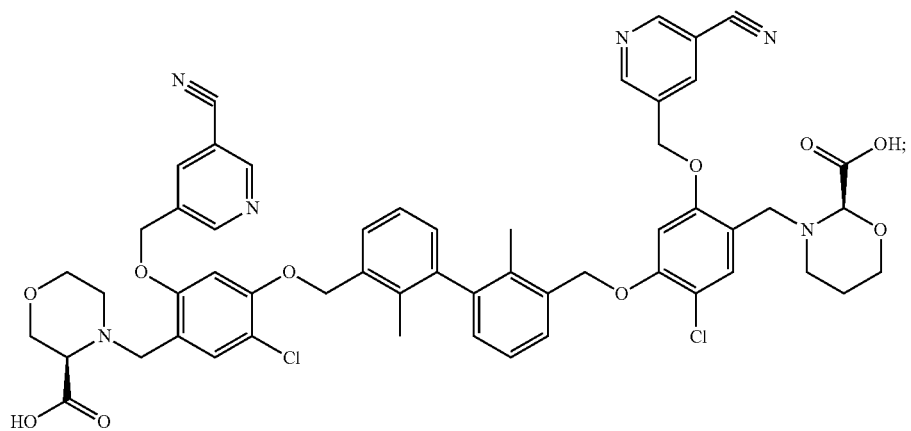
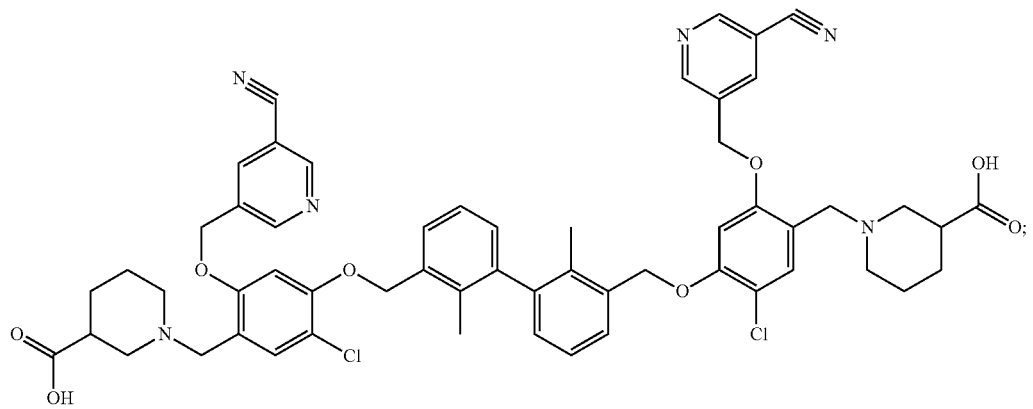

443
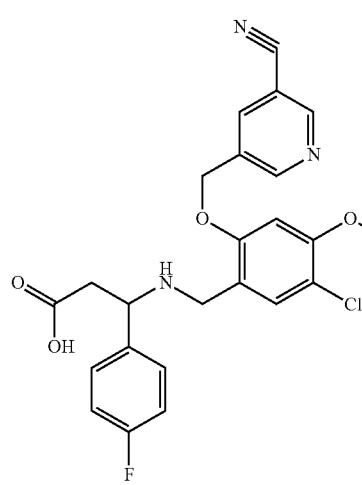
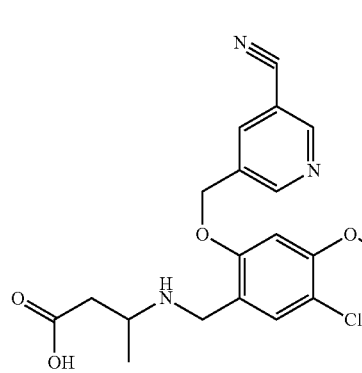
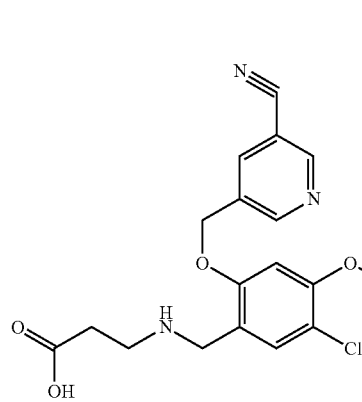
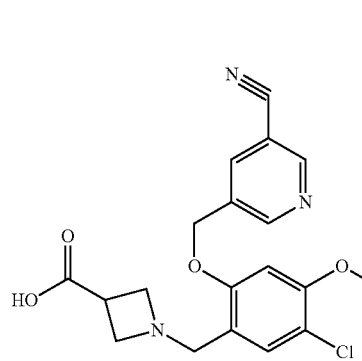
444
-continued
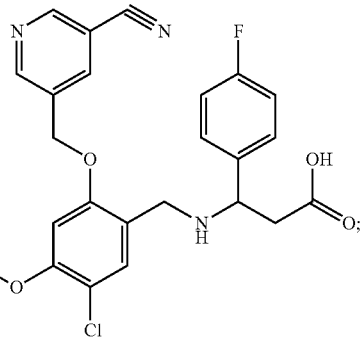
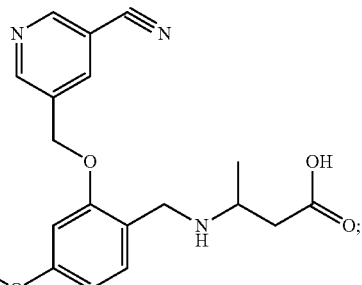
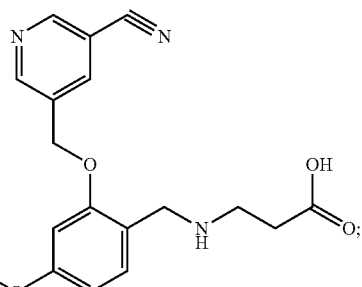
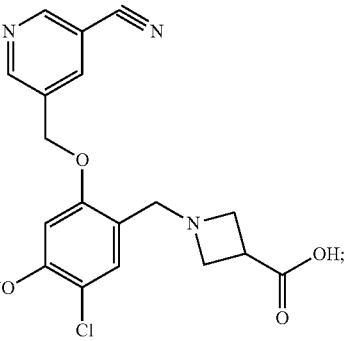

445
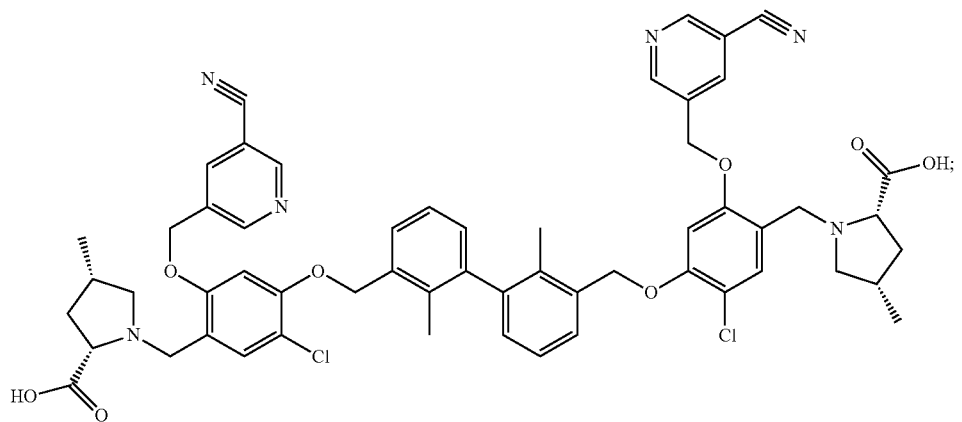
446
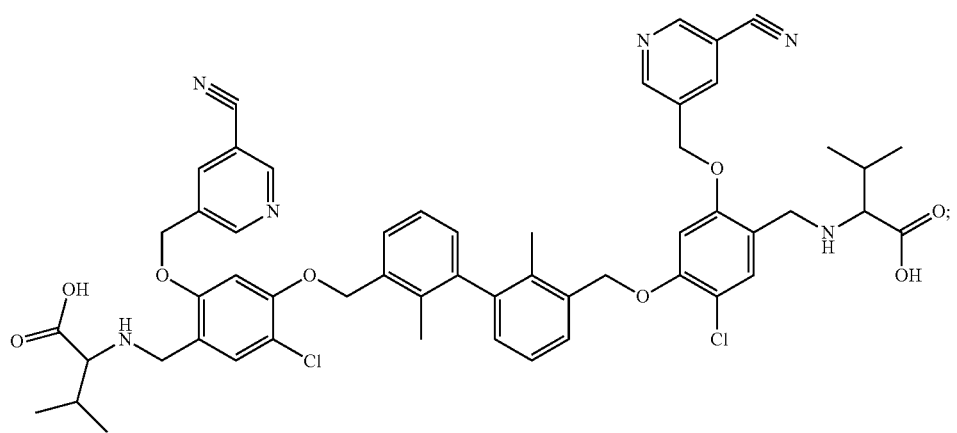
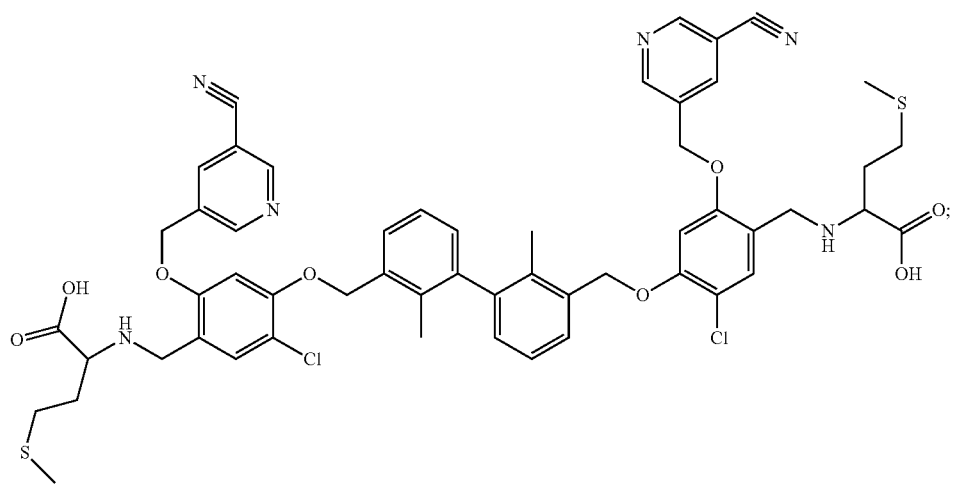

447
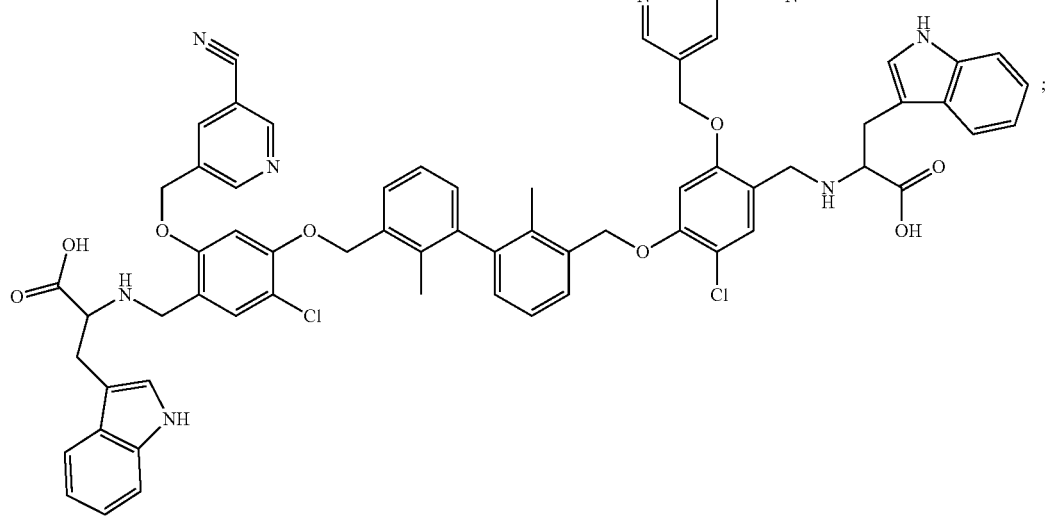
448
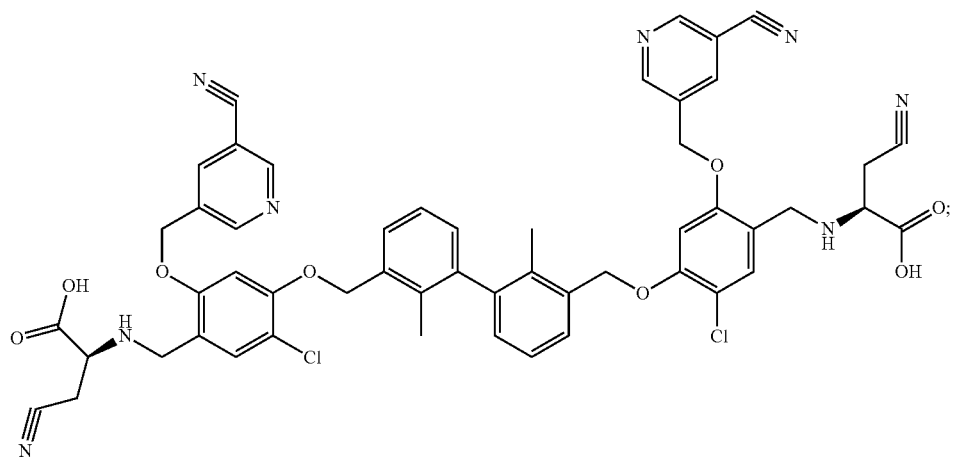
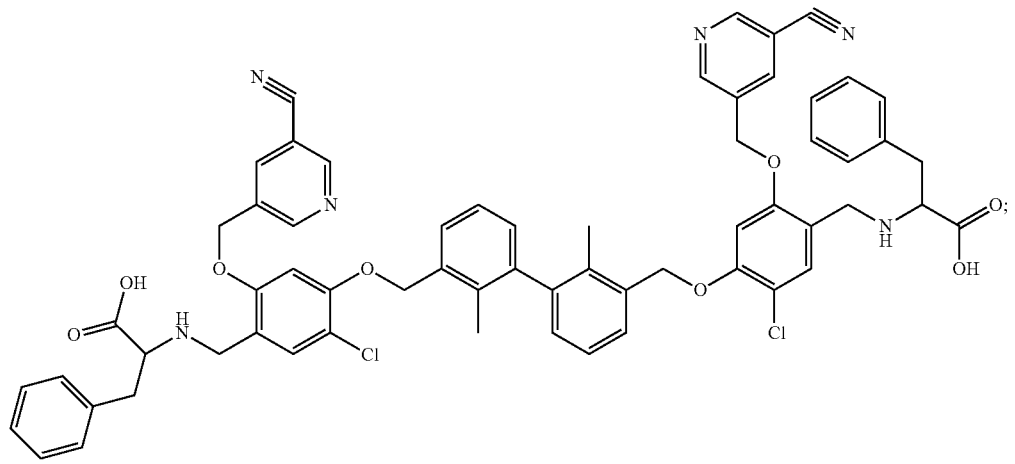

-continued
449
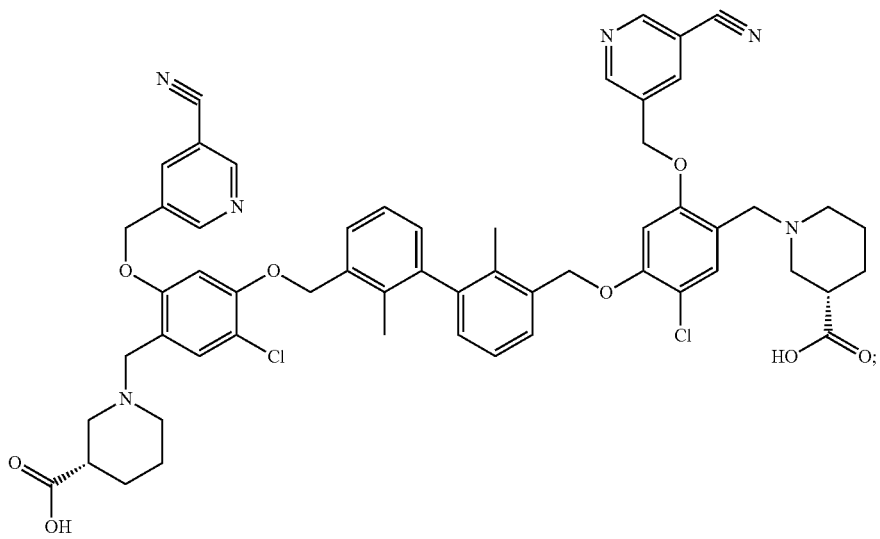
450
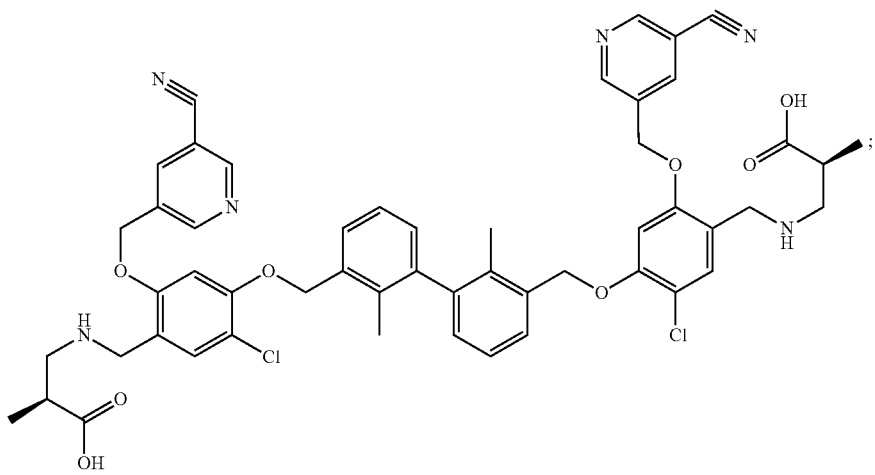
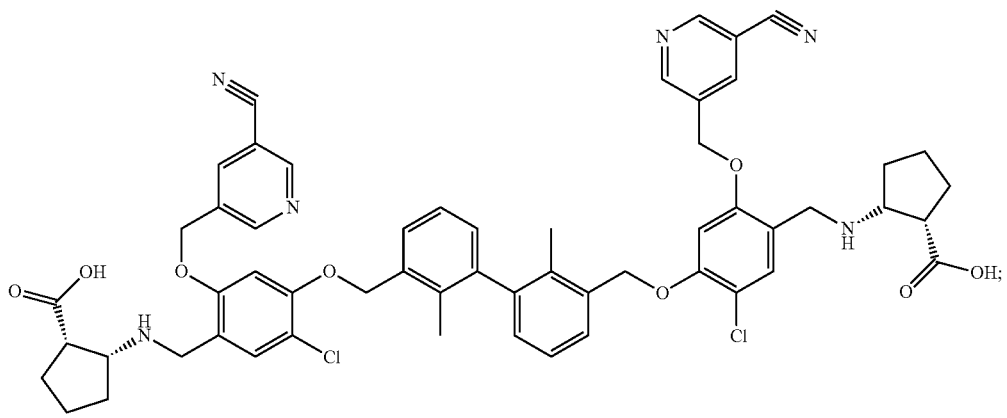

451
452
-continued
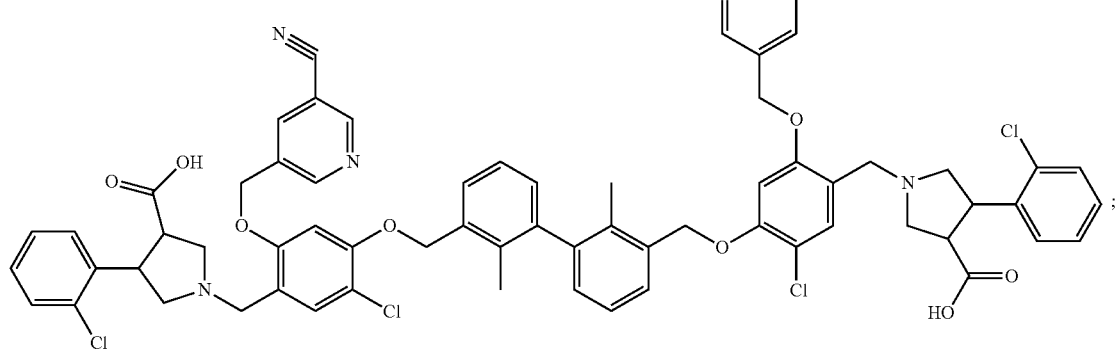
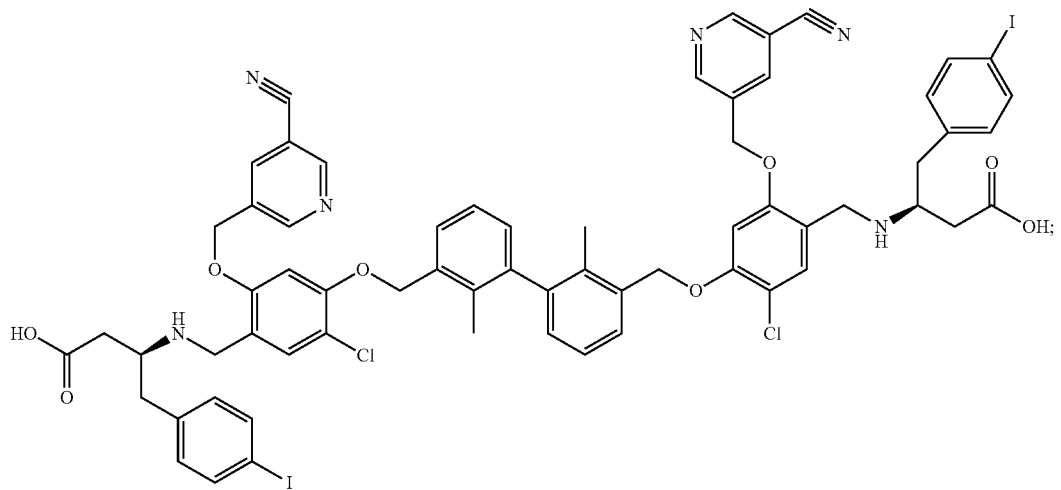
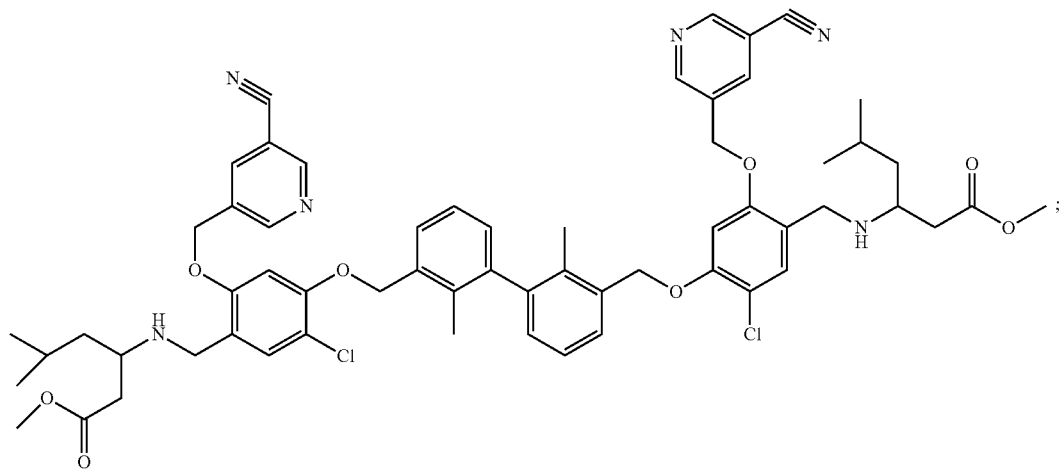

453 454
-continued
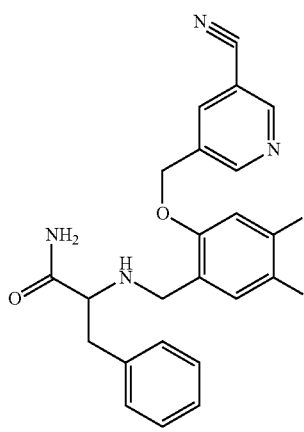
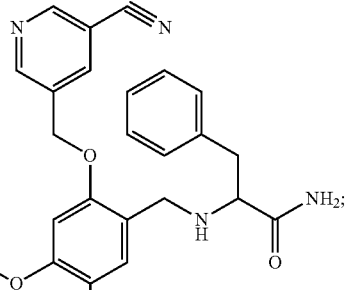
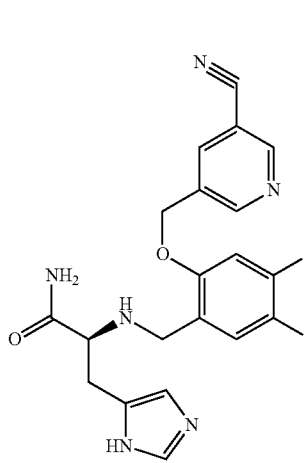
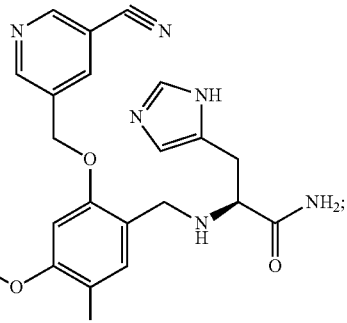
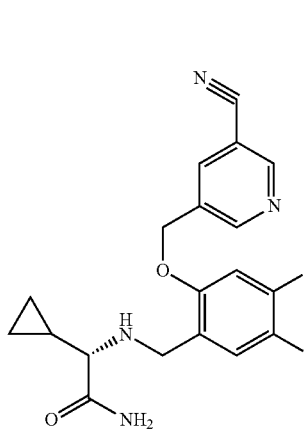
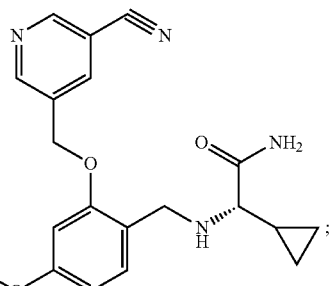

455
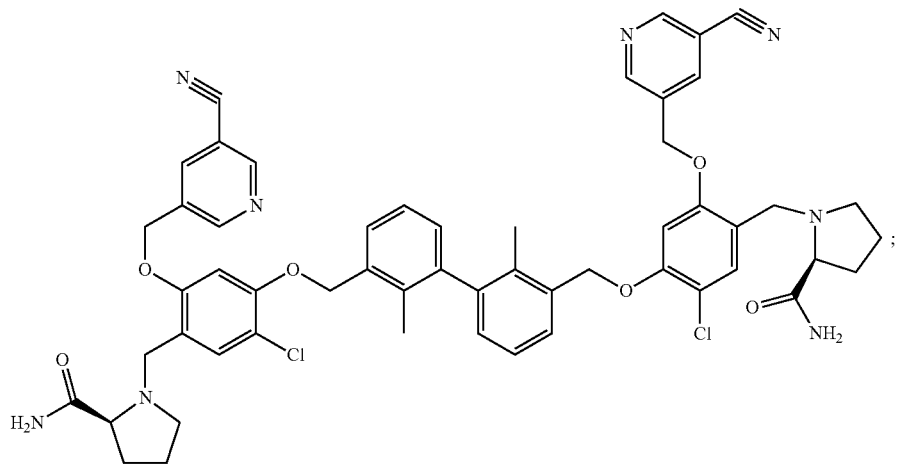
-continued
456
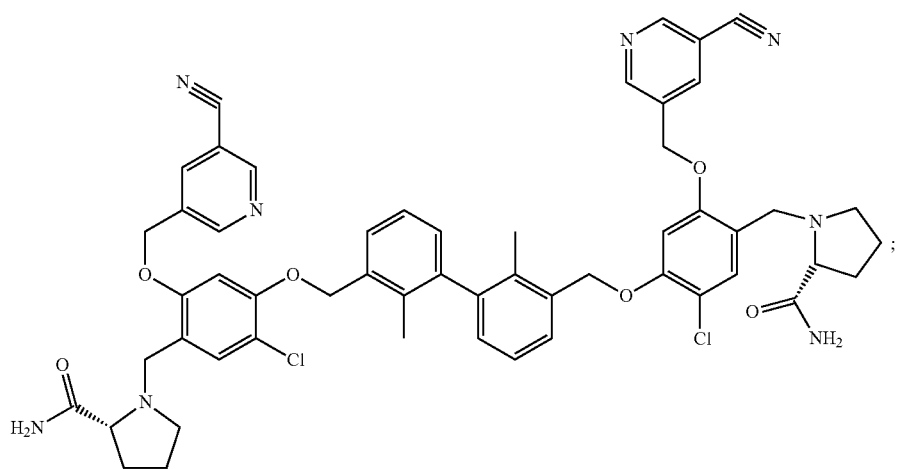
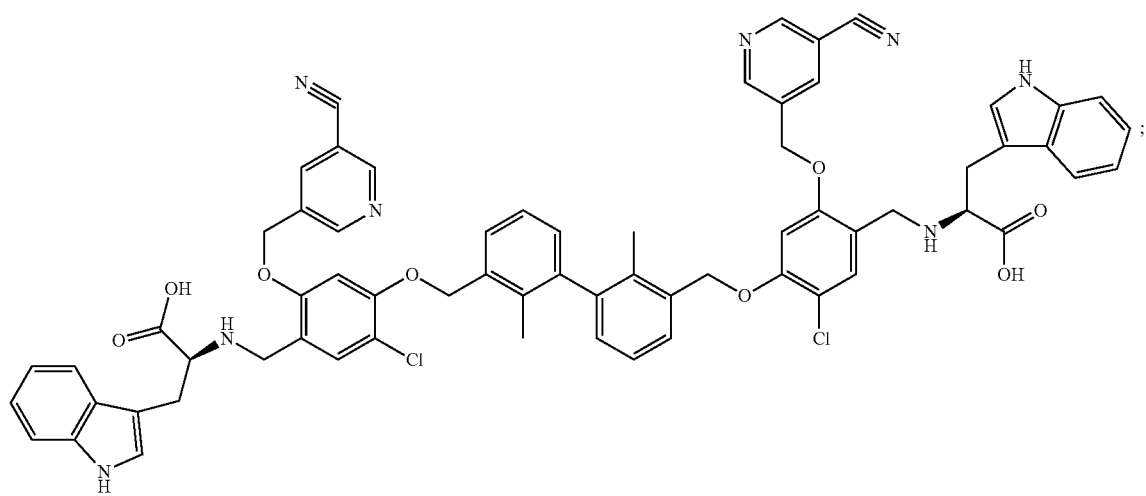

457 458
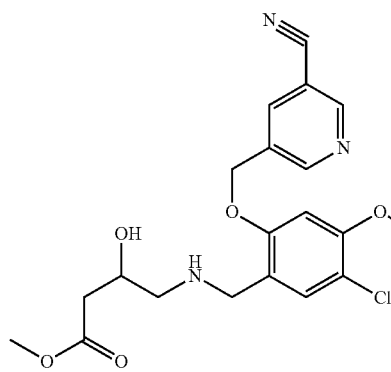
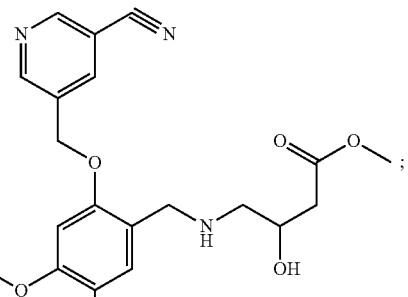
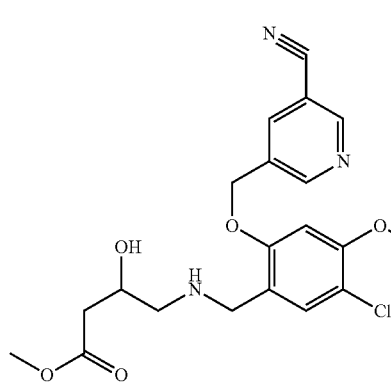
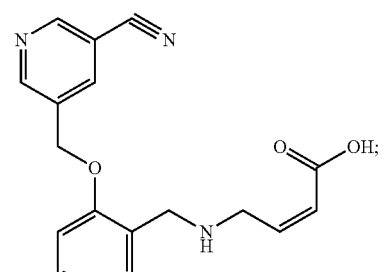
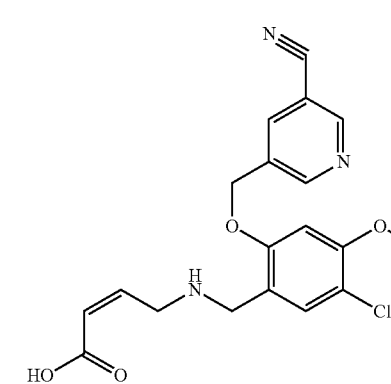
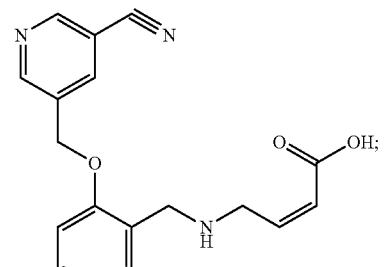
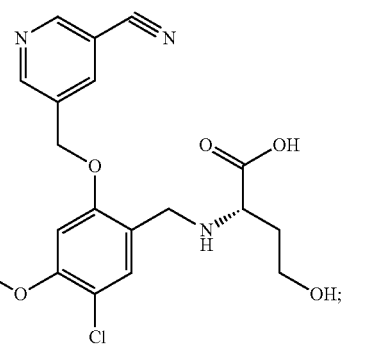
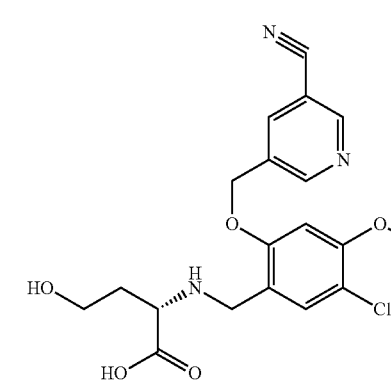

459 460
-continued
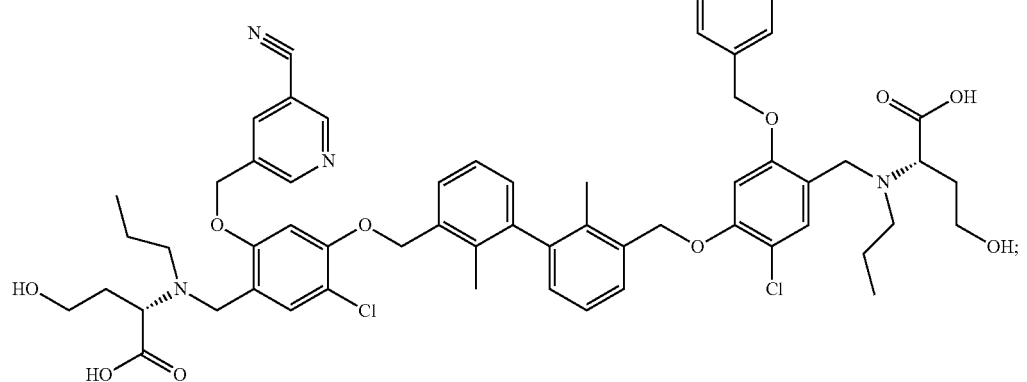
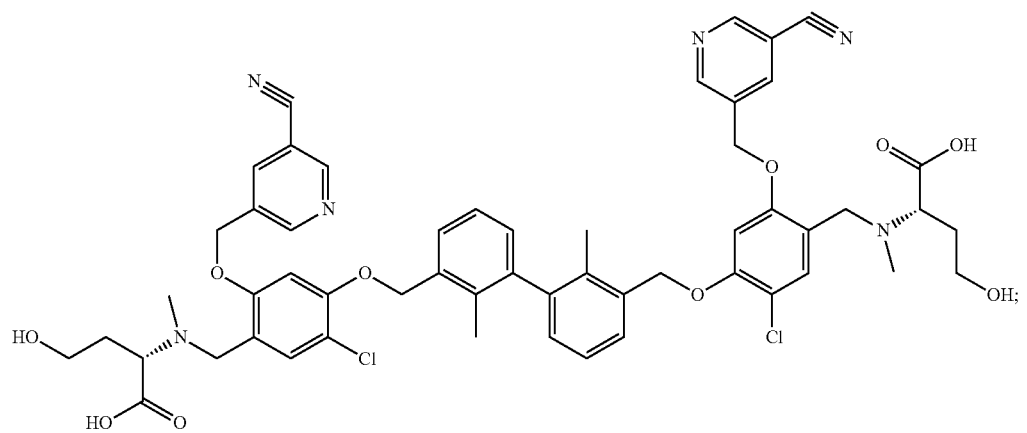
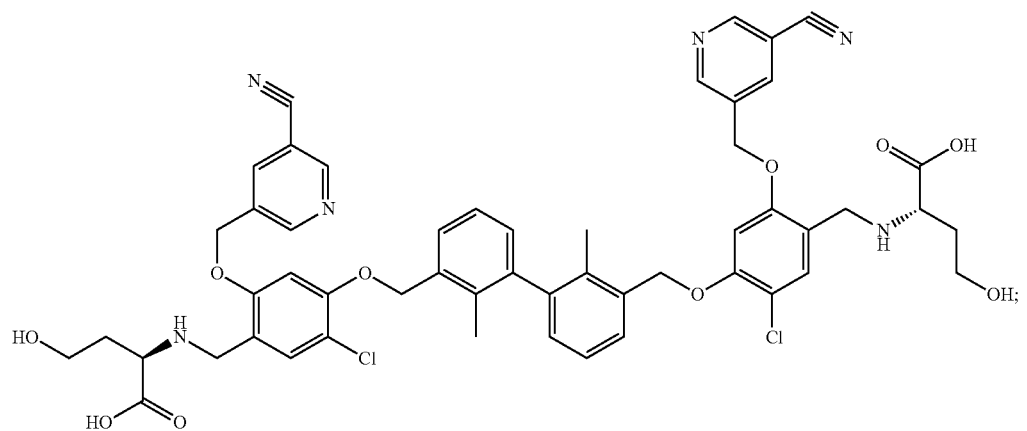
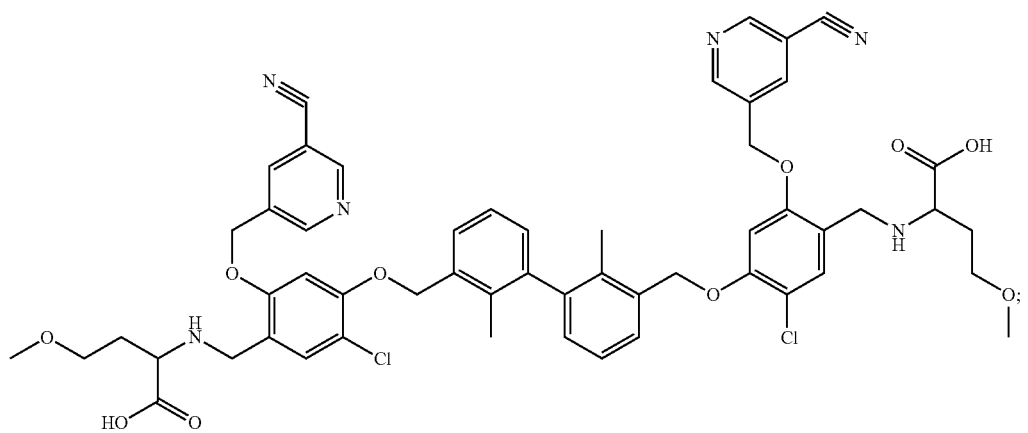

461 462
-continued
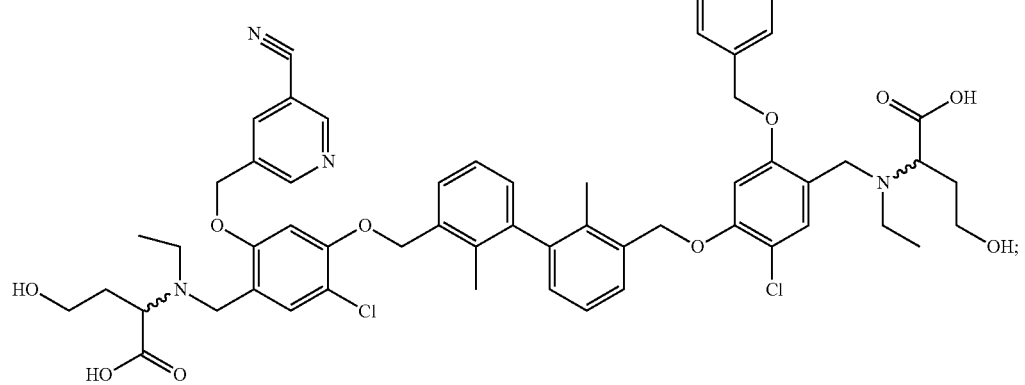
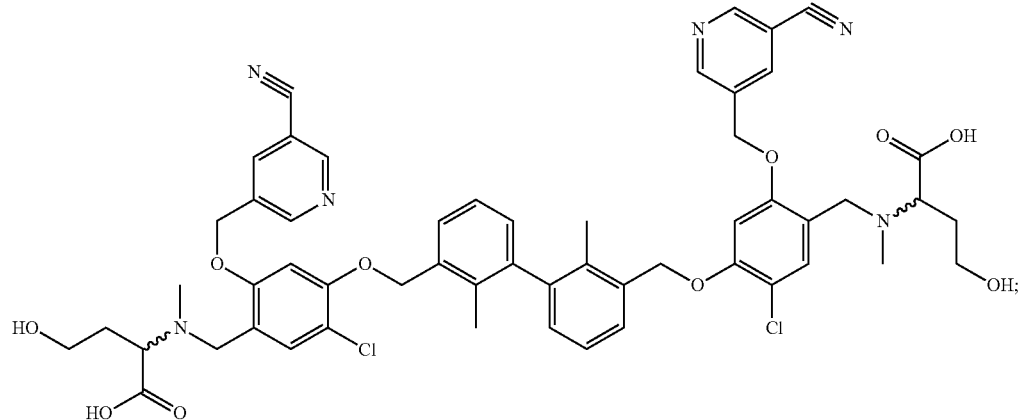
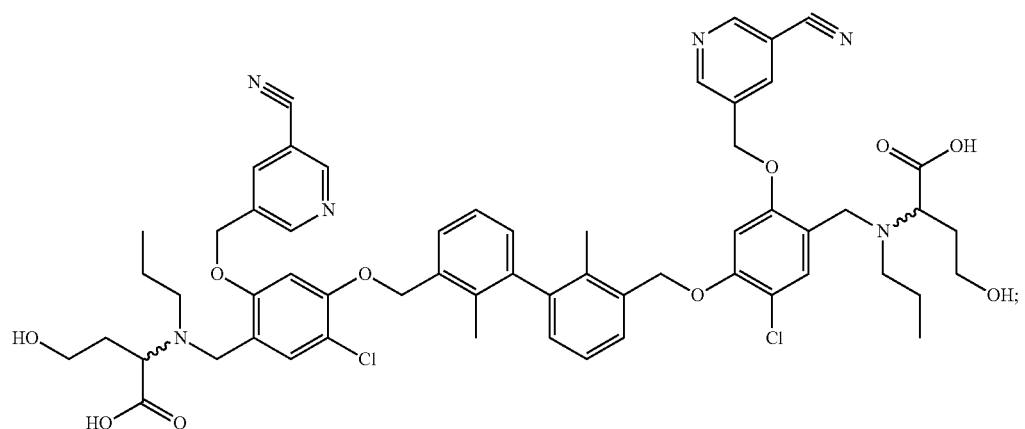
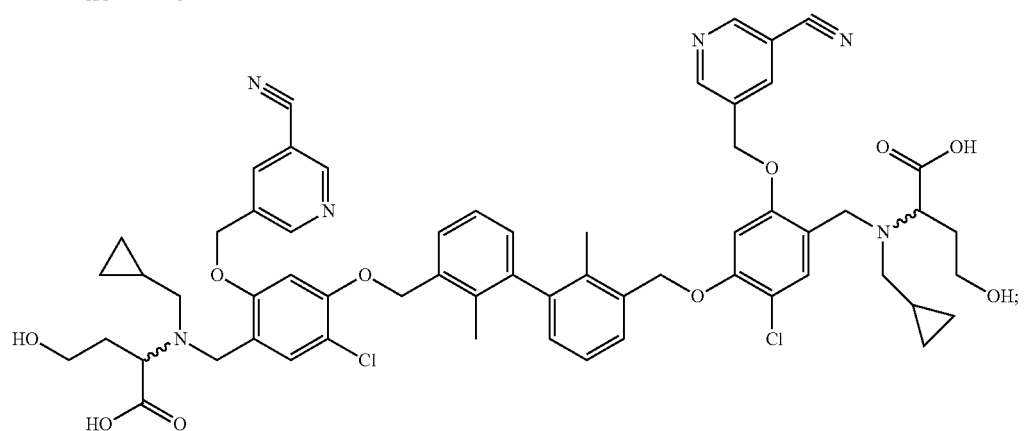

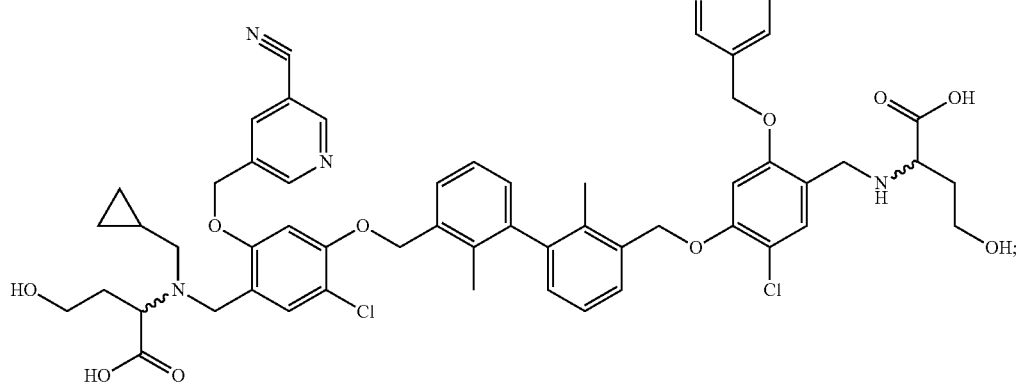
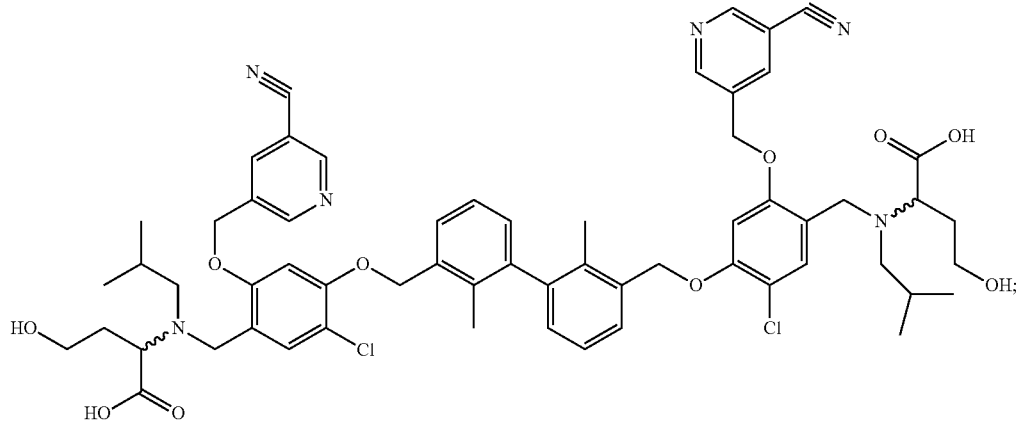
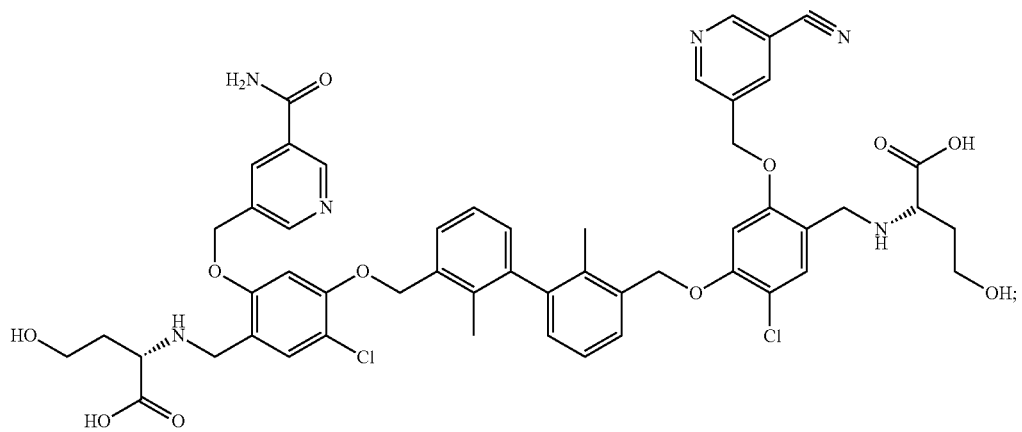
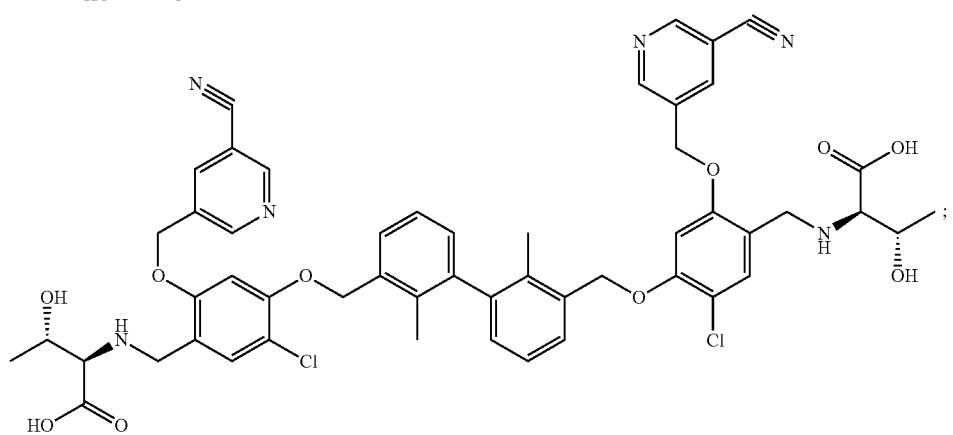

465
466
-continued
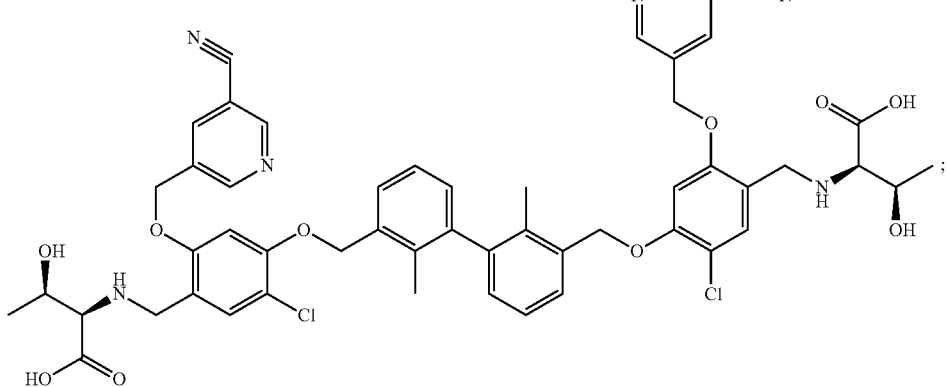
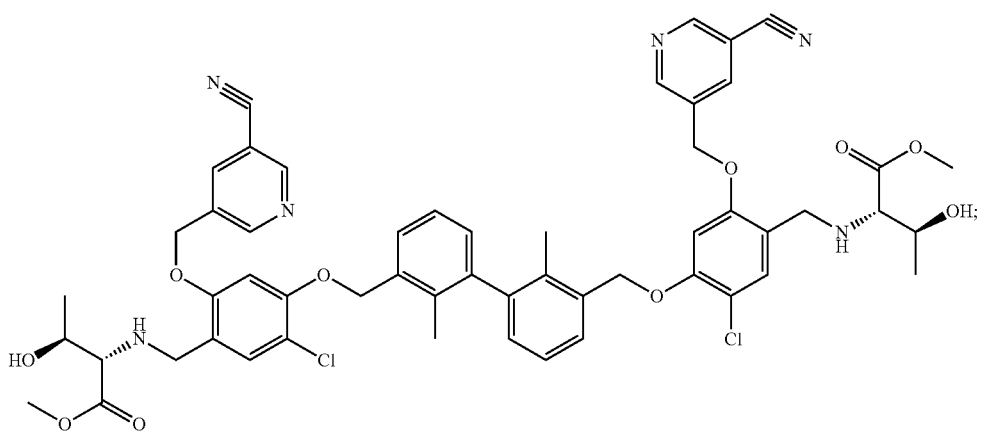
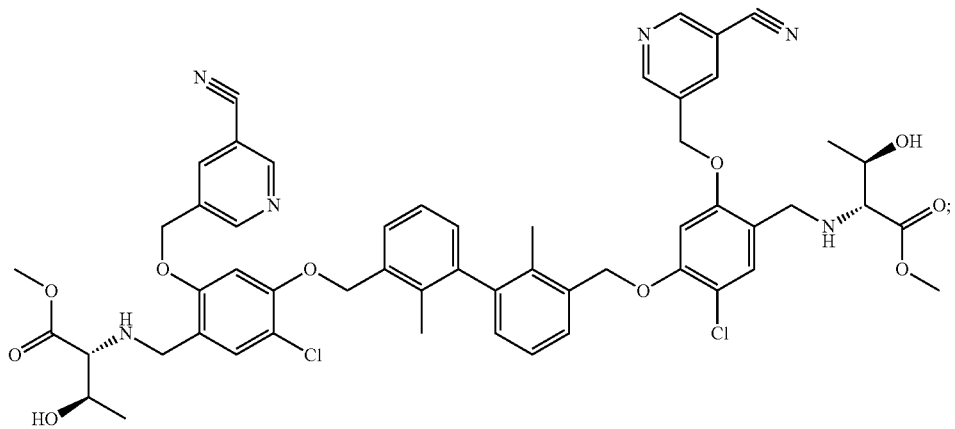

467
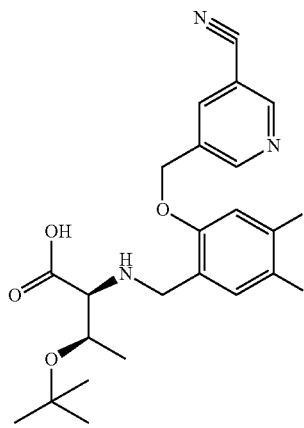
468
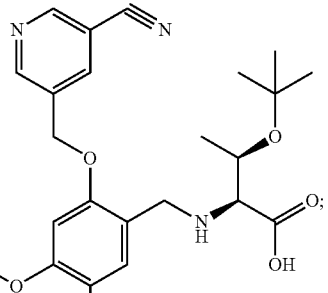
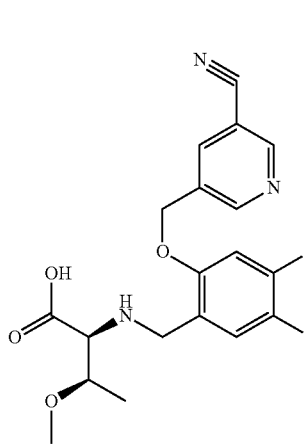
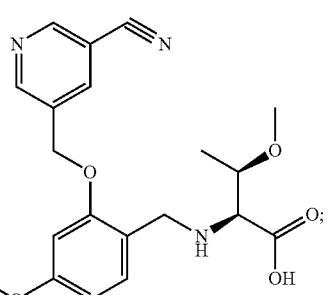
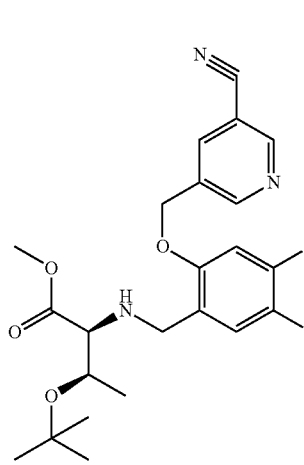
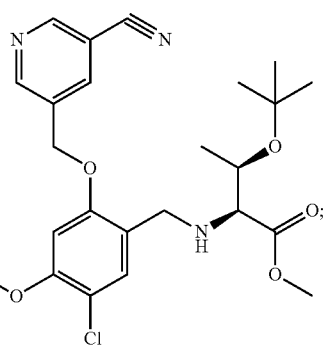

-continued
469
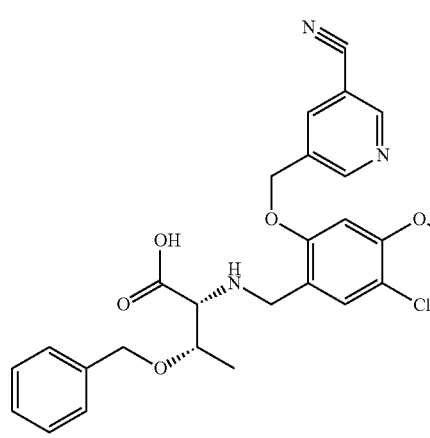
470
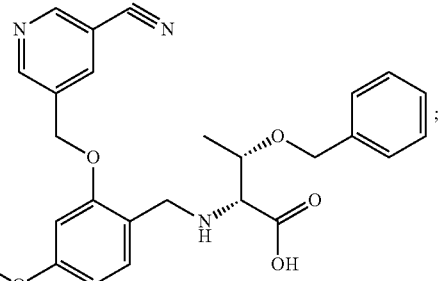
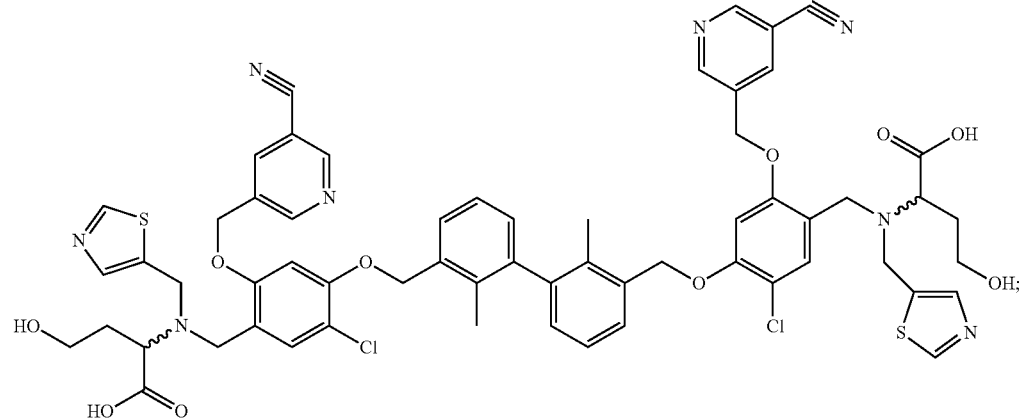
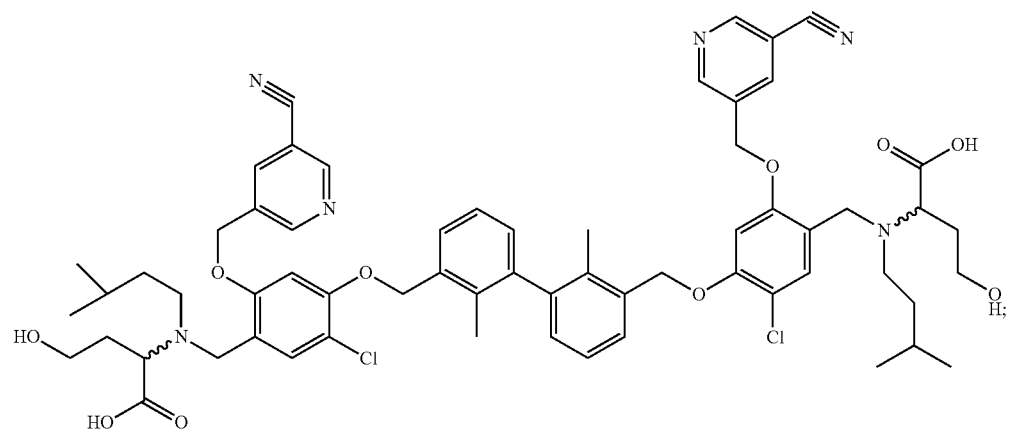

471
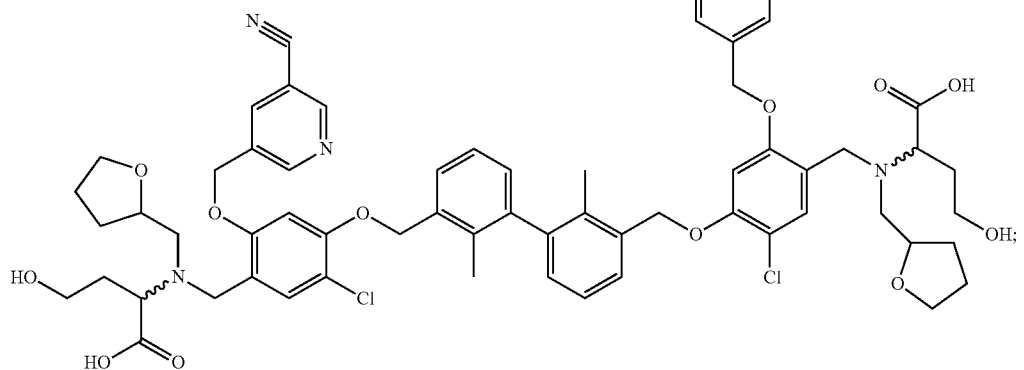
472
-continued
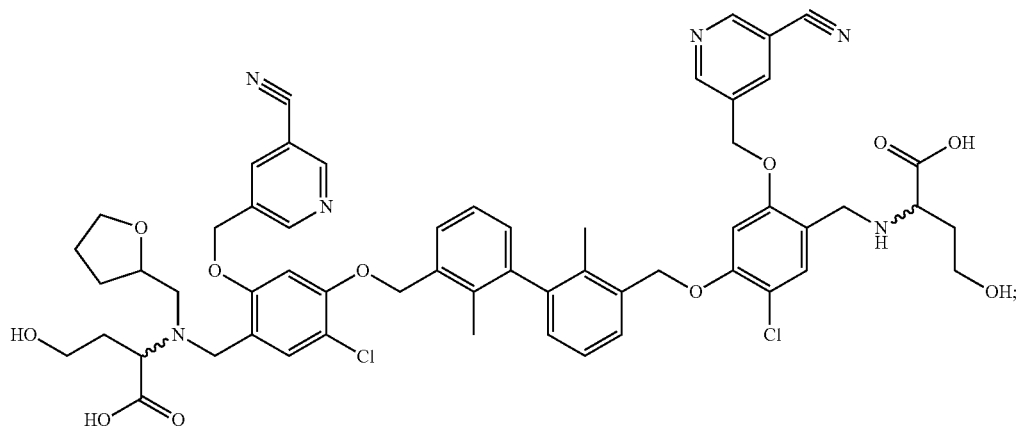
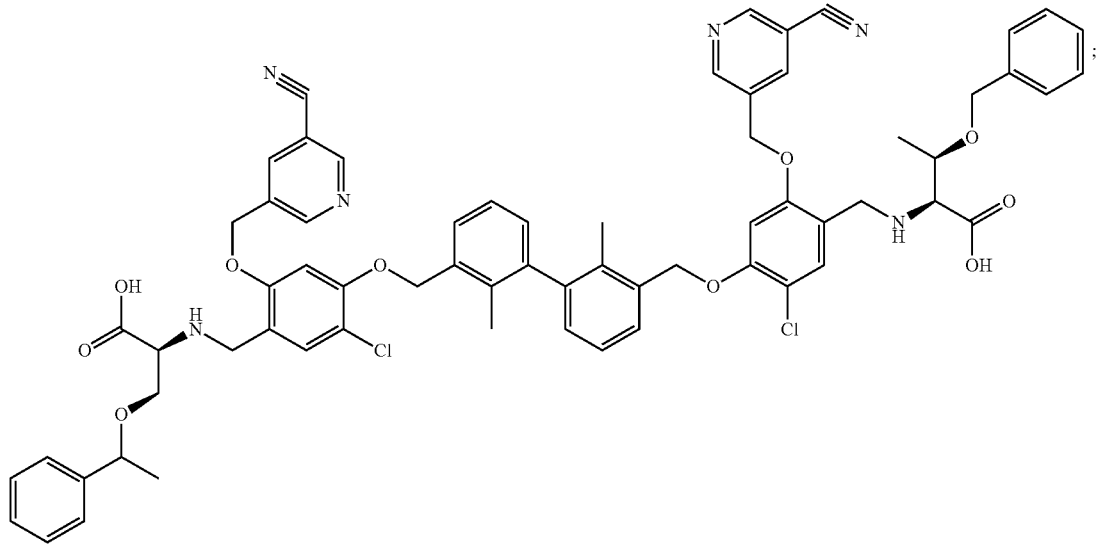

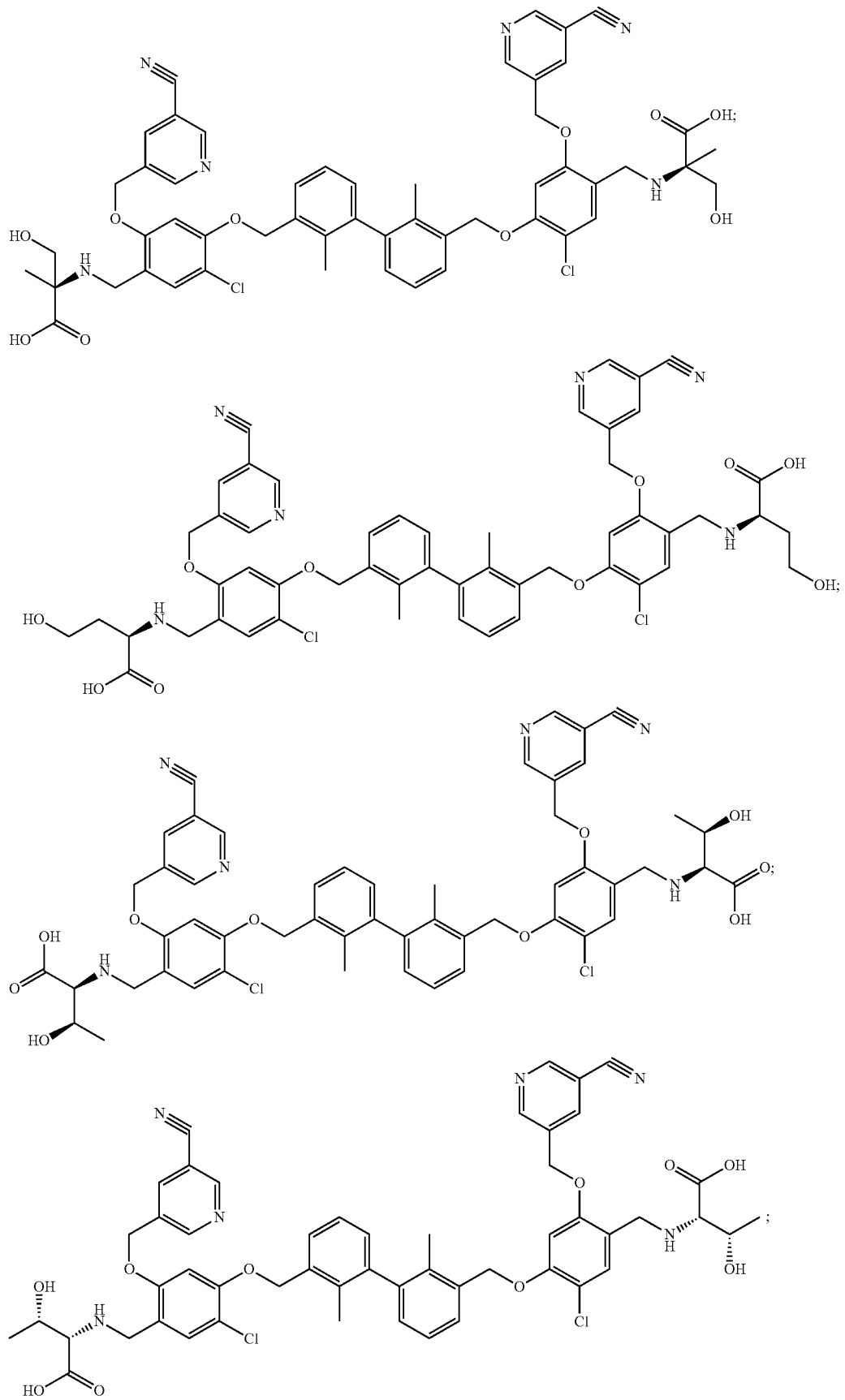

475
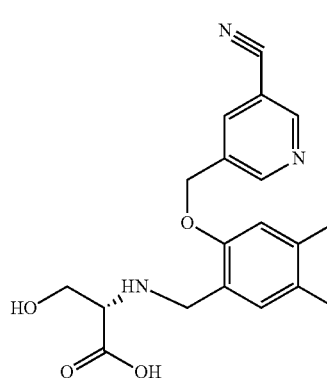
476
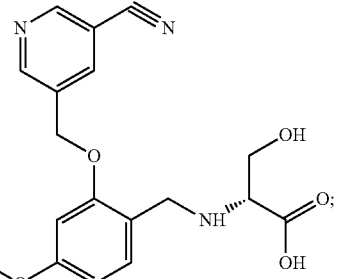
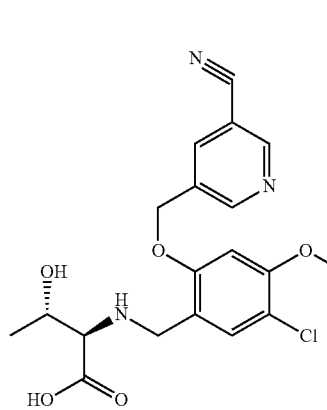
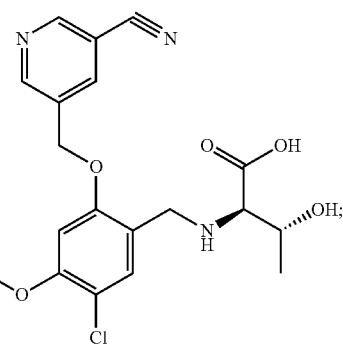
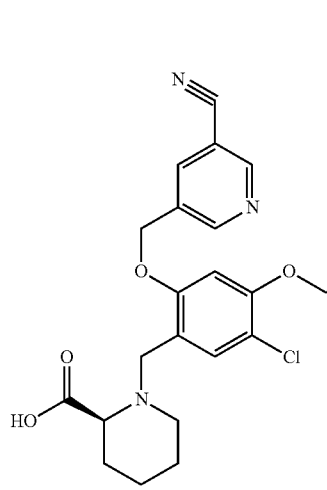
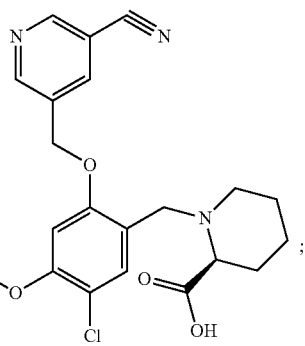

477
-continued
478
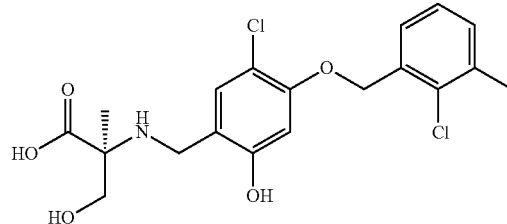
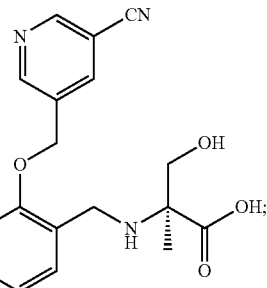
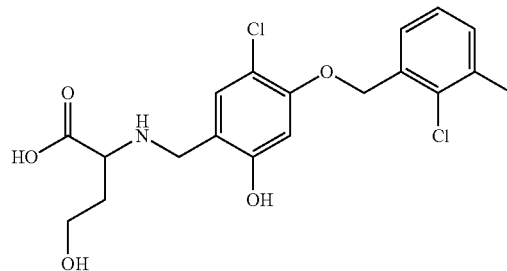
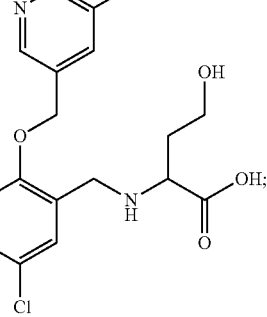
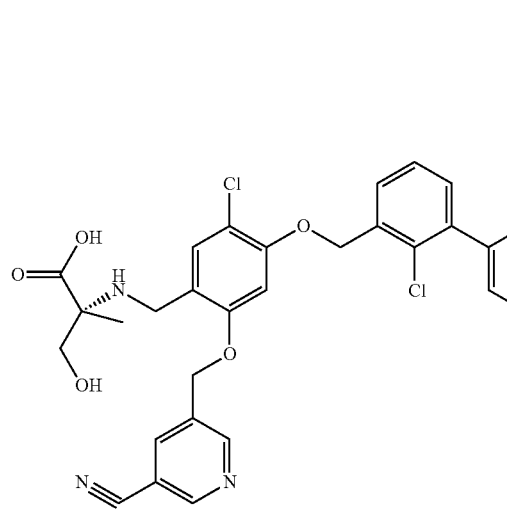
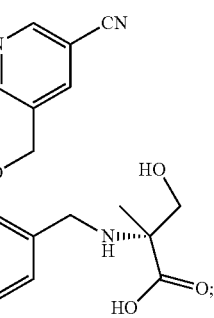

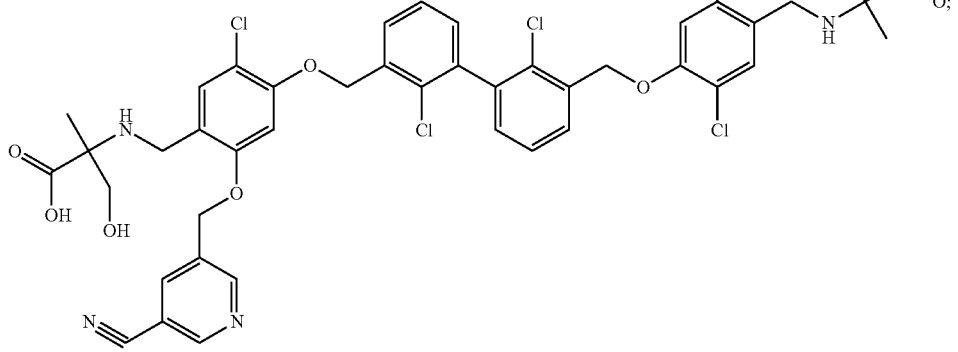
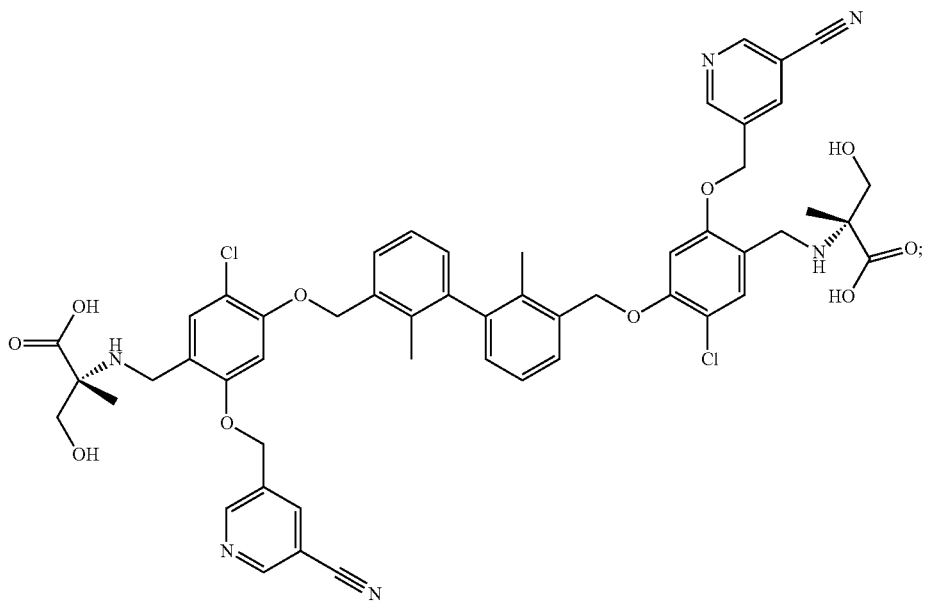
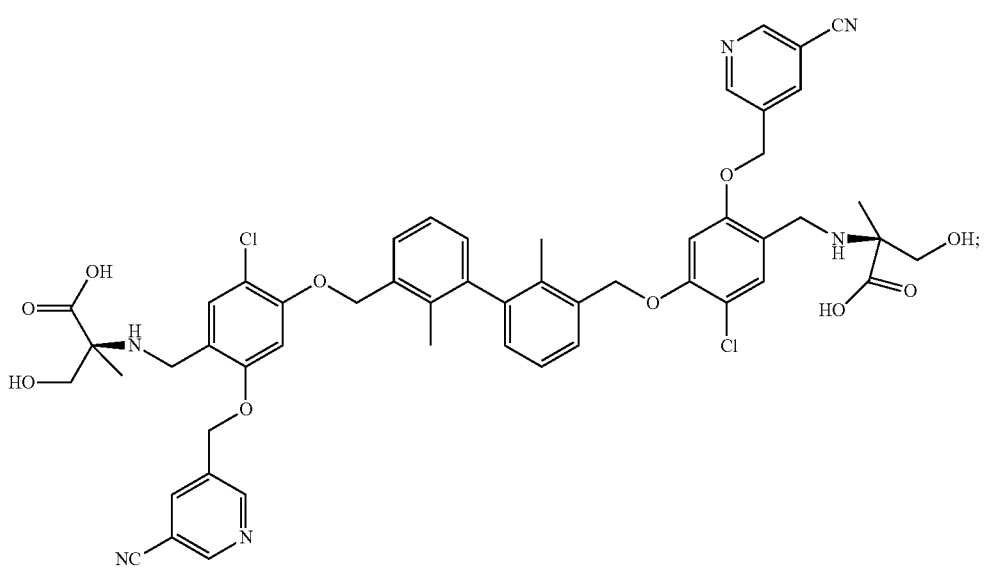

481 482
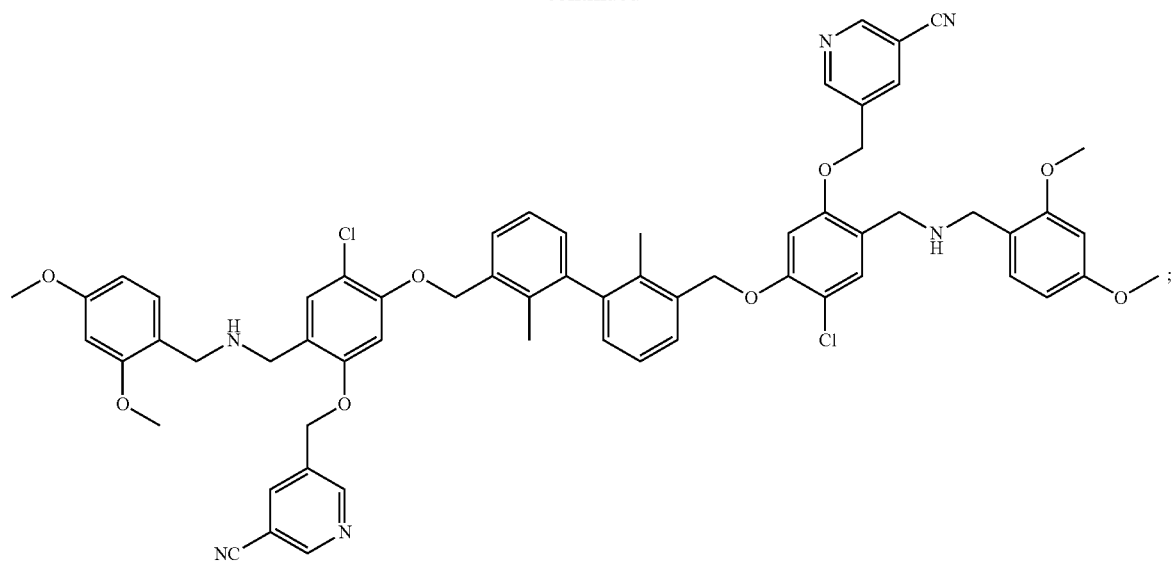
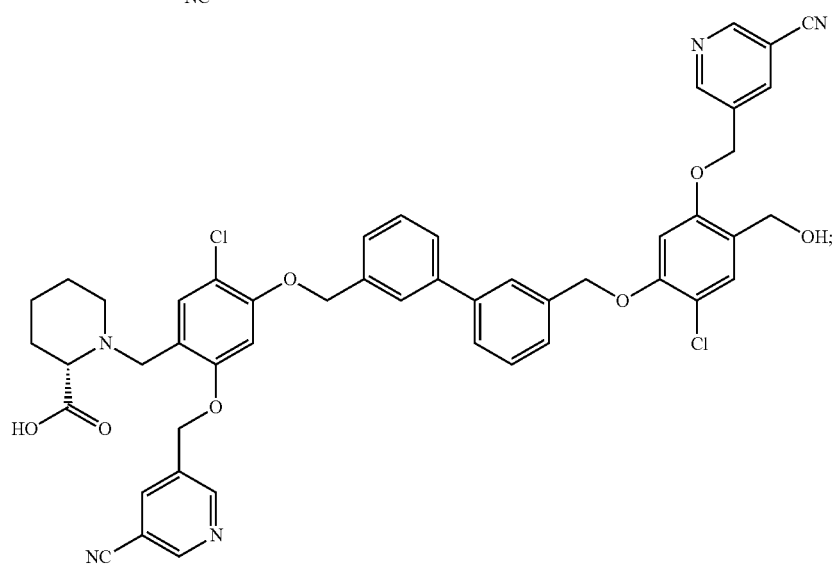
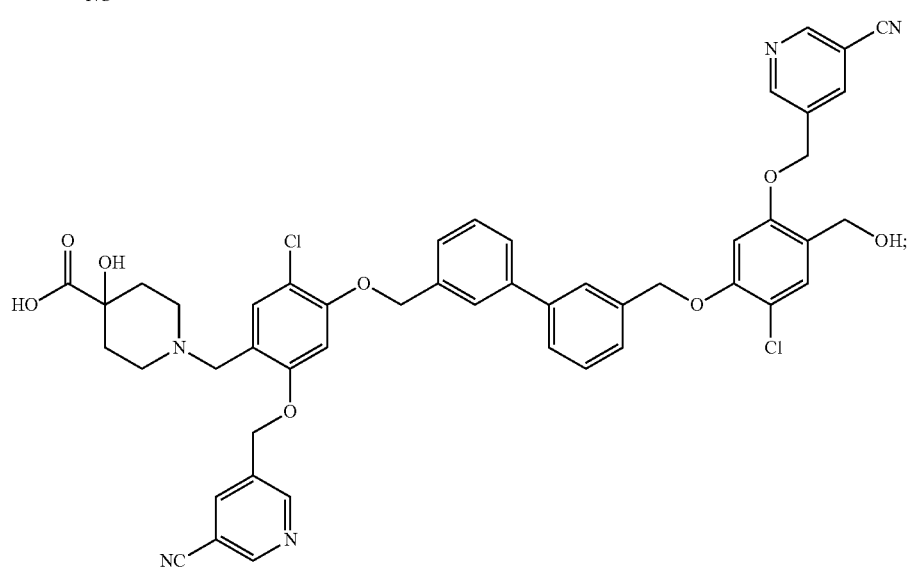

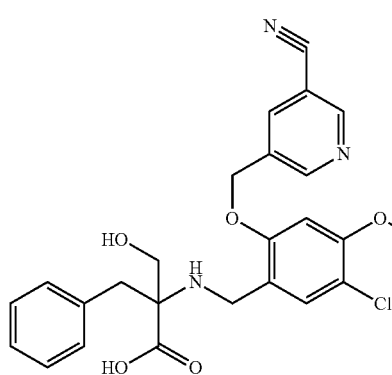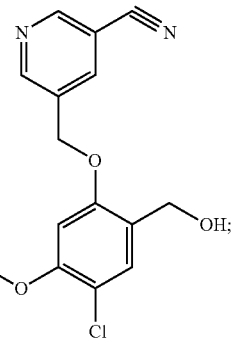
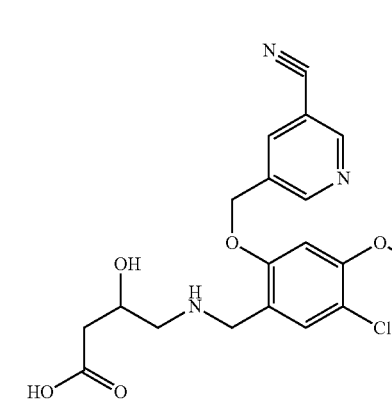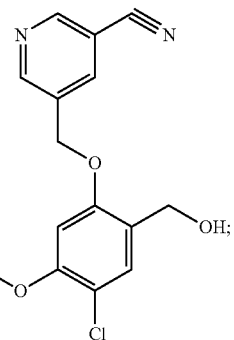
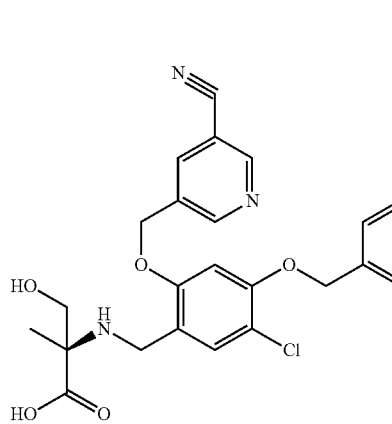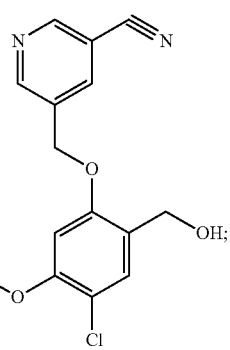
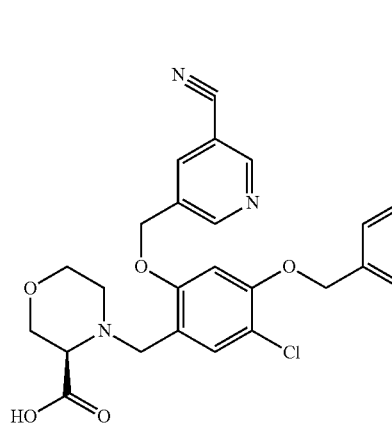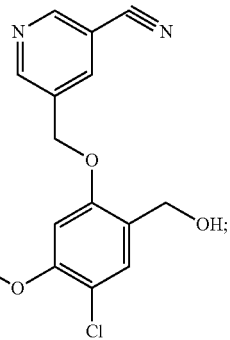

485
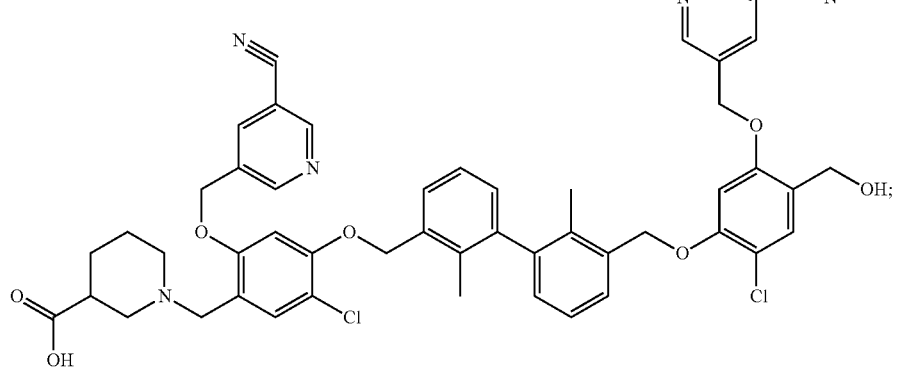
486
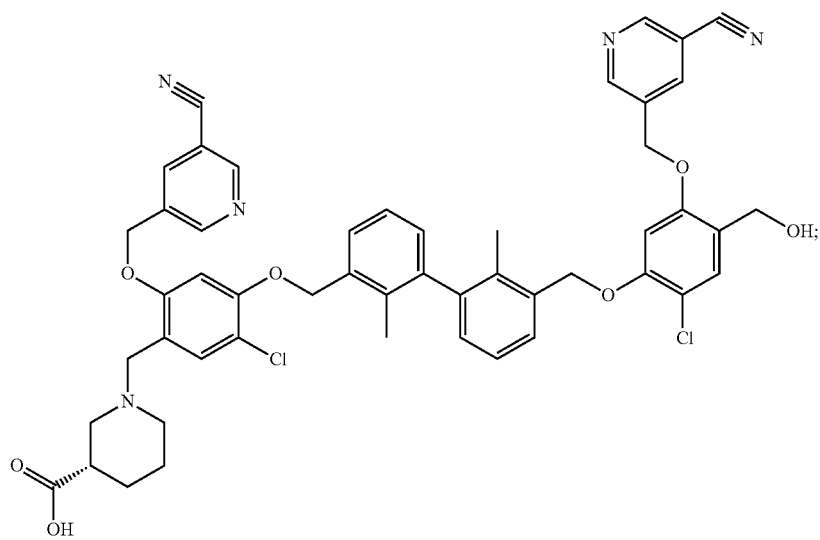
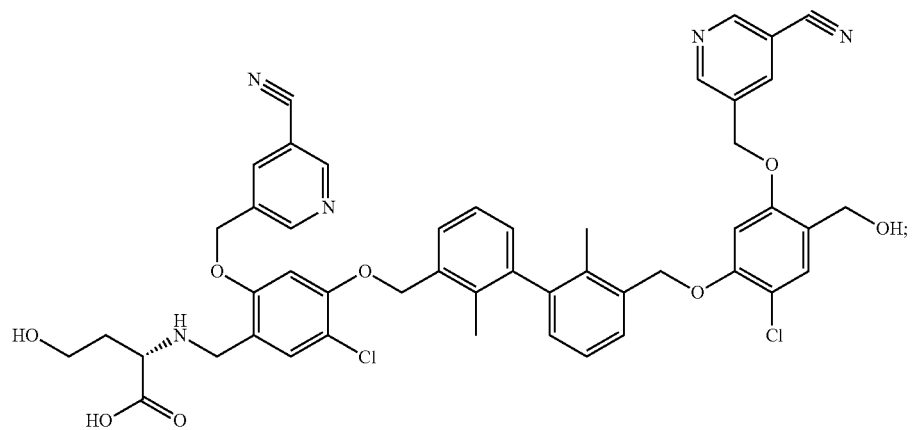

487 488
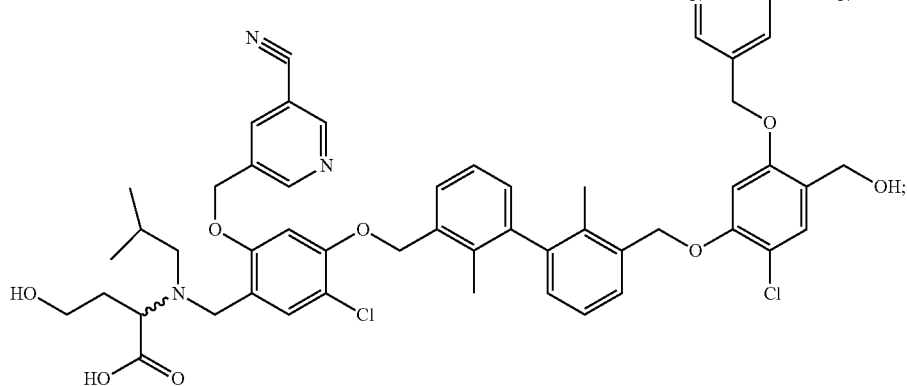
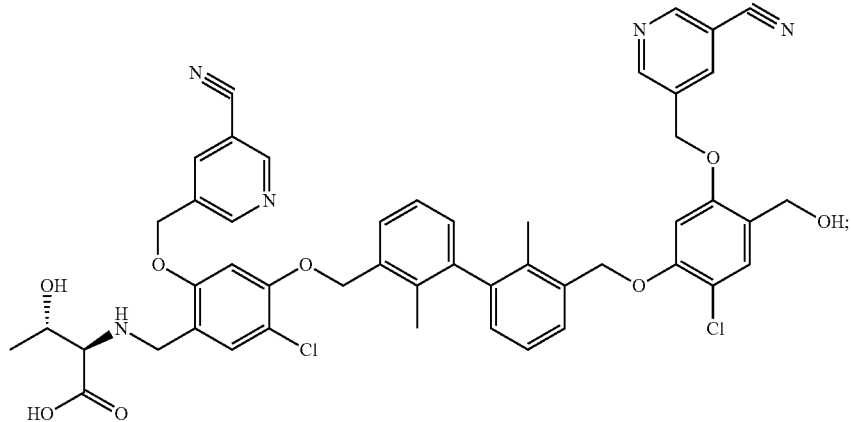
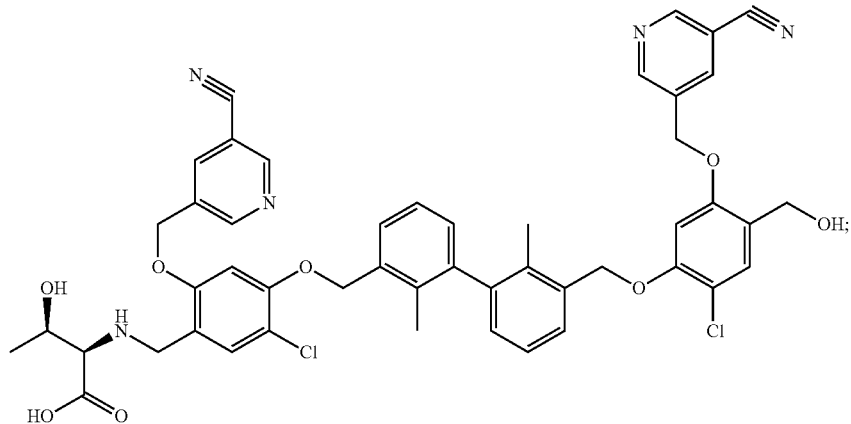
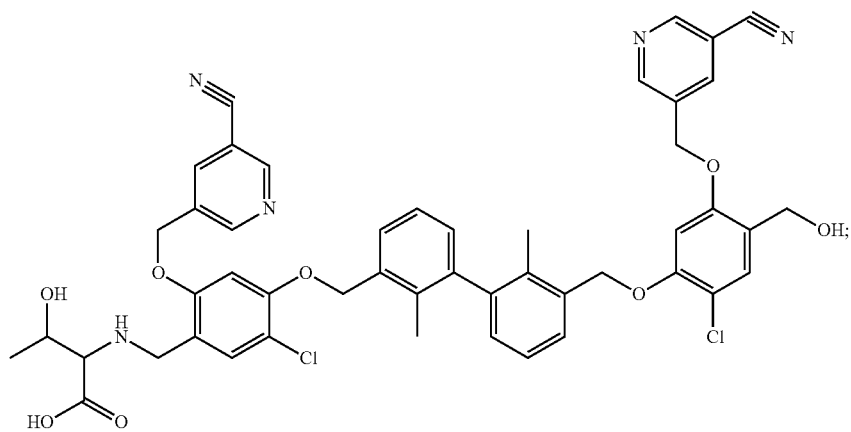

-continued
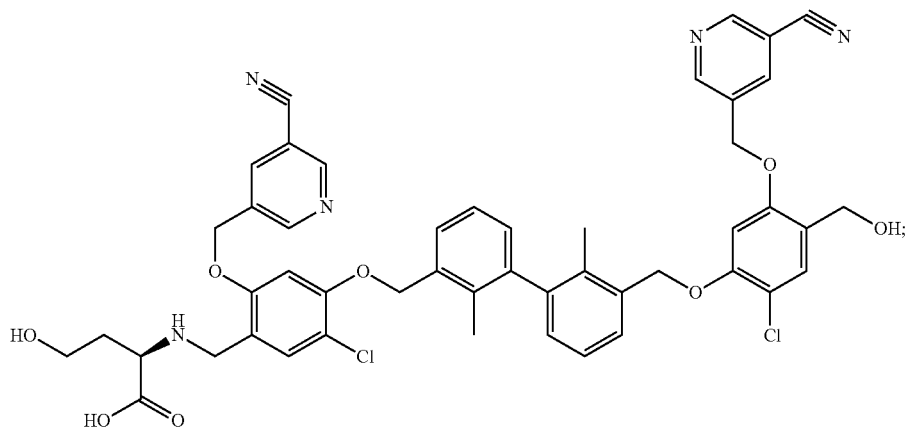
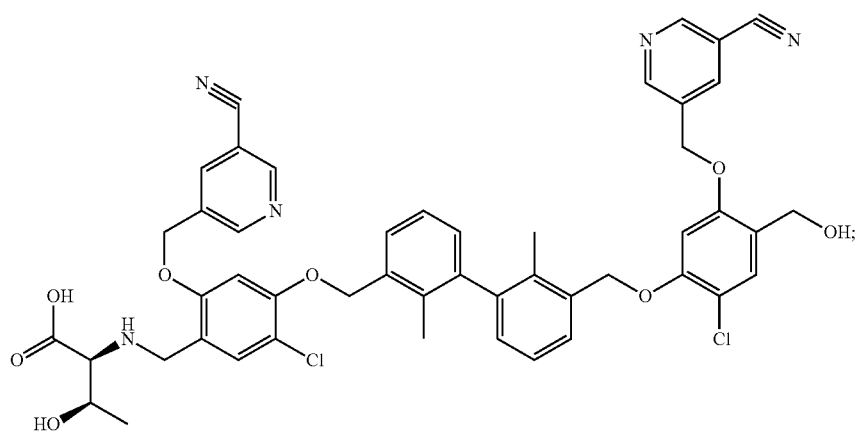
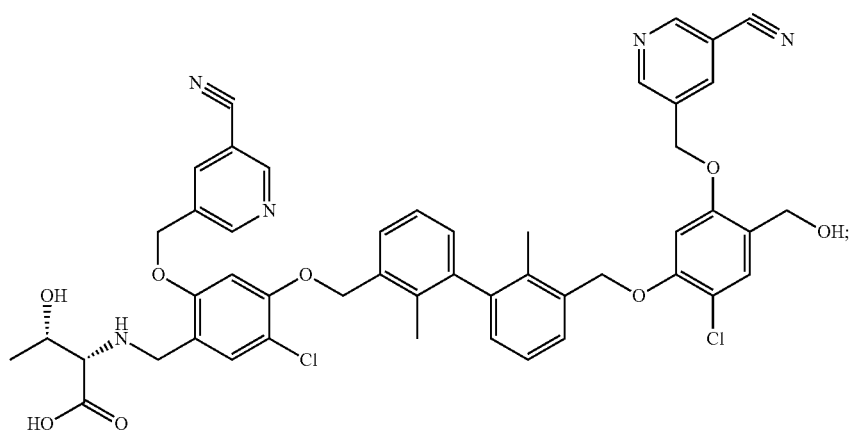
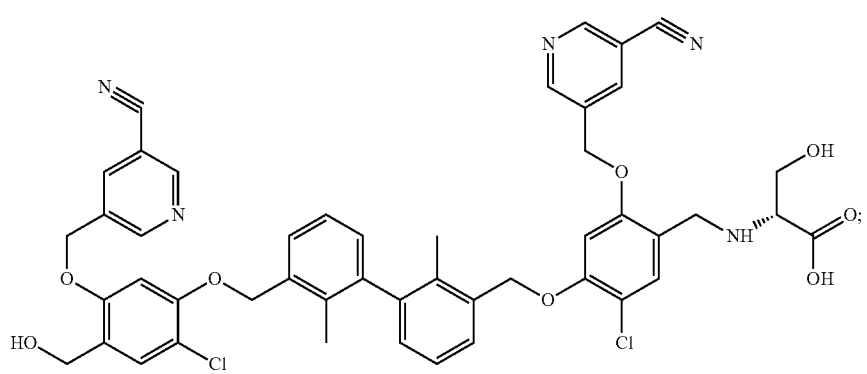

491
492
-continued
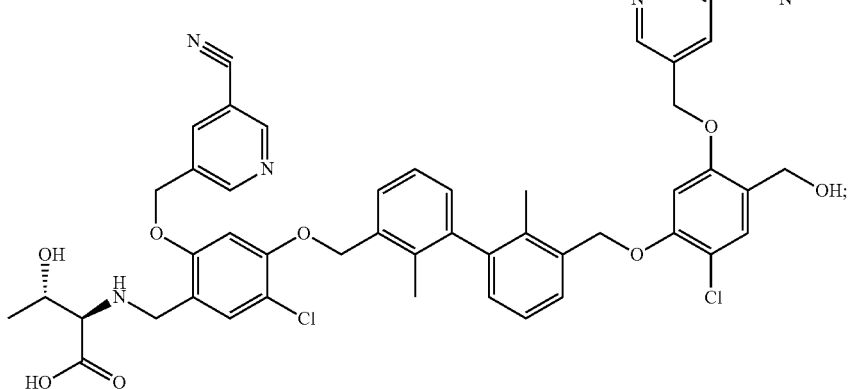
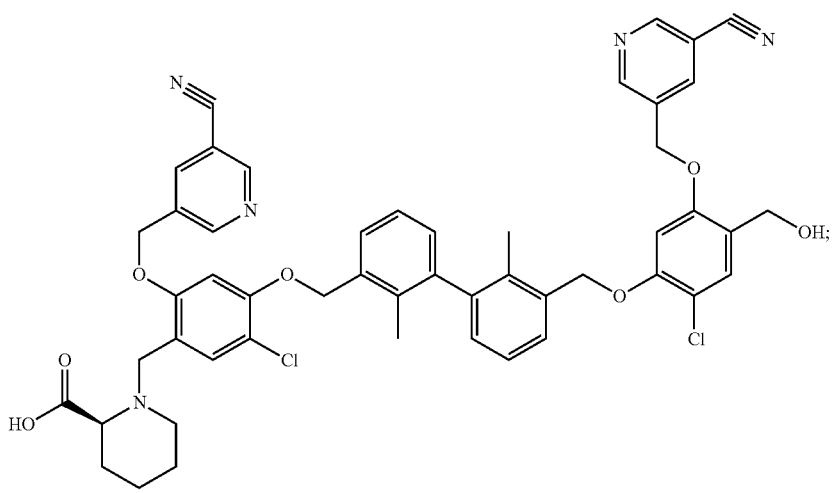
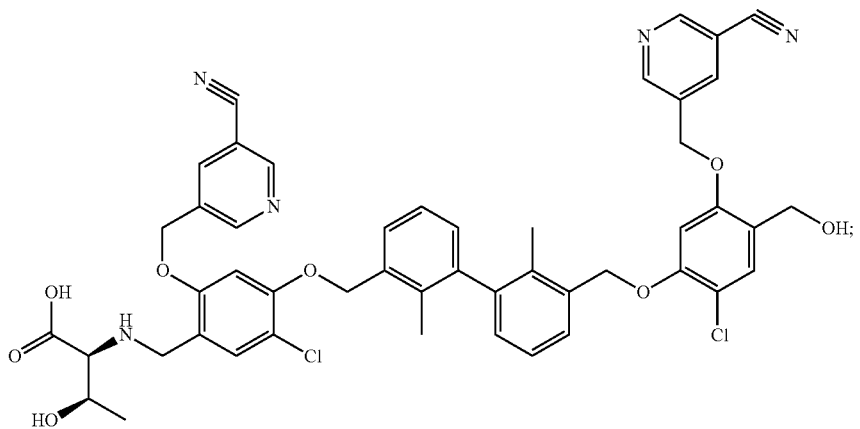

493 494
-continued
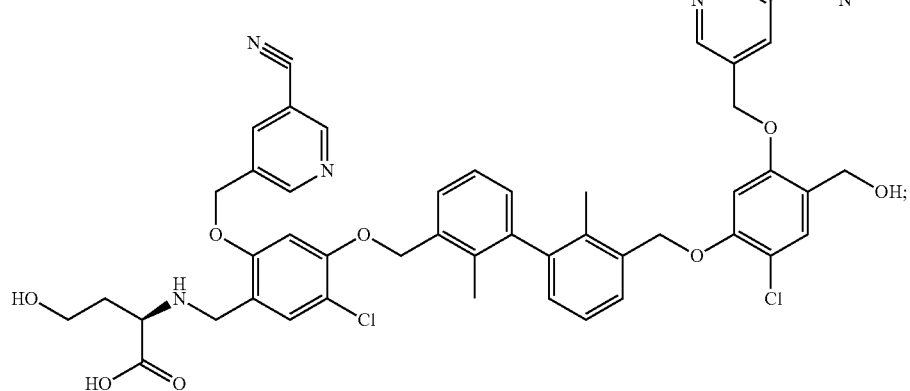
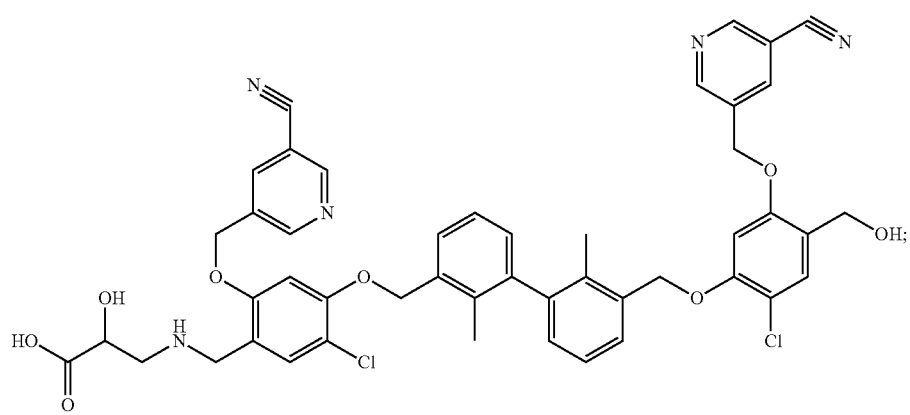
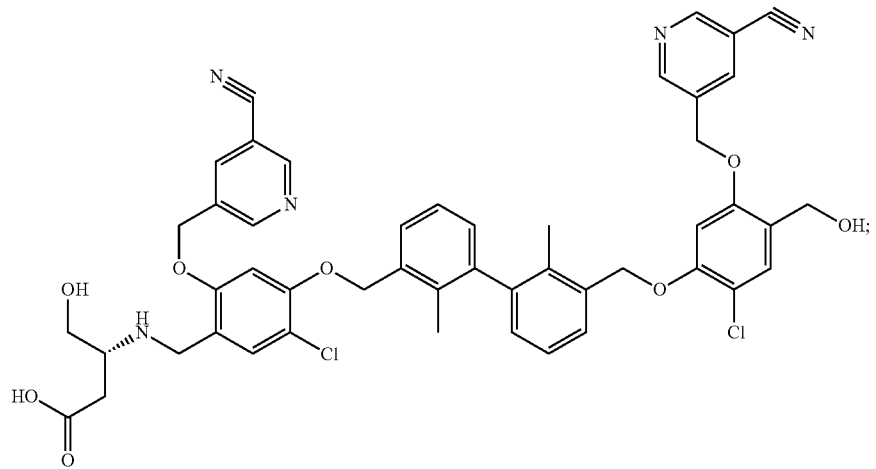

495
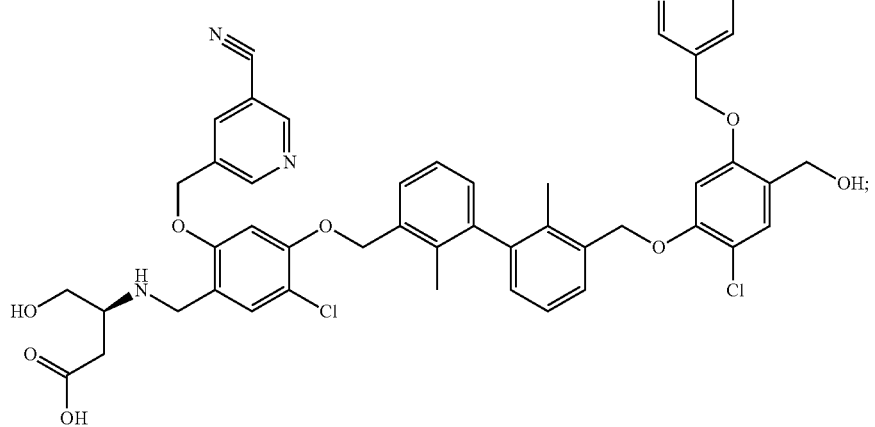
-continued
496
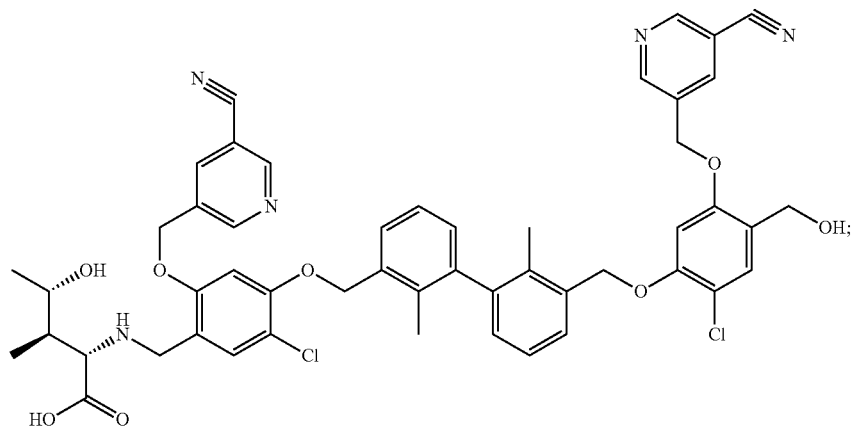
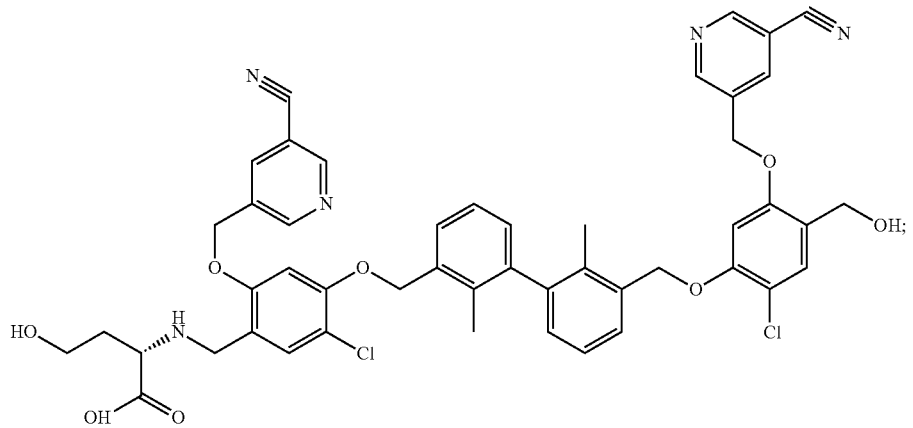

-continued
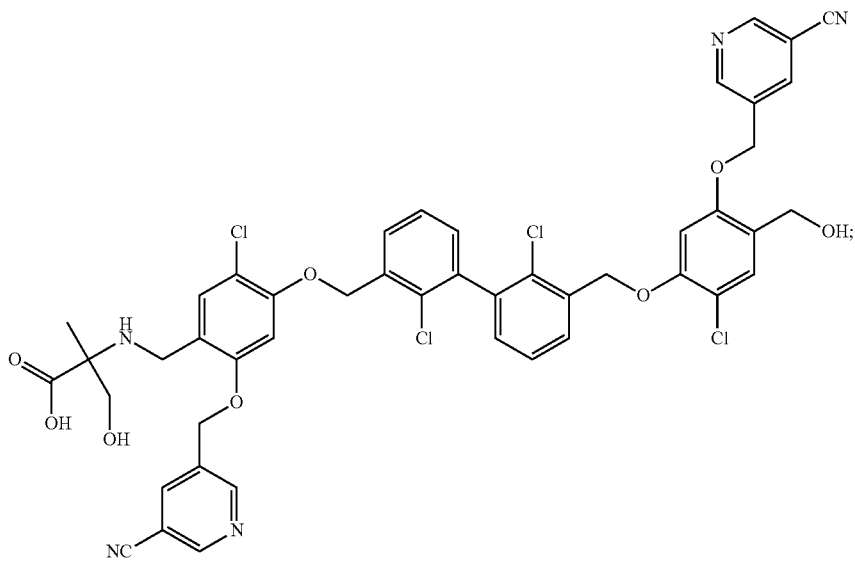
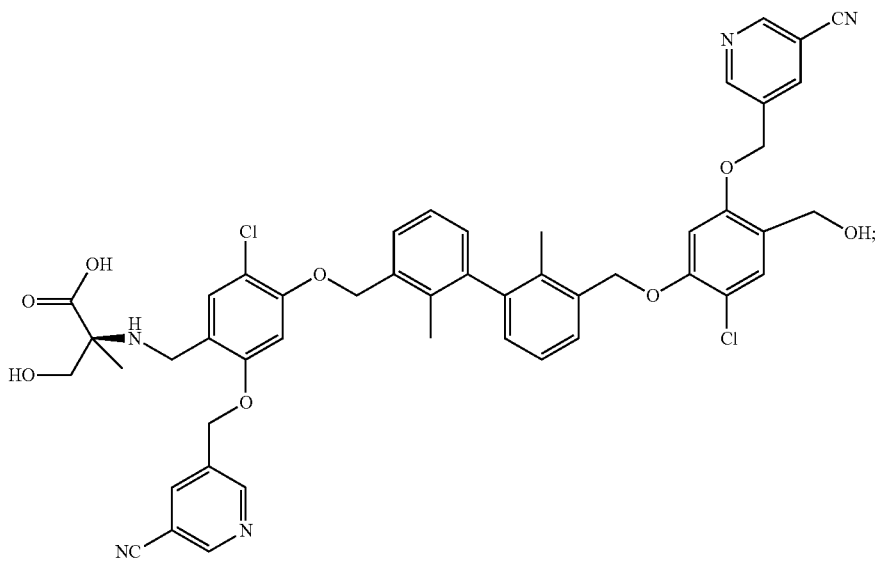
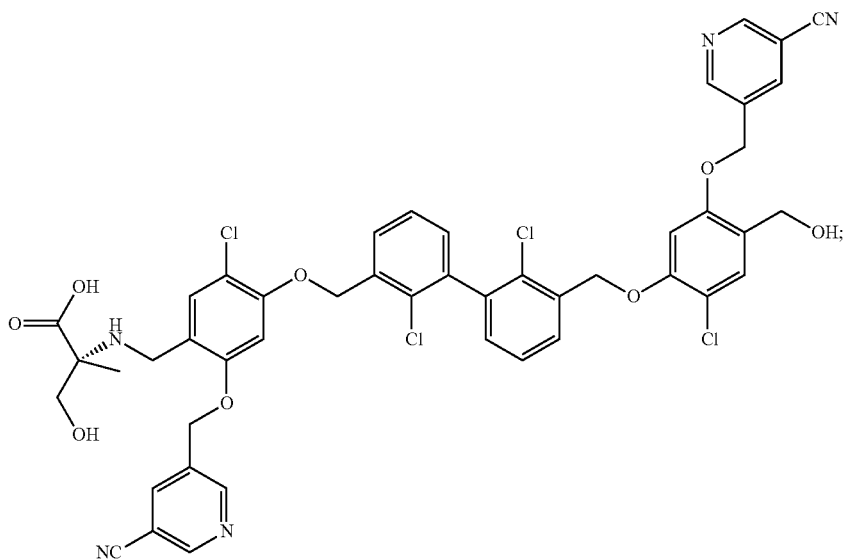

-continued
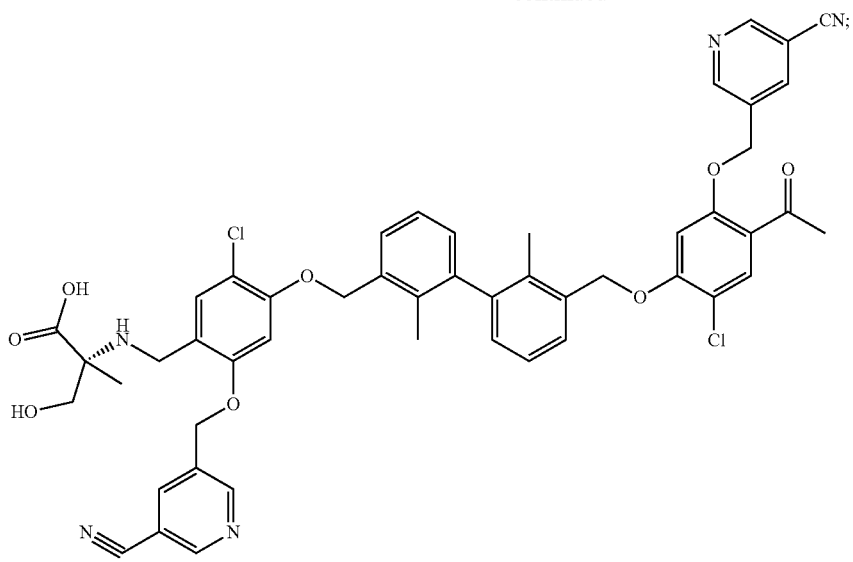
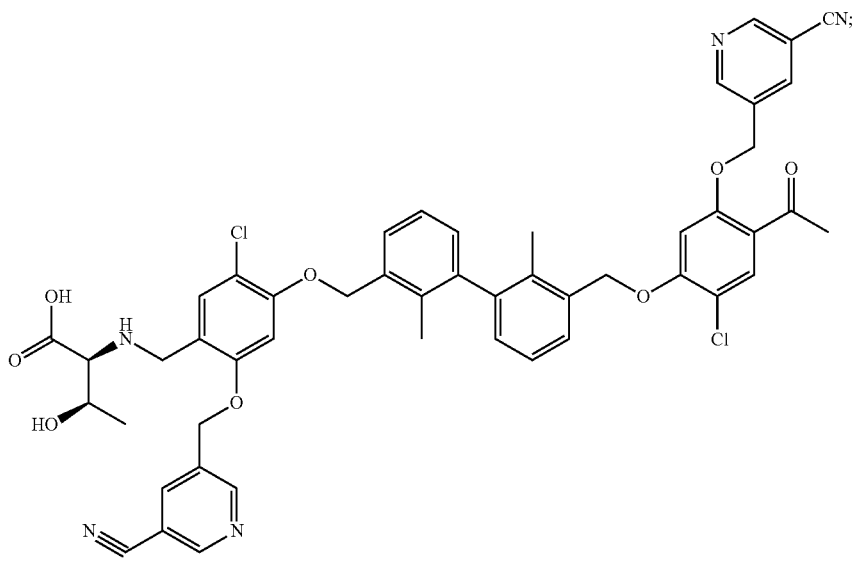
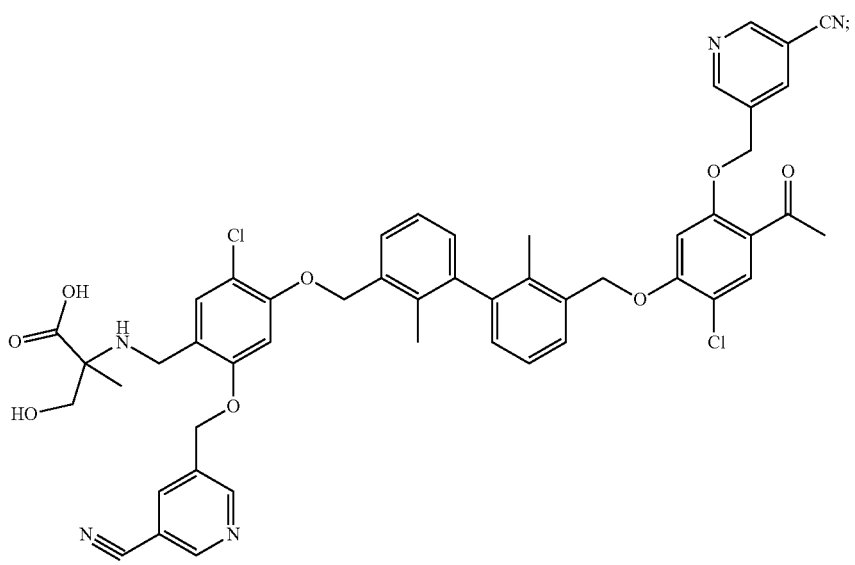

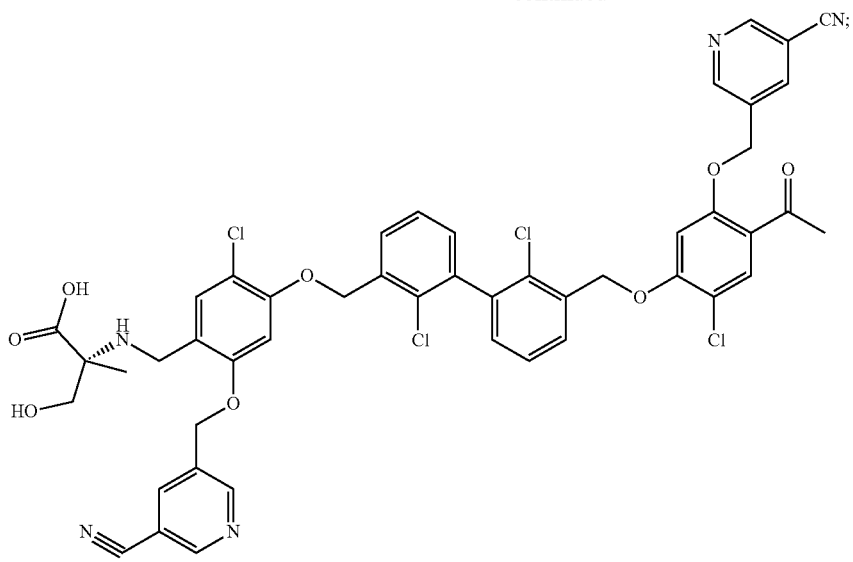
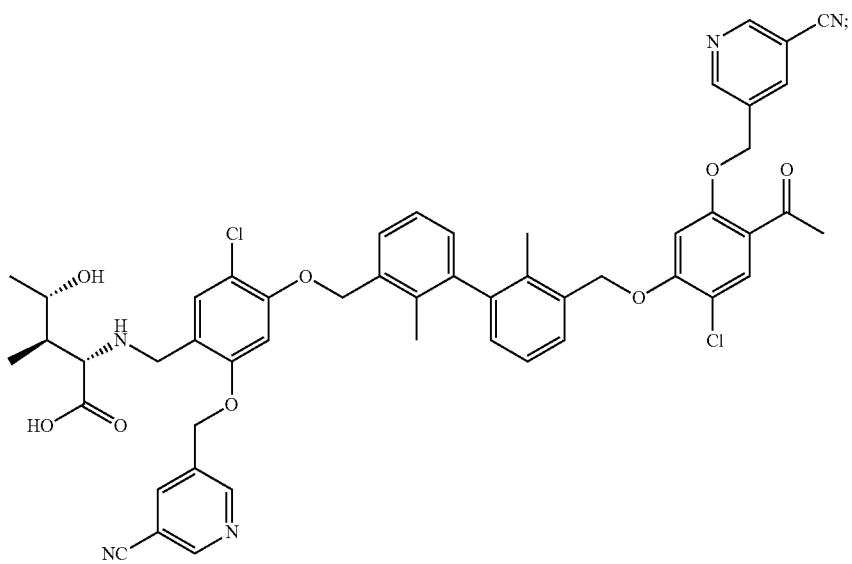
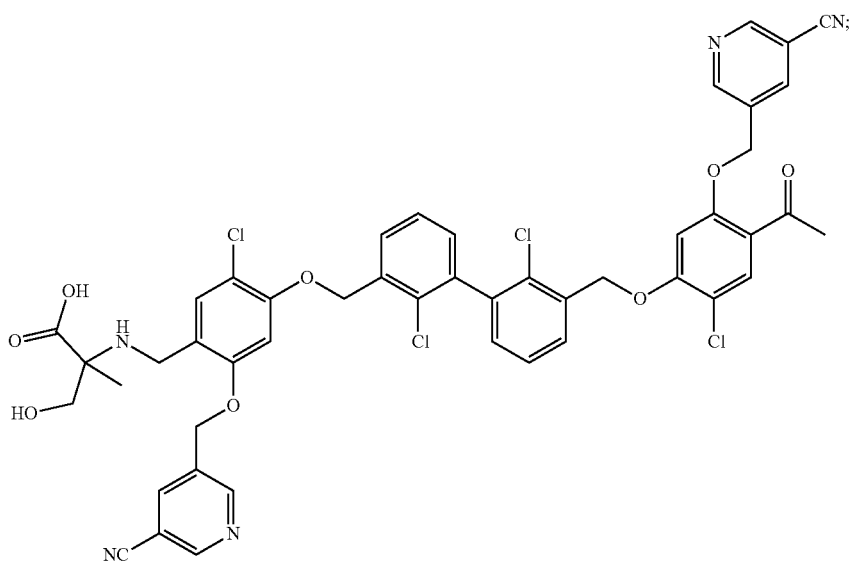

-continued
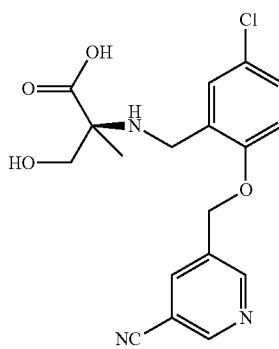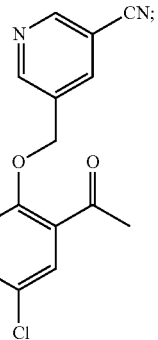
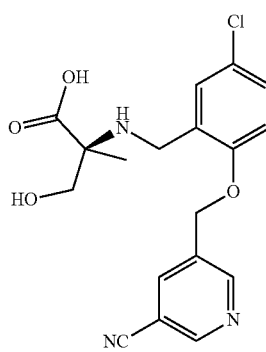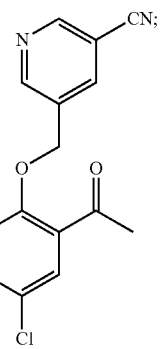
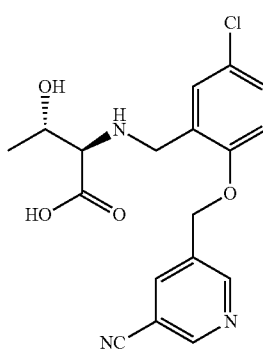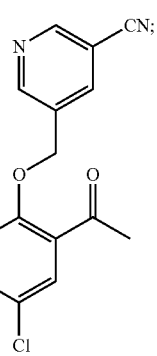

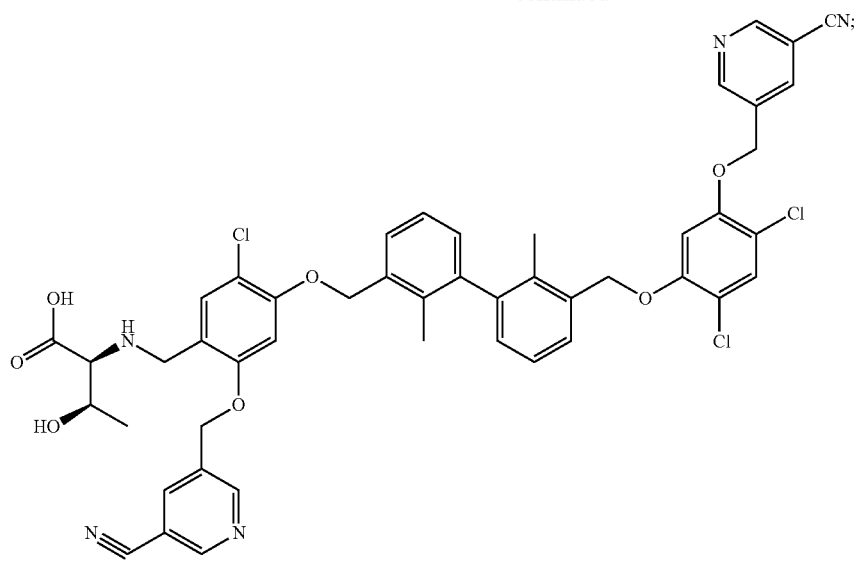
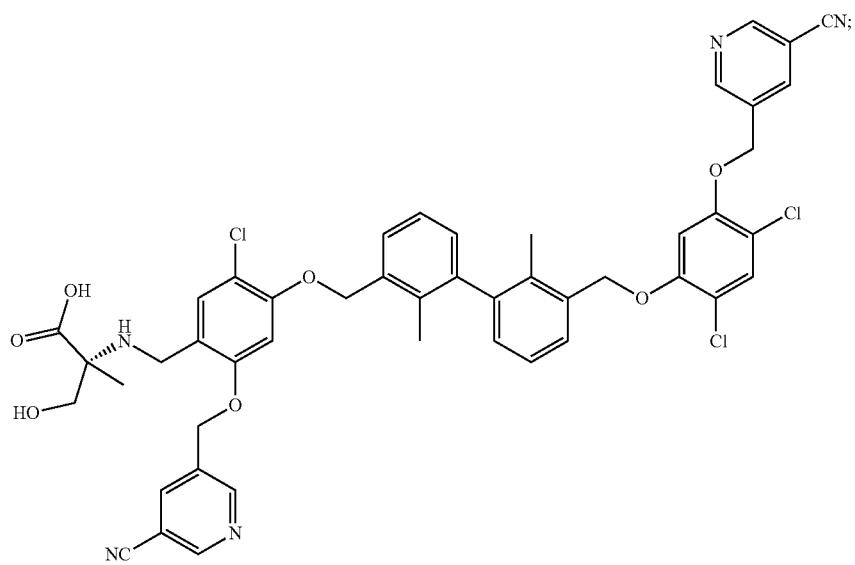
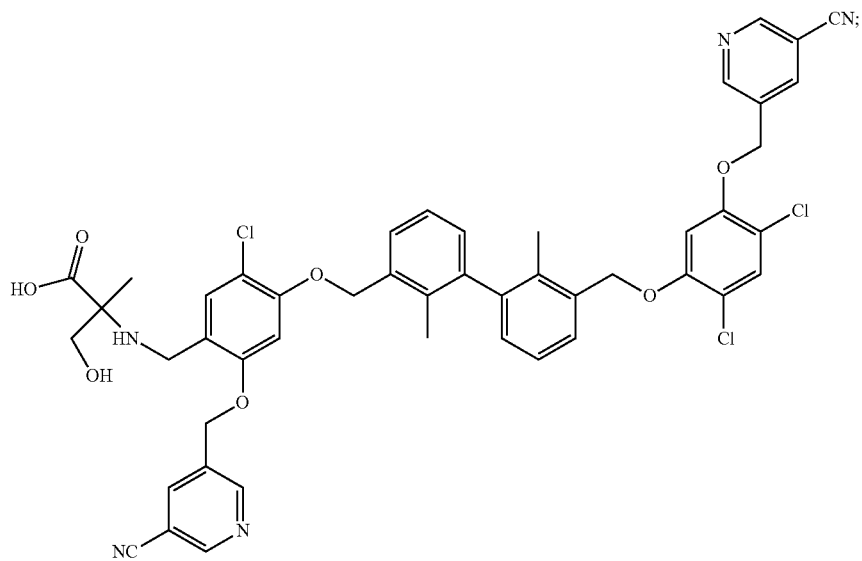

-continued
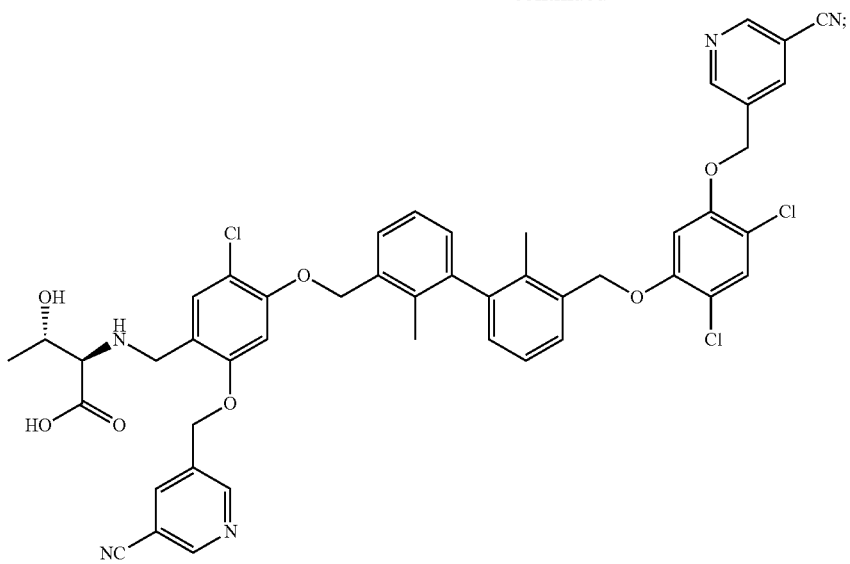
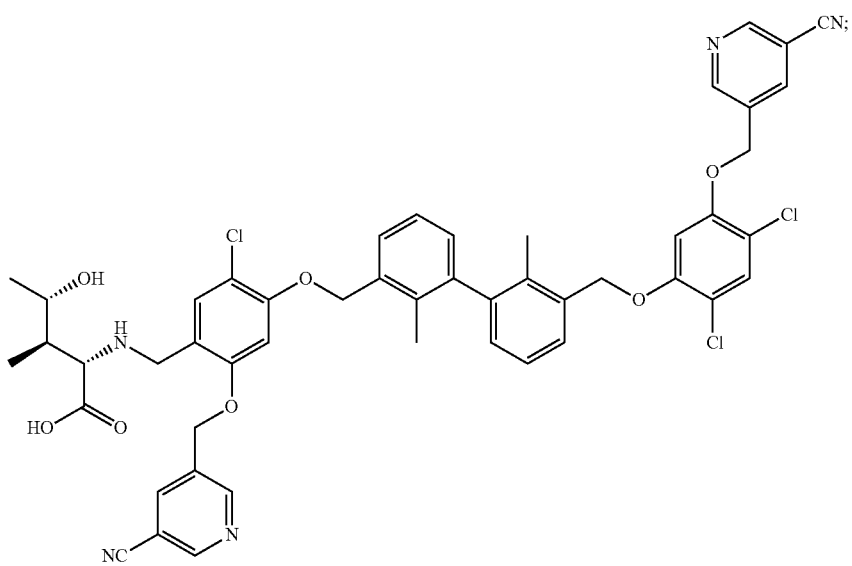
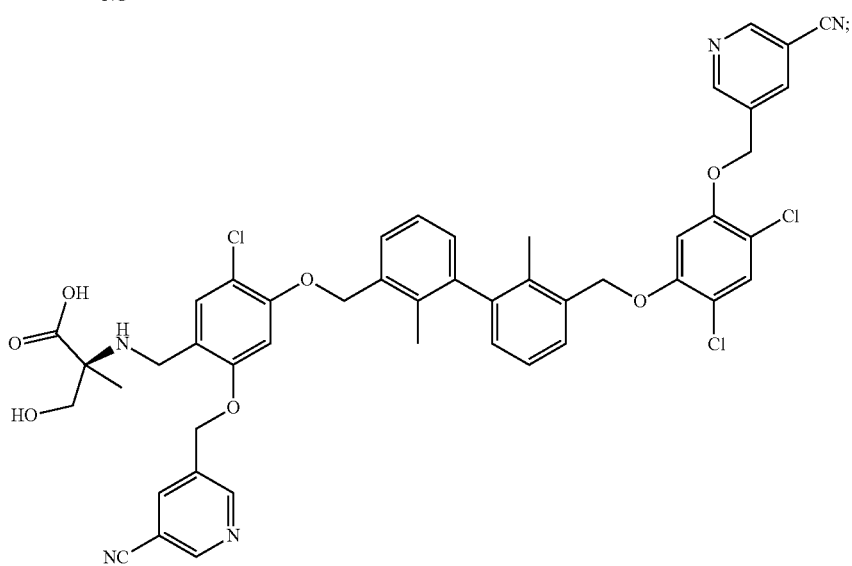

-continued
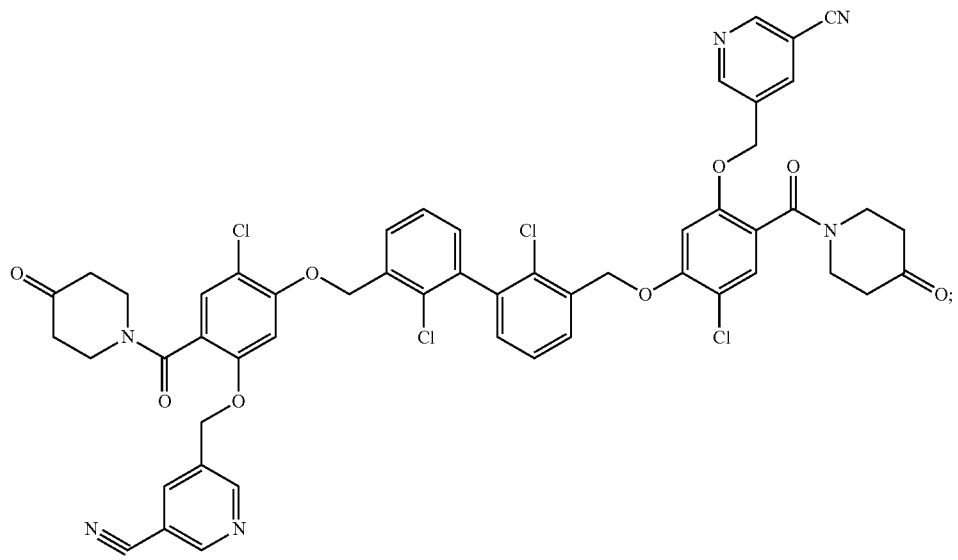
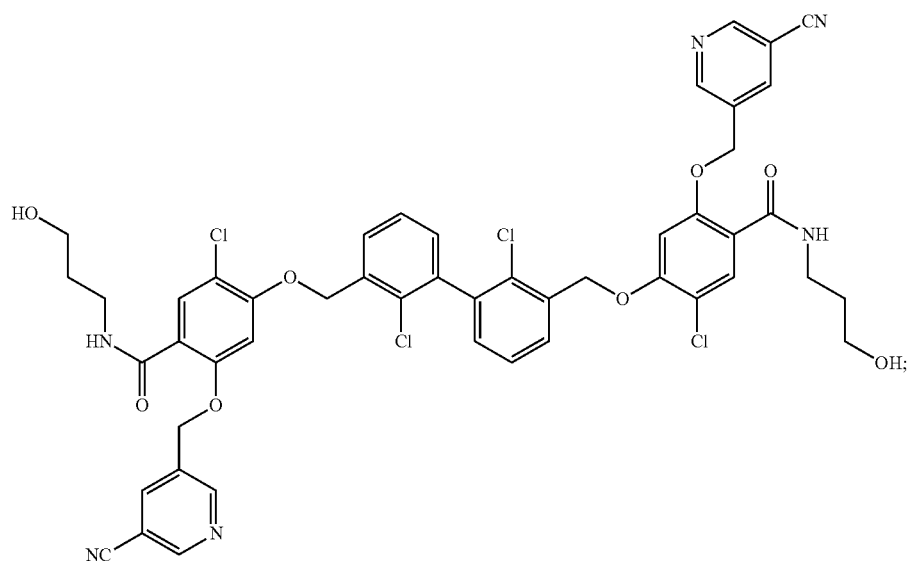
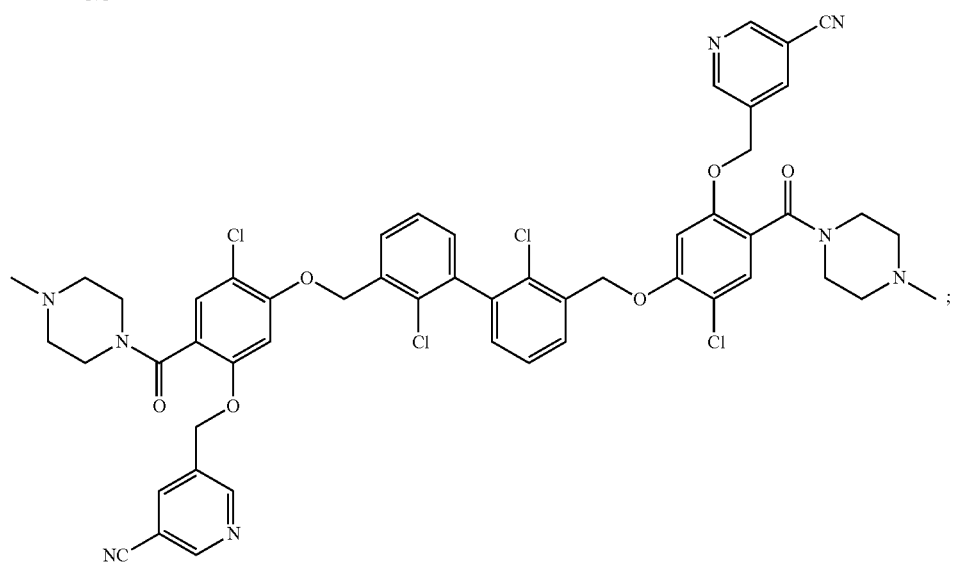

511
512
-continued
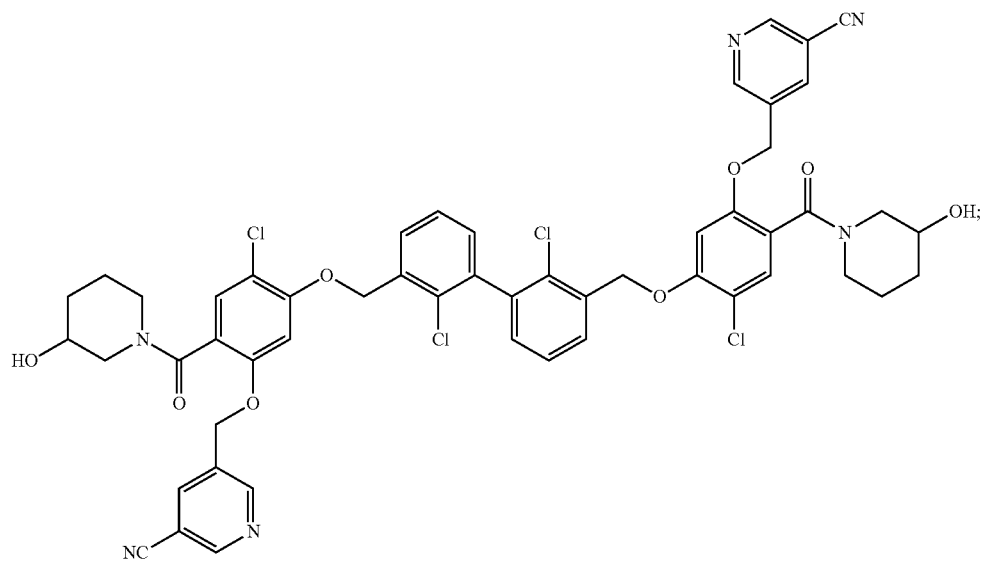
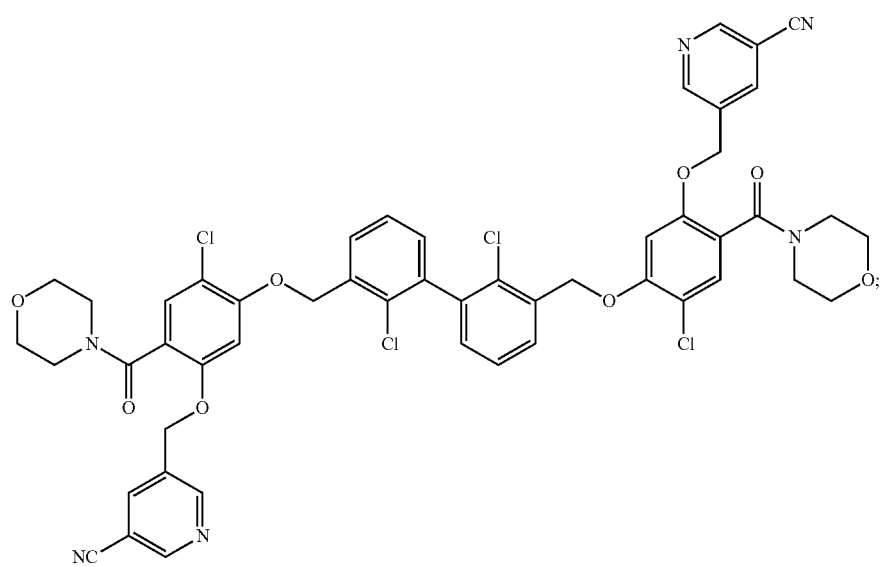
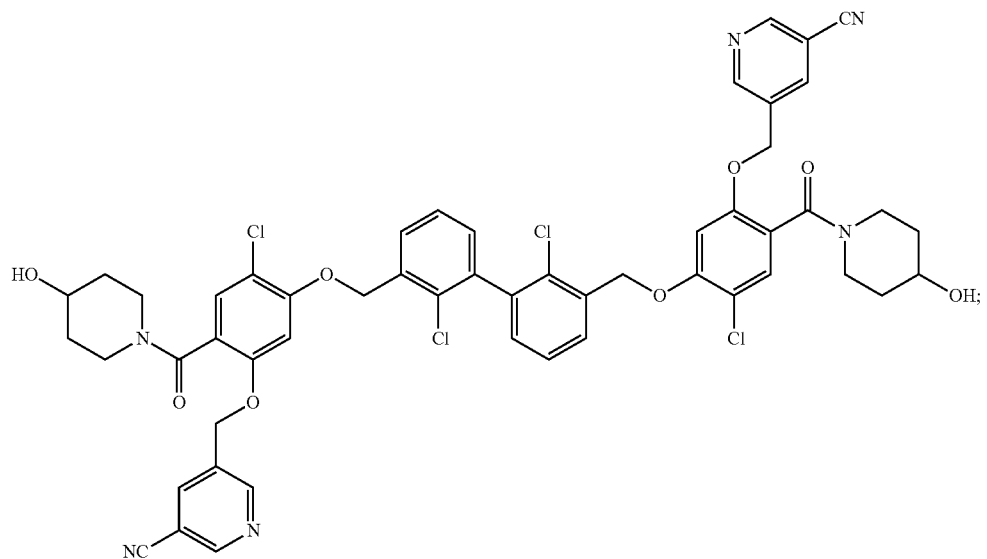

513
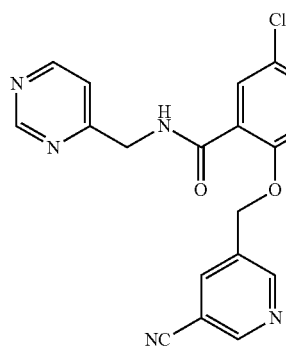
514
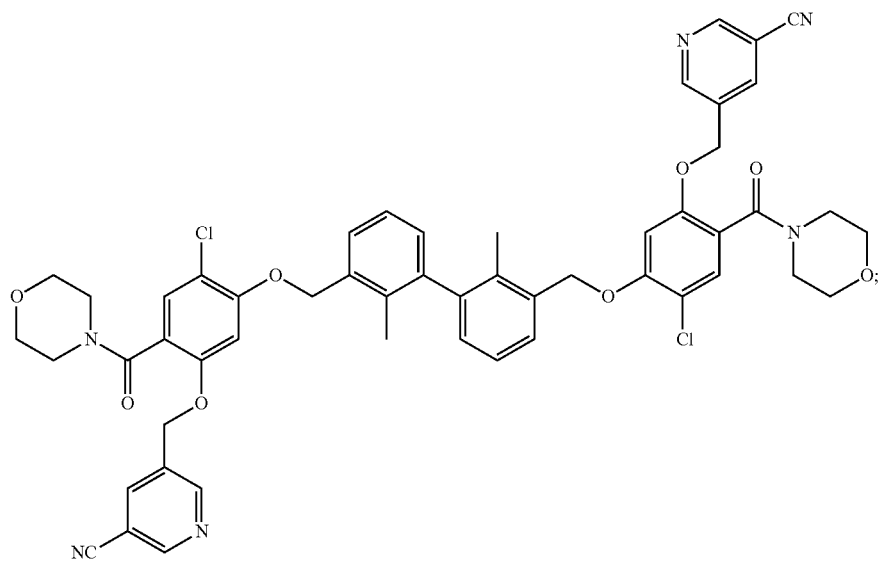
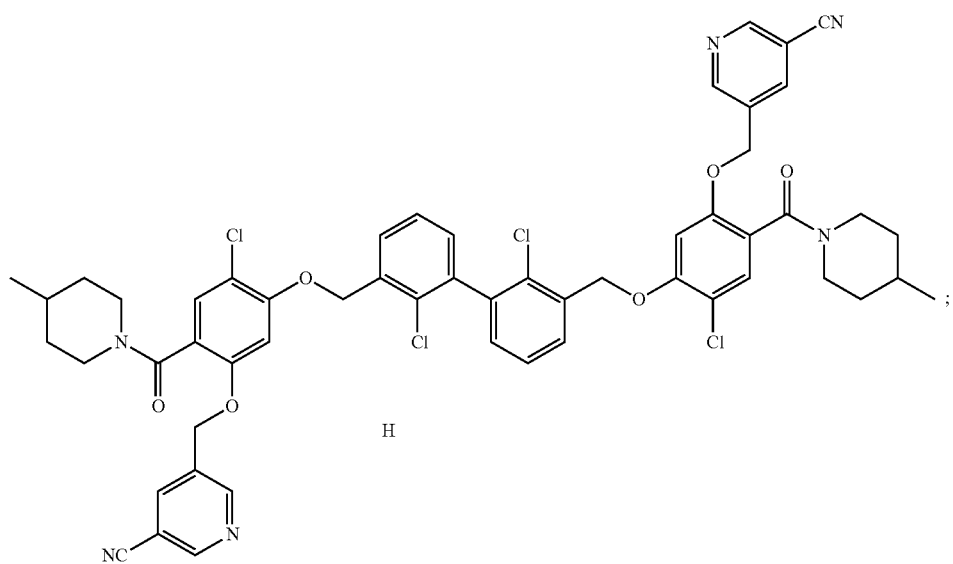

-continued
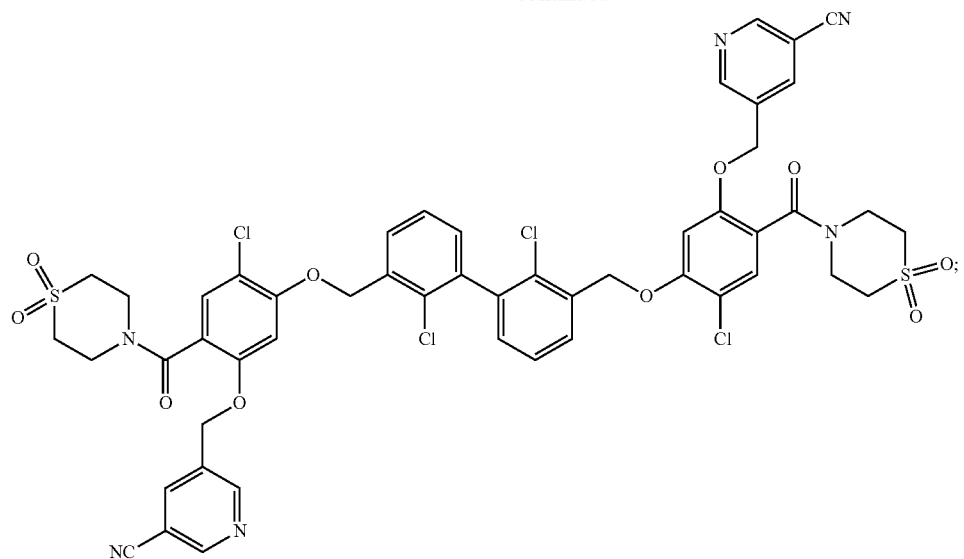
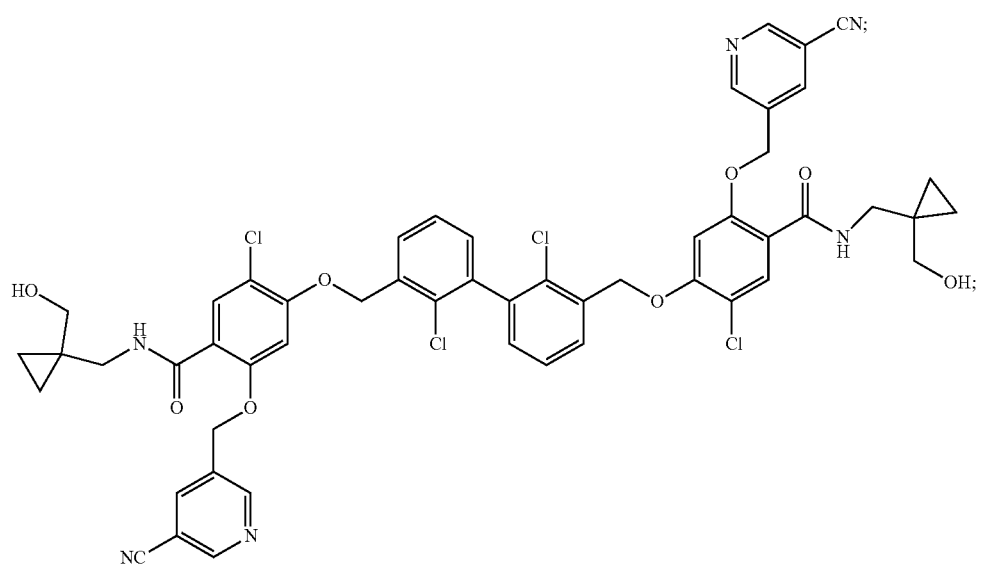
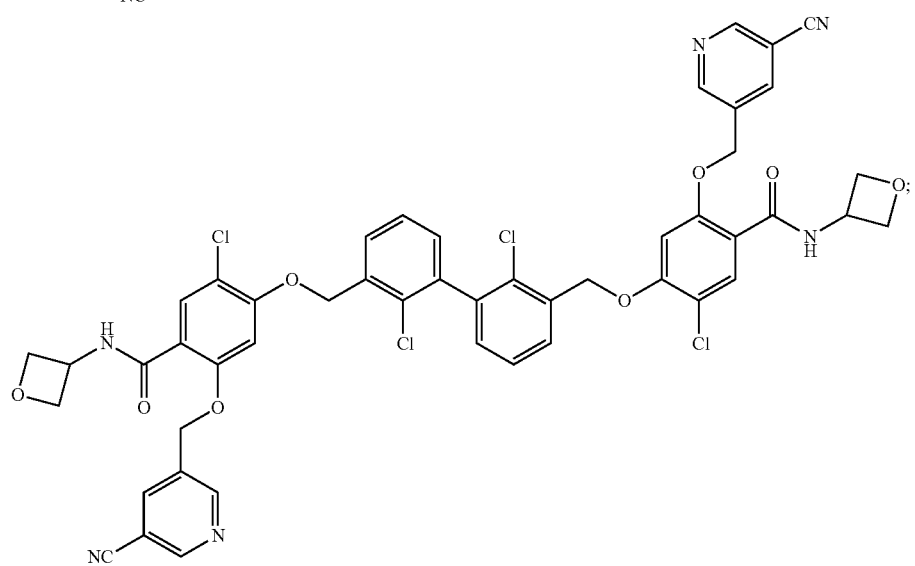

-continued
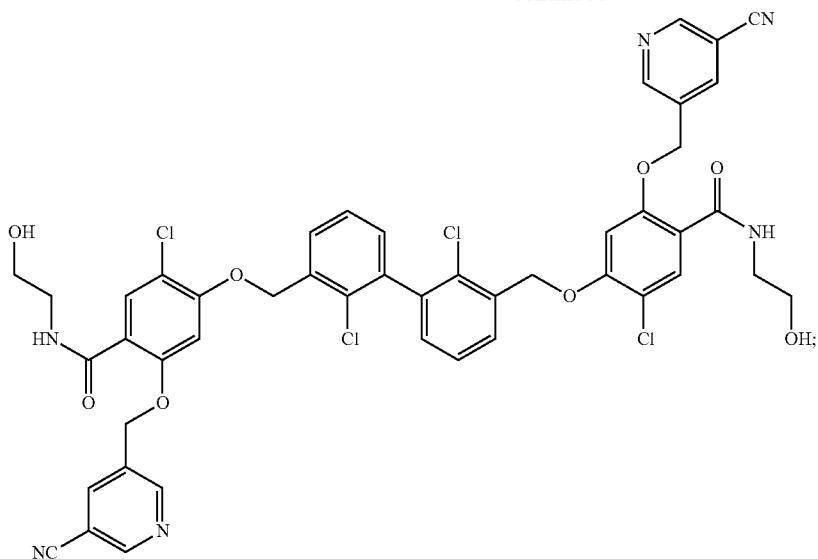
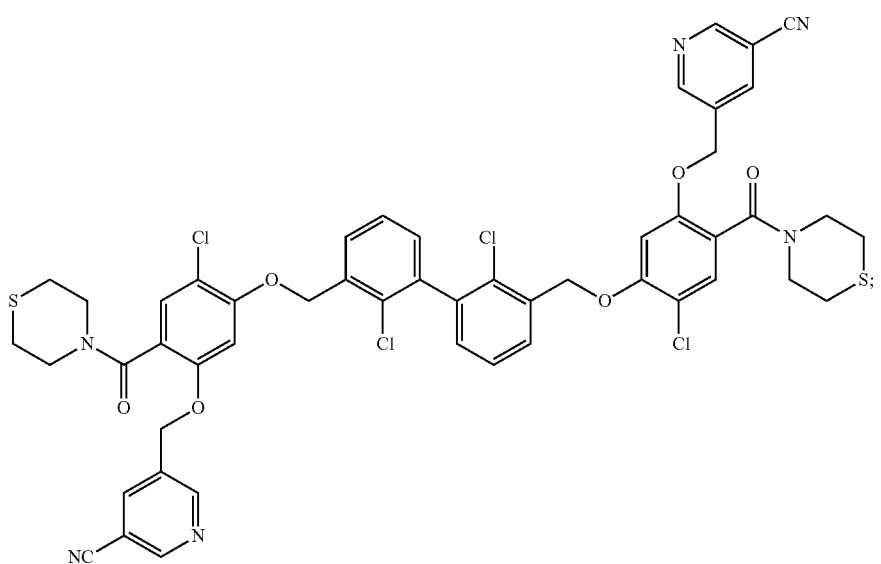
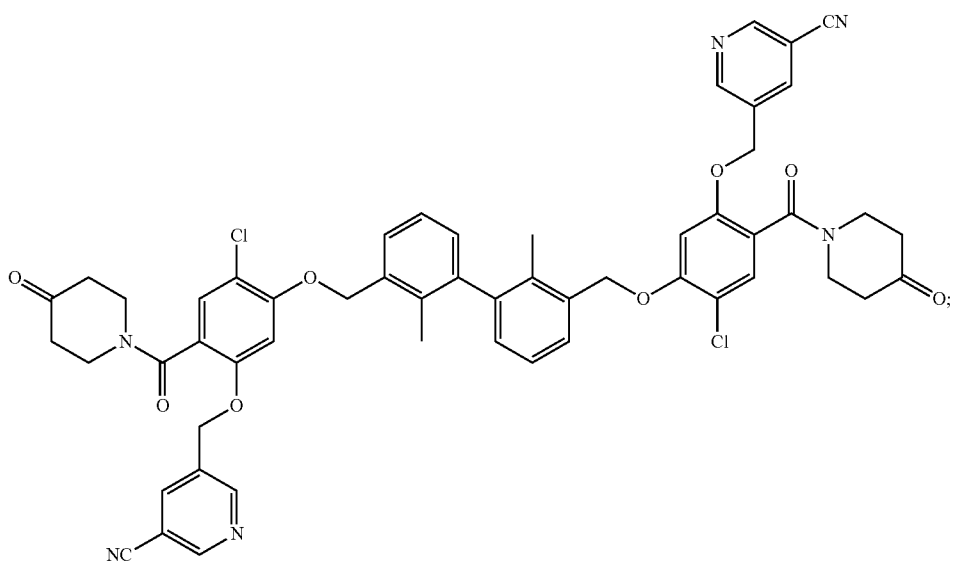

-continued
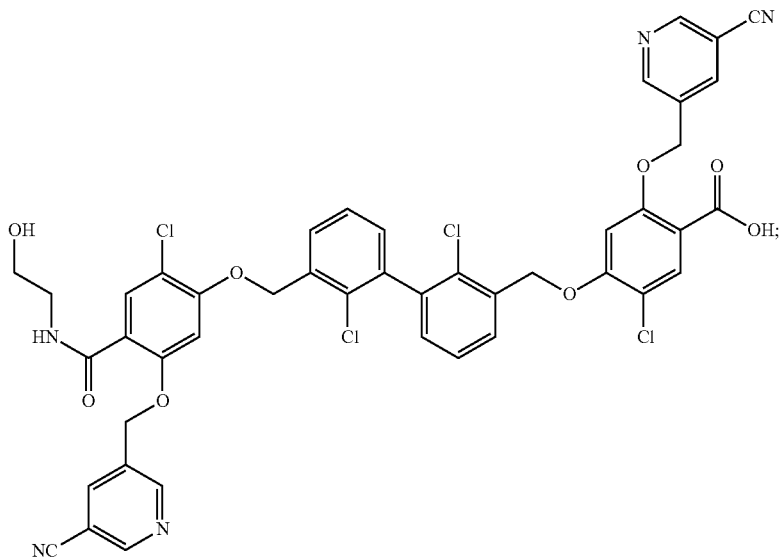
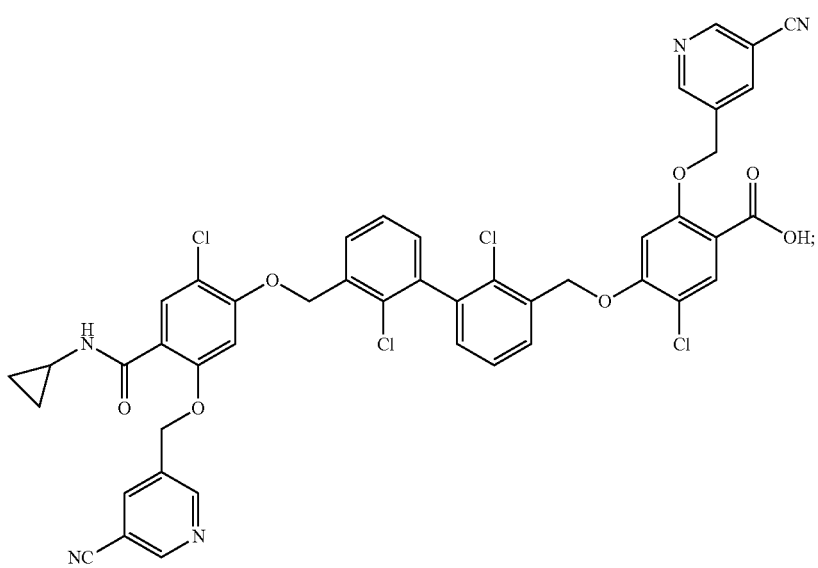
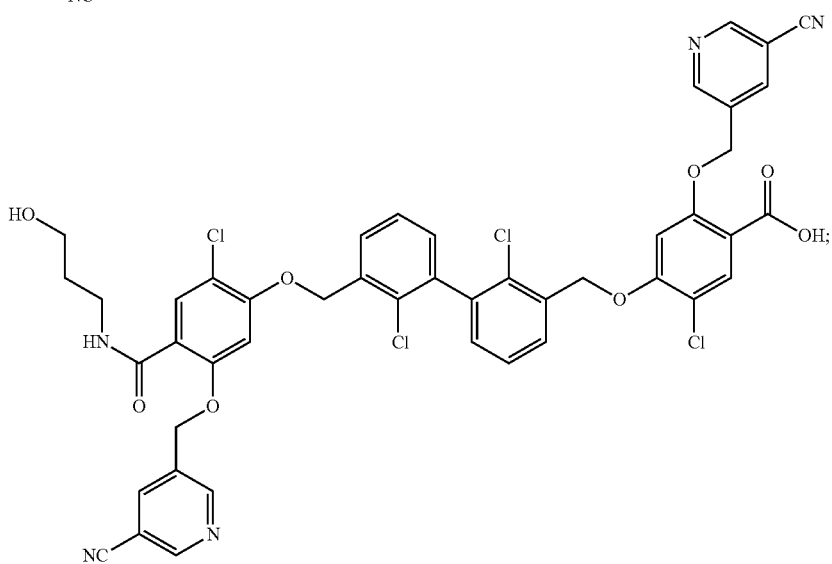

-continued
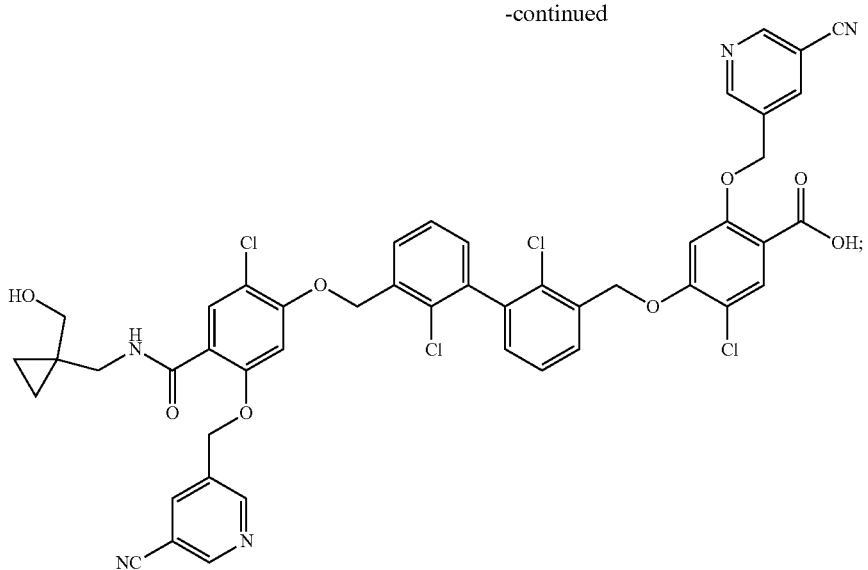
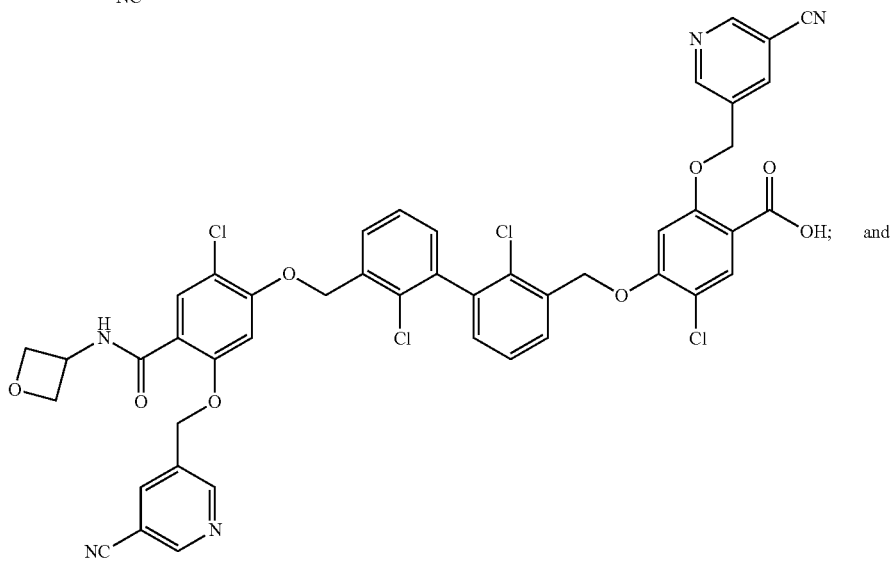
and
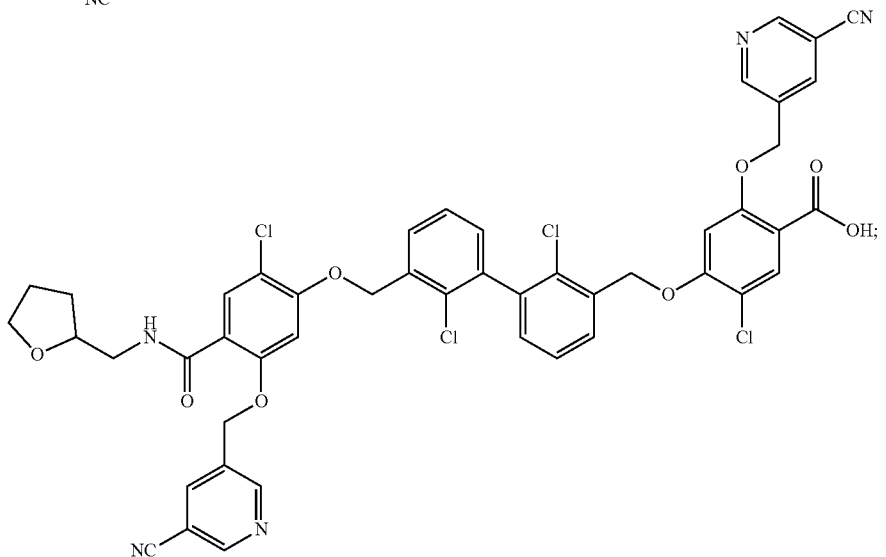
or a pharmaceutically acceptable salt thereof.

8. A pharmaceutical composition comprising a compound of claim 1, or a pharmaceutically acceptable salt thereof, and a pharmaceutically acceptable carrier.

* * * * *